US012528815B2

(12) United States Patent
Brown et al.

(10) Patent No.: US 12,528,815 B2
(45) Date of Patent: Jan. 20, 2026

(54) 5-AMINO-8-(4-PYRIDYL)-[1,2,4]TRIAZOLO [4,3-C]PYRIMIDIN-3-ONE COMPOUNDS FOR USE AGAINST CANCER

(71) Applicant: Nxera Pharma UK Limited, Cambridge (GB)

(72) Inventors: Giles Albert Brown, Cambridge (GB); Miles Stuart Congreve, Cambridge (GB); Christine Mary Richardson, Saffron Walden (GB); Rebecca Paul, St. Albans (GB); Stephen Philippe Andrews, Royston (GB); Jonathan Stephen Mason, Cambridge (GB); Francesca Deflorian, Cambridge (GB); Nigel Alan Swain, Cambridge (GB)

(73) Assignee: Nxera Pharma UK Limited, Cambridge (GB)

( * ) Notice: Subject to any disclaimer, the term of this patent is extended or adjusted under 35 U.S.C. 154(b) by 665 days.

(21) Appl. No.: 17/914,196

(22) PCT Filed: Mar. 25, 2021

(86) PCT No.: PCT/EP2021/057807

§ 371 (c)(1),
(2) Date: Sep. 23, 2022

(87) PCT Pub. No.: WO2021/191379

PCT Pub. Date: Sep. 30, 2021

(65) Prior Publication Data

US 2023/0146483 A1 May 11, 2023

Related U.S. Application Data

(60) Provisional application No. 62/994,970, filed on Mar. 26, 2020.

(51) Int. Cl.

| | |
|---|---|
| ***C07D 487/04*** | (2006.01) |
| ***A61K 31/501*** | (2006.01) |
| ***A61K 31/506*** | (2006.01) |
| ***A61K 31/5377*** | (2006.01) |
| ***A61K 31/55*** | (2006.01) |
| ***A61P 35/00*** | (2006.01) |
| ***C07D 519/00*** | (2006.01) |

(52) U.S. Cl.

CPC ......... *C07D 487/04* (2013.01); *C07D 519/00* (2013.01); *C07B 2200/05* (2013.01)

(58) Field of Classification Search

CPC ................ C07D 487/04; A61K 31/501; A61K 31/506; A61K 31/5377; A61K 31/55; A61P 35/00

See application file for complete search history.

(56) References Cited

FOREIGN PATENT DOCUMENTS

| | | | |
|---|---|---|---|
| EP | 3575301 | A1 | 12/2019 |
| JP | 2011513417 | A | 4/2011 |
| WO | 2006/138734 | A1 | 12/2006 |
| WO | 2009/111449 | A1 | 9/2009 |

OTHER PUBLICATIONS

International Search Report and Written Opinion for Application No. PCT/EP2021/057807, dated May 3, 2021, 10 pages.

*Primary Examiner* — Bruck Kifle

(74) *Attorney, Agent, or Firm* — Finnegan, Henderson, Farabow, Garrett & Dunner LLP

(57) ABSTRACT

Described herein are triazalone compounds of Formula (I): and pharmaceutically acceptable salts thereof. Methods of making and using compounds of Formula (I) are also described. Compounds of Formula (I) and pharmaceutically acceptable salts thereof can be useful as adenosine receptor antagonists, for example in the treatment of diseases or conditions mediated by the adenosine receptor, such as cancer, movement disorders, or attention disorders.

(I)

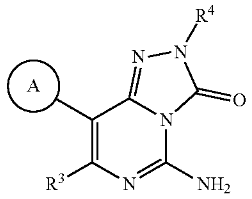

11 Claims, No Drawings

5-AMINO-8-(4-PYRIDYL)-[1,2,4]TRIAZOLO [4,3-C]PYRIMIDIN-3-ONE COMPOUNDS FOR USE AGAINST CANCER

CROSS-REFERENCE TO RELATED APPLICATIONS

This application is a 35 U.S.C. § 371 national stage filing of International Application No. PCT/EP2021/057807, filed on Mar. 25, 2021, which claims priority to U.S. Provisional Application No. 62/994,970, filed on Mar. 26, 2020.

BACKGROUND

Adenosine modulates of a number of physiological functions. Intracellularly, adenosine is involved in energy metabolism, nucleic acid metabolism, and the methionine cycle; extracellular adenosine engages in intercellular signaling. For example, extracellular adenosine is a potent immunosuppressor, preventing an overzealous immune response during inflammation and infection. Adenosine also acts on other systems, including the cardiovascular system, and the central nervous system.

The action of adenosine is mediated by a family of G-protein coupled receptors. At least four subtypes of adenosine receptors have been identified: A1R, A2aR, A2bR, and A3R. The A1R and A3 subtypes inhibit the activity of the enzyme adenylate cyclase, whereas the A2a and A2b subtypes stimulate the activity of the same enzyme, thereby modulating the level of cyclic AMP in cells.

In the immune system, engagement of A2a and A2b adenosine receptors is a critical regulatory mechanism that protects tissues against excessive immune reactions. In tumors, this pathway is hijacked and hinders antitumor immunity, promoting cancer progression. Furthermore, in many cases, the tumor microenvironment contains high levels of extracellular adenosine. Thus, the adenosine receptor, notably A2aR and A2bR, have been identified as targets for cancer therapies.

Numerous adenosine receptor antagonists have been reported. For example, international patent application WO 2006/138734 discloses triazolopyrimidine cannabinoid receptor 1 (CB-1) antagonists. WO 2008/002596 and WO 2009/111449 disclose adenosine A2a receptor antagonists which include a triazolone moiety. WO 2012/038980 discloses fused tricyclic compounds as adenosine receptor antagonists. WO 2016/161282 discloses heterocyclic compounds as LSD1 inhibitors. WO 2018/166493 discloses heteroaryl[4,3-c]pyrimidine-5-amine derivatives for use as A2a receptor antagonists.

There remains a need for adenosine receptor antagonists that are highly soluble, highly selective, and highly potent.

SUMMARY

In one aspect, a compound of Formula (I):

(I)

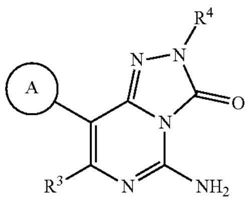

or a pharmaceutically acceptable salt thereof, is provided, wherein:

ring A can be:

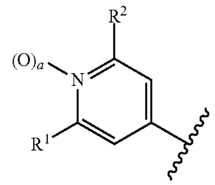

each $R^1$ and each $R^2$, independently, can be halo, $C_{1-3}$alkyl, —O—$C_{1-3}$alkyl, —$CO_2R^a$, or —$NR^7R^8$;

wherein alkyl is optionally substituted with one or more substituents independently selected from —$OR^a$ and halo;

$R^3$ can be $C_{1-6}$alkyl, $C_{2-6}$alkenyl, $C_{2-6}$alkynyl, aryl, heterocyclyl, heteroaryl, halo, —$OR^a$, —$NR^aR^b$, —$CO_2R^a$, —$CONR^aR^b$, —$NR^aC(O)$—$R^a$, or —NHC(O)—$OR^a$;

wherein heterocyclyl and heteroaryl, independently, include from 1 to 4 heteroatoms independently selected from N, O, and $S(O)_k$; and wherein $R^3$ is optionally substituted with from one to three substituents selected from halo, cyano, —$R^a$, and —$OR^a$;

$R^4$ can be absent or —$(CHR^c)_i$—$(NR^a)_j$—$R^5$;

$R^5$ can be:

(1) $C_{3-8}$cycloalkyl, aryl, 3-, 4-, 6-, or 7-membered heterocyclyl, or 3-, 4-, 6-, or 7-membered heteroaryl;

wherein heterocyclyl and heteroaryl, independently, include from 1 to 4 heteroatoms independently selected from N, O, and $S(O)_k$; and wherein one or two ring atoms of $R^5$ is optionally replaced by —C(═O)—;

(2) a multicyclic, 6- to 11-membered, cycloalkyl, aryl, heterocyclyl, or heteroaryl ring system;

wherein heterocyclyl and heteroaryl, independently, include from 1 to 4 heteroatoms independently selected from N, O, and $S(O)_k$; and wherein one or two ring atoms of $R^5$ is optionally replaced by —C(═O)—; or (3) $C_{1-6}$alkyl, —$OR^a$, —$NR^aR^b$, cyano, —$OS(O)_2$—$C_{1-3}$alkyl, —$CO_2R^a$, —$C(O)NR^aR^b$, —$NR^a$—C(O)—$OR^a$, or —O—C(O)—$NR^aR^b$; and wherein $R^5$ can be optionally substituted with from one to four groups —X—$R^6$.

each X, independently, can be a bond, —O—, —$NR^a$—, —$S(O)_k$—, —$(CH_2)_m$—, or —C(O)—;

each $R^6$, independently, can be H, halo, —$OR^a$, $C_{1-6}$alkyl, $C_{3-8}$cycloalkyl, heterocyclyl, heteroaryl, aryl, —$CO_2R^a$, —$C(O)NR^aR^b$, —$(CH_2)_n$—$NR^aR^b$, or cyano;

wherein heterocyclyl and heteroaryl, independently, include from 1 to 4 heteroatoms independently selected from N, O, and $S(O)_k$;

wherein one or two ring atoms of each $C_{3-8}$cycloalkyl, heterocyclyl, heteroaryl, or aryl, independently, is optionally replaced by —C(═O)—;

wherein each of alkyl, cycloalkyl, heterocyclyl, heteroaryl, and aryl is optionally substituted with one or more substituents independently selected from —$R^a$, —$OR^a$, —$(CH_2)_n$—$NR^aR^b$, and halo;

each $R^7$ and each $R^8$, independently, can be $R^a$;

or $R^7$ and $R^8$ together with the atom to which they are attached can form a 3- to 8-membered heterocyclyl optionally substituted with one or more substituents independently selected from —$OR^a$ and halo;

each $R^a$ and each $R^b$, independently, can be H, $C_{1-6}$alkyl, $C_{3-8}$cycloalkyl, or $C_{4-9}$cycloalkylalkyl;

wherein each $R^a$ and each $R^b$, independently, is optionally substituted with one or more substituents independently selected from —OH and halo;

each $R^c$, independently, can be H, halo, $C_{1-3}$alkyl, or —$(CH_2)_n$—$NR^aR^b$;

wherein alkyl is optionally substituted with one or more substituents independently selected from —$OR^a$ and halo;

a can be 0 or 1;

i can be 0, 1, 2, or 3;

j can be 0 or 1;

each k, independently, can be 0, 1, or 2;

each m, independently, can be 1 or 2; and each n, independently, can be 0 or 1.

The compound of Formula (I), can be a selective adenosine receptor antagonist with respect to CB-1. The compound can have a Ki for at least one of A2aR and A2bR of 100 nM or less, and has a Ki for CB-1 of 10,000 nM or more.

In some embodiments, $R^5$ can be $C_{1-6}$alkyl, —$OR^a$, —$NR^aR^b$, cyano, —$OS(O)_2$—$C_{1-3}$alkyl, —$CO_2R^a$, —C(O)$NR^aR^b$, —$NR^a$—C(O)—$OR^a$, or —O—C(O)—$NR^aR^b$.

In some embodiments, $R^5$ can be aryl, 6-membered heterocyclyl, or 6-membered heteroaryl.

In some embodiments, $R^5$ can be a multicyclic, 6- to 11-membered, cycloalkyl, aryl, heterocyclyl, or heteroaryl ring system.

In some embodiments, $R^3$ can be $C_{1-6}$alkyl, $C_{2-6}$alkenyl, $C_{2-6}$alkynyl, heterocyclyl, heteroaryl, halo, —$OR^a$, —$NR^aR^b$, —$CO_2R^a$, —$CONR^aR^b$, —$NR^a$C(O)—$R^a$, or —NHC(O)—$OR^a$.

In some embodiments, i can be 1 and $R^c$ can be H or $C_{1-3}$alkyl; or i can be 2 and each $R^c$ can be H.

In another aspect, a compound of Formula (II):

(II)

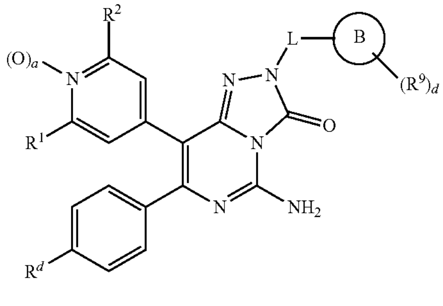

or a pharmaceutically acceptable salt thereof, is provided, wherein:

each $R^1$ and each $R^2$, independently, can be halo, $C_{1-3}$alkyl, or —O—$C_{1-3}$alkyl;

wherein alkyl is optionally substituted with one or more substituents independently selected from —OH and halo;

ring B can be $C_{3-8}$cycloalkyl, aryl, 6- or 7-membered heterocyclyl, or 6- or 7-membered heteroaryl;

wherein heterocyclyl and heteroaryl, independently, include from 1 to 4 heteroatoms independently selected from N and O;

each $R^9$, independently, can be halo, —$R^a$, or —$OR^a$;

each $R^a$ and each $R^b$, independently, can be H, $C_{1-6}$alkyl, $C_{3-8}$cycloalkyl, or $C_{4-9}$cycloalkylalkyl;

wherein each $R^a$ and each $R^b$, independently, is optionally substituted with one or more substituents independently selected from —OH and halo;

L can be —$(CHR^c)_e$—;

each $R^c$, independently, can be H, halo, $C_{1-3}$alkyl, or —$(CH_2)_n$—$NR^aR^b$;

wherein alkyl is optionally substituted with one or more substituents independently selected from —$OR^a$ and halo;

$R^d$ can be H or halo;

a can be 0 or 1;

b can be 0, 1, or 2;

d can be 0, 1, 2, 3, or 4;

e can be 1 or 2; and n can be 0 or 1.

In another aspect, a compound of Formula (III):

(III)

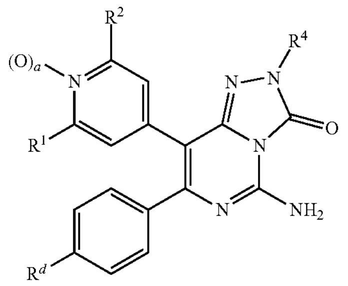

or a pharmaceutically acceptable salt thereof, is provided, wherein:

each $R^1$ and each $R^2$, independently, can be halo, $C_{1-3}$alkyl, —O—$C_{1-3}$alkyl, —$CO_2R^a$, or —$NR^7R^8$;

wherein alkyl is optionally substituted with one or more substituents independently selected from —$OR^a$ and halo;

$R^4$ can be —$(CHR^c)_2$—$R^5$;

$R^5$ can be H, halo, $C_{1-3}$alkyl, —$OR^e$, —$COR^e$, —$COOR^e$, —$OS(O)_2R^e$, —OCO—$NR^eR^f$, or —CO—$NR^eR^f$;

wherein alkyl is optionally substituted with one or more substituents independently selected from —OH and halo;

each $R^a$ and each $R^b$, independently, can be H, $C_{1-6}$alkyl, $C_{3-8}$cycloalkyl, or $C_{4-9}$cycloalkylalkyl;

wherein each $R^a$ and each $R^b$, independently, is optionally substituted with one or more substituents independently selected from —OH and halo;

each $R^c$, independently, can be H, halo, $C_{1-3}$alkyl, or —$(CH_2)_n$—$NR^aR^b$;

wherein alkyl is optionally substituted with one or more substituents independently selected from —$OR^a$ and halo;

$R^d$ can be H or halo;

each $R^e$ and each $R^f$, independently, can be H or $C_{1-6}$alkyl;

wherein alkyl is optionally substituted with one or more substituents independently selected from —OH and halo;

a can be 0 or 1; and each n, independently, can be 0 or 1.

In some embodiments, $R^5$ can be H, —$CH_3$, —$CH_2F$, —$CHF_2$, or —$CF_3$.

In another aspect, a compound, or pharmaceutically acceptable salt thereof, is provided, selected from the group consisting of:

5-amino-8-(2,6-dimethyl-4-pyridyl)-2-[(4-fluorophenyl)methyl]-7-phenyl-[1,2,4]triazolo[4,3-c]pyrimidin-3-one;

5-amino-8-(2,6-dimethyl-4-pyridyl)-2-[(5-fluoro-2-pyridyl)methyl]-7-phenyl-[1,2,4]triazolo[4,3-c]pyrimidin-3-one;

5-amino-8-(2,6-dimethyl-4-pyridyl)-2-[(4-methoxyphenyl)methyl]-7-phenyl-[1,2,4]triazolo[4,3-c]pyrimidin-3-one;

5-amino-8-(2,6-dimethyl-4-pyridyl)-2-[(4-hydroxyphenyl)methyl]-7-phenyl-[1,2,4]triazolo[4,3-c]pyrimidin-3-one;

5-amino-8-(2,6-dimethyl-4-pyridyl)-7-phenyl-2-(pyridazin-3-ylmethyl)-[1,2,4]triazolo[4,3-c]pyrimidin-3-one;

5-amino-8-(2,6-dimethyl-4-pyridyl)-2-[(6-methoxy-2-pyridyl)methyl]-7-phenyl-[1,2,4]triazolo[4,3-c]pyrimidin-3-one;

5-amino-8-(2,6-dimethyl-4-pyridyl)-2-[(5-fluoro-6-methoxy-2-pyridyl)methyl]-7-phenyl-[1,2,4]triazolo[4,3-c]pyrimidin-3-one;

5-amino-8-(2,6-dimethyl-4-pyridyl)-2-[(5-fluoro-6-oxo-1H-pyridin-2-yl)methyl]-7-phenyl-[1,2,4]triazolo[4,3-c]pyrimidin-3-one;

5-amino-8-(2,6-dimethyl-4-pyridyl)-2-[(6-oxo-1H-pyridin-2-yl)methyl]-7-phenyl-[1,2,4]triazolo[4,3-c]pyrimidin-3-one;

5-amino-8-(2,6-dimethyl-4-pyridyl)-2-[(5-fluoro-1-methyl-6-oxo-2-pyridyl)methyl]-7-phenyl-[1,2,4]triazolo[4,3-c]pyrimidin-3-one;

5-amino-2-[1-(2,4-difluorophenyl)ethyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-7-phenyl-2-(4-pyridylmethyl)-[1,2,4]triazolo[4,3-c]pyrimidin-3-one;

5-amino-8-(2,6-dimethyl-4-pyridyl)-2-isothiochroman-4-yl-7-phenyl-[1,2,4]triazolo[4,3-c]pyrimidin-3-one;

(R)-5-amino-8-(2,6-dimethyl-4-pyridyl)-2-(7-fluorotetralin-1-yl)-7-phenyl-[1,2,4]triazolo[4,3-c]pyrimidin-3-one;

5-amino-2-[1-(2,5-difluorophenyl)ethyl]-8-(2,6-dimethyl-4-pyridyl)-7-phenyl-[1,2,4]triazolo[4,3-c]pyrimidin-3-one;

5-amino-2-[[2-(difluoromethylsulfanyl)phenyl]methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-(o-tolylmethyl)-7-phenyl-[1,2,4]triazolo[4,3-c]pyrimidin-3-one;

5-amino-8-(2,6-dimethyl-4-pyridyl)-2-[(4-fluoro-2-methyl-phenyl)methyl]-7-phenyl-[1,2,4]triazolo[4,3-c]pyrimidin-3-one;

5-amino-8-(2,6-dimethyl-4-pyridyl)-7-phenyl-2-[(2-pyrazol-1-yl-3-pyridyl)methyl]-[1,2,4]triazolo[4,3-c]pyrimidin-3-one;

5-amino-8-(2,6-dimethyl-4-pyridyl)-7-phenyl-2-[1-(2-pyridyl)ethyl]-[1,2,4]triazolo[4,3-c]pyrimidin-3-one;

5-amino-2-[(2-chloro-3-fluoro-phenyl)methyl]-8-(2,6-dimethyl-4-pyridyl)-7-phenyl-[1,2,4]triazolo[4,3-c]pyrimidin-3-one;

5-amino-2-[[2-(cyclopropylmethoxy)phenyl]methyl]-8-(2,6-dimethyl-4-pyridyl)-7-phenyl-[1,2,4]triazolo[4,3-c]pyrimidin-3-one;

5-amino-2-[(2,6-difluorophenyl)methyl]-8-(2,6-dimethyl-4-pyridyl)-7-phenyl-[1,2,4]triazolo[4,3-c]pyrimidin-3-one;

5-amino-2-[[2-[(dimethylamino)methyl]phenyl]methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[(2-ethoxyphenyl)methyl]-7-phenyl-[1,2,4]triazolo[4,3-c]pyrimidin-3-one;

(R)-5-amino-8-(2,6-dimethyl-4-pyridyl)-7-phenyl-2-[1-(4-pyridyl)ethyl]-[1,2,4]triazolo[4,3-c]pyrimidin-3-one;

5-amino-8-(2,6-dimethyl-4-pyridyl)-7-phenyl-2-[1-(3-pyridyl)ethyl]-[1,2,4]triazolo[4,3-c]pyrimidin-3-one;

5-amino-8-(2,6-dimethyl-4-pyridyl)-2-[(2-methoxy-3-pyridyl)methyl]-7-phenyl-[1,2,4]triazolo[4,3-c]pyrimidin-3-one;

5-amino-8-(2,6-dimethyl-4-pyridyl)-2-[(4-methoxy-6-methyl-2-pyridyl)methyl]-7-phenyl-[1,2,4]triazolo[4,3-c]pyrimidin-3-one;

5-amino-8-(2,6-dimethyl-4-pyridyl)-7-phenyl-2-[[2-(4-piperidyl)phenyl]methyl]-[1,2,4]triazolo[4,3-c]pyrimidin-3-one;

5-amino-8-(2,6-dimethyl-4-pyridyl)-7-phenyl-2-[1-phenyl-2-(2,2,2-trifluoroethylamino)ethyl]-[1,2,4]triazolo[4,3-c]pyrimidin-3-one;

5-amino-8-(2,6-dimethyl-4-pyridyl)-7-phenyl-2-[[2-(4-piperidylmethyl)phenyl]methyl]-[1,2,4]triazolo[4,3-c]pyrimidin-3-one;

5-amino-8-(2,6-dimethyl-4-pyridyl)-2-[(6-methoxy-pyridazin-3-yl)methyl]-7-phenyl-[1,2,4]triazolo[4,3-c]pyrimidin-3-one;

5-amino-2-(2-amino-1-(2,6-difluorophenyl)ethyl)-8-(2,6-dimethylpyridin-4-yl)-7-phenyl-[1,2,4]triazolo[4,3-c]pyrimidin-3(2H)-one;

5-amino-8-(2,6-dimethyl-4-pyridyl)-2-[(5-fluoropyrimidin-2-yl)methyl]-7-phenyl-[1,2,4]triazolo[4,3-c]pyrimidin-3-one;

5-amino-2-[(6-amino-5-fluoro-2-pyridyl)methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[(6-hydroxy-pyridazin-3-yl)methyl]-7-phenyl-[1,2,4]triazolo[4,3-c]pyrimidin-3-one;

5-amino-8-(2,6-dimethyl-4-pyridyl)-2-[1-(5-fluoro-2-pyridyl)propyl]-7-phenyl-[1,2,4]triazolo[4,3-c]pyrimidin-3-one;

5-amino-8-(2,6-dimethyl-4-pyridyl)-2-[1-(5-fluoro-2-pyridyl)propyl]-7-phenyl-[1,2,4]triazolo[4,3-c]pyrimidin-3-one;

5-amino-8-(2,6-dimethyl-4-pyridyl)-2-[1-(5-fluoro-2-pyridyl)propyl]-7-phenyl-[1,2,4]triazolo[4,3-c]pyrimidin-3-one;

5-amino-2-[(3-chloro-5-fluoro-2-pyridyl)methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[(5-fluoro-2-methoxy-3-pyridyl)methyl]-7-phenyl-[1,2,4]triazolo[4,3-c]pyrimidin-3-one;

5-amino-8-(2,6-dimethyl-4-pyridyl)-7-(4-fluorophenyl)-2-(pyridazin-3-ylmethyl)-[1,2,4]triazolo[4,3-c]pyrimidin-3-one;

5-amino-8-(2,6-dimethyl-1-oxido-pyridin-1-ium-4-yl)-2-[(5-fluoro-2-pyridyl)methyl]-7-phenyl-[1,2,4]triazolo[4,3-c]pyrimidin-3-one;

5-amino-8-(2,6-dimethyl-1-oxido-pyridin-1-ium-4-yl)-7-phenyl-2-(pyridazin-3-ylmethyl)-[1,2,4]triazolo[4,3-c]pyrimidin-3-one;

5-amino-2-[(5-fluoro-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[(6-amino-5-fluoro-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[1-(5-fluoro-2-pyridyl)propyl]-8-[2-(hydroxymethyl)-6-methyl-4-pyridyl]-7-phenyl-[1,2,4]triazolo[4,3-c]pyrimidin-3-one;

5-amino-2-[1-(5-fluoro-2-pyridyl)propyl]-8-[2-(hydroxymethyl)-6-methyl-4-pyridyl]-7-phenyl-[1,2,4]triazolo[4,3-c]pyrimidin-3-one;
5-amino-2-[(3-fluoro-5-methoxy-2-pyridyl)methyl]-8-[2-(hydroxymethyl)-6-methyl-4-pyridyl]-7-phenyl-[1,2,4]triazolo[4,3-c]pyrimidin-3-one;
5-amino-2-[(5-fluoro-6-hydroxy-2-pyridyl)methyl]-8-[2-(hydroxymethyl)-6-methyl-4-pyridyl]-7-phenyl-[1,2,4]triazolo[4,3-c]pyrimidin-3-one;
5-amino-2-[(5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one;
5-amino-2-[(3-chloro-5-fluoro-2-pyridyl)methyl]-8-[2-(hydroxymethyl)-6-methyl-4-pyridyl]-7-phenyl-[1,2,4]triazolo[4,3-c]pyrimidin-3-one;
5-amino-2-[(6-amino-5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one;
5-amino-8-[2-(hydroxymethyl)-6-methyl-4-pyridyl]-2-[(5-methyl-2-pyridyl)methyl]-7-phenyl-[1,2,4]triazolo[4,3-c]pyrimidin-3-one;
5-amino-2-[(5-bromo-2-pyridyl)methyl]-8-[2-(hydroxymethyl)-6-methyl-4-pyridyl]-7-phenyl-[1,2,4]triazolo[4,3-c]pyrimidin-3-one;
6-[[5-amino-8-[2-(hydroxymethyl)-6-methyl-4-pyridyl]-3-oxo-7-phenyl-[1,2,4]triazolo[4,3-c]pyrimidin-2-yl]methyl]pyridine-3-carbonitrile;
5-amino-2-[(5-chloro-2-pyridyl)methyl]-8-[2-(hydroxymethyl)-6-methyl-4-pyridyl]-7-phenyl-[1,2,4]triazolo[4,3-c]pyrimidin-3-one;
5-amino-8-[2-(hydroxymethyl)-6-methyl-4-pyridyl]-7-phenyl-2-(pyridazin-3-ylmethyl)-[1,2,4]triazolo[4,3-c]pyrimidin-3-one;
5-amino-8-[2-(hydroxymethyl)-6-methyl-4-pyridyl]-2-[(2-methoxy-3-pyridyl)methyl]-7-phenyl-[1,2,4]triazolo[4,3-c]pyrimidin-3-one;
5-amino-7-(4-fluorophenyl)-8-[2-(hydroxymethyl)-6-methyl-4-pyridyl]-2-(pyridazin-3-ylmethyl)-[1,2,4]triazolo[4,3-c]pyrimidin-3-one;
5-amino-7-(4-fluorophenyl)-2-[(5-fluoro-2-pyridyl)methyl]-8-[2-(hydroxymethyl)-6-methyl-4-pyridyl]-[1,2,4]triazolo[4,3-c]pyrimidin-3-one;
5-amino-2-[(6-amino-5-fluoro-2-pyridyl)methyl]-7-(4-fluorophenyl)-8-[2-(hydroxymethyl)-6-methyl-4-pyridyl]-[1,2,4]triazolo[4,3-c]pyrimidin-3-one;
5-amino-7-(4-fluorophenyl)-8-[2-(hydroxymethyl)-6-methyl-4-pyridyl]-2-[(5-methyl-2-pyridyl)methyl]-[1,2,4]triazolo[4,3-c]pyrimidin-3-one;
5-amino-2-[(5-chloro-2-pyridyl)methyl]-7-(4-fluorophenyl)-8-[2-(hydroxymethyl)-6-methyl-4-pyridyl]-[1,2,4]triazolo[4,3-c]pyrimidin-3-one;
6-[[5-amino-7-(4-fluorophenyl)-8-[2-(hydroxymethyl)-6-methyl-4-pyridyl]-3-oxo-[1,2,4]triazolo[4,3-c]pyrimidin-2-yl]methyl]pyridine-3-carbonitrile;
5-amino-2-[(6-amino-5-fluoro-2-pyridyl)methyl]-8-[2-(hydroxymethyl)-6-methoxy-4-pyridyl]-7-phenyl-[1,2,4]triazolo[4,3-c]pyrimidin-3-one;
5-amino-2-[(5-chloro-2-pyridyl)methyl]-8-[2-(hydroxymethyl)-6-methoxy-4-pyridyl]-7-phenyl-[1,2,4]triazolo[4,3-c]pyrimidin-3-one;
5-amino-8-[2-(hydroxymethyl)-6-methoxy-4-pyridyl]-2-[(5-methyl-2-pyridyl)methyl]-7-phenyl-[1,2,4]triazolo[4,3-c]pyrimidin-3-one;
5-amino-7-(4-fluorophenyl)-8-[2-(hydroxymethyl)-6-methoxy-4-pyridyl]-2-[(5-methyl-2-pyridyl)methyl]-[1,2,4]triazolo[4,3-c]pyrimidin-3-one;
5-amino-2-[(5-chloro-2-pyridyl)methyl]-7-(4-fluorophenyl)-8-[2-(hydroxymethyl)-6-methoxy-4-pyridyl]-[1,2,4]triazolo[4,3-c]pyrimidin-3-one;
5-amino-8-[2-chloro-6-(hydroxymethyl)-4-pyridyl]-2-[(5-fluoro-2-pyridyl)methyl]-7-phenyl-[1,2,4]triazolo[4,3-c]pyrimidin-3-one;
5-amino-2-[(6-amino-5-fluoro-2-pyridyl)methyl]-8-[2-chloro-6-(hydroxymethyl)-4-pyridyl]-7-phenyl-[1,2,4]triazolo[4,3-c]pyrimidin-3-one;
5-amino-8-[2-(dimethylamino)-6-methyl-4-pyridyl]-2-[(5-fluoro-2-pyridyl)methyl]-7-phenyl-[1,2,4]triazolo[4,3-c]pyrimidin-3-one;
5-amino-2-[(5-fluoro-2-pyridyl)methyl]-8-[2-methyl-6-(trifluoromethyl)-4-pyridyl]-7-phenyl-[1,2,4]triazolo[4,3-c]pyrimidin-3-one;
5-amino-2-[(5-fluoro-2-pyridyl)methyl]-8-[2-(hydroxymethyl)-6-methoxy-4-pyridyl]-7-phenyl-[1,2,4]triazolo[4,3-c]pyrimidin-3-one;
5-amino-2-[(5-fluoro-2-pyridyl)methyl]-8-(2-hydroxy-6-methyl-4-pyridyl)-7-phenyl-[1,2,4]triazolo[4,3-c]pyrimidin-3-one;
5-amino-8-[2-(azetidin-1-yl)-6-methyl-4-pyridyl]-2-[(5-fluoro-2-pyridyl)methyl]-7-phenyl-[1,2,4]triazolo[4,3-c]pyrimidin-3-one;
5-amino-8-(2-chloro-6-methyl-4-pyridyl)-2-[(5-fluoro-2-pyridyl)methyl]-7-phenyl-[1,2,4]triazolo[4,3-c]pyrimidin-3-one;
5-amino-8-(2-chloro-6-methyl-4-pyridyl)-2-[(5-methoxy-2-pyridyl)methyl]-7-phenyl-[1,2,4]triazolo[4,3-c]pyrimidin-3-one;
5-amino-2-[(5-fluoro-2-pyridyl)methyl]-8-(2-methoxy-6-methyl-4-pyridyl)-7-phenyl-[1,2,4]triazolo[4,3-c]pyrimidin-3-one;
5-amino-8-[2-chloro-6-(trifluoromethyl)-4-pyridyl]-2-[(5-fluoro-2-pyridyl)methyl]-7-phenyl-[1,2,4]triazolo[4,3-c]pyrimidin-3-one;
5-amino-8-(2,6-dimethyl-4-pyridyl)-7-phenyl-2-(2-phenylethyl)-[1,2,4]triazolo[4,3-c]pyrimidin-3-one;
5-amino-8-(2,6-dimethyl-4-pyridyl)-2-(1-methyl-2-phenylethyl)-7-phenyl-[1,2,4]triazolo[4,3-c]pyrimidin-3-one;
5-amino-8-(2,6-dimethyl-4-pyridyl)-2-[2-(4-hydroxyphenyl)ethyl]-7-phenyl-[1,2,4]triazolo[4,3-c]pyrimidin-3-one;
5-amino-8-(2,6-dimethyl-4-pyridyl)-2-[2-(4-fluorophenyl)ethyl]-7-phenyl-[1,2,4]triazolo[4,3-c]pyrimidin-3-one;
methyl 4-[2-[5-amino-8-(2,6-dimethyl-4-pyridyl)-3-oxo-7-phenyl-[1,2,4]triazolo[4,3-c]pyrimidin-2-yl]ethyl]benzoate;
4-[2-[5-amino-8-(2,6-dimethyl-4-pyridyl)-3-oxo-7-phenyl-[1,2,4]triazolo[4,3-c]pyrimidin-2-yl]ethyl]benzoic acid;
5-amino-8-(2,6-dimethyl-4-pyridyl)-7-phenyl-2-[2-(2-pyridyl)ethyl]-[1,2,4]triazolo[4,3-c]pyrimidin-3-one;
5-amino-8-(2,6-dimethyl-4-pyridyl)-7-(4-fluorophenyl)-2-(2-phenylethyl)-[1,2,4]triazolo[4,3-c]pyrimidin-3-one;
5-amino-8-[2-methyl-6-(trifluoromethyl)-4-pyridyl]-7-phenyl-2-(2-phenylethyl)-[1,2,4]triazolo[4,3-c]pyrimidin-3-one;
5-amino-8-(2-chloro-6-methyl-4-pyridyl)-7-phenyl-2-(2-phenylethyl)-[1,2,4]triazolo[4,3-c]pyrimidin-3-one;
5-amino-8-[2-(azetidin-1-yl)-6-methyl-4-pyridyl]-7-phenyl-2-(2-phenylethyl)-[1,2,4]triazolo[4,3-c]pyrimidin-3-one;
5-[2-[5-amino-8-(2,6-dimethyl-4-pyridyl)-3-oxo-7-phenyl-[1,2,4]triazolo[4,3-c]pyrimidin-2-yl]ethylamino]-2-chloro-N-methyl-benzamide;
5-amino-8-(2,6-dimethyl-4-pyridyl)-7-phenyl-2-[2-[1-([1,2,4]triazolo[4,3-a]pyrimidin-3-yl)ethylamino]ethyl]-[1,2,4]triazolo[4,3-c]pyrimidin-3-one;

5-amino-8-(2,6-dimethyl-4-pyridyl)-2-[2-[methyl-(1-phenyl-4-piperidyl)amino]ethyl]-7-phenyl-[1,2,4]triazolo[4,3-c]pyrimidin-3-one;

5-amino-8-(2,6-dimethyl-4-pyridyl)-2-[2-[[(1S)-1-(6-methyl-2-pyridyl)ethyl]amino]ethyl]-7-phenyl-[1,2,4]triazolo[4,3-c]pyrimidin-3-one;

5-amino-8-(2,6-dimethyl-4-pyridyl)-2-[2-[[1-(3-methyl-1H-pyrazol-5-yl)-4-piperidyl]amino]ethyl]-7-phenyl-[1,2,4]triazolo[4,3-c]pyrimidin-3-one;

5-amino-8-(2,6-dimethyl-4-pyridyl)-2-[2-[2-(1-methylpyrrol-2-yl)azepan-1-yl]ethyl]-7-phenyl-[1,2,4]triazolo[4,3-c]pyrimidin-3-one;

5-amino-8-(2,6-dimethyl-4-pyridyl)-2-[2-[4-[(5-methyl-2-pyridyl)amino]-1-piperidyl]ethyl]-7-phenyl-[1,2,4]triazolo[4,3-c]pyrimidin-3-one;

5-amino-8-(2,6-dimethyl-4-pyridyl)-2-[2-[3-(3-methyl-5-oxo-4H-pyrazol-1-yl)anilino]ethyl]-7-phenyl-[1,2,4]triazolo[4,3-c]pyrimidin-3-one;

5-amino-8-(2,6-dimethyl-4-pyridyl)-2-[2-[[2-(hydroxymethyl)tetralin-2-yl]-methyl-amino]ethyl]-7-phenyl-[1,2,4]triazolo[4,3-c]pyrimidin-3-one;

5-amino-2-[1-(aminomethyl)-2-(2,4-difluorophenyl)ethyl]-8-(2,6-dimethyl-4-pyridyl)-7-phenyl-[1,2,4]triazolo[4,3-c]pyrimidin-3-one;

5-amino-2-[[(3R)-4-benzylmorpholin-3-yl]methyl]-8-(2,6-dimethyl-4-pyridyl)-7-phenyl-[1,2,4]triazolo[4,3-c]pyrimidin-3-one;

5-amino-2-[(4-benzyl-4-piperidyl)methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-(2-morpholin-3-yl-1-phenyl-ethyl)-7-phenyl-[1,2,4]triazolo[4,3-c]pyrimidin-3-one;

5-amino-2-(5-aminoindan-2-yl)-8-(2,6-dimethyl-4-pyridyl)-7-phenyl-[1,2,4]triazolo[4,3-c]pyrimidin-3-one;

5-amino-8-(2,6-dimethyl-4-pyridyl)-7-phenyl-2H-[1,2,4]triazolo[4,3-c]pyrimidin-3-one;

5-amino-8-(2,6-dimethyl-4-pyridyl)-2-methyl-7-phenyl-[1,2,4]triazolo[4,3-c]pyrimidin-3-one;

5-amino-8-(2,6-dimethyl-4-pyridyl)-2-ethyl-7-phenyl-[1,2,4]triazolo[4,3-c]pyrimidin-3-one;

5-amino-8-(2,6-dimethyl-4-pyridyl)-2-isopropyl-7-phenyl-[1,2,4]triazolo[4,3-c]pyrimidin-3-one;

5-amino-8-(2,6-dimethyl-4-pyridyl)-2-isopentyl-7-phenyl-[1,2,4]triazolo[4,3-c]pyrimidin-3-one;

5-amino-8-(2,6-dimethyl-4-pyridyl)-7-phenyl-2-(3,3,3-trifluoropropyl)-[1,2,4]triazolo[4,3-c]pyrimidin-3-one;

5-amino-8-(2,6-dimethyl-4-pyridyl)-2-(2-hydroxyethyl)-7-phenyl-[1,2,4]triazolo[4,3-c]pyrimidin-3-one;

5-amino-8-(2,6-dimethyl-4-pyridyl)-2-(3-fluoropropyl)-7-phenyl-[1,2,4]triazolo[4,3-c]pyrimidin-3-one;

2-[5-amino-8-(2,6-dimethyl-4-pyridyl)-3-oxo-7-phenyl-[1,2,4]triazolo[4,3-c]pyrimidin-2-yl]ethyl methanesulfonate;

5-amino-8-(2,6-dimethyl-4-pyridyl)-2-(2-methoxyethyl)-7-phenyl-[1,2,4]triazolo[4,3-c]pyrimidin-3-one;

3-[5-amino-8-(2,6-dimethyl-4-pyridyl)-3-oxo-7-phenyl-[1,2,4]triazolo[4,3-c]pyrimidin-2-yl]propanenitrile;

ethyl N-[2-[5-amino-8-(2,6-dimethyl-4-pyridyl)-3-oxo-7-phenyl-[1,2,4]triazolo[4,3-c]pyrimidin-2-yl]ethyl]carbamate;

ethyl N-[2-[5-amino-8-(2,6-dimethyl-4-pyridyl)-3-oxo-7-phenyl-[1,2,4]triazolo[4,3-c]pyrimidin-2-yl]ethyl]-N-methyl-carbamate;

tert-butyl N-[2-[5-amino-8-(2,6-dimethyl-4-pyridyl)-3-oxo-7-phenyl-[1,2,4]triazolo[4,3-c]pyrimidin-2-yl]ethyl]carbamate;

methyl 3-[5-amino-8-(2,6-dimethyl-4-pyridyl)-3-oxo-7-phenyl-[1,2,4]triazolo[4,3-c]pyrimidin-2-yl]propanoate;

2-[5-amino-8-(2,6-dimethyl-4-pyridyl)-3-oxo-7-phenyl-[1,2,4]triazolo[4,3-c]pyrimidin-2-yl]ethyl N-ethylcarbamate;

5-amino-2-(3,3-difluoropropyl)-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[2-[ethyl(methyl)amino]ethyl]-7-phenyl-[1,2,4]triazolo[4,3-c]pyrimidin-3-one;

5-amino-2-[2-[cyclopropyl(methyl)amino]ethyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-7-phenyl-2-propyl-[1,2,4]triazolo[4,3-c]pyrimidin-3-one;

5-amino-8-(2,6-dimethyl-4-pyridyl)-2-isobutyl-7-phenyl-[1,2,4]triazolo[4,3-c]pyrimidin-3-one;

2-[5-amino-8-(2,6-dimethyl-4-pyridyl)-3-oxo-7-phenyl-[1,2,4]triazolo[4,3-c]pyrimidin-2-yl]acetamide;

3-[5-amino-8-(2,6-dimethyl-4-pyridyl)-3-oxo-7-phenyl-[1,2,4]triazolo[4,3-c]pyrimidin-2-yl]-N,N-dimethyl-propanamide;

5-amino-8-(2,6-dimethyl-4-pyridyl)-2-[3-hydroxy-2-(hydroxymethyl)propyl]-7-phenyl-[1,2,4]triazolo[4,3-c]pyrimidin-3-one;

2-[5-amino-8-(2,6-dimethyl-4-pyridyl)-3-oxo-7-phenyl-[1,2,4]triazolo[4,3-c]pyrimidin-2-yl]-N,N-dimethyl-acetamide;

5-amino-2-[(3,3-difluorocyclopentyl)methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[(2-ethyl-2-methyl-cyclopropyl)methyl]-7-phenyl-[1,2,4]triazolo[4,3-c]pyrimidin-3-one;

2-[5-amino-8-(2,6-dimethyl-4-pyridyl)-3-oxo-7-phenyl-[1,2,4]triazolo[4,3-c]pyrimidin-2-yl]-N-cyclopropyl-N-methyl-acetamide;

methyl 1-[[5-amino-8-(2,6-dimethyl-4-pyridyl)-3-oxo-7-phenyl-[1,2,4]triazolo[4,3-c]pyrimidin-2-yl]methyl]cyclopentanecarboxylate;

5-amino-8-(2,6-dimethyl-4-pyridyl)-7-phenyl-2-[2-(trifluoromethoxy)ethyl]-[1,2,4]triazolo[4,3-c]pyrimidin-3-one;

3-[5-amino-8-(2,6-dimethyl-4-pyridyl)-3-oxo-7-phenyl-[1,2,4]triazolo[4,3-c]pyrimidin-2-yl]propanamide;

5-amino-8-(2,6-dimethyl-4-pyridyl)-7-(2,3,4,5,6-pentadeuteriophenyl)-2-(3,3,3-trifluoropropyl)-[1,2,4]triazolo[4,3-c]pyrimidin-3-one;

5-amino-8-(2,6-dimethyl-4-pyridyl)-7-(4-fluorophenyl)-2-(3,3,3-trifluoropropyl)-[1,2,4]triazolo[4,3-c]pyrimidin-3-one;

5-amino-7-(2,4-difluorophenyl)-8-(2,6-dimethyl-4-pyridyl)-2-(3,3,3-trifluoropropyl)-[1,2,4]triazolo[4,3-c]pyrimidin-3-one;

5-amino-8-(2,6-dimethyl-4-pyridyl)-7-(4-methoxyphenyl)-2-(3,3,3-trifluoropropyl)-[1,2,4]triazolo[4,3-c]pyrimidin-3-one;

4-[5-amino-8-(2,6-dimethyl-4-pyridyl)-3-oxo-2-(3,3,3-trifluoropropyl)-[1,2,4]triazolo[4,3-c]pyrimidin-7-yl]benzonitrile;

5-amino-8-(2,6-dimethyl-4-pyridyl)-7-(2-pyridyl)-2-(3,3,3-trifluoropropyl)-[1,2,4]triazolo[4,3-c]pyrimidin-3-one;

5-amino-8-(2,6-dimethyl-4-pyridyl)-7-(4-pyridyl)-2-(3,3,3-trifluoropropyl)-[1,2,4]triazolo[4,3-c]pyrimidin-3-one;

5-amino-8-(2,6-dimethyl-4-pyridyl)-7-(3-pyridyl)-2-(3,3,3-trifluoropropyl)-[1,2,4]triazolo[4,3-c]pyrimidin-3-one;

5-amino-8-(2,6-dimethyl-4-pyridyl)-7-(5-fluoro-2-pyridyl)-2-(3,3,3-trifluoropropyl)-[1,2,4]triazolo[4,3-c]pyrimidin-3-one;
5-amino-8-(2,6-dimethyl-4-pyridyl)-7-(4-methylpyrazol-1-yl)-2-(3,3,3-trifluoropropyl)-[1,2,4]triazolo[4,3-c]pyrimidin-3-one;
5-amino-8-(2,6-dimethyl-4-pyridyl)-7-(2-furyl)-2-(3,3,3-trifluoropropyl)-[1,2,4]triazolo[4,3-c]pyrimidin-3-one;
5-amino-8-(2,6-dimethyl-4-pyridyl)-7-(5-methyl-2-furyl)-2-(3,3,3-trifluoropropyl)-[1,2,4]triazolo[4,3-c]pyrimidin-3-one;
5-amino-8-(2,6-dimethyl-4-pyridyl)-7-(4-methylthiazol-2-yl)-2-(3,3,3-trifluoropropyl)-[1,2,4]triazolo[4,3-c]pyrimidin-3-one;
5-amino-8-[2-chloro-6-(hydroxymethyl)-4-pyridyl]-7-phenyl-2-(3,3,3-trifluoropropyl)-[1,2,4]triazolo[4,3-c]pyrimidin-3-one;
5-amino-8-[2-(hydroxymethyl)-6-methoxy-4-pyridyl]-7-phenyl-2-(3,3,3-trifluoropropyl)-[1,2,4]triazolo[4,3-c]pyrimidin-3-one;
5-amino-7-(4-fluorophenyl)-8-[2-(hydroxymethyl)-6-methoxy-4-pyridyl]-2-(3,3,3-trifluoropropyl)-[1,2,4]triazolo[4,3-c]pyrimidin-3-one;
5-amino-8-(2-chloro-6-methyl-4-pyridyl)-7-phenyl-2-(3,3,3-trifluoropropyl)-[1,2,4]triazolo[4,3-c]pyrimidin-3-one;
5-amino-8-(2-chloro-6-methyl-4-pyridyl)-7-(4-fluorophenyl)-2-methyl-[1,2,4]triazolo[4,3-c]pyrimidin-3-one;
5-amino-8-(2-chloro-6-methyl-4-pyridyl)-7-(4-fluorophenyl)-2-(3,3,3-trifluoropropyl)-[1,2,4]triazolo[4,3-c]pyrimidin-3-one;
5-amino-8-[2-(hydroxymethyl)-6-methyl-4-pyridyl]-7-phenyl-2-(3,3,3-trifluoropropyl)-[1,2,4]triazolo[4,3-c]pyrimidin-3-one;
methyl 4-[5-amino-3-oxo-7-phenyl-2-(3,3,3-trifluoropropyl)-[1,2,4]triazolo[4,3-c]pyrimidin-8-yl]-6-methyl-pyridine-2-carboxylate;
5-amino-8-[2-(hydroxymethyl)-6-(trifluoromethyl)-4-pyridyl]-7-phenyl-2-(3,3,3-trifluoropropyl)-[1,2,4]triazolo[4,3-c]pyrimidin-3-one;
tert-butyl 3-[5-amino-8-(2,6-dimethyl-4-pyridyl)-3-oxo-7-phenyl-[1,2,4]triazolo[4,3-c]pyrimidin-2-yl]piperidine-1-carboxylate;
5-amino-8-(2,6-dimethyl-4-pyridyl)-7-phenyl-2-(3-piperidyl)-[1,2,4]triazolo[4,3-c]pyrimidin-3-one;
5-amino-8-(2,6-dimethyl-1-oxido-pyridin-1-ium-4-yl)-7-phenyl-2-(3,3,3-trifluoropropyl)-[1,2,4]triazolo[4,3-c]pyrimidin-3-one;
5-amino-8-(2,6-dimethyl-1-oxido-pyridin-1-ium-4-yl)-2-isobutyl-7-phenyl-[1,2,4]triazolo[4,3-c]pyrimidin-3-one;
5-amino-8-(2,6-dimethyl-1-oxido-pyridin-1-ium-4-yl)-7-(4-fluorophenyl)-2-(3,3,3-trifluoropropyl)-[1,2,4]triazolo[4,3-c]pyrimidin-3-one;
5-amino-2-[(3-fluoro-1-bicyclo[1.1.1]pentanyl)methyl]-8-[2-(hydroxymethyl)-6-methyl-4-pyridyl]-7-phenyl-[1,2,4]triazolo[4,3-c]pyrimidin-3-one;
5-amino-2-[(4-fluorocuban-1-yl)methyl]-8-[2-(hydroxymethyl)-6-methyl-4-pyridyl]-7-phenyl-[1,2,4]triazolo[4,3-c]pyrimidin-3-one;
5-amino-8-[2-(hydroxymethyl)-6-methyl-4-pyridyl]-7-(2,3,4,5,6-pentadeuteriophenyl)-2-(3,3,3-trifluoropropyl)-[1,2,4]triazolo[4,3-c]pyrimidin-3-one;
5-amino-2-(cuban-1-ylmethyl)-8-[2-(hydroxymethyl)-6-methyl-4-pyridyl]-7-phenyl-[1,2,4]triazolo[4,3-c]pyrimidin-3-one;
5-amino-2-(3-bicyclo[1.1.1]pentanylmethyl)-8-[2-(hydroxymethyl)-6-methyl-4-pyridyl]-7-phenyl-[1,2,4]triazolo[4,3-c]pyrimidin-3-one;
5-amino-7-(4-fluorophenyl)-8-[2-(hydroxymethyl)-6-methyl-4-pyridyl]-2-(3,3,3-trifluoropropyl)-[1,2,4]triazolo[4,3-c]pyrimidin-3-one;
tert-butyl (R)-2-((5-amino-8-(2,6-dimethylpyridin-4-yl)-3-oxo-7-phenyl-[1,2,4]triazolo[4,3-c]pyrimidin-2(3H)-yl)methyl)morpholine-4-carboxylate;
(R)-5-amino-8-(2,6-dimethylpyridin-4-yl)-2-(morpholin-2-ylmethyl)-7-phenyl-[1,2,4]triazolo[4,3-c]pyrimidin-3(2H)-one;
tert-butyl 4-[[5-amino-8-(2,6-dimethyl-4-pyridyl)-3-oxo-7-phenyl-[1,2,4]triazolo[4,3-c]pyrimidin-2-yl]methyl]piperidine-1-carboxylate;
5-amino-8-(2,6-dimethyl-4-pyridyl)-7-phenyl-2-(4-piperidylmethyl)-[1,2,4]triazolo[4,3-c]pyrimidin-3-one;
tert-butyl (2S)-2-[[5-amino-8-(2,6-dimethyl-4-pyridyl)-3-oxo-7-phenyl-[1,2,4]triazolo[4,3-c]pyrimidin-2-yl]methyl]morpholine-4-carboxylate;
5-amino-8-(2,6-dimethyl-4-pyridyl)-2-(1-methyl-3-piperidyl)-7-phenyl-[1,2,4]triazolo[4,3-c]pyrimidin-3-one;
(S)-5-amino-8-(2,6-dimethylpyridin-4-yl)-2-(morpholin-2-ylmethyl)-7-phenyl-[1,2,4]triazolo[4,3-c]pyrimidin-3(2H)-one;
5-amino-8-(2,6-dimethyl-4-pyridyl)-2-[[(2S)-4-methylmorpholin-2-yl]methyl]-7-phenyl-[1,2,4]triazolo[4,3-c]pyrimidin-3-one;
5-amino-8-(2,6-dimethyl-4-pyridyl)-7-phenyl-2-(tetrahydropyran-4-ylmethyl)-[1,2,4]triazolo[4,3-c]pyrimidin-3-one;
5-amino-8-(2,6-dimethyl-4-pyridyl)-2-[[(2R)-4-methylmorpholin-2-yl]methyl]-7-phenyl-[1,2,4]triazolo[4,3-c]pyrimidin-3-one;
tert-butyl (3S)-3-[[5-amino-8-(2,6-dimethyl-4-pyridyl)-3-oxo-7-phenyl-[1,2,4]triazolo[4,3-c]pyrimidin-2-yl]methyl]morpholine-4-carboxylate;
5-amino-8-(2,6-dimethyl-4-pyridyl)-2-[[(3S)-morpholin-3-yl]methyl]-7-phenyl-[1,2,4]triazolo[4,3-c]pyrimidin-3-one;
5-amino-8-(2,6-dimethyl-4-pyridyl)-2-[[(3S)-4-methylmorpholin-3-yl]methyl]-7-phenyl-[1,2,4]triazolo[4,3-c]pyrimidin-3-one;
5-amino-8-(2,6-dimethyl-4-pyridyl)-2-[(1-methyl-4-piperidyl)methyl]-7-phenyl-[1,2,4]triazolo[4,3-c]pyrimidin-3-one;
(R)-5-amino-8-(2,6-dimethylpyridin-4-yl)-2-(morpholin-3-ylmethyl)-7-phenyl-[1,2,4]triazolo[4,3-c]pyrimidin-3(2H)-one;
5-amino-8-(2,6-dimethyl-4-pyridyl)-2-[[(3R)-4-methylmorpholin-3-yl]methyl]-7-phenyl-[1,2,4]triazolo[4,3-c]pyrimidin-3-one;
5-amino-8-(2,6-dimethyl-4-pyridyl)-7-phenyl-2-(tetrahydropyran-3-ylmethyl)-[1,2,4]triazolo[4,3-c]pyrimidin-3-one;
5-amino-8-(2,6-dimethyl-4-pyridyl)-7-phenyl-2-(tetrahydropyran-3-ylmethyl)-[1,2,4]triazolo[4,3-c]pyrimidin-3-one;
5-amino-8-(2,6-dimethyl-4-pyridyl)-7-phenyl-2-(tetrahydropyran-3-ylmethyl)-[1,2,4]triazolo[4,3-c]pyrimidin-3-one;
5-amino-8-(2,6-dimethyl-4-pyridyl)-7-phenyl-2-(tetrahydropyran-2-ylmethyl)-[1,2,4]triazolo[4,3-c]pyrimidin-3-one;
5-amino-8-(2,6-dimethyl-4-pyridyl)-7-phenyl-2-(tetrahydropyran-2-ylmethyl)-[1,2,4]triazolo[4,3-c]pyrimidin-3-one;
5-amino-8-(2,6-dimethyl-4-pyridyl)-7-phenyl-2-(tetrahydropyran-2-ylmethyl)-[1,2,4]triazolo[4,3-c]pyrimidin-3-one;

tert-butyl (S)-3-((5-amino-8-(2,6-dimethylpyridin-4-yl)-3-oxo-7-phenyl-[1,2,4]triazolo[4,3-c]pyrimidin-2(3H)-yl)methyl)-4-methylpiperazine-1-carboxylate;

tert-butyl (R)-3-((5-amino-8-(2,6-dimethylpyridin-4-yl)-3-oxo-7-phenyl-[1,2,4]triazolo[4,3-c]pyrimidin-2(3H)-yl)methyl)-4-methylpiperazine-1-carboxylate;

(R)-5-amino-2-((1,4-dimethylpiperazin-2-yl)methyl)-8-(2,6-dimethylpyridin-4-yl)-7-phenyl-[1,2,4]triazolo[4,3-c]pyrimidin-3(2H)-one;

5-amino-8-(2,6-dimethyl-4-pyridyl)-2-[[(2R)-1-methylpiperazin-2-yl]methyl]-7-phenyl-[1,2,4]triazolo[4,3-c]pyrimidin-3-one;

(S)-5-amino-2-((1,4-dimethylpiperazin-2-yl)methyl)-8-(2,6-dimethylpyridin-4-yl)-7-phenyl-[1,2,4]triazolo[4,3-c]pyrimidin-3(2H)-one;

5-amino-8-(2,6-dimethyl-4-pyridyl)-2-[[(2S)-1-methylpiperazin-2-yl]methyl]-7-phenyl-[1,2,4]triazolo[4,3-c]pyrimidin-3-one;

5-amino-8-(2,6-dimethyl-4-pyridyl)-2-[(1,1-dioxothian-3-yl)methyl]-7-phenyl-[1,2,4]triazolo[4,3-c]pyrimidin-3-one;

5-amino-8-(2,6-dimethyl-4-pyridyl)-2-[(1,1-dioxothian-3-yl)methyl]-7-phenyl-[1,2,4]triazolo[4,3-c]pyrimidin-3-one;

5-amino-8-(2,6-dimethyl-4-pyridyl)-2-[(1,1-dioxothietan-3-yl)methyl]-7-phenyl-[1,2,4]triazolo[4,3-c]pyrimidin-3-one;

5-amino-8-[2-(hydroxymethyl)-6-methyl-4-pyridyl]-7-phenyl-2-(tetrahydropyran-2-ylmethyl)-[1,2,4]triazolo[4,3-c]pyrimidin-3-one;

5-amino-8-[2-(hydroxymethyl)-6-methyl-4-pyridyl]-7-phenyl-2-(tetrahydropyran-2-ylmethyl)-[1,2,4]triazolo[4,3-c]pyrimidin-3-one;

5-amino-8-[2-(hydroxymethyl)-6-methyl-4-pyridyl]-7-phenyl-2-(tetrahydropyran-3-ylmethyl)-[1,2,4]triazolo[4,3-c]pyrimidin-3-one;

5-amino-8-[2-(hydroxymethyl)-6-methyl-4-pyridyl]-7-phenyl-2-(tetrahydropyran-3-ylmethyl)-[1,2,4]triazolo[4,3-c]pyrimidin-3-one;

5-amino-7-(4-fluorophenyl)-8-[2-(hydroxymethyl)-6-methyl-4-pyridyl]-2-(3,4,5,6-tetrahydropyridazin-3-ylmethyl)-[1,2,4]triazolo[4,3-c]pyrimidin-3-one;

5-amino-2-[2-(azetidin-1-yl)ethyl]-8-(2,6-dimethyl-4-pyridyl)-7-phenyl-[1,2,4]triazolo[4,3-c]pyrimidin-3-one;

2-(2-(2-azabicyclo[3.1.0]hexan-2-yl)ethyl)-5-amino-8-(2,6-dimethylpyridin-4-yl)-7-phenyl-[1,2,4]triazolo[4,3-c]pyrimidin-3(2H)-one;

5-amino-8-(2,6-dimethyl-4-pyridyl)-7-phenyl-2-[2-(1-piperidyl)ethyl]-[1,2,4]triazolo[4,3-c]pyrimidin-3-one;

5-amino-8-(2,6-dimethyl-4-pyridyl)-2-[2-(1-methyl-4-piperidyl)ethyl]-7-phenyl-[1,2,4]triazolo[4,3-c]pyrimidin-3-one;

5-amino-8-(2,6-dimethyl-4-pyridyl)-2-[2-(3-methyl-1-piperidyl)ethyl]-7-phenyl-[1,2,4]triazolo[4,3-c]pyrimidin-3-one;

5-amino-8-(2,6-dimethyl-4-pyridyl)-2-(2-morpholinoethyl)-7-phenyl-[1,2,4]triazolo[4,3-c]pyrimidin-3-one;

5-amino-2-[2-((cis)-2,6-dimethylmorpholin-4-yl)ethyl]-8-(2,6-dimethyl-4-pyridyl)-7-phenyl-[1,2,4]triazolo[4,3-c]pyrimidin-3-one;

5-amino-2-[2-(4,4-difluoro-1-piperidyl)ethyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[2-(4-methylpiperazin-1-yl)ethyl]-7-phenyl-[1,2,4]triazolo[4,3-c]pyrimidin-3-one;

5-amino-2-[2-(8-azabicyclo[3.2.1]octan-8-yl)ethyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-7-(4-fluorophenyl)-2-[2-(1-piperidyl)ethyl]-[1,2,4]triazolo[4,3-c]pyrimidin-3-one;

5-amino-8-(2-chloro-6-methyl-4-pyridyl)-7-(4-fluorophenyl)-2-[2-(1-piperidyl)ethyl]-[1,2,4]triazolo[4,3-c]pyrimidin-3-one;

methyl 3-[2-[5-amino-8-(2,6-dimethyl-4-pyridyl)-3-oxo-7-phenyl-[1,2,4]triazolo[4,3-c]pyrimidin-2-yl]ethylamino]piperidine-1-carboxylate;

5-amino-8-(2,6-dimethyl-4-pyridyl)-2-[2-[[2-(4-hydroxy-1-piperidyl)-2-oxo-ethyl]-methyl-amino]ethyl]-7-phenyl-[1,2,4]triazolo[4,3-c]pyrimidin-3-one;

3-[2-[5-amino-8-(2,6-dimethyl-4-pyridyl)-3-oxo-7-phenyl-[1,2,4]triazolo[4,3-c]pyrimidin-2-yl]ethylamino]-N-cyclopropyl-cyclohexanecarboxamide;

methyl 3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl]propanoate;

3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl]propanoic acid;

5-amino-8-(2,6-dimethyl-4-pyridyl)-7-phenyl-2-[3-(1-piperidyl)propyl]-[1,2,4]triazolo[4,3-c]pyrimidin-3-one;

5-amino-8-(2,6-dimethylpyridin-4-yl)-2-(3-(2-oxopyridin-1(2H)-yl)propyl)-7-phenyl-[1,2,4]triazolo[4,3-c]pyrimidin-3(2H)-one;

3-(5-amino-8-(2,6-dimethylpyridin-4-yl)-3-oxo-7-phenyl-[1,2,4]triazolo[4,3-c]pyrimidin-2(3H)-yl)-N-methylpropanamide;

5-amino-8-(2,6-dimethyl-4-pyridyl)-7-morpholino-2-(3,3,3-trifluoropropyl)-[1,2,4]triazolo[4,3-c]pyrimidin-3-one;

5-amino-8-(2,6-dimethyl-4-pyridyl)-7-(1-piperidyl)-2-(3,3,3-trifluoropropyl)-[1,2,4]triazolo[4,3-c]pyrimidin-3-one;

5-amino-8-(2,6-dimethyl-4-pyridyl)-7-ethoxy-2-(3,3,3-trifluoropropyl)-[1,2,4]triazolo[4,3-c]pyrimidin-3-one;

5-amino-8-(2,6-dimethyl-4-pyridyl)-7-[ethyl(methyl)amino]-2-(3,3,3-trifluoropropyl)-[1,2,4]triazolo[4,3-c]pyrimidin-3-one;

5-amino-7-chloro-8-(2,6-dimethyl-4-pyridyl)-2-(3,3,3-trifluoropropyl)-[1,2,4]triazolo[4,3-c]pyrimidin-3-one;

methyl 5-amino-8-(2,6-dimethyl-4-pyridyl)-3-oxo-2-(3,3,3-trifluoropropyl)-[1,2,4]triazolo[4,3-c]pyrimidine-7-carboxylate;

5-amino-8-(2,6-dimethyl-4-pyridyl)-7-prop-1-ynyl-2-(3,3,3-trifluoropropyl)-[1,2,4]triazolo[4,3-c]pyrimidin-3-one;

5-amino-8-(2,6-dimethyl-4-pyridyl)-7-methoxy-2-(3,3,3-trifluoropropyl)-[1,2,4]triazolo[4,3-c]pyrimidin-3-one;

5-amino-8-(2,6-dimethyl-4-pyridyl)-7-[(Z)-1-methylprop-1-enyl]-2-(3,3,3-trifluoropropyl)-[1,2,4]triazolo[4,3-c]pyrimidin-3-one; and 5-amino-8-(2,6-dimethyl-4-pyridyl)-7-[(E)-1-methylprop-1-enyl]-2-(3,3,3-trifluoropropyl)-[1,2,4]triazolo[4,3-c]pyrimidin-3-one.

In another aspect, a pharmaceutical composition including a compound of Formula (I), or a pharmaceutically acceptable salt thereof, and a pharmaceutically acceptable carrier, diluent, or excipient, is provided.

In another aspect, the use of a compound of Formula (I), or a pharmaceutically acceptable salt thereof, for the treatment of a disease or condition mediated by the adenosine receptor is provided.

In some embodiments, the disease or condition mediated by the adenosine receptor is lung cancer, pancreatic cancer, prostate cancer, ovarian cancer, cervical cancer, colorectal cancer, breast cancer, brain cancer, gastric cancer, liver cancer, renal cancer, endometrial cancer, thyroid cancer, bladder cancer, glial cancer, melanoma, or other solid tumor.

Other features, objects, and advantages will be apparent from the description and from the claims.

DESCRIPTION

Compounds of Formula (I), Formula (II), and Formula (III) are useful as adenosine receptor antagonists.

A compound of Formula (I):

(I)

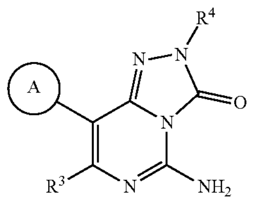

or a pharmaceutically acceptable salt thereof, is described herein.

Ring A is:

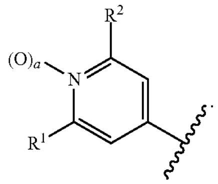

Each $R^1$ and each $R^2$, independently, is halo, $C_{1-3}$alkyl, —O—$C_{1-3}$alkyl, —$CO_2R^a$, or —$NR^7R^8$; wherein alkyl is optionally substituted with one or more substituents independently selected from —$OR^a$ and halo.

$R^3$ is $C_{1-6}$alkyl, $C_{2-6}$alkenyl, $C_{2-6}$alkynyl, aryl, heterocyclyl, heteroaryl, halo, —$OR^a$, —$NR^aR^b$, —$CO_2R^a$, —$CONR^aR^b$, —$NR^aC(O)$—$R^a$, or —NHC(O)—$OR^a$; wherein heterocyclyl and heteroaryl, independently, include from 1 to 4 heteroatoms independently selected from N, O, and $S(O)_k$; and wherein $R^3$ is optionally substituted with from one to three substituents selected from halo, cyano, —$R^a$, and —$OR^a$.

$R^4$ is absent or —$(CHR^c)_i$—$(NR^a)_j$—$R^5$.

$R^5$ is: (1) $C_{3-8}$cycloalkyl, aryl, 3-, 4-, 6-, or 7-membered heterocyclyl, or 3-, 4-, 6-, or 7-membered heteroaryl; wherein heterocyclyl and heteroaryl, independently, include from 1 to 4 heteroatoms independently selected from N, O, and $S(O)_k$; wherein one or two ring atoms of $R^5$ is optionally replaced by —C(═O)—; (2) a multicyclic, 6- to 11-membered, cycloalkyl, aryl, heterocyclyl, or heteroaryl ring system; wherein heterocyclyl and heteroaryl, independently, include from 1 to 4 heteroatoms independently selected from N, O, and $S(O)_k$; wherein one or two ring atoms of $R^5$ is optionally replaced by —C(═O)—; or (3) $C_{1-6}$alkyl, —$OR^a$, —$NR^aR^b$, cyano, —$OS(O)_2$—$C_{1-3}$alkyl, —$CO_2R^a$, —$C(O)NR^aR^b$, —$NR^a$—C(O)—$OR^a$, or —O—C(O)—$NR^aR^b$.

$R^5$ is optionally substituted with from one to four groups —X—$R^6$.

Each X, independently, is a bond, —O—, —$NR^a$—, —$S(O)_k$—, —$(CH_2)_m$—, or —C(O)—.

Each $R^6$, independently, is H, halo, —$OR^a$, $C_{1-6}$alkyl, $C_{3-8}$cycloalkyl, heterocyclyl, heteroaryl, aryl, —$CO_2R^a$, —$C(O)NR^aR^b$, —$(CH_2)_n$—$NR^aR^b$, or cyano; wherein heterocyclyl and heteroaryl, independently, include from 1 to 4 heteroatoms independently selected from N, O, and $S(O)_k$; wherein one or two ring atoms of each $C_{3-8}$cycloalkyl, heterocyclyl, heteroaryl, or aryl, independently, is optionally replaced by —C(═O)—; and wherein each of alkyl, cycloalkyl, heterocyclyl, heteroaryl, and aryl is optionally substituted with one or more substituents independently selected from —$R^a$, —$OR^a$, —$(CH_2)_n$—$NR^aR^b$, and halo.

Each $R^7$ and each $R^8$, independently, is $R^a$.

Or $R^7$ and $R^8$ together with the atom to which they are attached form a 3- to 8-membered heterocyclyl optionally substituted with one or more substituents independently selected from —$OR^a$ and halo.

Each $R^a$ and each $R^b$, independently, is H, $C_{1-6}$alkyl, $C_{3-8}$cycloalkyl, or $C_{4-9}$cycloalkylalkyl; wherein each $R^a$ and each $R^b$, independently, is optionally substituted with one or more substituents independently selected from —OH and halo.

Each $R^c$, independently, is H, halo, $C_{1-3}$alkyl, or —$(CH_2)_n$—$NR^aR^b$; wherein alkyl is optionally substituted with one or more substituents independently selected from —$OR^a$ and halo.

a is 0 or 1.

i is 0, 1, 2, or 3.

j is 0 or 1.

Each k, independently, is 0, 1, or 2.

Each m, independently, is 1 or 2.

Each n, independently, is 0 or 1.

In some embodiments, $R^5$ is $C_{1-6}$alkyl, —$OR^a$, —$NR^aR^b$, cyano, —$OS(O)_2$—$C_{1-3}$alkyl, —$CO_2R^a$, —$C(O)NR^aR^b$, —$NR^a$—C(O)—$OR^a$, or —O—C(O)—$NR^aR^b$.

In some embodiments, $R^5$ is aryl, 6-membered heterocyclyl, or 6-membered heteroaryl.

In some embodiments, $R^5$ is a multicyclic, 6- to 11-membered, cycloalkyl, aryl, heterocyclyl, or heteroaryl ring system.

In some embodiments, $R^3$ is $C_{1-6}$alkyl, $C_{2-6}$alkenyl, $C_{2-6}$alkynyl, heterocyclyl, heteroaryl, halo, —$OR^a$, —$NR^aR^b$, —$CO_2R^a$, —$CONR^aR^b$, —$NR^aC(O)$—$R^a$, or —NHC(O)—$OR^a$.

In some embodiments, i is 1 and $R^c$ is H or $C_{1-3}$alkyl; or i is 2 and each $R^c$ is H.

In some embodiments, $R^3$ is $C_{1-6}$alkyl, $C_{2-6}$alkenyl, $C_{2-6}$alkynyl, heterocyclyl, heteroaryl, halo, —$OR^a$, —$NR^aR^b$, —$CO_2R^a$, —$CONR^aR^b$, —$NR^aC(O)$—$R^a$, or —NHC(O)—$OR^a$; i is 1 or 2; and each $R^c$, independently, is H or $C_{1-3}$alkyl.

In some embodiments, $R^3$ is $C_{1-6}$alkyl, $C_{2-6}$alkenyl, $C_{2-6}$alkynyl, heterocyclyl, heteroaryl, halo, —$OR^a$, —$NR^aR^b$, —$CO_2R^a$, —$CONR^aR^b$, —$NR^aC(O)$—$R^a$, or —NHC(O)—$OR^a$; i is 1 or 2; each $R^c$, independently, is H or $C_{1-3}$alkyl; and $R^5$ is $C_{3-8}$cycloalkyl, aryl, 3-, 4-, 6-, or 7-membered heterocyclyl, or 3-, 4-, 6-, or 7-membered heteroaryl; wherein heterocyclyl and heteroaryl, independently, include from 1 to 4 heteroatoms independently selected from N, O, and $S(O)_k$; and wherein one or two ring atoms of $R^5$ is optionally replaced by —C(═O)—.

In some embodiments, $R^3$ is $C_{1-6}$alkyl, $C_{2-6}$alkenyl, $C_{2-6}$alkynyl, heterocyclyl, heteroaryl, halo, —$OR^a$, —$NR^aR^b$, —$CO_2R^a$, —$CONR^aR^b$, —$NR^aC(O)$—$R^a$, or —NHC(O)—$OR^a$; i is 1 or 2; each $R^c$, independently, is H or $C_{1-3}$alkyl; and $R^5$ is a multicyclic, 6- to 11-membered, cycloalkyl, aryl, heterocyclyl, or heteroaryl ring system; wherein heterocyclyl and heteroaryl, independently, include from 1 to 4 heteroatoms independently selected from N, O, and $S(O)_k$; and wherein one or two ring atoms of $R^5$ is optionally replaced by —C(═O)—.

In some embodiments, $R^5$ is a multicyclic, 6- to 11-membered, cycloalkyl, aryl, heterocyclyl, or heteroaryl ring system; wherein heterocyclyl and heteroaryl, independently, include from 1 to 4 heteroatoms independently selected from N, O, and $S(O)_k$; and wherein one or two ring atoms of $R^5$ is optionally replaced by —C(═O)—.

In some embodiments, $R^5$ is a multicyclic, 6- to 11-membered, cycloalkyl, aryl, heterocyclyl, or heteroaryl ring system; wherein heterocyclyl and heteroaryl, independently, include from 1 to 4 heteroatoms independently selected from N, O, and $S(O)_k$; and wherein one or two ring atoms of $R^5$ is optionally replaced by —C(═O)—; i is 0; and j is 0.

In some embodiments, $R^5$ is a multicyclic, 6- to 11-membered, cycloalkyl, aryl, heterocyclyl, or heteroaryl ring system; wherein heterocyclyl and heteroaryl, independently, include from 1 to 4 heteroatoms independently selected from N, O, and $S(O)_k$; and wherein one or two ring atoms of $R^5$ is optionally replaced by —C(═O)—; i is 1 or 2; and j is 0.

In some embodiments, j is 1.

In some embodiments, j is 1; and i is 1 or 2.

In some embodiments, j is 1; i is 1 or 2; and $R^5$ is $C_{3-8}$cycloalkyl, aryl, 3-, 4-, 6-, or 7-membered heterocyclyl, or 3-, 4-, 6-, or 7-membered heteroaryl; wherein heterocyclyl and heteroaryl, independently, include from 1 to 4 heteroatoms independently selected from N, O, and $S(O)_k$; and wherein one or two ring atoms of $R^5$ is optionally replaced by —C(═O)—.

In some embodiments, j is 1; i is 1 or 2; and $R^5$ is a multicyclic, 6- to 11-membered, cycloalkyl, aryl, heterocyclyl, or heteroaryl ring system; wherein heterocyclyl and heteroaryl, independently, include from 1 to 4 heteroatoms independently selected from N, O, and $S(O)_k$; and wherein one or two ring atoms of $R^5$ is optionally replaced by —C(═O)—.

In some embodiments, $R^5$ is $C_{1-6}$alkyl, —$OR^a$, —$NR^aR^b$, cyano, —$OS(O)_2$—$C_{1-3}$alkyl, —$CO_2R^a$, —C(O)$NR^aR^b$, —$NR^a$—C(O)—$OR^a$, or —O—C(O)—$NR^aR^b$.

In some embodiments, $R^5$ is $C_{1-6}$alkyl, —$OR^a$, —$NR^aR^b$, cyano, —$OS(O)_2$—$C_{1-3}$alkyl, —$CO_2R^a$, —C(O)$NR^aR^b$, —$NR^a$—C(O)—$OR^a$, or —O—C(O)—$NR^aR^b$; and j is 0.

A compound of Formula (II):

(II)

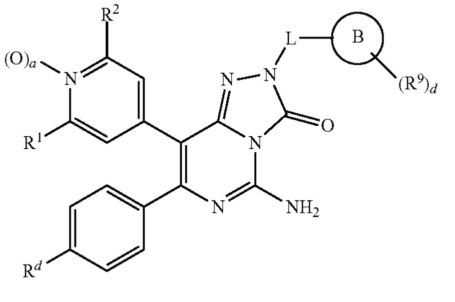

or a pharmaceutically acceptable salt thereof, is described herein.

Each $R^1$ and each $R^2$, independently, is halo, $C_{1-3}$alkyl, or —O—$C_{1-3}$alkyl; wherein alkyl is optionally substituted with one or more substituents independently selected from —OH and halo;

Ring B is $C_{3-8}$cycloalkyl, aryl, 6- or 7-membered heterocyclyl, or 6- or 7-membered heteroaryl; wherein heterocyclyl and heteroaryl, independently, include from 1 to 4 heteroatoms independently selected from N and O.

Each $R^9$, independently, is halo, —$R^a$, or —$OR^a$.

Each $R^a$ and each $R^b$, independently, is H, $C_{1-6}$alkyl, $C_{3-8}$cycloalkyl, or $C_{4-9}$cycloalkylalkyl; wherein each $R^a$ and each $R^b$, independently, is optionally substituted with one or more substituents independently selected from —OH and halo.

L is —$(CHR^c)_e$—.

Each $R^c$, independently, is H, halo, $C_{1-3}$alkyl, or —$(CH_2)_n$—$NR^aR^b$; wherein alkyl is optionally substituted with one or more substituents independently selected from —$OR^a$ and halo.

$R^d$ is H or halo.

a is 0 or 1.

b is 0, 1, or 2.

d is 0, 1, 2, 3, or 4.

e is 1 or 2.

n is 0 or 1.

Compounds of Formula (II) are encompassed by the broader Formula (I).

In some embodiments, ring B is phenyl, pyridyl, 2-oxo-pyridyl, pyrimidyl, or pyridazinyl.

In some embodiments, ring B is phenyl.

In some embodiments, e is 1; and ring B is phenyl.

In some embodiments, e is 2; and ring B is phenyl.

In some embodiments, ring B is phenyl, pyridyl, 2-oxo-pyridyl, pyrimidyl, or pyridazinyl; and each $R^9$, independently, is $C_{1-3}$alkyl, wherein alkyl is optionally substituted with one or more substituents independently selected from —OH and halo.

In some embodiments, e is 2; and ring B is phenyl, pyridyl, 2-oxo-pyridyl, pyrimidyl, or pyridazinyl.

A compound of Formula (III):

(III)

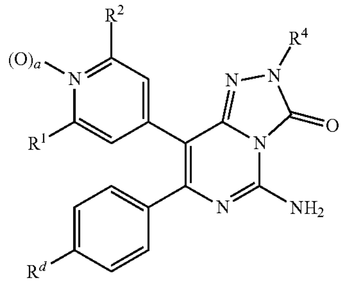

or a pharmaceutically acceptable salt thereof, is described herein.

Each $R^1$ and each $R^2$, independently, is halo, $C_{1-3}$alkyl, —O—$C_{1-3}$alkyl, —$CO_2R^a$, or —$NR^7R^8$; wherein alkyl is optionally substituted with one or more substituents independently selected from —$OR^a$ and halo.

$R^4$ is —$(CHR^c)_2$—$R^5$.

$R^5$ is H, halo, $C_{1-3}$alkyl, —$OR^e$, —$COR^e$, —$COOR^e$, —$OS(O)_2R^e$, —OCO—$NR^eR^f$, or —CO—$NR^eR^f$; wherein alkyl is optionally substituted with one or more substituents independently selected from —OH and halo.

Each $R^a$ and each $R^b$, independently, is H, $C_{1-6}$alkyl, $C_{3-8}$cycloalkyl, or $C_{4-9}$cycloalkylalkyl; wherein each $R^a$ and each $R^b$, independently, is optionally substituted with one or more substituents independently selected from —OH and halo.

Each $R^c$, independently, is H, halo, $C_{1-3}$alkyl, or —$(CH_2)_n$—$NR^aR^b$; wherein alkyl is optionally substituted with one or more substituents independently selected from —$OR^a$ and halo.

$R^d$ is H or halo.

Each $R^e$ and each $R^f$, independently, is H or $C_{1-6}$alkyl; wherein alkyl is optionally substituted with one or more substituents independently selected from —OH and halo.

a is 0 or 1.

Each n, independently, is 0 or 1.

Compounds of Formula (III) are encompassed by the broader Formula (I).

In some embodiments, $R^5$ is H, —$CH_3$, —$CH_2F$, —$CHF_2$, or —$CF_3$.

The term "halo" refers to fluoro, chloro, bromo and iodo.

The term "alkyl" refers to a fully saturated straight-chain or branched aliphatic group, having the number of carbon atoms specified, if designated (e.g., $C_{1-10}$alkyl refers to an alkyl group having one to ten carbons). Examples include as methyl, ethyl, n-propyl, isopropyl, n-butyl, t-butyl, isobutyl, sec-butyl, n-pentyl, n-hexyl, n-heptyl, n-octyl, and the like. If no size is designated, "alkyl" refers to a group having from 1 to 10 carbon atoms.

The term "alkenyl" refers to an unsaturated straight-chain or branched aliphatic group, which contain at least one carbon-carbon double bond, and having the number of carbon atoms specified, if designated. Examples of alkenyl groups include, but are not limited to, vinyl, allyl, 1-propenyl, 2-butenyl, 3-butenyl, 3-methylbut-1-enyl, 1-pentenyl and 4-hexenyl. If no size is designated, "alkenyl" refers to a group having from 2 to 10 carbon atoms.

The term "alkynyl" refers to an unsaturated straight-chain or branched aliphatic group, which contain at least one carbon-carbon triple bond, and having the number of carbon atoms specified, if designated. Examples of alkynyl groups include, but are not limited to, ethynyl, propargyl, and but-2-ynyl. If no size is designated, "alkynyl" refers to a group having from 2 to 10 carbon atoms.

Alkenyl and alkynyl groups can contain more than one unsaturated bond, or a mixture of double and triple bonds.

The term "cycloalkyl" refers to a saturated or unsaturated aliphatic ring containing from 3 to 10 carbon ring atoms, where one or more carbon ring atoms can optionally be replaced by —C(═O)—. A cycloalkyl group can contain fused and/or bridged rings, including where the fused or bridged ring(s) are cycloalkyl. Suitable examples of "cycloalkyl" include, but are not limited to, cyclopropyl, cyclopentyl, cyclobutyl, cyclohexyl, cyclohexenyl, cyclohexynyl, cycloheptyl, norbornyl, 4-oxocyclohex-1-yl and 3-oxocyclohept-5-en-1-yl.

The term "heterocyclyl" refers to a saturated or unsaturated heterocyclic ring containing from 3 to 10 ring atoms, where from 1 to 4 ring atoms are independently N, O, or S; and one or more carbon ring atoms can optionally be replaced by —C(═O)—. A ring nitrogen or a ring sulfur atom, independently, can optionally be oxidized, including for example —N(O)—, —S(O)—, or —$S(O)_2$—. A ring nitrogen atom in a heterocyclyl group can optionally be quaternized, for example, —$N^+(CH_3)_2$—. A heterocyclyl group can contain fused and/or bridged rings, including where the fused or bridged ring(s) are cycloalkyl or heterocyclyl groups. Examples of heterocyclic groups include, but are not limited to, pyrrolidinyl, piperidinyl, piperazinyl, tetrahydrofuranyl, morpholinyl, thiomorphonlinyl, dihydropyranyl, dihydropyridinyl, tetrahydropyranyl, octahydroquinolinyl, octahydroindolizinyl, and decahydroquinolinyl.

The term "aryl" refers to a monocyclic, bicyclic or tricyclic aromatic hydrocarbon group containing from 6 to 14 ring atoms. Aryl may contain fused rings, including aryl rings fused to cycloalkyl, heterocyclyl, or aryl rings. Examples of aryl groups include, but are not limited to, phenyl, naphthyl, anthracenyl, tetrahydronaphthyl, and dihydro-1H-indenyl.

The term "heteroaryl" refers to a monocyclic, bicyclic or tricyclic aromatic group containing from 6 to 14 ring atoms, where from 1 to 4 ring atoms are independently N, O, or S. A ring nitrogen or a ring sulfur atom, independently, can optionally be oxidized, including for example —N(O)—, —S(O)—, or —$S(O)_2$—. A heteroaryl group can contain fused and/or bridged rings, including where the fused or bridged ring(s) are cycloalkyl, heterocyclyl, aryl, or heteroaryl groups. Examples of heteroaryl groups include, but are not limited to, pyrrolyl, furanyl, pyridyl, imidazolyl, oxazolyl, thiazolyl, pyrimidinyl, 5,6,7,8-tetrahydroquinolinyl, benzofuranyl, pyrrolopyridinyl, pyrrolopyrimidinyl, triazinyl, and tetrazolyl.

The term "multicyclic ring system" refers to a cycloalkyl, heterocyclyl, aryl, or heteroaryl group which includes two or more fused and/or bridged rings.

Some compounds described herein can exist in more than one stereoisomeric form. Descriptions of such compounds, unless otherwise specified, are intended to encompass all geometric and optical isomers, including racemates.

Some compounds described herein can exhibit tautomerism. The structural drawings herein typically represent only one of the possible tautomeric forms of such compounds. It will be understood that the structural drawings are intended to encompass all tautomeric forms of such compounds.

The term "pharmaceutically acceptable salts" refers those salts of the compounds of Formula (I) which retain the biological activity of the free compounds and which can be administered as a pharmaceutical to humans and/or animals. The desired salt of a basic functional group of a compound may be prepared by treating the compound with an acid. Some examples of suitable inorganic acids include, but are not limited to, hydrochloric acid, hydrobromic acid, sulfuric acid, nitric acid, and phosphoric acid. Some examples of suitable organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. The desired salt of an acidic functional group of a compound can be prepared by treating the compound with a base. Some examples of suitable inorganic salts of acid compounds include, but are not limited to, alkali metal and alkaline earth salts, such as sodium salts, potassium salts, magnesium salts, and calcium salts; ammonium salts; and aluminum salts. Some examples of suitable of organic salts of acid compounds include, but are not limited to, procaine, dibenzylamine, N-ethylpiperidine, N,N'-dibenzylethylenediamine, and triethylamine salts.

Compounds of Formula (I) may contain the stated atoms in any of their isotopic forms. In this respect, embodiments of the invention that may be mentioned include those in which: (a) the compound of Formula (I) is not isotopically enriched or labelled with respect to any atoms of the compound; and (b) the compound of Formula (I) is isotopically enriched or labelled with respect to one or more atoms of the compound.

The use of "$\sim\sim$" in formulas herein denotes the point of attachment between different groups.

Illustrative compounds of Formula (I), or a pharmaceutically acceptable salt thereof, include:

5-amino-8-(2,6-dimethyl-4-pyridyl)-2-[(4-fluorophenyl)methyl]-7-phenyl-[1,2,4]triazolo[4,3-c]pyrimidin-3-one;

5-amino-8-(2,6-dimethyl-4-pyridyl)-2-[(5-fluoro-2-pyridyl)methyl]-7-phenyl-[1,2,4]triazolo[4,3-c]pyrimidin-3-one;

5-amino-8-(2,6-dimethyl-4-pyridyl)-2-[(4-methoxyphenyl)methyl]-7-phenyl-[1,2,4]triazolo[4,3-c]pyrimidin-3-one;

5-amino-8-(2,6-dimethyl-4-pyridyl)-2-[(4-hydroxyphenyl)methyl]-7-phenyl-[1,2,4]triazolo[4,3-c]pyrimidin-3-one;

5-amino-8-(2,6-dimethyl-4-pyridyl)-7-phenyl-2-(pyridazin-3-ylmethyl)-[1,2,4]triazolo[4,3-c]pyrimidin-3-one;

5-amino-8-(2,6-dimethyl-4-pyridyl)-2-[(6-methoxy-2-pyridyl)methyl]-7-phenyl-[1,2,4]triazolo[4,3-c]pyrimidin-3-one;

5-amino-8-(2,6-dimethyl-4-pyridyl)-2-[(5-fluoro-6-methoxy-2-pyridyl)methyl]-7-phenyl-[1,2,4]triazolo[4,3-c]pyrimidin-3-one;

5-amino-8-(2,6-dimethyl-4-pyridyl)-2-[(5-fluoro-6-oxo-1H-pyridin-2-yl)methyl]-7-phenyl-[1,2,4]triazolo[4,3-c]pyrimidin-3-one;

5-amino-8-(2,6-dimethyl-4-pyridyl)-2-[(6-oxo-1H-pyridin-2-yl)methyl]-7-phenyl-[1,2,4]triazolo[4,3-c]pyrimidin-3-one;

5-amino-8-(2,6-dimethyl-4-pyridyl)-2-[(5-fluoro-1-methyl-6-oxo-2-pyridyl)methyl]-7-phenyl-[1,2,4]triazolo[4,3-c]pyrimidin-3-one;

5-amino-2-[1-(2,4-difluorophenyl)ethyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-7-phenyl-2-(4-pyridylmethyl)-[1,2,4]triazolo[4,3-c]pyrimidin-3-one;

5-amino-8-(2,6-dimethyl-4-pyridyl)-2-isothiochroman-4-yl-7-phenyl-[1,2,4]triazolo[4,3-c]pyrimidin-3-one;

(R)-5-amino-8-(2,6-dimethyl-4-pyridyl)-2-(7-fluorotetralin-1-yl)-7-phenyl-[1,2,4]triazolo[4,3-c]pyrimidin-3-one;

5-amino-2-[1-(2,5-difluorophenyl)ethyl]-8-(2,6-dimethyl-4-pyridyl)-7-phenyl-[1,2,4]triazolo[4,3-c]pyrimidin-3-one;

5-amino-2-[[2-(difluoromethylsulfanyl)phenyl]methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-(o-tolylmethyl)-7-phenyl-[1,2,4]triazolo[4,3-c]pyrimidin-3-one;

5-amino-8-(2,6-dimethyl-4-pyridyl)-2-[(4-fluoro-2-methylphenyl)methyl]-7-phenyl-[1,2,4]triazolo[4,3-c]pyrimidin-3-one;

5-amino-8-(2,6-dimethyl-4-pyridyl)-7-phenyl-2-[(2-pyrazol-1-yl-3-pyridyl)methyl]-[1,2,4]triazolo[4,3-c]pyrimidin-3-one;

5-amino-8-(2,6-dimethyl-4-pyridyl)-7-phenyl-2-[1-(2-pyridyl)ethyl]-[1,2,4]triazolo[4,3-c]pyrimidin-3-one;

5-amino-2-[(2-chloro-3-fluoro-phenyl)methyl]-8-(2,6-dimethyl-4-pyridyl)-7-phenyl-[1,2,4]triazolo[4,3-c]pyrimidin-3-one;

5-amino-2-[[2-(cyclopropylmethoxy)phenyl]methyl]-8-(2,6-dimethyl-4-pyridyl)-7-phenyl-[1,2,4]triazolo[4,3-c]pyrimidin-3-one;

5-amino-2-[(2,6-difluorophenyl)methyl]-8-(2,6-dimethyl-4-pyridyl)-7-phenyl-[1,2,4]triazolo[4,3-c]pyrimidin-3-one;

5-amino-2-[[2-[(dimethylamino)methyl]phenyl]methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[(2-ethoxyphenyl)methyl]-7-phenyl-[1,2,4]triazolo[4,3-c]pyrimidin-3-one;

(R)-5-amino-8-(2,6-dimethyl-4-pyridyl)-7-phenyl-2-[1-(4-pyridyl)ethyl]-[1,2,4]triazolo[4,3-c]pyrimidin-3-one;

5-amino-8-(2,6-dimethyl-4-pyridyl)-7-phenyl-2-[1-(3-pyridyl)ethyl]-[1,2,4]triazolo[4,3-c]pyrimidin-3-one;

5-amino-8-(2,6-dimethyl-4-pyridyl)-2-[(2-methoxy-3-pyridyl)methyl]-7-phenyl-[1,2,4]triazolo[4,3-c]pyrimidin-3-one;

5-amino-8-(2,6-dimethyl-4-pyridyl)-2-[(4-methoxy-6-methyl-2-pyridyl)methyl]-7-phenyl-[1,2,4]triazolo[4,3-c]pyrimidin-3-one;

5-amino-8-(2,6-dimethyl-4-pyridyl)-7-phenyl-2-[[2-(4-piperidyl)phenyl]methyl]-[1,2,4]triazolo[4,3-c]pyrimidin-3-one;

5-amino-8-(2,6-dimethyl-4-pyridyl)-7-phenyl-2-[1-phenyl-2-(2,2,2-trifluoroethylamino)ethyl]-[1,2,4]triazolo[4,3-c]pyrimidin-3-one;

5-amino-8-(2,6-dimethyl-4-pyridyl)-7-phenyl-2-[[2-(4-piperidylmethyl)phenyl]methyl]-[1,2,4]triazolo[4,3-c]pyrimidin-3-one;

5-amino-8-(2,6-dimethyl-4-pyridyl)-2-[(6-methoxypyridazin-3-yl)methyl]-7-phenyl-[1,2,4]triazolo[4,3-c]pyrimidin-3-one;

5-amino-2-(2-amino-1-(2,6-difluorophenyl)ethyl)-8-(2,6-dimethylpyridin-4-yl)-7-phenyl-[1,2,4]triazolo[4,3-c]pyrimidin-3(2H)-one;

5-amino-8-(2,6-dimethyl-4-pyridyl)-2-[(5-fluoropyrimidin-2-yl)methyl]-7-phenyl-[1,2,4]triazolo[4,3-c]pyrimidin-3-one;

5-amino-2-[(6-amino-5-fluoro-2-pyridyl)methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[(6-hydroxypyridazin-3-yl)methyl]-7-phenyl-[1,2,4]triazolo[4,3-c]pyrimidin-3-one;

5-amino-8-(2,6-dimethyl-4-pyridyl)-2-[1-(5-fluoro-2-pyridyl)propyl]-7-phenyl-[1,2,4]triazolo[4,3-c]pyrimidin-3-one;

5-amino-8-(2,6-dimethyl-4-pyridyl)-2-[1-(5-fluoro-2-pyridyl)propyl]-7-phenyl-[1,2,4]triazolo[4,3-c]pyrimidin-3-one;

5-amino-8-(2,6-dimethyl-4-pyridyl)-2-[1-(5-fluoro-2-pyridyl)propyl]-7-phenyl-[1,2,4]triazolo[4,3-c]pyrimidin-3-one;

5-amino-2-[(3-chloro-5-fluoro-2-pyridyl)methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[(5-fluoro-2-methoxy-3-pyridyl)methyl]-7-phenyl-[1,2,4]triazolo[4,3-c]pyrimidin-3-one;

5-amino-8-(2,6-dimethyl-4-pyridyl)-7-(4-fluorophenyl)-2-(pyridazin-3-ylmethyl)-[1,2,4]triazolo[4,3-c]pyrimidin-3-one;

5-amino-8-(2,6-dimethyl-1-oxido-pyridin-1-ium-4-yl)-2-[(5-fluoro-2-pyridyl)methyl]-7-phenyl-[1,2,4]triazolo[4,3-c]pyrimidin-3-one;

5-amino-8-(2,6-dimethyl-1-oxido-pyridin-1-ium-4-yl)-7-phenyl-2-(pyridazin-3-ylmethyl)-[1,2,4]triazolo[4,3-c]pyrimidin-3-one;

5-amino-2-[(5-fluoro-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[(6-amino-5-fluoro-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[1-(5-fluoro-2-pyridyl)propyl]-8-[2-(hydroxymethyl)-6-methyl-4-pyridyl]-7-phenyl-[1,2,4]triazolo[4,3-c]pyrimidin-3-one;

5-amino-2-[1-(5-fluoro-2-pyridyl)propyl]-8-[2-(hydroxymethyl)-6-methyl-4-pyridyl]-7-phenyl-[1,2,4]triazolo[4,3-c]pyrimidin-3-one;

5-amino-2-[(3-fluoro-5-methoxy-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[(5-fluoro-6-hydroxy-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[(5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one;

5-amino-2-[(3-chloro-5-fluoro-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[(6-amino-5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one;

5-amino-8-[2-(hydroxymethyl)-6-methyl-4-pyridyl]-2-[(5-methyl-2-pyridyl)methyl]-7-phenyl-[1,2,4]triazolo[4,3-c]pyrimidin-3-one;

5-amino-2-[(5-bromo-2-pyridyl)methyl]-8-[2-(hydroxymethyl)-6-methyl-4-pyridyl]-7-phenyl-[1,2,4]triazolo[4,3-c]pyrimidin-3-one;

6-[[5-amino-8-[2-(hydroxymethyl)-6-methyl-4-pyridyl]-3-oxo-7-phenyl-[1,2,4]triazolo[4,3-c]pyrimidin-2-yl]methyl]pyridine-3-carbonitrile;

5-amino-2-[(5-chloro-2-pyridyl)methyl]-8-[2-(hydroxymethyl)-6-methyl-4-pyridyl]-7-phenyl-[1,2,4]triazolo[4,3-c]pyrimidin-3-one;

5-amino-8-[2-(hydroxymethyl)-6-methyl-4-pyridyl]-7-phenyl-2-(pyridazin-3-ylmethyl)-[1,2,4]triazolo[4,3-c]pyrimidin-3-one;

5-amino-8-[2-(hydroxymethyl)-6-methyl-4-pyridyl]-2-[(2-methoxy-3-pyridyl)methyl]-7-phenyl-[1,2,4]triazolo[4,3-c]pyrimidin-3-one;

5-amino-7-(4-fluorophenyl)-8-[2-(hydroxymethyl)-6-methyl-4-pyridyl]-2-(pyridazin-3-ylmethyl)-[1,2,4]triazolo[4,3-c]pyrimidin-3-one;

5-amino-7-(4-fluorophenyl)-2-[(5-fluoro-2-pyridyl)methyl]-8-[2-(hydroxymethyl)-6-methyl-4-pyridyl]-[1,2,4]triazolo[4,3-c]pyrimidin-3-one;

5-amino-2-[(6-amino-5-fluoro-2-pyridyl)methyl]-7-(4-fluorophenyl)-8-[2-(hydroxymethyl)-6-methyl-4-pyridyl]-[1,2,4]triazolo[4,3-c]pyrimidin-3-one;

5-amino-7-(4-fluorophenyl)-8-[2-(hydroxymethyl)-6-methyl-4-pyridyl]-2-[(5-methyl-2-pyridyl)methyl]-[1,2,4]triazolo[4,3-c]pyrimidin-3-one;

5-amino-2-[(5-chloro-2-pyridyl)methyl]-7-(4-fluorophenyl)-8-[2-(hydroxymethyl)-6-methyl-4-pyridyl]-[1,2,4]triazolo[4,3-c]pyrimidin-3-one;

6-[[5-amino-7-(4-fluorophenyl)-8-[2-(hydroxymethyl)-6-methyl-4-pyridyl]-3-oxo-[1,2,4]triazolo[4,3-c]pyrimidin-2-yl]methyl]pyridine-3-carbonitrile;

5-amino-2-[(6-amino-5-fluoro-2-pyridyl)methyl]-8-[2-(hydroxymethyl)-6-methoxy-4-pyridyl]-7-phenyl-[1,2,4]triazolo[4,3-c]pyrimidin-3-one;

5-amino-2-[(5-chloro-2-pyridyl)methyl]-8-[2-(hydroxymethyl)-6-methoxy-4-pyridyl]-7-phenyl-[1,2,4]triazolo[4,3-c]pyrimidin-3-one;

5-amino-8-[2-(hydroxymethyl)-6-methoxy-4-pyridyl]-2-[(5-methyl-2-pyridyl)methyl]-7-phenyl-[1,2,4]triazolo[4,3-c]pyrimidin-3-one;

5-amino-7-(4-fluorophenyl)-8-[2-(hydroxymethyl)-6-methoxy-4-pyridyl]-2-[(5-methyl-2-pyridyl)methyl]-[1,2,4]triazolo[4,3-c]pyrimidin-3-one;

5-amino-2-[(5-chloro-2-pyridyl)methyl]-7-(4-fluorophenyl)-8-[2-(hydroxymethyl)-6-methoxy-4-pyridyl]-[1,2,4]triazolo[4,3-c]pyrimidin-3-one;

5-amino-8-[2-chloro-6-(hydroxymethyl)-4-pyridyl]-2-[(5-fluoro-2-pyridyl)methyl]-7-phenyl-[1,2,4]triazolo[4,3-c]pyrimidin-3-one;

5-amino-2-[(6-amino-5-fluoro-2-pyridyl)methyl]-8-[2-chloro-6-(hydroxymethyl)-4-pyridyl]-7-phenyl-[1,2,4]triazolo[4,3-c]pyrimidin-3-one;

5-amino-8-[2-(dimethylamino)-6-methyl-4-pyridyl]-2-[(5-fluoro-2-pyridyl)methyl]-7-phenyl-[1,2,4]triazolo[4,3-c]pyrimidin-3-one;

5-amino-2-[(5-fluoro-2-pyridyl)methyl]-8-[2-methyl-6-(trifluoromethyl)-4-pyridyl]-7-phenyl-[1,2,4]triazolo[4,3-c]pyrimidin-3-one;

5-amino-2-[(5-fluoro-2-pyridyl)methyl]-8-[2-(hydroxymethyl)-6-methoxy-4-pyridyl]-7-phenyl-[1,2,4]triazolo[4,3-c]pyrimidin-3-one;

5-amino-2-[(5-fluoro-2-pyridyl)methyl]-8-(2-hydroxy-6-methyl-4-pyridyl)-7-phenyl-[1,2,4]triazolo[4,3-c]pyrimidin-3-one;

5-amino-8-[2-(azetidin-1-yl)-6-methyl-4-pyridyl]-2-[(5-fluoro-2-pyridyl)methyl]-7-phenyl-[1,2,4]triazolo[4,3-c]pyrimidin-3-one;

5-amino-8-(2-chloro-6-methyl-4-pyridyl)-2-[(5-fluoro-2-pyridyl)methyl]-7-phenyl-[1,2,4]triazolo[4,3-c]pyrimidin-3-one;

5-amino-8-(2-chloro-6-methyl-4-pyridyl)-2-[(5-methoxy-2-pyridyl)methyl]-7-phenyl-[1,2,4]triazolo[4,3-c]pyrimidin-3-one;

5-amino-2-[(5-fluoro-2-pyridyl)methyl]-8-(2-methoxy-6-methyl-4-pyridyl)-7-phenyl-[1,2,4]triazolo[4,3-c]pyrimidin-3-one;

5-amino-8-[2-chloro-6-(trifluoromethyl)-4-pyridyl]-2-[(5-fluoro-2-pyridyl)methyl]-7-phenyl-[1,2,4]triazolo[4,3-c]pyrimidin-3-one;

5-amino-8-(2,6-dimethyl-4-pyridyl)-7-phenyl-2-(2-phenylethyl)-[1,2,4]triazolo[4,3-c]pyrimidin-3-one;

5-amino-8-(2,6-dimethyl-4-pyridyl)-2-(1-methyl-2-phenylethyl)-7-phenyl-[1,2,4]triazolo[4,3-c]pyrimidin-3-one;

5-amino-8-(2,6-dimethyl-4-pyridyl)-2-[2-(4-hydroxyphenyl)ethyl]-7-phenyl-[1,2,4]triazolo[4,3-c]pyrimidin-3-one;

5-amino-8-(2,6-dimethyl-4-pyridyl)-2-[2-(4-fluorophenyl)ethyl]-7-phenyl-[1,2,4]triazolo[4,3-c]pyrimidin-3-one;

methyl 4-[2-[5-amino-8-(2,6-dimethyl-4-pyridyl)-3-oxo-7-phenyl-[1,2,4]triazolo[4,3-c]pyrimidin-2-yl]ethyl]benzoate;

4-[2-[5-amino-8-(2,6-dimethyl-4-pyridyl)-3-oxo-7-phenyl-[1,2,4]triazolo[4,3-c]pyrimidin-2-yl]ethyl]benzoic acid;

5-amino-8-(2,6-dimethyl-4-pyridyl)-7-phenyl-2-[2-(2-pyridyl)ethyl]-[1,2,4]triazolo[4,3-c]pyrimidin-3-one;

5-amino-8-(2,6-dimethyl-4-pyridyl)-7-(4-fluorophenyl)-2-(2-phenylethyl)-[1,2,4]triazolo[4,3-c]pyrimidin-3-one;

5-amino-8-[2-methyl-6-(trifluoromethyl)-4-pyridyl]-7-phenyl-2-(2-phenylethyl)-[1,2,4]triazolo[4,3-c]pyrimidin-3-one;

5-amino-8-(2-chloro-6-methyl-4-pyridyl)-7-phenyl-2-(2-phenylethyl)-[1,2,4]triazolo[4,3-c]pyrimidin-3-one;

5-amino-8-[2-(azetidin-1-yl)-6-methyl-4-pyridyl]-7-phenyl-2-(2-phenylethyl)-[1,2,4]triazolo[4,3-c]pyrimidin-3-one;

5-[2-[5-amino-8-(2,6-dimethyl-4-pyridyl)-3-oxo-7-phenyl-[1,2,4]triazolo[4,3-c]pyrimidin-2-yl]ethylamino]-2-chloro-N-methyl-benzamide;

5-amino-8-(2,6-dimethyl-4-pyridyl)-7-phenyl-2-[2-[1-([1,2,4]triazolo[4,3-a]pyrimidin-3-yl)ethylamino]ethyl]-[1,2,4]triazolo[4,3-c]pyrimidin-3-one;

5-amino-8-(2,6-dimethyl-4-pyridyl)-2-[2-[methyl-(1-phenyl-4-piperidyl)amino]ethyl]-7-phenyl-[1,2,4]triazolo[4,3-c]pyrimidin-3-one;

5-amino-8-(2,6-dimethyl-4-pyridyl)-2-[2-[[(1S)-1-(6-methyl-2-pyridyl)ethyl]amino]ethyl]-7-phenyl-[1,2,4]triazolo[4,3-c]pyrimidin-3-one;
5-amino-8-(2,6-dimethyl-4-pyridyl)-2-[2-[[1-(3-methyl-1H-pyrazol-5-yl)-4-piperidyl]amino]ethyl]-7-phenyl-[1,2,4]triazolo[4,3-c]pyrimidin-3-one;
5-amino-8-(2,6-dimethyl-4-pyridyl)-2-[2-[2-(1-methylpyrrol-2-yl)azepan-1-yl]ethyl]-7-phenyl-[1,2,4]triazolo[4,3-c]pyrimidin-3-one;
5-amino-8-(2,6-dimethyl-4-pyridyl)-2-[2-[4-[(5-methyl-2-pyridyl)amino]-1-piperidyl]ethyl]-7-phenyl-[1,2,4]triazolo[4,3-c]pyrimidin-3-one;
5-amino-8-(2,6-dimethyl-4-pyridyl)-2-[2-[3-(3-methyl-5-oxo-4H-pyrazol-1-yl)anilino]ethyl]-7-phenyl-[1,2,4]triazolo[4,3-c]pyrimidin-3-one;
5-amino-8-(2,6-dimethyl-4-pyridyl)-2-[2-[[2-(hydroxymethyl)tetralin-2-yl]-methyl-amino]ethyl]-7-phenyl-[1,2,4]triazolo[4,3-c]pyrimidin-3-one;
5-amino-2-[1-(aminomethyl)-2-(2,4-difluorophenyl)ethyl]-8-(2,6-dimethyl-4-pyridyl)-7-phenyl-[1,2,4]triazolo[4,3-c]pyrimidin-3-one;
5-amino-2-[[(3R)-4-benzylmorpholin-3-yl]methyl]-8-(2,6-dimethyl-4-pyridyl)-7-phenyl-[1,2,4]triazolo[4,3-c]pyrimidin-3-one;
5-amino-2-[(4-benzyl-4-piperidyl)methyl]-8-(2,6-dimethyl-4-pyridyl)-7-phenyl-[1,2,4]triazolo[4,3-c]pyrimidin-3-one;
5-amino-8-(2,6-dimethyl-4-pyridyl)-2-(2-morpholin-3-yl-1-phenyl-ethyl)-7-phenyl-[1,2,4]triazolo[4,3-c]pyrimidin-3-one;
5-amino-2-(5-aminoindan-2-yl)-8-(2,6-dimethyl-4-pyridyl)-7-phenyl-[1,2,4]triazolo[4,3-c]pyrimidin-3-one;
5-amino-8-(2,6-dimethyl-4-pyridyl)-7-phenyl-2H-[1,2,4]triazolo[4,3-c]pyrimidin-3-one;
5-amino-8-(2,6-dimethyl-4-pyridyl)-2-methyl-7-phenyl-[1,2,4]triazolo[4,3-c]pyrimidin-3-one;
5-amino-8-(2,6-dimethyl-4-pyridyl)-2-ethyl-7-phenyl-[1,2,4]triazolo[4,3-c]pyrimidin-3-one;
5-amino-8-(2,6-dimethyl-4-pyridyl)-2-isopropyl-7-phenyl-[1,2,4]triazolo[4,3-c]pyrimidin-3-one;
5-amino-8-(2,6-dimethyl-4-pyridyl)-2-isopentyl-7-phenyl-[1,2,4]triazolo[4,3-c]pyrimidin-3-one;
5-amino-8-(2,6-dimethyl-4-pyridyl)-7-phenyl-2-(3,3,3-trifluoropropyl)-[1,2,4]triazolo[4,3-c]pyrimidin-3-one;
5-amino-8-(2,6-dimethyl-4-pyridyl)-2-(2-hydroxyethyl)-7-phenyl-[1,2,4]triazolo[4,3-c]pyrimidin-3-one;
5-amino-8-(2,6-dimethyl-4-pyridyl)-2-(3-fluoropropyl)-7-phenyl-[1,2,4]triazolo[4,3-c]pyrimidin-3-one;
2-[5-amino-8-(2,6-dimethyl-4-pyridyl)-3-oxo-7-phenyl-[1,2,4]triazolo[4,3-c]pyrimidin-2-yl]ethyl methanesulfonate;
5-amino-8-(2,6-dimethyl-4-pyridyl)-2-(2-methoxyethyl)-7-phenyl-[1,2,4]triazolo[4,3-c]pyrimidin-3-one;
3-[5-amino-8-(2,6-dimethyl-4-pyridyl)-3-oxo-7-phenyl-[1,2,4]triazolo[4,3-c]pyrimidin-2-yl]propanenitrile;
ethyl N-[2-[5-amino-8-(2,6-dimethyl-4-pyridyl)-3-oxo-7-phenyl-[1,2,4]triazolo[4,3-c]pyrimidin-2-yl]ethyl]carbamate;
ethyl N-[2-[5-amino-8-(2,6-dimethyl-4-pyridyl)-3-oxo-7-phenyl-[1,2,4]triazolo[4,3-c]pyrimidin-2-yl]ethyl]-N-methyl-carbamate;
tert-butyl N-[2-[5-amino-8-(2,6-dimethyl-4-pyridyl)-3-oxo-7-phenyl-[1,2,4]triazolo[4,3-c]pyrimidin-2-yl]ethyl]carbamate;
methyl 3-[5-amino-8-(2,6-dimethyl-4-pyridyl)-3-oxo-7-phenyl-[1,2,4]triazolo[4,3-c]pyrimidin-2-yl]propanoate;
2-[5-amino-8-(2,6-dimethyl-4-pyridyl)-3-oxo-7-phenyl-[1,2,4]triazolo[4,3-c]pyrimidin-2-yl]ethyl N-ethylcarbamate;
5-amino-2-(3,3-difluoropropyl)-8-(2,6-dimethyl-4-pyridyl)-7-phenyl-[1,2,4]triazolo[4,3-c]pyrimidin-3-one;
5-amino-8-(2,6-dimethyl-4-pyridyl)-2-[2-[ethyl(methyl)amino]ethyl]-7-phenyl-[1,2,4]triazolo[4,3-c]pyrimidin-3-one;
5-amino-2-[2-[cyclopropyl(methyl)amino]ethyl]-8-(2,6-dimethyl-4-pyridyl)-7-phenyl-[1,2,4]triazolo[4,3-c]pyrimidin-3-one;
5-amino-8-(2,6-dimethyl-4-pyridyl)-7-phenyl-2-propyl-[1,2,4]triazolo[4,3-c]pyrimidin-3-one;
5-amino-8-(2,6-dimethyl-4-pyridyl)-2-isobutyl-7-phenyl-[1,2,4]triazolo[4,3-c]pyrimidin-3-one;
2-[5-amino-8-(2,6-dimethyl-4-pyridyl)-3-oxo-7-phenyl-[1,2,4]triazolo[4,3-c]pyrimidin-2-yl]acetamide;
3-[5-amino-8-(2,6-dimethyl-4-pyridyl)-3-oxo-7-phenyl-[1,2,4]triazolo[4,3-c]pyrimidin-2-yl]-N,N-dimethyl-propanamide;
5-amino-8-(2,6-dimethyl-4-pyridyl)-2-[3-hydroxy-2-(hydroxymethyl)propyl]-7-phenyl-[1,2,4]triazolo[4,3-c]pyrimidin-3-one;
2-[5-amino-8-(2,6-dimethyl-4-pyridyl)-3-oxo-7-phenyl-[1,2,4]triazolo[4,3-c]pyrimidin-2-yl]-N,N-dimethyl-acetamide;
5-amino-2-[(3,3-difluorocyclopentyl)methyl]-8-(2,6-dimethyl-4-pyridyl)-7-phenyl-[1,2,4]triazolo[4,3-c]pyrimidin-3-one;
5-amino-8-(2,6-dimethyl-4-pyridyl)-2-[(2-ethyl-2-methyl-cyclopropyl)methyl]-7-phenyl-[1,2,4]triazolo[4,3-c]pyrimidin-3-one;
2-[5-amino-8-(2,6-dimethyl-4-pyridyl)-3-oxo-7-phenyl-[1,2,4]triazolo[4,3-c]pyrimidin-2-yl]-N-cyclopropyl-N-methyl-acetamide;
methyl 1-[[5-amino-8-(2,6-dimethyl-4-pyridyl)-3-oxo-7-phenyl-[1,2,4]triazolo[4,3-c]pyrimidin-2-yl]methyl]cyclopentanecarboxylate;
5-amino-8-(2,6-dimethyl-4-pyridyl)-7-phenyl-2-[2-(trifluoromethoxy)ethyl]-[1,2,4]triazolo[4,3-c]pyrimidin-3-one;
3-[5-amino-8-(2,6-dimethyl-4-pyridyl)-3-oxo-7-phenyl-[1,2,4]triazolo[4,3-c]pyrimidin-2-yl]propanamide;
5-amino-8-(2,6-dimethyl-4-pyridyl)-7-(2,3,4,5,6-pentadeuteriophenyl)-2-(3,3,3-trifluoropropyl)-[1,2,4]triazolo[4,3-c]pyrimidin-3-one;
5-amino-8-(2,6-dimethyl-4-pyridyl)-7-(4-fluorophenyl)-2-(3,3,3-trifluoropropyl)-[1,2,4]triazolo[4,3-c]pyrimidin-3-one;
5-amino-7-(2,4-difluorophenyl)-8-(2,6-dimethyl-4-pyridyl)-2-(3,3,3-trifluoropropyl)-[1,2,4]triazolo[4,3-c]pyrimidin-3-one;
5-amino-8-(2,6-dimethyl-4-pyridyl)-7-(4-methoxyphenyl)-2-(3,3,3-trifluoropropyl)-[1,2,4]triazolo[4,3-c]pyrimidin-3-one;
4-[5-amino-8-(2,6-dimethyl-4-pyridyl)-3-oxo-2-(3,3,3-trifluoropropyl)-[1,2,4]triazolo[4,3-c]pyrimidin-7-yl]benzonitrile;
5-amino-8-(2,6-dimethyl-4-pyridyl)-7-(2-pyridyl)-2-(3,3,3-trifluoropropyl)-[1,2,4]triazolo[4,3-c]pyrimidin-3-one;
5-amino-8-(2,6-dimethyl-4-pyridyl)-7-(4-pyridyl)-2-(3,3,3-trifluoropropyl)-[1,2,4]triazolo[4,3-c]pyrimidin-3-one;
5-amino-8-(2,6-dimethyl-4-pyridyl)-7-(3-pyridyl)-2-(3,3,3-trifluoropropyl)-[1,2,4]triazolo[4,3-c]pyrimidin-3-one;
5-amino-8-(2,6-dimethyl-4-pyridyl)-7-(5-fluoro-2-pyridyl)-2-(3,3,3-trifluoropropyl)-[1,2,4]triazolo[4,3-c]pyrimidin-3-one;

5-amino-8-(2,6-dimethyl-4-pyridyl)-7-(4-methylpyrazol-1-yl)-2-(3,3,3-trifluoropropyl)-[1,2,4]triazolo[4,3-c]pyrimidin-3-one;

5-amino-8-(2,6-dimethyl-4-pyridyl)-7-(2-furyl)-2-(3,3,3-trifluoropropyl)-[1,2,4]triazolo[4,3-c]pyrimidin-3-one;

5-amino-8-(2,6-dimethyl-4-pyridyl)-7-(5-methyl-2-furyl)-2-(3,3,3-trifluoropropyl)-[1,2,4]triazolo[4,3-c]pyrimidin-3-one;

5-amino-8-(2,6-dimethyl-4-pyridyl)-7-(4-methylthiazol-2-yl)-2-(3,3,3-trifluoropropyl)-[1,2,4]triazolo[4,3-c]pyrimidin-3-one;

5-amino-8-[2-chloro-6-(hydroxymethyl)-4-pyridyl]-7-phenyl-2-(3,3,3-trifluoropropyl)-[1,2,4]triazolo[4,3-c]pyrimidin-3-one;

5-amino-8-[2-(hydroxymethyl)-6-methoxy-4-pyridyl]-7-phenyl-2-(3,3,3-trifluoropropyl)-[1,2,4]triazolo[4,3-c]pyrimidin-3-one;

5-amino-7-(4-fluorophenyl)-8-[2-(hydroxymethyl)-6-methoxy-4-pyridyl]-2-(3,3,3-trifluoropropyl)-[1,2,4]triazolo[4,3-c]pyrimidin-3-one;

5-amino-8-(2-chloro-6-methyl-4-pyridyl)-7-phenyl-2-(3,3,3-trifluoropropyl)-[1,2,4]triazolo[4,3-c]pyrimidin-3-one;

5-amino-8-(2-chloro-6-methyl-4-pyridyl)-7-(4-fluorophenyl)-2-methyl-[1,2,4]triazolo[4,3-c]pyrimidin-3-one;

5-amino-8-(2-chloro-6-methyl-4-pyridyl)-7-(4-fluorophenyl)-2-(3,3,3-trifluoropropyl)-[1,2,4]triazolo[4,3-c]pyrimidin-3-one;

5-amino-8-[2-(hydroxymethyl)-6-methyl-4-pyridyl]-7-phenyl-2-(3,3,3-trifluoropropyl)-[1,2,4]triazolo[4,3-c]pyrimidin-3-one;

methyl 4-[5-amino-3-oxo-7-phenyl-2-(3,3,3-trifluoropropyl)-[1,2,4]triazolo[4,3-c]pyrimidin-8-yl]-6-methyl-pyridine-2-carboxylate;

5-amino-8-[2-(hydroxymethyl)-6-(trifluoromethyl)-4-pyridyl]-7-phenyl-2-(3,3,3-trifluoropropyl)-[1,2,4]triazolo[4,3-c]pyrimidin-3-one;

tert-butyl 3-[5-amino-8-(2,6-dimethyl-4-pyridyl)-3-oxo-7-phenyl-[1,2,4]triazolo[4,3-c]pyrimidin-2-yl]piperidine-1-carboxylate;

5-amino-8-(2,6-dimethyl-4-pyridyl)-7-phenyl-2-(3-piperidyl)-[1,2,4]triazolo[4,3-c]pyrimidin-3-one;

5-amino-8-(2,6-dimethyl-1-oxido-pyridin-1-ium-4-yl)-7-phenyl-2-(3,3,3-trifluoropropyl)-[1,2,4]triazolo[4,3-c]pyrimidin-3-one;

5-amino-8-(2,6-dimethyl-1-oxido-pyridin-1-ium-4-yl)-2-isobutyl-7-phenyl-[1,2,4]triazolo[4,3-c]pyrimidin-3-one;

5-amino-8-(2,6-dimethyl-1-oxido-pyridin-1-ium-4-yl)-7-(4-fluorophenyl)-2-(3,3,3-trifluoropropyl)-[1,2,4]triazolo[4,3-c]pyrimidin-3-one;

5-amino-2-[(3-fluoro-1-bicyclo[1.1.1]pentanyl)methyl]-8-[2-(hydroxymethyl)-6-methyl-4-pyridyl]-7-phenyl-[1,2,4]triazolo[4,3-c]pyrimidin-3-one;

5-amino-2-[(4-fluorocuban-1-yl)methyl]-8-[2-(hydroxymethyl)-6-methyl-4-pyridyl]-7-phenyl-[1,2,4]triazolo[4,3-c]pyrimidin-3-one;

5-amino-8-[2-(hydroxymethyl)-6-methyl-4-pyridyl]-7-(2,3,4,5,6-pentadeuteriophenyl)-2-(3,3,3-trifluoropropyl)-[1,2,4]triazolo[4,3-c]pyrimidin-3-one;

5-amino-2-(cuban-1-ylmethyl)-8-[2-(hydroxymethyl)-6-methyl-4-pyridyl]-7-phenyl-[1,2,4]triazolo[4,3-c]pyrimidin-3-one;

5-amino-2-(3-bicyclo[1.1.1]pentanylmethyl)-8-[2-(hydroxymethyl)-6-methyl-4-pyridyl]-7-phenyl-[1,2,4]triazolo[4,3-c]pyrimidin-3-one;

5-amino-7-(4-fluorophenyl)-8-[2-(hydroxymethyl)-6-methyl-4-pyridyl]-2-(3,3,3-trifluoropropyl)-[1,2,4]triazolo[4,3-c]pyrimidin-3-one;

tert-butyl (R)-2-((5-amino-8-(2,6-dimethylpyridin-4-yl)-3-oxo-7-phenyl-[1,2,4]triazolo[4,3-c]pyrimidin-2(3H)-yl)methyl)morpholine-4-carboxylate;

(R)-5-amino-8-(2,6-dimethylpyridin-4-yl)-2-(morpholin-2-ylmethyl)-7-phenyl-[1,2,4]triazolo[4,3-c]pyrimidin-3(2H)-one;

tert-butyl 4-[[5-amino-8-(2,6-dimethyl-4-pyridyl)-3-oxo-7-phenyl-[1,2,4]triazolo[4,3-c]pyrimidin-2-yl]methyl]piperidine-1-carboxylate;

5-amino-8-(2,6-dimethyl-4-pyridyl)-7-phenyl-2-(4-piperidylmethyl)-[1,2,4]triazolo[4,3-c]pyrimidin-3-one;

tert-butyl (2S)-2-[[5-amino-8-(2,6-dimethyl-4-pyridyl)-3-oxo-7-phenyl-[1,2,4]triazolo[4,3-c]pyrimidin-2-yl]methyl]morpholine-4-carboxylate;

5-amino-8-(2,6-dimethyl-4-pyridyl)-2-(1-methyl-3-piperidyl)-7-phenyl-[1,2,4]triazolo[4,3-c]pyrimidin-3-one;

(S)-5-amino-8-(2,6-dimethylpyridin-4-yl)-2-(morpholin-2-ylmethyl)-7-phenyl-[1,2,4]triazolo[4,3-c]pyrimidin-3(2H)-one;

5-amino-8-(2,6-dimethyl-4-pyridyl)-2-[[(2S)-4-methylmorpholin-2-yl]methyl]-7-phenyl-[1,2,4]triazolo[4,3-c]pyrimidin-3-one;

5-amino-8-(2,6-dimethyl-4-pyridyl)-7-phenyl-2-(tetrahydropyran-4-ylmethyl)-[1,2,4]triazolo[4,3-c]pyrimidin-3-one;

5-amino-8-(2,6-dimethyl-4-pyridyl)-2-[[(2R)-4-methylmorpholin-2-yl]methyl]-7-phenyl-[1,2,4]triazolo[4,3-c]pyrimidin-3-one;

tert-butyl (3S)-3-[[5-amino-8-(2,6-dimethyl-4-pyridyl)-3-oxo-7-phenyl-[1,2,4]triazolo[4,3-c]pyrimidin-2-yl]methyl]morpholine-4-carboxylate;

5-amino-8-(2,6-dimethyl-4-pyridyl)-2-[[(3S)-morpholin-3-yl]methyl]-7-phenyl-[1,2,4]triazolo[4,3-c]pyrimidin-3-one;

5-amino-8-(2,6-dimethyl-4-pyridyl)-2-[[(3S)-4-methylmorpholin-3-yl]methyl]-7-phenyl-[1,2,4]triazolo[4,3-c]pyrimidin-3-one;

5-amino-8-(2,6-dimethyl-4-pyridyl)-2-[(1-methyl-4-piperidyl)methyl]-7-phenyl-[1,2,4]triazolo[4,3-c]pyrimidin-3-one;

(R)-5-amino-8-(2,6-dimethylpyridin-4-yl)-2-(morpholin-3-ylmethyl)-7-phenyl-[1,2,4]triazolo[4,3-c]pyrimidin-3(2H)-one;

5-amino-8-(2,6-dimethyl-4-pyridyl)-2-[[(3R)-4-methylmorpholin-3-yl]methyl]-7-phenyl-[1,2,4]triazolo[4,3-c]pyrimidin-3-one;

5-amino-8-(2,6-dimethyl-4-pyridyl)-7-phenyl-2-(tetrahydropyran-3-ylmethyl)-[1,2,4]triazolo[4,3-c]pyrimidin-3-one;

5-amino-8-(2,6-dimethyl-4-pyridyl)-7-phenyl-2-(tetrahydropyran-3-ylmethyl)-[1,2,4]triazolo[4,3-c]pyrimidin-3-one;

5-amino-8-(2,6-dimethyl-4-pyridyl)-7-phenyl-2-(tetrahydropyran-3-ylmethyl)-[1,2,4]triazolo[4,3-c]pyrimidin-3-one;

5-amino-8-(2,6-dimethyl-4-pyridyl)-7-phenyl-2-(tetrahydropyran-2-ylmethyl)-[1,2,4]triazolo[4,3-c]pyrimidin-3-one;

5-amino-8-(2,6-dimethyl-4-pyridyl)-7-phenyl-2-(tetrahydropyran-2-ylmethyl)-[1,2,4]triazolo[4,3-c]pyrimidin-3-one;

5-amino-8-(2,6-dimethyl-4-pyridyl)-7-phenyl-2-(tetrahydropyran-2-ylmethyl)-[1,2,4]triazolo[4,3-c]pyrimidin-3-one;

tert-butyl (S)-3-((5-amino-8-(2,6-dimethylpyridin-4-yl)-3-oxo-7-phenyl-[1,2,4]triazolo[4,3-c]pyrimidin-2(3H)-yl)methyl)-4-methylpiperazine-1-carboxylate;

tert-butyl (R)-3-((5-amino-8-(2,6-dimethylpyridin-4-yl)-3-oxo-7-phenyl-[1,2,4]triazolo[4,3-c]pyrimidin-2(3H)-yl)methyl)-4-methylpiperazine-1-carboxylate;

(R)-5-amino-2-((1,4-dimethylpiperazin-2-yl)methyl)-8-(2,6-dimethylpyridin-4-yl)-7-phenyl-[1,2,4]triazolo[4,3-c]pyrimidin-3(2H)-one;

5-amino-8-(2,6-dimethyl-4-pyridyl)-2-[[(2R)-1-methylpiperazin-2-yl]methyl]-7-phenyl-[1,2,4]triazolo[4,3-c]pyrimidin-3-one;

(S)-5-amino-2-((1,4-dimethylpiperazin-2-yl)methyl)-8-(2,6-dimethylpyridin-4-yl)-7-phenyl-[1,2,4]triazolo[4,3-c]pyrimidin-3(2H)-one;

5-amino-8-(2,6-dimethyl-4-pyridyl)-2-[[(2S)-1-methylpiperazin-2-yl]methyl]-7-phenyl-[1,2,4]triazolo[4,3-c]pyrimidin-3-one;

5-amino-8-(2,6-dimethyl-4-pyridyl)-2-[(1,1-dioxothian-3-yl)methyl]-7-phenyl-[1,2,4]triazolo[4,3-c]pyrimidin-3-one;

5-amino-8-(2,6-dimethyl-4-pyridyl)-2-[(1,1-dioxothian-3-yl)methyl]-7-phenyl-[1,2,4]triazolo[4,3-c]pyrimidin-3-one;

5-amino-8-(2,6-dimethyl-4-pyridyl)-2-[(1,1-dioxothietan-3-yl)methyl]-7-phenyl-[1,2,4]triazolo[4,3-c]pyrimidin-3-one;

5-amino-8-[2-(hydroxymethyl)-6-methyl-4-pyridyl]-7-phenyl-2-(tetrahydropyran-2-ylmethyl)-[1,2,4]triazolo[4,3-c]pyrimidin-3-one;

5-amino-8-[2-(hydroxymethyl)-6-methyl-4-pyridyl]-7-phenyl-2-(tetrahydropyran-2-ylmethyl)-[1,2,4]triazolo[4,3-c]pyrimidin-3-one;

5-amino-8-[2-(hydroxymethyl)-6-methyl-4-pyridyl]-7-phenyl-2-(tetrahydropyran-3-ylmethyl)-[1,2,4]triazolo[4,3-c]pyrimidin-3-one;

5-amino-8-[2-(hydroxymethyl)-6-methyl-4-pyridyl]-7-phenyl-2-(tetrahydropyran-3-ylmethyl)-[1,2,4]triazolo[4,3-c]pyrimidin-3-one;

5-amino-7-(4-fluorophenyl)-8-[2-(hydroxymethyl)-6-methyl-4-pyridyl]-2-(3,4,5,6-tetrahydropyridazin-3-ylmethyl)-[1,2,4]triazolo[4,3-c]pyrimidin-3-one;

5-amino-2-[2-(azetidin-1-yl)ethyl]-8-(2,6-dimethyl-4-pyridyl)-7-phenyl-[1,2,4]triazolo[4,3-c]pyrimidin-3-one;

2-(2-(2-azabicyclo[3.1.0]hexan-2-yl)ethyl)-5-amino-8-(2,6-dimethylpyridin-4-yl)-7-phenyl-[1,2,4]triazolo[4,3-c]pyrimidin-3(2H)-one;

5-amino-8-(2,6-dimethyl-4-pyridyl)-7-phenyl-2-[2-(1-piperidyl)ethyl]-[1,2,4]triazolo[4,3-c]pyrimidin-3-one;

5-amino-8-(2,6-dimethyl-4-pyridyl)-2-[2-(1-methyl-4-piperidyl)ethyl]-7-phenyl-[1,2,4]triazolo[4,3-c]pyrimidin-3-one;

5-amino-8-(2,6-dimethyl-4-pyridyl)-2-[2-(3-methyl-1-piperidyl)ethyl]-7-phenyl-[1,2,4]triazolo[4,3-c]pyrimidin-3-one;

5-amino-8-(2,6-dimethyl-4-pyridyl)-2-(2-morpholinoethyl)-7-phenyl-[1,2,4]triazolo[4,3-c]pyrimidin-3-one;

5-amino-2-[2-((cis)-2,6-dimethylmorpholin-4-yl)ethyl]-8-(2,6-dimethyl-4-pyridyl)-7-phenyl-[1,2,4]triazolo[4,3-c]pyrimidin-3-one;

5-amino-2-[2-(4,4-difluoro-1-piperidyl)ethyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[2-(4-methylpiperazin-1-yl)ethyl]-7-phenyl-[1,2,4]triazolo[4,3-c]pyrimidin-3-one;

5-amino-2-[2-(8-azabicyclo[3.2.1]octan-8-yl)ethyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-7-(4-fluorophenyl)-2-[2-(1-piperidyl)ethyl]-[1,2,4]triazolo[4,3-c]pyrimidin-3-one;

5-amino-8-(2-chloro-6-methyl-4-pyridyl)-7-(4-fluorophenyl)-2-[2-(1-piperidyl)ethyl]-[1,2,4]triazolo[4,3-c]pyrimidin-3-one;

methyl 3-[2-[5-amino-8-(2,6-dimethyl-4-pyridyl)-3-oxo-7-phenyl-[1,2,4]triazolo[4,3-c]pyrimidin-2-yl]ethylamino]piperidine-1-carboxylate;

5-amino-8-(2,6-dimethyl-4-pyridyl)-2-[2-[[2-(4-hydroxy-1-piperidyl)-2-oxo-ethyl]-methyl-amino]ethyl]-7-phenyl-[1,2,4]triazolo[4,3-c]pyrimidin-3-one;

3-[2-[5-amino-8-(2,6-dimethyl-4-pyridyl)-3-oxo-7-phenyl-[1,2,4]triazolo[4,3-c]pyrimidin-2-yl]ethylamino]-N-cyclopropyl-cyclohexanecarboxamide;

methyl 3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl]propanoate;

3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl]propanoic acid;

5-amino-8-(2,6-dimethyl-4-pyridyl)-7-phenyl-2-[3-(1-piperidyl)propyl]-[1,2,4]triazolo[4,3-c]pyrimidin-3-one;

5-amino-8-(2,6-dimethylpyridin-4-yl)-2-(3-(2-oxopyridin-1(2H)-yl)propyl)-7-phenyl-[1,2,4]triazolo[4,3-c]pyrimidin-3(2H)-one;

3-(5-amino-8-(2,6-dimethylpyridin-4-yl)-3-oxo-7-phenyl-[1,2,4]triazolo[4,3-c]pyrimidin-2(3H)-yl)-N-methylpropanamide;

5-amino-8-(2,6-dimethyl-4-pyridyl)-7-morpholino-2-(3,3,3-trifluoropropyl)-[1,2,4]triazolo[4,3-c]pyrimidin-3-one;

5-amino-8-(2,6-dimethyl-4-pyridyl)-7-(1-piperidyl)-2-(3,3,3-trifluoropropyl)-[1,2,4]triazolo[4,3-c]pyrimidin-3-one;

5-amino-8-(2,6-dimethyl-4-pyridyl)-7-ethoxy-2-(3,3,3-trifluoropropyl)-[1,2,4]triazolo[4,3-c]pyrimidin-3-one;

5-amino-8-(2,6-dimethyl-4-pyridyl)-7-[ethyl(methyl)amino]-2-(3,3,3-trifluoropropyl)-[1,2,4]triazolo[4,3-c]pyrimidin-3-one;

5-amino-7-chloro-8-(2,6-dimethyl-4-pyridyl)-2-(3,3,3-trifluoropropyl)-[1,2,4]triazolo[4,3-c]pyrimidin-3-one;

methyl 5-amino-8-(2,6-dimethyl-4-pyridyl)-3-oxo-2-(3,3,3-trifluoropropyl)-[1,2,4]triazolo[4,3-c]pyrimidine-7-carboxylate;

5-amino-8-(2,6-dimethyl-4-pyridyl)-7-prop-1-ynyl-2-(3,3,3-trifluoropropyl)-[1,2,4]triazolo[4,3-c]pyrimidin-3-one;

5-amino-8-(2,6-dimethyl-4-pyridyl)-7-methoxy-2-(3,3,3-trifluoropropyl)-[1,2,4]triazolo[4,3-c]pyrimidin-3-one;

5-amino-8-(2,6-dimethyl-4-pyridyl)-7-[(Z)-1-methylprop-1-enyl]-2-(3,3,3-trifluoropropyl)-[1,2,4]triazolo[4,3-c]pyrimidin-3-one; and 5-amino-8-(2,6-dimethyl-4-pyridyl)-7-[(E)-1-methylprop-1-enyl]-2-(3,3,3-trifluoropropyl)-[1,2,4]triazolo[4,3-c]pyrimidin-3-one.

Compounds of Formula (I) can be adenosine receptor antagonists, i.e. antagonists of one or more of A1R, A2aR, A2bR, and A3R. The term "adenosine receptor antagonist" refers to a compound, e.g., a compound of Formula (I) that binds to the adenosine receptor and antagonizes its activity.

In some cases, the compound of Formula (I) is a selective adenosine receptor antagonist. The term "selective" refers the property of a compound of Formula (I) that is an adenosine receptor antagonist but is substantially inactive at other biological targets. The term "substantially inactive" as used herein describes a compound that (i) has significantly weaker affinity for a given receptor as compared to its affinity for the adenosine receptor; (ii) does not show substantial agonist or antagonist activity at a given receptor; or both (i) and (ii).

The term “selective adenosine receptor antagonist” refers to a compound that shows binding affinity for one or more adenosine receptor subtypes that is at least 100 times greater, at least 1,000 times greater, or at least 10,000 times greater than its affinity for a given receptor. In other words, the ratio of binding Ki values (given receptor:adenosine receptor) can be at least 100, at least 1,000, or at least 10,000.

In particular, a selective adenosine receptor antagonist can be substantially inactive toward other G-protein coupled receptors, such as the cannabinoid receptors, referred to as CB-1 and CB-2.

A compound of Formula (I) can have a binding affinity Ki for A2aR of, e.g., 100 nM or less, 10 nM or less, or 1 nM or less.

A compound of Formula (I) can have a binding affinity Ki for A2bR of, e.g., 100 nM or less, 10 nM or less, or 1 nM or less.

A compound of Formula (I) can have a binding affinity $K_i$ for CB-1 of, e.g., 1,000 nM or greater, 10,000 nM or greater, 13,000 nM or greater.

A compound of Formula (I) can be a selective adenosine receptor antagonist with respect to CB-1.

A compound of Formula (I) can be active as an adenosine receptor antagonist but substantially inactive at CB-1.

The compounds of Formula (I) can also be selective between the different subtypes of adenosine receptor. In some embodiments, the compounds of Formula (I) are A2aR-selective; A2bR-selective; or dual A2aR/A2bR-selective.

An A2aR-selective compound shows a binding affinity for A2aR that is at least 100 times stronger, at least 1,000 times stronger, or at least 10,000 times stronger than its binding affinity for each of A1R, A2bR, and A3R.

An A2bR-selective compound that is at least 100 times stronger, at least 1,000 times stronger, or at least 10,000 times stronger than its binding affinity for each of A1R, A2aR, and A3R.

A dual A2aR/A2bR-selective compound shows a binding affinity for A2aR that is at least 100 times stronger, at least 1,000 times stronger, or at least 10,000 times stronger than its binding affinity for each of A1R and A3R. A dual A2aR/A2bR-selective also shows a binding affinity for A2bR that is at least 100 times stronger, at least 1,000 times stronger, or at least 10,000 times stronger than its binding affinity for each of A1R and A3R. In addition, for a dual A2aR/A2bR-selective compound, the ratio of binding affinity for A2aR to binding affinity for A2bR is less than 100.

In one embodiment, there is provided a pharmaceutical composition which includes a compound of Formula (I), or a pharmaceutically acceptable salt thereof, and a pharmaceutically acceptable carrier, diluent, or excipient.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Compounds of Formula (I) are useful in the treatment of diseases or conditions mediated by the adenosine receptor. In one embodiment, there is provided a compound of Formula (I) or a pharmaceutically acceptable salt thereof, for use in the treatment of diseases or conditions mediated by the adenosine receptor. In some embodiments the disease or condition is mediated by A2aR; in other embodiments, by A2bR; in still other embodiments, by both A2aR and A2bR.

Some examples of disease or conditions mediated by the adenosine receptor include cancer, including lung cancer, pancreatic cancer, prostate cancer, ovarian cancer, cervical cancer, colorectal cancer, breast cancer, brain cancer, gastric cancer, liver cancer, renal cancer, endometrial cancer, thyroid cancer, bladder cancer, glial cancer, melanoma, or other solid tumor; movement disorders, including Parkinson’s disease and Huntington’s disease; and attention disorders, including attention deficit disorder and attention deficit-hyperactivity disorder. Other diseases and conditions mediated by the adenosine receptor are known.

In one embodiment, there is provided a compound of Formula (I), or a pharmaceutically acceptable salt thereof, for use in the treatment of a disease or condition mediated by the adenosine receptor.

In one embodiment, there is provided a compound of Formula (I), or a pharmaceutically acceptable salt thereof, for use in the treatment of cancer (including lung cancer, pancreatic cancer, prostate cancer, ovarian cancer, cervical cancer, colorectal cancer, breast cancer, brain cancer, gastric cancer, liver cancer, renal cancer, endometrial cancer, thyroid cancer, bladder cancer, glial cancer, melanoma, or other solid tumor).

In one embodiment, there is provided a compound of Formula (I), or a pharmaceutically acceptable salt thereof, for use in the treatment of a disease or condition mediated by the adenosine receptor, wherein the compound is a selective adenosine receptor antagonist with respect to CB-1.

In one embodiment, there is provided a compound of Formula (I), or a pharmaceutically acceptable salt thereof, for use in the treatment of cancer (including lung cancer, pancreatic cancer, prostate cancer, ovarian cancer, cervical cancer, colorectal cancer, breast cancer, brain cancer, gastric cancer, liver cancer, renal cancer, endometrial cancer, thyroid cancer, bladder cancer, glial cancer, melanoma, or other solid tumor, wherein the compound is a selective adenosine receptor antagonist with respect to CB-1.

In one embodiment, there is provided a method of treating a disease or condition mediated by the adenosine receptor, which includes administering an effective amount of a compound of Formula (I), or a pharmaceutically acceptable salt thereof, to a subject in need of such treatment.

In one embodiment, there is provided a method of treating cancer (including lung cancer, pancreatic cancer, prostate cancer, ovarian cancer, cervical cancer, colorectal cancer, breast cancer, brain cancer, gastric cancer, liver cancer, renal cancer, endometrial cancer, thyroid cancer, bladder cancer, glial cancer, melanoma, or other solid tumor) which includes administering an effective amount of a compound of Formula (I), or a pharmaceutically acceptable salt thereof, to a subject in need of such treatment.

In one embodiment, there is provided a method of treating a disease or condition mediated by the adenosine receptor, which includes administering an effective amount of a compound of Formula (I), or a pharmaceutically acceptable salt thereof, to a subject in need of such treatment, wherein the compound is a selective adenosine receptor antagonist with respect to CB-1.

In one embodiment, there is provided a method of treating cancer (including lung cancer, pancreatic cancer, prostate cancer, ovarian cancer, cervical cancer, colorectal cancer, breast cancer, brain cancer, gastric cancer, liver cancer, renal cancer, endometrial cancer, thyroid cancer, bladder cancer, glial cancer, melanoma, or other solid tumor), which includes administering an effective amount of a compound of Formula (I), or a pharmaceutically acceptable salt thereof, to a subject in need of such treatment, wherein the compound is a selective adenosine receptor antagonist with respect to CB-1.

In one embodiment, there is provided a compound of Formula (I), or a pharmaceutically acceptable salt thereof, for use in the manufacture of a medicament for use in the treatment of a disease or condition mediated by the adenosine receptor.

In one embodiment, there is provided a compound of Formula (I), or a pharmaceutically acceptable salt thereof, for use in the manufacture of a medicament for use in the treatment of cancer (including lung cancer, pancreatic cancer, prostate cancer, ovarian cancer, cervical cancer, colorectal cancer, breast cancer, brain cancer, gastric cancer, liver cancer, renal cancer, endometrial cancer, thyroid cancer, bladder cancer, glial cancer, melanoma, or other solid tumor).

In one embodiment, there is provided a compound of Formula (I), or a pharmaceutically acceptable salt thereof, for use in the manufacture of a medicament for use in the treatment of a disease or condition mediated by the adenosine receptor, wherein the compound is a selective adenosine receptor antagonist with respect to CB-1.

In one embodiment, there is provided a compound of Formula (I), or a pharmaceutically acceptable salt thereof, for use in the manufacture of a medicament for use in the treatment of cancer (including lung cancer, pancreatic cancer, prostate cancer, ovarian cancer, cervical cancer, colorectal cancer, breast cancer, brain cancer, gastric cancer, liver cancer, renal cancer, endometrial cancer, thyroid cancer, bladder cancer, glial cancer, melanoma, or other solid tumor, wherein the compound is a selective adenosine receptor antagonist with respect to CB-1.

Compounds of Formula (I) can be prepared according to the following general schemes.

Schemes 1a and 1b illustrate the preparation of intermediate 6-substituted-4-hydrazino-2-aminopyrimidine compounds of Formula (IV).

Scheme 1a

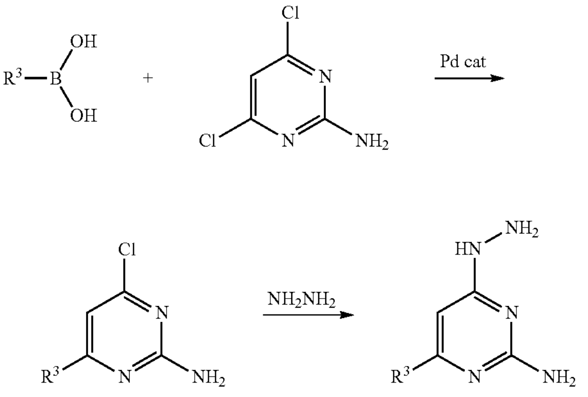

(IV)

Scheme 1b

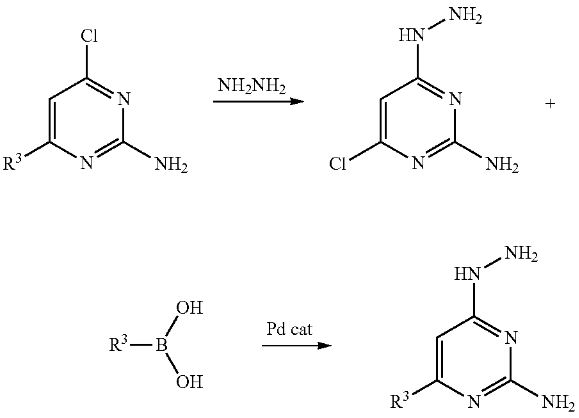

(IV)

Scheme 2 illustrates the conversion of compounds of Formula (IV) into the intermediate 7-substituted-5-amino-8-bromo-[1,2,4]triazolo[4,3-c]pyrimidin-3-one compounds of Formula (V). Briefly, the compound of Formula (IV) is treated with triphosgene to effect closure of the triazolone ring, followed by bromination with $(CH_3)_3PhN^+Br_3^-$.

Scheme 2

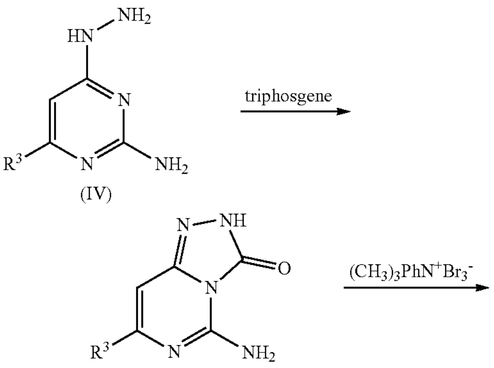

-continued

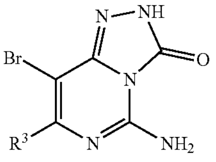

(V)

Scheme 3a illustrates the conversion of compounds of Formula (V) into compound of Formula (I). The alkylation of the compound of Formula (V) with $R^4$ can be carried out using a variety of methods, for example, Mitsonobu reaction; alcohol mesylation followed by an alkylation reaction; alcohol tosylation followed by an alkylation reaction; or alcohol chlorination followed by an alkylation reaction.

Scheme 3a

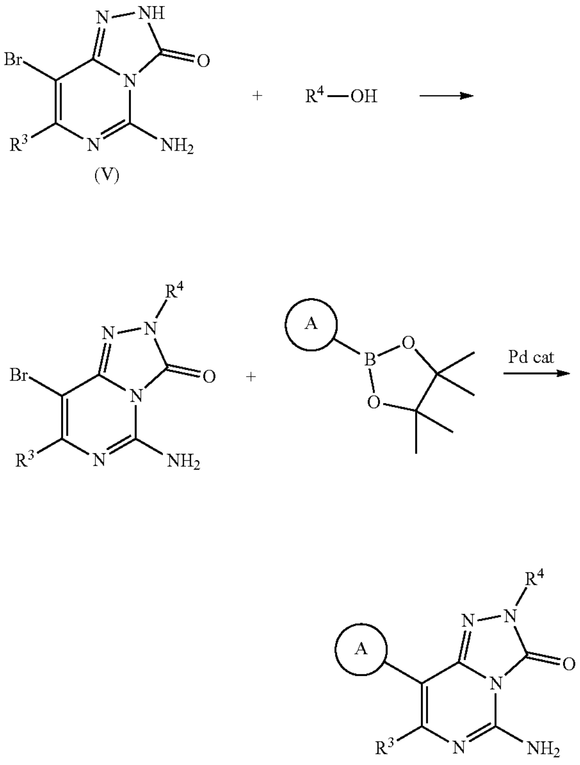

(I)

Alternatively, a compound such as $R^4$—Br may be used in a direct alkylation of the compound of Formula (V).

Optionally, $R^4$ can be further modified after alkylation of the compound of Formula (V).

Scheme 3b illustrates an alternate route for the conversion of compounds of Formula (V) into compounds of Formula (I). In Scheme 3b, [Pg] represents a suitable reagent for installing the protecting group denoted Pg. The alkylation of the compound of Formula (Va) with $R^4$ can be carried out using a variety of methods, for example, Mitsonobu reaction; alcohol mesylation followed by an alkylation reaction; alcohol tosylation followed by an alkylation reaction; alcohol chlorination followed by an alkylation reaction.

Scheme 3b

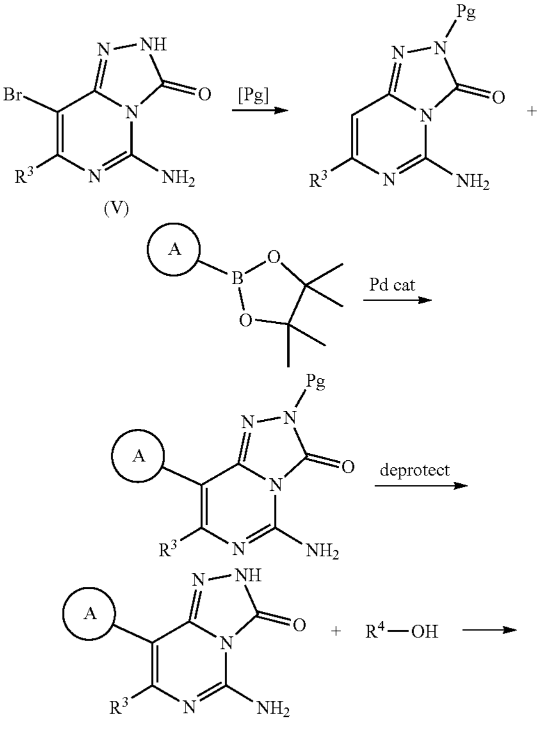

(Va)

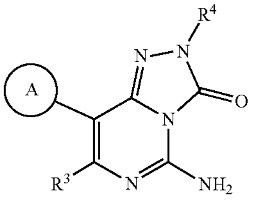

(I)

Alternatively, a compound such as $R^4$—Br may be used in a direct alkylation of the compound of Formula (Va).

Optionally, $R^4$ can be further modified after alkylation of the compound of Formula (V).

Optionally, a compound of Formula (I) can be further modified, for example, to form a different compound of Formula (I).

EXAMPLES

General Techniques

LCMS Method A

Instrument: Agilent Technologies 1200 Series, Agilent LC/MSD SL, Column: Waters XBridge C8 3.5 μm, 4.6×50 mm. Gradient [time (min)/solvent B (%)]:0.0/5,8.0/100,8.1/100,8.5/5,10.0/5. (Solvent A=1 mL of TFA in 1000 mL of Milli-Q Water; Solvent B=1 mL of TFA in 1000 mL of MeCN); Injection volume 1 μL (may vary); UV detection 220 to 400 nm; Column temperature 25° C.; 2.0 mL/min.

For UV inactive compounds an ELSD detector (Polymer Laboratories PL-ELS 2100 ICE) is connected with the above instrument.

LCMS Method B

Instrument: Agilent Technologies 1200 Series, Agilent LC/MSD SL, Column: Atlantis dC18 5 μm, 4.6×50 mm.

Gradient [time (min)/solvent B (%)]:0.0/10, 2.5/95, 4.5/95, 4.6/10, 6.0/10. (Solvent A=1 mL of TFA in 1000 mL of Milli-Q Water; Solvent B=1 mL of TFA in 1000 mL of MeCN); Injection volume 1 μL (may vary); UV detection 210 to 400 nm; Column temperature 25° C.; 1.5 mL/min.

LCMS Method C

Instrument: Agilent Technologies 1200 Series, Agilent 6130 Quadrupole LC/MS, Column: Zorbax C18 5 μm, 4.6×50 mm. Gradient [time (min)/solvent B (%)]:0.0/10, 2.5/95, 4.5/95,4.6/10, 6.0/10. (Solvent A=1 mL of Formic Acid in 1000 mL of Milli-Q Water; Solvent B=MeCN); Injection volume 1 μL (may vary); UV detection 210 to 400 nm; column temperature 25° C.; 1.5 mL/min.

LCMS Method D

Instrument: Agilent Technologies 1200 Series, Agilent 6130 Quadrupole LC/MS, Column: Zorbax C18 5 μm, 4.6×50 mm. Gradient [time (min)/solvent B (%)]:0.0/10, 4.0/95, 5.0/95, 5.5/10, 7.0/10. (Solvent A=770.08 mg of Ammonium acetate in 1000 mL of Milli-Q Water; Solvent B=MeCN); Injection volume 1 μL (may vary); UV detection 210 to 400 nm; column temperature 25° C.; 1.2 mL/min.

LCMS Method E

Instrument: Agilent Technologies 1200 Series, Agilent 6130 Quadrupole LC/MS, Column: XBridge C8 3.5 μm, 4.6×50 mm. Gradient [time (min)/solvent B (%)]:0.0/5, 8.0/100, 8.1/100, 8.5/5, 10.0/5. (Solvent A=790.06 mg of Ammonium bicarbonate is added to 1000 mL of Milli-Q Water; Solvent B=MeCN); Injection volume 1 μL (may vary); UV detection 210 to 400 nm; column temperature 25° C.; 1.0 mL/min.

LCMS Method F

Instrument: Agilent 1100 Series LC/MSD. Column: Zorbax SB-C18 1.8 μm 4.6×15 mm. Gradient [time (min)/solvent A (%)]:0.0/100; 0.01/100; 1.5/0; 1.8/0; 1.81/100. (Solvent A=$H_2O$; Solvent B=MeCN, both modified with 0.1% formic acid). Injection volume 1 μL (may vary). UV detection 215 nm. Column temperature 60° C.

Prep-HPLC Method A

Instrument: Agilent Technologies 1260 Infinity II Series LC. Solvent: A—0.1% TFA in $H_2O$, B-MeOH, Column: YMC Actus Triart $C_{18}$ (30 mm×250 mm) 5 μm. Gradient [time (min)/solvent B (%)]:0.0/10, 20/95, 23/95, 24/10, 26/10.

Prep-HPLC Method B

Instrument: Agilent Technologies 1260 Infinity II Series LC. Solvent: A—0.1% HCOOH in $H_2O$, B— MeCN, Column: YMC Actus Triart $C_8$ (20 mm×250 mm) 5 μm. Gradient [time (min)/solvent B (%)]:0.0/10, 20/95, 23/95, 24/10, 26/10.

Prep-HPLC Method C

Instrument: Agilent Technologies 1260 Infinity II Series LC. Solvent: A—10 mM $NH_4HCO_3$ in $H_2O$, B-MeOH or MeCN, Column: XBridge C8 (19 mm×150 mm), 5 μm or YMC Actus Triart C18 (30 mm×250 mm) 5 μm. Gradient [time (min)/solvent B (%)]:0.0/10, 15/95, 18/95, 19/10, 21/10.

Prep-HPLC Method D

Instrument: Agilent Technologies 1260 Infinity II Series LC. Mobile Phase: HEXANE B: IPA (60:40), Column: YMC Silica (19×150) mm, 5 μm, Flow: 15 mL/min. Note: Gradient may vary from sample to sample based on sample separation and Polarity.

Prep-HPLC Method E

Instrument: Agilent Technologies 1260 Infinity II Series LC. Solvent: A—$H_2O$, B-MeOH or MeCN. Column: Waters Sunfire C18 OBD Prep Column, 100 Å, 5 μm, 19 mm×100 mm. Gradient [time (min)/solvent B (%)]:0.0/10, 20/95, 23/95, 24/10, 26/10.

MD Auto-Prep Method A

Instrument: Agilent Technologies 1260 Infinity II Series LC/6125 Quadrupole MSD.

Solvent: A—0.1% TFA in $H_2O$, B-MeOH, Column: X Bridge C8 (19 mm×150 mm), 5 μm, Gradient; [time (min)/solvent B (%)]: 0.0/10, 15/95, 18/95, 19/10, 21/10.

Chiral SFC Method A

Instrument: SFC Investigator-Waters. Solvent: A—$CO_2$, B—20 mM Ammonia in MeOH. Column: LUX C2 (cellulose) (250×4.6) mm, 5 μm. Isocratic 40%. Outlet Pressure; 100 bar. Column temperature 25° C.; 1.6 mL/min.

Chiral SFC Method B

Instrument: SFC Investigator-Waters. Solvent: A—$C_{02}$, B—0.1% DEA in n-hexane: EtOH: 70:30. Column: CHIRALCEL C4 (cellulose) (250×4.6) mm, 5 μm. Outlet Pressure; 100 bar. Column temperature 25° C.; 1.0 mL/min.

Chiral SFC Method C

Instrument: SFC Investigator-Waters. Solvent: A—$CO_2$, B—20 mM Ammonia in MeOH. Column: Lux A1 (Amylose); (250×4.6) mm, 5 sm. Isocratic 30%. Outlet Pressure; 100 bar. Column temperature 35° C.; 3.0 mL/min.

Chiral SFC Method D

Instrument: SFC Investigator-Waters. Solvent: A—$CO_2$, B—20 mM Ammonia in MeOH. Column: Chiralcel ODH (Cellulose); (250×4.6) mm, 5 μm. Isocratic 40%. Outlet Pressure; 100 bar. Column temperature 35° C.; 4.0 mL/min.

Chiral SFC Method E

Instrument: SFC Investigator-Waters. Solvent: A—$CO_2$, B—20 mM Ammonia in MeOH. Column: Lux A1 (Amylose); (250×4.6) mm, 5 μm. Isocratic 30%. Outlet Pressure; 100 bar. Column temperature 35° C.; 3.0 mU/min.

Synthetic Routes for Intermediates

Synthetic Routes 1 to 10, used to prepare Intermediates used in the synthesis of compounds of Formula (I), are described below. The details of Synthetic Routes 1 to 10 are illustrative of the techniques used in the preparation of other Intermediates as detailed in Table 2 below.

Synthetic Route 1: Procedure for the Preparation of Intermediate 1

Intermediate 1, 5-amino-8-bromo-7-phenyl-[1,2,4]triazolo[4,3-c]pyrimidin-3(2H)-one

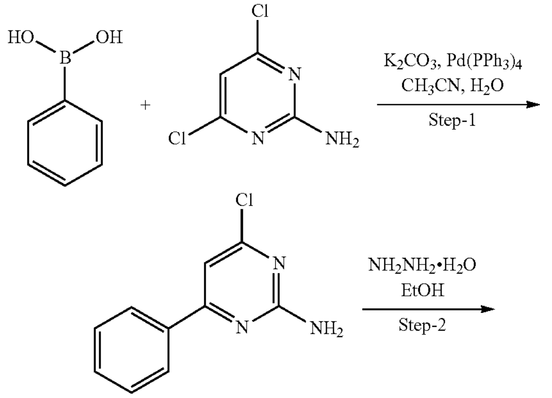

-continued

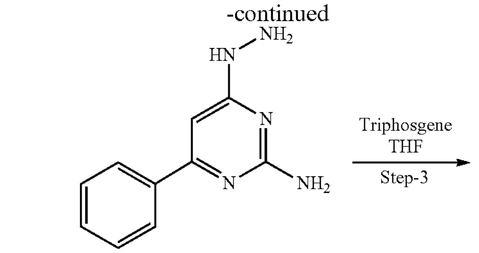

Intermediate 74

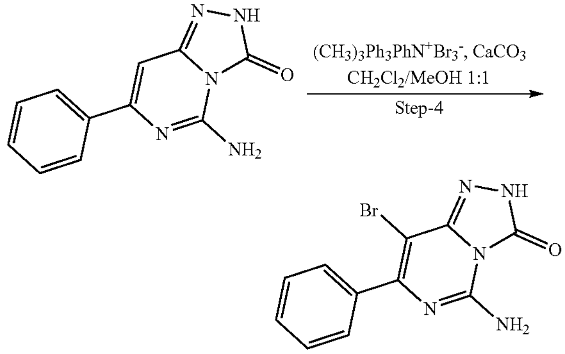

Intermediate 1

Step 1; This reaction was performed as 2×250 g batches. To a degassed suspension of phenyl boronic acid (250 g, 2.05 mol), 4,6-dichloro-2-aminopyrimidine (672 g, 4.10 mol) and $K_2CO_3$ (848 g, 6.15 mol) in $CH_3CN$ (15 L) and $H_2O$ (2 L) at room temperature was added $Pd(PPh_3)_4$ (118 g, 0.10 mol) and the resultant reaction mixture was heated to 90° C. for 6 h. The reaction mixture was concentrated under reduced pressure. The residue obtained was vigorously stirred with $H_2O$ (4 L) and DCM (10 L), undissolved solids were filtered-off through a Buchner funnel and rinsed with DCM (3 L). The filtrate was taken in a separating funnel, the organic layer was separated, dried over anhydrous $Na_2SO_4$ and concentrated under reduced pressure. The crude product was purified by flash chromatography using 230-400 silica mesh and was eluted with 0-15% EtOAc in Pet-Ether to afford 4-chloro-6-phenylpyrimidin-2-amine (350 g, 41%) as an off-white solid.

LCMS (Method A): m/z 206 $(M+H)^+$ $(ES^+)$, at 2.53 min, UV active.

$^1H$ NMR: (400 MHz, DMSO-d6) δ: 8.05-8.03 (m, 2H), 7.52-7.47 (m, 3H), 7.21 (s, 1H). Exchangeable —NH2 protons were not observed.

Step 2; To a stirred suspension of 4-chloro-6-phenylpyrimidin-2-amine (350 g, 1.70 mol) in EtOH (4.0 L), hydrazine hydrate (255 g, 5.1 mol) was added and the mixture was heated to 90° C. for 15 h. The reaction was concentrated under reduced pressure. The residue obtained was triturated with diethyl ether (1 L) and 10% sodium bicarbonate solution (1 L). The solid obtained was collected by filtration through a Buchner funnel, rinsed with Diethyl ether (200 mL) and dried under vacuum to afford 4-hydrazinyl-6-phenylpyrimidin-2-amine (250 g, 73%) as an off-white solid.

LCMS (Method C): m/z 202 $(M+H)^+$ $(ES^+)$, at 0.69 min, UV active.

$^1H$ NMR: (400 MHz, DMSO-d6) δ: 7.94-7.91 (m, 2H), 7.84 (s, 1H), 7.48-7.42 (m, 3H), 6.47 (s, 1H), 6.00 (s, 2H), 4.25 (s, 2H).

Step 3; To a solution of 4-hydrazinyl-6-phenylpyrimidin-2-amine (250 g, 1.24 mol) in dry THF (3.0 L) under $N_2$, cooled to −30° C. was added triphosgene (735 g, 2.48 mol) portion wise and the mixture was stirred at same temperature for 45 min. The reaction was quenched cautiously into ice cold water (10 L) with vigorous stirring. After the effervescence stopped, the reaction mass was concentrated under reduced pressure. The resulting solid was collected by filtration through a Buchner funnel, rinsed with water (1 L) and dried under vacuum to afford 5-amino-7-phenyl-[1,2,4]triazolo[4,3-c]pyrimidin-3(2H)-one (200 g, 70%) as a yellow solid.

LCMS (Method C): m/z 228 $(M+H)^+$ $(ES^+)$, at 1.64 min, UV active.

$^1H$ NMR: (400 MHz, DMSO-d6) δ: 12.46 (s, 1H), 8.05-7.98 (m, 3H), 7.65 (s, 1H), 7.50-7.44 (m, 3H), 6.93 (s, 1H).

Step 4; To a suspension of 5-amino-7-phenyl-[1,2,4]triazolo[4,3-c]pyrimidin-3(2H)-one (200 g, 0.88 mol) in DCM/MeOH 1:1 (2 L) under $N_2$ atmosphere, $CaCO_3$ (88 g, 0.88 mol) followed by $(CH_3)_3PhN^+\ Br_3^-$ (331 g, 0.88 mol) were added and the mixture was stirred at room temperature for 1 h. The reaction mixture was filtered through a Buchner funnel, rinsed with small portions of MeOH/DCM (1:1) and dried under vacuum to afford Intermediate 1, 5-amino-8-bromo-7-phenyl-[1,2,4]triazolo[4,3-c]pyrimidin-3(2H)-one (160 g, 59%) as a light brown solid. The data for the title compound are in Table 2.

Synthetic Route 2: Procedure for the Preparation of Intermediate 7

Intermediate 7: 5-amino-8-(2,6-dimethylpyridin-4-yl)-7-phenyl-[1,2,4]triazolo[4,3-c]pyrimidin-3(2H)-one

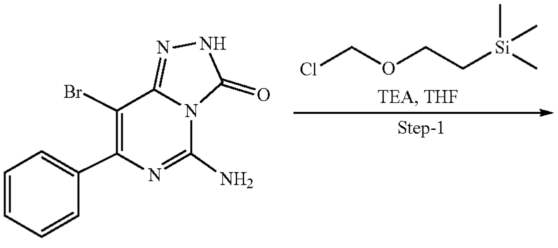

Intermediate 1

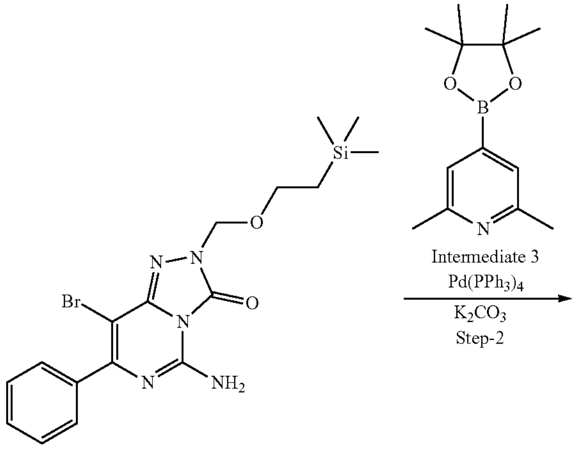

Intermediate 9

-continued

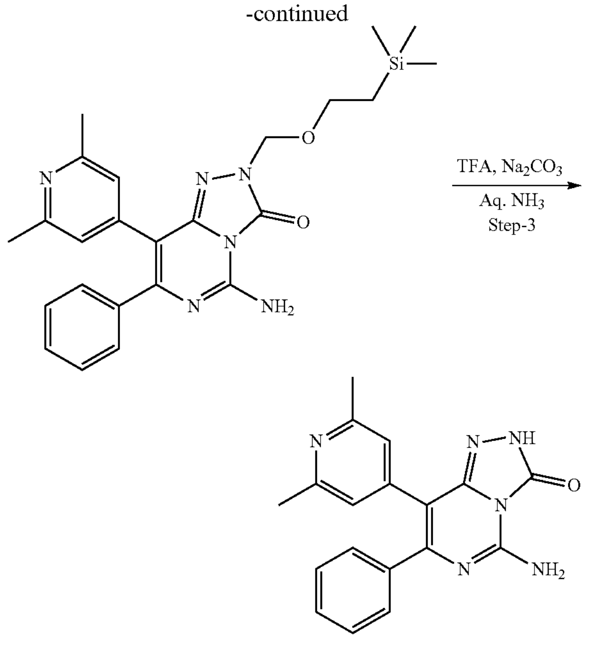

Intermediate 7

Step 1; To a suspension of 5-amino-8-bromo-7-phenyl-[1,2,4]triazolo[4,3-c]pyrimidin-3(2H)-one (16.2 g, 53 mmol) in THF (200 mL) at 0° C. was added TEA (19 mL, 136.3 mmol) followed by the dropwise addition of (2-(chloromethoxy)ethyl)trimethylsilane (11.3 g, 67.8 mmol). The reaction was stirred at 0° C. for 1 h then partitioned between EtOAc (250 mL) and $H_2O$ (200 mL). The organic layer was separated, dried over anhydrous $Na_2SO_4$ and concentrated under reduced pressure. The crude product was purified by Biotage-Isolera using 100 g silica snap and eluted with gradient 0-30% EtOAc in hexane to afford 5-amino-8-bromo-7-phenyl-2-((2-(trimethylsilyl)ethoxy)methyl)-[1,2,4]triazolo[4,3-c]pyrimidin-3(2H)-one (12 g, 52%) as an off-white solid. The data for the title compound are in Table 2.

Step 2; To a degassed suspension of 5-amino-8-bromo-7-phenyl-2-((2-(trimethylsilyl)ethoxy)methyl)-[1,2,4]triazolo[4,3-c]pyrimidin-3(2H)-one (11 g, 25 mmol), 2,6-dimethyl-4-(4,4,5,5-tetramethyl-1,3,2-dioxaborolan-2-yl)pyridine (6.5 g, 28 mmol) and $K_2CO_3$ (8.6 g, 62.5 mmol) in 1,4-Dioxane (150 mL) and $H_2O$ (30 mL) at room temperature was added $Pd(PPh_3)_4$ (1.44 g, 1.25 mmol) and the reaction mixture was heated at 120° C. for 5 h. The reaction mixture was partitioned between EtOAc (300 mL) and water (200 mL). The organic layer was separated, dried over anhydrous $Na_2SO_4$ and concentrated under reduced pressure. The crude product was purified by Biotage-Isolera using 100 g silica snap and eluted with gradient 0-80% EtOAc in Hexane to afford 5-amino-8-(2,6-dimethylpyridin-4-yl)-7-phenyl-2-((2-(trimethylsilyl)ethoxy)methyl)-[1,2,4]triazolo[4,3-c]pyrimidin-3(2H)-one (7.5 g, 64%) as a yellow solid.

LCMS (Method B): m/z 462 $(M+H)^+$ $(ES^+)$, at 2.55 min, UV active.

$^1H$ NMR: (400 MHz, DMSO-d6) δ: 7.30-7.26 (m, 5H), 6.82 (s, 2H), 5.13 (s, 2H), 3.63 (t, J=7.4 Hz, 2H), 2.29 (s, 6H), 0.88 (t, J=7.4 Hz, 2H), 0.06 (s, 9H). Exchangeable —$NH_2$ protons were not observed.

Step 3; 5-amino-8-(2,6-dimethylpyridin-4-yl)-7-phenyl-2-((2-(trimethylsilyl)ethoxy)methyl)-[1,2,4]triazolo[4,3-c]pyrimidin-3(2H)-one (7 g, 15 mmol) was dissolved in TFA (40 mL) and stirred at room temperature for 30 min. The reaction mixture was concentrated under reduced pressure and dried under hi-vacuum. The residue obtained was taken in EtOH (30 mL) and cautiously added Aq. NH4OH (50 mL) and the reaction mixture was heated at 60° C. for 2 h. The solid was collected by filtration through a Buchner funnel, washed with water (10 mL) and EtOH (10 mol) and dried under vacuum to afford 5-amino-8-(2,6-dimethylpyridin-4-yl)-7-phenyl-[1,2,4]triazolo[4,3-c]pyrimidin-3(2H)-one (4.5 g, 89%) as a yellow solid. The data for the title compound are in Table 2.

Synthetic Route 3: Procedure for the Preparation of Intermediate 11

Intermediate 11: 6-(bromomethyl)-3-fluoro-2-methoxypyridine

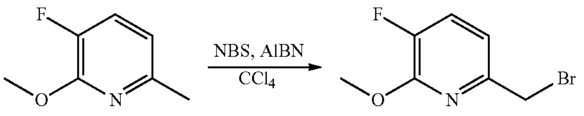

Intermediate 11

To a stirred solution of 3-fluoro-2-methoxy-6-methylpyridine (500 mg, 3.54 mmol) in $CCl_4$ (10 mL) at 0° C. was added N-bromosuccinamide (700 mg, 3.89 mmol) and AIBN (57 mg, 0.35 mmol). The reaction mixture was heated to 80° C. for 16 h. The reaction mixture was partitioned between DCM (20 mL) and $H_2O$ (20 mL), the organic layer was separated and concentrated under reduced pressure. The crude product was purified by Biotage-Isolera using 10 g silica snap and eluted with pet-ether to afford 6-(bromomethyl)-3-fluoro-2-methoxypyridine (720 mg, 89%) as pale yellow gum. The data for the title compound are in Table 2.

Synthetic Route 4: Procedure for the Preparation of Intermediate 38

Intermediate 38: N,N-ditert-butoxy carbonyl (6-(bromomethyl)-3-fluoropyridin-2-yl)-amine

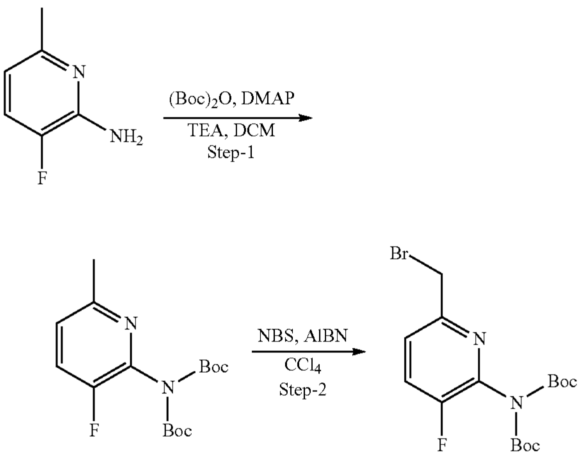

Intermediate 38

Step 1; To a stirred solution of 3-fluoro-6-methylpyridin-2-amine (100 mg, 0.79 mmol) in DCM (10 mL) was added TEA (240 mg, 2.37 mmol), DMAP (9 mg, 0.08 mmol) and Boc-anhydride (432 mg, 1.98 mmol). The reaction mixture was stirred at room temperature for 16 h. The reaction mixture was partitioned between DCM (20 mL) and water (20 mL), the organic layer was separated and concentrated under reduced pressure. The crude product was purified by Biotage-Isolera using 10 g silica snap and eluted with gradient 0-10% EtOAc in pet-ether to afford N,N-di-tert-butoxy carbonyl (3-fluoro-6-methylpyridin-2-yl)amine as white liquid.

LCMS (Method B): m/z 327 $(M+H)^+$ $(ES^+)$, at 2.82 min, UV active.

$^1$H NMR: (400 MHz, DMSO-d6) δ: 7.79-7.73 (m, 1H), 7.38-7.34 (m, 1H), 2.44 (s, 3H), 1.38 (s, 18H).

Step 2; To a stirred solution of N,N-di-tert-butoxy carbonyl (3-fluoro-6-methylpyridin-2-yl)amine (160 mg, 0.49 mmol) in $CCl_4$ (10 mL) was added N-bromosuccinamide (174 mg, 0.98 mmol) and AIBN (16 mg, 0.10 mmol). The reaction mixture was heated to 80° C. for 16 h. The reaction mixture was partitioned between DCM (20 mL) and water (20 mL), the organic layer was separated and concentrated under reduced pressure to afford N,N-ditert-butoxy carbonyl (6-(bromomethyl)-3-fluoropyridin-2-yl)-amine (crude) as brown gummy solid, that was taken onto the next step without purification. The data for the title compound are in Table 2.

Synthetic Route 5: Procedure for the Preparation of Intermediate 41

Intermediate 41: 5-amino-8-bromo-7-(4-fluorophenyl)-[1,2,4]triazolo[4,3-c]pyrimidin-3(2H)-one

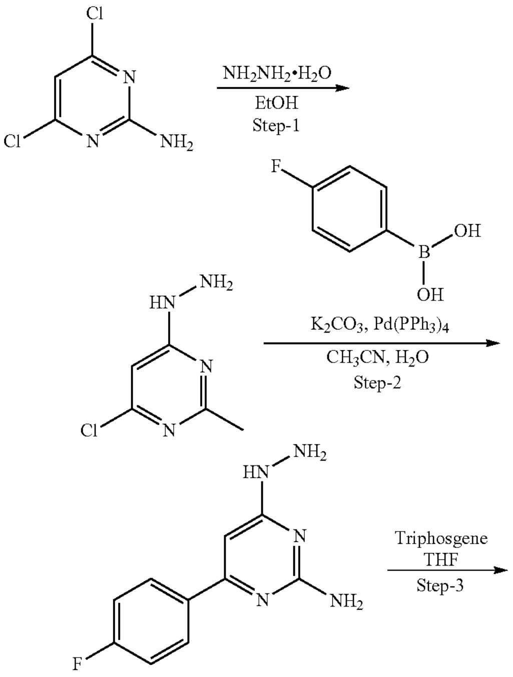

-continued

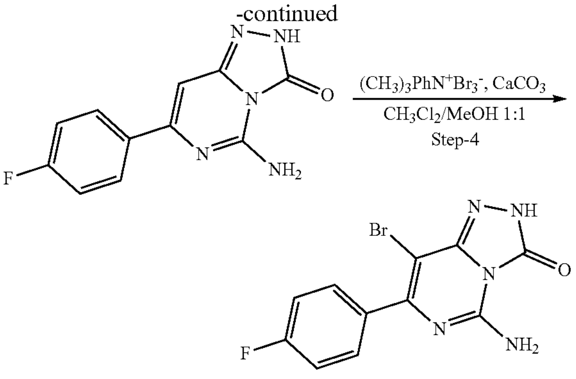

Intermediate 41

Step 1; To a stirred suspension of 4,6-dichloropyrimidin-2-amine (400 g, 2.43 mol) in EtOH (5 L), was added hydrazine hydrate (365 g, 7.31 mol) and the mixture was heated to 90° C. for 15 h. The reaction mass was concentrated under reduced pressure. The residue obtained was triturated with diethyl ether (1 L) and 10% sodium bicarbonate solution (1 L). The solid obtained was collected by filtration through a Buchner funnel, rinsed with Diethyl ether (200 mL) and dried under vacuum to afford 4-chloro-6-hydrazineylpyrimidin-2-amine (300 g, 77%) as an off-white solid.

LCMS (Method C): m/z 160 $(M+H)^+$ $(ES^+)$, at 0.37 min, UV active.

$^1$H NMR: (400 MHz, DMSO-d6) δ: 8.10 (s, 1H), 6.36 (s, 2H), 5.97 (s, 1H), 4.26 (s, 2H).

Step 2; To a degassed suspension of 4-chloro-6-hydrazineylpyrimidin-2-amine (300 g, 1.87 mol), 4-Fluorophenyl boronic acid (313 g, 2.24 mol), and $K_2CO_3$ (774 g, 5.61 mol) in 1,4-dioxane (6 L) and $H_2O$ (1 L) at room temperature was added $Pd(PPh_3)_4$ (107 g, 0.093 mol) and the resultant reaction mixture was heated to 110° C. for 15 h. The reaction mixture was concentrated under reduced pressure to remove the 1,4-dioxane. The residue obtained was vigorously stirred with $H_2O$ (4 L) to obtain a solid, which was filtered through Buchner funnel and rinsed with MeOH (1 L). The solid was dried under vacuum to afford 4-(4-fluorophenyl)-6-hydrazineylpyrimidin-2-amine (200 g, 49%) as a green solid.

LCMS (Method C): m/z 220 $(M+H)^+$ $(ES^+)$, at 0.76 min, UV active.

$^1$H NMR: (400 MHz, DMSO-d6) δ: 8.00-7.96 (m, 2H), 7.854 (s, 1H), 7.29-7.24 (m, 2H), 6.45 (s, 1H), 6.01 (s, 2H), 4.24 (s, 2H).

Step 3; To a solution of 4-(4-fluorophenyl)-6-hydrazineylpyrimidin-2-amine (200 g, 0.91 mol) in dry THF (3.0 L) under $N_2$, cooled to −30° C. was added triphosgene (538 g, 1.82 mol) portionwise and the mixture was stirred at same temperature for 1 h. The reaction was quenched cautiously into ice cold water (10 L) with vigorous stirring. After the effervescence stopped, the reaction mass was concentrated under reduced pressure. The resulting solid was collected by filtration through a Buchner funnel, rinsed with water (1 L) and dried under vacuum to afford 5-amino-7-(4-fluorophenyl)-[1,2,4]triazolo[4,3-c]pyrimidin-3(2H)-one (150 g, 67%) as yellow solid.

LCMS (Method C): m/z 246 $(M+H)^+$ $(ES^+)$, at 1.77 min, UV active.

$^1$H NMR: (400 MHz, DMSO-d6) δ:12.43 (s, 1H), 8.19-8.01 (m, 2H), 7.95-7.52 (m, 2H), 7.50-7.27 (m, 2H), 6.92 (s, 1H).

Step 4; This reaction was performed on 2×75 g batches. To a suspension of 5-amino-7-(4-fluorophenyl)-[1,2,4]triazolo[4,3-c]pyrimidin-3(2H)-one (150 g, 0.66 mol) in DCM/MeOH 1:1 (2 L) under $N_2$ atmosphere, $CaCO_3$ (66 g, 0.66 mol) followed by $(CH_3)_3PhN^+ Br_3^-$ (250 g, 0.66 mol) were added and the mixture was stirred at room temperature for 1 h. The reaction mixture was filtered through a Buchner funnel, rinsed with small portions of MeOH/DCM (1:1) and dried under vacuum to afford 5-amino-8-bromo-7-(4-fluorophenyl)-[1,2,4]triazolo[4,3-c]pyrimidin-3(2H)-one (120 g, 60%) as light brown solid. The data for the title compound are in Table 2.

Synthetic Route 6: Procedure for the Preparation of Intermediate 42

Intermediate 42: methyl-6-methyl-4-(4,4,5,5-tetramethyl-1,3,2-dioxaborolan-2-yl)picolinate

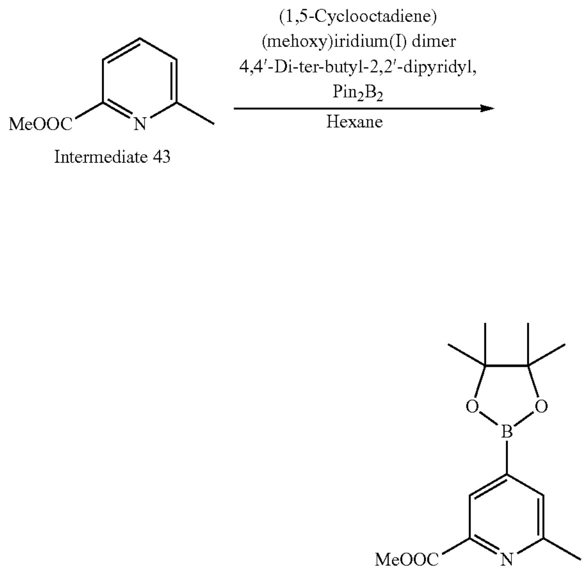

Intermediate 43

Intermediate 42

A degassed solution of (1,5-Cyclooctadiene)(methoxy) iridium(I) dimer (51 mg, 0.33 mmol), 4,4'-Di-tert-butyl-2,2'-dipyridyl (41 mg, 0.155 mmol) and bis-pinacolato diborane (600 mg, 2.48 mmol) in hexane was heated at 55° C. for 10 min. methyl 6-methylpyridine-2-carboxylate (500 mg, 3.1 mmol) was added to the mixture via syringe and heated at 60° C. for 14 h. The reaction was concentrated under reduced pressure to afford methyl 6-methyl-4-(4,4,5,5-tetramethyl-1,3,2-dioxaborolan-2-yl)picolinate as a brown gum, which was used crude without purification. The data for the title compound are in Table 2.

Synthetic Route 7: Typical Procedure for the Preparation of Triazolopyrimidine Analogues Via Suzuki Coupling, Utilising SEM-Protection Intermediate 45: methyl 4-(5-amino-3-oxo-7-phenyl-2,3-dihydro-[1,2,4]triazolo[4,3-c]pyrimidin-8-yl)-6-methylpicolinate

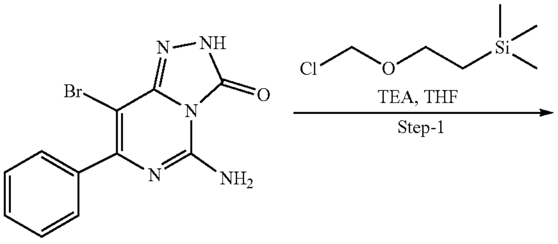

Intermediate 1

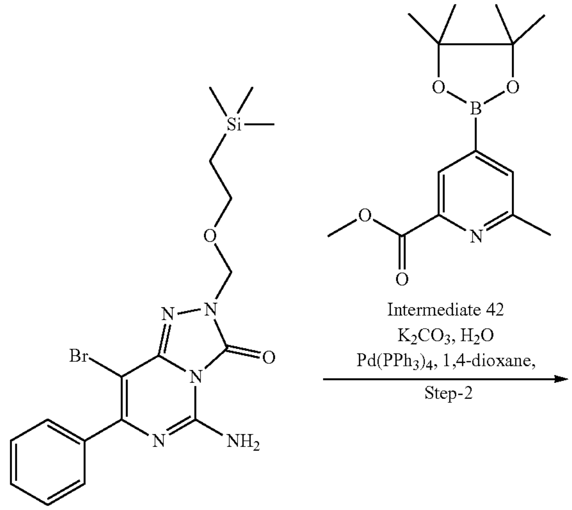

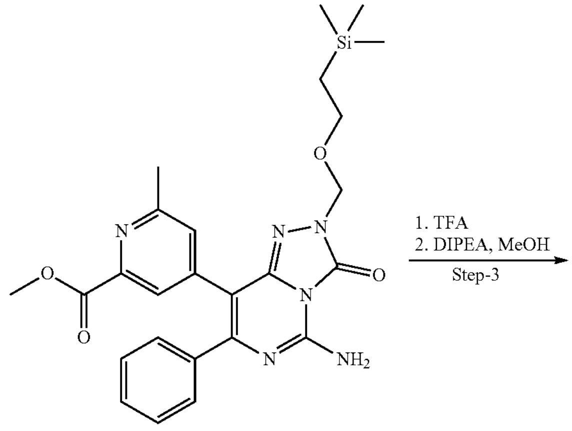

Intermediate 52

-continued

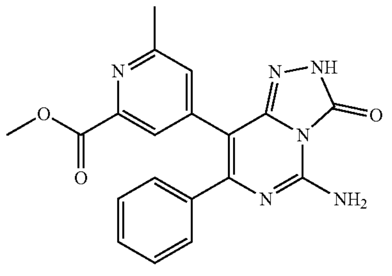

Intermediate 45

Step 1; To a suspension of 5-amino-8-bromo-7-phenyl-[1,2,4]triazolo[4,3-c]pyrimidin-3(2H)-one (16.2 g, 53 mmol) in THF (200 mL) at 0° C. was added TEA (19 mL, 136.3 mmol) followed by the dropwise addition of (2-(chloromethoxy)ethyl)trimethylsilane (11.3 g, 67.8 mmol). The reaction was stirred at 0° C. for 1 h then partitioned between EtOAc (250 mL) and water (200 mL). The organic layer was separated, dried over anhydrous $Na_2SO_4$ and concentrated under reduced pressure. The crude product was purified by Biotage-Isolera using 100 g silica snap and eluted with gradient 0-30% EtOAc in Hexane to afford 5-amino-8-bromo-7-phenyl-2-((2-(trimethylsilyl)ethoxy)methyl)-[1,2,4]triazolo[4,3-c]pyrimidin-3(2H)-one (12 g, 52%) as an off-white solid.

LCMS (Method B): m/z 436 (M+H)+(ES+), at 3.25 min, UV active.

$^1$H NMR: (400 MHz, DMSO-d6) δ: 8.56 (s, 2H), 7.62 (d, J=7.1 Hz, 2H), 7.45 (d, J=6.6 Hz, 3H), 5.18 (s, 2H), 3.66 (t, J=8.2 Hz, 2H), 0.91 (t, J=8.2 Hz, 2H), 0.04 (s, 9H).

Step 2; Prepared in a similar fashion to route a, step 2, using intermediate 34, to afford methyl 4-(5-amino-3-oxo-7-phenyl-2-((2-(trimethylsilyl)ethoxy)methyl)-2,3-dihydro-[1,2,4]triazolo[4,3-c]pyrimidin-8-yl)-6-methyl picolinate (6 g, 64%) as a yellow solid. The data for the title compound are in table 2.

Step 3; A solution of methyl 4-(5-amino-3-oxo-7-phenyl-2-((2-(trimethylsilyl)ethoxy)methyl)-2,3-dihydro-[1,2,4]triazolo[4,3-c]pyrimidin-8-yl)-6-methylpicolinate (1 g, 1.9 mmol) in TFA (15 mL) was stirred at room temperature for 30 min. After the completion of starting material, monitored by TLC, reaction mixture was concentrated under reduced pressure. The residue obtained was dissolved in MeOH (20 mL), DIPEA (1.7 mL, 9.8 mmol) was added and the resultant reaction mixture was heated to 60° C. for 4 h. The precipitate was collected by filtration, washed with MeOH (2×2 mL) and dried under vacuum to afford methyl 4-(5-amino-3-oxo-7-phenyl-2,3-dihydro-[1,2,4]triazolo[4,3-c]pyrimidin-8-yl)-6-methylpicolinate (0.55 g, 67%) as a yellow solid. The data for the title compound are in Table 2.

Synthetic Route 8: Typical Procedure for the Preparation of Triazolopyrimidine Analogues Using a SEM-Protection Strategy

Intermediate 53: 5-amino-8-(2-(hydroxymethyl)-6-methylpyridin-4-yl)-7-phenyl-[1,2,4]triazolo[4,3-c]pyrimidin-3(2H)-one

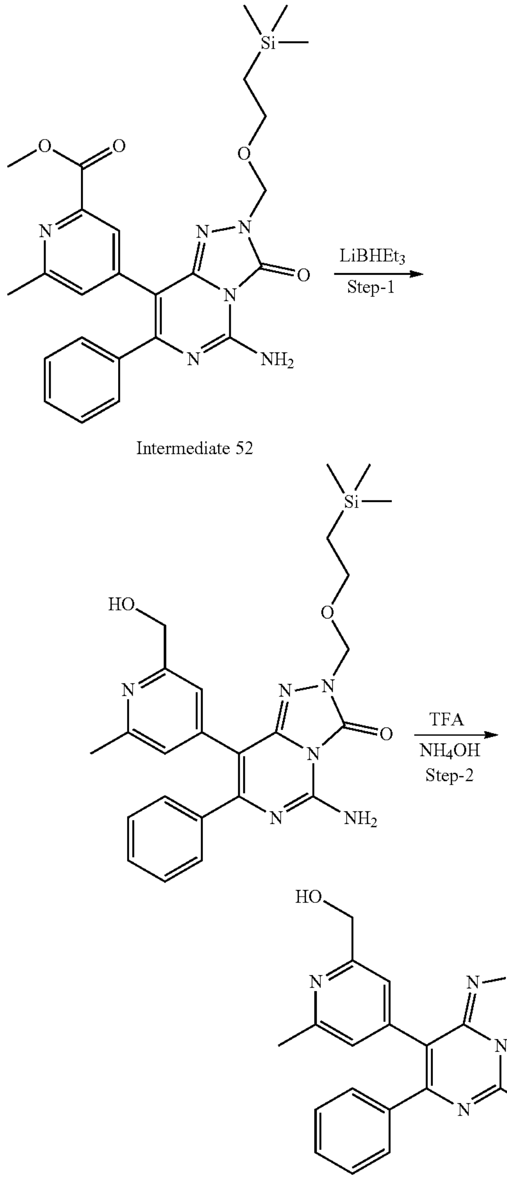

Intermediate 52

Intermediate 53

Step 1; To a solution of methyl 4-(5-amino-3-oxo-7-phenyl-2-((2-(trimethylsilyl)ethoxy)methyl)-2,3-dihydro-[1,2,4]triazolo[4,3-c]pyrimidin-8-yl)-6-methylpicolinate (3.5 g, 6.90 mmol) in THF (30 mL) at 0° C., lithium triethyl borohydride (1M in THF, 13.8 mL, 13.81 mmol) was added dropwise and the reaction mixture was stirred at room temperature for 1 h. The reaction mixture was partitioned between EtOAc (50 mL) and $H_2O$ (50 mL). The organic layer was separated, washed with brine solution (20 mL), dried over anhydrous $Na_2SO_4$ and concentrated under reduced pressure. The crude product was purified by flash column chromatography by using silica (230-400) mesh and eluted with 0-3% MeOH in DCM gradient to afford 5-amino-8-(2-(hydroxymethyl)-6-methylpyridin-4-yl)-7-phenyl-2-((2-(trimethylsilyl)ethoxy)methyl)-[1,2,4]triazolo[4,3-c]pyrimidin-3(2H)-one (2.2 g, 66%) as a yellow solid.

LCMS (Method C): m/z 479 $(M+H)^+$ $(ES^+)$, at 1.82 min, UV active.

$^1H$ NMR: (400 MHz, DMSO-d6) δ: 8.42-8.26 (m, 2H), 7.29-7.25 (m, 5H), 7.09 (s, 1H), 6.88 (s, 1H), 5.25 (t, J=5.7 Hz, 1H), 5.12 (s, 2H), 4.42 (d, J=5.7 Hz, 2H), 3.65-3.61 (m, 2H), 2.31 (s, 3H), 0.88 (t, J=8.0 Hz, 2H), 0.01 (s, 9H).

Step 2; A suspension of 5-amino-8-(2-(hydroxymethyl)-6-methylpyridin-4-yl)-7-phenyl-2-((2-(trimethylsilyl)ethoxy)methyl)-[1,2,4]triazolo[4,3-c]pyrimidin-3(2H)-one (1.1 g, 2.29 mmol) in TFA (10 mL) was heated to 60° C. for 1 h. The reaction mixture was concentrated under reduced pressure. The crude product was diluted with EtOH and cooled to 0° C., ammonium hydroxide solution (50 mL) was added dropwise and heated to 60° C. for 1 h. The reaction mixture was concentrated under reduced pressure and the volume reduced to approximately half. The precipitate was filtered, washed with EtOH and dried to afford 5-amino-8-(2-(hydroxymethyl)-6-methylpyridin-4-yl)-7-phenyl-[1,2,4]triazolo[4,3-c]pyrimidin-3(2H)-one (450 mg, 56%) as a yellow solid. The data for the title compound are in table 2.

Synthetic Route 9: Procedure for the Preparation of Intermediate 83

Intermediate 83: 2-(5-amino-8-(2,6-dimethylpyridin-4-yl)-3-oxo-7-phenyl-[1,2,4]triazolo[4,3-c]pyrimidin-2(3H)-yl)ethyl methanesulfonate

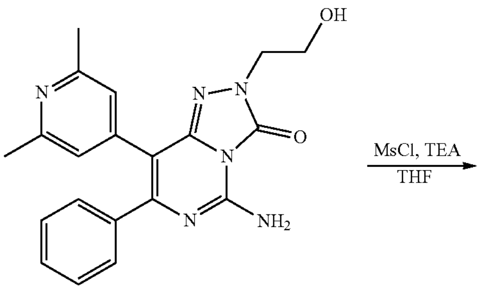

Intermediate 84

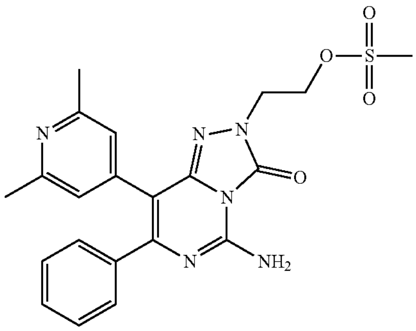

Intermediate 83

To a suspension 5-amino-8-(2,6-dimethylpyridin-4-yl)-2-(2-hydroxyethyl)-7-phenyl-[1,2,4]triazolo[4,3-c]pyrimidin-3(2H)-one (4 g, 0.01 mol) and TEA (4 mL, 0.03 mol) in THF (60 mL) at 0° C. was added methane sulfonyl chloride (1 mL, 0.012 mol) dropwise over 10 min. The reaction mixture was partitioned between EtOAc (50 mL) and brine solution (50 mL). The organic layer was separated, dried over anhydrous $Na_2SO_4$ and concentrated under reduced pressure. The crude product was triturated with n-Hexane (2×20 mL), decanted and dried to afford 2-(5-amino-8-(2,6-dimethylpyridin-4-yl)-3-oxo-7-phenyl-[1,2,4]triazolo[4,3-c]pyrimidin-2(3H)-yl)ethyl methanesulfonate (3.4 g, 70%) as a yellow solid. The data for the title compound are in Table 2.

Synthetic Route 10: Procedure for the Preparation of Intermediate 138

Intermediate 138: 4-methyl-2-(trimethylstannyl)thiazole

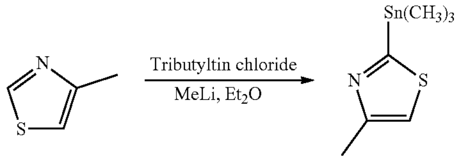

To a solution of 4-methylthiazole (150 mg, 1.51 mmol) in diethyl ether (20 mL) at −78° C. was added methyl lithium (470 mg, 2.25 mmol) dropwise and the reaction was stirred at same temperature for 1 h. Tributyltin chloride (180 mg, 1.65 mmol) was added at −78° C. and the reaction was stirred at room temperature for 16 h. The reaction mixture was partitioned between EtOAc (10 mL) and $H_2O$ (10 mL). The organic layer was separated, dried over anhydrous $Na_2SO_4$ and concentrated under reduced pressure to afford 4-methyl-2-(trimethylstannyl)thiazole which was used in the next step without further purification.

Synthetic Routes for Examples

Route a: Typical Procedure for the Preparation of Alkylated Triazolopyrimidinones Via an Alkylation Reaction Followed by Suzuki Coupling Example 1-1, 5-amino-8-(2,6-dimethyl-4-pyridyl)-2-[(4-fluorophenyl)methyl]-7-phenyl-[1,2,4]triazolo[4,3-c]pyrimidin-3-one

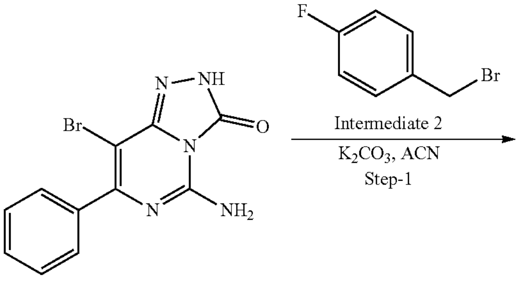

Intermediate 1

-continued

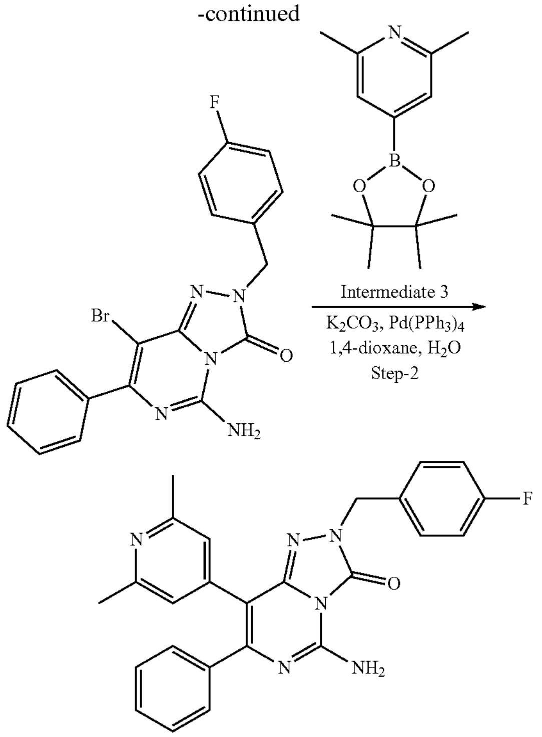

Example 1-1

Step 1; To a suspension of 5-amino-8-bromo-7-phenyl-[1,2,4]triazolo[4,3-c]pyrimidin-3(2H)-one (0.3 g, 0.98 mmol) and $K_2CO_3$ (0.4 g, 2.94 mmol) in MeCN at room temperature was added 1-(bromomethyl)-4-fluorobenzene (0.18 g, 1.18 mol) and the reaction mixture was heated at 50° C. for 5 h. (In some analogues a mixture of MeCN/DMSO was used as solvent.) The reaction mixture was partitioned between EtOAc (15 mL) and $H_2O$ (15 mL). The organic layer was separated, dried over anhydrous $Na_2SO_4$ and concentrated under reduced pressure. The crude product was purified by Biotage-Isolera by using 10 g silica snap and gradient 0-20% EtOAc in hexane to afford 5-amino-8-bromo-2-(4-fluorobenzyl)-7-phenyl-[1,2,4]triazolo[4,3-c]pyrimidin-3(2H)-one (100 mg, 24%) as a white solid.

LCMS (Method C): m/z 413 $(M+H)^+$ $(ES^+)$, at 2.85 min, UV active.

$^1H$ NMR: (400 MHz, DMSO-d6) δ: 7.61 (d, J=6.0 Hz, 2H), 7.46-7.38 (m, 5H), 7.23-7.18 (m, 2H), 5.05 (s, 2H). Exchangeable —$NH_2$ protons not observed Step 2; A mixture of 5-amino-8-bromo-2-(4-fluorobenzyl)-7-phenyl-[1,2,4]triazolo[4,3-c]pyrimidin-3(2H)-one (100 mg, 0.38 mmol), 2,6-dimethylpyridine-4-boronic acid pinacol ester (108 mg, 0.46 mmol) and $K_2CO_3$ (104 mg, 0.76 mmol) in 1,4-dioxane (4 mL) and $H_2O$ (1 mL) was degassed for few minutes, $Pd(PPh_3)_4$ (22 mg, 0.02 mmol) was added, the vessel was sealed and heated to 120° C. for 6 h. After cooling to room temperature, the reaction mixture was partitioned between $H_2O$ (25 mL) and EtOAc (50 mL). The organic layer was separated, dried over anhydrous $Na_2SO_4$, concentrated under reduced pressure and purified by Biotage-Isolera using 10 g silica snap and eluted with hexane/EtOAc (50:50) to afford 5-amino-8-(2,6-dimethyl-4-pyridyl)-2-[(4-fluorophenyl)methyl]-7-phenyl-[1,2,4]triazolo[4,3-c]pyrimidin-3-one (46 mg, 43%) as a yellow solid. The data for the title compound are in Table 3.

Route b: Typical Procedure for the Preparation of Alkylated Triazolopyrimidinones Via an Alcohol Mesylation and Displacement Reaction Followed by Suzuki Coupling

Example 1-2, 5-amino-8-(2,6-dimethyl-4-pyridyl)-2-[(5-fluoro-2-pyridyl)methyl]-7-phenyl-[1,2,4]triazolo[4,3-c]pyrimidin-3-one

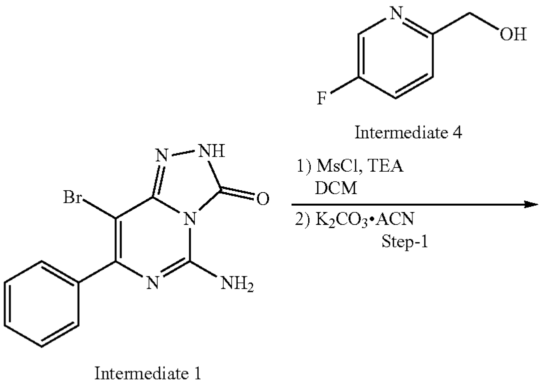

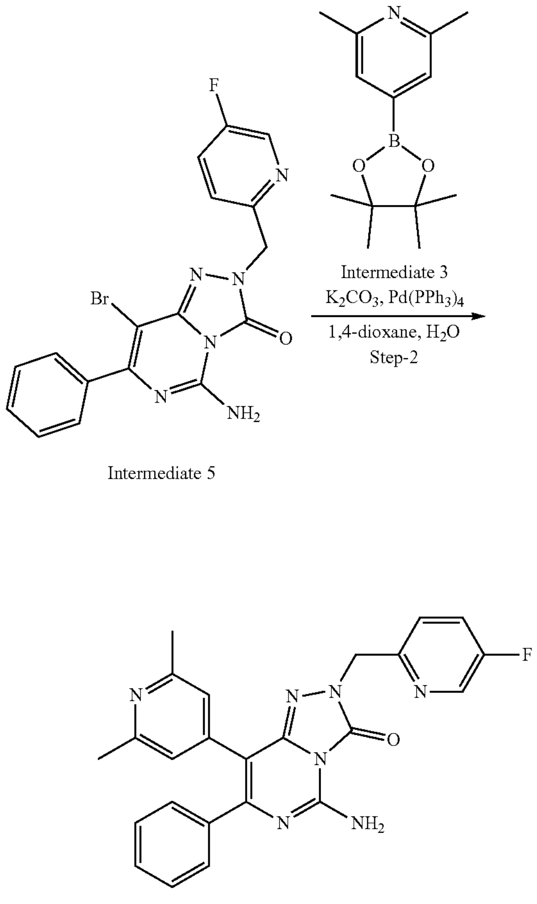

Example 1-2

Step 1; To a solution of (5-fluoropyridin-2-yl)methanol (150 mg, 1.18 mmol) and TEA (395 mg, 3.92 mmol) in DCM (20 mL) at 0° C. was added mesyl chloride (135 mg, 1.18 mmol) and the reaction mixture was stirred at room temperature for 1 h. The reaction mixture was partitioned between DCM (20 mL) and $H_2O$ (20 mL), the organic layer was separated and concentrated under reduced pressure to obtain the mesylated intermediate. This intermediate was taken in MeCN (20 mL) and 5-amino-8-bromo-7-phenyl-[1,2,4]triazolo[4,3-c]pyrimidin-3(2H)-one (300 mg, 0.98 mmol) and $K_2CO_3$ (405 mg, 2.94 mmol) were added and heated to 70° C. for 16 h in sealed tube. (For other analogues DMSO was used as solvent, or a MeCN/DMSO mixture.) The reaction mixture was partitioned between EtOAc (20 mL) and $H_2O$ (20 mL), the organic layer was separated and concentrated under reduced pressure. The crude product was purified by Biotage-Isolera using 25 g silica snap and was eluted with gradient 0-100% EtOAc in pet-ether to afford 5-amino-8-bromo-2-((5-fluoropyridin-2-yl)methyl)-7-phenyl-[1,2,4]triazolo[4,3-c]pyrimidin-3(2H)-one as an off-white solid. The data for the title compound are in Table 2.

Step 2; A mixture of 5-amino-8-bromo-2-((5-fluoropyridin-2-yl)methyl)-7-phenyl-[1,2,4]triazolo[4,3-c]pyrimidin-3(2H)-one (0.17 g, 0.41 mmol), 2,6-dimethylpyridine-4-boronic acid pinacol ester (113 mg, 0.49 mmol) and $K_2CO_3$ (169 mg, 1.22 mmol) in 1,4-dioxane (15 mL) and $H_2O$ (5 mL) was degassed for few minutes, $Pd(PPh_3)_4$ (46 mg, 0.04 mmol) was added, the vessel was sealed and heated to 120° C. for 5 h. The reaction mixture was partitioned between $H_2O$ (25 mL) and EtOAc (50 mL). The organic layer was separated, dried over anhydrous $Na_2SO_4$ and concentrated. The crude product was purified by Biotage-Isolera using 10 g silica snap and eluted with gradient 0-100% EtOAc in Pet-ether to afford 5-amino-8-(2,6-dimethyl-4-pyridyl)-2-[(5-fluoro-2-pyridyl)methyl]-7-phenyl-[1,2,4]triazolo[4,3-c]pyrimidin-3-one (82 mg, 44%) as a yellow solid. The data for the title compound are in Table 3.

Route c

Example 1-3, 5-amino-8-(2,6-dimethyl-4-pyridyl)-2-[(4-methoxyphenyl)methyl]-7-phenyl-[1,2,4]triazolo[4,3-c]pyrimidin-3-one

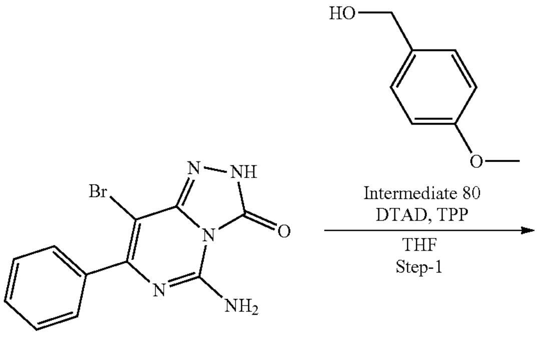

Intermediate 1

-continued

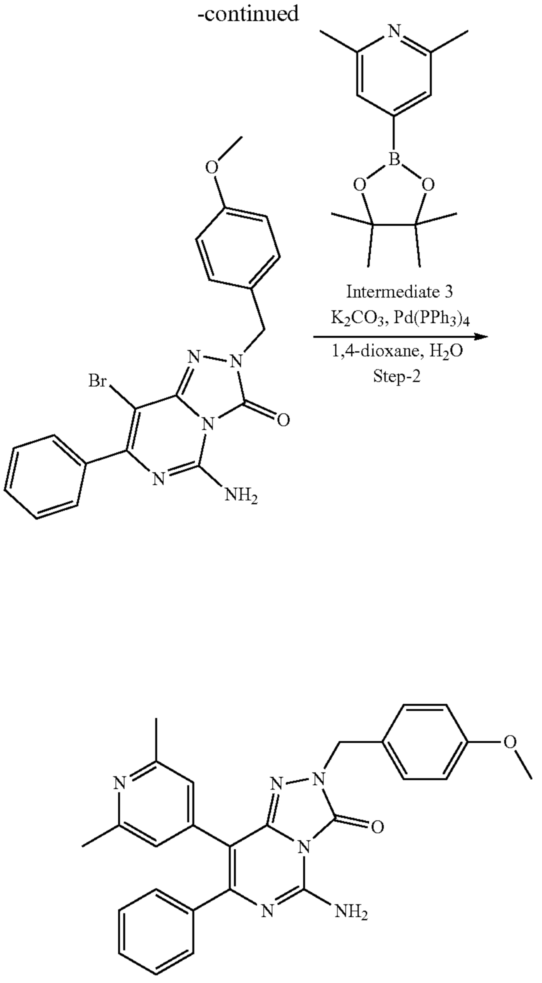

Example 1-3

Step 1; To a suspension of 5-amino-8-bromo-7-phenyl-[1,2,4]triazolo[4,3-c]pyrimidin-3(2H)-one (300 mg, 0.98 mmol), (4-methoxyphenyl)methanol (162 mg, 1.1 mmol) and triphenyl phosphine (385 mg, 1.4 mmol) in THF (10 mL) at room temperature was added di-tertiary butyl azodicarboxylate (332 mg, 1.4 mmol) and the reaction mixture was stirred at room temperature for 1 h. The reaction mixture was concentrated under reduced pressure and purified by Biotage-Isolera using 10 g silica snap and was eluted with gradient 30-100% EtOAc in pet ether to afford 5-amino-8-bromo-2-(4-methoxybenzyl)-7-phenyl-[1,2,4]triazolo[4,3-c]pyrimidin-3(2H)-one (180 mg, 44%) as an off-white solid.

LCMS (Method B): m/z 426 $(M+H)^+$ $(ES^+)$, at 2.93 min, UV active.

$^1H$ NMR: (400 MHz, DMSO-d6) δ: 7.60-7.44 (m, 5H), 7.29 (d, J=10.8 Hz, 2H), 6.93 (d, J=10.8 Hz, 2H), 4.98 (s, 2H), 3.75 (s, 3H). Exchangeable —$NH_2$ protons not observed Step 2; Prepared in a similar fashion to route a, step 2, to afford 5-amino-8-(2,6-dimethyl-4-pyridyl)-2-[(4-methoxyphenyl)methyl]-7-phenyl-[1,2,4]triazolo[4,3-c]pyrimidin-3-one (70 mg, 37%) as a yellow solid. The data for the title compound are in Table 3.

Route d: Typical Procedure for the Preparation of Alkylated Triazolopyrimidinones Via an Alcohol Mesylation and Displacement Reaction

Example 1-5, 5-amino-8-(2,6-dimethyl-4-pyridyl)-7-phenyl-2-(pyridazin-3-ylmethyl)-[1,2,4]triazolo[4,3-c]pyrimidin-3-one

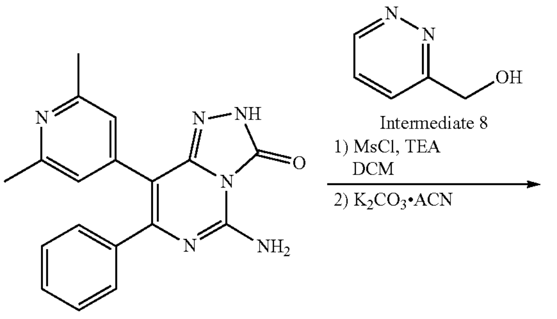

Intermediate 7

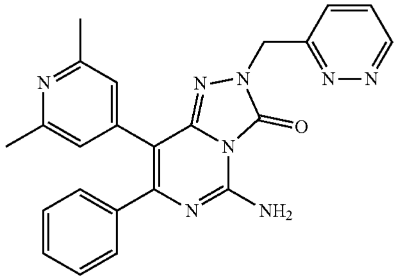

Example 1-5

To a solution of pyridazin-3-ylmethanol (40 mg, 0.36 mmol) and TEA (90 mg, 0.90 mmol) in DCM (10 mL) at 0° C. was added mesyl chloride (45 mg, 0.39 mmol) and the reaction mixture was stirred at room temperature for 1 h. The reaction mixture was partitioned between DCM (20 mL) and $H_2O$ (20 mL), the organic layer was separated and concentrated under reduced pressure to obtain mesylated intermediate. This intermediate was taken in MeCN (20 mL) and 5-amino-8-(2,6-dimethylpyridin-4-yl)-7-phenyl-[1,2,4]triazolo[4,3-c]pyrimidin-3(2H)-one (100 mg, 0.30 mmol) and $K_2CO_3$ (124 mg, 0.90 mmol) were added and heated to 80° C. for 6 h in sealed tube. (In other examples the reaction may be performed in a mixture of MeCN/DMSO or just DMSO). The reaction mixture was partitioned between EtOAc (20 mL) and $H_2O$ (20 mL), the organic layer was separated and concentrated under reduced pressure. The crude product was purified by Biotage-Isolera using 10 g silica snap and was eluted with gradient 0-100% EtOAc in pet-ether to afford 5-amino-8-(2,6-dimethyl-4-pyridyl)-7-phenyl-2-(pyridazin-3-ylmethyl)-[1,2,4]triazolo[4,3-c]pyrimidin-3-one (33 mg, 26%) as yellow solid. The data for the title compound are in Table 3.

Route e: Typical Procedure for the Preparation of Triazolopyrimidinones Via a Demethylation Reaction

Example 1-8, 5-amino-8-(2,6-dimethyl-4-pyridyl)-2-[(5-fluoro-6-oxo-1H-pyridin-2-yl)methyl]-7-phenyl-[1,2,4]triazolo[4,3-c]pyrimidin-3-one

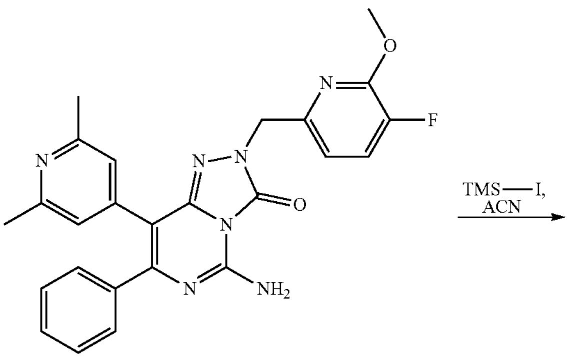

Example 1-7

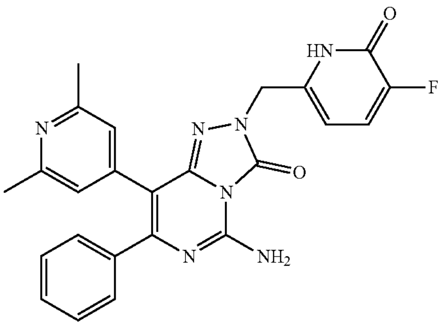

Example 1-8

A mixture of 5-amino-8-(2,6-dimethylpyridin-4-yl)-2-((5-fluoro-6-methoxypyridin-2-yl)methyl)-7-phenyl-[1,2,4]triazolo[4,3-c]pyrimidin-3(2H)-one (200 mg, 0.42 mmol) in MeCN (10 mL) was cooled to 0° C., iodo trimethyl silane (212 mg, 1.06 mmol) was added and stirred for 2 h at room temperature. The reaction mixture was partitioned between EtOAc (20 mL) and saturated $NaHCO_3$ (20 mL), the organic layer was separated and washed with saturated sodium bisulphate solution (20 mL), dried over anhydrous $Na_2SO_4$ and concentrated under reduced pressure. The crude product was triturated with MeOH to afford 5-amino-8-(2,6-dimethyl-4-pyridyl)-2-[(5-fluoro-6-oxo-1H-pyridin-2-yl)methyl]-7-phenyl-[1,2,4]triazolo[4,3-c]pyrimidin-3-one (130 mg, 67%) as a yellow solid. The data for the title compound are in Table 3.

Route f

Example 1-10, 5-amino-8-(2,6-dimethyl-4-pyridyl)-2-[(5-fluoro-1-methyl-6-oxo-2-pyridyl)methyl]-7-phenyl-[1,2,4]triazolo[4,3-c]pyrimidin-3-one

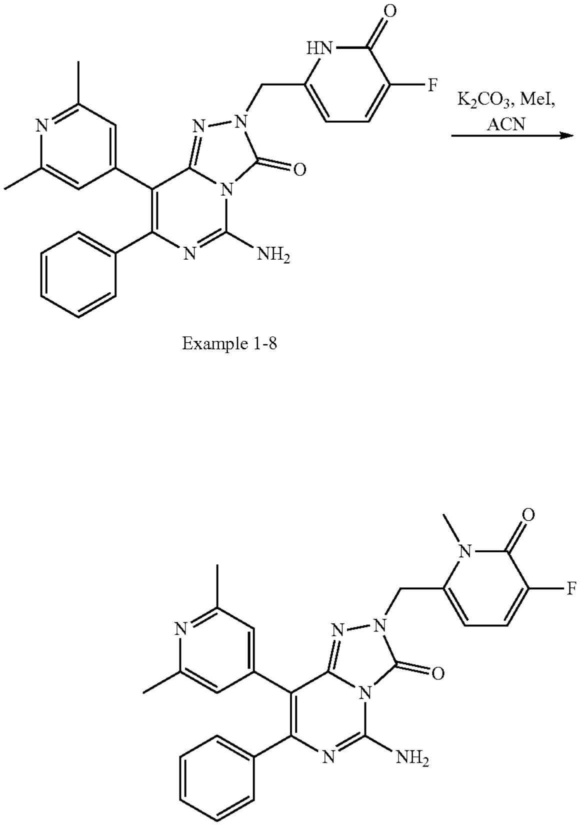

Example 1-8

Example 1-10

To a solution of 5-amino-8-(2,6-dimethyl-4-pyridyl)-2-[(5-fluoro-6-oxo-1H-pyridin-2-yl)methyl]-7-phenyl-[1,2,4]triazolo[4,3-c]pyrimidin-3-one (40 mg, 0.08 mmol) in MeCN (5 mL) was added $K_2CO_3$ (33.1 mg, 0.24 mmol) and methyl iodide (14.8 mg, 0.10 mmol) and the reaction mixture was stirred at room temperature for 16 h. The reaction mixture was partitioned between EtOAc (10 mL) and $H_2O$ (10 mL), the organic layer was separated and concentrated under reduced pressure. The crude product was purified by Biotage isolera using 10 g silica snap, eluting with 0-100% EtOAc in pet-ether to afford 5-amino-8-(2,6-dimethyl-4-pyridyl)-2-[(5-fluoro-1-methyl-6-oxo-2-pyridyl)methyl]-7-phenyl-[1,2,4]triazolo[4,3-c]pyrimidin-3-one (9 mg, 25%) as yellow solid. The data for the title compound are in Table 3.

Route g: Typical Procedure for the Preparation of Alkylated Triazolopyrimidinones Via a Mitsunobu Reaction Example 1-11, 5-amino-2-[1-(2,4-difluorophenyl)ethyl]-8-(2,6-dimethyl-4-pyridyl)-7-phenyl-[1,2,4]triazolo[4,3-c]pyrimidin-3-one

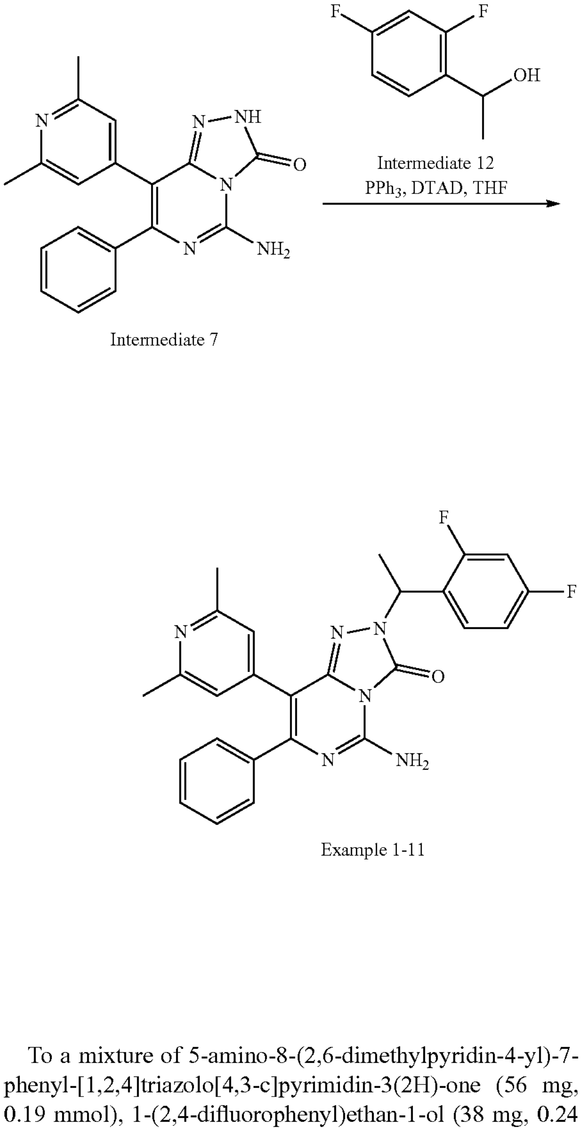

Intermediate 7

Example 1-11

To a mixture of 5-amino-8-(2,6-dimethylpyridin-4-yl)-7-phenyl-[1,2,4]triazolo[4,3-c]pyrimidin-3(2H)-one (56 mg, 0.19 mmol), 1-(2,4-difluorophenyl)ethan-1-ol (38 mg, 0.24 mmol) and $PPh_3$ (62 mg, 0.24 mmol) in THF (3 mL), was added di-tert-butyl-azodicarboxylate (55 mg, 0.24 mmol). The reaction mixture was stirred at room temperature for 16-18 h. The mixture was concentrated and the product was purified by prep HPLC (method E) to afford 5-amino-2-[1-(2,4-difluorophenyl)ethyl]-8-(2,6-dimethyl-4-pyridyl)-7-phenyl-[1,2,4]triazolo[4,3-c]pyrimidin-3-one (16 mg, 20%). The data for the title compound are in Table 3.

Route h: Typical Procedure for the Preparation of Alkylated Triazolopyrimidinones Via a Mitsunobu Reaction and Utilising a Boc Protection Strategy Example 1-30, 5-amino-8-(2,6-dimethyl-4-pyridyl)-7-phenyl-2-[[2-(4-piperidyl)phenyl]methyl]-[1,2,4]triazolo[4,3-c]pyrimidin-3-one

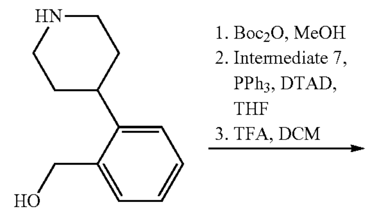

Intermediate 32

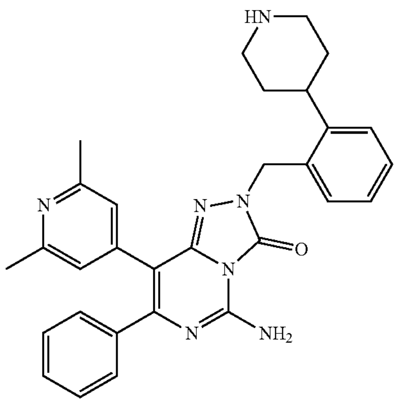

Example 1-30

$Boc_2O$ (229 mg, 1.05 mmol) was added to a solution of [2-(piperidin-4-yl)phenyl]methanol (191 mg, 1 mmol) in MeOH (2 mL), at 0° C. The reaction mixture was stirred for 2 h at room temperature. The mixture was concentrated under reduced pressure and the residue was crystallized from a mixture of i-Propanol/hexane to give the Boc protected amine.

Di-tert-butyl-azodicarboxylate (51 mg, 0.22 mmol) was added to a mixture of 5-amino-8-(2,6-dimethylpyridin-4-yl)-7-phenyl-[1,2,4]triazolo[4,3-c]pyrimidin-3(2H)-one (66 mg, 0.20 mmol), Boc protected amine (42 mg, 0.22 mol) and $PPh_3$ (68 mg, 0.26 mmol) in THF (3 mL). The reaction was stirred at room temperature for 18 h. The mixture was concentrated under reduced pressure, the residue was dissolved in DCM (3 mL) and TFA (0.5 mL) was added and the reaction sonicated for 2 h at room temperature. The mixture was concentrated in vacuo and the product was purified by prep HPLC (method E) to afford 5-amino-8-(2,6-dimethyl-4-pyridyl)-7-phenyl-2-[[2-(4-piperidyl)phenyl]methyl]-[1,2,4]triazolo[4,3-c]pyrimidin-3-one (51 mg, 50%). The data for the title compound are in Table 3.

Route i

Example 1-36, 5-amino-2-[(6-amino-5-fluoro-2-pyridyl)methyl]-8-(2,6-dimethyl-4-pyridyl)-7-phenyl-[1,2,4]triazolo[4,3-c]pyrimidin-3-one

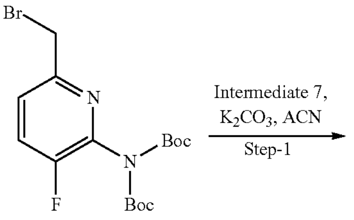

Intermediate 38

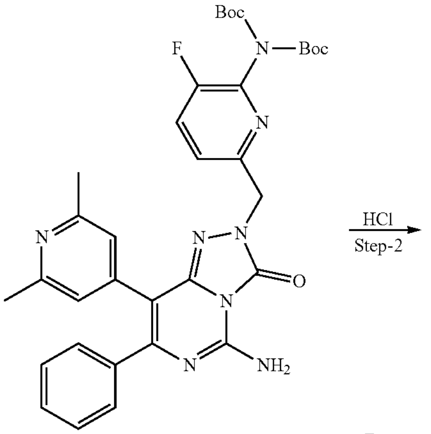

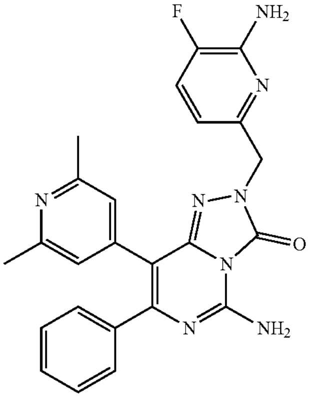

Example 1-36

Step 1; Performed in a similar fashion to route a step-1, heating the reaction to 80° C. for 16 h, to afford N,N-di-tert-butoxycarbonyl(6-((5-amino-8-(2,6-dimethylpyridin-4-yl)-3-oxo-7-phenyl-[1,2,4]triazolo[4,3-c]pyrimidin-2(3H)-yl)methyl)-3-fluoropyridin-2-yl)amine (30 mg, 15%) as pale yellow solid.

LCMS (Method B): m/z 657 $(M+H)^+$ $(ES^+)$, at 2.57 min, UV active.

$^1H$ NMR: (400 MHz, DMSO-d6) δ: 7.92-7.86 (m, 1H), 7.52-7.49 (m, 1H), 7.26-7.25 (m, 5H), 6.76 (s, 2H), 5.11 (s, 2H), 2.25 (s, 6H), 1.29 (s, 18H). Exchangeable $—NH_2$ protons not observed.

Step 2; To a stirred solution of N,N-di-tert-butoxycarbonyl(6-((5-amino-8-(2,6-dimethylpyridin-4-yl)-3-oxo-7-phenyl-[1,2,4]triazolo[4,3-c]pyrimidin-2(3H)-yl)methyl)-3-fluoropyridin-2-yl)amine (30 mg, 0.04 mmol) in diethyl ether (3 mL) was added 2 M HCl in diethyl ether (2 mL) and stirred at room temperature for 16 h. The reaction mixture was concentrated under reduced pressure The crude product was loaded onto an SCX column and eluted with 20% ammonia in MeOH solution to afford 5-amino-2-((6-amino-5-fluoropyridin-2-yl)methyl)-8-(2,6-dimethylpyridin-4-yl)-7-phenyl-[1,2,4]triazolo[4,3-c]pyrimidin-3(2H)-one (5 mg, 27%) as a pale yellow solid. The data for the title compound are in Table 3.

Route j

Examples 1-38, 5-amino-8-(2,6-dimethyl-4-pyridyl)-2-[1-(5-fluoro-2-pyridyl)propyl]-7-phenyl-[1,2,4]triazolo[4,3-c]pyrimidin-3-one and chiral separation into the enantiomers 1-38 iso-1 and 1-38 iso-2

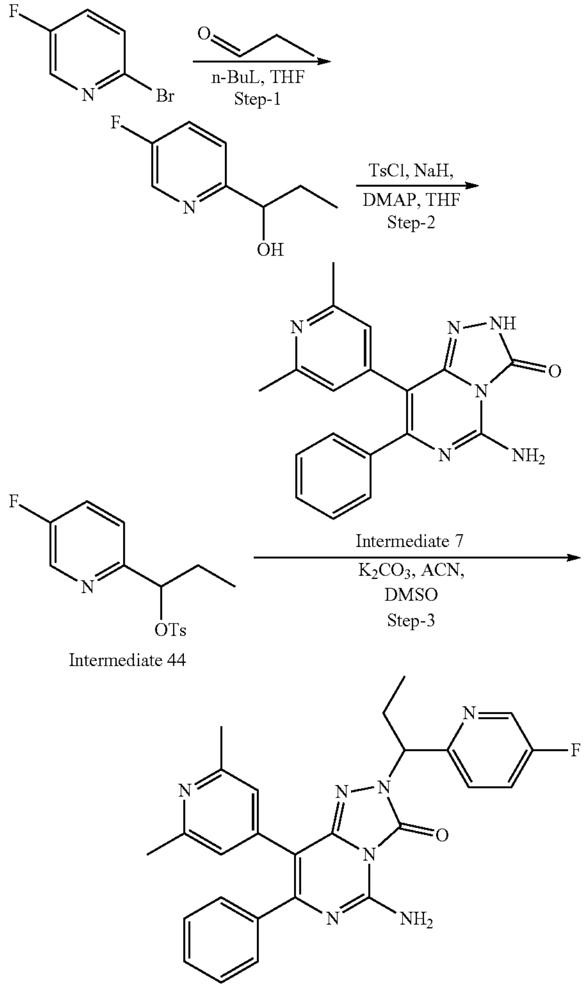

Example 1-38

Step 1; To a suspension of 2-bromo-5-fluoropyridine (5 g, 28.4 mmol) in THF (100 mL) at −78° C. was added n-butyl lithium (2 M in THF, 17 mL, 34.09 mmol) and the reaction stirred at −78° C. for 1 h. Propionaldehyde (2.5 mL, 34.09 mmol) was added dropwise at the same temperature and stirred at room temperature for 2 h. The reaction was quenched by the dropwise addition of $NH_4Cl$ solution (100 mL) and extracted with EtOAc (100 mL). The organic layer was separated, dried over $Na_2SO_4$ and concentrated under reduced pressure. The crude product was purified by Biotage-Isolera using 50 g silica snap and was eluted with (0-100%) EtOAc in pet ether gradient to afford 1-(5-fluoropyridin-2-yl)propan-1-ol (1.5 g, 39%) as a brown liquid.

LCMS (Method A): m/z 156 $(M+H)^+$ $(ES^+)$, at 0.86 min, UV active.

Step 2; To a suspension of tosyl chloride (2.78 g, 14.61 mmol) and catalytic amount of DMAP at 0° C. in THF (30 mL) was added NaH (60% dispersion in mineral oil, 280 mg, 11.68 mmol) portion wise followed by the addition of 1-(5-fluoropyridin-2-yl)propan-1-ol (1.5 g, 9.67 mmol) in THF (10 mL) at 0° C. and then stirred at room temperature for 1 h. The reaction mixture was quenched by $NH_4Cl$ solution (100 mL) and extracted with EtOAc (100 mL). The organic layer was separated, dried over $Na_2SO_4$ and concentrated under reduced. The crude product was purified by Biotage-Isolera using 25 g silica snap and was eluted with (0-100%) EtOAc in pet-ether gradient to afford 1-(5-fluoropyridin-2-yl)propyl 4-methylbenzenesulfonate (1.5 g, 34%) as off-white solid. The data are in table 2.

Step 3; To a suspension of 5-amino-8-(2,6-dimethylpyridin-4-yl)-7-phenyl-[1,2,4]triazolo[4,3-c]pyrimidin-3(2H)-one (250 mg, 0.75 mmol) in MeCN (10 mL) and DMSO (2 mL) was added 1-(5-fluoropyridin-2-yl)propyl 4-methylbenzenesulfonate (232 mg, 0.75 mmol) and $K_2CO_3$ (311 mg, 0.22 mmol). The reaction was heated to 80° C. for 2 h. The reaction mixture was partitioned between EtOAc (20 mL) and $H_2O$ (10 mL). The organic layer was separated, dried over $Na_2SO_4$ and concentrated under reduced pressure. The crude product was purified by Biotage-Isolera using 10 g silica snap and was eluted with (0-100%) EtOAc in pet ether gradient to afford 5-amino-8-(2,6-dimethyl-4-pyridyl)-2-[1-(5-fluoro-2-pyridyl)propyl]-7-phenyl-[1,2,4]triazolo[4,3-c]pyrimidin-3-one (110 mg, 29%) as yellow solid. The data for the title compound are in Table 3.

The racemic compound was purified by Chiral SFC (method A) to afford 1-38 iso-1 as the first eluting peak and 1-38 iso-2 as the second eluting peak. The data for the title compounds are in Table 3.

Route k: Typical Procedure for the Preparation of Pyridine N-Oxides Via an Oxidation Using mCPBA Example 1-42, 5-amino-8-(2,6-dimethyl-1-oxido-pyridin-1-ium-4-yl)-2-[(5-fluoro-2-pyridyl)methyl]-7-phenyl-[1,2,4]triazolo[4,3-c]pyrimidin-3-one

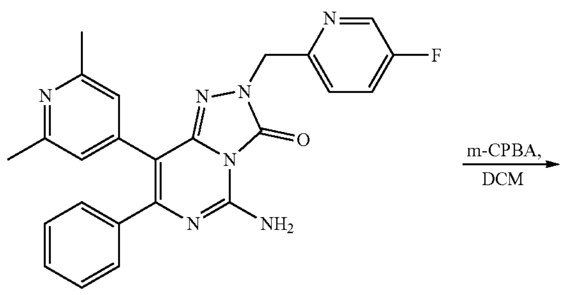

Example 1-2

-continued

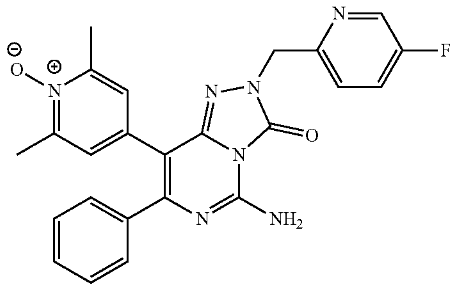

Example 1-42

To a solution of 5-amino-8-(2,6-dimethyl-4-pyridyl)-2-[(5-fluoro-2-pyridyl)methyl]-7-phenyl-[1,2,4]triazolo[4,3-c]pyrimidin-3-one (100 mg, 0.22 mmol) in DCM (10 mL) was added 3-chlorobenzoperoxoic acid (50 mg, 0.18 mmol) and reaction mixture was stirred at room temperature for 2 h. The reaction mixture was quenched with 10% sodium bicarbonate solution (10 mL) and extracted with EtOAc (10 mL). The organic layer was separated, dried over anhydrous $Na_2SO_4$ and concentrated under reduced pressure. The crude product was purified by Biotage-Isolera using 10 g silica snap and was eluted with 0-100% EtOAc in hexane gradient to afford 5-amino-8-(2,6-dimethyl-1-oxido-pyridin-1-ium-4-yl)-2-[(5-fluoro-2-pyridyl)methyl]-7-phenyl-[1,2,4]triazolo[4,3-c]pyrimidin-3-one (28 mg, 27%) as yellow solid. The data for the title compound are in Table 3.

Route 1

Example 1-44, 5-amino-2-[(5-fluoro-2-pyridyl)methyl]-8-[2-(hydroxymethyl)-6-methyl-4-pyridyl]-7-phenyl-[1,2,4]triazolo[4,3-c]pyrimidin-3-one

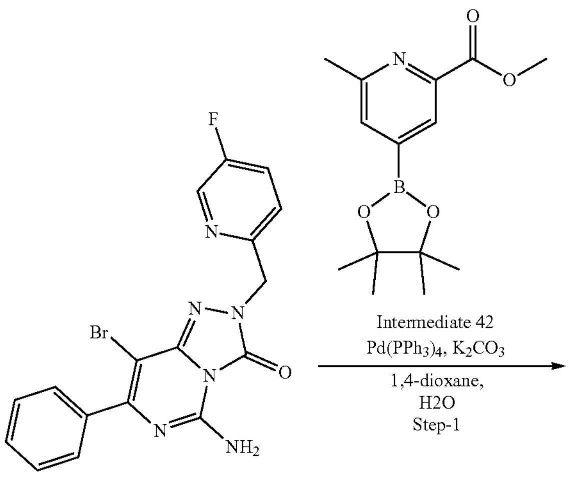

Intermediate 5

-continued

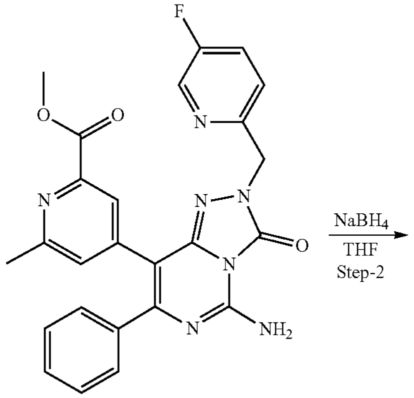

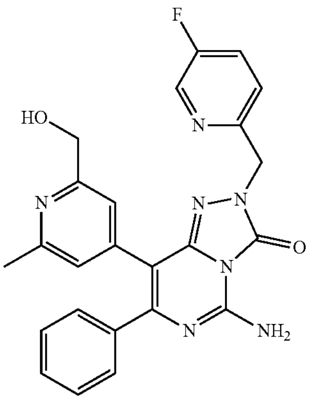

Example 1-44

Step 1; Performed in a similar fashion to route a step-2 to afford methyl 4-(5-amino-2-((5-fluoropyridin-2-yl)methyl)-3-oxo-7-phenyl-2,3-dihydro-[1,2,4]triazolo[4,3-c]pyrimidin-8-yl)-6-methylpicolinate (70 mg, 19%) as a yellow solid.

LCMS (Method B): m/z 485 $(M+H)^+$ $(ES^+)$, at 2.38 min, UV active.

$^1H$ NMR: (400 MHz, DMSO-d6) δ: 8.54-8.52 (m, 1H), 7.77-7.75 (m, 1H), 7.73-7.71 (m, 1H), 7.47-7.42 (m, 1H), 7.31-7.21 (m, 6H), 5.16-5.13 (m, 2H), 3.81 (s, 3H), 2.01 (s, 3H). Exchangeable —$NH_2$ Protons were not Observed.

Step 2; To a degassed solution methyl 4-(5-amino-2-((5-fluoropyridin-2-yl)methyl)-3-oxo-7-phenyl-2,3-dihydro-[1,2,4]triazolo[4,3-c]pyrimidin-8-yl)-6-methylpicolinate (70 mg, 0.14 mmol) in MeOH at room temperature was added $NaBH_4$ (24 mg, 0.9 mmol) portionwise and stirred for 15 h. The reaction mixture was partitioned between DCM (20 mL) and saturated $NaHCO_3$ solution (10 mL). The organic layer was separated, dried over anhydrous $Na_2SO_4$ and concentrated under reduced pressure. The crude product was purified by Biotage-Isolera by using 230-400 silica snap and was eluted with 0-100% EtOAc in hexane gradient to 5-amino-2-[(5-fluoro-2-pyridyl)methyl]-8-[2-(hydroxymethyl)-6-methyl-4-pyridyl]-7-phenyl-[1,2,4]triazolo[4,3-c]pyrimidin-3-one (10 mg, 15%) as a yellow solid. The data for the title compound are in Table 3.

Route m
Examples 1-45, 5-amino-2-[(6-amino-5-fluoro-2-pyridyl)methyl]-8-[2-(hydroxymethyl)-6-methyl-4-pyridyl]-7-phenyl-[1,2,4]triazolo[4,3-c]pyrimidin-3-one
Example 1-48, 5-amino-2-[(5-fluoro-6-hydroxy-2-pyridyl)methyl]-8-[2-(hydroxymethyl)-6-methyl-4-pyridyl]-7-phenyl-[1,2,4]triazolo[4,3-c]pyrimidin-3-one
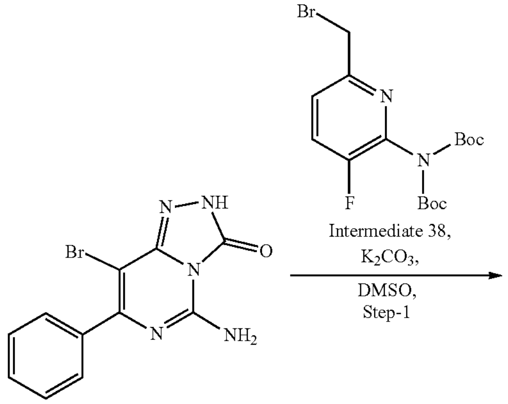
Intermediate 1
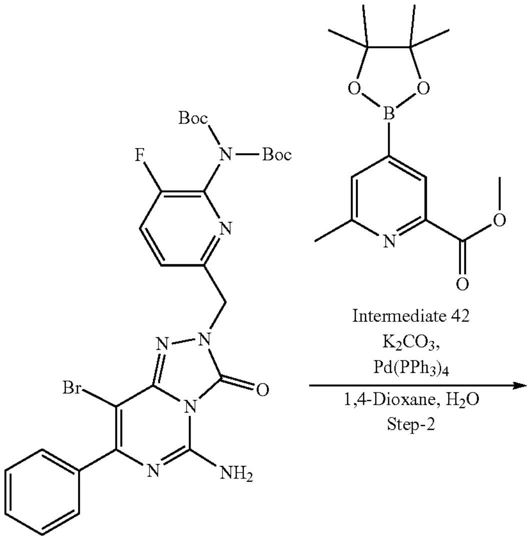
-continued
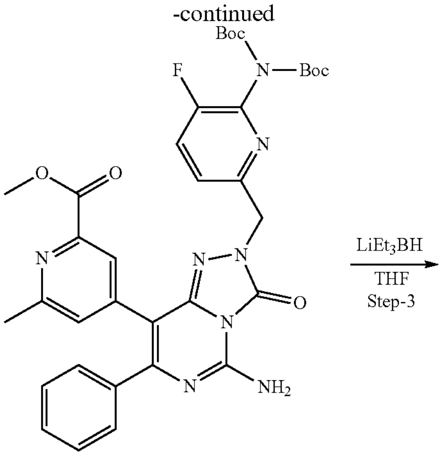
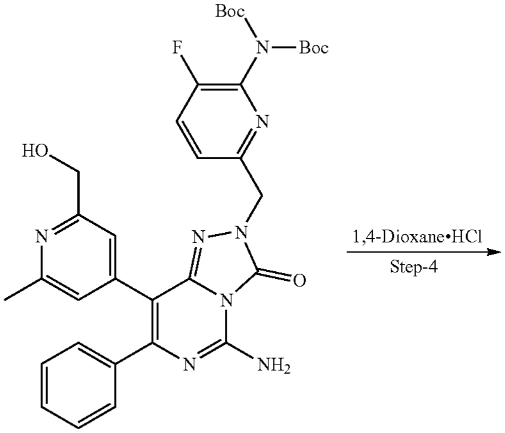
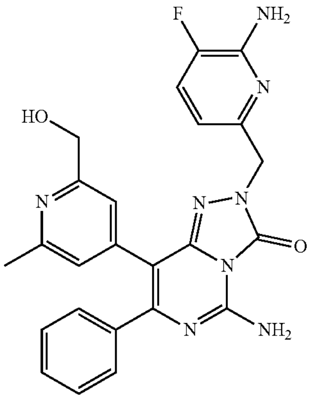
Example 1-45

-continued

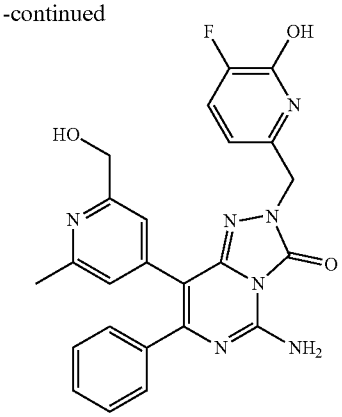

Example 1-48

Step 1; To a solution of 5-amino-8-bromo-7-phenyl-[1,2,4]triazolo[4,3-c]pyrimidin-3(2H)-one (350 mg, 1.143 mmol) and N,N-di-tert-butoxy carbonyl (6-(bromomethyl)-3-fluoropyridin-2-yl)-amine (507 mg, 1.258 mmol) in DMSO (10 mL) was added $K_2CO_3$ (473 mg, 3.430 mmol) and the reaction was heated at 80° C. for 2 h. The reaction mixture was quenched with ice cold water. The precipitate was filtered and dried under vacuum to afford 5-amino-2-((6-Di-Boc protected amino-5-fluoropyridin-2-yl)methyl)-8-bromo-7-phenyl-[1,2,4]triazolo[4,3-c]pyrimidin-3(2H)-one (600 mg, 83%) as yellow solid.

LCMS (Method A): m/z 431 $(M+H-2\times Boc)^+$ $(ES^+)$, at 3.02 min, UV active.

$^1H$ NMR: (400 MHz, DMSO-d6) δ: 7.92 (s, 2H), 7.61-7.56 (m, 3H), 7.46-7.45 (m, 4H), 5.15 (s, 2H), 1.37 (s, 18H).

Step 2; Prepared in a similar fashion to route a step-2, to afford methyl 4-(5-amino-2-((6-di-Boc protected amino-5-fluoropyridin-2-yl)methyl)-3-oxo-7-phenyl-2,3-dihydro-[1,2,4]triazolo[4,3-c]pyrimidin-8-yl)-6-methylpicolinate (250 mg, 37%) as yellow solid.

LCMS (Method A): m/z 701 $(M+H)^+$ $(ES^+)$, at 2.76 min, UV active.

$^1H$ NMR: (400 MHz, DMSO-d6) δ: 7.91-7.87 (m, 2H), 7.65-7.56 (m, 3H), 7.32-7.20 (m, 5H), 5.12 (s, 2H), 3.78 (s, 3H), 2.36 (s, 3H), 1.29 (s, 18H). Exchangeable $—NH_2$ protons were not observed.

Step 3; To a solution of methyl 4-(5-amino-2-((6-di-Boc protected amino-5-fluoropyridin-2-yl)methyl)-3-oxo-7-phenyl-2,3-dihydro-[1,2,4]triazolo[4,3-c]pyrimidin-8-yl)-6-methylpicolinate (250 mg, 0.357 mmol) in THF (10 mL) at 0° C. was added lithium triethyl borohydride (1 M solution in THF, 75.7 mg, 0.714 mmol) dropwise. The reaction was stirred at room temperature for 2 h. The reaction mixture was partitioned between EtOAc (20 mL) and $H_2O$ (10 mL). The organic layer was separated, washed with brine (10 mL), dried over $Na_2SO_4$ and concentrated under reduced pressure to afford 5-amino-2-((6-di-Boc protected amino-5-fluoropyridin-2-yl)methyl)-8-(2-(hydroxymethyl)-6-methylpyridin-4-yl)-7-phenyl-[1,2,4]triazolo[4,3-c]pyrimidin-3(2H)-one (100 mg, 41%) as yellow solid. The crude product was used in the next step without purification.

LCMS (Method A): m/z 673 $(M+H)^+$ $(ES^+)$, at 4.09 min, UV active.

$^1H$ NMR: (400 MHz, DMSO-d6) δ: 7.91-7.87 (m, 2H), 7.66-7.50 (m, 3H), 7.25-7.13 (m, 5H), 5.15 (s, 2H), 4.85 (s, 2H), 2.19 (s, 3H), 1.24 (s, 18H). Exchangeable $—NH_2$ protons were not observed.

Step 4; To a solution of 5-amino-2-((6-di-Boc protected amino-5-fluoropyridin-2-yl)methyl)-8-(2-(hydroxymethyl)-6-methylpyridin-4-yl)-7-phenyl-[1,2,4]triazolo[4,3-c]pyrimidin-3(2H)-one (100 mg, 0.14 mmol) in 1,4-dioxane (2 mL) at room temperature was added 4.0 M HCl in dioxane (3 mL) at 0° C. and the reaction mixture was stirred at room temperature for 2 h. The reaction mixture was concentrated under reduced pressure. The crude product was purified by Prep HPLC (Method A), where 2 peaks were observed. Collected fractions were concentrated and the residue was partitioned between EtOAc (10 mL) and 10% sodium bicarbonate solution (10 mL). Organic layer was separated, dried over anhydrous $Na_2SO_4$ and concentrated to dryness to afford 5-amino-2-[(6-amino-5-fluoro-2-pyridyl)methyl]-8-[2-(hydroxymethyl)-6-methyl-4-pyridyl]-7-phenyl-[1,2,4]triazolo[4,3-c]pyrimidin-3-one (30 mg, 45%) as an off white solid and 5-amino-2-[(5-fluoro-6-hydroxy-2-pyridyl)methyl]-8-[2-(hydroxymethyl)-6-methyl-4-pyridyl]-7-phenyl-[1,2,4]triazolo[4,3-c]pyrimidin-3-one (1.5 mg, 2%) as an off-white solid. The data for the title compounds are in Table 3.

Route n

Example 1-46 isomers 1 and 2, 5-amino-2-[1-(5-fluoro-2-pyridyl)propyl]-8-[2-(hydroxymethyl)-6-methyl-4-pyridyl]-7-phenyl-[1,2,4]triazolo[4,3-c]pyrimidin-3-one

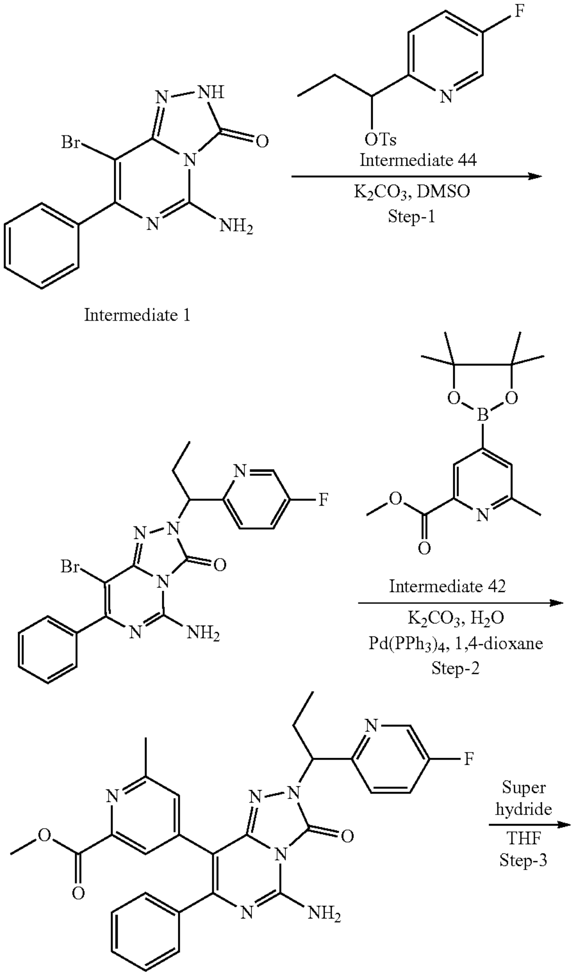

-continued

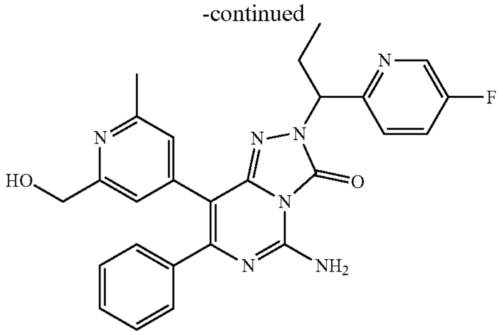

Examples 1-46 iso-1 and iso-2

Step 1; To a stirred solution of 1-(6-fluoropyridin-2-yl) propyl 4-methylbenzenesulfonate (506 mg, 1.63 mmol) in DMSO (5 mL), was added 5-amino-8-bromo-7-phenyl-[1,2,4]triazolo[4,3-c]pyrimidin-3(2H)-one (500 mg, 1.63 mmol) and $K_2CO_3$ (674 mg, 4.89 mmol) and the resultant reaction mixture was heated to 80° C. for 2 h. The reaction mixture was poured into ice and the precipitate was filtered and dried to afford 5-amino-8-bromo-2-(1-(6-fluoropyridin-3-yl)propyl)-7-phenyl-[1,2,4]triazolo[4,3-c]pyrimidin-3(2H)-one as brown solid.

LCMS (Method A): m/z 442 $(M+H)^+$ $(ES^+)$, at 2.69 min, UV active.

Step 2; Prepared in a similar fashion to route a step-2, to afford methyl 4-(5-amino-2-(1-(6-fluoropyridin-3-yl)propyl)-3-oxo-7-phenyl-2,3-dihydro-[1,2,4]triazolo[4,3-c]pyrimidin-8-yl)-6-methylpicolinate (300 mg, 41%) as a yellow solid.

LCMS (Method A): m/z 514 $(M+H)^+$ $(ES^+)$, at 3.32 min, UV active.

$^1$H NMR: (400 MHz, DMSO-d6) δ: 8.47 (d, J=6.4 Hz, 2H), 7.61-7.60 (m, 3H), 7.58-7.45 (m, 3H), 7.32 (d, J=2.4 Hz, 2H), 5.50 (s, 1H), 4.04-4.03 (m, 2H), 3.93 (s, 3H), 2.38 (s, 3H), 0.91 (t, J=7.2 Hz, 3H). Exchangeable —$NH_2$ protons were not observed.

Step 3; To a solution of methyl 4-(5-amino-2-(1-(6-fluoropyridin-3-yl)propyl)-3-oxo-7-phenyl-2,3-dihydro-[1,2,4]triazolo[4,3-c]pyrimidin-8-yl)-6-methylpicolinate (300 mg, 0.58 mmol) in THF (20 mL) at 0° C. was added lithium triethyl borohydride (1 M in THF, 1.16 mL, 1.16 mmol) and the resultant reaction mixture was stirred at room temperature for 1 h. The reaction mixture was quenched by the drop wise addition of water (20 mL) and extracted with EtOAc (10 mL). The organic layer was separated and concentrated under reduced pressure. The crude product was purified by Biotage-Isolera using 25 g silica gel snap and eluted with 0-100% EtOAc in Pet ether gradient to afford 5-amino-2-[1-(5-fluoro-2-pyridyl)propyl]-8-[2-(hydroxymethyl)-6-methyl-4-pyridyl]-7-phenyl-[1,2,4]triazolo[4,3-c]pyrimidin-3-one as a yellow solid. The racemic compound was purified by Chiral SFC (method B) to afford 1-46 iso-1 as the first eluting peak and 1-46 iso-2 as the second eluting peak. The data for the title compounds are in Table 3.

Route o: Typical Procedure for the Preparation of Alkylated Triazolopyrimidinones Via an Alcohol Tosylation and Displacement, Followed by an Ester Reduction

Example 1-47, 5-amino-2-[(3-fluoro-5-methoxy-2-pyridyl)methyl]-8-[2-(hydroxymethyl)-6-methyl-4-pyridyl]-7-phenyl-[1,2,4]triazolo[4,3-c]pyrimidin-3-one

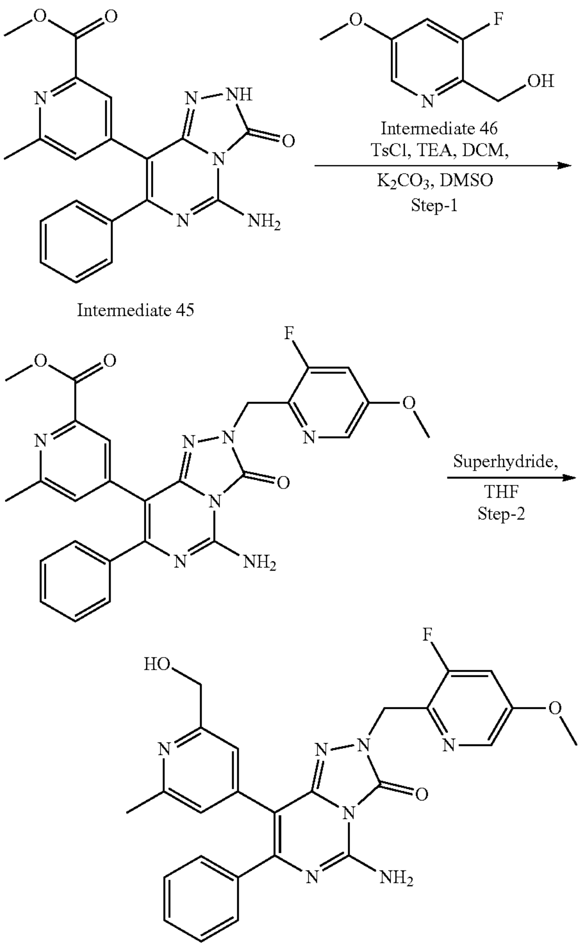

Example 1-47

Step 1; To a solution of tosyl chloride (120 mg, 0.63 mmol), TEA (0.2 mL, 1.7 mmol) and a catalytic amount of DMAP in DCM (5 mL) at 0° C., was added (3-fluoro-5-methoxypyridin-2-yl)methanol (90 mg, 0.57 mmol) and the resultant reaction mixture was stirred at room temperature for 1 h. The reaction mixture was partitioned between DCM (10 mL) and $H_2O$ (10 mL). The organic layer was separated and concentrated under reduced pressure to afford the tosylated intermediate. The tosylated intermediate was taken in DMSO (2 mL) and methyl 4-(5-amino-3-oxo-7-phenyl-2,3-dihydro-[1,2,4]triazolo[4,3-c]pyrimidin-8-yl)-6-methylpicolinate (192 mg, 0.51 mmol), $K_2CO_3$ (235 mg, 1.71 mmol) were added and the resultant reaction mixture was heated to 80° C. for 2 h in a sealed tube. The reaction mixture was partitioned between EtOAc (10 mL) and $H_2O$ (10 mL). The organic layer was separated and concentrated under reduced pressure. The crude product was purified by Biotage-Isolera using 10 g silica snap and eluted with 0-100% EtOAc in Pet-ether gradient to afford methyl 4-(5-amino-2-((3-fluoro-5-methoxypyridin-2-yl)methyl)-3-oxo-7-phenyl-2,3-dihydro-[1,2,4]triazolo[4,3-c]pyrimidin-8-yl)-6-methylpicolinate (60 mg, 23%) as a yellow solid.

LCMS (Method A): m/z 516 $(M+H)^+$ $(ES^+)$, at 2.56 min, UV active.

Step 2; Performed in a similar fashion to route m step-3 and purified by prep-HPLC (Method A). Fractions were concentrated and the residue obtained was diluted with EtOAc (10 mL), washed with 10% sodium bicarbonate solution (10 mL). The organic layer was separated, dried over anhydrous $Na_2SO_4$ and concentrated to afford 5-amino-2-[(3-fluoro-5-methoxy-2-pyridyl)methyl]-8-[2-(hydroxymethyl)-6-methyl-4-pyridyl]-7-phenyl-[1,2,4]triazolo[4,3-c]pyrimidin-3-one (10 mg, 18%) as a yellow solid. The data for the title compound are in Table 3.

Route p: Typical Procedure for the Preparation of Alkylated Triazolopyrimidinones Via an Alcohol Mesylation and Displacement Reaction, Followed by a Suzuki Coupling and Ester Reduction Example 1-49, 5-amino-2-[(5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one

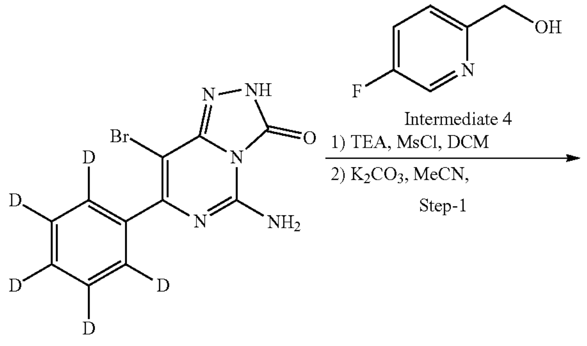

Intermediate 47

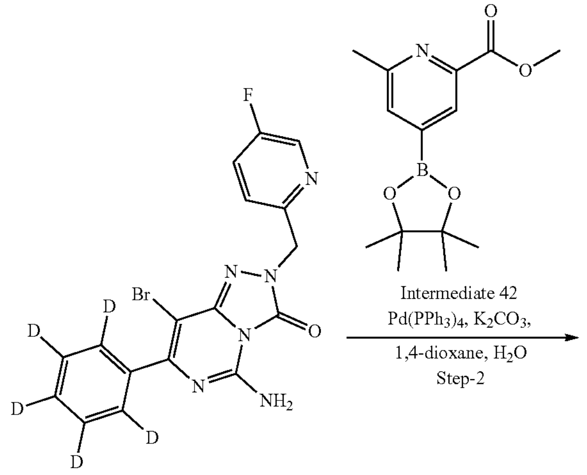

-continued

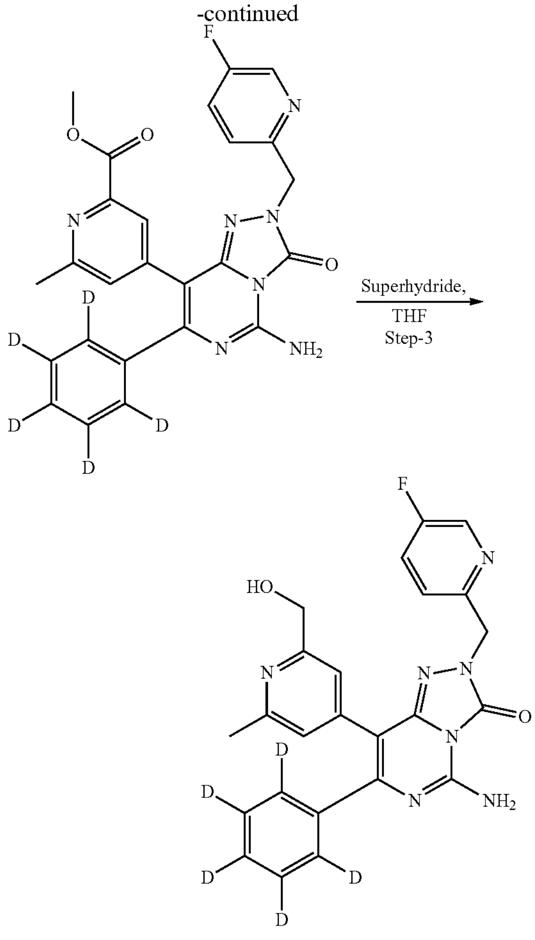

Example 1-49

Step 1; Performed in a similar fashion to route b step-1, using intermediates 47 and 4, to afford 5-amino-8-bromo-2-((5-fluoropyridin-2-yl)methyl)-7-(phenyl-d5)-[1,2,4]triazolo[4,3-c]pyrimidin-3(2H)-one (450 mg, 83%) as a brown solid.

LCMS (Method C): m/z 421 $(M+H)^+$ $(ES^+)$, at 2.06 min, UV active.

$^1H$ NMR: (400 MHz, DMSO-d6) δ: 8.55 (d, J=3.2 Hz, 1H), 7.76 (d, J=2.8 Hz, 1H), 7.50 (d, J=4.4 Hz, 1H), 5.17 (s, 2H). Exchangeable —$NH_2$ protons were not observed.

Step 2; Performed in a similar fashion to route a step-2, to afford methyl 4-(5-amino-2-((5-fluoropyridin-2-yl)methyl)-3-oxo-7-(phenyl-d5)-2,3-dihydro-[1,2,4]triazolo[4,3-c]pyrimidin-8-yl)-6-methylpicolinate (160 mg, 30%) as a yellow solid.

LCMS (Method C): m/z 491 $(M+H)^+$ $(ES^+)$, at 2.06 min, UV active.

Step 3; Performed in a similar fashion to route m step-3 and purified by prep-HPLC (Method A). Fractions were concentrated and the residue obtained was diluted with EtOAc (10 mL), washed with 10% sodium bicarbonate solution (10 mL). The organic layer was separated, dried over anhydrous $Na_2SO_4$ and concentrated to afford 5-amino-2-[(5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one (40 mg, 26%) as a yellow solid. The data for the title compound are in Table 3.

Route q: Typical Procedure for the Preparation of Alkylated Triazolopyrimidinones Via a Mitsunobu Reaction, Followed by an Ester Reduction

Example 1-50, 5-amino-2-[(3-chloro-5-fluoro-2-pyridyl)methyl]-8-[2-(hydroxymethyl)-6-methyl-4-pyridyl]-7-phenyl-[1,2,4]triazolo[4,3-c]pyrimidin-3-one

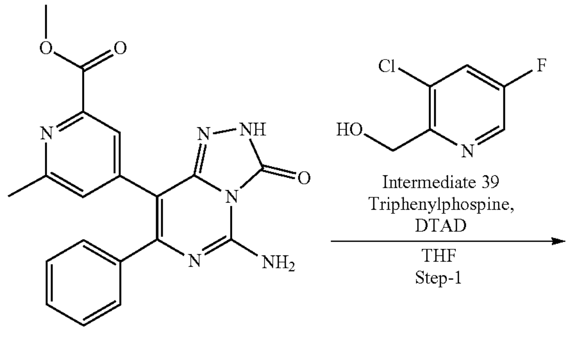

Intermediate 45

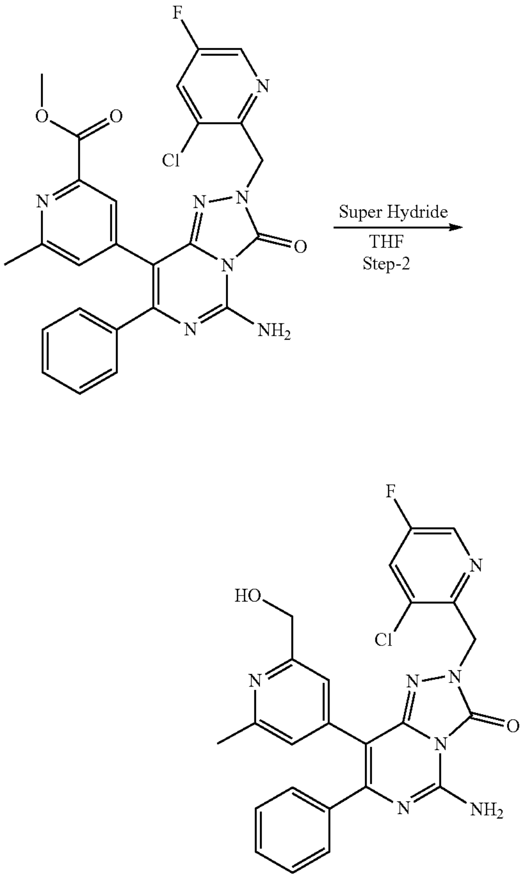

Example 1-50

Step 1; Performed in a similar fashion to route c step-1, using intermediates 45 and 39 to afford methyl 4-(5-amino-2-((3-chloro-5-fluoropyridin-2-yl) methyl)-3-oxo-7-phenyl-2, 3-dihydro-[1, 2, 4] triazolo [4,3-c] pyrimidin-8-yl)-6-methylpicolinate (25 mg, 14%) as a yellow solid.

LCMS (Method C): m/z 520 $(M+H)^+$ $(ES^+)$, at 2.01 min, UV active.

$^1H$ NMR: (400 MHz, DMSO-d6) δ: 8.56 (d, J=2.8 Hz, 1H), 8.19-8.16 (m, 1H), 7.64 (s, 1H), 7.32-7.20 (m, 5H), 7.20 (s, 1H), 5.25 (s, 2H), 3.79 (s, 3H), 2.35 (s, 3H). Exchangeable —$NH_2$ protons were not observed.

Step 2; Performed in a similar fashion to route m step-3 and purified by prep-HPLC (Method A). Fractions were concentrated and the residue obtained was diluted with EtOAc (10 mL), washed with 10% sodium bicarbonate solution (10 mL). The organic layer was separated, dried over anhydrous $Na_2SO_4$ and concentrated to afford 5-amino-2-[(3-chloro-5-fluoro-2-pyridyl)methyl]-8-[2-(hydroxymethyl)-6-methyl-4-pyridyl]-7-phenyl-[1,2,4]triazolo[4,3-c]pyrimidin-3-one (4 mg, 17%) as a yellow solid. The data for the title compound are in Table 3.

Route r: Typical Procedure for the Preparation of Alkylated Triazolopyrimidinones Via an Alkylation Reaction, Followed by an Ester Reduction and Boc Deprotection

Example 1-51, 5-amino-2-[(6-amino-5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one

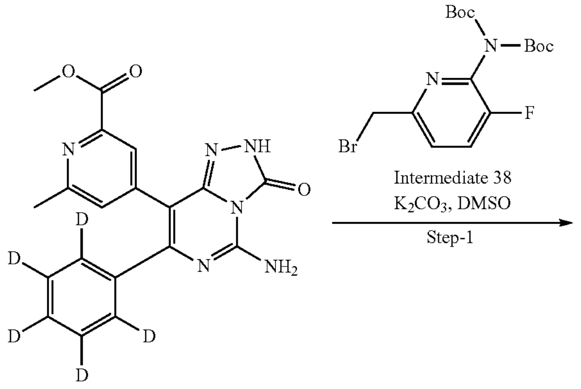

Intermediate 49

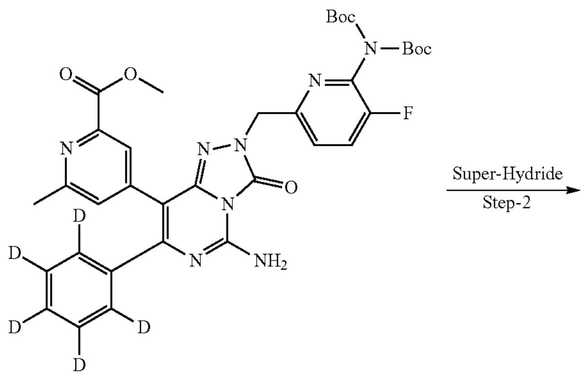

-continued

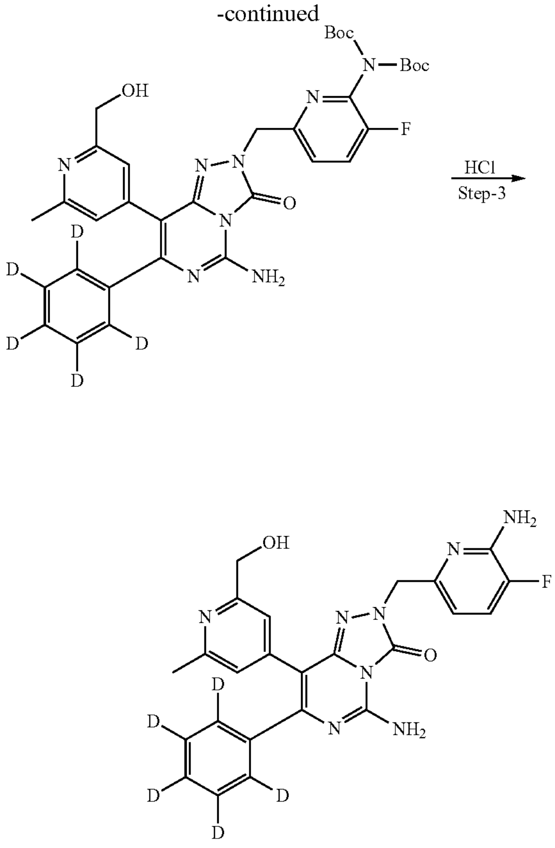

Example 1-51

Step 1; Performed in a similar fashion to route m step-1, using intermediates 49 and 38, to afford methyl 4-(5-amino-2-((6-di-boc amino-5-fluoropyridin-2-yl)methyl)-3-oxo-7-(phenyl-d5)-2,3-dihydro-[1,2,4]triazolo[4,3-c]pyrimidin-8-yl)-6-methylpicolinate (80 mg, 57%) as yellow solid.

LCMS (Method C): m/z 706 $(M+H)^+$ $(ES^+)$, at 2.44 min, UV active.

$^1H$ NMR: (400 MHz, DMSO-d6) δ: 7.90-7.85 (m, 1H), 7.60 (s, 1H), 7.51 (s, 1H), 7.18 (s, 1H), 5.10 (s, 2H), 3.77 (s, 3H), 2.34 (s, 3H), 1.27 (s, 18H). Exchangeable —$NH_2$ protons were not observed.

Step 2; Performed in a similar fashion to route m step-3, and purified by flash column chromatography by using silica (230-400) mesh and eluted with 0-40% EtOAc in pet ether gradient to afford 5-amino-2-((6-diboc-amino-5-fluoropyridin-2-yl)methyl)-8-(2-(hydroxymethyl)-6-methylpyridin-4-yl)-7-(phenyl-d5)-[1,2,4]triazolo[4,3-c]pyrimidin-3(2H)-one (70 mg, 92%) as a yellow solid.

LCMS (Method C): m/z 578 $(M+H\text{-}Boc)^+$ $(ES^+)$, at 1.43 min, UV active.

Step 3; Performed in a similar fashion to route m step-4 to afford 5-amino-2-[(6-amino-5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one (10 g 20%) as a yellow solid. The data for the title compound are in table 3.

Route s: Typical Procedure for the Preparation of Alkylated Triazolopyrimidinones Via an Alcohol Mesylation and Displacement Reaction, Followed by an Ester Reduction Example 1-53, 5-amino-2-[(5-bromo-2-pyridyl)methyl]-8-[2-(hydroxymethyl)-6-methyl-4-pyridyl]-7-phenyl-[1,2,4]triazolo[4,3-c]pyrimidin-3-one

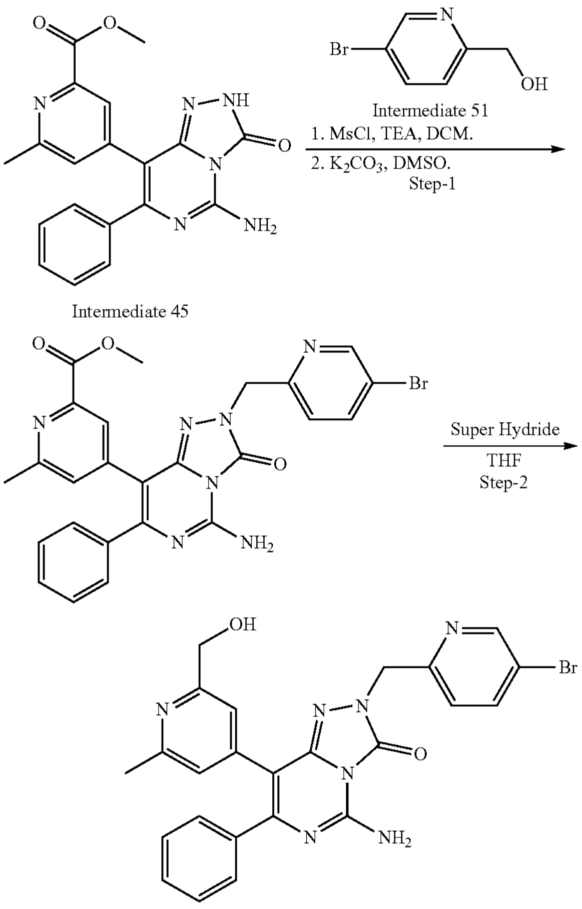

Example 1-53

Step 1; Performed in a similar fashion to route b step-1, to afford methyl 4-(5-amino-2-((5-bromopyridin-2-yl)methyl)-3-oxo-7-phenyl-2,3-dihydro-[1,2,4]triazolo[4,3-c]pyrimidin-8-yl)-6-methylpicolinate (120 mg, 36%) as a pale yellow solid.

LCMS (Method C): m/z 547 $(M+H)^+$ $(ES^+)$, at 2.16 min, UV active.

$^1H$ NMR: (400 MHz, DMSO-d6) δ: 8.64 (s, 1H), 7.99 (s, 1H), 7.49 (s, 1H), 7.32-7.26 (m, 7H), 5.18-5.14 (m, 2H), 3.86 (s, 3H), 2.42 (s, 3H). Exchangeable —$NH_2$ protons were not observed.

Step 2; Performed in a similar fashion to route o step-2 to afford 5-amino-2-[(5-bromo-2-pyridyl)methyl]-8-[2-(hydroxymethyl)-6-methyl-4-pyridyl]-7-phenyl-[1,2,4]triazolo[4,3-c]pyrimidin-3-one (12 mg, 10%) as a yellow solid. The data for the title compound are in table 3.

Route t: Typical Procedure for the Preparation of Alkylated Triazolopyrimidinones Via an Alkylation Reaction

Example 1-54, 6-[[5-amino-8-[2-(hydroxymethyl)-6-methyl-4-pyridyl]-3-oxo-7-phenyl-[1,2,4]triazolo[4,3-c]pyrimidin-2-yl]methyl]pyridine-3-carbonitrile

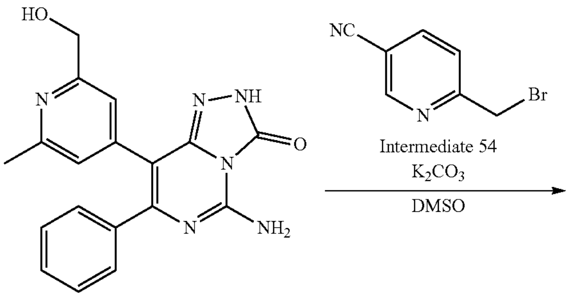

Intermediate 53

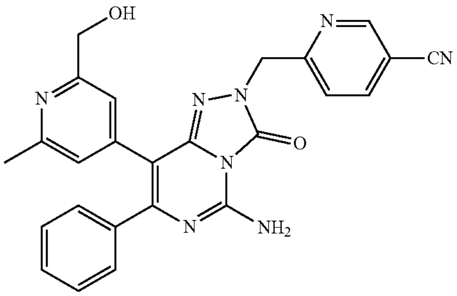

Example 1-54

To a stirred solution of 5-amino-8-(2-(hydroxymethyl)-6-methylpyridin-4-yl)-7-phenyl-[1,2,4]triazolo[4,3-c]pyrimidin-3(2H)-one (450 mg, 1.29 mmol) in DMSO (10 mL), were added 6-(bromomethyl)nicotinonitrile (254 mg, 1.29 mmol) and $K_2CO_3$ (535 mg, 3.87 mmol) and the reaction mixture was heated to 70° C. for 1 h. The reaction mixture was partitioned between EtOAc (20 mL) and $H_2O$ (20 mL). The organic layer was separated and concentrated under reduced pressure. The crude product was purified by flash column chromatography by using silica (230-400) mesh and eluted with 0-3% MeOH in DCM gradient to afford 6-[[5-amino-8-[2-(hydroxymethyl)-6-methyl-4-pyridyl]-3-oxo-7-phenyl-[1,2,4]triazolo[4,3-c]pyrimidin-2-yl]methyl]pyridine-3-carbonitrile (290 mg, 48%) as a yellow solid. The data for the title compound are in table 3.

Route u: Typical Procedure for the Preparation of Alkylated Triazolopyrimidinones Via an Ester Reduction, Followed by an Alkylation Reaction

Example 1-63, 6-[[5-amino-7-(4-fluorophenyl)-8-[2-(hydroxymethyl)-6-methyl-4-pyridyl]-3-oxo-[1,2,4]triazolo[4,3-c]pyrimidin-2-yl]methyl]pyridine-3-carbonitrile

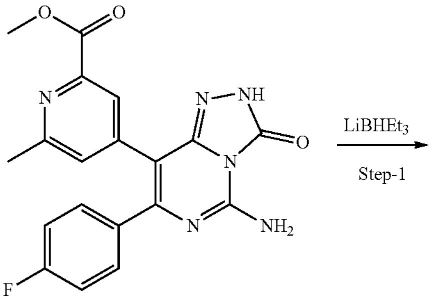

Intermediate 56

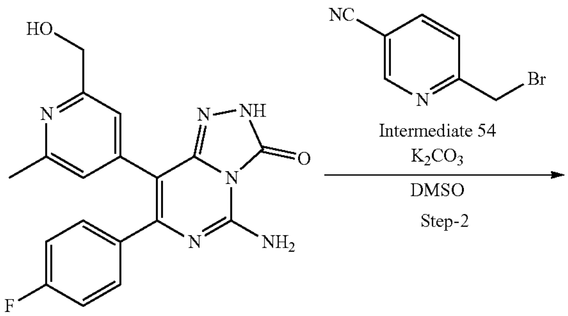

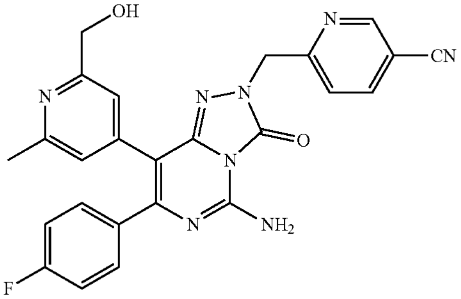

Example 1-63

Step 1; Performed in a similar fashion to route o step-2, to afford 5-amino-7-(4-fluorophenyl)-8-(2-(hydroxymethyl)-6-methylpyridin-4-yl)-[1,2,4]triazolo[4,3-c]pyrimidin-3(2H)-one (460 mg, 48%) as a yellow solid.

LCMS (Method C): m/z 367 $(M+H)^+$ $(ES^+)$, at 2.16 min, UV active.

$^1H$ NMR: (400 MHz, DMSO-d6) δ: 12.42 (s, 1H), 7.33-7.29 (m, 2H), 7.12-7.08 (m, 3H), 6.87 (s, 1H), 5.26 (t, J=5.8 Hz, 1H), 4.43 (d, J=5.8 Hz, 2H), 2.32 (s, 3H). Exchangeable —$NH_2$ protons were not observed.

Step 2; Performed in a similar fashion to route t, to afford 6-[[5-amino-7-(4-fluorophenyl)-8-[2-(hydroxymethyl)-6-methyl-4-pyridyl]-3-oxo-[1,2,4]triazolo[4,3-c]pyrimidin-2-yl]methyl]pyridine-3-carbonitrile (250 g, 41%) as a yellow solid. The data for the title compound are in table 3.

Route v: Typical Procedure for the Preparation of Alkylated Triazolopyrimidinones Via a Suzuki Coupling and an $S_NAr$ Displacement

Example 1-71, 5-amino-8-[2-(dimethylamino)-6-methyl-4-pyridyl]-2-[(5-fluoro-2-pyridyl)methyl]-7-phenyl-[1,2,4]triazolo[4,3-c]pyrimidin-3-one

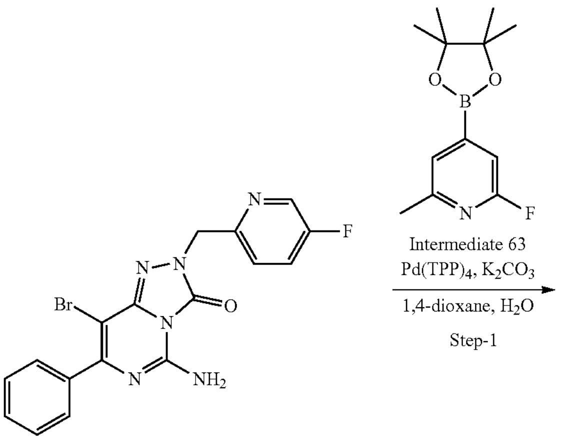

Intermediate 5

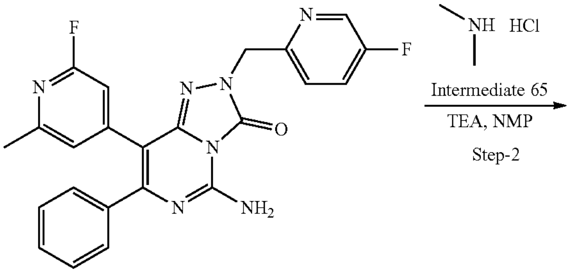

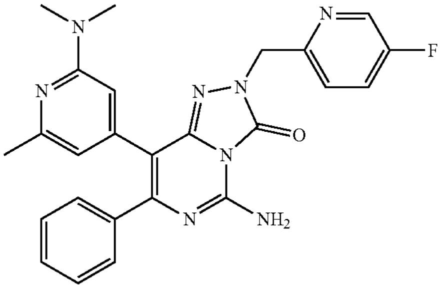

Example 1-71

Step 1; Performed in a similar fashion to route a step-2, to afford 5-amino-8-(2-fluoro-6-methylpyridin-4-yl)-2-((5-fluoropyridin-2-yl)methyl)-7-phenyl-[1,2,4]triazolo[4,3-c]pyrimidin-3(2H)-one (700 mg, 33%) as a yellow solid.

LCMS (Method C): m/z 446 $(M+H)^+$ $(ES^+)$, at 1.93 min, UV active.

$^1H$ NMR: (400 MHz, DMSO-d6) δ:8.55-8.02 (m, 1H), 8.00 (s, 1H), 7.77-7.72 (m, 2H), 7.29-6.93 (m, 5H), 6.68 (s, 1H), 5.15-5.11 (m, 2H), 2.26 (s, 3H). Exchangeable —$NH_2$ protons were not observed.

Step 2; To a solution of 5-amino-8-(2-fluoro-6-methylpyridin-4-yl)-2-((5-fluoropyridin-2-yl)methyl)-7-phenyl-[1,2,4]triazolo[4,3-c]pyrimidin-3(2H)-one (350 mg, 0.78 mmol) in NMP (5 mL), were added TEA (0.3 mL, 2.34 mmol) and N,N-dimethylamine hydrochloride (130 mg, 0.56 mmol) and the resultant reaction mixture was heated to 120° C. for 16 h. (In other analogues TEA can be omitted and an excess of the amine (free base) is used.) The reaction mixture was partitioned between $H_2O$ (20 mL) and EtOAc (40 mL). The organic layer was separated, dried over anhydrous $Na_2SO_4$ and concentrated. The crude product was purified by Prep-HPLC (Method A). Collected fractions were concentrated under reduced pressure and the residue obtained was diluted with EtOAc (10 mL), washed with 10% sodium bicarbonate solution (10 mL). The organic layer was separated, dried over anhydrous $Na_2SO_4$ and concentrated to afford 5-amino-8-(2-(dimethylamino)-6-methylpyridin-4-yl)-2-((5-fluoropyridin-2-yl)methyl)-7-phenyl-[1,2,4]triazolo[4,3-c]pyrimidin-3(2H)-one (45 mg, 12%) as a yellow solid. The data for the title compound are in table 3.

Route w

Example 1-77, 5-amino-8-(2-chloro-6-methyl-4-pyridyl)-2-[(5-methoxy-2-pyridyl)methyl]-7-phenyl-[1,2,4]triazolo[4,3-c]pyrimidin-3-one

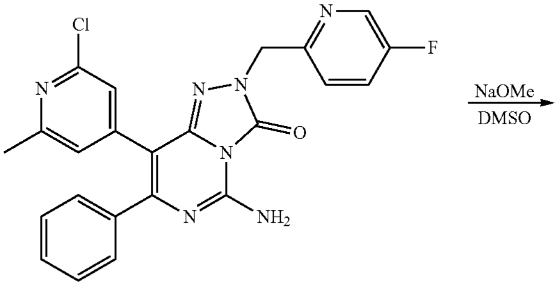

Example 1-76

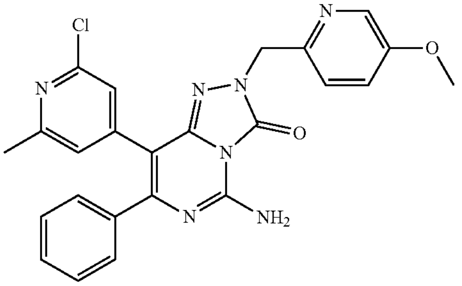

Example 1-77

To a stirred solution of 5-amino-8-(2-chloro-6-methylpyridin-4-yl)-2-((5-fluoropyridin-2-yl)methyl)-7-phenyl-[1,2,4]triazolo[4,3-c]pyrimidin-3(2H)-one (100 mg, 0.2 mmol) in DMSO (1 mL) was added NaOMe (35 mg, 0.6 mmol) and the reaction was heated to 120° C. for 5 h. The reaction mixture was partitioned between $H_2O$ (10 mL) and EtOAc (10 mL). The organic layer was separated, dried over anhydrous $Na_2SO_4$ and concentrated. The crude product was purified by Prep-HPLC (Method A). Fractions were concentrated and the residue obtained was diluted with EtOAc (10 mL), washed with 10% sodium bicarbonate solution (10 mL). The organic layer was separated, dried over anhydrous $Na_2SO_4$ and concentrated to afford 5-amino-8-(2-chloro-6-methylpyridin-4-yl)-2-((5-methoxypyridin-2-yl)methyl)-7-phenyl-[1,2,4]triazolo[4,3-c]pyrimidin-3(2H)-one (12 mg, 12%) as an off white solid. The data for the title compound are in table 3.

Route x: Typical Procedure for the Preparation of Alkylated Triazolopyrimidinones Via an Aldehyde Condensation Reaction

Example 1-80, 5-amino-8-(2,6-dimethyl-4-pyridyl)-7-phenyl-2-(2-phenylethyl)-[1,2,4]triazolo[4,3-c]pyrimidin-3-one

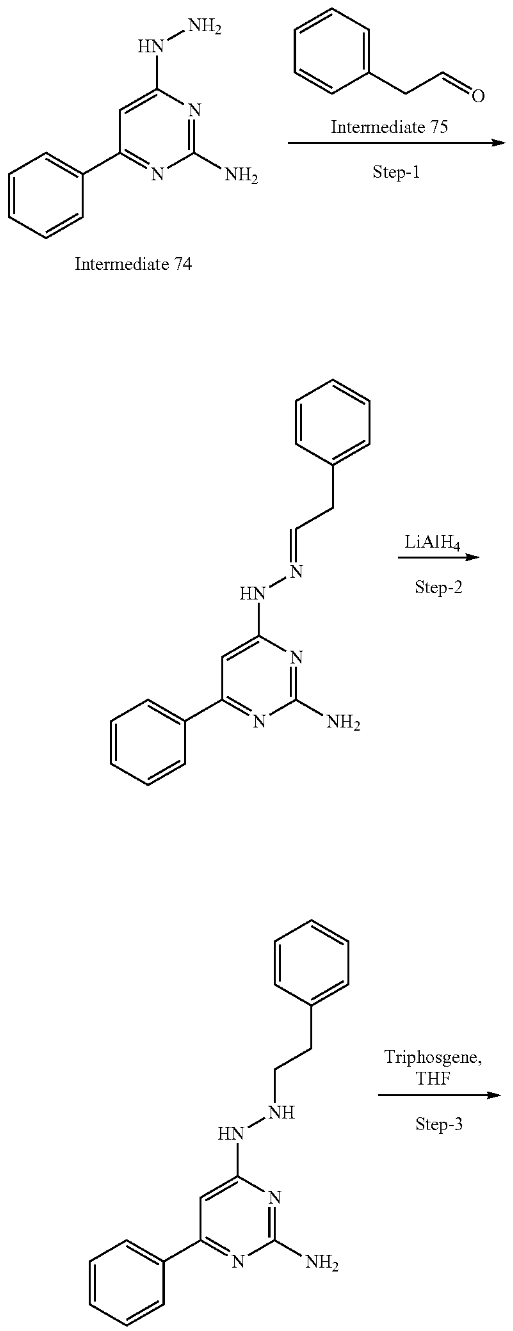

-continued

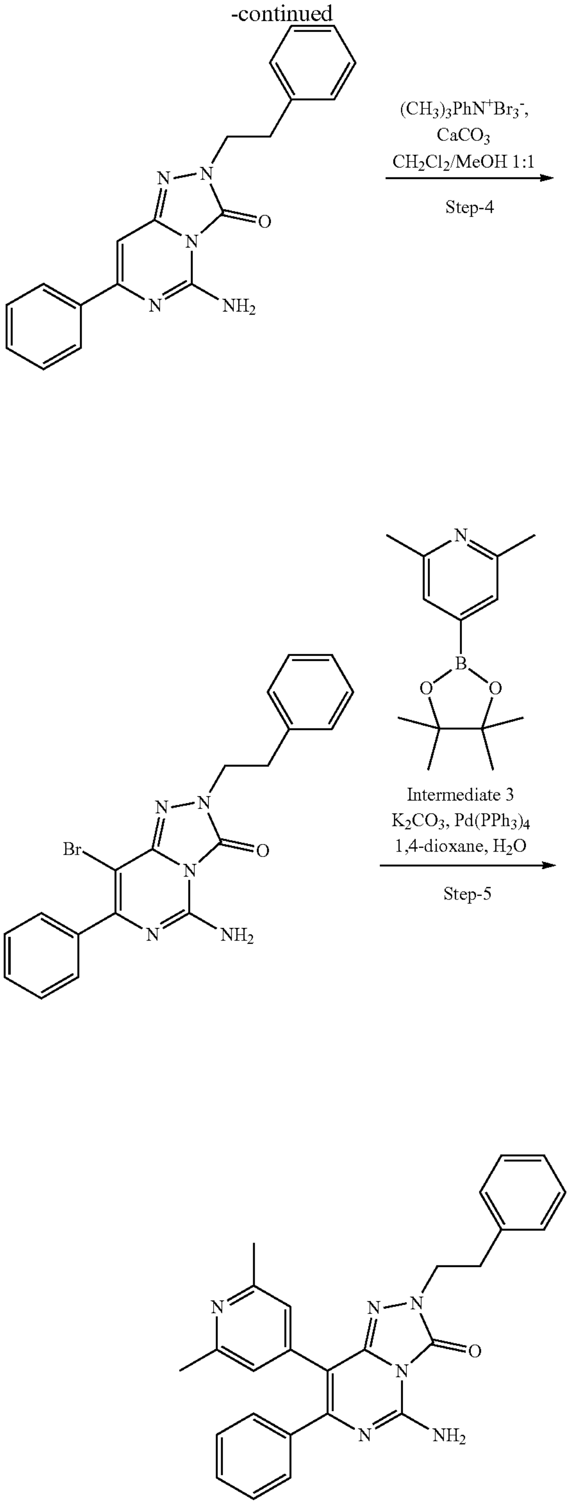

Example 1-80

Step 1; To a solution of 4-hydrazinyl-6-phenylpyrimidin-2-amine (0.6 g, 2.98 mmol) in MeOH (5 mL) at room temperature was added phenyl acetaldehyde (0.357 g, 2.98 mmol) and the resulting reaction was stirred for 3 h. The mixture was concentrated under reduced pressure and dried under vacuum. The residue obtained was triturated with petroleum ether (3×3 mL), decanted and dried under hi-vacuum to afford (E)-4-phenyl-6-(2-(2-phenylethylidene) hydrazinyl) pyrimidin-2-amine (0.62 g, 68%) as an off-white solid.

LCMS (Method D): m/z 304 $(M+H)^+$ $(ES^+)$, at 3.86 min, UV active.

$^1H$ NMR: (400 MHz, DMSO-d6) δ: 10.55 (br s, 1H), 7.98-7.96 (m, 2H), 7.49-7.46 (m, 4H), 7.37-7.32 (m, 2H), 7.30-7.23 (m, 3H), 6.76 (s, 1H), 6.20 (br s, 2H), 3.61 (d, J=5.8 Hz, 2H)

Step 2; To a solution of 4-phenyl-6-(2-(2-phenylethylidene)hydrazinyl)pyrimidin-2-amine (0.6 g, 1.98 mmol) in THF (20 mL) at −30° C. was added lithium aluminium hydride (1 M in THF, 9.9 mL, 9.9 mmol) dropwise over 2 min. The reaction mixture was stirred at room temperature for 2 h. The reaction was quenched with saturated $Na_2SO_4$ solution (20 mL) and extracted with EtOAc (2×15 mL). The combined organic layers were dried over anhydrous $Na_2SO_4$ and concentrated to afford 4-(2-phenethylhydrazinyl)-6-phenylpyrimidin-2-amine as a brown gum that was used immediately in the next step without purification.

Step 3; To a solution of 4-(2-phenethylhydrazinyl)-6-phenylpyrimidin-2-amine (600 mg, 1.96 mmol) in dry THF (10 mL) under $N_2$ cooled to −20° C., was added triphosgene (1152 mg, 3.92 mmol) and the mixture was stirred for 45 min. The reaction was concentrated and purified by gradient flash chromatography eluting with $CH_2Cl_2$/MeOH 95:5 to afford 5-amino-2-phenethyl-7-phenyl-[1,2,4]triazolo[4,3-c] pyrimidin-3(2H)-one (350 mg, 53%) as a pale yellow solid.

LCMS (Method D): m/z 332 $(M+H)^+$ $(ES^+)$, at 3.86 min, UV active.

$^1H$ NMR: (400 MHz, DMSO-d6) δ: 7.91 (d, J=9.6 Hz, 2H), 7.49-7.46 (m, 3H), 7.35-7.31 (m, 2H), 7.27-7.24 (m, 3H), 6.70 (s, 1H), 4.17-4.13 (m, 2H), 3.18-3.15 (m, 2H)

Exchangeable —$NH_2$ protons were not observed.

Step 4; To a suspension of 5-amino-2-phenethyl-7-phenyl-[1,2,4]triazolo[4,3-c]pyrimidin-3(2H)-one (350 mg, 1.05) in $CH_2Cl_2$/MeOH 1:1 (10 mL) under $N_2$, were added $CaCO_3$ (105 mg, 1.05 mmol) and $(CH_3)_3PhN^+$ $Br_3^-$ (392 mg, 1.05 mmol) and the mixture was stirred at room temperature for 1 h. The reaction was quenched with $H_2O$ and extracted with $CH_2Cl_2$. The organic layer was dried over $Na_2SO_4$ and concentrated. The crude product was purified by gradient flash chromatography eluting with $CH_2Cl_2$/MeOH 95:5 to afford 5-amino-8-bromo-2-phenethyl-7-phenyl-[1,2,4]triazolo[4,3-c]pyrimidin-3(2H)-one (140 mg, 30%) as a yellow solid.

LCMS (Method D): m/z 409 $(M+H)^+$ $(ES^+)$, at 4.19 min, UV active.

$^1H$ NMR: (400 MHz, DMSO-d6) δ: 7.64-7.61 (m, 2H), 7.49-7.44 (m, 3H), 7.33-7.21 (m, 5H), 4.06 (t, J=14.4 Hz, 2H), 3.06 (t, J=14.4 Hz, 2H) Exchangeable —$NH_2$ protons were not observed.

Step 5; Performed in a similar fashion to route a step-2, to afford 5-amino-8-(2,6-dimethylpyridin-4-yl)-2-phenethyl-7-phenyl-[1,2,4]triazolo[4,3-c]pyrimidin-3(2H)-one (68 mg, 45%) as a pale yellow solid. The data for the title compound are in table 3.

Route y

Example 1-85, 4-[2-[5-amino-8-(2,6-dimethyl-4-pyridyl)-3-oxo-7-phenyl-[1,2,4]triazolo[4,3-c]pyrimidin-2-yl]ethyl]benzoic acid

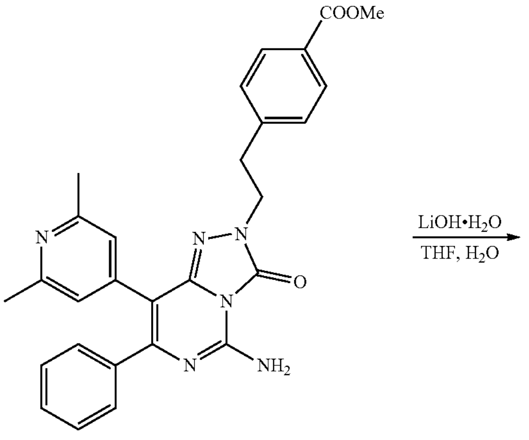

Example 1-84

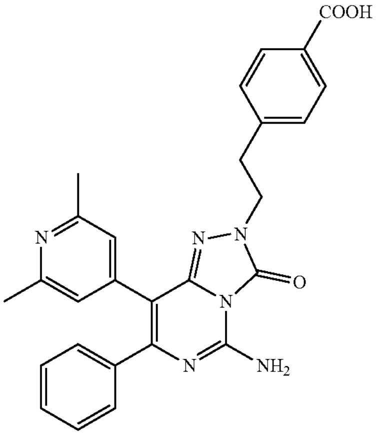

Example 1-85

To a solution of methyl 4-(2-(5-amino-8-(2,6-dimethylpyridin-4-yl)-3-oxo-7-phenyl-[1,2,4]triazolo[4,3-c]pyrimidin-2(3H)-yl)ethyl)benzoate (50 mg, 0.1 mmol) in THF (2 mL) and $H_2O$ (1 mL) was added $LiOH.H_2O$ (9 mg, 0.20 mmol) and reaction was stirred at room temperature for 6 h. The reaction mixture was acidified to pH-6 and concentrated. The crude product was purified by passing through an SCX cartridge (SolEx SCX, 6 mL, 500 mg), eluted with methanolic ammonia and dried to afford 4-(2-(5-amino-8-(2,6-dimethylpyridin-4-yl)-3-oxo-7-phenyl-[1,2,4]triazolo [4,3-c]pyrimidin-2(3H)-yl)ethyl)benzoic acid (12 mg, 25%) as a yellow solid. The data for the title compound are in table 3.

Route z

Example 1-90, 5-amino-8-[2-(azetidin-1-yl)-6-methyl-4-pyridyl]-7-phenyl-2-(2-phenylethyl)-[1,2,4]triazolo[4,3-c]pyrimidin-3-one

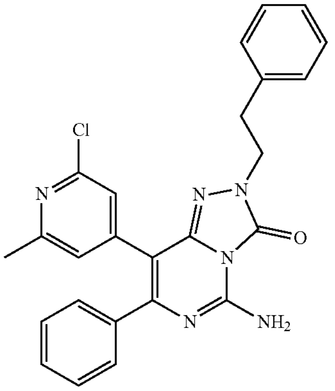

Example 1-89

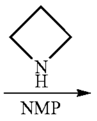

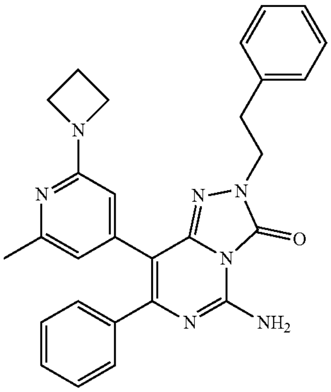

Example 1-90

A solution of 5-amino-8-(2-chloro-6-methylpyridin-4-yl)-2-phenethyl-7-phenyl-[1,2,4]triazolo[4,3-c]pyrimidin-3(2H)-one (60 mg, 0.13 mmol) and azetidine (12 mg, 0.19 mmol) in NMP (2 mL) was heated at 150° C. for 16 h. The reaction mixture was partitioned between EtOAc (10 mL) and $H_2O$ (10 mL). The organic layer was separated, dried over anhydrous $Na_2SO_4$ and concentrated under reduced pressure. The crude compound was purified by Biotage-Isolera by using 10 g silica snap and gradient EtOAc in Hexane to afford 5-amino-8-(2-(azetidin-1-yl)-6-methylpyridin-4-yl)-2-phenethyl-7-phenyl-[1,2,4]triazolo[4,3-c]pyrimidin-3(2H)-one (7 mg, 10%) as pale yellow solid. The data for the title compound are in table 3.

Route aa: Typical Procedure for the Preparation of Alkylated Triazolopyrimidinones Via a Displacement Reaction Example 1-91, 5-[2-[5-amino-8-(2,6-dimethyl-4-pyridyl)-3-oxo-7-phenyl-[1,2,4]triazolo[4,3-c]pyrimidin-2-yl]ethylamino]-2-chloro-N-methyl-benzamide

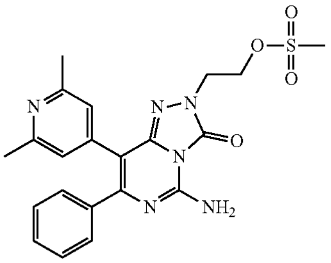

Intermediate 83

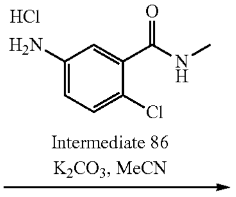

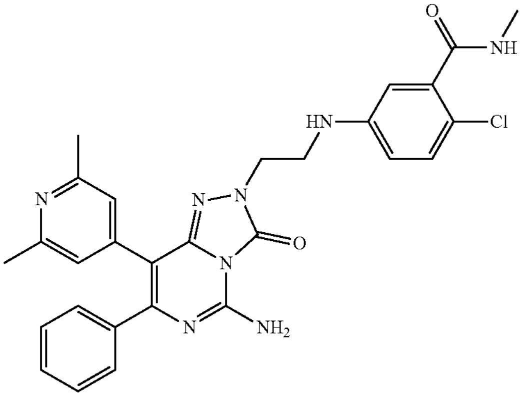

Example 1-91

To a suspension 2-(5-amino-8-(2,6-dimethylpyridin-4-yl)-3-oxo-7-phenyl-[1,2,4]triazolo[4,3-c]pyrimidin-2(3H)-yl)ethyl methanesulfonate 1 (73 mg, 0.16 mmol) in MeCN (2 mL) was added $K_2CO_3$ (66 mg, 0.48 mmol) and 5-amino-2-chloro-N-methylbenzamide hydrochloride (42 mg, 0.19 mmol). The reaction mixture was heated at 100° C. for 15 h. The mixture was partitioned between EtOAc (5 mL) and $H_2O$ (5 mL). The organic layer was separated, dried over anhydrous $Na_2SO_4$ and concentrated under reduced pressure. The crude product was purified by prep HPLC (Method E) to afford 5-[2-[5-amino-8-(2,6-dimethyl-4-pyridyl)-3-oxo-7-phenyl-[1,2,4]triazolo[4,3-c]pyrimidin-2-yl]ethylamino]-2-chloro-N-methyl-benzamide (7 mg, 8%). The data for the title compound are in table 3.

Route ab

Example 2-16, 2-[5-amino-8-(2,6-dimethyl-4-pyridyl)-3-oxo-7-phenyl-[1,2,4]triazolo[4,3-c]pyrimidin-2-yl]ethyl N-ethylcarbamate

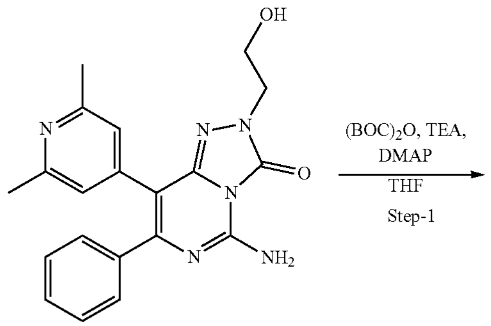

Intermediate 84

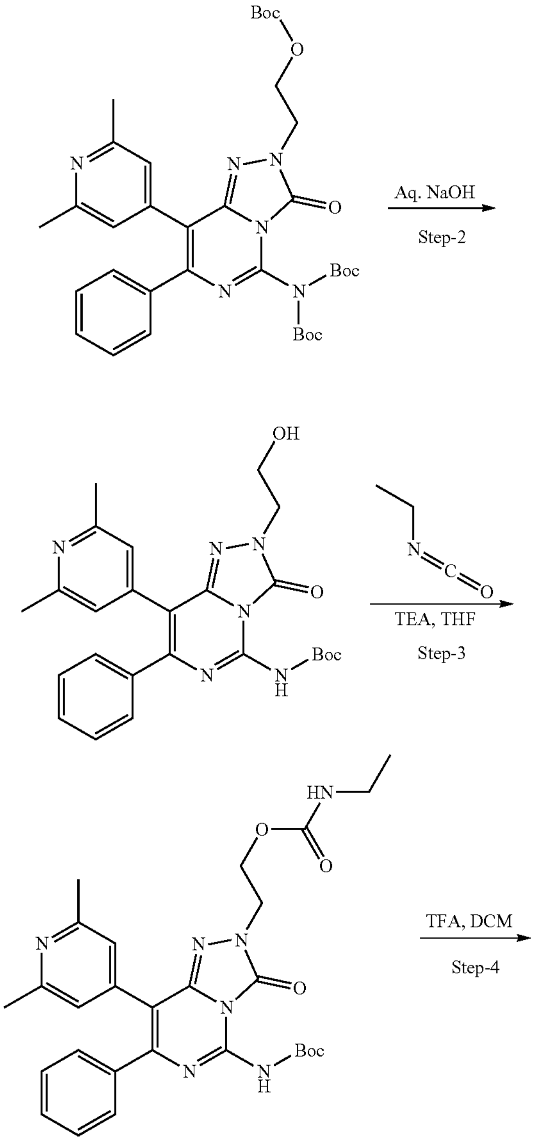

-continued

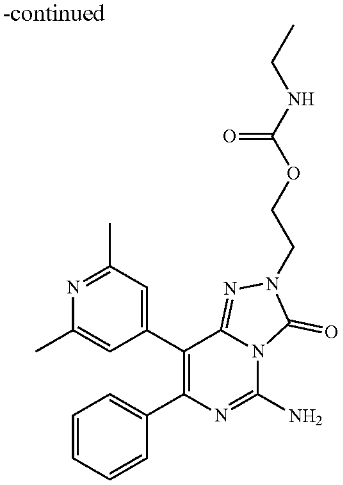

Example 2-16

Step 1; To a suspension of 5-amino-8-(2,6-dimethylpyridin-4-yl)-2-(2-hydroxyethyl)-7-phenyl-[1,2,4]triazolo[4,3-c]pyrimidin-3(2H)-one (50 mg, 0.13 mmol), di-tert-butyl-dicarbonate (31 mg, 0.014 mmol), TEA (0.69 ml, 0.52 mmol) in THF (5 mL) at room temperature was added DMAP (8 mg, 0.006 mmol). The reaction mixture was stirred for 48 h at room temperature. The reaction mixture was partitioned between EtOAc (20 mL) and sodium bicarbonate (10 mL). The organic layer was dried over anhydrous $Na_2SO_4$, concentrated under reduced pressure to afford tert-butyl (2-(2-((tert-butoxycarbonyl)oxy)ethyl)-8-(2,6-dimethylpyridin-4-yl)-3-oxo-7-phenyl-2,3-dihydro-[1,2,4]triazolo[4,3-c]pyrimidin-5-yl)carbamate (80 mg, crude) as a yellow solid that as taken on without purification.

LCMS (Method B): m/z 677 $(M+H)^+$ $(ES^+)$, at 2.89 min, UV active.

Step 2; To a suspension of tert-butyl (2-(2-((tert-butoxycarbonyl)oxy)ethyl)-8-(2,6-dimethylpyridin-4-yl)-3-oxo-7-phenyl-2,3-dihydro-[1,2,4]triazolo[4,3-c]pyrimidin-5-yl) carbamate (80 mg, 0.118) in 1,4-dioxane (2 mL) was added 2 N aq. NaOH solution (3 mL). The reaction mixture was stirred for 48 h at room temperature, then was partitioned between EtOAc (10 mL) and water (10 mL). The organic layer was dried over anhydrous $Na_2SO_4$, concentrated under reduced pressure and purified by Biotage-Isolera using 10 g silica snap and eluted with gradient 10% MeOH in DCM to afford tert-butyl (8-(2,6-dimethylpyridin-4-yl)-2-(2-hydroxyethyl)-3-oxo-7-phenyl-2,3-dihydro-[1,2,4]triazolo[4,3-c]pyrimidin-5-yl)carbamate (40 mg, 21%) as yellow solid.

LCMS (Method B): m/z 477 $(M+H)^+$ $(ES^+)$, at 2.32 min, UV active.

$^1H$ NMR: (400 MHz, DMSO-d6) δ:10.24 (s, 1H), 7.38-7.27 (m, 5H), 6.91 (s, 2H), 4.89 (s, 1H), 3.87 (t, J=7.6 Hz, 2H), 3.63 (t, J=7.6 Hz, 2H), 2.35 (s, 6H), 1.51-1.49 (m, 9H).

Step 3; To a suspension of tert-butyl (8-(2,6-dimethylpyridin-4-yl)-2-(2-hydroxyethyl)-3-oxo-7-phenyl-2,3-dihydro-[1,2,4]triazolo[4,3-c]pyrimidin-5-yl)carbamate (35 mg, 0.073 mmol) and TEA (0.02 ml, 0.014 mmol) in THF (5 mL) at room temperature was added ethyl isocyanate (5 mg, 0.066 mmol). The reaction mixture was heated to 60° C. for 12 h. The reaction mixture was cooled to room temperature and partitioned between EtOAc (10 mL) and $H_2O$ (10 mL). The organic layer was dried over anhydrous $Na_2SO_4$, concentrated under reduced pressure and purified by Biotage-Isolera using 10 g silica snap and eluted with gradient 10%

MeOH in DCM to afford tert-butyl (tert-butoxycarbonyl)(8-(2,6-dimethylpyridin-4-yl)-2-(2-((ethylcarbamoyl)oxy)ethyl)-3-oxo-7-phenyl-2,3-dihydro-[1,2,4]triazolo[4,3-c]pyrimidin-5-yl)carbamate (30 mg, 74%) as a yellow solid.

LCMS (Method B): m/z 547 $(M+H)^+$ $(ES^+)$, at 2.50 min, UV active.

Step 4; To a suspension of tert-butyl (tert-butoxycarbonyl)(8-(2,6-dimethylpyridin-4-yl)-2-(2-((ethylcarbamoyl)oxy)ethyl)-3-oxo-7-phenyl-2,3-dihydro-[1,2,4]triazolo[4,3-c]pyrimidin-5-yl)carbamate (30 mg, 0.054 mmol) in DCM was added 5 mL of 20% TFA in DCM. The reaction mixture was stirred at room temperature for 15 h. The reaction mixture was concentrated under reduced pressure, loaded on SCX cartridge and eluted with 2 M methanolic ammonia to afford 2-(5-amino-8-(2,6-dimethylpyridin-4-yl)-3-oxo-7-phenyl-[1,2,4]triazolo[4,3-c]pyrimidin-2(3H)-yl)ethyl ethyl carbamate (4 mg, 7%) as a yellow solid. The data for the title compound are in table 3.

Route ac

Example 2-17, 5-amino-2-(3,3-difluoropropyl)-8-(2,6-dimethyl-4-pyridyl)-7-phenyl-[1,2,4]triazolo[4,3-c]pyrimidin-3-one

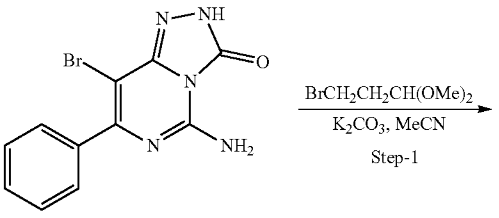

Intermediate 1

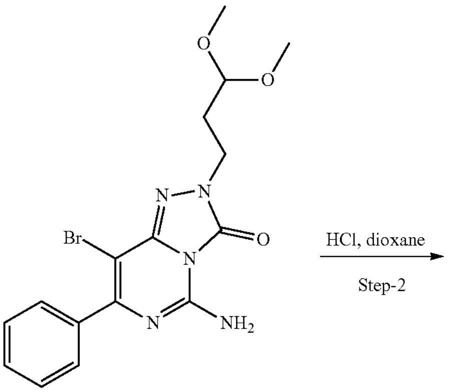

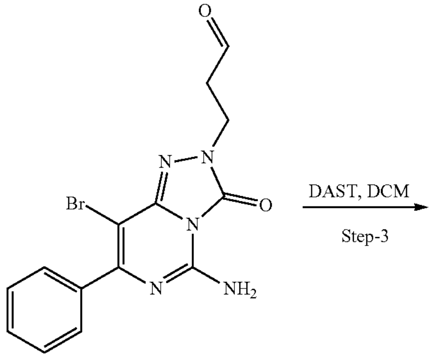

-continued

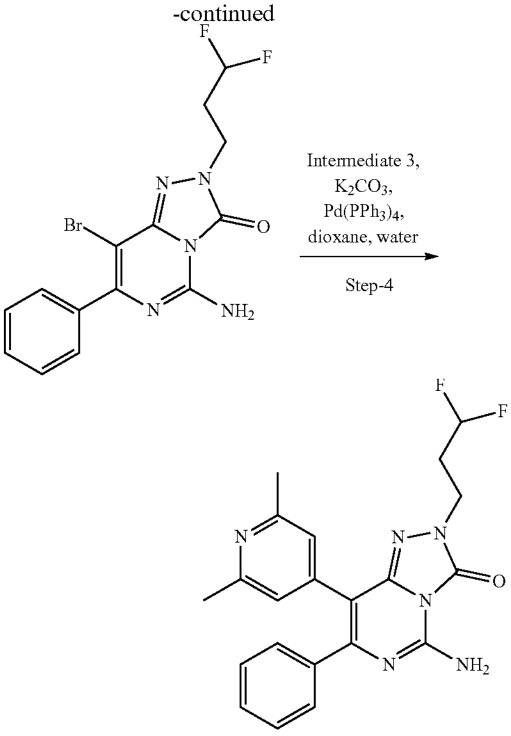

Example 2-17

Step 1; Prepared in a similar fashion to route a step 1, with purification by trituration with diethyl ether, to afford 5-amino-8-bromo-2-(3,3-dimethoxypropyl)-7-phenyl-[1,2,4]triazolo[4,3-c]pyrimidin-3(2H)-one (1.2 g, 45%) as an off-white solid.

LCMS (Method B): m/z 408 $(M+H)^+$ $(ES^+)$, at 2.68 min, UV active.

$^1$H NMR: (400 MHz, DMSO-d6) δ: 7.62-7.61 (m, 2H), 7.48-7.43 (m, 3H), 4.47 (t, J=5.6 Hz, 1H), 3.85 (t, J=7.2 Hz, 2H), 3.26 (s, 6H), 1.99-1.94 (m, 2H). Exchangeable —$NH_2$ protons were not observed.

Step 2; To a solution of 5-amino-8-bromo-2-(3,3-dimethoxypropyl)-7-phenyl-[1,2,4]triazolo[4,3-c]pyrimidin-3(2H)-one (1.2 g, 2.94 mmol) in 1,4-dioxane (10 mL) at room temperature was added 2 N HCl (30 mL) and the reaction stirred for 2 h. The reaction was concentrated under reduced pressure and partitioned between EtOAc (30 mL) and saturated $NaHCO_3$ solution (20 mL). The organic layer was separated, dried over anhydrous $Na_2SO_4$ and concentrated under reduced pressure to afford 3-(5-amino-8-bromo-3-oxo-7-phenyl-[1,2,4]triazolo[4,3-c]pyrimidin-2(3H)-yl)propanal (0.6 g) as a brown gum which was used immediately in the next step.

LCMS (Method B): m/z 362 $(M+H)^+$ $(ES^+)$, at 2.32 min, UV active.

Step 3; To a solution of 3-(5-amino-8-bromo-3-oxo-7-phenyl-[1,2,4]triazolo[4,3-c]pyrimidin-2(3H)-yl)propanal (0.6 g, 1.65 mmol) in DCM (15 mL) at −78° C. was added DAST (0.58 g, 3.63 mmol) and stirred at room temperature for 15 h. The reaction mass was cautiously quenched by the drop wise addition of saturated sodium bicarbonate solution (40 mL) and extracted with DCM (2×30 mL). The combined organic layers were dried over anhydrous $Na_2SO_4$ and concentrated under reduced pressure. The crude product was purified by Biotage-Isolera using 25 g silica snap and was eluted with gradient 0-40% EtOAc in hexane to afford 5-amino-8-bromo-2-(3,3-difluoropropyl)-7-phenyl-[1,2,4]triazolo[4,3-c]pyrimidin-3(2H)-one (0.2 g, 31%) as an off-white solid.

LCMS (Method B): m/z 384 $(M+H)^+$ $(ES^+)$, at 2.80 min, UV active.

$^1$H NMR: (400 MHz, DMSO-d6) δ: 7.63-7.61 (m, 2H), 7.48-7.45 (m, 3H), 6.35-6.05 (m, 1H), 3.99 (t, J=6.8 Hz, 2H), 2.39-2.22 (m, 2H). Exchangeable —$NH_2$ protons were not observed Step 4; Performed in a similar fashion to route a step 2, to afford 5-amino-2-(3,3-difluoropropyl)-8-(2,6-dimethyl-4-pyridyl)-7-phenyl-[1,2,4]triazolo[4,3-c]pyrimidin-3-one (100 mg, 47%) as a yellow solid. The data for the title compound are in table 3.

Route ad: Typical Procedure for the Preparation of Alkylated Triazolopyrimidinones Via an Alkylation Reaction Example 2-20, 5-amino-8-(2,6-dimethyl-4-pyridyl)-7-phenyl-2-propyl-[1,2,4]triazolo[4,3-c]pyrimidin-3-one

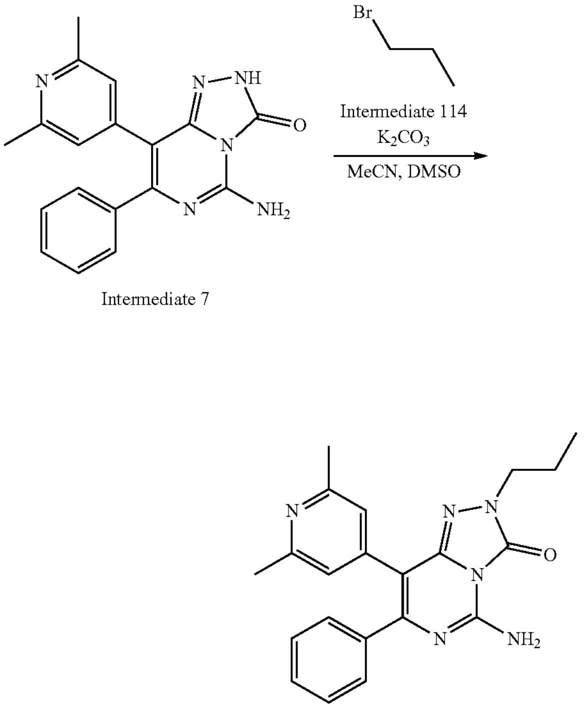

Intermediate 7

Example 2-20

Performed in a similar fashion to route a step 1, to afford 5-amino-8-(2,6-dimethyl-4-pyridyl)-7-phenyl-2-propyl-[1,2,4]triazolo[4,3-c]pyrimidin-3-one (45 mg, 40%) as a yellow solid. The data for the title compound are in table 3.

Route ae: Typical Procedure for the Preparation of Amides

Example 2-23, 3-[5-amino-8-(2,6-dimethyl-4-pyridyl)-3-oxo-7-phenyl-[1,2,4]triazolo[4,3-c]pyrimidin-2-yl]-N,N-dimethyl-propanamide

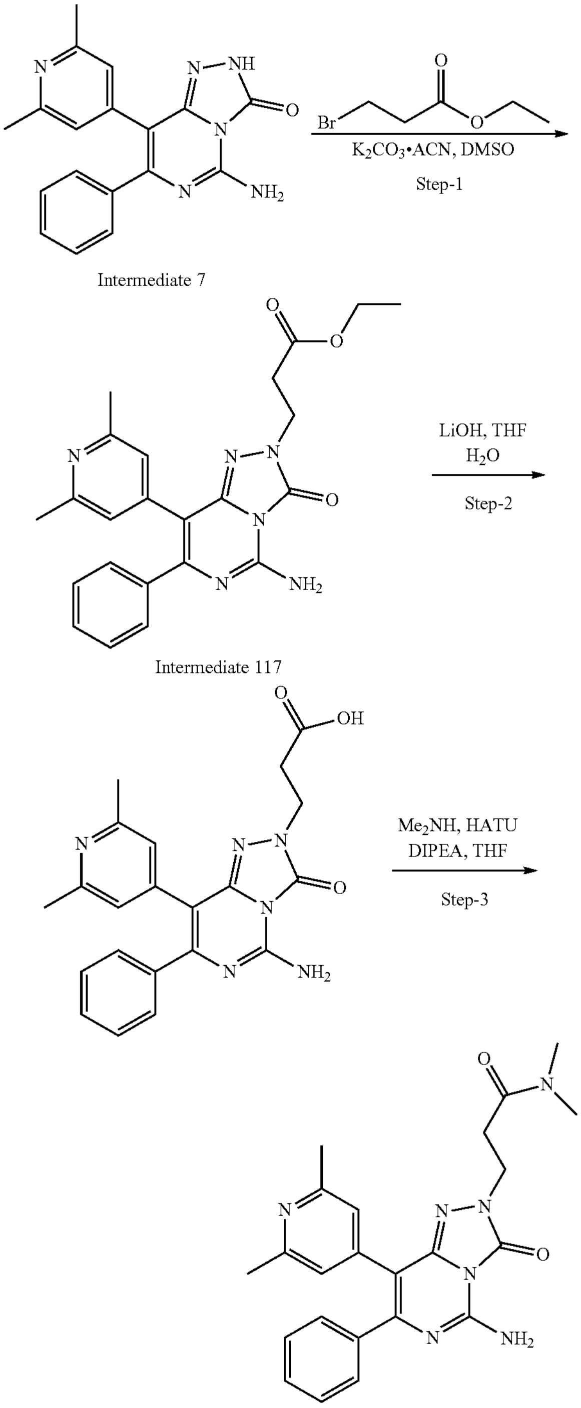

Intermediate 7

Intermediate 117

Example 2-23

Step 1; Performed in a similar fashion to route a, step 1, using ethyl 3-bromopropanoate and intermediate 7, to afford ethyl 3-(5-amino-8-(2,6-dimethylpyridin-4-yl)-3-oxo-7-phenyl-[1,2,4]triazolo[4,3-c]pyrimidin-2(3H)-yl)propanoate (180 mg, 69%) as yellow solid. The data for this compound are in table 2.

Step 2; To a suspension of ethyl 3-(5-amino-8-(2,6-dimethylpyridin-4-yl)-3-oxo-7-phenyl-[1,2,4]triazolo[4,3-c]pyrimidin-2(3H)-yl)propanoate (90 mg, 0.20 mmol) in THF (5 mL), $H_2O$ (5 mL) and MeOH (1 mL) was added lithium hydroxide monohydrate (43 mg, 1.04 mmol) and the reaction mixture was stirred at room temperature for 45 min. The reaction was partitioned between EtOAc (5 mL) and $H_2O$ (5 mL). The aqueous layer was separated and acidified with 6 N HCl (2 mL) and extracted with EtOAc (10 mL). The organic layer was dried over anhydrous $Na_2SO_4$ and concentrated under reduced pressure to afford 3-(5-amino-8-(2,6-dimethylpyridin-4-yl)-3-oxo-7-phenyl-[1,2,4]triazolo[4,3-c]pyrimidin-2(3H)-yl)propanoic acid (80 mg, 84%) as a yellow solid.

LCMS (Method A): m/z 405 $(M+H)^+$ $(ES^+)$, at 2.11 min, UV active.

$^1H$ NMR: (400 MHz, DMSO-d6) δ: 7.26-7.23 (m, 5H), 6.82 (s, 2H), 3.98 (t, J=8.0 Hz, 2H), 2.74 (t, J=8.0 Hz, 2H), 2.30 (s, 6H). Exchangeable protons were not observed Step 3; To a suspension of 3-(5-amino-8-(2,6-dimethylpyridin-4-yl)-3-oxo-7-phenyl-[1,2,4]triazolo[4,3-c]pyrimidin-2(3H)-yl)propanoic acid (80 mg, 0.19 mmol) in THF (10 mL) was added DIPEA (196 mg 1.5 mmol), dimethyl amine hydrochloride (100 mg, 1.14 mmol) and HATU (108 mg, 0.28 mmol) and stirred at room temperature for 1 h. The reaction mixture was partitioned between EtOAc (10 mL) and $H_2O$ (5 mL). The organic layer was separated, dried over anhydrous $Na_2SO_4$ and concentrated under reduced pressure. The crude product was dissolved in MeOH (5 mL), passed through SCX column and eluted with 2 N methanolic ammonia (10 mL) and concentrated to afford 3-[5-amino-8-(2,6-dimethyl-4-pyridyl)-3-oxo-7-phenyl-[1,2,4]triazolo[4,3-c]pyrimidin-2-yl]-N,N-dimethyl-propanamide (29 mg, 33%) as a yellow solid. The data for the title compound are in table 3.

Route af

Example 2-24, 5-amino-8-(2,6-dimethyl-4-pyridyl)-2-[3-hydroxy-2-(hydroxymethyl)propyl]-7-phenyl-[1,2,4]triazolo[4,3-c]pyrimidin-3-one

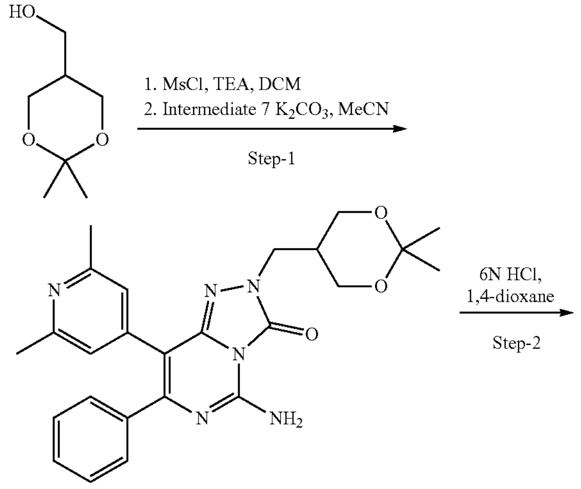

-continued

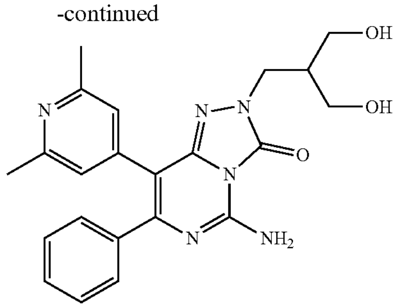

Example 2-24

Step 1; Performed in a similar fashion to route b step 1, using (2,2-dimethyl-1,3-dioxan-5-yl)methanol and Intermediate 7, to afford 5-amino-2-((2,2-dimethyl-1,3-dioxan-5-yl)methyl)-8-(2,6-dimethylpyridin-4-yl)-7-phenyl-[1,2,4]triazolo[4,3-c]pyrimidin-3(2H)-one (55 mg, 20%) as white solid.

LCMS (Method B): m/z 461 $(M+H)^+$ $(ES^+)$, at 2.08 min, UV active.

$^1H$ NMR: (400 MHz, DMSO-d6) δ: 7.26-7.24 (m, 5H), 6.82 (s, 2H), 3.90-3.85 (m, 4H), 3.65-3.63 (m, 2H), 2.30 (s, 6H), 2.00-1.88 (m, 1H), 1.33 (s, 6H). Exchangeable —$NH_2$ protons were not observed.

Step 2; To a solution of 5-amino-2-((2,2-dimethyl-1,3-dioxan-5-yl)methyl)-8-(2,6-dimethylpyridin-4-yl)-7-phenyl-[1,2,4]triazolo[4,3-c]pyrimidin-3(2H)-one (50 mg, 0.1 mmol) in 1,4-dioxane (5 mL) was added 6 N HCl (2 mL) and the reaction stirred at room temperature for 6 h. The mixture was concentrated under reduced pressure and partitioned between 10% sodium bicarbonate (15 mL) and EtOAc (15 mL). The organic layer was separated, dried over anhydrous $Na_2SO_4$ and concentrated. The crude product was recrystallized from diethyl ether to afford 5-amino-8-(2,6-dimethylpyridin-4-yl)-2-(3-hydroxy-2-(hydroxymethyl)propyl)-7-phenyl-[1,2,4]triazolo[4,3-c]pyrimidin-3(2H)-one (40 mg, 88%) as a yellow solid. The data for the title compound are in table 3.

Route ag

Example 2-31, 3-[5-amino-8-(2,6-dimethyl-4-pyridyl)-3-oxo-7-phenyl-[1,2,4]triazolo[4,3-c]pyrimidin-2-yl]propanamide

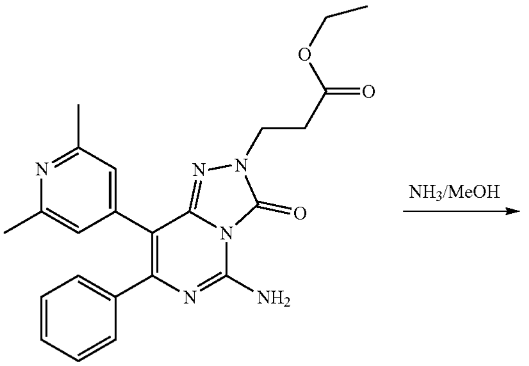

Intermediate 117

-continued

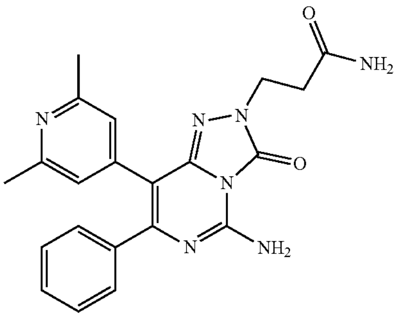

Example 2-31

A suspension of ethyl 2-(5-amino-8-(2,6-dimethylpyridin-4-yl)-3-oxo-7-phenyl-[1,2,4]triazolo[4,3-c]pyrimidin-2(3H)-yl)acetate (90 mg, 0.28 mmol) in 2 N methanolic ammonia was heated to 100° C. for 16 h. The reaction was concentrated, dissolved in MeOH (5 mL), passed through an SCX column and eluted with 2 N methanolic ammonia (10 mL) and concentrated to afford 3-[5-amino-8-(2,6-dimethyl-4-pyridyl)-3-oxo-7-phenyl-[1,2,4]triazolo[4,3-c]pyrimidin-2-yl]propanamide (35 mg, 35%) as a yellow solid. The data for the title compound are in table 3.

Route ah: Typical Procedure for the Preparation of Alkylated Triazolopyrimidinones Via an Alkylation Reaction

Example 2-37, 5-amino-8-(2,6-dimethyl-4-pyridyl)-7-(2-pyridyl)-2-(3,3,3-trifluoropropyl)-[1,2,4]triazolo[4,3-c]pyrimidin-3-one

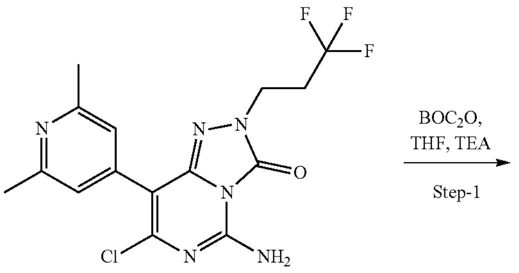

Intermediate 131

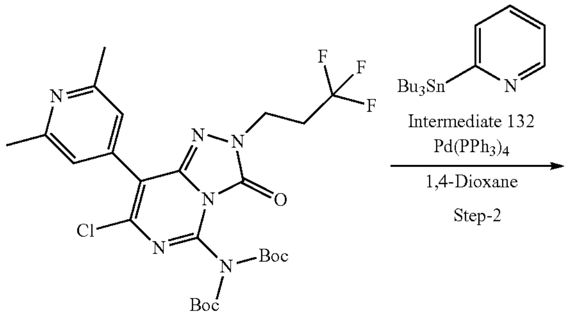

Intermediate 181

-continued

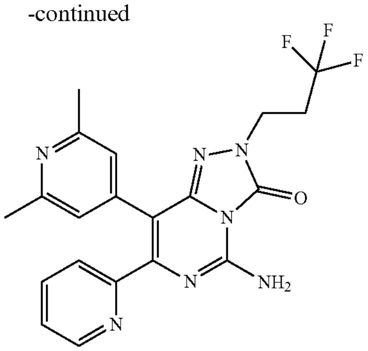

Example 2-37

Step 1; To a suspension of 5-amino-7-chloro-8-(2,6-dimethylpyridin-4-yl)-2-(3,3,3-trifluoropropyl)-[1,2,4]triazolo[4,3-c]pyrimidin-3(2H)-one (100 mg, 0.25 mmol) in THF (10 mL) was added TEA (0.07 mL, 0.77 mmol), Boc anhydride (218 mg, 0.77 mmol) and a catalytic amount of DMAP. The reaction was heated to 50° C. for 5 h. The reaction mixture was partitioned between EtOAc (10 mL) and $H_2O$ (10 mL). The organic layer was separated, dried over anhydrous $Na_2SO_4$ and concentrated under reduced pressure to afford di-boc protected-5-amino-7-chloro-8-(2,6-dimethylpyridin-4-yl)-2-(3,3,3-trifluoropropyl)-[1,2,4]triazolo[4,3-c]pyrimidin-3(2H)-one (200 mg, 14%), that was used in the next step without purification.

LCMS (Method A): m/z 587 $(M+H)^+$ $(ES^+)$, at 2.66 min, UV active.

Step 2; To a solution of di-boc protected-5-amino-7-chloro-8-(2,6-dimethylpyridin-4-yl)-2-(3,3,3-trifluoropropyl)-[1,2,4]triazolo[4,3-c]pyrimidin-3(2H)-one (100 mg, 0.17 mmol) in 1,4-dioxane (20 mL) was added 2-(tributylstannyl)pyridine (75.3 mg, 0.20 mmol) and $Pd(PPh_3)_4$ (19.6 mg, 0.01 mmol). The reaction was heated to 120° C. for 4 h in a sealed vial, then partitioned between EtOAc (20 mL) and $H_2O$ (15 mL). The organic layer was separated dried over $Na_2SO_4$ and concentrated under reduced pressure. The crude product was purified by Biotage-Isolera using 10 g silica snap, eluted with 0-100% EtOAc in hexane gradient to afford 5-amino-8-(2,6-dimethyl-4-pyridyl)-7-(2-pyridyl)-2-(3,3,3-trifluoropropyl)-[1,2,4]triazolo[4,3-c]pyrimidin-3-one (20 mg, 27%) as a yellow solid. The data for the title compound are in table 3.

Route ai

Example 2-41, 5-amino-8-(2,6-dimethyl-4-pyridyl)-7-(4-methylpyrazol-1-yl)-2-(3,3,3-trifluoropropyl)-[1,2,4]triazolo[4,3-c]pyrimidin-3-one

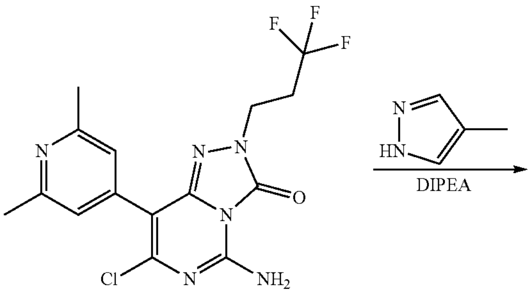

Intermediate 131

-continued

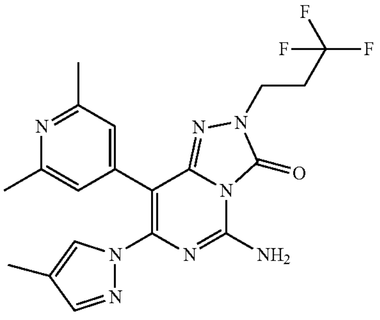

Example 2-41

A suspension of 5-amino-7-chloro-8-(2,6-dimethylpyridin-4-yl)-2-(3,3,3-trifluoropropyl)-[1,2,4]triazolo[4,3-c]pyrimidin-3(2H)-one (100 mg, 0.25 mmol), 4-methyl-1H-pyrazole (0.5 mL) and DIPEA (0.5 mL) were taken in a sealed vial and heated to 120° C. for 16 h. The reaction mixture was partitioned between EtOAc (10 mL) and $H_2O$ (10 mL). The organic layer was separated, dried over anhydrous $Na_2SO_4$ and concentrated under reduced pressure. The crude product was re-crystallized from hexane to afford 5-amino-8-(2,6-dimethyl-4-pyridyl)-7-(4-methylpyrazol-1-yl)-2-(3,3,3-trifluoropropyl)-[1,2,4]triazolo[4,3-c]pyrimidin-3-one (11 mg, 11%) as a yellow solid. The data for the title compound are in table 3.

Route aj

Example 2-51, 5-amino-8-[2-(hydroxymethyl)-6-methyl-4-pyridyl]-7-phenyl-2-(3,3,3-trifluoropropyl)-[1,2,4]triazolo[4,3-c]pyrimidin-3-one

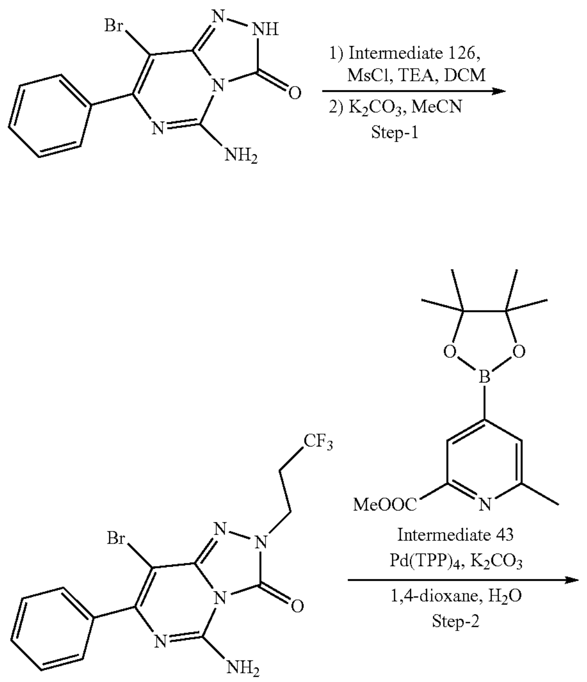

-continued

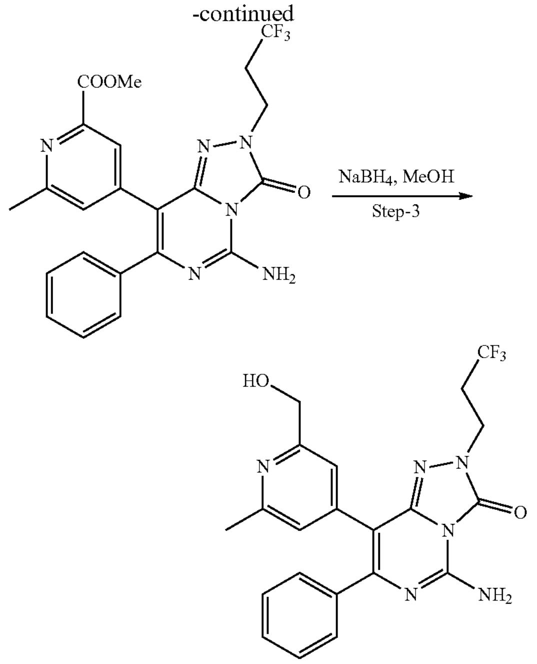

Example 2-51

Step 1; To a solution of 3,3,3-trifluoropropan-1-ol (400 mg, 3.6 mmol) in DCM (10 mL) at 0° C. was added TEA (1.3 mL, 9.6 mmol) followed by the dropwise addition of mesyl chloride (0.4 mL, 4.8 mmol). The reaction mixture was stirred at 0° C. for 1 h then partitioned between DCM (20 mL) and brine solution (20 mL). The organic layer was separated, dried over anhydrous $Na_2SO_4$ and concentrated under reduced pressure to afford 3,3,3-trifluoropropyl methanesulfonate. This intermediate was added to a suspension of 5-amino-8-bromo-7-phenyl-[1,2,4]triazolo[4,3-c]pyrimidin-3(2H)-one (1 g, 3.2 mmol) and $K_2CO_3$ (1.3 g, 9.6 mmol) in MeCN (20 mL) and the reaction mixture was stirred at 80° C. for 15 h. The reaction was partitioned between EtOAc (50 mL) and $H_2O$ (50 mL). The organic layer was separated, dried over anhydrous $Na_2SO_4$ and concentrated under reduced pressure. The crude product was triturated with MeOH (5 mL), filtered through a Buchner funnel and dried under vacuum to afford 5-amino-8-bromo-7-phenyl-2-(3,3,3-trifluoropropyl)-[1,2,4]triazolo[4,3-c]pyrimidin-3(2H)-one (700 mg, 53%) as an off-white solid.

LCMS (Method B): m/z 402 $(M+H)^+$ $(ES^+)$, at 2.69 min, UV active.

$^1H$ NMR: (400 MHz, DMSO-d6) δ: 8.26 (s, 2H), 7.64-7.61 (m, 2H), 7.47-7.44 (m, 3H), 4.10 (t, J=8.8 Hz, 2H), 2.84-2.76 (m, 2H).

Step 2; A mixture of 5-amino-8-bromo-7-phenyl-2-(3,3,3-trifluoropropyl)-[1,2,4]triazolo[4,3-c]pyrimidin-3(2H)-one (0.6 g, 1.49 mmol), methyl 6-methyl-4-(4,4,5,5-tetramethyl-1,3,2-dioxaborolan-2-yl)picolinate (1 g, 3.6 mmol) and $K_2CO_3$ (0.61 g, 4.47 mmol) in 1,4-dioxane (20 mL) and $H_2O$ (2 mL) was degassed for few minutes, $Pd(PPh_3)_4$ (17 mg, 0.015 mmol) was added, the vessel was sealed and heated to 120° C. for 5 h. The reaction mixture was partitioned between $H_2O$ (20 mL) and EtOAc (30 mL). The organic layer was separated, dried over anhydrous $Na_2SO_4$ and concentrated. The crude product was purified by Biotage-Isolera using 10 g silica snap and eluted with 0-80% EtOAc in hexane gradient to afford methyl 4-(5-amino-3-oxo-7-phenyl-2-(3,3,3-trifluoropropyl)-2,3-dihydro-[1,2,4]triazolo[4,3-c]pyrimidin-8-yl)-6-methylpicolinate (150 mg, 22%) as a yellow solid.

LCMS (Method A): m/z 472 $(M+H)^+$ $(ES^+)$, at 3.52 min, UV active.

$^1H$ NMR: (400 MHz, DMSO-d6) δ: 7.67 (s, 1H), 7.30-7.26 (m, 6H), 4.06 (t, J=6.5 Hz, 2H), 3.81 (s, 3H), 2.76-2.73 (m, 2H), 2.41 (s, 3H). Exchangeable —$NH_2$ Protons were not observed.

Step 3; To a solution of methyl 4-(5-amino-3-oxo-7-phenyl-2-(3,3,3-trifluoropropyl)-2,3-dihydro-[1,2,4]triazolo[4,3-c]pyrimidin-8-yl)-6-methylpicolinate (120 mg, 0.25 mmol) in MeOH at room temperature was added $NaBH_4$ (48 mg, 1.27 mmol) portionwise and the reaction stirred for 15 h. The reaction mixture was partitioned between DCM (20 mL) and saturated $NaHCO_3$ solution (10 mL). The organic layer was separated, dried over anhydrous sodium sulphate and concentrated under reduced pressure. The crude product was purified by Biotage-Isolera using 230-400 silica snap and was eluted with 0-100% EtOAc in hexane gradient to afford 5-amino-8-[2-(hydroxymethyl)-6-methyl-4-pyridyl]-7-phenyl-2-(3,3,3-trifluoropropyl)-[1,2,4]triazolo[4,3-c]pyrimidin-3-one (63 mg, 55%) as a yellow solid. The data for the title compound are in table 3.

Route ak: Typical Procedure for Boc Deprotection Using TFA

Example 2-55, 5-amino-8-(2,6-dimethyl-4-pyridyl)-7-phenyl-2-(3-piperidyl)-[1,2,4]triazolo[4,3-c]pyrimidin-3-one

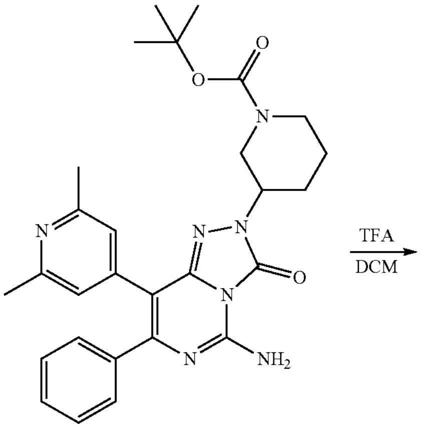

Example 2-54

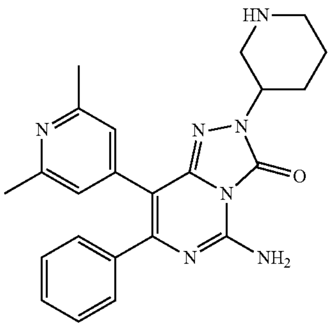

Example 2-55

A solution of tert-butyl 3-(5-amino-8-(2,6-dimethylpyridin-4-yl)-3-oxo-7-phenyl-[1,2,4]triazolo[4,3-c]pyrimidin-2(3H)-yl)piperidine-1-carboxylate (70 mg, 0.13 mmol) in 20% TFA in DCM (5 mL) was stirred at room temperature for 15 h, then concentrated. The crude mass was dissolved in MeOH (2 mL) and was passed through a DSC-SCX column (6 mL), washed with water (5 mL) and finally compound was eluted with 2M ammonia in MeOH (10 mL), concentrated and lyophilized to afford 5-amino-8-(2,6-dimethyl-4-pyridyl)-7-phenyl-2-(3-piperidyl)-[1,2,4]triazolo[4,3-c]pyrimidin-3-one (34 mg, 60%) as a yellow solid. The data for the title compound are in table 3.

Route al: Typical Procedure for the Preparation of Pyridine N-Oxides

Example 2-56, 5-amino-8-(2,6-dimethyl-1-oxido-pyridin-1-ium-4-yl)-7-phenyl-2-(3,3,3-trifluoropropyl)-[1,2,4]triazolo[4,3-c]pyrimidin-3-one

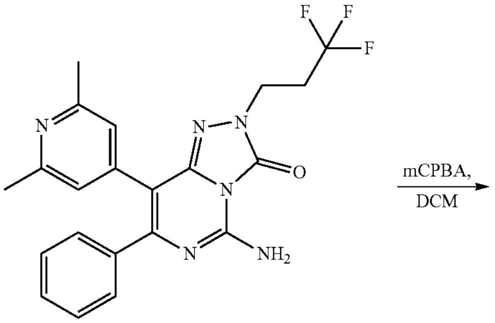

Example 2-6

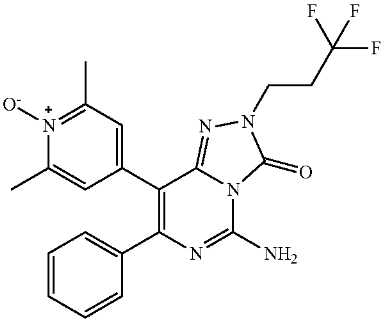

Example 2-56

To a stirred solution of 5-amino-8-(2,6-dimethyl-4-pyridyl)-7-phenyl-2-(3,3,3-trifluoropropyl)-[1,2,4]triazolo[4,3-c]pyrimidin-3-one (60 mg, 0.14 mmol) in DCM at 0° C. was added m-CPBA (30 mg, 0.16 mmol) portionwise and stirred at room temperature for 30 min. The reaction mixture was partitioned between EtOAc (20 mL) and $H_2O$ (10 mL). The organic layer was separated, dried over anhydrous $Na_2SO_4$ and concentrated under reduced pressure. The crude product was purified by Prep-HPLC (Method A). The collected fractions were concentrated under reduced pressure and the residue obtained was diluted with EtOAc (10 mL) and washed with 10% sodium bicarbonate solution (10 mL). The organic layer was separated, dried over anhydrous $Na_2SO_4$ and concentrated to afford 5-amino-8-(2,6-dimethyl-1-oxido-pyridin-1-ium-4-yl)-7-phenyl-2-(3,3,3-trifluoropropyl)-[1,2,4]triazolo[4,3-c]pyrimidin-3-one (30 mg, 48%) as a yellow solid. The data for the title compound are in table 3.

Route am: Typical Procedure for the Alkylation of Amines Via Reductive Amination Example 2-72, 5-amino-8-(2,6-dimethyl-4-pyridyl)-2-[[(2S)-4-methylmorpholin-2-yl]methyl]-7-phenyl-[1,2,4]triazolo[4,3-c]pyrimidin-3-one

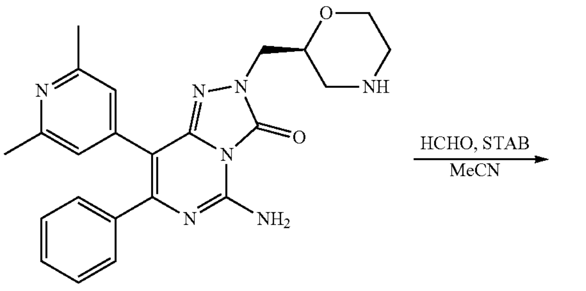

Example 2-71

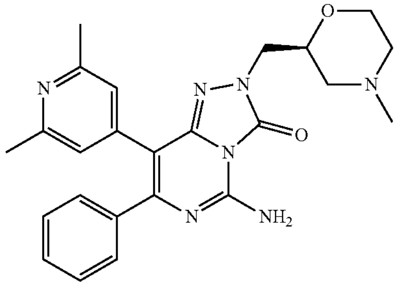
Example 2-72

To a suspension of (S)-5-amino-8-(2,6-dimethylpyridin-4-yl)-2-(morpholin-2-ylmethyl)-7-phenyl-[1,2,4]triazolo[4,3-c]pyrimidin-3(2H)-one (80 mg, 0.185 mmol) in MeCN was added 35% aqueous formaldehyde solution (16 mg, 0.185 mmol) and stirred for 10 min. Sodium triacetoxyborohydride (76 mg, 0.36 mmol) was added to the reaction mixture and stirred at room temperature for 15 min. The reaction mixture was partitioned between $H_2O$ (10 mL) and EtOAc (10 mL), the organic layer was separated, dried over anhydrous $Na_2SO_4$ and concentrated. The crude product was purified by Biotage-Isolera using 10 g silica snap and eluted with gradient 0-20% EtOAc in MeOH to afford (S)-5-amino-8-(2,6-dimethylpyridin-4-yl)-2-((4-methylmorpholin-2-yl)methyl)-7-phenyl-[1,2,4]triazolo[4,3-c]pyrimidin-3(2H)-one (30 mg, 38%) as yellow solid. The data for the title compound are in table 3.

Route an

Example 2-79, (R)-5-amino-8-(2,6-dimethylpyridin-4-yl)-2-(morpholin-3-ylmethyl)-7-phenyl-[1,2,4]triazolo[4,3-c]pyrimidin-3(2H)-one

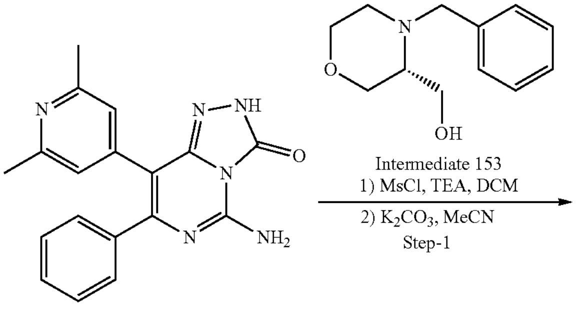

Intermediate 7

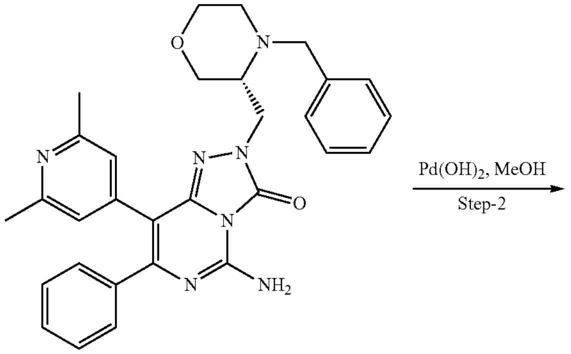

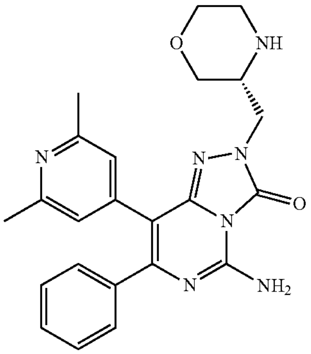

Step 1; Performed in a similar fashion to route b step 1, and purified by Prep-HPLC (Method-C) to afford (R)-5-amino-2-((4-benzylmorpholin-3-yl)methyl)-8-(2,6-dimethylpyridin-4-yl)-7-phenyl-[1,2,4]triazolo[4,3-c]pyrimidin-3(2H)-one (320 mg, 40%) as yellow solid.

LCMS (Method A): m/z 522 $(M+H)^+$ $(ES^+)$, at 2.37 min, UV active.

Step 2; To a mixture of (R)-5-amino-2-((4-benzylmorpholin-3-yl)methyl)-8-(2,6-dimethylpyridin-4-yl)-7-phenyl-[1,2,4]triazolo[4,3-c]pyrimidin-3(2H)-one (300 mg, 0.57 mmol) in MeOH (10 mL) was added $Pd(OH)_2$ and the reaction mixture was stirred for 15 h under an atmosphere of $H_2$ (balloon pressure). The reaction mixture was filtered through celite and washed with MeOH. The filtrate was concentrated under reduced pressure. The crude product was purified by Biotage isolera using 25 g silica snap, eluting with gradient 0-10% MeOH in EtOAc to afford (R)-5-amino-8-(2,6-dimethylpyridin-4-yl)-2-(morpholin-3-ylmethyl)-7-phenyl-[1,2,4]triazolo[4,3-c]pyrimidin-3(2H)-one (120 mg, 48%) as a yellow solid. The data for the title compound are in table 3.

Route ao: Typical Procedure for the Preparation of Alkylated Triazolopyrimidinones Via an Alcohol Tosylation and Displacement Reaction Example 2-81, 5-amino-8-(2,6-dimethyl-4-pyridyl)-7-phenyl-2-(tetrahydropyran-3-ylmethyl)-[1,2,4]triazolo[4,3-c]pyrimidin-3-one (Followed by Chiral Separation into its Enantiomers, 2-81 iso-1 and 2-81 iso-2)

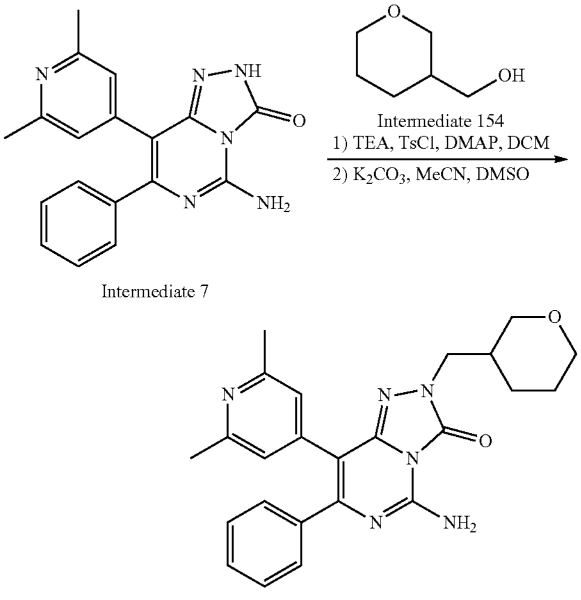

Intermediate 7

Example 2-81

To a solution of tosyl chloride (189.4 mg, 0.99 mmol), DMAP (11 mg, 0.09) and TEA (0.4 mL, 2.71 mmol) in DCM (10 mL) at 0° C. was added (tetrahydro-2H-pyran-3-yl) methanol (126 mg, 1.08 mmol) in DCM (1 mL) dropwise and the resultant reaction mixture was stirred at room temperature for 30 min. The reaction mixture was partitioned between DCM (20 mL) and $H_2O$ (20 mL). The organic layer was separated, dried over anhydrous $Na_2SO_4$ and concentrated under reduced pressure to obtain tosylated intermediate. This tosylated intermediate was taken in MeCN (20 mL) with 5-amino-8-(2,6-dimethylpyridin-4-yl)-7-phenyl-[1,2,4]triazolo[4,3-c]pyrimidin-3(2H)-one (300 mg, 0.90 mmol) and $K_2CO_3$ (374 mg, 2.71 mmol) and the resultant reaction mixture was heated to 50° C. for 6 h in sealed vial. The reaction mixture was partitioned between EtOAc (20 mL) and $H_2O$ (20 mL). The organic layer was separated, dried over anhydrous $Na_2SO_4$ and concentrated under reduced pressure. The crude product was purified by Biotage-Isolera using 10 g silica gel snap, and was eluted with 0-100% EtOAc in Pet ether gradient to afford 5-amino-8-(2,6-dimethyl-4-pyridyl)-7-phenyl-2-(tetrahydropyran-3-ylmethyl)-[1,2,4]triazolo[4,3-c]pyrimidin-3-one as a yellow solid.

The racemic compound was purified by Chiral SFC (method C) to afford 2-81 iso-1 as the first eluting peak and 2-81 iso-2 as the second eluting peak. The data for the title compounds are in Table 3.

Route ap: Typical Procedure for Boc Deprotection Using HCl

Example 2-86, 5-amino-8-(2,6-dimethyl-4-pyridyl)-2-[[(2R)-1-methylpiperazin-2-yl]methyl]-7-phenyl-[1,2,4]triazolo[4,3-c]pyrimidin-3-one

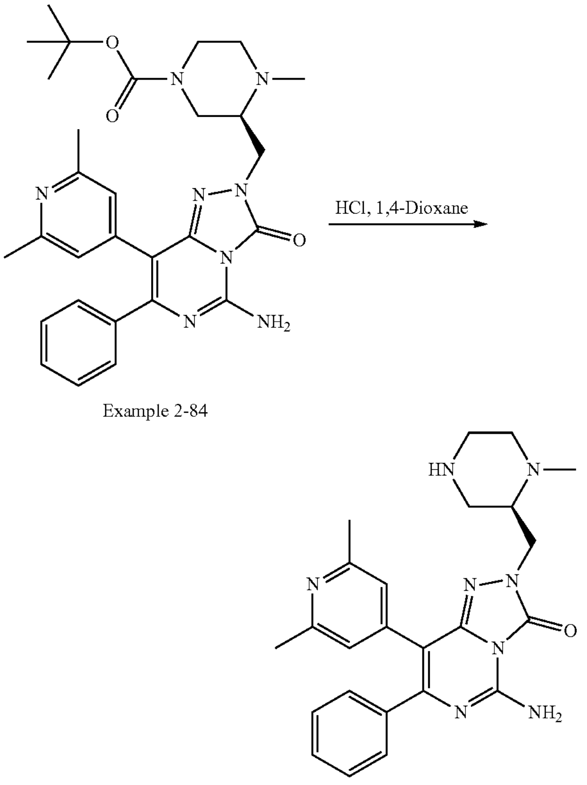

Example 2-84

Example 2-86

To a solution of tert-butyl (R)-3-((5-amino-8-(2,6-dimethylpyridin-4-yl)-3-oxo-7-phenyl-[1,2,4]triazolo[4,3-c]pyrimidin-2(3H)-yl)methyl)-4-methylpiperazine-1-carboxylate (250 mg, 0.45 mmol) in 1,4-dioxane (10 mL) at 0° C. was added HCl in 1,4-dioxane (4 N solution, 5 mL) and stirred at room temperature for 6 h. The mixture was concentrated and the residue was washed with diethyl ether (10 mL) and decanted. The crude product was purified by Prep-HPLC (Method A), the pure fractions were concentrated and the residue was diluted with 10% MeOH in DCM (10 mL) and loaded on SCX cartridge. Cartridge was washed with $H_2O$ and MeOH and the product was eluted with 20% ammonia in MeOH (10 mL) and concentrated under reduced pressure to afford 5-amino-8-(2,6-dimethyl-4-pyridyl)-2-[[(2R)-1-methylpiperazin-2-yl]methyl]-7-phenyl-[1,2,4]triazolo[4,3-c]pyrimidin-3-one (175 mg, 87%) as a yellow solid. The data for the title compound are in table 3.

Route aq: Typical Procedure for the Preparation of Alkylated Triazolopyrimidinones Via an Alcohol Tosylation and Displacement Reaction, Followed by a Suzuki Coupling and Ester Reduction Examples 2-91 ios-1 and 2-91 iso-2, 5-amino-8-[2-(hydroxymethyl)-6-methyl-4-pyridyl]-7-phenyl-2-(tetrahydropyran-2-ylmethyl)-[1,2,4]triazolo[4,3-c]pyrimidin-3-one

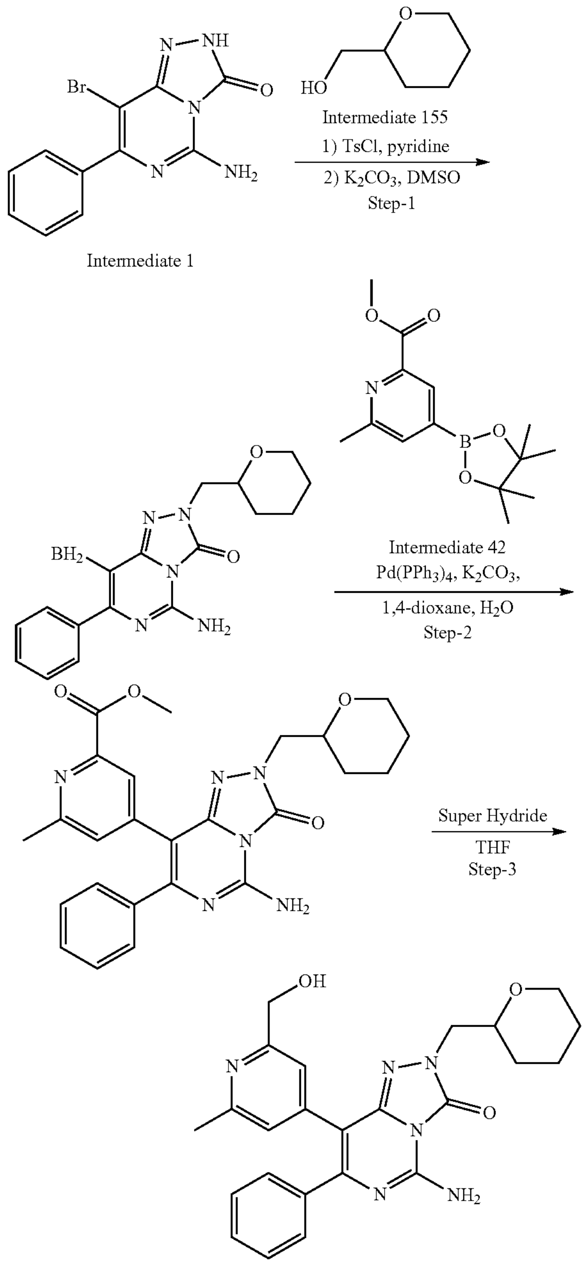

Example 2-91

Step 1; To a solution of tetrahydro-2H-pyran-2-yl)methanol (500 mg, 4.30 mmol) in pyridine (5 mL) was added 4-toluene sulfonyl chloride (984 mg, 5.16 mmol) at 0° C. and resultant reaction mixture was stirred at room temperature for 16 h. The mixture was concentrated and diluted with $H_2O$ (10 mL). The reaction was extracted with EtOAc (2×10 mL), the combined organic layers were washed with brine solution (20 mL), dried over $Na_2SO_4$ and concentrated to obtain tosylated intermediate. The obtained tosylated intermediate was taken in DMSO with 5-amino-8-bromo-7-phenyl-[1,2,4]triazolo[4,3-c]pyrimidin-3(2H)-one (770 mg, 2.52 mmol) and $K_2CO_3$ (1.04 g, 7.57 mmol) and the resultant reaction mixture was heated to 70° C. for 7 h. The reaction mixture was partitioned between EtOAc (20 mL) and $H_2O$ (20 mL). The organic layer was separated and concentrated under reduced pressure. The crude product was purified by Biotage Isolera column chromatography using silica (230-400) mesh, eluted with 0-100% EtOAc in Pet ether gradient to afford 5-amino-8-bromo-7-phenyl-2-((tetrahydro-2H-pyran-2-yl)methyl)-[1,2,4]triazolo[4,3-c]pyrimidin-3(2H)-one (420 mg, 41%) as a white solid.

LCMS (Method A): m/z 404 $(M+H)^+$ $(ES^+)$, at 2.26 min, UV active.

$^1H$ NMR: (400 MHz, DMSO-d6) δ: 7.63-7.61 (m, 2H), 7.48-7.44 (m, 3H), 3.92-3.83 (m, 2H), 3.76-3.69 (m, 2H), 3.34 (m, 1H), 1.79 (s, 1H), 1.67 (d, J=12.40 Hz, 1H), 1.47 (s, 3H), 1.27-1.18 (m, 1H). Exchangeable —$NH_2$ Protons were not observed.

Step 2; Performed in a similar fashion to route a step 2, to afford methyl 4-(5-amino-3-oxo-7-phenyl-2-((tetrahydro-2H-pyran-2-yl)methyl)-2,3-dihydro-[1,2,4]triazolo[4,3-c]pyrimidin-8-yl)picolinate (350 mg, 70%) as a yellow solid.

LCMS (Method A): m/z 473 $(M-H)^-$ $(ES^-)$, at 2.26 min, UV active.

Step 3; Performed in a similar fashion to route o step 2, to afford 5-amino-8-(2-(hydroxymethyl)-6-methylpyridin-4-yl)-7-phenyl-2-((tetrahydro-2H-pyran-2-yl)methyl)-[1,2,4]triazolo[4,3-c]pyrimidin-3(2H)-one as yellow solid.

The racemic compound was purified by Chiral SFC (method D) to afford 2-91 iso-1 as the first eluting peak and 2-91 iso-2 as the second eluting peak. The data for the title compounds are in Table 3.

Route ar: Typical Procedure for the Preparation of Amine Analogues Via an Alcohol Tosylation and Displacement Reaction, Followed by a Suzuki Coupling Example 2-98, 5-amino-8-(2,6-dimethyl-4-pyridyl)-2-[2-(3-methyl-1-piperidyl)ethyl]-7-phenyl-[1,2,4]triazolo[4,3-c]pyrimidin-3-one

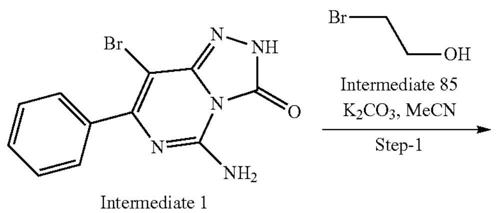

-continued

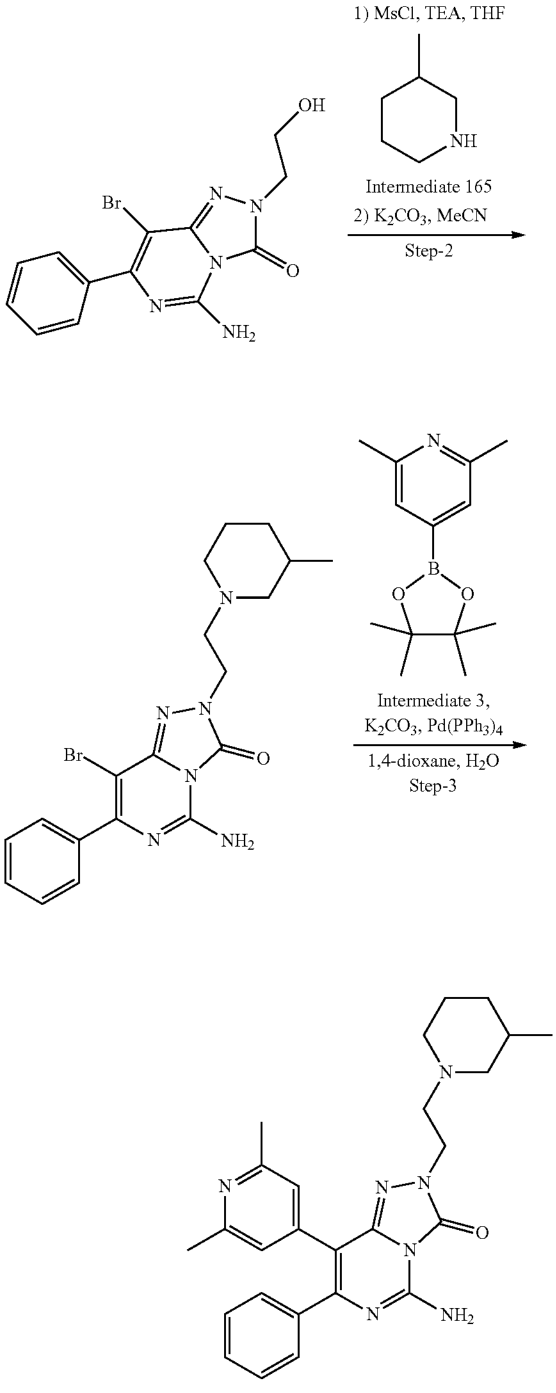

Example 2-98

Step 1; To a suspension of 5-amino-8-bromo-7-phenyl-[1,2,4]triazolo[4,3-c]pyrimidin-3(2H)-one (2 g, 6.56 mmol) and $K_2CO_3$ (1.81 g, 13.12 mmol) in MeCN (40 mL) at room temperature was added 2-bromoethan-1-ol (0.98 g, 7.87 mol) and the reaction mixture was heated at 80° C. for 15 h. The reaction mixture was partitioned between EtOAc (50 mL) and $H_2O$ (30 mL). The organic layer was separated, dried over anhydrous $Na_2SO_4$ and concentrated under reduced pressure to afford 5-amino-8-bromo-2-(2-hydroxy-ethyl)-7-phenyl-[1,2,4]triazolo[4,3-c]pyrimidin-3(2H)-one (1 g, 44%) as an off-white solid.

LCMS (Method B): m/z 350 $(M+H)^+$ $(ES^+)$, at 2.26 min, UV active.

$^1H$ NMR: (400 MHz, DMSO-d6) δ: 7.62-7.60 (m, 2H), 7.46-7.44 (m, 3H), 4.83 (t, J=6.0 Hz, 1H), 3.86 (t, J=5.6 Hz, 2H), 3.72-3.68 (m, 2H). Exchangeable —$NH_2$ Protons were not observed.

Step 2; To a suspension 5-amino-8-bromo-2-(2-hydroxy-ethyl)-7-phenyl-[1,2,4]triazolo[4,3-c]pyrimidin-3(2H)-one (0.3 g, 0.86 mmol) and TEA (0.17 g, 1.72 mmol) in THF (5 mL) at 0° C. was added methane sulfonylchloride (0.14 g, 1.03 mol) slowly and the reaction mixture was stirred at 0° C. for 20 min. The reaction mixture was concentrated under reduced pressure. The residue obtained was taken in MeCN (5 mL) and $K_2CO_3$ (0.36 g, 2.58 mmol) and 3-methylpiperidine (0.11 g, 1.29 mmol) were added. The reaction mixture was heated at 100° C. for 15 h. The reaction mixture was partitioned between EtOAc (15 mL) and $H_2O$ (15 mL). The organic layer was separated, dried over anhydrous $Na_2SO_4$ and concentrated then purified by Biotage-Isolera using 10 g silica snap and eluted with gradient 1-100% EtOAc in Hexane to afford 5-amino-8-bromo-2-(2-(3-methylpiperidin-1-yl)ethyl)-7-phenyl-[1,2,4]triazolo[4,3-c]pyrimidin-3(2H)-one (120 mg, 32%) as an off-white solid.

LCMS (Method B): m/z 431 $(M+H)^+$ $(ES^+)$, at 2.26 min, UV active.

$^1H$ NMR: (400 MHz, DMSO-d6) δ: 7.62-7.60 (m, 2H), 7.45-7.44 (m, 3H), 3.92 (t, J=5.2 Hz, 2H), 2.78 (t, J=5.2 Hz, 2H), 2.66-2.60 (m, 4H), 1.62-1.52 (m, 4H), 1.41-1.38 (m, 1H), 0.81 (d, J=6.4 Hz, 3H). Exchangeable —$NH_2$ Protons were not observed.

Step 3; Prepared in a similar fashion to route a step 2, to afford 5-amino-8-(2,6-dimethyl-4-pyridyl)-2-[2-(3-methyl-1-piperidyl)ethyl]-7-phenyl-[1,2,4]triazolo[4,3-c]pyrimidin-3-one as a yellow solid. The data for the title compound are in table 3.

Route as

Examples 2-109, methyl 3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl]propanoate Example 2-110, 3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl]propanoic acid

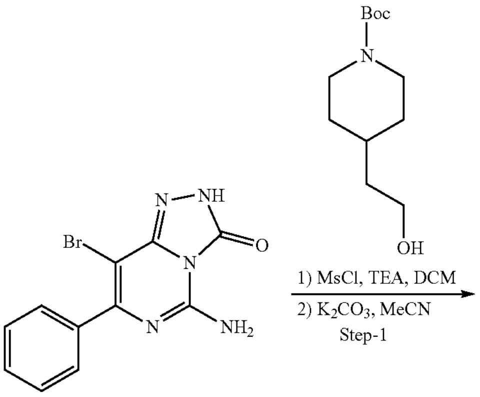

-continued

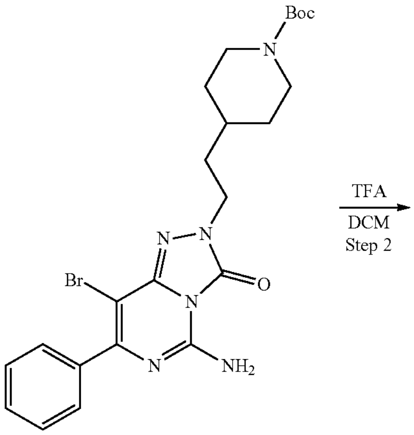

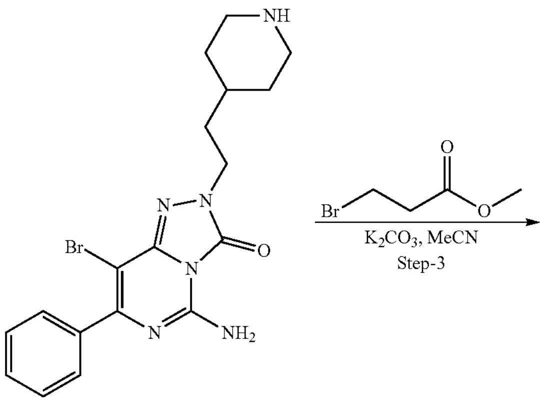

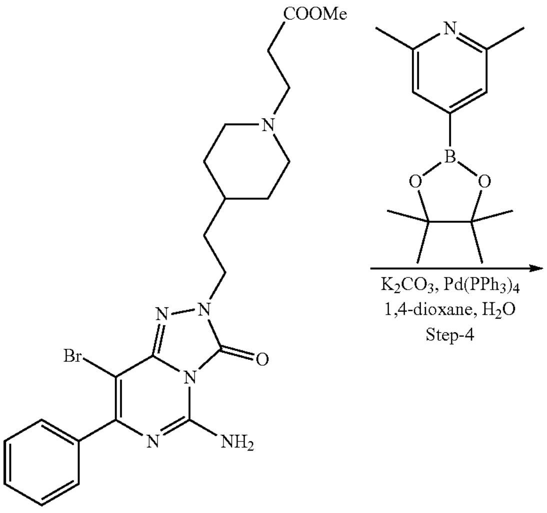

-continued

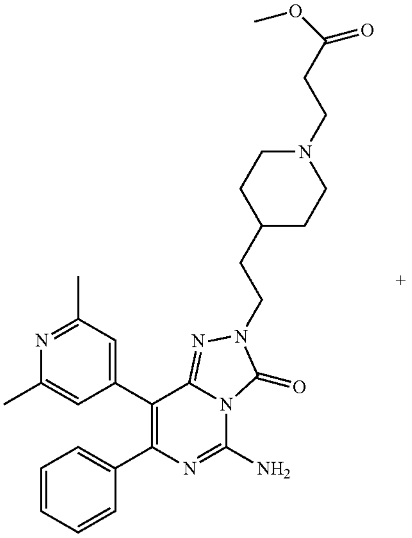

Example 2-109

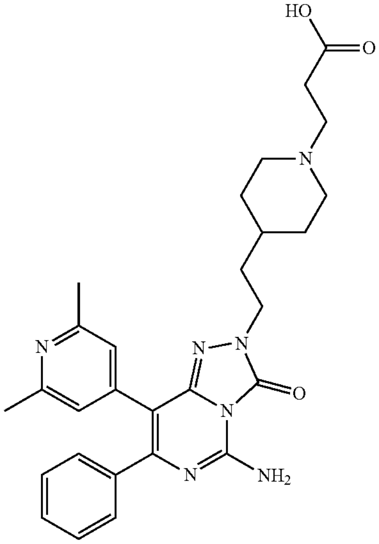

Example 2-110

Step 1; Performed in a similar fashion to route b step 1, to afford tert-butyl 4-(2-(5-amino-8-bromo-3-oxo-7-phenyl-[1,2,4]triazolo[4,3-c]pyrimidin-2(3H)-yl)ethyl)piperidine-1-carboxylate (400 mg, 57%) as yellow solid.

LCMS (Method A): m/z 417 $(M+H\text{-}Boc)^+$ $(ES^+)$, at 3.23 min, UV active.

$^1H$ NMR: (400 MHz, DMSO-d6) δ: 7.62-7.61 (m, 2H), 7.46-7.44 (m, 3H), 3.88-3.86 (m, 4H), 2.51 (t, J=2.0 Hz, 2H), 1.72-1.68 (m, 4H), 1.66 (t, J=1.6 Hz, 1H), 1.65 (s, 9H), 1.39-1.38 (m, 2H). Exchangeable $—NH_2$ Protons were not observed.

Step 2; To a solution of tert-butyl 4-(2-(5-amino-8-bromo-3-oxo-7-phenyl-[1,2,4]triazolo[4,3-c]pyrimidin-2(3H)-yl) ethyl)piperidine-1-carboxylate (400 mg, 0.77 mmol) in DCM (10 mL) was added TFA (2 mL) and stirred for 2 h at room temperature. The reaction mixture was partitioned between DCM (10 mL) and 1.5 N sodium bicarbonate solution (5 mL). The organic layer was separated, dried over anhydrous $Na_2SO_4$ and concentrated to afford 5-amino-8-bromo-7-phenyl-2-(2-(piperidin-4-yl)ethyl)-[1,2,4]triazolo [4,3-c]pyrimidin-3(2H)-one (300 mg, 90%) as a yellow solid.

LCMS (Method A): m/z 417 $(M+H)^+$ $(ES^+)$, at 3.23 min, UV active.

$^1H$ NMR: (400 MHz, DMSO-d6) δ: 7.62-7.61 (m, 2H), 7.46-7.44 (m, 3H), 3.88-3.86 (m, 4H), 2.51 (t, J=2.0 Hz, 2H), 1.72-1.68 (m, 4H), 1.66 (t, J=1.6 Hz, 2H), 1.39-1.38 (m, 2H). Exchangeable —$NH_2$ Protons were not observed.

Step 3; Performed in a similar fashion to route a step 1, to afford methyl 3-(4-(2-(5-amino-8-bromo-3-oxo-7-phenyl-[1,2,4]triazolo[4,3-c]pyrimidin-2(3H)-yl)ethyl)piperidin-1-yl)propanoate (200 mg, 45%) as a yellow solid.

LCMS (Method A): m/z 503 $(M+H)^+$ $(ES^+)$, at 2.28 min, UV active.

Step 4; Performed in a similar fashion to route a step 2 and purified by prep HPLC (Method-A). Fractions were concentrated under reduced pressure, the residue obtained was partitioned between 10% MeOH in DCM (15 mL) and 10% $NaHCO_3$ solution (10 mL). The organic layer was separated, dried over anhydrous $Na_2SO_4$ and concentrated under reduced pressure to afford methyl 3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl]propanoate as a yellow solid (22 mg, 21%). Also isolated during the purification was 3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl]propanoic acid (20 mg, 20%) as a yellow solid. The data for the title compounds are in table 3.

Route at: Typical Procedure for the Preparation of Analogues Via an $S_NAr$ Reaction Example 3-1, 5-amino-8-(2,6-dimethyl-4-pyridyl)-7-morpholino-2-(3,3,3-trifluoropropyl)-[1,2,4]triazolo[4,3-c]pyrimidin-3-one

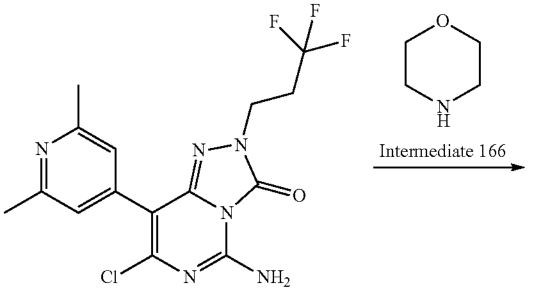

Intermediate 131

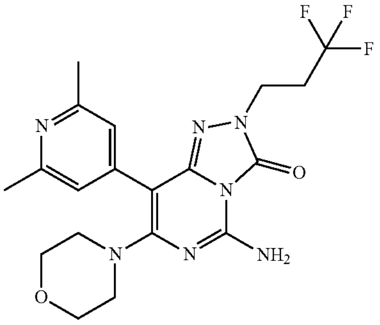

Example 3-1

5-amino-7-chloro-8-(2,6-dimethylpyridin-4-yl)-2-(3,3,3-trifluoropropyl)-[1,2,4]triazolo[4,3-c]pyrimidin-3(2H)-one (100 mg, 0.25 mmol) in morpholine (2 mL) was taken in a sealed tube and heated in a pre-heated oil bath at 120° C. and stirred for 15 h. The reaction mixture was partitioned between $H_2O$ (20 mL) and EtOAc (30 mL). The organic layer was separated, dried over anhydrous $Na_2SO_4$ and concentrated. The crude compound was purified by Biotage-Isolera using 10 g silica snap and was eluted with 0-100% EtOAc in hexane gradient to afford 5-amino-8-(2,6-dimethyl-4-pyridyl)-7-morpholino-2-(3,3,3-trifluoropropyl)-[1,2,4]triazolo[4,3-c]pyrimidin-3-one (55 mg, 45%) as a yellow solid. The data for the title compound are in table 3.

Route au

Example 3-6, methyl 5-amino-8-(2,6-dimethyl-4-pyridyl)-3-oxo-2-(3,3,3-trifluoropropyl)-[1,2,4]triazolo[4,3-c]pyrimidine-7-carboxylate

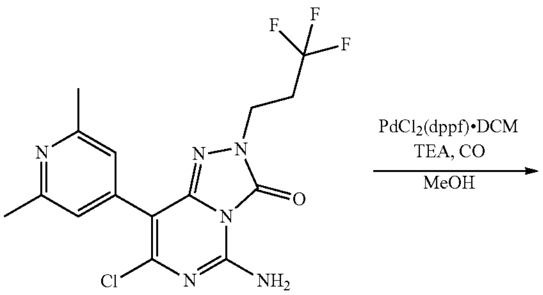

Intermediate 131

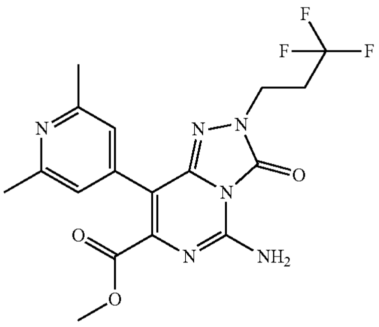

Example 3-6

To a suspension of 5-amino-7-chloro-8-(2,6-dimethylpyridin-4-yl)-2-(3,3,3-trifluoropropyl)-[1,2,4]triazolo[4,3-c]pyrimidin-3(2H)-one (100 mg, 0.25 mmol) in MeOH (10 mL) was added TEA (0.3 mL, 0.35 mmol) and $PdCl_2$ (dppf)·DCM (50 mg, 1.09 mmol). The reaction mass was stirred at 100° C. under 5 $kg/cm^2$ carbon monoxide pressure in an autoclave for 16 h. The reaction mixture was partitioned between EtOAc (10 mL) and $H_2O$ (10 mL). The organic layer was separated, dried over anhydrous $Na_2SO_4$ and concentrated under reduced pressure. The crude product was purified by Biotage-Isolera using 10 g silica snap and was eluted with 0-100% EtOAc in hexane gradient to afford methyl 5-amino-8-(2,6-dimethyl-4-pyridyl)-3-oxo-2-(3,3,3-trifluoropropyl)-[1,2,4]triazolo[4,3-c]pyrimidine-7-carboxylate (14 mg, 14%) as a yellow solid. The data for the title compound are in table 3.

/Route av

Example 3-8, 5-amino-8-(2,6-dimethyl-4-pyridyl)-7-methoxy-2-(3,3,3-trifluoropropyl)-[1,2,4]triazolo[4,3-c]pyrimidin-3-one

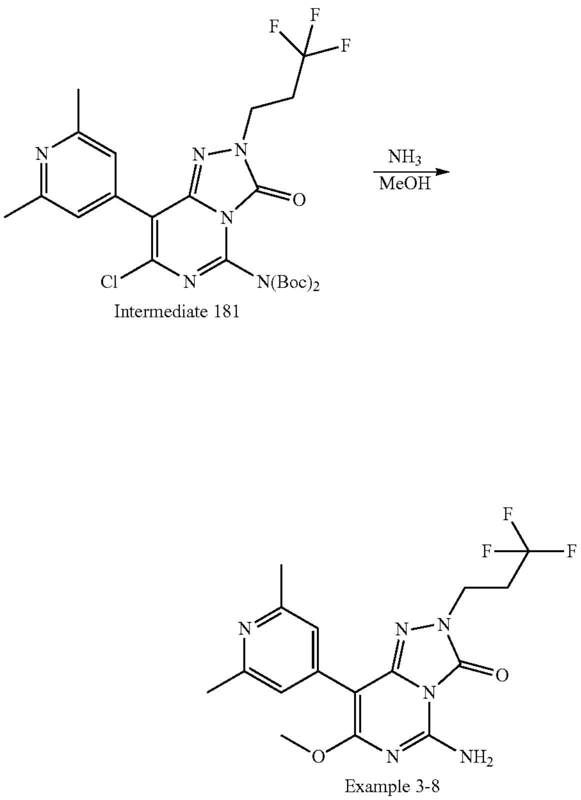

A suspension of Di-boc protected 5-amino-7-chloro-8-(2,6-dimethylpyridin-4-yl)-2-(3,3,3-trifluoropropyl)-[1,2,4]triazolo[4,3-c]pyrimidin-3(2H)-one (100 mg, 0.25 mmol) in MeOH (10 mL) was cooled to −20° C. and purged with ammonia gas for 5 min in an autoclave vessel. The vessel was sealed and heated to 100° C. for 16 h. The reaction mixture was concentrated under reduced pressure. The crude was purified by Prep-HPLC (Method A). Collected fractions were concentrated and the residue obtained was diluted with EtOAc (10 mL), washed with 10% sodium bicarbonate solution (10 mL). The organic layer was separated, dried over anhydrous $Na_2SO_4$ and concentrated to afford 5-amino-8-(2,6-dimethyl-4-pyridyl)-7-methoxy-2-(3,3,3-trifluoropropyl)-[1,2,4]triazolo[4,3-c]pyrimidin-3-one (16 mg, 24%) as a yellow solid. The data for the title compound are in table 3.

Route aw

Example 3-9, 5-amino-8-(2,6-dimethyl-4-pyridyl)-7-[(Z)-1-methylprop-1-enyl]-2-(3,3,3-trifluoropropyl)-[1,2,4]triazolo[4,3-c]pyrimidin-3-one Example 3-10, 5-amino-8-(2,6-dimethyl-4-pyridyl)-7-[(E)-1-methylprop-1-enyl]-2-(3,3,3-trifluoropropyl)-[1,2,4]triazolo[4,3-c]pyrimidin-3-one

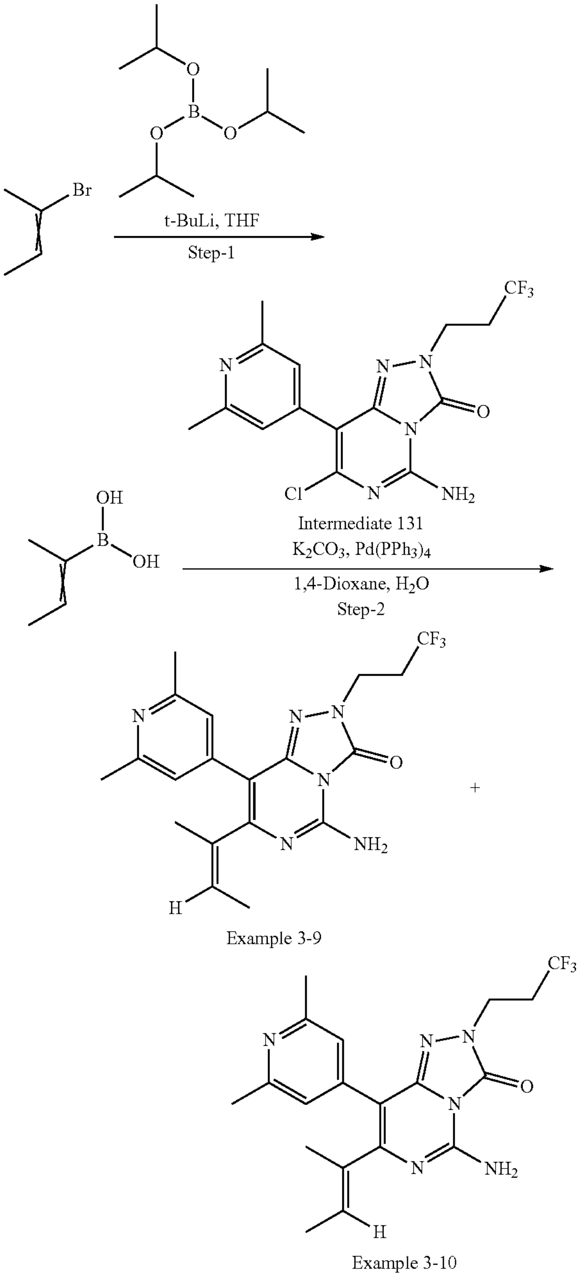

Step 1; To a solution of 2-bromobut-2-ene (100 mg, 0.740 mmol) in THF (5 mL) was added t-BuLi (1.7 M in Pentane, 0.43 mL, 1.629 mmol) dropwise at −78° C. The solution was stirred at −78° C. for 1 h and then tri-isopropylborate (0.26 mL, 1.111 mmol) was added. The reaction mixture was stirred at −78° C. for 4 h. The reaction mixture was quenched with saturated $NH_4C_1$ (5 mL) and was extracted with diethyl ether (10 mL). The organic layer was separated, dried over $Na_2SO_4$ and concentrated to afford but-2-en-2-ylboronic acid as a white solid. The crude product was taken on to the next step without purification or analysis.

Step 2; Performed in a similar fashion to route a step 2 to give a mixture of alkene regioisomers. These were separated by MD Auto-prep (method A) to afford 5-amino-8-(2,6-dimethyl-4-pyridyl)-7-[(Z)-1-methylprop-1-enyl]-2-(3,3,3-trifluoropropyl)-[1,2,4]triazolo[4,3-c]pyrimidin-3-one (50 mg, 13%) and 5-amino-8-(2,6-dimethyl-4-pyridyl)-7-[(E)-1-methylprop-1-enyl]-2-(3,3,3-trifluoropropyl)-[1,2,4]triazolo[4,3-c]pyrimidin-3-one (16 mg, 4%). The data for the title compounds are in table 3. Alkene geometry assigned by NOE.

TABLE 1

| Examples 1-1 to 3-10 | |
|---|---|
| 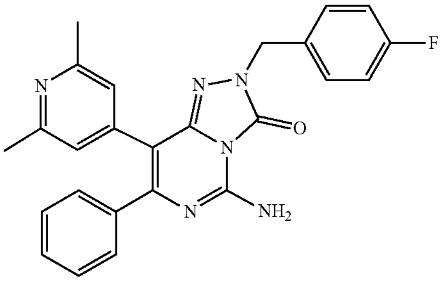 [SMILES: Cc1cc(-c2c(-c3ccccc3)nc(N)n3c(=O)n(Cc4ccc(F)cc4)nc23)cc(C)n1] | Example 1-1 |
| 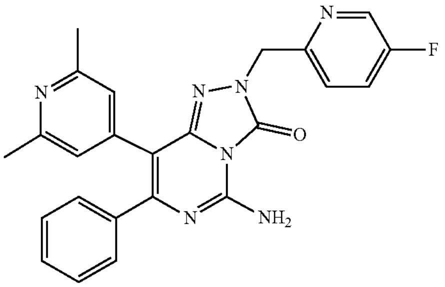 [SMILES: Cc1cc(-c2c(-c3ccccc3)nc(N)n3c(=O)n(Cc4ccc(F)cn4)nc23)cc(C)n1] | Example 1-2 |
| 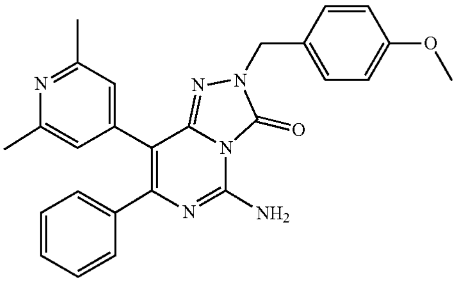 | Example 1-3 |
| 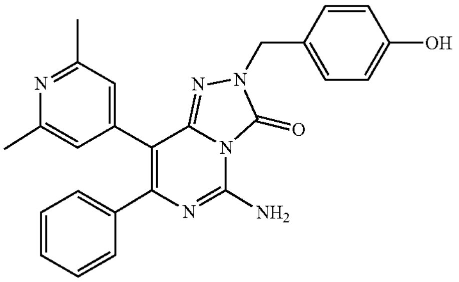 [SMILES: Cc1cc(-c2c(-c3ccccc3)nc(N)n3c(=O)n(Cc4ccc(O)cc4)nc23)cc(C)n1] | Example 1-4 |

TABLE 1-continued
| Examples 1-1 to 3-10 | |
|---|---|
| 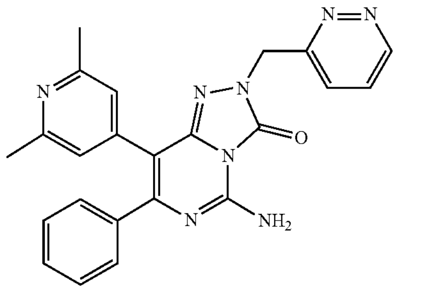 [SMILES: Cc1cc(-c2c(-c3ccccc3)nc(N)n3c(=O)n(Cc4cccnn4)nc23)cc(C)n1] | Example 1-5 |
| 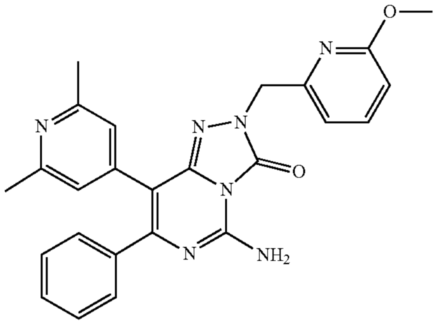 | Example 1-6 |
| 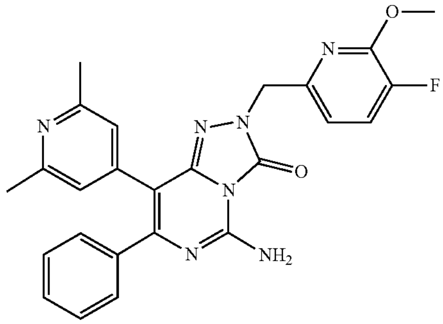 [SMILES: COc1nc(Cn2nc3c(-c4cc(C)nc(C)c4)c(-c4ccccc4)nc(N)n3c2=O)ccc1F] | Example 1-7 |
| 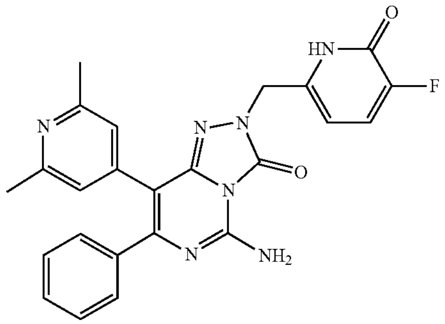 [SMILES: Cc1cc(-c2c(-c3ccccc3)nc(N)n3c(=O)n(Cc4ccc(F)c(=O)[nH]4)nc23)cc(C)n1] | Example 1-8 |
| 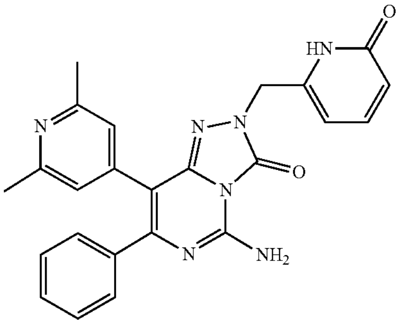 [SMILES: Cc1cc(-c2c(-c3ccccc3)nc(N)n3c(=O)n(Cc4cccc(=O)[nH]4)nc23)cc(C)n1] | Example 1-9 |

TABLE 1-continued
| Examples 1-1 to 3-10 |
| --- |
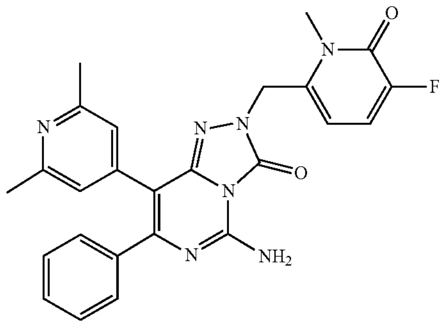 [SMILES: Cc1cc(-c2c(-c3ccccc3)nc(N)n3c(=O)n(Cc4ccc(F)c(=O)n4C)nc23)cc(C)n1]
Example 1-10
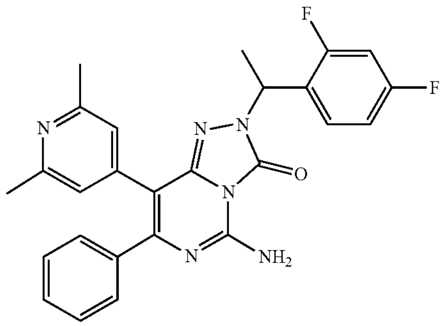 [SMILES: Cc1cc(-c2c(-c3ccccc3)nc(N)n3c(=O)n(C(C)c4ccc(F)cc4F)nc23)cc(C)n1]
Example 1-11
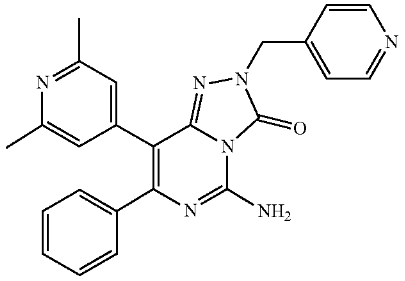 [SMILES: Cc1cc(-c2c(-c3ccccc3)nc(N)n3c(=O)n(Cc4ccncc4)nc23)cc(C)n1]
Example 1-12
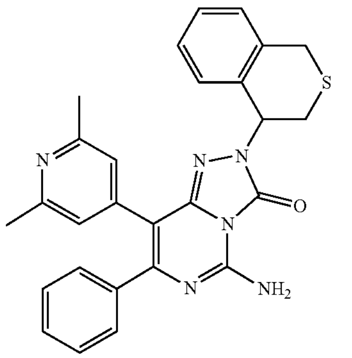 [SMILES: Cc1cc(-c2c(-c3ccccc3)nc(N)n3c(=O)n(C4CSCc5ccccc54)nc23)cc(C)n1]
Example 1-13

TABLE 1-continued
| Examples 1-1 to 3-10 | |
|---|---|
| 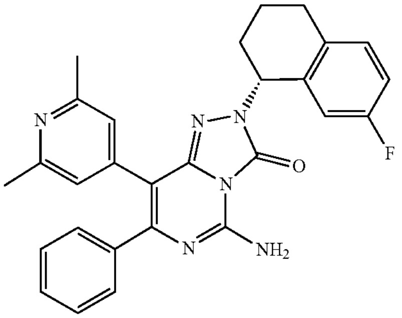 [SMILES: Cc1cc(-c2c(-c3ccccc3)nc(N)n3c(=O)n([C@@H]4CCCc5ccc(F)cc54)nc23)cc(C)n1] | Example 1-14 |
| 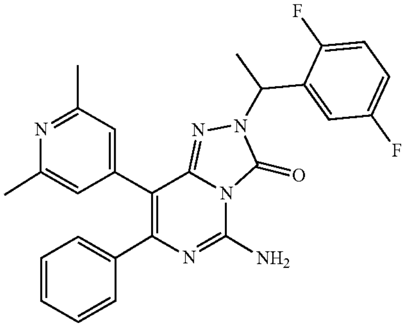 [SMILES: Cc1cc(-c2c(-c3ccccc3)nc(N)n3c(=O)n(C(C)c4cc(F)ccc4F)nc23)cc(C)n1] | Example 1-15 |
| 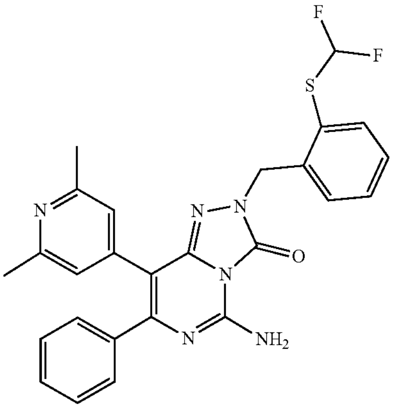 [SMILES: Cc1cc(-c2c(-c3ccccc3)nc(N)n3c(=O)n(Cc4ccccc4SC(F)F)nc23)cc(C)n1] | Example 1-16 |
| 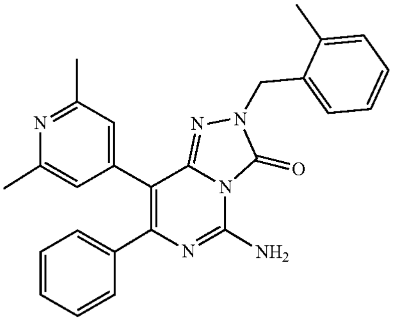 [SMILES: Cc1cc(-c2c(-c3ccccc3)nc(N)n3c(=O)n(Cc4ccccc4C)nc23)cc(C)n1] | Example 1-17 |

TABLE 1-continued
| Examples 1-1 to 3-10 | |
|---|---|
| 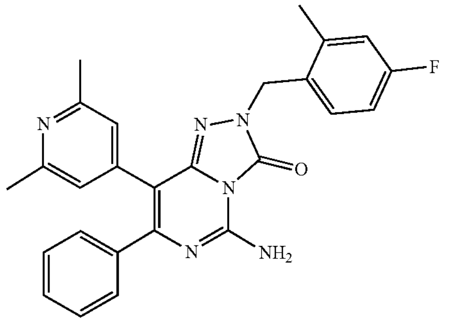 [SMILES: Cc1cc(-c2c(-c3ccccc3)nc(N)n3c(=O)n(Cc4ccc(F)cc4C)nc23)cc(C)n1] | Example 1-18 |
| 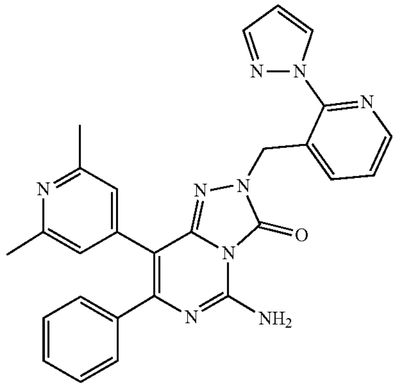 [SMILES: Cc1cc(-c2c(-c3ccccc3)nc(N)n3c(=O)n(Cc4cccnc4-n4cccn4)nc23)cc(C)n1] | Example 1-19 |
| 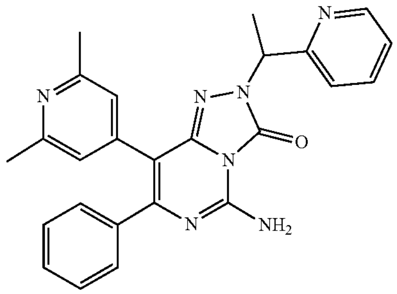 [SMILES: Cc1cc(-c2c(-c3ccccc3)nc(N)n3c(=O)n(C(C)c4ccccn4)nc23)cc(C)n1] | Example 1-20 |
| 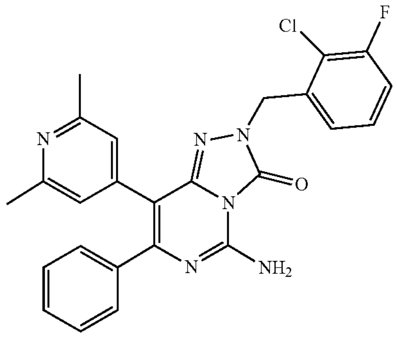 [SMILES: Cc1cc(-c2c(-c3ccccc3)nc(N)n3c(=O)n(Cc4cccc(F)c4Cl)nc23)cc(C)n1] | Example 1-21 |

TABLE 1-continued
| Examples 1-1 to 3-10 |
|---|
| 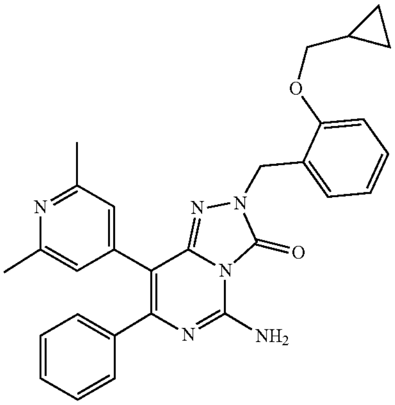 [SMILES: Cc1cc(-c2c(-c3ccccc3)nc(N)n3c(=O)n(Cc4ccccc4OCC4CC4)nc23)cc(C)n1] Example 1-22 |
| 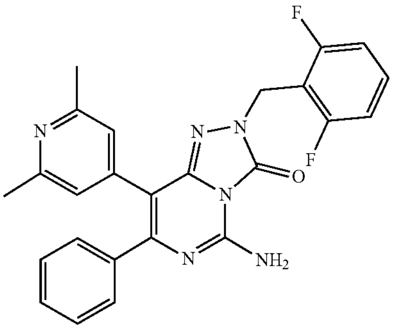 [SMILES: Cc1cc(-c2c(-c3ccccc3)nc(N)n3c(=O)n(Cc4c(F)cccc4F)nc23)cc(C)n1] Example 1-23 |
| 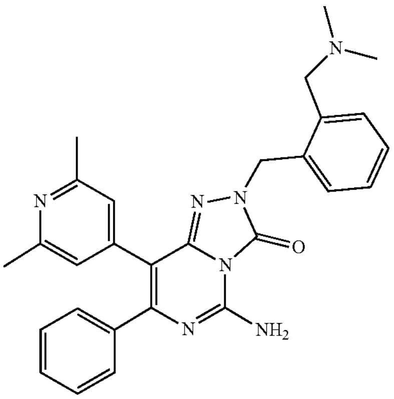 [SMILES: Cc1cc(-c2c(-c3ccccc3)nc(N)n3c(=O)n(Cc4ccccc4CN(C)C)nc23)cc(C)n1] Example 1-24 |
| 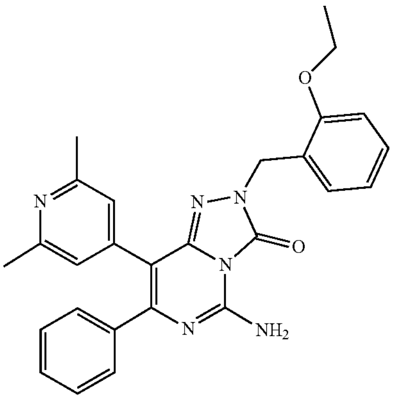 [SMILES: CCOc1ccccc1Cn1nc2c(-c3cc(C)nc(C)c3)c(-c3ccccc3)nc(N)n2c1=O] Example 1-25 |

TABLE 1-continued
Examples 1-1 to 3-10
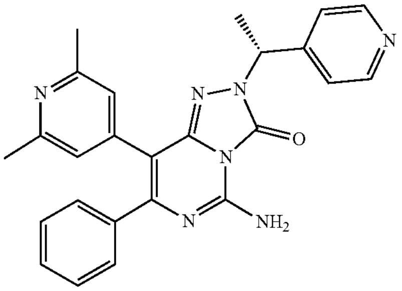 [SMILES: Cc1cc(-c2c(-c3ccccc3)nc(N)n3c(=O)n([C@H](C)c4ccncc4)nc23)cc(C)n1]
Example 1-26
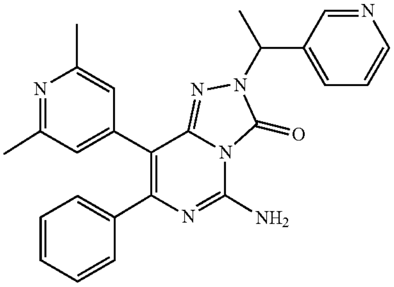 [SMILES: Cc1cc(-c2c(-c3ccccc3)nc(N)n3c(=O)n(C(C)c4cccnc4)nc23)cc(C)n1]
Example 1-27
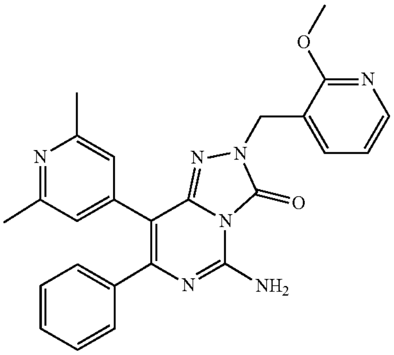 [SMILES: COc1ncccc1Cn1nc2c(-c3cc(C)nc(C)c3)c(-c3ccccc3)nc(N)n2c1=O]
Example 1-28
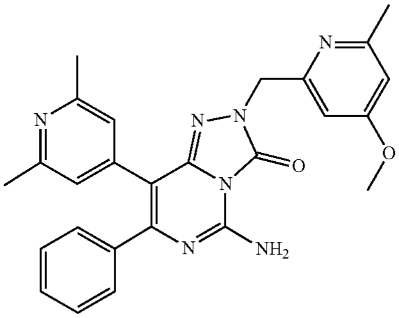
Example 1-29

TABLE 1-continued
| Examples 1-1 to 3-10 | |
|---|---|
| 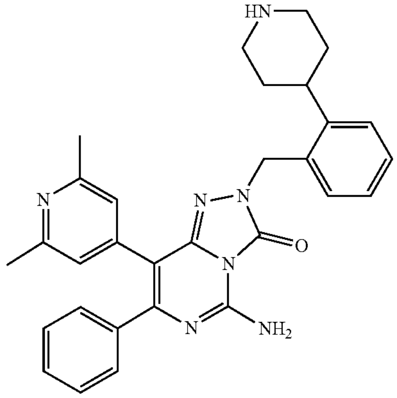 [SMILES: Cc1cc(-c2c(-c3ccccc3)nc(N)n3c(=O)n(Cc4ccccc4C4CCNCC4)nc23)cc(C)n1] | Example 1-30 |
| 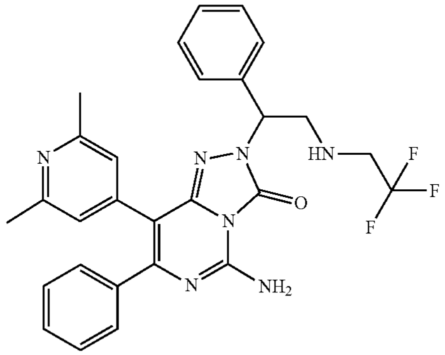 [SMILES: Cc1cc(-c2c(-c3ccccc3)nc(N)n3c(=O)n(C(CNCC(F)(F)F)c4ccccc4)nc23)cc(C)n1] | Example 1-31 |
| 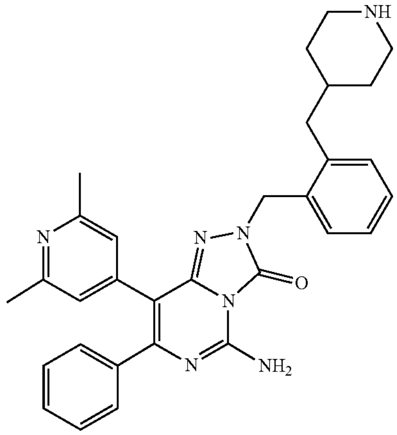 [SMILES: Cc1cc(-c2c(-c3ccccc3)nc(N)n3c(=O)n(Cc4ccccc4CC4CCNCC4)nc23)cc(C)n1] | Example 1-32 |
| 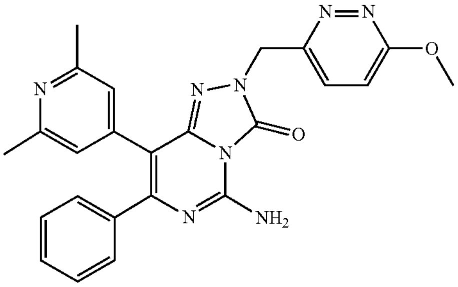 | Example 1-33 |

TABLE 1-continued
| Examples 1-1 to 3-10 | |
|---|---|
| 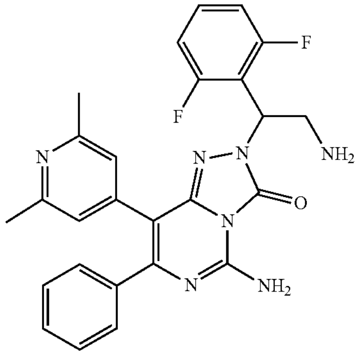 [SMILES: Cc1cc(-c2c(-c3ccccc3)nc(N)n3c(=O)n(C(CN)c4c(F)cccc4F)nc23)cc(C)n1] | Example 1-34 |
| 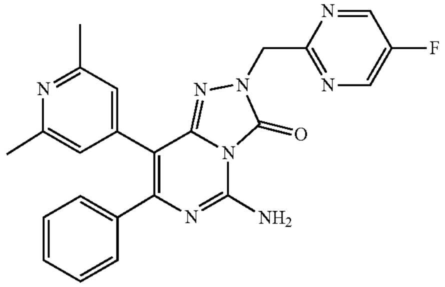 [SMILES: Cc1cc(-c2c(-c3ccccc3)nc(N)n3c(=O)n(Cc4ncc(F)cn4)nc23)cc(C)n1] | Example 1-35 |
| 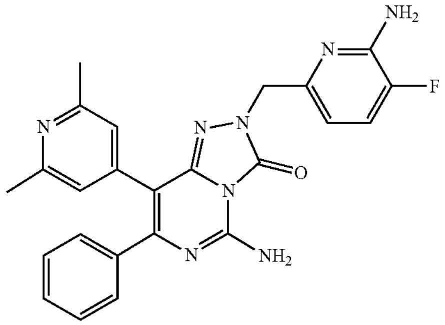 [SMILES: Cc1cc(-c2c(-c3ccccc3)nc(N)n3c(=O)n(Cc4ccc(F)c(N)n4)nc23)cc(C)n1] | Example 1-36 |
| 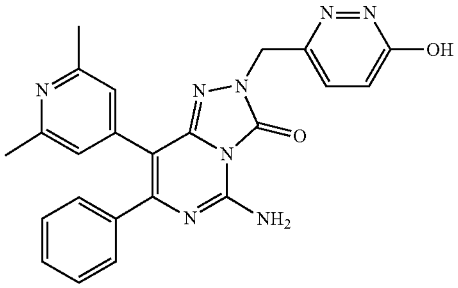 [SMILES: Cc1cc(-c2c(-c3ccccc3)nc(N)n3c(=O)n(Cc4ccc(O)nn4)nc23)cc(C)n1] | Example 1-37 |

TABLE 1-continued
| Examples 1-1 to 3-10 | |
| --- | --- |
| 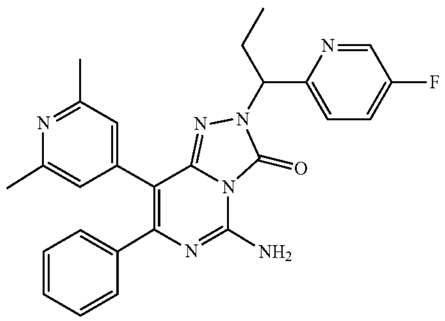 (And iso-1, iso-2) | Example 1-38 |
| 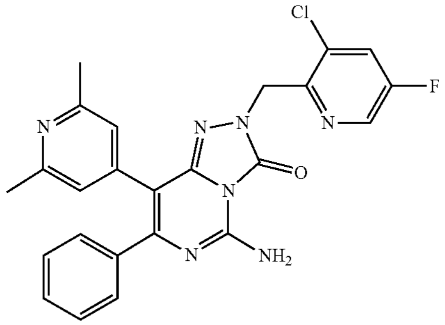 [SMILES: Cc1cc(-c2c(-c3ccccc3)nc(N)n3c(=O)n(Cc4ncc(F)cc4Cl)nc23)cc(C)n1] | Example 1-39 |
| 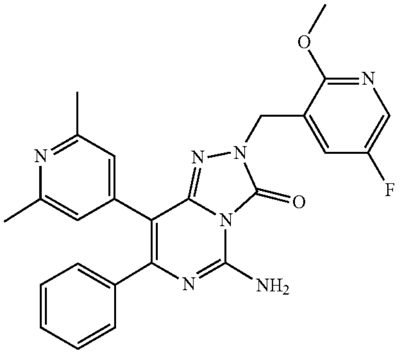 [SMILES: COc1ncc(F)cc1Cn1nc2c(-c3cc(C)nc(C)c3)c(-c3ccccc3)nc(N)n2c1=O] | Example 1-40 |
| 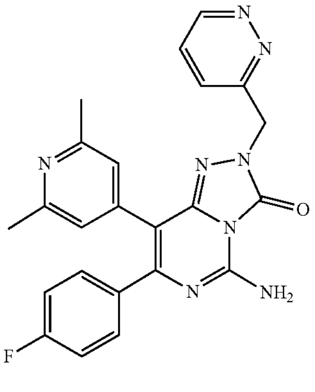 [SMILES: Cc1cc(-c2c(-c3ccc(F)cc3)nc(N)n3c(=O)n(Cc4cccnn4)nc23)cc(C)n1] | Example 1-41 |

TABLE 1-continued
Examples 1-1 to 3-10
Example 1-42
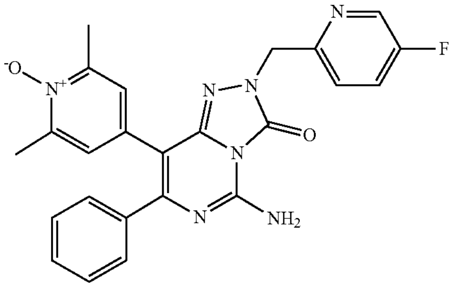
Example 1-43
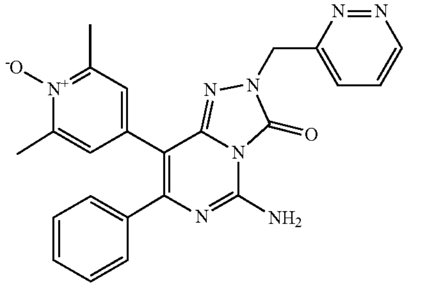
Example 1-44
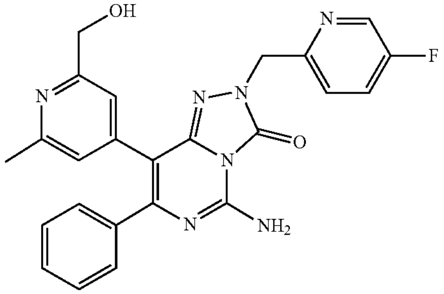 [SMILES: Cc1cc(-c2c(-c3ccccc3)nc(N)n3c(=O)n(Cc4ccc(F)cn4)nc23)cc(CO)n1]
Example 1-45
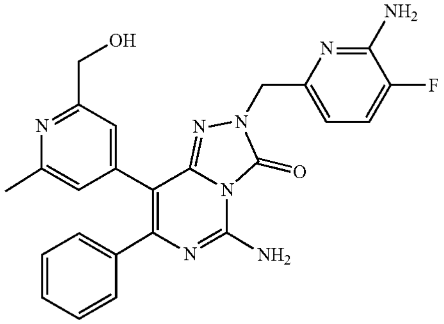 [SMILES: Cc1cc(-c2c(-c3ccccc3)nc(N)n3c(=O)n(Cc4ccc(F)c(N)n4)nc23)cc(CO)n1]
Example 1-46
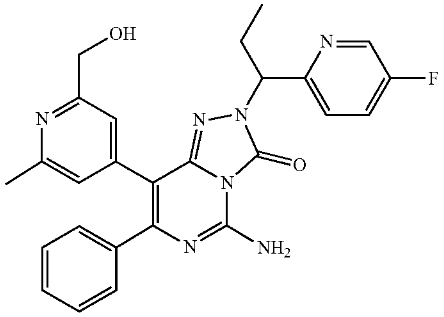
-iso1 and iso-2

TABLE 1-continued
| Examples 1-1 to 3-10 | |
| --- | --- |
| 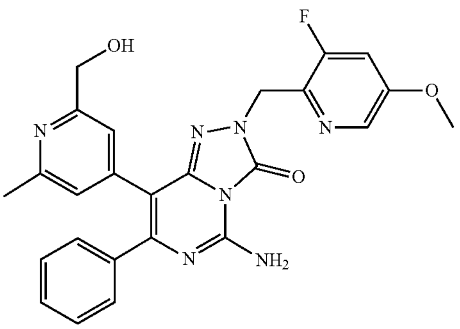 | Example 1-47 |
| 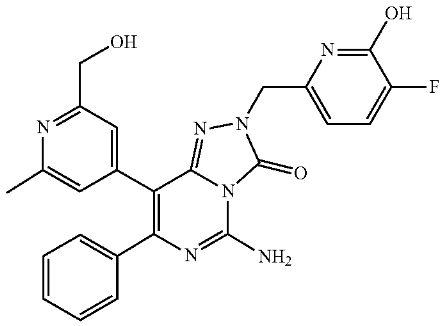 [SMILES: Cc1cc(-c2c(-c3ccccc3)nc(N)n3c(=O)n(Cc4ccc(F)c(O)n4)nc23)cc(CO)n1] | Example 1-48 |
| 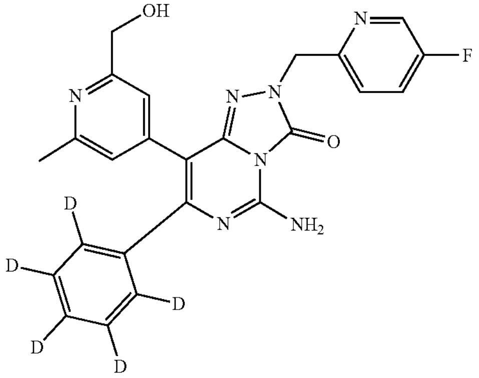 [SMILES: [2H]c1c([2H])c([2H])c(-c2nc(N)n3c(=O)n(Cc4ccc(F)cn4)nc3c2-c2cc(C)nc(CO)c2)c([2H])c1[2H]] | Example 1-49 |
| 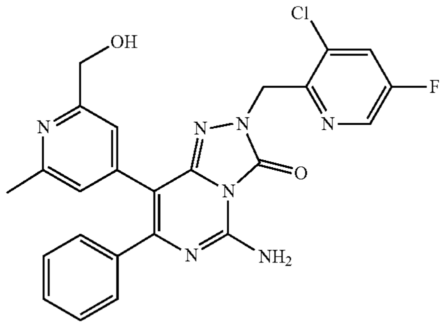 [SMILES: Cc1cc(-c2c(-c3ccccc3)nc(N)n3c(=O)n(Cc4ncc(F)cc4Cl)nc23)cc(CO)n1] | Example 1-50 |

TABLE 1-continued
Examples 1-1 to 3-10
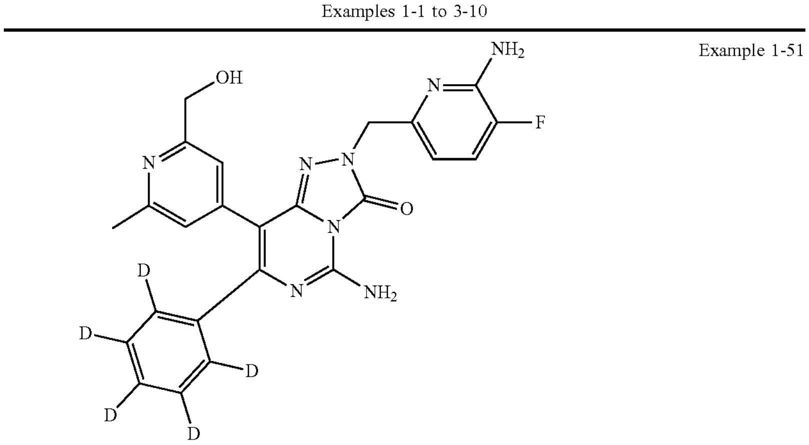
Example 1-51
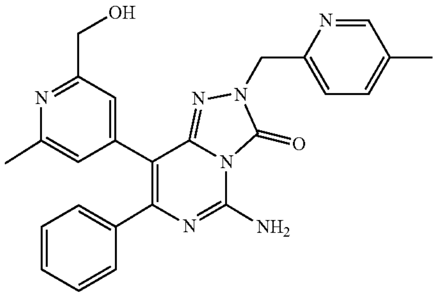
Example 1-52
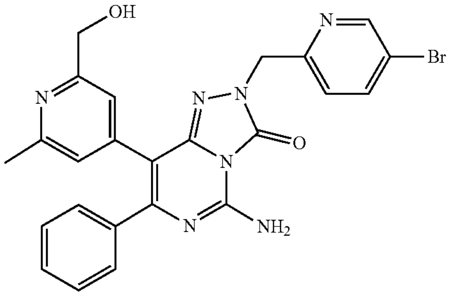 [SMILES: Cc1cc(-c2c(-c3ccccc3)nc(N)n3c(=O)n(Cc4ccc(Br)cn4)nc23)cc(CO)n1]
Example 1-53
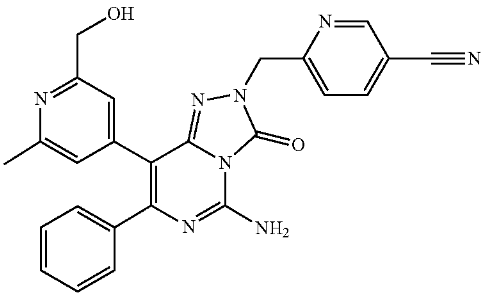 [SMILES: Cc1cc(-c2c(-c3ccccc3)nc(N)n3c(=O)n(Cc4ccc(C#N)cn4)nc23)cc(CO)n1]
Example 1-54
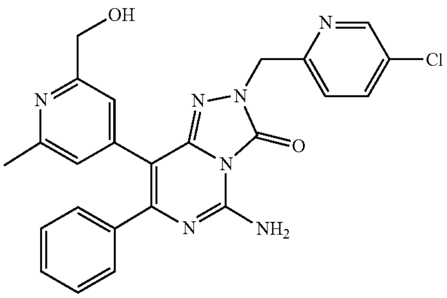 [SMILES: Cc1cc(-c2c(-c3ccccc3)nc(N)n3c(=O)n(Cc4ccc(Cl)cn4)nc23)cc(CO)n1]
Example 1-55

TABLE 1-continued
| Examples 1-1 to 3-10 | |
| --- | --- |
| 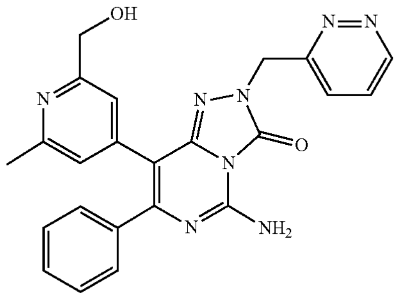 [SMILES: Cc1cc(-c2c(-c3ccccc3)nc(N)n3c(=O)n(Cc4cccnn4)nc23)cc(CO)n1] | Example 1-56 |
| 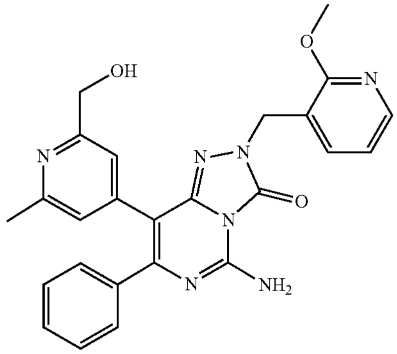 [SMILES: COc1ncccc1Cn1nc2c(-c3cc(C)nc(CO)c3)c(-c3ccccc3)nc(N)n2c1=O] | Example 1-57 |
| 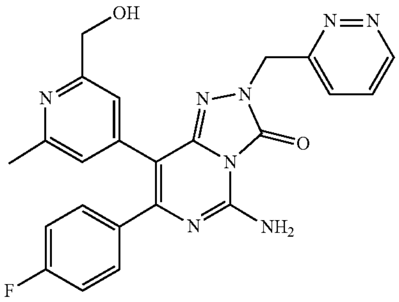 [SMILES: Cc1cc(-c2c(-c3ccc(F)cc3)nc(N)n3c(=O)n(Cc4cccnn4)nc23)cc(CO)n1] | Example 1-58 |
| 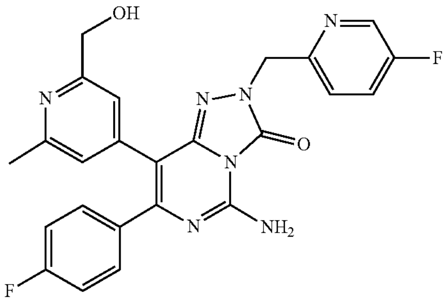 [SMILES: Cc1cc(-c2c(-c3ccc(F)cc3)nc(N)n3c(=O)n(Cc4ccc(F)cn4)nc23)cc(CO)n1] | Example 1-59 |

TABLE 1-continued
| Examples 1-1 to 3-10 | |
|---|---|
| 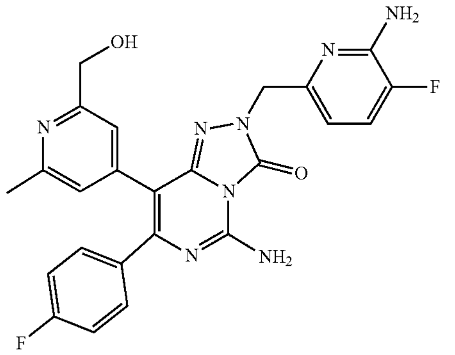 [SMILES: Cc1cc(-c2c(-c3ccc(F)cc3)nc(N)n3c(=O)n(Cc4ccc(F)c(N)n4)nc23)cc(CO)n1] | Example 1-60 |
| 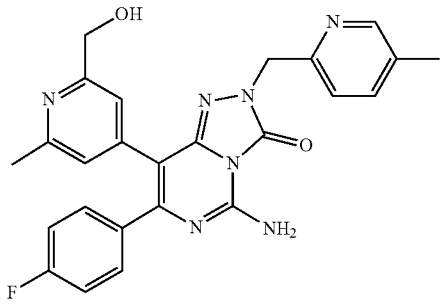 [SMILES: Cc1ccc(Cn2nc3c(-c4cc(C)nc(CO)c4)c(-c4ccc(F)cc4)nc(N)n3c2=O)nc1] | Example 1-61 |
| 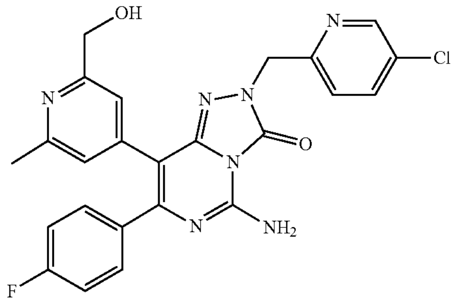 [SMILES: Cc1cc(-c2c(-c3ccc(F)cc3)nc(N)n3c(=O)n(Cc4ccc(Cl)cn4)nc23)cc(CO)n1] | Example 1-62 |
| 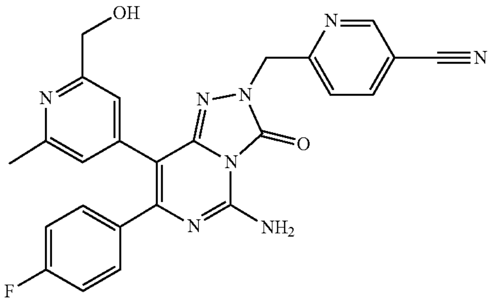 [SMILES: Cc1cc(-c2c(-c3ccc(F)cc3)nc(N)n3c(=O)n(Cc4ccc(C#N)cn4)nc23)cc(CO)n1] | Example 1-63 |
| 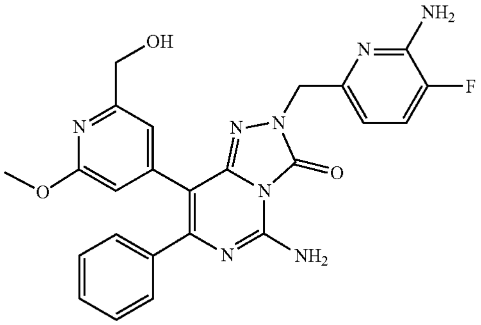 [SMILES: COc1cc(-c2c(-c3ccccc3)nc(N)n3c(=O)n(Cc4ccc(F)c(N)n4)nc23)cc(CO)n1] | Example 1-64 |

TABLE 1-continued
| Examples 1-1 to 3-10 | |
|---|---|
| 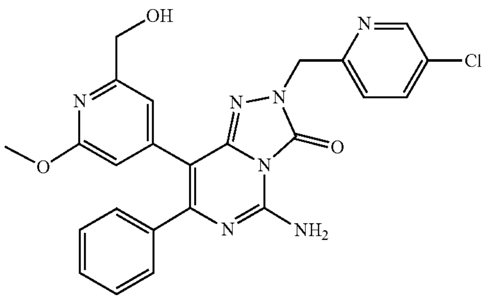 [SMILES: COc1cc(-c2c(-c3ccccc3)nc(N)n3c(=O)n(Cc4ccc(Cl)cn4)nc23)cc(CO)n1] | Example 1-65 |
| 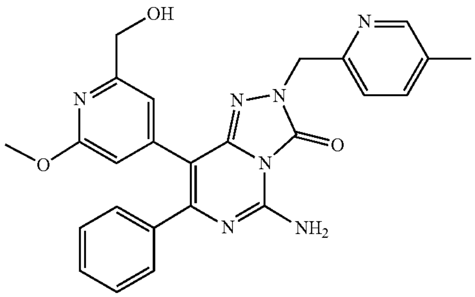 | Example 1-66 |
| 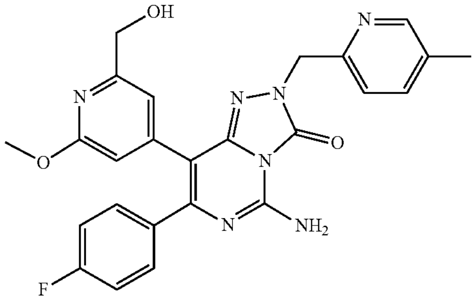 | Example 1-67 |
| 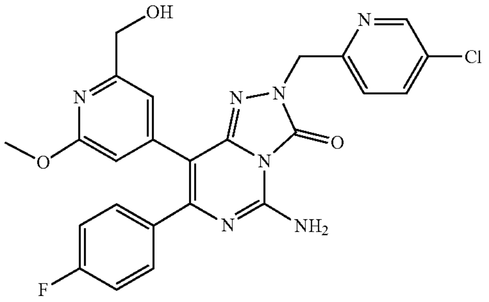 [SMILES: COc1cc(-c2c(-c3ccc(F)cc3)nc(N)n3c(=O)n(Cc4ccc(Cl)cn4)nc23)cc(CO)n1] | Example 1-68 |
| 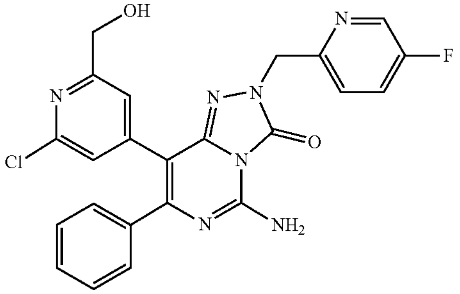 [SMILES: Nc1nc(-c2ccccc2)c(-c2cc(Cl)nc(CO)c2)c2nn(Cc3ccc(F)cn3)c(=O)n12] | Example 1-69 |

TABLE 1-continued
| Examples 1-1 to 3-10 | |
| --- | --- |
| 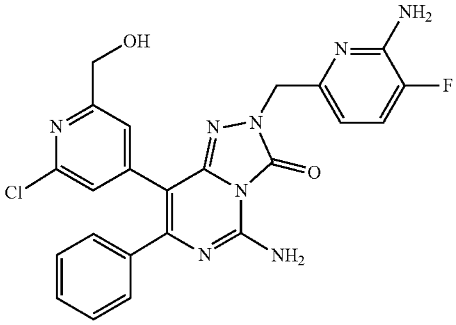 [SMILES: Nc1nc(Cn2nc3c(-c4cc(Cl)nc(CO)c4)c(-c4ccccc4)nc(N)n3c2=O)ccc1F] | Example 1-70 |
| 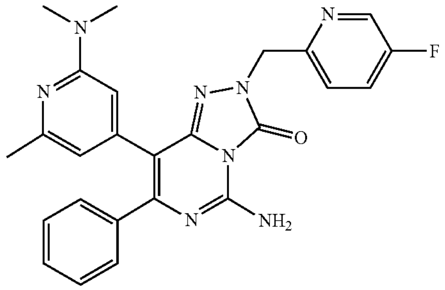 [SMILES: Cc1cc(-c2c(-c3ccccc3)nc(N)n3c(=O)n(Cc4ccc(F)cn4)nc23)cc(N(C)C)n1] | Example 1-71 |
| 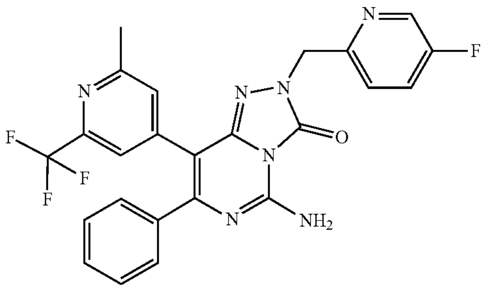 [SMILES: Cc1cc(-c2c(-c3ccccc3)nc(N)n3c(=O)n(Cc4ccc(F)cn4)nc23)cc(C(F)(F)F)n1] | Example 1-72 |
| 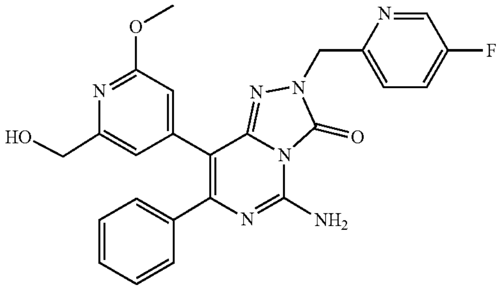 [SMILES: COc1cc(-c2c(-c3ccccc3)nc(N)n3c(=O)n(Cc4ccc(F)cn4)nc23)cc(CO)n1] | Example 1-73 |
| 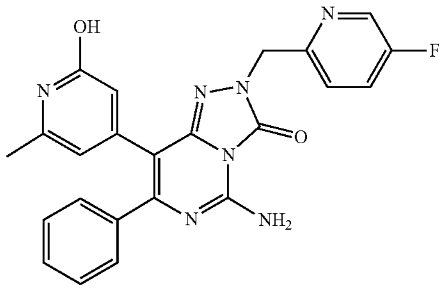 | Example 1-74 |

TABLE 1-continued
| Examples 1-1 to 3-10 | |
|---|---|
| 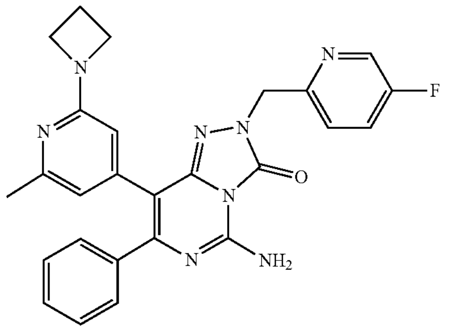 [SMILES: Cc1cc(-c2c(-c3ccccc3)nc(N)n3c(=O)n(Cc4ccc(F)cn4)nc23)cc(N2CCC2)n1] | Example 1-75 |
| 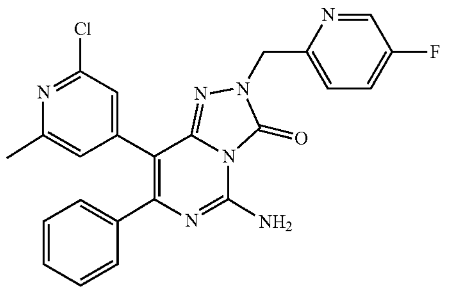 | Example 1-76 |
| 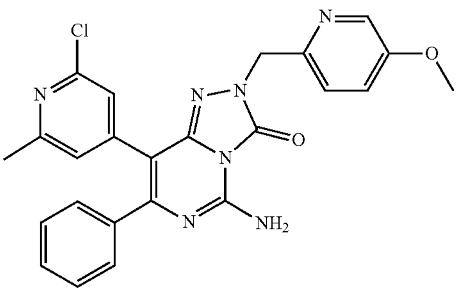 | Example 1-77 |
| 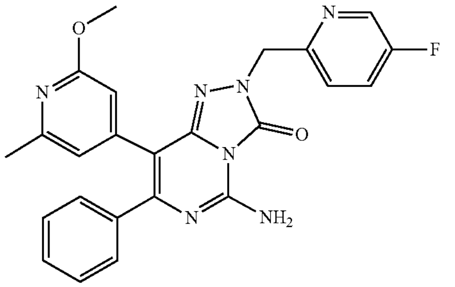 [SMILES: COc1cc(-c2c(-c3ccccc3)nc(N)n3c(=O)n(Cc4ccc(F)cn4)nc23)cc(C)n1] | Example 1-78 |
| 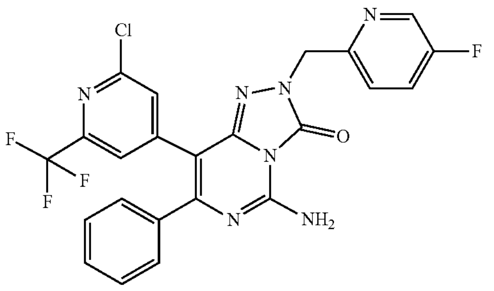 [SMILES: Nc1nc(-c2ccccc2)c(-c2cc(Cl)nc(C(F)(F)F)c2)c2nn(Cc3ccc(F)cn3)c(=O)n12] | Example 1-79 |

TABLE 1-continued
| Examples 1-1 to 3-10 |
|---|
| 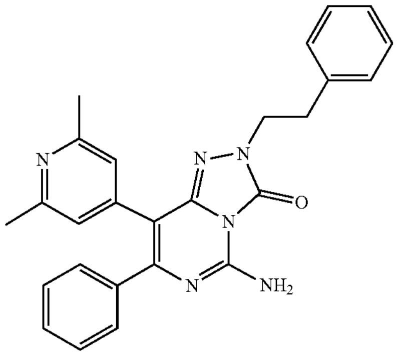 [SMILES: Cc1cc(-c2c(-c3ccccc3)nc(N)n3c(=O)n(CCc4ccccc4)nc23)cc(C)n1] Example 1-80 |
| 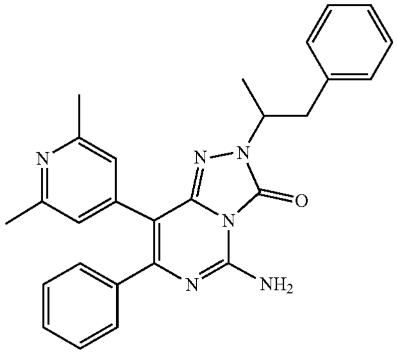 [SMILES: Cc1cc(-c2c(-c3ccccc3)nc(N)n3c(=O)n(C(C)Cc4ccccc4)nc23)cc(C)n1] Example 1-81 |
| 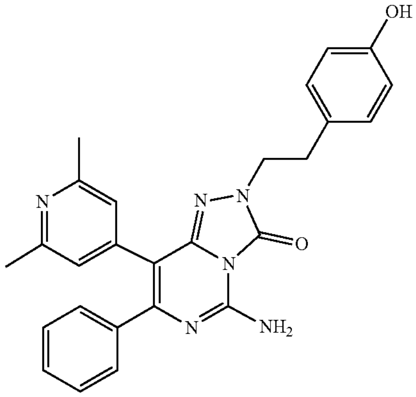 [SMILES: Cc1cc(-c2c(-c3ccccc3)nc(N)n3c(=O)n(CCc4ccc(O)cc4)nc23)cc(C)n1] Example 1-82 |
| 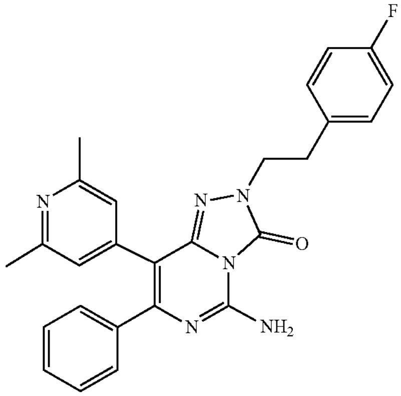 [SMILES: Cc1cc(-c2c(-c3ccccc3)nc(N)n3c(=O)n(CCc4ccc(F)cc4)nc23)cc(C)n1] Example 1-83 |

TABLE 1-continued
Examples 1-1 to 3-10
Example 1-84
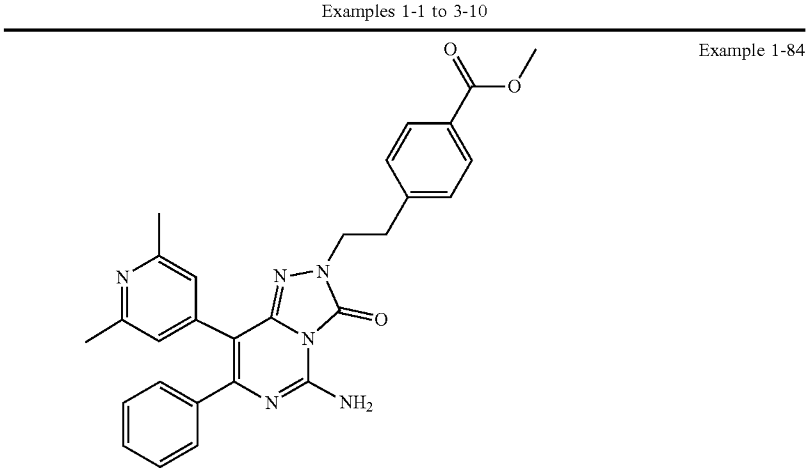
Example 1-85
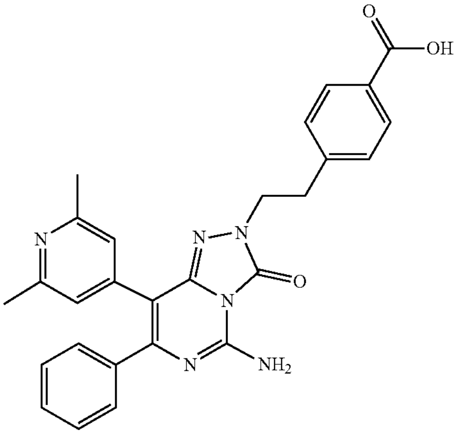 [SMILES: Cc1cc(-c2c(-c3ccccc3)nc(N)n3c(=O)n(CCc4ccc(C(=O)O)cc4)nc23)cc(C)n1]
Example 1-86
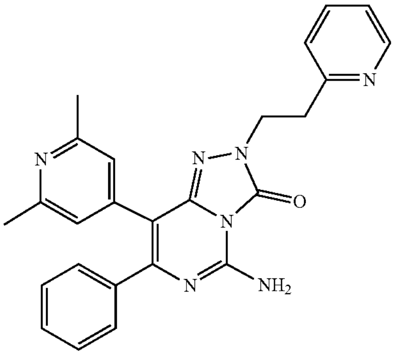 [SMILES: Cc1cc(-c2c(-c3ccccc3)nc(N)n3c(=O)n(CCc4ccccn4)nc23)cc(C)n1]
Example 1-87
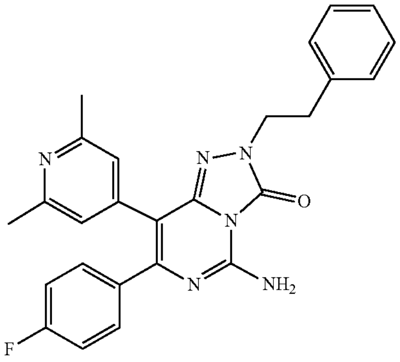 [SMILES: Cc1cc(-c2c(-c3ccc(F)cc3)nc(N)n3c(=O)n(CCc4ccccc4)nc23)cc(C)n1]

TABLE 1-continued
| Examples 1-1 to 3-10 |
|---|
| 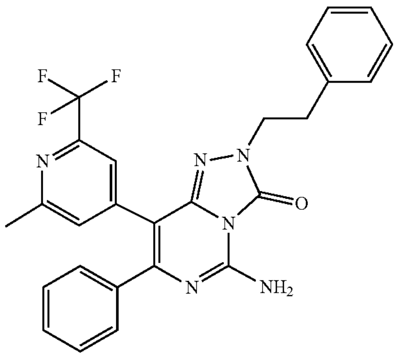 [SMILES: Cc1cc(-c2c(-c3ccccc3)nc(N)n3c(=O)n(CCc4ccccc4)nc23)cc(C(F)(F)F)n1] Example 1-88 |
| 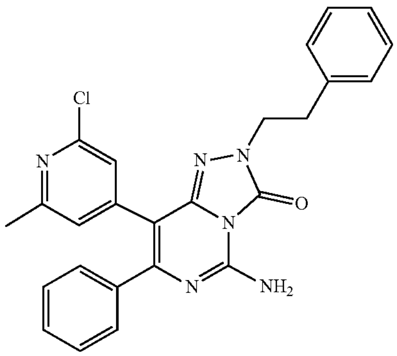 Example 1-89 |
| 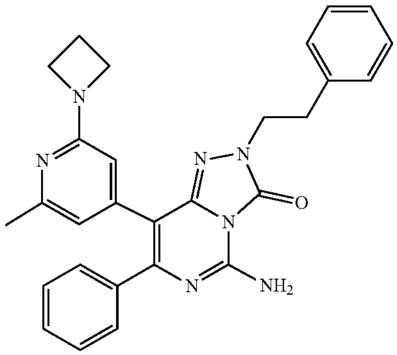 [SMILES: Cc1cc(-c2c(-c3ccccc3)nc(N)n3c(=O)n(CCc4ccccc4)nc23)cc(N2CCC2)n1] Example 1-90 |
| 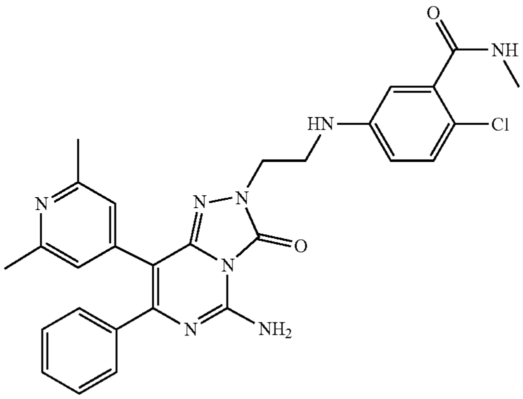 Example 1-91 |

TABLE 1-continued
| Examples 1-1 to 3-10 |
| --- |
| 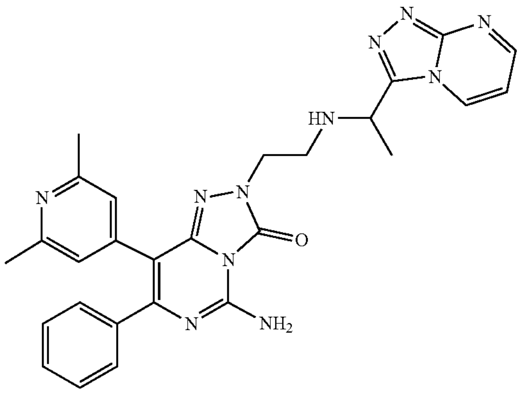 [SMILES: Cc1cc(-c2c(-c3ccccc3)nc(N)n3c(=O)n(CCNC(C)c4nnc5ncccn45)nc23)cc(C)n1] Example 1-92 |
| 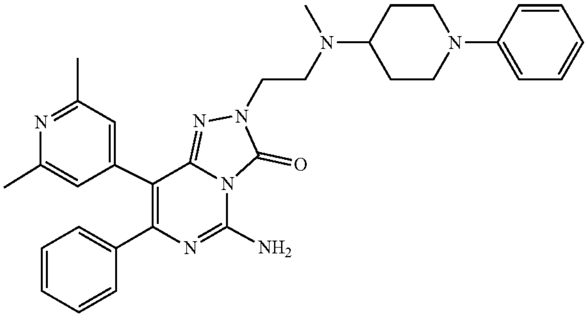 [SMILES: Cc1cc(-c2c(-c3ccccc3)nc(N)n3c(=O)n(CCN(C)C4CCN(c5ccccc5)CC4)nc23)cc(C)n1] Example 1-93 |
| 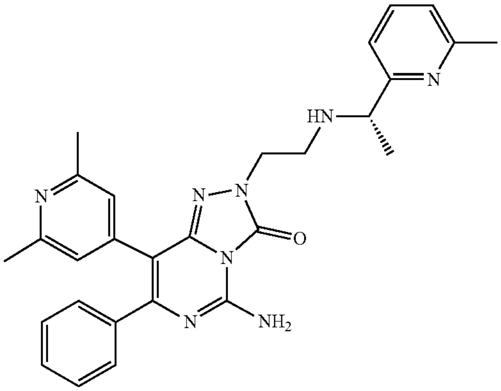 Example 1-94 |
| 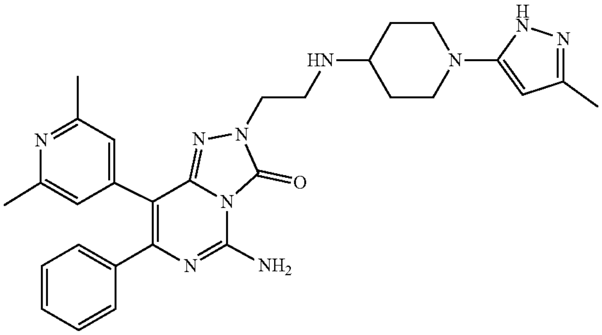 Example 1-95 |

TABLE 1-continued
| Examples 1-1 to 3-10 |
| --- |
| 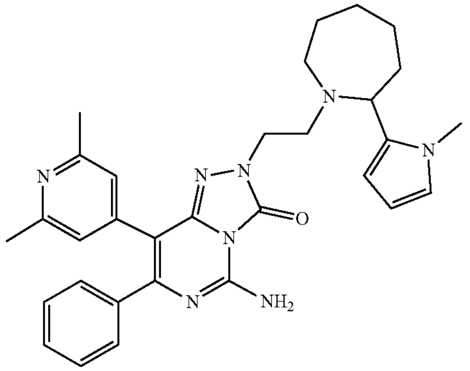 Example 1-96 |
| 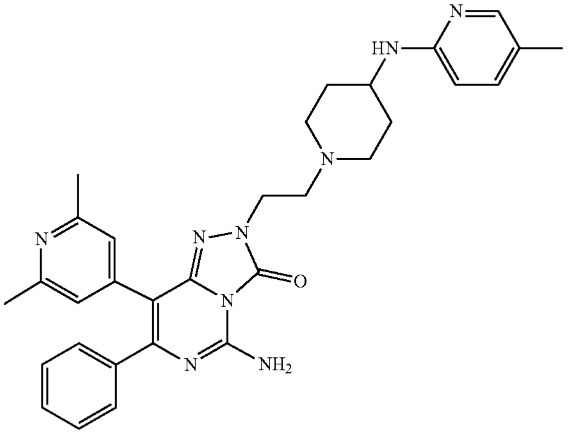 Example 1-97 |
| 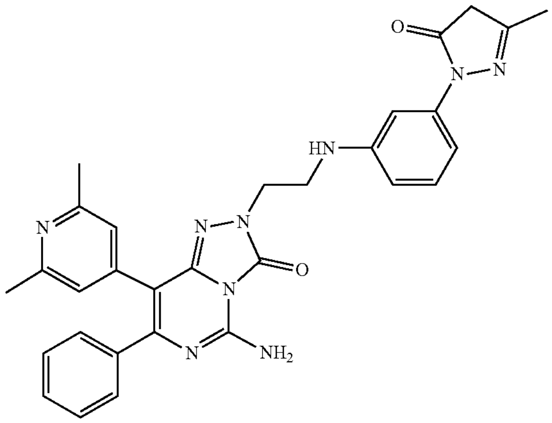 Example 1-98 |
| 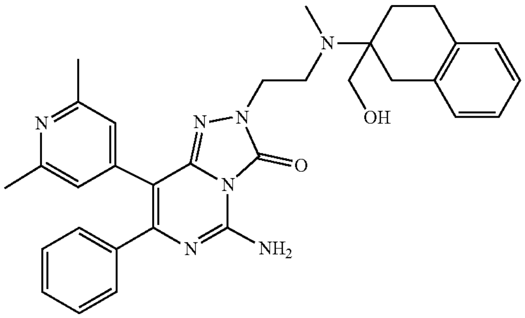 [SMILES: Cc1cc(-c2c(-c3ccccc3)nc(N)n3c(=O)n(CCN(C)C4(CO)CCc5ccccc5C4)nc23)cc(C)n1] Example 1-99 |

TABLE 1-continued
| Examples 1-1 to 3-10 | |
|---|---|
| 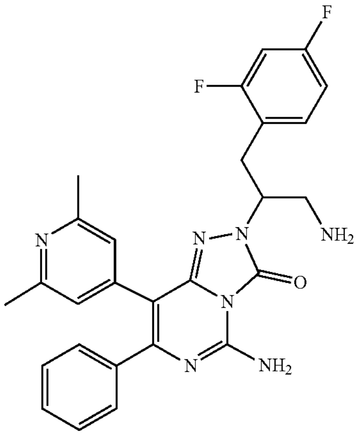 [SMILES: Cc1cc(-c2c(-c3ccccc3)nc(N)n3c(=O)n(C(CN)Cc4ccc(F)cc4F)nc23)cc(C)n1] | Example 1-100 |
| 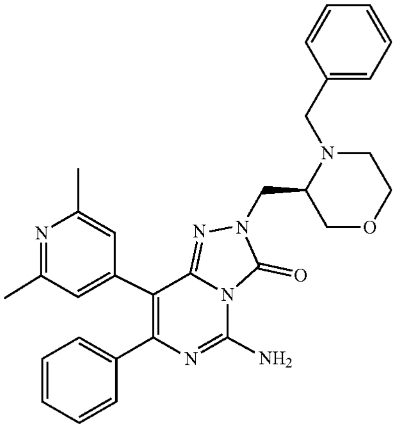 [SMILES: Cc1cc(-c2c(-c3ccccc3)nc(N)n3c(=O)n(C[C@@H]4COCCN4Cc4ccccc4)nc23)cc(C)n1] | Example 1-101 |
| 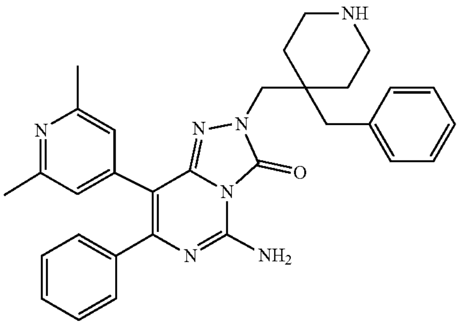 [SMILES: Cc1cc(-c2c(-c3ccccc3)nc(N)n3c(=O)n(CC4(Cc5ccccc5)CCNCC4)nc23)cc(C)n1] | Example 1-102 |
| 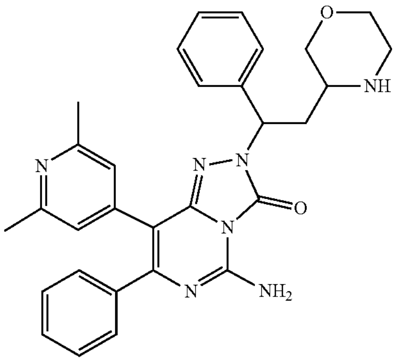 [SMILES: Cc1cc(-c2c(-c3ccccc3)nc(N)n3c(=O)n(C(CC4COCCN4)c4ccccc4)nc23)cc(C)n1] | Example 1-103 |

TABLE 1-continued
| Examples 1-1 to 3-10 | |
|---|---|
| 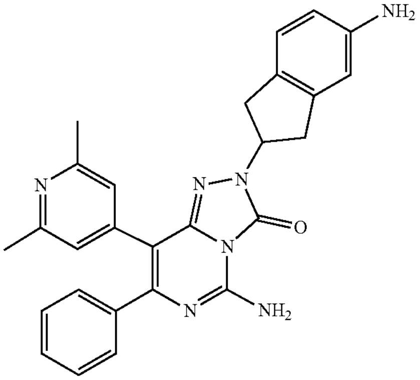 [SMILES: Cc1cc(-c2c(-c3ccccc3)nc(N)n3c(=O)n(C4Cc5ccc(N)cc5C4)nc23)cc(C)n1] | Example 1-104 |
| 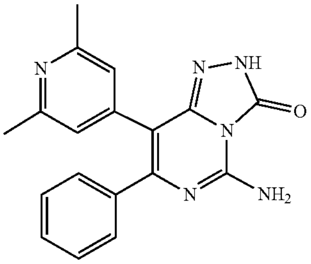 [SMILES: Cc1cc(-c2c(-c3ccccc3)nc(N)n3c(=O)[nH]nc23)cc(C)n1] | Example 2-1 |
| 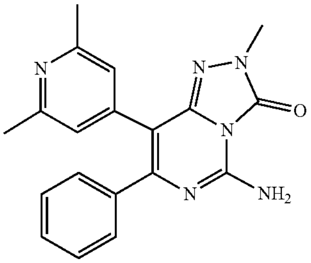 [SMILES: Cc1cc(-c2c(-c3ccccc3)nc(N)n3c(=O)n(C)nc23)cc(C)n1] | Example 2-2 |
| 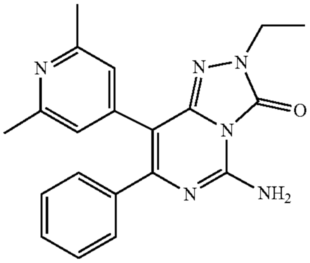 [SMILES: CCn1nc2c(-c3cc(C)nc(C)c3)c(-c3ccccc3)nc(N)n2c1=O] | Example 2-3 |
| 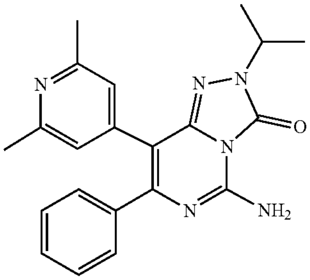 [SMILES: Cc1cc(-c2c(-c3ccccc3)nc(N)n3c(=O)n(C(C)C)nc23)cc(C)n1] | Example 2-4 |

TABLE 1-continued
| Examples 1-1 to 3-10 | |
|---|---|
| 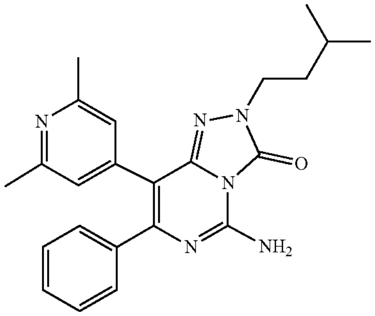 [SMILES: Cc1cc(-c2c(-c3ccccc3)nc(N)n3c(=O)n(CCC(C)C)nc23)cc(C)n1] | Example 2-5 |
| 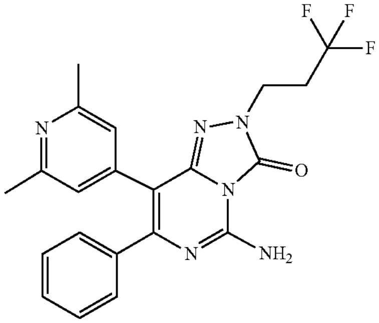 [SMILES: Cc1cc(-c2c(-c3ccccc3)nc(N)n3c(=O)n(CCC(F)(F)F)nc23)cc(C)n1] | Example 2-6 |
| 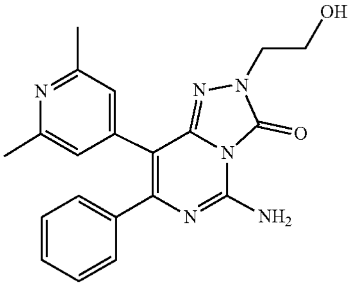 [SMILES: Cc1cc(-c2c(-c3ccccc3)nc(N)n3c(=O)n(CCO)nc23)cc(C)n1] | Example 2-7 |
| 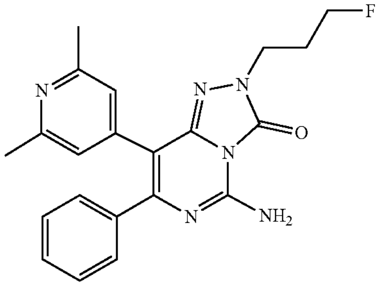 [SMILES: Cc1cc(-c2c(-c3ccccc3)nc(N)n3c(=O)n(CCCF)nc23)cc(C)n1] | Example 2-8 |
| 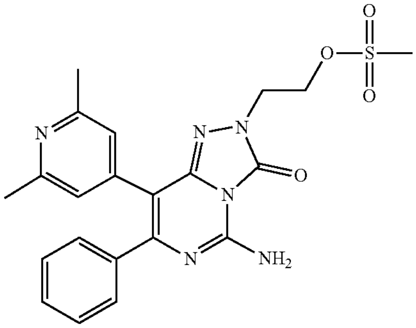 | Example 2-9 |

TABLE 1-continued
| Examples 1-1 to 3-10 | |
|---|---|
| 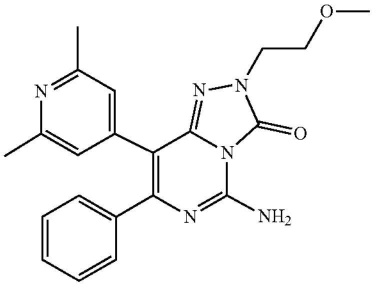 | Example 2-10 |
| 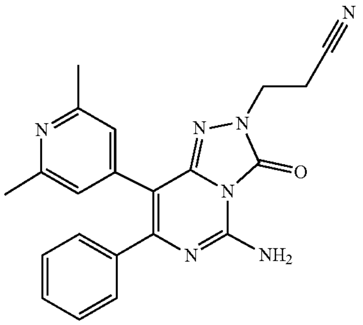 [SMILES: Cc1cc(-c2c(-c3ccccc3)nc(N)n3c(=O)n(CCC#N)nc23)cc(C)n1] | Example 2-11 |
| 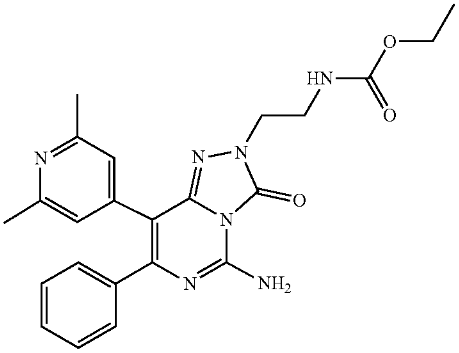 [SMILES: CCOC(=O)NCCn1nc2c(-c3cc(C)nc(C)c3)c(-c3ccccc3)nc(N)n2c1=O] | Example 2-12 |
| 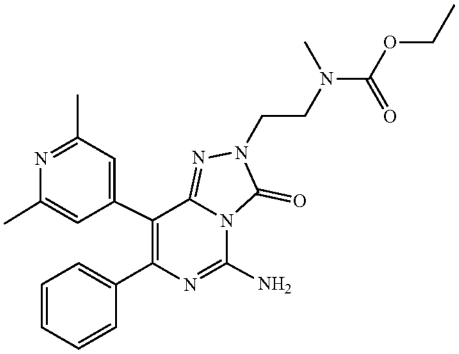 [SMILES: CCOC(=O)N(C)CCn1nc2c(-c3cc(C)nc(C)c3)c(-c3ccccc3)nc(N)n2c1=O] | Example 2-13 |

TABLE 1-continued
| Examples 1-1 to 3-10 | |
|---|---|
| 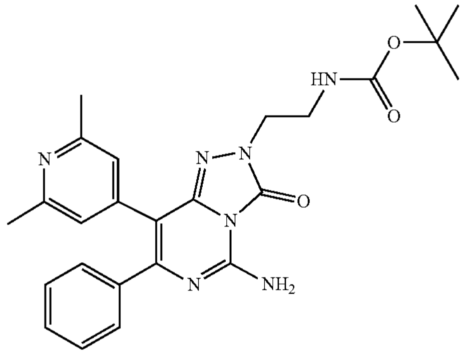 [SMILES: Cc1cc(-c2c(-c3ccccc3)nc(N)n3c(=O)n(CCNC(=O)OC(C)(C)C)nc23)cc(C)n1] | Example 2-14 |
| 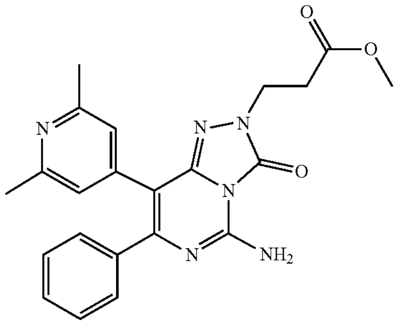 | Example 2-15 |
| 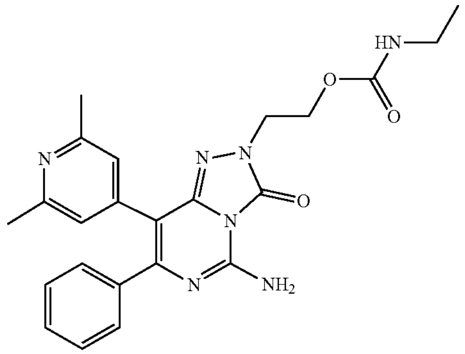 [SMILES: CCNC(=O)OCCn1nc2c(-c3cc(C)nc(C)c3)c(-c3ccccc3)nc(N)n2c1=O] | Example 2-16 |
| 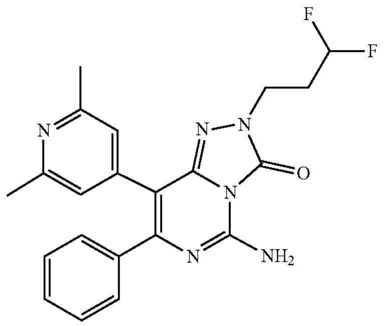 [SMILES: Cc1cc(-c2c(-c3ccccc3)nc(N)n3c(=O)n(CCC(F)F)nc23)cc(C)n1] | Example 2-17 |

TABLE 1-continued
| Examples 1-1 to 3-10 | |
|---|---|
| 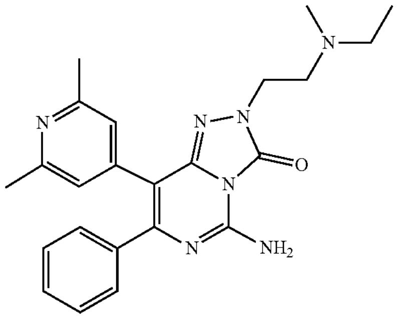 [SMILES: CCN(C)CCn1nc2c(-c3cc(C)nc(C)c3)c(-c3ccccc3)nc(N)n2c1=O] | Example 2-18 |
| 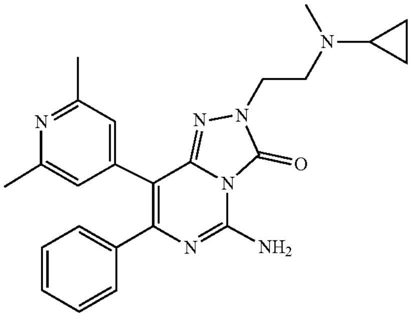 [SMILES: Cc1cc(-c2c(-c3ccccc3)nc(N)n3c(=O)n(CCN(C)C4CC4)nc23)cc(C)n1] | Example 2-19 |
| 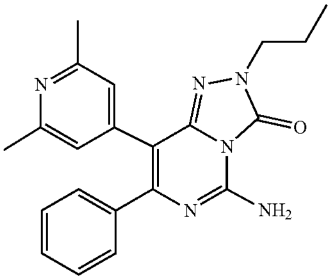 [SMILES: CCCn1nc2c(-c3cc(C)nc(C)c3)c(-c3ccccc3)nc(N)n2c1=O] | Example 2-20 |
| 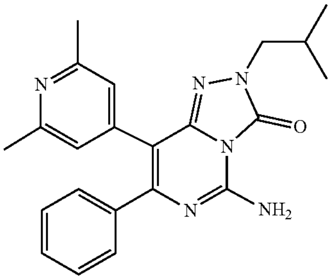 [SMILES: Cc1cc(-c2c(-c3ccccc3)nc(N)n3c(=O)n(CC(C)C)nc23)cc(C)n1] | Example 2-21 |
| 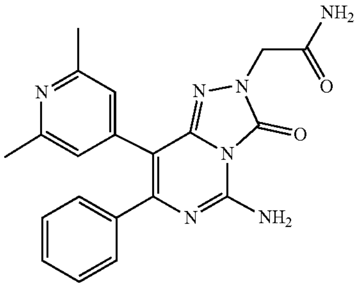 [SMILES: Cc1cc(-c2c(-c3ccccc3)nc(N)n3c(=O)n(CC(N)=O)nc23)cc(C)n1] | Example 2-22 |

TABLE 1-continued
| Examples 1-1 to 3-10 | |
|---|---|
| 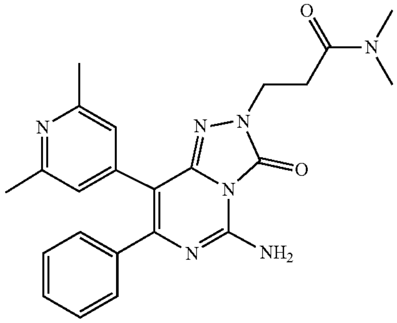 | Example 2-23 |
| 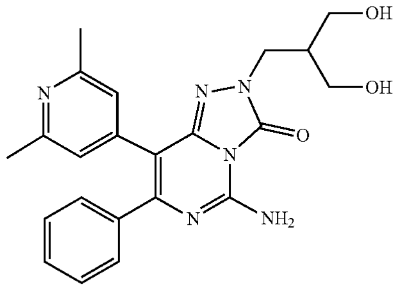 [SMILES: Cc1cc(-c2c(-c3ccccc3)nc(N)n3c(=O)n(CC(CO)CO)nc23)cc(C)n1] | Example 2-24 |
| 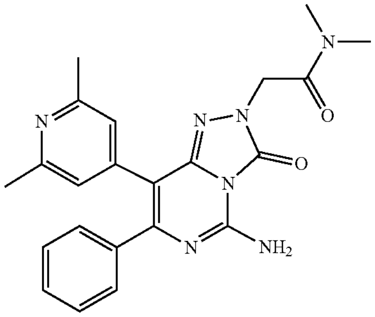 | Example 2-25 |
| 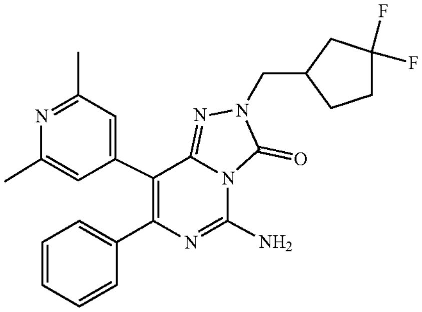 [SMILES: Cc1cc(-c2c(-c3ccccc3)nc(N)n3c(=O)n(CC4CCC(F)(F)C4)nc23)cc(C)n1] | Example 2-26 |
| 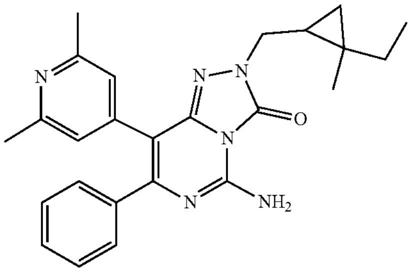 [SMILES: CCC1(C)CC1Cn1nc2c(-c3cc(C)nc(C)c3)c(-c3ccccc3)nc(N)n2c1=O] | Example 2-27 |

TABLE 1-continued
| Examples 1-1 to 3-10 | |
|---|---|
| 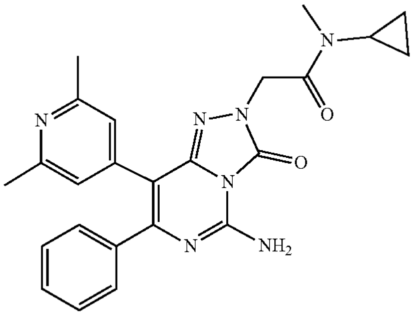 [SMILES: Cc1cc(-c2c(-c3ccccc3)nc(N)n3c(=O)n(CC(=O)N(C)C4CC4)nc23)cc(C)n1] | Example 2-28 |
| 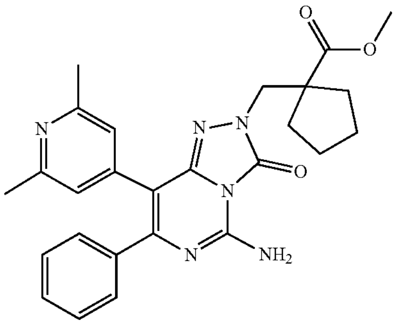 | Example 2-29 |
| 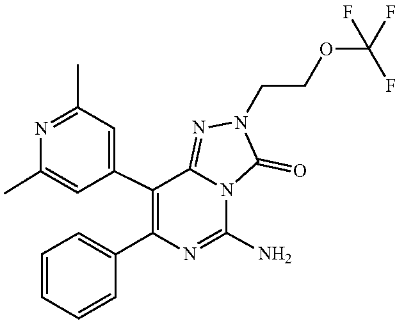 [SMILES: Cc1cc(-c2c(-c3ccccc3)nc(N)n3c(=O)n(CCOC(F)(F)F)nc23)cc(C)n1] | Example 2-30 |
| 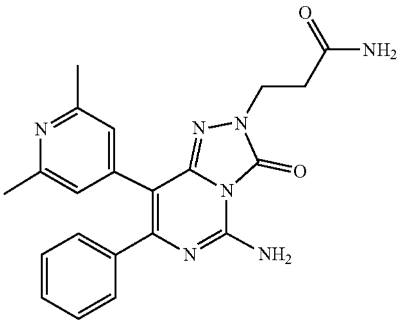 [SMILES: Cc1cc(-c2c(-c3ccccc3)nc(N)n3c(=O)n(CCC(N)=O)nc23)cc(C)n1] | Example 2-31 |

TABLE 1-continued
| Examples 1-1 to 3-10 | |
|---|---|
| 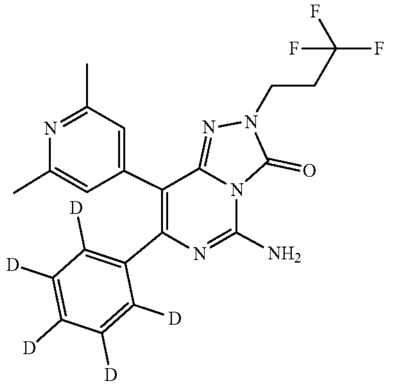 [SMILES: [2H]c1c([2H])c([2H])c(-c2nc(N)n3c(=O)n(CCC(F)(F)F)nc3c2-c2cc(C)nc(C)c2)c([2H])c1[2H]] | Example 2-32 |
| 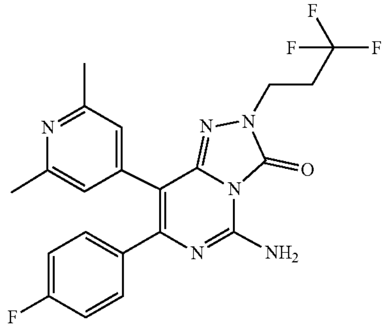 [SMILES: Cc1cc(-c2c(-c3ccc(F)cc3)nc(N)n3c(=O)n(CCC(F)(F)F)nc23)cc(C)n1] | Example 2-33 |
| 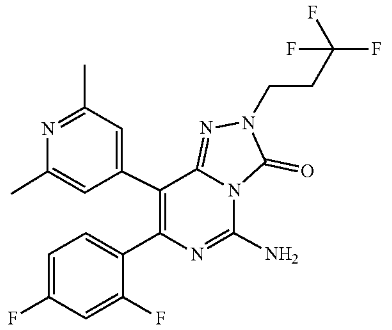 [SMILES: Cc1cc(-c2c(-c3ccc(F)cc3F)nc(N)n3c(=O)n(CCC(F)(F)F)nc23)cc(C)n1] | Example 2-34 |
| 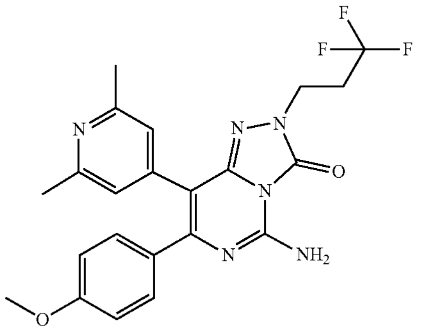 [SMILES: COc1ccc(-c2nc(N)n3c(=O)n(CCC(F)(F)F)nc3c2-c2cc(C)nc(C)c2)cc1] | Example 2-35 |

TABLE 1-continued
| Examples 1-1 to 3-10 | |
|---|---|
| 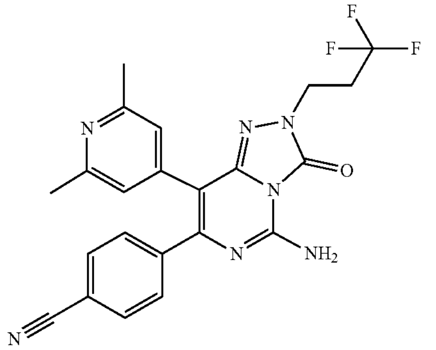 [SMILES: Cc1cc(-c2c(-c3ccc(C#N)cc3)nc(N)n3c(=O)n(CCC(F)(F)F)nc23)cc(C)n1] | Example 2-36 |
| 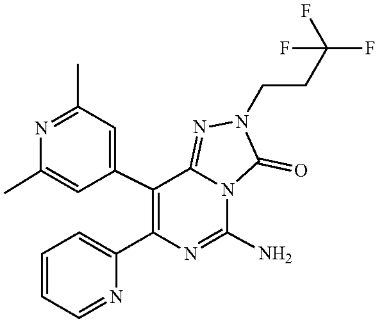 [SMILES: Cc1cc(-c2c(-c3ccccn3)nc(N)n3c(=O)n(CCC(F)(F)F)nc23)cc(C)n1] | Example 2-37 |
| 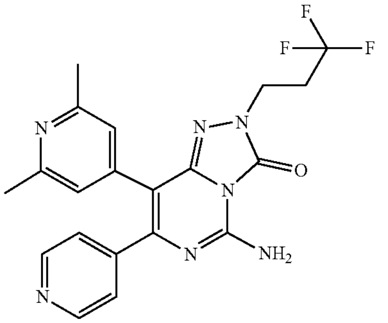 | Example 2-38 |
| 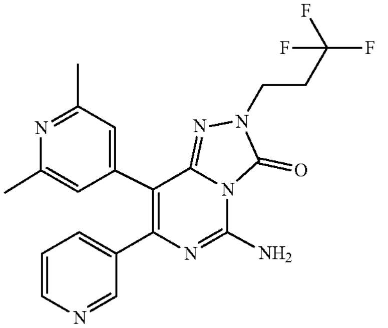 [SMILES: Cc1cc(-c2c(-c3cccnc3)nc(N)n3c(=O)n(CCC(F)(F)F)nc23)cc(C)n1] | Example 2-39 |

TABLE 1-continued
| Examples 1-1 to 3-10 |
| --- |
| 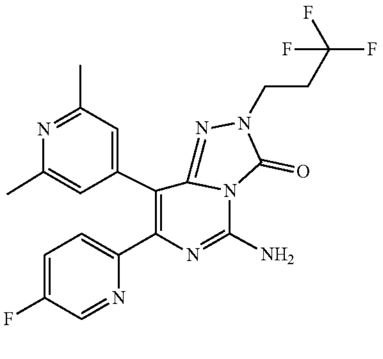 [SMILES: Cc1cc(-c2c(-c3ccc(F)cn3)nc(N)n3c(=O)n(CCC(F)(F)F)nc23)cc(C)n1] Example 2-40 |
| 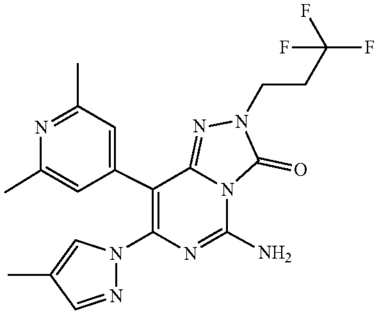 [SMILES: Cc1cnn(-c2nc(N)n3c(=O)n(CCC(F)(F)F)nc3c2-c2cc(C)nc(C)c2)c1] Example 2-41 |
| 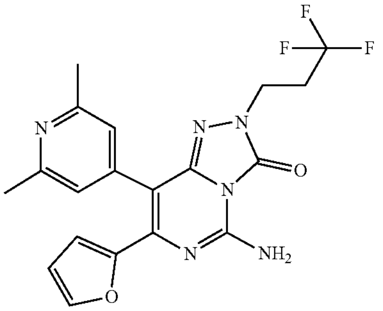 [SMILES: Cc1cc(-c2c(-c3ccco3)nc(N)n3c(=O)n(CCC(F)(F)F)nc23)cc(C)n1] Example 2-42 |
| 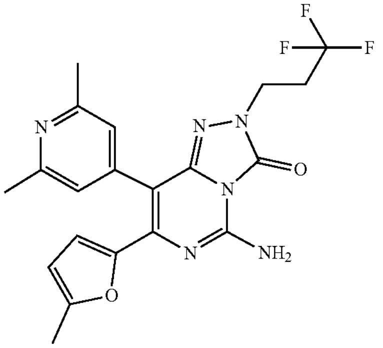 [SMILES: Cc1cc(-c2c(-c3ccc(C)o3)nc(N)n3c(=O)n(CCC(F)(F)F)nc23)cc(C)n1] Example 2-43 |

TABLE 1-continued
| Examples 1-1 to 3-10 | |
|---|---|
| 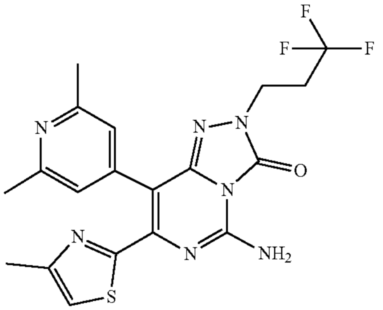 [SMILES: Cc1cc(-c2c(-c3nc(C)cs3)nc(N)n3c(=O)n(CCC(F)(F)F)nc23)cc(C)n1] | Example 2-44 |
| 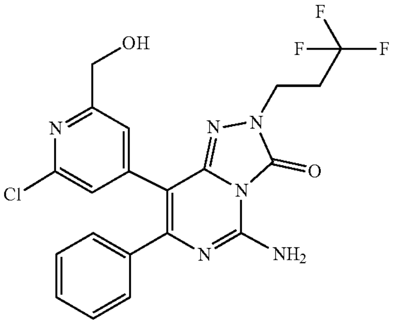 [SMILES: Nc1nc(-c2ccccc2)c(-c2cc(Cl)nc(CO)c2)c2nn(CCC(F)(F)F)c(=O)n12] | Example 2-45 |
| 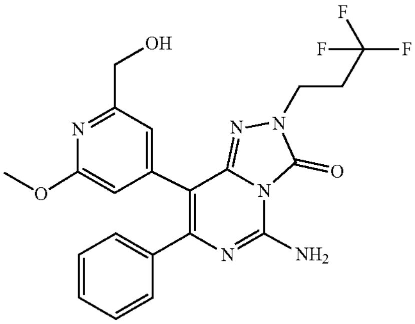 [SMILES: COc1cc(-c2c(-c3ccccc3)nc(N)n3c(=O)n(CCC(F)(F)F)nc23)cc(CO)n1] | Example 2-46 |
| 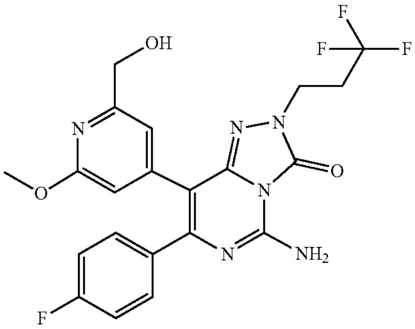 [SMILES: COc1cc(-c2c(-c3ccc(F)cc3)nc(N)n3c(=O)n(CCC(F)(F)F)nc23)cc(CO)n1] | Example 2-47 |

TABLE 1-continued
| Examples 1-1 to 3-10 |
| --- |
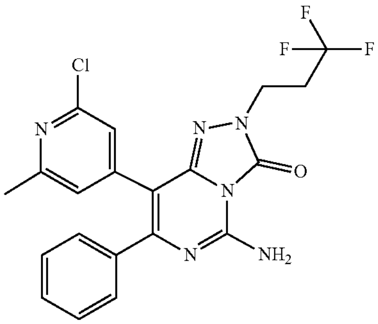 [SMILES: Cc1cc(-c2c(-c3ccccc3)nc(N)n3c(=O)n(CCC(F)(F)F)nc23)cc(Cl)n1]
Example 2-48
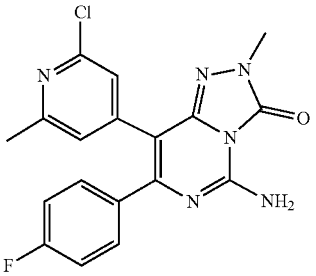 [SMILES: Cc1cc(-c2c(-c3ccc(F)cc3)nc(N)n3c(=O)n(C)nc23)cc(Cl)n1]
Example 2-49
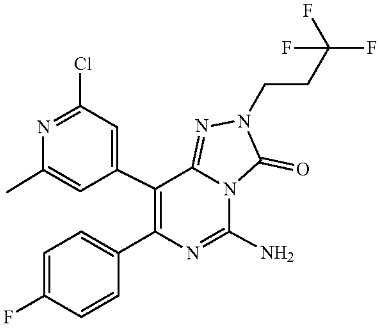 [SMILES: Cc1cc(-c2c(-c3ccc(F)cc3)nc(N)n3c(=O)n(CCC(F)(F)F)nc23)cc(Cl)n1]
Example 2-50
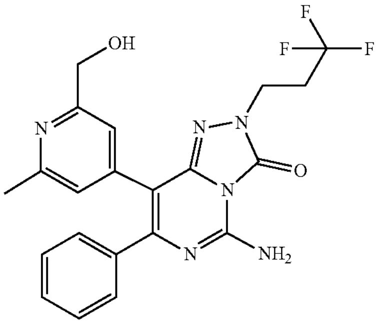 [SMILES: Cc1cc(-c2c(-c3ccccc3)nc(N)n3c(=O)n(CCC(F)(F)F)nc23)cc(CO)n1]
Example 2-51
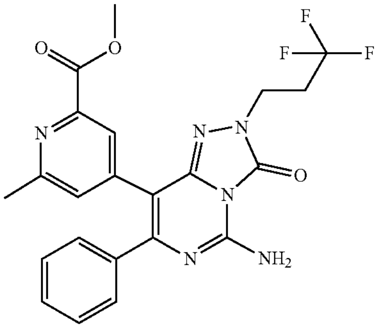 [SMILES: COC(=O)c1cc(-c2c(-c3ccccc3)nc(N)n3c(=O)n(CCC(F)(F)F)nc23)cc(C)n1]
Example 2-52

TABLE 1-continued
| Examples 1-1 to 3-10 | |
|---|---|
| 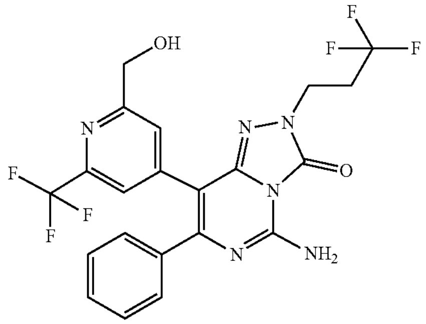 [SMILES: Nc1nc(-c2ccccc2)c(-c2cc(CO)nc(C(F)(F)F)c2)c2nn(CCC(F)(F)F)c(=O)n12] | Example 2-53 |
| 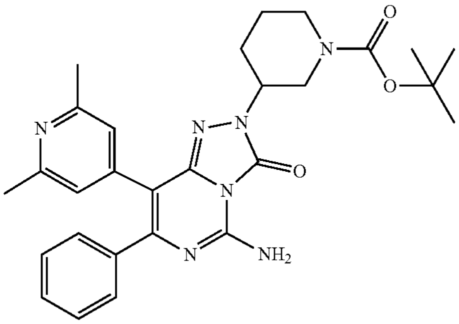 [SMILES: Cc1cc(-c2c(-c3ccccc3)nc(N)n3c(=O)n(C4CCCN(C(=O)OC(C)(C)C)C4)nc23)cc(C)n1] | Example 2-54 |
| 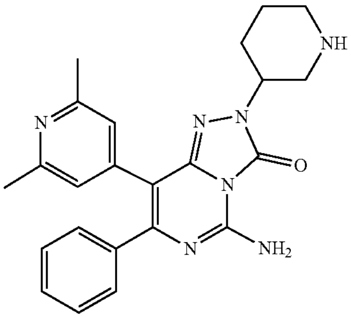 [SMILES: Cc1cc(-c2c(-c3ccccc3)nc(N)n3c(=O)n(C4CCCNC4)nc23)cc(C)n1] | Example 2-55 |
| 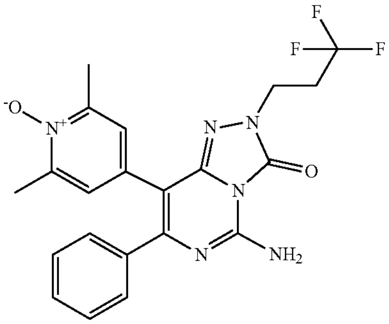 | Example 2-56 |
| 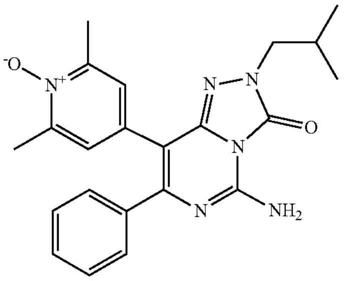 | Example 2-57 |

TABLE 1-continued
| Examples 1-1 to 3-10 | |
| --- | --- |
| 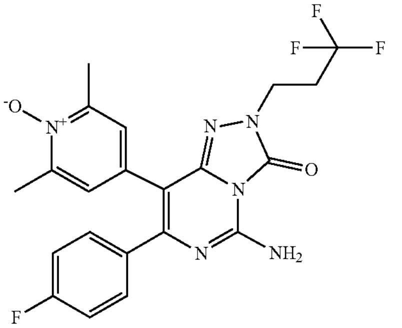 | Example 2-58 |
| 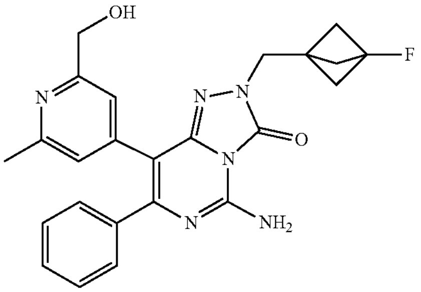 [SMILES: Cc1cc(-c2c(-c3ccccc3)nc(N)n3c(=O)n(CC45CC(F)(C4)C5)nc23)cc(CO)n1] | Example 2-59 |
| 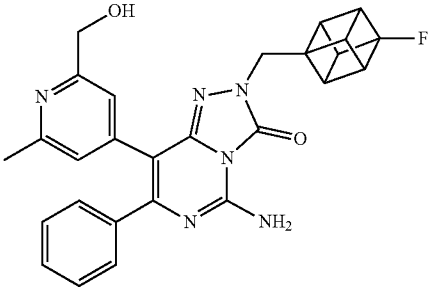 [SMILES: Cc1cc(-c2c(-c3ccccc3)nc(N)n3c(=O)n(CC45C6C7C4C4C5C6C74F)nc23)cc(CO)n1] | Example 2-60 |
| 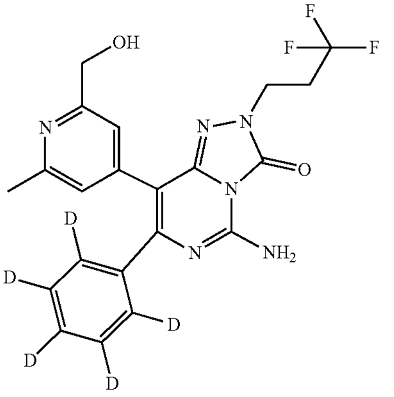 [SMILES: [2H]c1c([2H])c([2H])c(-c2nc(N)n3c(=O)n(CCC(F)(F)F)nc3c2-c2cc(C)nc(CO)c2)c([2H])c1[2H]] | Example 2-61 |

TABLE 1-continued
| Examples 1-1 to 3-10 | |
|---|---|
| 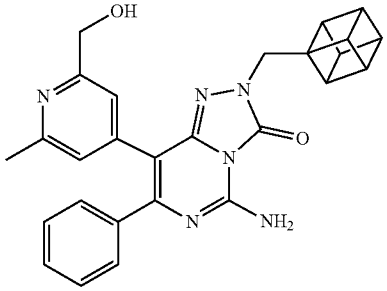 [SMILES: Cc1cc(-c2c(-c3ccccc3)nc(N)n3c(=O)n(CC45C6C7C8C6C4C8C75)nc23)cc(CO)n1] | Example 2-62 |
| 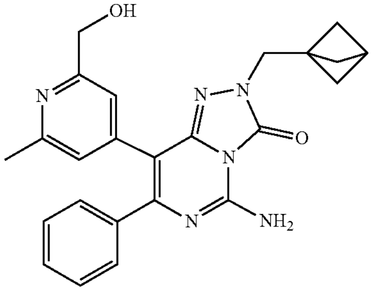 [SMILES: Cc1cc(-c2c(-c3ccccc3)nc(N)n3c(=O)n(CC45CC(C4)C5)nc23)cc(CO)n1] | Example 2-63 |
| 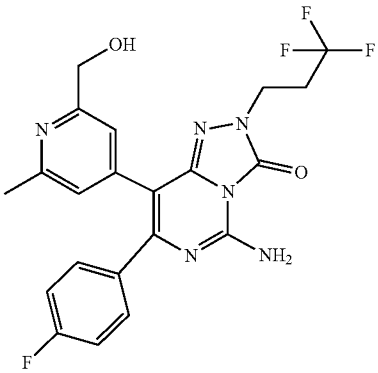 [SMILES: Cc1cc(-c2c(-c3ccc(F)cc3)nc(N)n3c(=O)n(CCC(F)(F)F)nc23)cc(CO)n1] | Example 2-64 |
| 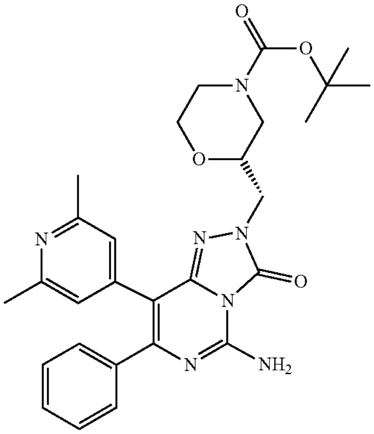 | Example 2-65 |

TABLE 1-continued
| Examples 1-1 to 3-10 | |
|---|---|
| 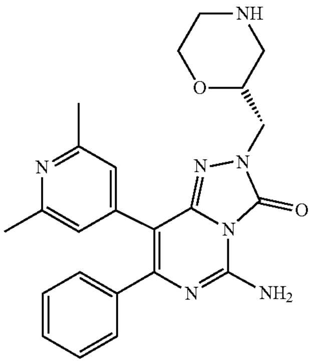 | Example 2-66 |
| 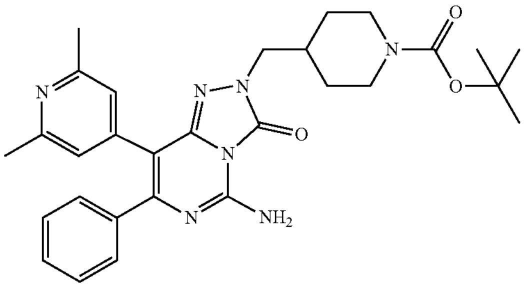 [SMILES: Cc1cc(-c2c(-c3ccccc3)nc(N)n3c(=O)n(CC4CCN(C(=O)OC(C)(C)C)CC4)nc23)cc(C)n1] | Example 2-67 |
| 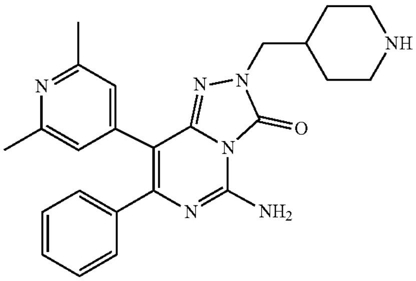 [SMILES: Cc1cc(-c2c(-c3ccccc3)nc(N)n3c(=O)n(CC4CCNCC4)nc23)cc(C)n1] | Example 2-68 |
| 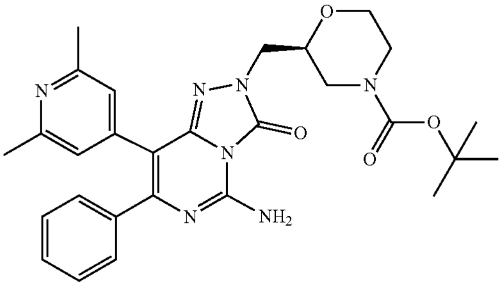 [SMILES: Cc1cc(-c2c(-c3ccccc3)nc(N)n3c(=O)n(C[C@@H]4CN(C(=O)OC(C)(C)C)CCO4)nc23)cc(C)n1] | Example 2-69 |
| 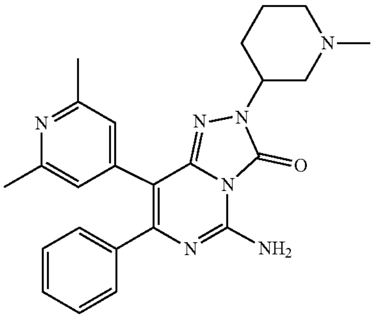 | Example 2-70 |

TABLE 1-continued
| Examples 1-1 to 3-10 |
| --- |
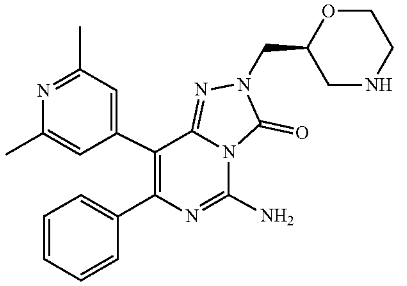 [SMILES: Cc1cc(-c2c(-c3ccccc3)nc(N)n3c(=O)n(C[C@@H]4CNCCO4)nc23)cc(C)n1]
Example 2-71
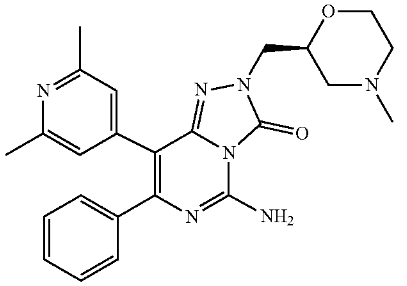
Example 2-72
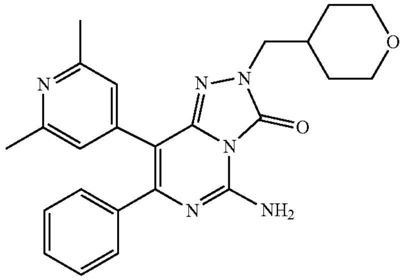 [SMILES: Cc1cc(-c2c(-c3ccccc3)nc(N)n3c(=O)n(CC4CCOCC4)nc23)cc(C)n1]
Example 2-73
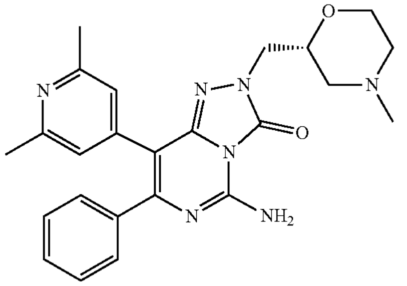
Example 2-74
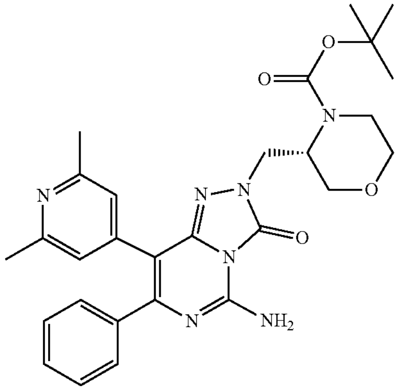 [SMILES: Cc1cc(-c2c(-c3ccccc3)nc(N)n3c(=O)n(C[C@H]4COCCN4C(=O)OC(C)(C)C)nc23)cc(C)n1]
Example 2-75

TABLE 1-continued
Examples 1-1 to 3-10
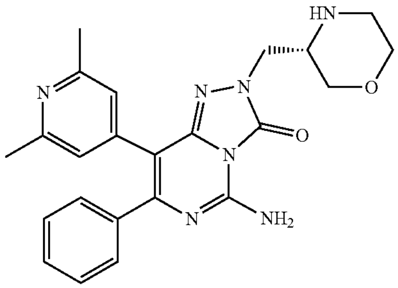 [SMILES: Cc1cc(-c2c(-c3ccccc3)nc(N)n3c(=O)n(C[C@H]4COCCN4)nc23)cc(C)n1]
Example 2-76
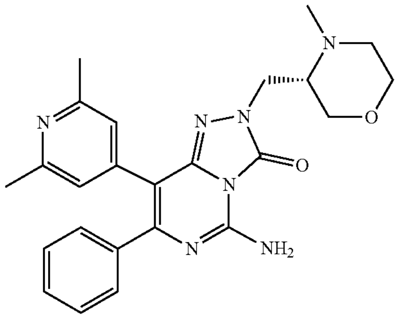 [SMILES: Cc1cc(-c2c(-c3ccccc3)nc(N)n3c(=O)n(C[C@H]4COCCN4C)nc23)cc(C)n1]
Example 2-77
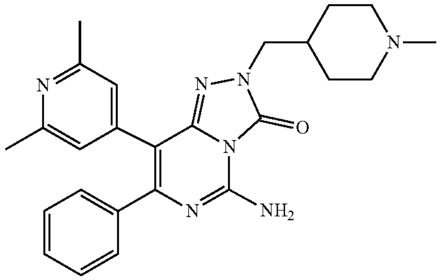
Example 2-78
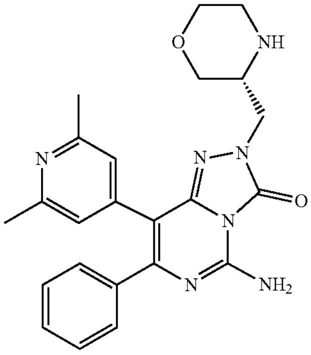 [SMILES: Cc1cc(-c2c(-c3ccccc3)nc(N)n3c(=O)n(C[C@@H]4COCCN4)nc23)cc(C)n1]
Example 2-79
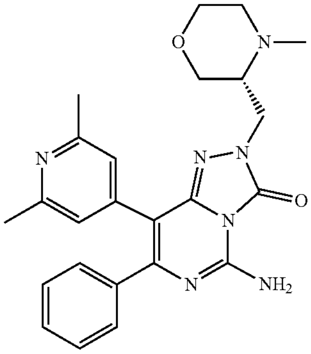
Example 2-80

TABLE 1-continued
| Examples 1-1 to 3-10 | |
|---|---|
| 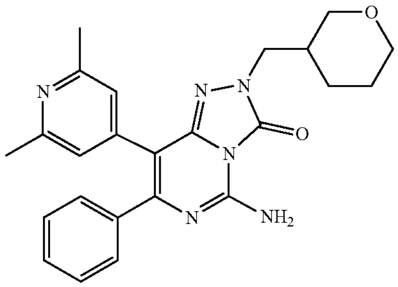<br>(and iso-1, iso-2) | Example 2-81 |
| 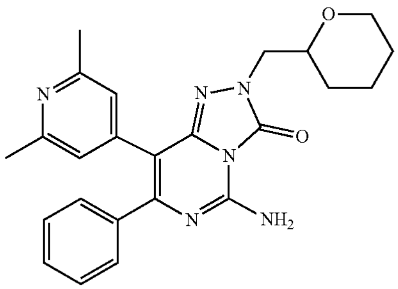<br>(and iso-1, iso-2) | Example 2-82 |
| 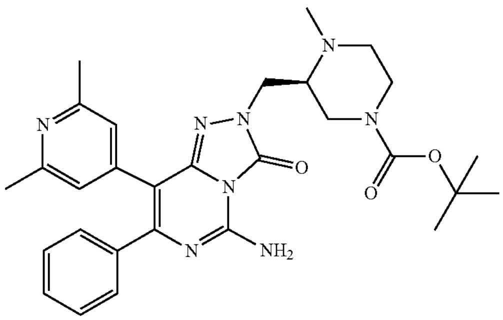 [SMILES: Cc1cc(-c2c(-c3ccccc3)nc(N)n3c(=O)n(C[C@@H]4CN(C(=O)OC(C)(C)C)CCN4C)nc23)cc(C)n1] | Example 2-83 |
| 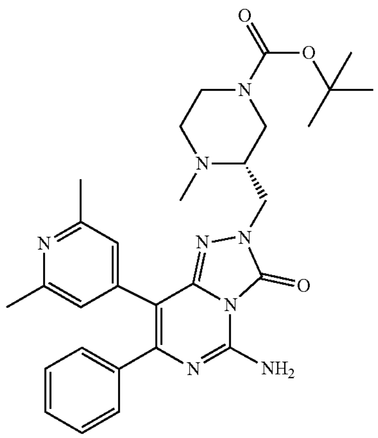 [SMILES: Cc1cc(-c2c(-c3ccccc3)nc(N)n3c(=O)n(C[C@H]4CN(C(=O)OC(C)(C)C)CCN4C)nc23)cc(C)n1] | Example 2-84 |

TABLE 1-continued
| Examples 1-1 to 3-10 | |
|---|---|
| 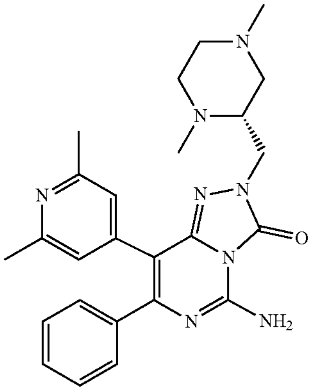 [SMILES: Cc1cc(-c2c(-c3ccccc3)nc(N)n3c(=O)n(C[C@H]4CN(C)CCN4C)nc23)cc(C)n1] | Example 2-85 |
| 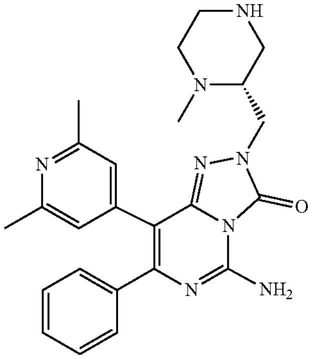 [SMILES: Cc1cc(-c2c(-c3ccccc3)nc(N)n3c(=O)n(C[C@H]4CNCCN4C)nc23)cc(C)n1] | Example 2-86 |
| 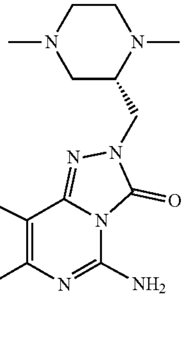 | Example 2-87 |
| 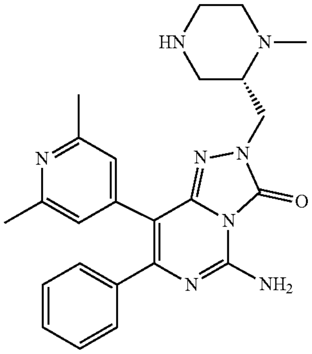 | Example 2-88 |

TABLE 1-continued
Examples 1-1 to 3-10
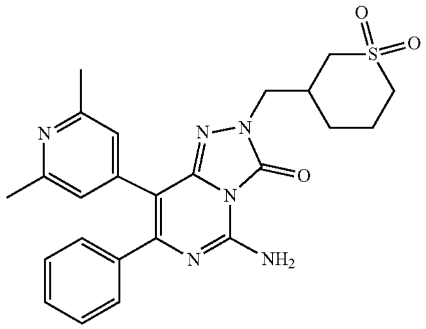
-iso 1 and iso-2
Example 2-89
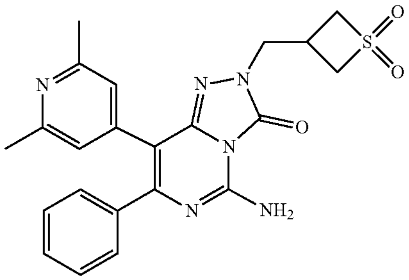 [SMILES: Cc1cc(-c2c(-c3ccccc3)nc(N)n3c(=O)n(CC4CS(=O)(=O)C4)nc23)cc(C)n1]
Example 2-90
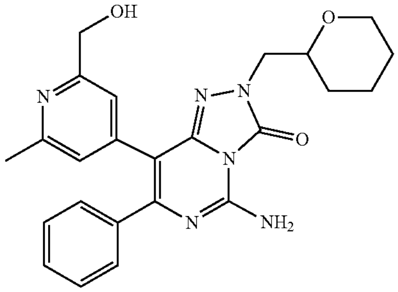
-iso 1 and iso-2
Example 2-91
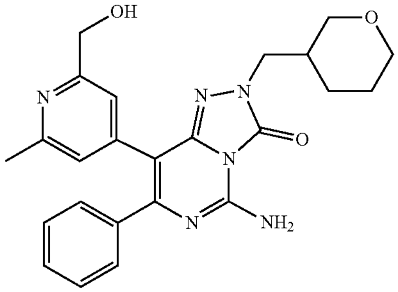
-iso 1 and iso-2
Example 2-92

TABLE 1-continued
| Examples 1-1 to 3-10 | |
|---|---|
| 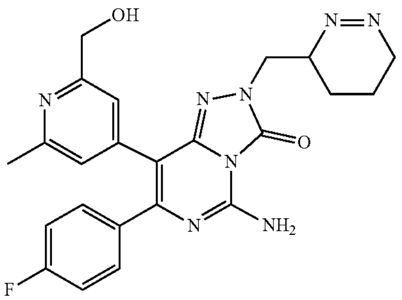 [SMILES: Cc1cc(-c2c(-c3ccc(F)cc3)nc(N)n3c(=O)n(CC4CCCN=N4)nc23)cc(CO)n1] | Example 2-93 |
| 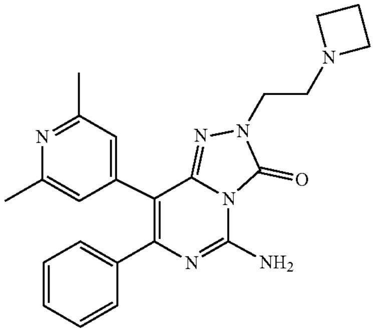 [SMILES: Cc1cc(-c2c(-c3ccccc3)nc(N)n3c(=O)n(CCN4CCC4)nc23)cc(C)n1] | Example 2-94 |
| 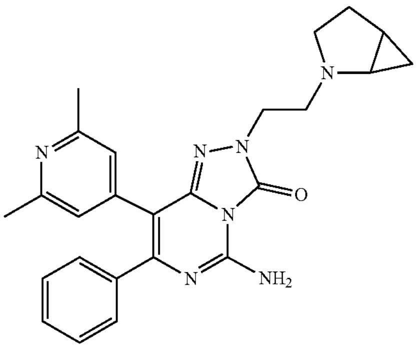 [SMILES: Cc1cc(-c2c(-c3ccccc3)nc(N)n3c(=O)n(CCN4CCC5CC54)nc23)cc(C)n1] | Example 2-95 |
| 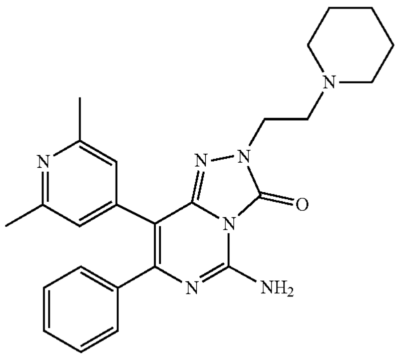 [SMILES: Cc1cc(-c2c(-c3ccccc3)nc(N)n3c(=O)n(CCN4CCCCC4)nc23)cc(C)n1] | Example 2-96 |

TABLE 1-continued
| Examples 1-1 to 3-10 |
| --- |
| 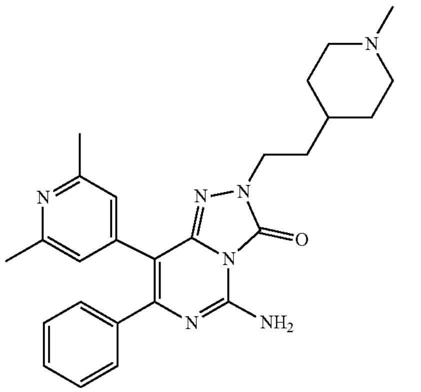 Example 2-97 |
| 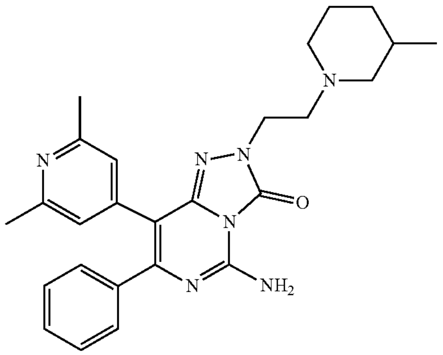 Example 2-98 |
| 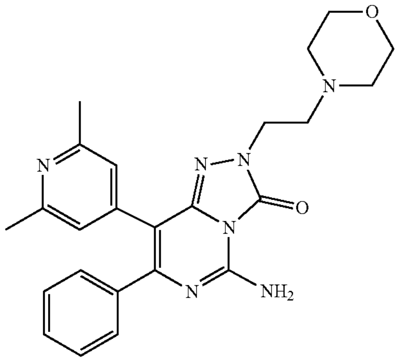 [SMILES: Cc1cc(-c2c(-c3ccccc3)nc(N)n3c(=O)n(CCN4CCOCC4)nc23)cc(C)n1] Example 2-99 |
| 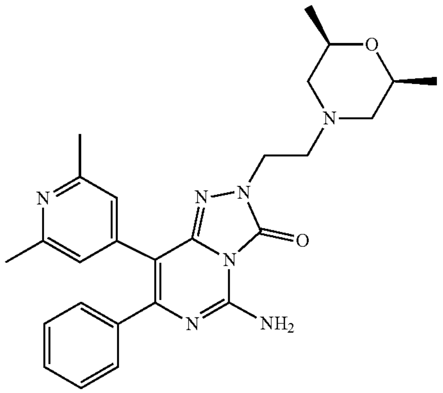 Example 2-100 |

TABLE 1-continued
| Examples 1-1 to 3-10 |
| --- |
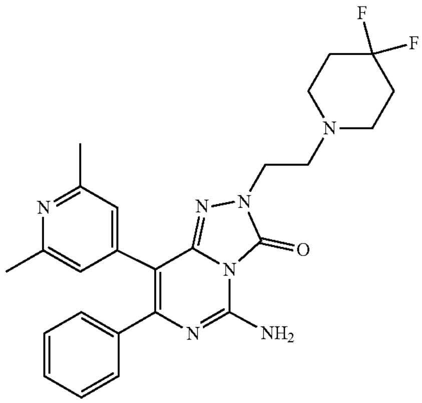 [SMILES: Cc1cc(-c2c(-c3ccccc3)nc(N)n3c(=O)n(CCN4CCC(F)(F)CC4)nc23)cc(C)n1]
Example 2-101
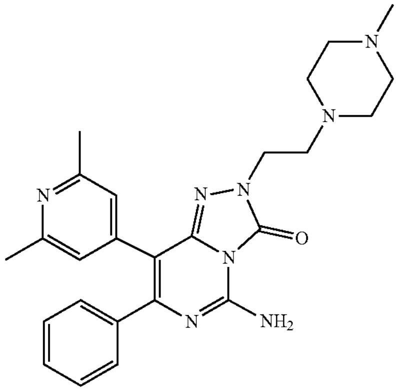
Example 2-102
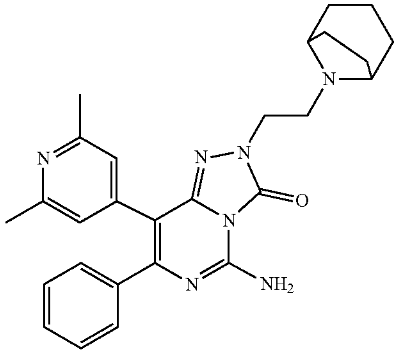 [SMILES: Cc1cc(-c2c(-c3ccccc3)nc(N)n3c(=O)n(CCN4C5CCCC4CC5)nc23)cc(C)n1]
Example 2-103
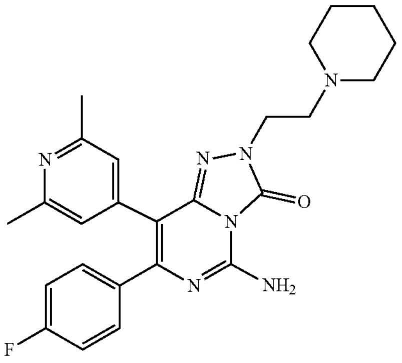 [SMILES: Cc1cc(-c2c(-c3ccc(F)cc3)nc(N)n3c(=O)n(CCN4CCCCC4)nc23)cc(C)n1]
Example 2-104

TABLE 1-continued
Examples 1-1 to 3-10
Example 2-105
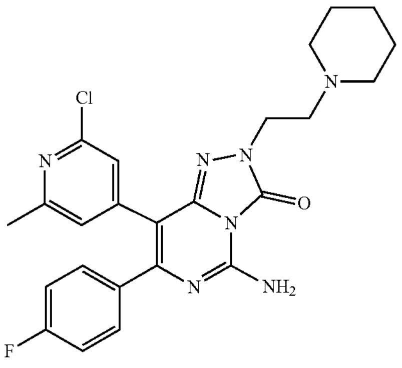 [SMILES: Cc1cc(-c2c(-c3ccc(F)cc3)nc(N)n3c(=O)n(CCN4CCCCC4)nc23)cc(Cl)n1]
Example 2-106
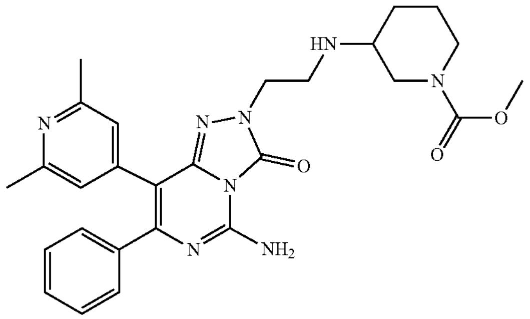
Example 2-107
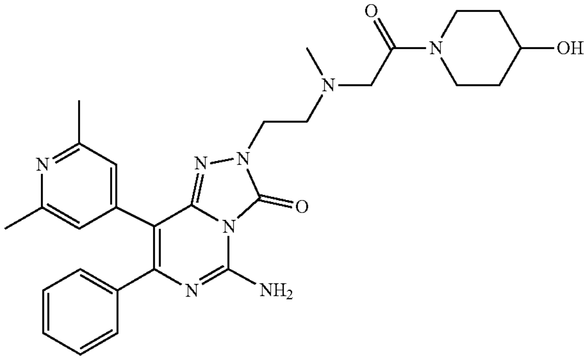 [SMILES: Cc1cc(-c2c(-c3ccccc3)nc(N)n3c(=O)n(CCN(C)CC(=O)N4CCC(O)CC4)nc23)cc(C)n1]
Example 2-108
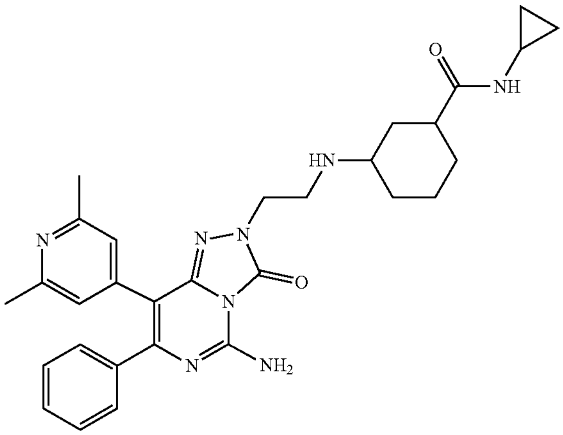 [SMILES: Cc1cc(-c2c(-c3ccccc3)nc(N)n3c(=O)n(CCNC4CCCC(C(=O)NC5CC5)C4)nc23)cc(C)n1]

TABLE 1-continued
| Examples 1-1 to 3-10 |
| --- |
| 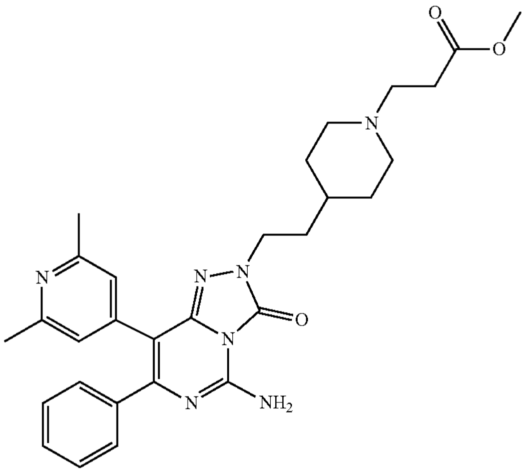 Example 2-109 |
| 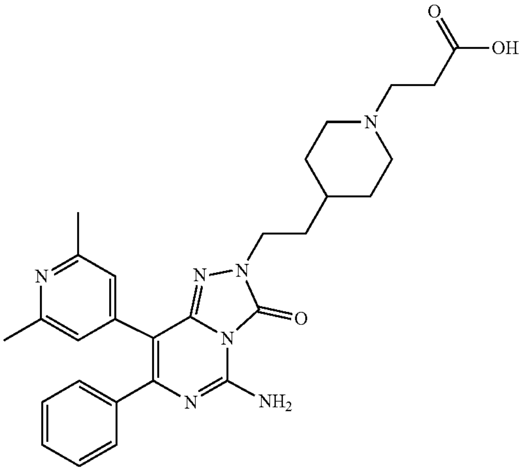 [SMILES: Cc1cc(-c2c(-c3ccccc3)nc(N)n3c(=O)n(CCC4CCN(CCC(=O)O)CC4)nc23)cc(C)n1] Example 2-110 |
| 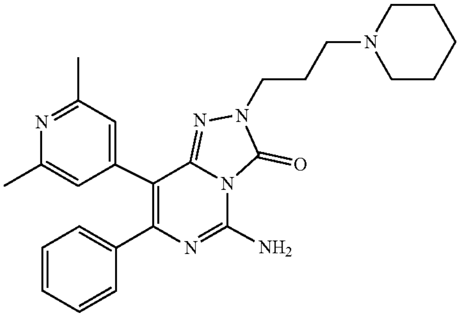 [SMILES: Cc1cc(-c2c(-c3ccccc3)nc(N)n3c(=O)n(CCCN4CCCCC4)nc23)cc(C)n1] Example 2-111 |

TABLE 1-continued
| Examples 1-1 to 3-10 | |
|---|---|
| 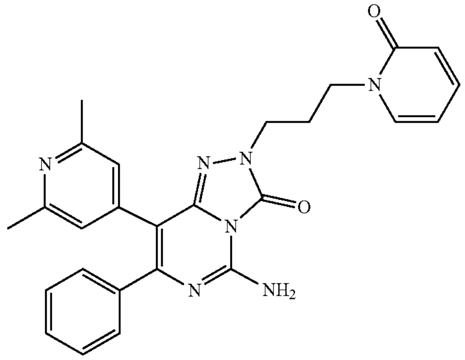 [SMILES: Cc1cc(-c2c(-c3ccccc3)nc(N)n3c(=O)n(CCCn4ccccc4=O)nc23)cc(C)n1] | Example 2-112 |
| 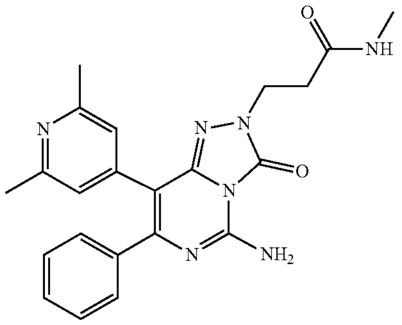 | Example 2-113 |
| 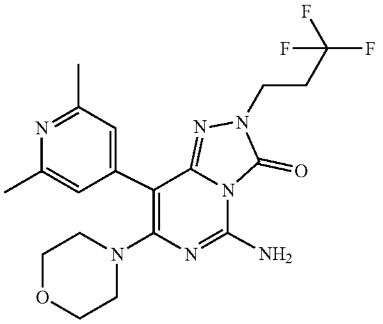 [SMILES: Cc1cc(-c2c(N3CCOCC3)nc(N)n3c(=O)n(CCC(F)(F)F)nc23)cc(C)n1] | Example 3-1 |
| 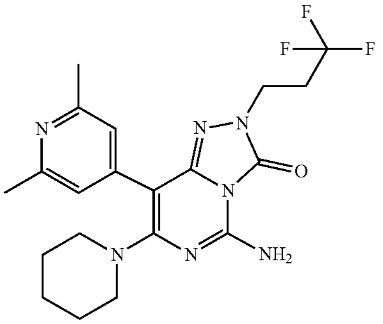 [SMILES: Cc1cc(-c2c(N3CCCCC3)nc(N)n3c(=O)n(CCC(F)(F)F)nc23)cc(C)n1] | Example 3-2 |

TABLE 1-continued
| Examples 1-1 to 3-10 |
| --- |
| 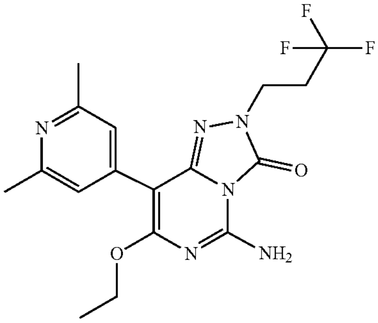 [SMILES: CCOc1nc(N)n2c(=O)n(CCC(F)(F)F)nc2c1-c1cc(C)nc(C)c1] Example 3-3 |
| 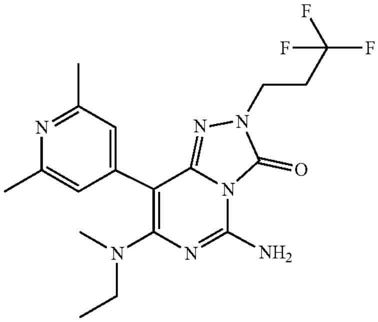 [SMILES: CCN(C)c1nc(N)n2c(=O)n(CCC(F)(F)F)nc2c1-c1cc(C)nc(C)c1] Example 3-4 |
| 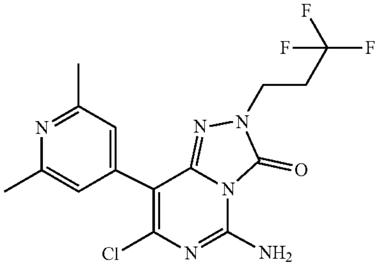 [SMILES: Cc1cc(-c2c(Cl)nc(N)n3c(=O)n(CCC(F)(F)F)nc23)cc(C)n1] Example 3-5 |
| 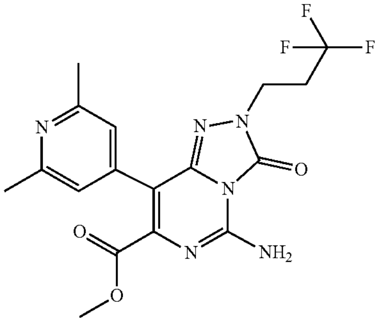 [SMILES: COC(=O)c1nc(N)n2c(=O)n(CCC(F)(F)F)nc2c1-c1cc(C)nc(C)c1] Example 3-6 |
| 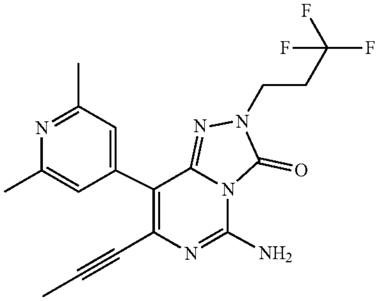 [SMILES: CC#Cc1nc(N)n2c(=O)n(CCC(F)(F)F)nc2c1-c1cc(C)nc(C)c1] Example 3-7 |

TABLE 1-continued

| Examples 1-1 to 3-10 | |
|---|---|
| 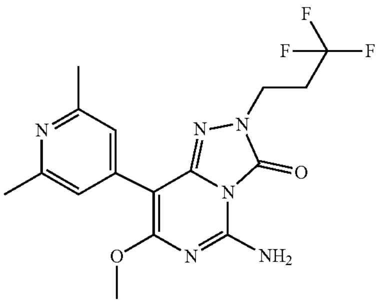 [SMILES: COc1nc(N)n2c(=O)n(CCC(F)(F)F)nc2c1-c1cc(C)nc(C)c1] | Example 3-8 |
| 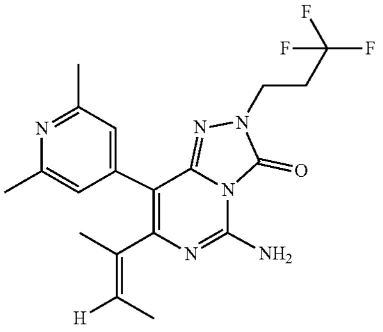 [SMILES: C/C=C(/C)c1nc(N)n2c(=O)n(CCC(F)(F)F)nc2c1-c1cc(C)nc(C)c1] | Example 3-9 |
| 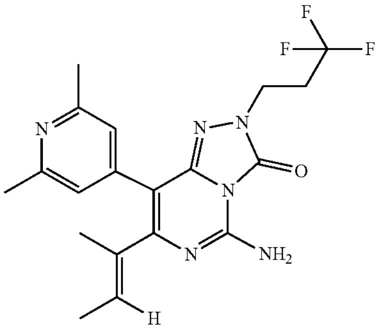 [SMILES: C/C=C(\C)c1nc(N)n2c(=O)n(CCC(F)(F)F)nc2c1-c1cc(C)nc(C)c1] | Example 3-10 |

Intermediates used in the preparation of the Examples are listed in Table 2. Compounds were prepared according to the methods of the synthetic route indicated ("Rte."). Where no route number or data is shown, commercially available materials were used. LCMS and $^1$H NMR data are shown for purified products (or indicated as 'used crude' if no purification was performed). In some cases, intermediates used for the preparation of another intermediate are shown in parentheses; for example, intermediates 41 & 42 were used in the preparation of intermediate 56.

TABLE 2

| Intermediates | | | |
|---|---|---|---|
| Int. | Rte. | Name | Data |
| 1 | 1 | 5-amino-8-bromo-7-phenyl-[1,2,4]triazolo[4,3-c]pyrimidin-3(2H)-one | LCMS (Method C): m/z 306 $(M + H)^+$ $(ES^+)$, at 1.78 min, UV active. $^1$H NMR: (400 MHz, DMSO-d6) δ: 12.57 (s, 1H), 7.62-7.60 (m, 2H), 7.45-7.41 (m, 3H). Exchangeable —$NH_2$ protons were not observed. |
| 2 | | 1-(bromomethyl)-4-fluorobenzene | |
| 3 | | 2,6-dimethylpyridine-4-boronic acid pinacol ester | |
| 4 | | (5-fluoropyridin-2-yl)methanol | |
| 5 | b (step 1) | 5-amino-8-bromo-2-((5-fluoropyridin-2-yl)methyl)-7-phenyl-[1,2,4]triazolo[4,3-c]pyrimidin-3(2H)-one | LCMS (Method C): m/z 415 $(M + H)^+$ $(ES^+)$, at 2.64 min, UV active. $^1$H NMR: (400 MHz, DMSO-d6) δ: 8.48 (s, 1H), 7.70 (d, J = 7.8 Hz, 2H), 7.47- |

TABLE 2-continued

| Intermediates | | | |
|---|---|---|---|
| Int. | Rte. | Name | Data |
| | | | 7.44 (m, 4H), 7.37-7.31 (m, 1H), 5.28 (s, 2H). Exchangeable —$NH_2$ protons were not observed |
| 6 | | 4-(bromomethyl)phenol | |
| 7 | 2 | 5-amino-8-(2,6-dimethylpyridin-4-yl)-7-phenyl-[1,2,4]triazolo[4,3-c]pyrimidin-3(2H)-one | LCMS (Method A): m/z 333 $(M + H)^+$ $(ES^+)$, at 1.98 min, UV active. $^1H$ NMR: (400 MHz, DMSO-d6) δ: 12.25 (s, 1H), 8.14 (s, 2H), 7.29-7.25 (m, 5H), 6.82 (s, 2H), 2.29 (s, 6H). |
| 8 | | pyridazin-3-ylmethanol | |
| 9 | 2 (step 1) | 5-amino-8-bromo-7-phenyl-2-((2-(trimethylsilyl)ethoxy)methyl)-[1,2,4]triazolo[4,3-c]pyrimidin-3(2H)-one | LCMS (Method B): m/z 436 (M + H)+ (ES+), at 3.25 min, UV active. $^1H$ NMR: (400 MHz, DMSO-d6) δ: 8.56 (s, 2H), 7.62 (d, J = 7.1 Hz, 2H), 7.45 (d, J = 6.6 Hz, 3H), 5.18 (s, 2H), 3.66 (t, J = 8.2 Hz, 2H), 0.91 (t, J = 8.2 Hz, 2H), 0.04 (s, 9H). |
| 10 | | (6-methoxypyridin-2-yl) methanol | |
| 11 | 3 | 6-(bromomethyl)-3-fluoro-2-methoxypyridine | LCMS (Method B): m/z 220 $(M + H)^+$ $(ES^+)$, at 2.97 min, UV active. $^1H$ NMR: (400 MHz, DMSO-d6) δ: 7.69-7.64 (m, 1H), 7.20-7.17 (m, 1H), 4.62 (s, 2H), 3.95 (s, 3H). |
| 12 | | 1-(2,4-difluorophenyl)ethan-1-ol | |
| 13 | | 4-(Hydroxymethyl)pyridine | |
| 14 | | 3,4-dihydro-1H-2-benzothiopyran-4-ol | |
| 15 | | (1S)-7-fluoro-1,2,3,4-tetrahydronaphthalen-1-ol | |
| 16 | | 1-(2,5-difluorophenyl)ethan-1-ol | |
| 17 | | {2-[(difluoromethyl)sulfanyl]phenyl} methanol | |
| 18 | | (2-methylphenyl)methanol | |
| 19 | | (4-fluoro-2-methylphenyl)methanol | |
| 20 | | [2-(1H-pyrazol-1-yl)pyridin-3-yl]methanol | |
| 21 | | 1-(pyridin-2-yl)ethan-1-ol | |
| 22 | | (2-chloro-3-fluorophenyl)methanol | |
| 23 | | [2-(cyclopropylmethoxy)phenyl]methanol | |
| 24 | | (2,6-difluorophenyl)methanol | |
| 25 | | {2-[(dimethylamino)methyl]phenyl} methanol | |
| 26 | | (2-ethoxyphenyl)methanol | |
| 27 | | (1S)-1-(pyridin-4-yl)ethan-1-ol | |
| 28 | | 1-(pyridin-3-yl)ethan-1-ol | |
| 29 | | (2-methoxypyridin-3-yl)methanol | |
| 30 | | (4-methoxy-6-methylpyridin-2-yl)methanol | |
| 31 | | 1-(2-chloro-6-fluorophenyl)propan-1-ol | |
| 32 | | [2-(piperidin-4-yl)phenyl]methanol | |
| 33 | | 1-phenyl-2-[(2,2,2-trifluoroethyl)amino]ethan-1-ol | |
| 34 | | [2-(piperidin-4-ylmethyl)phenyl]methanol | |
| 35 | | (6-methoxypyridazin-3-yl)methanol | |
| 36 | | 2-amino-1-(2,6-difluorophenyl)ethan-1-ol | |
| 37 | | (5-fluoropyrimidin-2-yl)methanol | |
| 38 | 4 | N,N-di-tert-butoxy carbonyl (6-(bromomethyl)-3-fluoropyridin-2-yl)-amine | LCMS (Method B): m/z 305 $(M - Boc)^+$ $(ES^+)$, at 3.00 min, UV active. |
| 39 | | (3-chloro-5-fluoropyridin-2-yl)methanol | |
| 40 | | (5-Fluoro-2-methoxypyridin-3-yl)methanol | |
| 41 | 5 | 5-amino-8-bromo-7-(4-fluorophenyl)-[1,2,4]triazolo[4,3- | LCMS (Method C): m/z 323 $(M + H)^+$ $(ES^+)$, at 1.87 min, UV active. |

TABLE 2-continued

| Intermediates | | | |
|---|---|---|---|
| Int. | Rte. | Name | Data |
| | | c]pyrimidin-3(2H)-one | $^1$H NMR: (400 MHz, DMSO-d6) δ: 12.58 (s, 1H), 8.19-8.01 (m, 2H), 7.70-7.67 (m, 2H), 7.32-7.27 (m, 2H). |
| 42 | 6 | Methyl-6-methyl-4-(4,4,5,5-tetramethyl-1,3,2-dioxaborolan-2-yl)picolinate | $^1$H NMR: (400 MHz, DMSO-d6) δ: 7.87 (s, 1H), 7.51 (s, 1H), 3.88 (s, 3H), 2.54 (s, 3H), 1.08 (s, 12H). |
| 43 | | methyl 6-methylpyridine-2-carboxylate | |
| 44 | j (steps 1 & 2) | 1-(5-fluoropyridin-2-yl)propyl 4-methylbenzenesulfonate | LCMS (Method A): m/z 310 $(M + H)^+$ $(ES^+)$, at 2.65 min, UV active. $^1$H NMR: (400 MHz, DMSO-d6) δ: 8.48 (s, 2H), 7.72-7.66 (m, 2H), 7.42-7.34 (m, 4H), 5.52 (d, J = 7.2 Hz, 2H), 2.36-2.33 (m, 6H). |
| 45 | 7 | methyl 4-(5-amino-3-oxo-7-phenyl-2,3-dihydro-[1,2,4]triazolo[4,3-c]pyrimidin-8-yl)-6-methylpicolinate | LCMS (Method A): m/z 377 $(M + H)^+$ $(ES^+)$, at 1.65 min, UV active. $^1$H NMR: (400 MHz, DMSO-d6) δ: 12.46 (s, 1H), 8.41 (s, 1H), 7.70 (s, 1H), 7.32-7.25 (m, 6H), 3.85 (s, 3H), 2.47 (s, 3H). One of the exchangeable —$NH_2$ protons was not observed. |
| 46 | | (3-fluoro-5-methoxypyridin-2-yl)methanol | |
| 47 | 1 (Intermediate 48) | 5-amino-8-bromo-7-(phenyl-d5)-[1,2,4]triazolo[4,3-c]pyrimidin-3(2H)-one | $^1$H NMR: (400 MHz, DMSO-d6) δ: 12.57 (s, 1H), 8.30 (s, 1H), 7.59 (s, 1H). |
| 48 | | (phenyl-d5)boronic acid | |
| 49 | 2 (Intermediates 47 & 42) | methyl 4-(5-amino-3-oxo-7-(phenyl-d5)-2,3-dihydro-[1,2,4]triazolo[4,3-c]pyrimidin-8-yl)-6-methylpicolinate | $^1$H NMR: (400 MHz, DMSO-d6) δ: 12.45 (s, 1H), 8.32 (s, 2H), 7.79 (s, 1H), 7.24 (s, 1H), 3.90 (s, 3H), 2.38 (s, 3H). |
| 50 | | 5-Methyl-2-pyridinemethanol | |
| 51 | | (5-Bromopyridin-2-yl)methanol | |
| 52 | 7 (steps 1 & 2) | methyl 4-(5-amino-3-oxo-7-phenyl-2-((2-(trimethylsilyl)ethoxy)methyl)-2,3-dihydro-[1,2,4]triazolo[4,3-c]pyrimidin-8-yl)-6-methyl picolinate | LCMS (Method A): m/z 507 $(M + H)^+$ $(ES^+)$, at 2.46 min, UV active. $^1$H NMR: (400 MHz, DMSO-d6) δ: 7.67 (s, 1H), 7.32-7.27 (m, 6H), 5.14 (s, 2H), 3.81 (s, 3H), 3.64 (t, J = 7.8 Hz, 2H), 2.40 (s, 3H), 0.89 (t, J = 7.8 Hz, 2H), 0.01 (s, 9H). Exchangeable —$NH_2$ protons were not observed. |
| 53 | 8 | 5-amino-8-(2-(hydroxymethyl)-6-methylpyridin-4-yl)-7-phenyl-[1,2,4]triazolo[4,3-c]pyrimidin-3(2H)-one | LCMS (Method C): m/z 347 $(M - H)^-$ (ES), at 1.11 min, UV active. $^1$H NMR: (400 MHz, DMSO-d6) δ: 12.42 (s, 1H), 8.43-7.87 (m, 2H), 7.27-7.25 (m, 5H), 7.14 (s, 1H), 6.84 (s, 1H), 5.25 (t, J = 5.7 Hz, 1H), 4.42 (d, J = 5.7 Hz, 2H), 2.29 (s, 3H). |
| 54 | | 6-(bromomethyl)nicotinonitrile | |
| 55 | | (5-chloropyridin-2-yl)methanol | |
| 56 | 2 (Intermediates 41 & 42) | methyl 4-(5-amino-7-(4-fluorophenyl)-3-oxo-2,3-dihydro-[1,2,4]triazolo[4,3-c]pyrimidin-8-yl)-6-methylpicolinate | LCMS (Method C): m/z 395 $(M + H)^+$ $(ES^+)$, at 1.51 min, UV active. $^1$H NMR: (400 MHz, DMSO-d6) δ: 12.45 (s, 1H), 8.41 (s, 2H), 7.68 (s, 1H), 7.32-7.26 (m, 3H), 7.11 (m, 2H), 3.81 (s, 3H), 2.40 (s, 3H). |
| 57 | 6 (Intermediate 58) | methyl 6-methoxy-4-(4,4,5,5-tetramethyl-1,3,2-dioxaborolan-2-yl)picolinate | Used crude |
| 58 | | methyl 6-methoxypicolinate | |
| 59 | 7 (Intermediate 57, step 2) Steps 1 & 2 | methyl 4-(5-amino-3-oxo-7-phenyl-2-((2-(trimethylsilyl)ethoxy)methyl)-2,3-dihydro-[1,2,4]triazolo[4,3-c]pyrimidin-8-yl)-6-methoxypicolinate | LCMS (Method C): m/z 523 $(M + H)^+$ $(ES^+)$, at 2.66 min, UV active. $^1$H NMR: (400 MHz, DMSO-d6) δ: 7.90 (s, 1H), 7.87 (s, 1H), 7.56 (s, 1H), 7.43-7.42 (m, 3H), 7.29 (s, 1H), 3.57 (s, 3H), 3.32 (s, 3H), 3.31 (s, 2H), 1.17 (s, 2H), 1.06 (s, 2H), 0.01 (s, 9H). Exchangeable —$NH_2$ protons were not observed. |
| 60 | 8 (Intermediate 59) | 5-amino-8-(2-(hydroxymethyl)-6-methoxypyridin-4-yl)-7-phenyl-[1,2,4]triazolo[4,3-c]pyrimidin-3(2H)-one | LCMS (Method C): m/z 365 $(M + H)^+$ $(ES^+)$, at 1.60 min, UV active. $^1$H NMR: (400 MHz, DMSO-d6) δ: 12.41 (s, 1H), 7.53 (s, 2H), 7.51-7.25 (m, 6H), 6.99 (s, 1H), 5.26 (t, J = 8.0 Hz, 2H), 4.54-4.51 (m, 1H), 3.88 (s, 3H). |

TABLE 2-continued

| Intermediates | | | |
|---|---|---|---|
| Int. | Rte. | Name | Data |
| 61 | 6 (Intermediate 62) | methyl 6-chloro-4-(4,4,5,5-tetramethyl-1,3,2-dioxaborolan-2-yl)picolinate | Used crude |
| 62 | | methyl 6-chloropicolinate | |
| 63 | 6 (Intermediate 64) | 2-fluoro-6-methyl-4-(4,4,5,5-tetramethyl-1,3,2-dioxaborolan-2-yl)pyridine | Used crude |
| 64 | | 2-fluoro-6-methylpyridine | |
| 65 | | N,N-dimethylamine hydrochloride | |
| 66 | 6 (Intermediate 67) purified by Biotage-Isolera using 10 g silica snap and was eluted with gradient 1-10% EtOAc in Hexane | 2-methyl-4-(4,4,5,5-tetramethyl-1,3,2-dioxaborolan-2-yl)-6-(trifluoromethyl)pyridine | $^1$H NMR: (400 MHz, $CDCl_3$) δ: 7.85 (s, 1H), 7.72 (s, 1H), 2.66 (s, 3H), 1.39 (s, 12H). |
| 67 | | 2-methyl-6-(trifluoromethyl)pyridine | |
| 68 | | azetidine | |
| 69 | | 2-Chloro-6-methyl-4-(4,4,5,5-tetramethyl-1,3,2-dioxaborolan-2-yl)pyridine | |
| 70 | 6 (Intermediate 71) | 2-methoxy-6-methyl-4-(4,4,5,5-tetramethyl-1,3,2-dioxaborolan-2-yl)pyridine | Used crude |
| 71 | | 2-methoxy-6-methylpyridine | |
| 72 | 6 (Intermediate 73) | 2-chloro-4-(4,4,5,5-tetramethyl-1,3,2-dioxaborolan-2-yl)-6-(trifluoromethyl)pyridine | Used crude |
| 73 | | 2-chloro-6-(trifluoromethyl)pyridine | |
| 74 | 1 (steps 1 & 2) | 4-hydrazinyl-6-phenylpyrimidin-2-amine | LCMS (Method C): m/z 202 $(M + H)^+$ $(ES^+)$, at 0.69 min, UV active. $^1$H NMR: (400 MHz, DMSO-d6) δ: 7.94-7.91 (m, 2H), 7.84 (s, 1H), 7.48-7.42 (m, 3H), 6.47 (s, 1H), 6.00 (s, 2H), 4.25 (s, 2H). |
| 75 | | phenyl acetaldehyde | |
| 76 | | phenyl acetone | |
| 77 | | 4-(2-bromoethyl)phenol | |
| 78 | | 1-(2-bromoethyl)-4-fluorobenzene | |
| 79 | | methyl 4-(2-bromoethyl)benzoate | |
| 80 | | (4-methoxyphenyl)methanol | |
| 81 | | 2-(pyridin-2-yl)ethan-1-ol | |
| 82 | | (2-bromoethyl)benzene | |
| 83 | 9 | 2-(5-amino-8-(2,6-dimethylpyridin-4-yl)-3-oxo-7-phenyl-[1,2,4]triazolo[4,3-c]pyrimidin-2(3H)-yl)ethyl methanesulfonate | LCMS (Method A): m/z 455 (M + H)+ (ES+), at 2.34 min, UV active. $^1$H NMR: (400 MHz, DMSO-d6 δ: 7.28-7.27 (m, 5H), 6.84 (s, 2H), 4.47 (t, J = 4.5 Hz, 2H), 4.13 (t, J = 4.5 Hz, 2H), 3.17 (s, 3H), 2.30 (s, 6H). Exchangeable —$NH_2$ protons not observed. |
| 84 | a (Intermediates 1 & 85 (step 1), 3 (step 2)) | 5-amino-8-(2,6-dimethylpyridin-4-yl)-2-(2-hydroxyethyl)-7-phenyl-[1,2,4]triazolo[4,3-c]pyrimidin-3(2H)-one | LCMS (Method A): m/z 377 (M + H)+ (ES+), at 1.94 min, UV active. $^1$H NMR: (400 MHz, DMSO-d6) δ: 7.27-7.25 (m, 5H), 6.83 (s, 2H), 4.80 (t, J = 6.0 Hz, 1H), 3.82 (t, J = 6.0 Hz, 2H), 3.65 (t, J = 5.6 Hz, 2H), 2.30 (s, 6H). Exchangeable —$NH_2$ protons not observed. |
| 85 | | 2-bromoethan-1-ol | |
| 86 | | 5-amino-2-chloro-N-methylbenzamide hydrochloride | |
| 87 | | 1-([1,2,4]triazolo[4,3-a]pyrimidin-3-yl)ethan-1-amine hydrochloride | |
| 88 | | N-methyl-1-phenylpiperidin-4-amine dihydrochloride | |
| 89 | | (1S)-1-(6-methylpyridin-2-yl)ethan-1-amine | |
| 90 | | 1-(3-methyl-1H-pyrazol-5-yl)piperidin-4-amine | |
| 91 | | 2-(1-methyl-1H-pyrrol-2-yl)azepane | |
| 92 | | 5-methyl-N-(piperidin-4-yl)pyridin-2-amine | |

TABLE 2-continued

| Intermediates | | | |
|---|---|---|---|
| Int. | Rte. | Name | Data |
| 93 | | 1-(3-aminophenyl)-3-methyl-4,5-dihydro-1H-pyrazol-5-one | |
| 94 | | [2-(methylamino)-1, 2,3,4-tetrahydronaphthalen-2-yl]methanol hydrochloride | |
| 95 | | 1-amino-3-(2,4-difluorophenyl)propan-2-ol | |
| 96 | | (R)-(4-benzylmorpholin-3-yl)methanol | |
| 97 | | (4-benzylpiperidin-4-yl)methanol | |
| 98 | | 2-(morpholin-3-yl)-1-phenylethan-1-ol | |
| 99 | | 5-amino-2,3-dihydro-1H-inden-2-ol | |
| 100 | | methyl iodide | |
| 101 | | ethyl iodide | |
| 102 | | 2-iodopropane | |
| 103 | | 1-bromo-3-methylbutane | |
| 104 | | 3,3,3-trifluoropropanal | |
| 105 | | 3-fluoropropan-1-ol | |
| 106 | | 1-bromo-2-methoxyethane | |
| 107 | | 3-bromopropanenitrile | |
| 108 | | ethyl (2-bromoethyl)carbamate | |
| 109 | | ethyl (2-hydroxyethyl)(methyl)carbamate | |
| 110 | | tert-butyl (2-bromoethyl)carbamate | |
| 111 | | methyl 3-bromopropanoate | |
| 112 | | ethyl(methyl)amine hydrochloride | |
| 113 | | N-methylcyclopropanamine | |
| 114 | | 1-bromopropane | |
| 115 | | 1-bromo-2-methylpropane | |
| 116 | | 1-bromo-acetamide | |
| 117 | ae (step 1) | ethyl 3-(5-amino-8-(2,6-dimethylpyridin-4-yl)-3-oxo-7-phenyl-[1,2,4]triazolo[4,3-c]pyrimidin-2(3H)-yl)propanoate | LCMS (Method A): m/z 433 (M + H)+ (ES+), at 2.11 min, UV active. $^1$H NMR: (400 MHz, DMSO-d6 δ: 7.28-7.27 (m, 5H), 6.80 (s, 2H), 4.05-4.03 (m, 4H), 2.74-2.72 (m, 2H), 2.51 (s, 6H), 1.12-1.10 (t, J = 8.0, 3H). Exchangeable —$NH_2$ protons not observed. |
| 118 | | 2-bromo-N,N-dimethylacetamide | |
| 119 | | (3,3-difluorocyclopentyl)methanol | |
| 120 | | (2-ethyl-2-methylcyclopropyl)methanol | |
| 121 | | N-cyclopropyl-2-hydroxy-N-methylacetamide | |
| 122 | | methyl 1-(hydroxymethyl)cyclopentane-1-carboxylate | |
| 123 | | 1-bromo-2-(trifluoromethoxy)ethane | |
| 124 | | 4,6-dichloro-5-iodopyrimidin-2-amine | |
| 125 | 1 (intermediate 124 & 3, steps 1-3 only) | 5-amino-7-chloro-8-(2,6-dimethylpyridin-4-yl)-[1,2,4]triazolo[4,3-c]pyrimidin-3(2H)-one | LCMS (Method B): m/z 291 $(M + H)^+$ (ES+), at 1.58 min, UV active. $^1$H NMR: (400 MHz, DMSO-d6 δ: 8.43 (s, 1H), 8.04 (s, 1H), 7.25 (s, 1H), 7.11 (s, 2H), 2.44 (s, 6H). |
| 126 | | 3,3,3-trifluoropropan-1-ol | |
| 127 | 1 (intermediate 128) | 5-amino-8-bromo-7-(2,4-difluorophenyl)-[1,2,4]triazolo[4,3-c]pyrimidin-3(2H)-one | LCMS (Method A): m/z 342 $(M + H)^+$ (ES+), at 2.39 min, UV active. $^1$H NMR: (400 MHz, DMSO-d6) δ: 7.49 (d, J = 7.0 Hz, 1H), 7.46 (d, J = 2.3 Hz, 1H), 7.08 (s, 1H). Exchangeable NH, $NH_2$— Protons were not observed. |
| 128 | | (2,4-difluorophenyl)boronic acid | |
| 129 | | (4-methoxy-phenyl)boronic acid | |
| 130 | | (4-cyanophenyl)boronic acid | |
| 131 | b (intermediate 125 and 126 step 1 only) | 5-amino-7-chloro-8-(2,6-dimethylpyridin-4-yl)-2-(3,3,3-trifluoropropyl)-[1,2,4]triazolo[4,3-c]pyrimidin-3(2H)-one | LCMS (Method A): m/z 387 $(M + H)^+$ (ES+), at 2.39 min, UV active. $^1$H NMR: (400 MHz, DMSO-d6) δ: 8.82 (s, 1H), 7.86 (s, 1H), 7.09 (s, 2H), 4.00 (t, J = 9.2 Hz, 2H), 2.71 (t, J = 4.0 Hz, 2H), 2.50 (s, 6H). |
| 132 | | 2-(tributylstannyl)pyridine | |
| 133 | | 4-(Tributylstannyl)pyridine | |

TABLE 2-continued

| Intermediates | | | |
|---|---|---|---|
| Int. | Rte. | Name | Data |
| 134 | | 3-(Tributylstannyl) pyridine | |
| 135 | | 5-fluoro-2-(trimethylstannyl) pyridine | Prepared as described in Journal of Medicinal Chemistry, 2015, vol. 58, # 16, p. 6653-6664. Used crude |
| 136 | | 2-(Tributylstannyl)furan | |
| 137 | | 5 methyl-2-(tributylstannyl) furan | |
| 138 | 10 | 4-methyl-2-(trimethylstannyl)thiazole | Used crude |
| 139 | | (2-chloro-6-methylpyridin-4-yl)boronic acid | |
| 140 | 6 (intermediate 141) | methyl 4-(4,4,5,5-tetramethyl-1,3,2-dioxaborolan-2-yl)-6-(trifluoromethyl)picolinate | Used crude |
| 141 | | methyl 6-(trifluoromethyl)picolinate | |
| 142 | | tert-butyl 3-hydroxypiperidine-1-carboxylate | |
| 143 | | bicyclo[1.1.1]pentan-1-ylmethanol | |
| 144 | | (4-fluorocuban-1-yl)methanol | |
| 145 | | cuban-1-ylmethanol | |
| 146 | | bicyclo[1.1.1]pentan-1-ylmethanol | |
| 147 | | tert-butyl (R)-2-(hydroxymethyl)morpholine-4-carboxylate | |
| 148 | | tert-butyl 4-(hydroxymethyl)piperidine-1-carboxylate | |
| 149 | | tert-butyl (S)-2-(hydroxymethyl)morpholine-4-carboxylate | |
| 150 | | 1-methylpiperidin-3-ol | |
| 151 | | (tetrahydro-2H-pyran-4-yl)methanol | |
| 152 | | tert-butyl (S)-3-(hydroxymethyl)morpholine-4-carboxylate | |
| 153 | | (R)-(4-benzylmorpholin-3-yl)methanol | |
| 154 | | (tetrahydro-2H-pyran-3-yl)methanol | |
| 155 | | (tetrahydro-2H-pyran-2-yl)methanol | |
| 156 | | tert-butyl (S)-3-(hydroxymethyl)-4-methylpiperazine-1-carboxylate | Prepared as described in WO2011073263 A1 |
| 157 | | tert-butyl (R)-3-(hydroxymethyl)-4-methylpiperazine-1-carboxylate | Prepared as described in WO2011073263 A1 |
| 158 | | (1,1-Dioxidotetrahydro-2H-thiopyran-3-yl)methanol | |
| 159 | | 3-(hydroxymethyl)thietane 1,1-dioxide | |
| 160 | | pyridazin-3-ylmethanol | |
| 161 | | azetidine hydrochloride | |
| 162 | | 2-azabicyclo[3.1.0]hexane hydrochloride | |
| 163 | | 1-(2-chloroethyl)piperidine hydrochloride | |
| 164 | | 2-(1-methylpiperidin-4-yl)ethan-1-ol | |
| 165 | | 3-methylpiperidine | |
| 166 | | morpholine | |
| 167 | | (cis)-2,6-dimethylmorpholine | |
| 168 | | 4,4-difluoropiperidine | |
| 169 | | 1-methylpiperazine | |
| 170 | | 8-azabicyclo[3.2.1]octane | |
| 171 | | methyl 3-aminopiperidine-1-carboxylate | |
| 172 | | 1-(4-hydroxypiperidin-1-yl)-2-(methylamino)ethan-1-one hydrochloride | |
| 173 | | 3-amino-N-cyclopropylcyclohexane-1-carboxamide | |

TABLE 2-continued

| Intermediates | | | |
|---|---|---|---|
| Int. | Rte. | Name | Data |
| 174 | | 3-(piperidin-1-yl)propan-1-ol | |
| 175 | | 1-(3-hydroxypropyl)-1,2-dihydropyridin-2-one | |
| 176 | | methylamine | |
| 177 | | piperidine | |
| 178 | | sodium ethoxide | |
| 179 | | N-methylethanamine | |
| 180 | | Tributyl(1-propyn-1-yl)stannane | |
| 181 | ab using Intermediate 131 (step 1 only) | Di-Boc protected 5-amino-7-chloro-8-(2,6-dimethylpyridin-4-yl)-2-(3,3,3-trifluoropropyl)-[1,2,4]triazolo[4,3-c]pyrimidin-3(2H)-one | LCMS (Method A): m/z 587 $(M + H)^+$ $(ES^+)$, at 2.89 min, UV active. |

TABLE 3

| Data for Examples 1-1 to 3-10 | | |
|---|---|---|
| Ex. | Name | Details |
| 1-1 | 5-amino-8-(2,6-dimethyl-4-pyridyl)-2-[(4-fluorophenyl)methyl]-7-phenyl-[1,2,4]triazolo[4,3-c]pyrimidin-3-one | Route a<br>$^1H$ NMR: (MHz, DMSO-d6) δ: 8.50 (br s, 2H), 7.37-7.14 (m, 9H), 6.79 (s, 2H), 5.01 (s, 2H), 2.27 (s, 6H)<br>LCMS Method A: m/z 441 $(M + H)^+$ (ES+), at 3.16 min, UV active |
| 1-2 | 5-amino-8-(2,6-dimethyl-4-pyridyl)-2-[(5-fluoro-2-pyridyl)methyl]-7-phenyl-[1,2,4]triazolo[4,3-c]pyrimidin-3-one | Route b<br>$^1H$ NMR: (MHz, DMSO-d6) δ: 8.52 (d, J = 2.8 Hz, 1H), 7.75-7.70 (m, 1H), 7.44-7.41 (m, 1H), 7.30-7.27 (m, 5H), 6.79 (s, 2H), 5.13 (s, 2H), 2.26 (s, 6H). Exchangeable —NH2 protons were not observed.<br>LCMS Method A: m/z 442 $(M + H)^+$ (ES+), at 2.61 min, UV active |
| 1-3 | 5-amino-8-(2,6-dimethyl-4-pyridyl)-2-[(4-methoxyphenyl)methyl]-7-phenyl-[1,2,4]triazolo[4,3-c]pyrimidin-3-one | Route c<br>$^1H$ NMR: (MHz, DMSO-d6) δ: 8.15 (s, 2H), 7.25-7.22 (m, 5H), 7.20-7.01 (m, 2H), 6.91-6.89 (m, 2H), 6.79 (s, 2H), 4.93 (s, 2H), 3.73 (s, 3H), 2.27 (s, 6H).<br>LCMS Method A: m/z 453 $(M + H)^+$ (ES+), at 3.16 min, UV active |
| 1-4 | 5-amino-8-(2,6-dimethyl-4-pyridyl)-2-[(4-hydroxyphenyl)methyl]-7-phenyl-[1,2,4]triazolo[4,3-c]pyrimidin-3-one | Intermediates 1 & 6 (step 1), 3 (step 2)<br>Route a<br>$^1H$ NMR: (MHz, DMSO-d6) δ: 9.42 (s, 1H), 7.29-7.27 (m, 5H), 7.11 (d, J = 8.4 Hz, 2H), 6.80 (s, 2H), 6.72 (d, J = 8.4 Hz, 2H), 4.88 (s, 2H), 2.28 (s, 6H). Exchangeable —$NH_2$ protons were not observed.<br>LCMS Method A: m/z 439 $(M + H)^+$ (ES+), at 2.63 min, UV active |
| 1-5 | 5-amino-8-(2,6-dimethyl-4-pyridyl)-7-phenyl-2-(pyridazin-3-ylmethyl)-[1,2,4]triazolo[4,3-c]pyrimidin-3-one | Route d<br>$^1H$ NMR: (MHz, DMSO-d6) δ: 9.19-9.17 (m, 1H), 7.72-7.64 (m, 2H), 7.30-7.26 (m, 5H), 6.79 (s, 2H), 5.36 (s, 2H), 2.26 (s, 6H). Exchangeable —$NH_2$ protons were not observed.<br>LCMS Method A: m/z 425 $(M + H)^+$ (ES+), at 2.08 min, UV active |
| 1-6 | 5-amino-8-(2,6-dimethyl-4-pyridyl)-2-[(6-methoxy-2-pyridyl)methyl]-7-phenyl-[1,2,4]triazolo[4,3-c]pyrimidin-3-one | Intermediates 1 & 10 (step 1), 3 (step 2)<br>Route b<br>$^1H$ NMR: (MHz, DMSO-d6) δ: 7.68-7.64 (m, 1H), 7.27-7.25 (m, 5H), 6.85-6.80 (m, 3H), 6.72-6.70 (m, 1H), 5.03 (s, 2H), 3.80 (s, 3H), 2.27 (s, 6H). Exchangeable —$NH_2$ protons were not observed.<br>LCMS Method A: m/z 454 $(M + H)^+$ (ES+), at 2.92 min, UV active |
| 1-7 | 5-amino-8-(2,6-dimethyl-4-pyridyl)-2-[(5-fluoro-6-methoxy-2-pyridyl)methyl]-7-phenyl-[1,2,4]triazolo[4,3-c]pyrimidin-3-one | Intermediates 1 & 11 (step 1), 3 (step 2)<br>Route a<br>$^1H$ NMR: (MHz, DMSO-d6) δ: 7.66-7.62 (m, 1H), 7.45-7.43 (m, 5H), 6.89 (d, J = 8.0 Hz, 1H), 6.80 (s, 2H), 5.02 (s, 2H), 3.90 (s, 3H), 2.27 (s, 6H). Exchangeable —$NH_2$ protons were not observed.<br>LCMS Method A: m/z 472 $(M + H)^+$ (ES+), at 3.18 min, UV active |

TABLE 3-continued

| Data for Examples 1-1 to 3-10 | | |
|---|---|---|
| Ex. | Name | Details |
| 1-8 | 5-amino-8-(2,6-dimethyl-4-pyridyl)-2-[(5-fluoro-6-oxo-1H-pyridin-2-yl)methyl]-7-phenyl-[1,2,4]triazolo[4,3-c]pyrimidin-3-one | Route e<br>$^1$H NMR: (MHz, DMSO-d6) δ: 12.15 (s, 1H), 8.23 (s, 2H), 7.36-7.27 (m, 6H), 6.79 (s, 2H), 6.04 (s, 1H), 4.88 (s, 2H), 2.27 (s, 6H).<br>LCMS Method A: m/z 458 $(M + H)^+$ (ES+), at 2.25 min, UV active |
| 1-9 | 5-amino-8-(2,6-dimethyl-4-pyridyl)-2-[(6-oxo-1H-pyridin-2-yl)methyl]-7-phenyl-[1,2,4]triazolo[4,3-c]pyrimidin-3-one | Intermediates: Example 1-6 (reaction heated to 70° C for 16 h and purified by SCX cartridge)<br>Route e<br>$^1$H NMR: (MHz, DMSO-d6) δ: 11.49 (s, 1H), 7.39 (s, 1H), 7.31-7.29 (m, 5H), 6.80-6.79 (m, 2H), 6.26 (d, J = 5.8 Hz, 2H), 4.89-4.73 (m, 2H), 2.27 (s, 6H). Exchangeable —$NH_2$ protons were not observed.<br>LCMS Method A: m/z 440 $(M + H)^+$ (ES+), at 2.14 min, UV active |
| 1-10 | 5-amino-8-(2,6-dimethyl-4-pyridyl)-2-[(5-fluoro-1-methyl-6-oxo-2-pyridyl)methyl]-7-phenyl-[1,2,4]triazolo[4,3-c]pyrimidin-3-one | Route f<br>$^1$H NMR: (MHz, DMSO-d6) δ: 7.94 (s, 2H), 7.35-7.27 (m, 6H), 6.79 (s, 2H), 6.08-6.04 (m, 1H), 5.11 (s, 2H), 3.56 (s, 3H), 2.27 (s, 6H).<br>LCMS Method A: m/z 472 $(M + H)^+$ (ES+), at 2.31 min, UV active |
| 1-11 | 5-amino-2-[1-(2,4-difluorophenyl)ethyl]-8-(2,6-dimethyl-4-pyridyl)-7-phenyl-[1,2,4]triazolo[4,3-c]pyrimidin-3-one | Route g<br>$^1$H NMR: (MHz, Chloroform-d) δ: 7.52-7.48 (m, 1H), 7.35-7.20 (m, 5H), 6.91-6.79 (m, 2H) 6.80 (s, 2H), 5.84 (q, J = 7.1 Hz, 1H), 2.40 (s, 6H), 1.75 (d, J = 7.1 Hz, 3H). Exchangeable —$NH_2$ protons were not observed.<br>LCMS Method F: m/z 473 $(M + H)^+$ (ES+), at 1.17 min, UV active |
| 1-12 | 5-amino-8-(2,6-dimethyl-4-pyridyl)-7-phenyl-2-(4-pyridylmethyl)-[1,2,4]triazolo[4,3-c]pyrimidin-3-one | Intermediate 13<br>Route g<br>$^1$H NMR: (MHz, DMSO-d6) δ: 8.49 (d, J = 5.4 Hz, 2H), 7.65 (br. s, 2H), 7.38-7.03 (m, 7H), 6.70 (s, 2H), 5.05 (s, 2H), 2.31 (s, 6H).<br>LCMS Method F:m/z 424 $(M + H)^+$ (ES+), at 0.78 min, UV active |
| 1-13 | 5-amino-8-(2,6-dimethyl-4-pyridyl)-2-isothiochroman-4-yl-7-phenyl-[1,2,4]triazolo[4,3-c]pyrimidin-3-one | Intermediates: 14<br>Route g<br>$^1$H NMR: (MHz, Chloroform-d) δ: 7.34-7.17 (m, 7H), 7.16-7.12 (m, 1H), 7.03 (d, J = 7.0 Hz, 1H), 6.82 (br s, 2H), 5.78-5.73 (m, 1H) 4.09 (d, J = 15.8 Hz, 1H), 3.66 (d, J = 16.0 Hz, 1H), 3.49-3.43 (m, 1H), 3.12-30 (m, 1H), 2.41 (s, 6H). Exchangeable —NH2 protons were not observed.<br>LCMS Method F:m/z 481 $(M + H)^+$ (ES+), at 1.10 min, UV active |
| 1-14 | (R)-5-amino-8-(2,6-dimethyl-4-pyridyl)-2-(7-fluorotetralin-1-yl)-7-phenyl-[1,2,4]triazolo[4,3-c]pyrimidin-3-one | Intermediates: 15<br>Route g<br>$^1$H NMR: (MHz, Chloroform-d) δ: 7.38-7.26 (m, 4H), 7.14-7.05 (m, 1H), 7.00-6.82 (m, 3H), 6.73-6.70 (m, 1H), 5.51 (d, J = 7.3 Hz, 1H), 2.79 (t, J = 18.5 Hz, 2H), 2.50 (s, 6H), 2.32-2.05 (m, 3H), 1.85 (s, 2H). Exchangeable —NH2 protons were not observed.<br>LCMS Method F:m/z 481 $(M + H)^+$ (ES+), at 1.14 min, UV active |
| 1-15 | 5-amino-2-[1-(2,5-difluorophenyl)ethyl]-8-(2,6-dimethyl-4-pyridyl)-7-phenyl-[1,2,4]triazolo[4,3-c]pyrimidin-3-one | Intermediates: 16<br>Route g<br>$^1$H NMR: (MHz, Chloroform-d) δ: 7.38-7.26 (m, 3H), 7.08-6.93 (m, 3H), 6.92-6.86 (m, 4H), 5.87 (d, J = 7.1 Hz, 1H), 2.49 (s, 6H), 1.75 (d, J = 7.1 Hz, 3H). Exchangeable —$NH_2$ protons were not observed.<br>LCMS Method F:m/z 473 $(M + H)^+$ (ES+), at 1.10 min, UV active |
| 1-16 | 5-amino-2-[[2-(difluoromethylsulfanyl)phenyl]methyl]-8-(2,6-dimethyl-4-pyridyl)-7-phenyl-[1,2,4]triazolo[4,3-c]pyrimidin-3-one | Intermediates: 17<br>Route g<br>$^1$H NMR: (MHz, DMSO-d6) δ: 7.73-7.60 (m, 1H), 7.54-7.32 (m, 3H), 7.28-7.15 (m, 6H), 6.68 (s, 2H), 5.29 (s, 2H), 2.29 (s, 6H). Exchangeable —$NH_2$ protons were not observed.<br>LCMS Method F:m/z 505 $(M + H)^+$ (ES+), at 1.15 min, UV active |
| 1-17 | 5-amino-8-(2,6-dimethyl-4-pyridyl)-2-(o-tolylmethyl)-7-phenyl-[1,2,4]triazolo[4,3-c]pyrimidin-3-one | Intermediates: 18<br>Route g<br>$^1$H NMR: (MHz, Chloroform-d) δ: 7.36-7.12 (m, 9H), 6.80 (s, 2H), 5.05 (s, 2H), 2.47 (s, 3H), 2.39 (s, 6H). Exchangeable —$NH_2$ protons were not observed.<br>LCMS Method F:m/z 437 $(M + H)^+$ (ES+), at 1.10 min, UV active |

TABLE 3-continued

| Data for Examples 1-1 to 3-10 | | |
|---|---|---|
| Ex. | Name | Details |
| 1-18 | 5-amino-8-(2,6-dimethyl-4-pyridyl)-2-[(4-fluoro-2-methyl-phenyl)methyl]-7-phenyl-[1,2,4]triazolo[4,3-c]pyrimidin-3-one | Intermediate: 19<br>Route g<br>$^1$H NMR: (MHz, DMSO-d6) δ 7.35-7.12 (m, 6H), 6.99-6.78 (m, 2H), 6.69 (s, 2H), 4.95 (s, 2H), 2.46 (s, 3H), 2.30 (s, 6H). Exchangeable —$NH_2$ protons were not observed.<br>LCMS Method F:m/z 455 $(M + H)^+$ (ES+), at 1.11 min, UV active |
| 1-19 | 5-amino-8-(2,6-dimethyl-4-pyridyl)-7-phenyl-2-[(2-pyrazol-1-yl-3-pyridyl)methyl]-[1,2,4]triazolo[4,3-c]pyrimidin-3-one | Intermediate: 20<br>Route g<br>$^1$H NMR: (MHz, Chloroform-d) δ: 8.44-8.37 (m, 2H), 7.78-7.72 (m, 1H), 7.59-7.54 (m, 1H), 7.33-7.19 (m, 6H), 6.77 (s, 2H), 6.49-6.43 (m, 1H), 5.63 (s, 2H), 2.37 (s, 6H). Exchangeable —$NH_2$ protons were not observed.<br>LCMS Method F:m/z 490 $(M + H)^+$ (ES+), at 1.00 min, UV active |
| 1-20 | 5-amino-8-(2,6-dimethyl-4-pyridyl)-7-phenyl-2-[1-(2-pyridyl)ethyl]-[1,2,4]triazolo[4,3-c]pyrimidin-3-one | Intermediate: 21<br>Route g<br>$^1$H NMR: (MHz, Chloroform-d) δ: 8.61-8.54 (m, 1H), 7.71-7.63 (m, 1H), 7.35-7.17 (m, 7H), 6.82 (s, 2H), 5.65 (q, J = 7.2 Hz, 1H), 2.39 (s, 6H), 1.88 (d, J = 7.2 Hz, 3H). Exchangeable —$NH_2$ protons were not observed.<br>LCMS Method F:m/z 438 $(M + H)^+$ (ES+), at 0.95 min, UV active |
| 1-21 | 5-amino-2-[(2-chloro-3-fluoro-phenyl)methyl]-8-(2,6-dimethyl-4-pyridyl)-7-phenyl-[1,2,4]triazolo[4,3-c]pyrimidin-3-one | Intermediate: 22<br>Route g<br>$^1$H NMR: (MHz, DMSO-d6) δ: 8.42 (br. s, 1H), 7.62 (br. s, 1H), 7.34-7.16 (m, 7H), 7.06 (d, J = 7.7 Hz, 1H), 6.69 (s, 2H), 5.13 (s, 2H), 2.29 (s, 6H).<br>LCMS Method F: m/z 475 $(M + H)^+$ (ES+), at 1.15 min, UV active |
| 1-22 | 5-amino-2-[[2-(cyclopropylmethoxy)phenyl]methyl]-8-(2,6-dimethyl-4-pyridyl)-7-phenyl-[1,2,4]triazolo[4,3-c]pyrimidin-3-one | Intermediate: 23<br>Route g<br>$^1$H NMR: (MHz, DMSO-d6) δ: 8.31 (br. s, 1H), 7.67 (br. s, 1H), 7.28-7.16 (m, 6H), 7.05 (d, J = 7.3 Hz, 1H), 6.89-6.82 (m, 2H), 6.69 (s, 2H), 5.02 (s, 2H), 3.85 (d, J = 6.7 Hz, 2H), 2.28 (s, 6H), 1.24 (s, 1H), 0.59-0.53 (m, 2H), 0.34 (d, J = 5.1 Hz, 2H).<br>LCMS Method F: m/z 493 $(M + H)^+$ (ES+), at 1.21 min, UV active |
| 1-23 | 5-amino-2-[(2,6-difluorophenyl)methyl]-8-(2,6-dimethyl-4-pyridyl)-7-phenyl-[1,2,4]triazolo[4,3-c]pyrimidin-3-one | Intermediate: 24<br>Route g<br>$^1$H NMR: (MHz, Chloroform-d) δ: 7.36-7.22 (m, 6H), 6.97-6.90 (m, 2H), 6.80 (s, 2H), 5.16 (s, 2H), 2.40 (s, 6H). Exchangeable —$NH_2$ protons were not observed.<br>LCMS Method F: m/z 459 $(M + H)^+$ (ES+), at 1.01 min, UV active |
| 1-24 | 5-amino-2-[[2-[(dimethylamino)methyl]phenyl]methyl]-8-(2,6-dimethyl-4-pyridyl)-7-phenyl-[1,2,4]triazolo[4,3-c]pyrimidin-3-one | Intermediate: 25<br>Route g<br>$^1$H NMR: (MHz, Chloroform-d) δ 7.44-7.17 (m, 11H), 6.81 (s, 2H), 5.28 (s, 2H), 2.46-2.24 (m, 12H). Exchangeable —$NH_2$ protons were not observed.<br>LCMS Method F: m/z 480 $(M + H)^+$ (ES+), at 0.77 min, UV active |
| 1-25 | 5-amino-8-(2,6-dimethyl-4-pyridyl)-2-[(2-ethoxyphenyl)methyl]-7-phenyl-[1,2,4]triazolo[4,3-c]pyrimidin-3-one | Intermediate: 26<br>Route g<br>$^1$H NMR: (MHz, Chloroform-d) δ: 7.33-7.22 (m, 6H), 7.20-7.15 (m, 1H), 6.95-6.83 (m, 4H), 5.11 (s, 2H), 4.05 (q, J = 7.0 Hz, 2H), 2.43 (s, 6H), 1.41 (t, J = 7.0 Hz, 3H). Exchangeable —$NH_2$ protons were not observed.<br>LCMS Method F: m/z 467 $(M + H)^+$ (ES+), at 1.07 min, UV active |
| 1-26 | (R)-5-amino-8-(2,6-dimethyl-4-pyridyl)-7-phenyl-2-[1-(4-pyridyl)ethyl]-[1,2,4]triazolo[4,3-c]pyrimidin-3-one | Intermediate: 27<br>Route g<br>$^1$H NMR: (MHz, Chloroform-d) δ: 8.61-8.55 (m, 2H), 7.34-7.22 (m, 7H), 6.89 (s, 2H), 5.49 (q, J = 7.2 Hz, 1H), 2.49 (s, 6H), 1.80 (d, J = 7.2 Hz, 3H). Exchangeable —$NH_2$ protons were not observed.<br>LCMS Method F: m/z 438 $(M + H)^+$ (ES+), at 0.76 min, UV active |
| 1-27 | 5-amino-8-(2,6-dimethyl-4-pyridyl)-7-phenyl-2-[1-(3-pyridyl)ethyl]-[1,2,4]triazolo[4,3-c]pyrimidin-3-one | Intermediate: 28<br>Route g<br>$^1$H NMR: (MHz, Chloroform-d) δ: 8.61-8.58 (m, 1H), 8.49-8.44 (m, 1H), 7.81-7.74 (m, 1H), 7.33-7.18 (m, 6H), 6.72 (s, 2H), 5.56 (q, J = 7.1 Hz, 1H), 2.50 (s, 6H), 1.78 (d, J = 7.1 Hz, 3H). Exchangeable —$NH_2$ protons were not observed. |

TABLE 3-continued

| Data for Examples 1-1 to 3-10 | | |
|---|---|---|
| Ex. | Name | Details |
| | | LCMS Method F: m/z 438 (M + H)+ (ES+), at 0.87 min, UV active |
| 1-28 | 5-amino-8-(2,6-dimethyl-4-pyridyl)-2-[(2-methoxy-3-pyridyl)methyl]-7-phenyl-[1,2,4]triazolo[4,3-c]pyrimidin-3-one | Intermediate: 29<br>Route g<br>$^1$H NMR: (MHz, Chloroform-d) δ: 8.11 (dd, J = 5.1, 1.9 Hz, 1H), 7.41 (dd, J = 7.2, 1.9 Hz, 1H), 7.33-7.19 (m, 5H), 6.86 (dd, J = 7.2, 5.1 Hz, 1H), 6.82 (s, 2H), 5.04 (s, 2H), 3.98 (s, 3H), 2.41 (s, 6H). Exchangeable —$NH_2$ protons were not observed.<br>LCMS Method F: m/z 454 (M + H)+ (ES+), at 0.94 min, UV active |
| 1-29 | 5-amino-8-(2,6-dimethyl-4-pyridyl)-2-[(4-methoxy-6-methyl-2-pyridyl)methyl]-7-phenyl-[1,2,4]triazolo[4,3-c]pyrimidin-3-one | Intermediate: 30<br>Route g<br>$^1$H NMR: (MHz, Chloroform-d) δ: 8.31 (br. s, 1H), 7.67 (br. s, 1H), 7.23 (m, 5H), 6.71 (s, 2H), 6.63 (s, 1H), 6.57 (s, 1H), 4.96 (s, 2H), 3.80 (s, 3H), 2.50 (s, 6H), 2.43 (s, 3H).<br>LCMS Method F: m/z 468 (M + H)+ (ES+), at 0.75 min, UV active |
| 1-30 | 5-amino-8-(2,6-dimethyl-4-pyridyl)-7-phenyl-2-[[2-(4-piperidyl)phenyl]methyl]-[1,2,4]triazolo[4,3-c]pyrimidin-3-one | Route h<br>$^1$H NMR: (MHz, Chloroform-d) δ 7.41-7.11 (m, 11H), 6.76 (s, 2H), 5.10 (s, 2H), 3.46 (s, 1H), 3.23-3.00 (m, 3H), 2.72-2.57 (m, 2H), 2.38 (s, 6H), 1.73-1.55 (m, 4H).<br>LCMS Method F: m/z 506 (M + H)+ (ES+), at 0.95 min, UV active |
| 1-31 | 5-amino-8-(2,6-dimethyl-4-pyridyl)-7-phenyl-2-[1-phenyl-2-(2,2,2-trifluoroethylamino)ethyl]-[1,2,4]triazolo[4,3-c]pyrimidin-3-one | Intermediate: 33<br>Route h<br>$^1$H NMR: (MHz, Chloroform-d) δ 7.43-7.20 (m, 12H), 6.82 (s, 2H), 5.39-5.35 (m, 1H), 3.68-3.62 (m, 1H), 3.23-3.17 (m, 3H), 2.42 (s, 6H). Exchangeable NH— proton was not observed.<br>LCMS Method F: m/z 534 (M + H)+ (ES+), at 1.23 min, UV active |
| 1-32 | 5-amino-8-(2,6-dimethyl-4-pyridyl)-7-phenyl-2-[[2-(4-piperidylmethyl)phenyl]methyl]-[1,2,4]triazolo[4,3-c]pyrimidin-3-one | Intermediate: 34<br>Route h<br>$^1$H NMR: (MHz, Chloroform-d) δ: 7.36-7.09 (m, 9H), 6.78 (s, 2H), 5.06 (s, 2H), 3.04-3.00 (m, 2H) 2.75-2.71 (m, 2H), 2.51-2.41 (m, 2H) 2.37 (s, 6H), 1.68-1.59 (m, 3H), 1.27-1.11 (m, 2H). Exchangeable protons were not observed.<br>LCMS Method F: m/z 520 (M + H)+ (ES+), at 0.97 min, UV active |
| 1-33 | 5-amino-8-(2,6-dimethyl-4-pyridyl)-2-[(6-methoxypyridazin-3-yl)methyl]-7-phenyl-[1,2,4]triazolo[4,3-c]pyrimidin-3-one | Intermediate: 35<br>Route d (Purified by Prep-HPLC (Method A). The product was partitioned between EtOAc (5 mL) and 10% sodium bicarbonate solution (5 mL). The organic layer was separated, dried over anhydrous $Na_2SO_4$ and concentrated under reduced pressure<br>$^1$H NMR: (MHz, DMSO-d6) δ: 7.60 (d, J = 9.2 Hz, 2H), 7.31-7.30 (m, 5H), 7.24 (d, J = 8.8 Hz, 2H), 5.26 (s, 2H), 4.00 (s, 3H), 2.49 (s, 6H). Exchangeable $NH_2$— protons were not observed.<br>LCMS Method A: m/z 455 (M + H)+ (ES+), at 2.42 min, UV active |
| 1-34 | 5-amino-2-(2-amino-1-(2,6-difluorophenyl)ethyl)-8-(2,6-dimethylpyridin-4-yl)-7-phenyl-[1,2,4]triazolo[4,3-c]pyrimidin-3(2H)-one | Intermediate: 36<br>Route h<br>$^1$H NMR: (MHz, Chloroform-d) δ: 7.35-7.15 (m, 8H), 6.98-6.76 (m, 4H), 5.72-5.60 (m, 1H), 3.87-3.67 (m, 1H), 3.39-3.22 (m, 1H), 2.41 (s, 6H). 1 × exchangeable —$NH_2$ protons not observed.<br>LCMS Method F: m/z 488 (M + H)+ (ES+), at 0.93 min, UV active |
| 1-35 | 5-amino-8-(2,6-dimethyl-4-pyridyl)-2-[(5-fluoropyrimidin-2-yl)methyl]-7-phenyl-[1,2,4]triazolo[4,3-c]pyrimidin-3-one | Intermediate: 37<br>Route d<br>$^1$H NMR: (MHz, DMSO-d6) δ: 8.89 (s, 2H), 8.14-8.11 (m, 2H), 7.29-7.27 (m, 5H), 6.79 (s, 2H), 5.27 (s, 2H), 2.26 (s, 6H).<br>LCMS Method A: m/z 443 (M + H)+ (ES+), at 2.31 min, UV active |
| 1-36 | 5-amino-2-[(6-amino-5-fluoro-2-pyridyl)methyl]-8-(2,6-dimethyl-4-pyridyl)-7-phenyl-[1,2,4]triazolo[4,3-c]pyrimidin-3-one | Route i<br>$^1$H NMR: (MHz, DMSO-d6) δ: 7.82 (s, 2H), 7.30-7.25 (m, 6H), 6.80 (s, 2H), 6.38-6.35 (m, 1H), 6.27 (s, 2H), 4.84 (s, 2H), 2.27 (s, 6H).<br>LCMS Method A: m/z 457 (M + H)+ (ES+), at 2.18 min, UV active |
| 1-37 | 5-amino-8-(2,6-dimethyl-4-pyridyl)-2-[(6-hydroxypyridazin- | Intermediate: Example 1-33<br>Route e (Purified by Prep-HPLC (Method A). The product |

TABLE 3-continued

| Data for Examples 1-1 to 3-10 | | |
|---|---|---|
| Ex. | Name | Details |
| | 3-yl)methyl]-7-phenyl-[1,2,4]triazolo[4,3-c]pyrimidin-3-one | was partitioned between EtOAc (5 mL) and 10% sodium bicarbonate solution (5 mL). The organic layer was separated, dried over anhydrous $Na_2SO_4$ and concentrated under reduced pressure<br>$^1H$ NMR: (MHz, DMSO-d6) δ: 12.97 (s, 1H), 7.39 (s, 1H), 7.30-7.26 (m, 5H), 6.91 (s, 1H), 6.84 (m, 2H), 4.95 (s, 2H), 2.51 (s, 6H). Exchangeable —$NH_2$ protons were not observed.<br>LCMS Method A: m/z 441 $(M + H)^+$ (ES+), at 2.01 min, UV active |
| 1-38 | 5-amino-8-(2,6-dimethyl-4-pyridyl)-2-[1-(5-fluoro-2-pyridyl)propyl]-7-phenyl-[1,2,4]triazolo[4,3-c]pyrimidin-3-one | Route j<br>$^1H$ NMR: (MHz, DMSO-d6) δ: 8.60 (d, J = 1.2 Hz, 1H), 8.45 (d, J = 4.8 Hz, 1H), 7.51 (t, J = 5.6 Hz, 1H), 7.33-7.29 (m, 5H), 6.82 (s, 2H), 5.49 (s, 1H), 2.34 (s, 6H), 2.29-2.86 (m, 1H), 2.04-2.00 (m, 1H), 0.90 (t, J = 7.2 Hz, 3H). Exchangeable —$NH_2$ protons were not observed.<br>LCMS Method A: m/z 470 $(M + H)^+$ (ES+), at 2.73 min, UV active |
| 1-38 iso-1 | 5-amino-8-(2,6-dimethyl-4-pyridyl)-2-[1-(5-fluoro-2-pyridyl)propyl]-7-phenyl-[1,2,4]triazolo[4,3-c]pyrimidin-3-one | Route j<br>$^1H$ NMR: (MHz, DMSO-d6) δ: 8.60 (d, J = 1.2 Hz, 1H), 8.45 (d, J = 4.8 Hz, 1H), 7.51 (t, J = 5.6 Hz, 1H), 7.33-7.29 (m, 5H), 6.82 (s, 2H), 5.49 (s, 1H), 2.34 (s, 6H), 2.29-2.86 (m, 1H), 2.04-2.00 (m, 1H), 0.90 (t, J = 7.2 Hz, 3H). Exchangeable —$NH_2$ protons were not observed.<br>LCMS Method A: m/z 470 $(M + H)^+$ (ES+), at 2.73 min, UV active |
| 1-38 iso-2 | 5-amino-8-(2,6-dimethyl-4-pyridyl)-2-[1-(5-fluoro-2-pyridyl)propyl]-7-phenyl-[1,2,4]triazolo[4,3-c]pyrimidin-3-one | Route j<br>$^1H$ NMR: (MHz, DMSO-d6) δ: 8.60 (d, J = 1.2 Hz, 1H), 8.45 (d, J = 4.8 Hz, 1H), 7.51 (t, J = 5.6 Hz, 1H), 7.33-7.29 (m, 5H), 6.82 (s, 2H), 5.49 (s, 1H), 2.34 (s, 6H), 2.29-2.86 (m, 1H), 2.04-2.00 (m, 1H), 0.90 (t, J = 7.2 Hz, 3H). Exchangeable —$NH_2$ protons were not observed.<br>LCMS Method A: m/z 470 $(M + H)^+$ (ES+), at 2.74 min, UV active |
| 1-39 | 5-amino-2-[(3-chloro-5-fluoro-2-pyridyl)methyl]-8-(2,6-dimethyl-4-pyridyl)-7-phenyl-[1,2,4]triazolo[4,3-c]pyrimidin-3-one | Intermediate: 39<br>Route d<br>$^1H$ NMR: (MHz, DMSO-d6) δ: 8.56 (s, 1H), 8.18 (d, J = 9.6 Hz, 1H), 7.28-7.27 (m, 5H), 6.78 (s, 2H), 5.24 (s, 2H), 2.26 (s, 6H). Exchangeable —$NH_2$ protons were not observed.<br>LCMS Method A: m/z 476 $(M + H)^+$ (ES+), at 2.84 min, UV active |
| 1-40 | 5-amino-8-(2,6-dimethyl-4-pyridyl)-2-[(5-fluoro-2-methoxy-3-pyridyl)methyl]-7-phenyl-[1,2,4]triazolo[4,3-c]pyrimidin-3-one | Intermediate: 40<br>Route d (Purified by Prep-HPLC (Method A). The product was partitioned between EtOAc (5 mL) and 10% sodium bicarbonate solution (5 mL). The organic layer was separated, dried over anhydrous $Na_2SO_4$ and concentrated under reduced pressure<br>$^1H$ NMR: (MHz, DMSO-d6) δ: 8.36 (s, 1H), 8.10 (d, J = 2.9 Hz, 1H), 7.77 (s, 1H), 7.60-7.57 (m, 1H), 7.31-7.26 (m, 5H), 6.80 (s, 2H), 4.94 (s, 2H), 3.91 (s, 3H), 2.26 (s, 6H).<br>LCMS Method A: m/z 472 $(M + H)^+$ (ES+), at 2.97 min, UV active |
| 1-41 | 5-amino-8-(2,6-dimethyl-4-pyridyl)-7-(4-fluorophenyl)-2-(pyridazin-3-ylmethyl)-[1,2,4]triazolo[4,3-c]pyrimidin-3-one | Intermediate: 41 & 8 (step 1)<br>Route b<br>$^1H$ NMR: (MHz, DMSO-d6) δ: 9.18 (d, J = 4.8 Hz, 1H), 7.71 (s, 1H), 7.69 (s, 1H), 7.32-7.30 (m, 2H), 7.29-7.13 (m, 2H), 6.80 (s, 2H), 5.35 (s, 2H), 2.28 (s, 6H). Exchangeable —$NH_2$ Protons were not observed.<br>LCMS Method A: m/z 443 $(M + H)^+$ (ES+), at 2.18 min, UV active |
| 1-42 | 5-amino-8-(2,6-dimethyl-1-oxido-pyridin-1-ium-4-yl)-2-[(5-fluoro-2-pyridyl)methyl]-7-phenyl-[1,2,4]triazolo[4,3-c]pyrimidin-3-one | Route k<br>$^1H$ NMR: (MHz, DMSO-d6) δ: 8.52 (d, J = 3.2 Hz, 1H), 7.77-7.73 (m, 1H), 7.72-7.70 (m, 1H), 7.46-7.42 (m, 5H), 7.33 (s, 2H), 5.14 (s, 2H), 2.21 (s, 6H). Exchangeable —$NH_2$ Protons were not observed.<br>LCMS Method A: m/z 458 $(M + H)^+$ (ES+), at 2.74 min, UV active |
| 1-43 | 5-amino-8-(2,6-dimethyl-1-oxido-pyridin-1-ium-4-yl)-7-phenyl-2-(pyridazin-3-ylmethyl)-[1,2,4]triazolo[4,3-c]pyrimidin-3-one | Intermediate: Example 1-5<br>Route k (Purified by Prep-HPLC (Method A). The product was partitioned between EtOAc (5 mL) and 10% sodium bicarbonate solution (5 mL). The organic layer was separated, dried over anhydrous $Na_2SO_4$ and concentrated under reduced pressure)<br>$^1H$ NMR: (MHz, DMSO-d6) δ: 9.19 (d, J = 4.0 Hz, 1H), 7.73-7.65 (m, 2H), 7.32 (d, J = 4.0 Hz, 5H), 7.08 (s, 2H), |

TABLE 3-continued

| Data for Examples 1-1 to 3-10 | | |
|---|---|---|
| Ex. | Name | Details |
| | | 5.37 (s, 2H), 2.20 (s, 6H). Exchangeable —$NH_2$ Protons were not observed. LCMS Method C: m/z 441 $(M + H)^+$ (ES+), at 1.16 min, UV active |
| 1-44 | 5-amino-2-[(5-fluoro-2-pyridyl)methyl]-8-[2-(hydroxymethyl)-6-methyl-4-pyridyl]-7-phenyl-[1,2,4]triazolo[4,3-c]pyrimidin-3-one | Route l $^1$H NMR: (MHz, DMSO-d6) δ: 8.51 (d, J = 2.9 Hz, 1H), 7.76-7.65 (m, 1H), 7.46-7.37 (m, 1H), 7.32-7.19 (m, 5H), 7.08 (s, 1H), 6.80 (s, 1H), 5.23 (t, J = 5.7 Hz, 1H), 5.12 (s, 2H), 4.39 (d, J = 5.7 Hz, 2H), 2.26 (s, 3H). Exchangeable —$NH_2$ Protons were not observed. LCMS Method A: m/z 458 $(M + H)^+$ (ES+), at 2.42 min, UV active |
| 1-45 | 5-amino-2-[(6-amino-5-fluoro-2-pyridyl)methyl]-8-[2-(hydroxymethyl)-6-methyl-4-pyridyl]-7-phenyl-[1,2,4]triazolo[4,3-c]pyrimidin-3-one | Route m $^1$H NMR: (MHz, DMSO-d6) δ: 8.15 (s, 2H), 7.66 (s, 6H), 7.30-7.23 (m, 1H), 7.11 (s, 1H), 6.83 (s, 1H), 6.39-6.36 (m, 1H), 6.28 (s, 1H), 5.27-5.23 (m, 1H), 4.84 (s, 2H), 4.41 (d, J = 4.0 Hz, 2H), 2.28 (s, 3H). LCMS Method A: m/z 473 $(M + H)^+$ (ES+), at 1.92 min, UV active |
| 1-46 iso-1 | 5-amino-2-[1-(5-fluoro-2-pyridyl)propyl]-8-[2-(hydroxymethyl)-6-methyl-4-pyridyl]-7-phenyl-[1,2,4]triazolo[4,3-c]pyrimidin-3-one | Route n $^1$H NMR: (MHz, DMSO-d6) δ: 8.60 (s, 1H), 8.44 (d, J = 4.8 Hz, 1H), 7.57 (t, J = 6.0 Hz, 1H), 7.31-7.28 (m, 6H), 7.27 (s, 1H), 5.50 (t, J = 6.0 Hz, 1H), 4.48 (s, 2H), 2.33 (s, 3H), 2.21 (s, 1H), 2.03 (s, 1H), 0.89 (t, J = 7.2 Hz, 3H). Exchangeable —$NH_2$ and OH Protons were not observed. LCMS Method A: m/z 486 $(M + H)^+$ (ES+), at 2.53 min, UV active |
| 1-46 iso-2 | 5-amino-2-[1-(5-fluoro-2-pyridyl)propyl]-8-[2-(hydroxymethyl)-6-methyl-4-pyridyl]-7-phenyl-[1,2,4]triazolo[4,3-c]pyrimidin-3-one | Route n $^1$H NMR: (MHz, DMSO-d6) δ: 8.60 (s, 1H), 8.44 (d, J = 4.8 Hz, 1H), 7.57 (t, J = 6.0 Hz, 1H), 7.31-7.28 (m, 6H), 7.27 (s, 1H), 5.50 (t, J = 6.0 Hz, 1H), 4.48 (s, 2H), 2.33 (s, 3H), 2.21 (s, 1H), 2.03 (s, 1H), 0.89 (t, J = 7.2 Hz, 3H). Exchangeable —$NH_2$ and OH Protons were not observed. LCMS Method A: m/z 486 $(M + H)^+$ (ES+), at 2.53 min, UV active |
| 1-47 | 5-amino-2-[(3-fluoro-5-methoxy-2-pyridyl)methyl]-8-[2-(hydroxymethyl)-6-methyl-4-pyridyl]-7-phenyl-[1,2,4]triazolo[4,3-c]pyrimidin-3-one | Route o $^1$H NMR: (MHz, DMSO-d6) δ: 8.12 (s, 1H), 7.48 (s, 1H), 7.45-7.26 (m, 5H), 7.05 (s, 1H), 6.81 (s, 1H), 5.23 (s, 1H), 5.12 (s, 2H), 4.39 (d, J = 5.7 Hz, 2H), 3.84 (d, J = 2.3 Hz, 3H), 2.27 (s, 3H). Exchangeable —$NH_2$ Protons were not observed. LCMS Method C: m/z 488 $(M + H)^+$ (ES+), at 1.53 min, UV active |
| 1-48 | 5-amino-2-[(5-fluoro-6-hydroxy-2-pyridyl)methyl]-8-[2-(hydroxymethyl)-6-methyl-4-pyridyl]-7-phenyl-[1,2,4]triazolo[4,3-c]pyrimidin-3-one | Route m $^1$H NMR: (MHz, DMSO-d6) δ: 11.30 (s, 1H), 7.39-7.23 (m, 6H), 7.05 (s, 1H), 6.77 (s, 1H), 6.33-6.31 (m, 1H), 6.26 (s, 2H), 5.24 (t, J = 5.6 Hz, 1H), 4.77 (s, 2H), 4.38 (d, J = 5.2 Hz, 2H), 2.08 (s, 3H). LCMS Method A: m/z 474 $(M + H)^+$ (ES+), at 1.77 min, UV active |
| 1-49 | 5-amino-2-[(5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one | Route p $^1$H NMR: (MHz, DMSO-d6) δ: 8.52 (d, J = 2.8 Hz, 1H), 7.76-7.72 (m, 1H), 7.42 (m, 1H), 7.13 (s, 1H), 6.86 (s, 1H), 5.23 (s, 1H), 5.13 (s, 2H), 4.42 (s, 2H), 2.29 (s, 3H). Exchangeable —$NH_2$ protons were not observed. LCMS Method C: m/z 463 $(M + H)^+$ (ES+), at 1.37 min, UV active |
| 1-50 | 5-amino-2-[(3-chloro-5-fluoro-2-pyridyl)methyl]-8-[2-(hydroxymethyl)-6-methyl-4-pyridyl]-7-phenyl-[1,2,4]triazolo[4,3-c]pyrimidin-3-one | Route q $^1$H NMR: (MHz, DMSO-d6) δ: 8.55 (s, 1H), 8.18-8.15 (m, 1H), 7.29-7.25 (m, 5H), 7.07 (s, 1H), 6.81 (s, 1H), 5.24-5.20 (m, 3H), 4.39 (d, J = 5.6 Hz, 2H), 2.27 (s, 3H). Exchangeable —$NH_2$ protons were not observed. LCMS Method A: m/z 492 $(M + H)^+$ (ES+), at 2.04 min, UV active |
| 1-51 | 5-amino-2-[(6-amino-5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one | Route r $^1$H NMR: (MHz, DMSO-d6) δ: 7.42-8.40 (m, 2H), 7.28-7.23 (m, 1H), 7.08 (s, 1H), 6.81 (s, 1H), 6.37-6.34 (m, 1H), 6.26 (s, 2H), 5.24-5.21 (m, 1H), 4.82 (s, 2H), 4.39 (d, J = 8.0 Hz, 2H), 2.26 (s, 3H). LCMS Method C: m/z 478 $(M + H)^+$ (ES+), at 1.06 min, UV active |
| 1-52 | 5-amino-8-[2-(hydroxymethyl)-6-methyl-4-pyridyl]-2-[(5-methyl-2-pyridyl)methyl]-7-phenyl-[1,2,4]triazolo[4,3-c]pyrimidin-3-one | Intermediate: 1 & 50 (step 1), 42 (step 2) Route p (step 3 purified by flash column chromatography by using silica (230-400) mesh and was eluted with 0-80% EtOAc in pet-ether) $^1$H NMR: (MHz, DMSO-d6) δ: 8.34 (s, 1H), 7.58 (d, J = 8.5 |

TABLE 3-continued

| Ex. | Name | Details |
|---|---|---|
| | | Hz, 1H), 7.27-7.19 (m, 6H), 7.09 (s, 1H), 6.81 (s, 1H), 5.24 (t, J = 5.7 Hz, 1H), 5.06 (s, 2H), 4.39 (d, J = 5.7 Hz, 2H), 2.27 (s, 6H). Exchangeable —$NH_2$ protons were not observed.<br>LCMS Method C: m/z 454 $(M + H)^+$ (ES+), at 1.26 min, UV active |
| 1-53 | 5-amino-2-[(5-bromo-2-pyridyl)methyl]-8-[2-(hydroxymethyl)-6-methyl-4-pyridyl]-7-phenyl-[1,2,4]triazolo[4,3-c]pyrimidin-3-one | Route s<br>$^1H$ NMR: (MHz, DMSO-d6) δ: 8.65 (d, J = 2.0 Hz, 1H), 8.05-8.02 (m, 1H), 7.34-7.29 (m, 1H), 7.27-7.24 (m, 5H), 7.09 (s, 1H), 6.81 (s, 1H), 5.25-5.23 (m, 1H), 5.10 (s, 2H), 4.40 (d, J = 4.0 Hz, 2H), 2.27 (s, 3H). Exchangeable —$NH_2$ protons were not observed.<br>LCMS Method C: m/z 518 $(M + H)^+$ (ES+), at 1.22 min, UV active |
| 1-54 | 6-[[5-amino-8-[2-(hydroxymethyl)-6-methyl-4-pyridyl]-3-oxo-7-phenyl-[1,2,4]triazolo[4,3-c]pyrimidin-2-yl]methyl]pyridine-3-carbonitrile | Route t<br>$^1H$ NMR: (MHz, DMSO-d6) δ: 8.87 (d, J = 1.4 Hz, 1H), 7.99-7.97 (m, 1H), 7.39 (d, J = 8.0 Hz, 1H), 7.32-7.26 (m, 5H), 6.89 (s, 2H), 5.30 (s, 2H), 4.58 (d, J = 4.8 Hz, 2H), 3.75 (t, J = 4.8 Hz, 1H), 2.43 (s, 3H). Exchangeable —$NH_2$ protons were not observed.<br>LCMS Method C: m/z 465 $(M + H)^+$ (ES+), at 1.16 min, UV active |
| 1-55 | 5-amino-2-[(5-chloro-2-pyridyl)methyl]-8-[2-(hydroxymethyl)-6-methyl-4-pyridyl]-7-phenyl-[1,2,4]triazolo[4,3-c]pyrimidin-3-one | Intermediate: 53 & 55<br>Route d<br>$^1H$ NMR: (MHz, DMSO-d6) δ: 8.57 (d, J = 2.4 Hz, 1H), 7.94-7.91 (m, 1H), 7.39 (d, J = 8.4 Hz, 1H), 7.27-7.25 (m, 5H), 7.09 (s, 1H), 6.81 (s, 1H), 5.22 (t, J = 5.6 Hz, 1H), 5.13 (s, 2H), 4.40 (d, J = 5.6 Hz, 2H), 2.27 (s, 3H). Exchangeable —$NH_2$ protons were not observed.<br>LCMS Method C: m/z 474 $(M + H)^+$ (ES+), at 1.43 min, UV active |
| 1-56 | 5-amino-8-[2-(hydroxymethyl)-6-methyl-4-pyridyl]-7-phenyl-2-(pyridazin-3-ylmethyl)-[1,2,4]triazolo[4,3-c]pyrimidin-3-one | Intermediate: 1 & 8 (step 1), 42 (step 2)<br>Route p<br>$^1H$ NMR: (MHz, DMSO-d6) δ: 9.18 (s, 1H), 8.10 (s, 2H), 7.72-7.64 (m, 2H), 7.29-7.23 (m, 5H), 7.11 (s, 1H), 6.82 (s, 1H), 5.35 (s, 2H), 5.25 (s, 1H), 4.40 (s, 2H), 2.27 (s, 3H).<br>LCMS Method A: m/z 441 $(M + H)^+$ (ES+), at 1.90 min, UV active |
| 1-57 | 5-amino-8-[2-(hydroxymethyl)-6-methyl-4-pyridyl]-2-[(2-methoxy-3-pyridyl)methyl]-7-phenyl-[1,2,4]triazolo[4,3-c]pyrimidin-3-one | Intermediate: 1 & 29 (step 1), 42 (step 2)<br>Route p (step 3 using $NaBH_4$ as reducing agent)<br>$^1H$ NMR: (MHz, DMSO-d6) δ: 8.11 (t, J = 4.8 Hz, 1H), 7.49 (d, J = 7.6 Hz, 1H), 7.29-7.25 (m, 5H), 7.10 (s, 1H), 6.97-6.94 (m, 1H), 6.82 (s, 1H), 5.21 (s, 1H), 4.94 (s, 2H), 4.39 (d, J = 5.6 Hz, 2H), 3.91 (s, 3H), 2.27 (s, 3H). Exchangeable —$NH_2$ protons were not observed.<br>LCMS Method A: m/z 470 $(M + H)^+$ (ES+), at 2.55 min, UV active |
| 1-58 | 5-amino-7-(4-fluorophenyl)-8-[2-(hydroxymethyl)-6-methyl-4-pyridyl]-2-(pyridazin-3-ylmethyl)-[1,2,4]triazolo[4,3-c]pyrimidin-3-one | Intermediate: 41 & 8 (step 1), 42 (step 2)<br>Route p<br>$^1H$ NMR: (MHz, DMSO-d6) δ: 9.19-9.17 (m, 1H), 7.72-7.65 (m, 2H), 7.33-7.29 (m, 2H), 7.13-7.08 (m, 3H), 6.86 (s, 1H), 5.35 (s, 2H), 5.24 (s, 1H), 4.41 (s, 2H), 2.30 (s, 3H). Exchangeable —$NH_2$ protons were not observed.<br>LCMS Method A: m/z 459 $(M + H)^+$ (ES+), at 2.03 min, UV active |
| 1-59 | 5-amino-7-(4-fluorophenyl)-2-[(5-fluoro-2-pyridyl)methyl]-8-[2-(hydroxymethyl)-6-methyl-4-pyridyl]-[1,2,4]triazolo[4,3-c]pyrimidin-3-one | Intermediate: 56 & 4 (step 1)<br>Route s<br>$^1H$ NMR: (MHz, DMSO-d6) δ: 8.52 (d, J = 2.9 Hz, 1H), 7.75-7.70 (m, 1H), 7.44-7.41 (m, 1H), 7.33-7.33 (m, 2H), 7.12-7.07 (m, 3H), 6.85 (s, 1H), 5.25 (t, J = 5.7 Hz, 1H), 5.12 (s, 2H), 4.41 (d, J = 5.7 Hz, 2H), 2.30 (s, 3H). Exchangeable —$NH_2$ protons were not observed.<br>LCMS Method A: m/z 476 $(M + H)^+$ (ES+), at 1.97 min, UV active |
| 1-60 | 5-amino-2-[(6-amino-5-fluoro-2-pyridyl)methyl]-7-(4-fluorophenyl)-8-[2-(hydroxymethyl)-6-methyl-4-pyridyl]-[1,2,4]triazolo[4,3-c]pyrimidin-3-one | Intermediate: 56 & 38 (step 1)<br>Route r<br>$^1H$ NMR: (MHz, DMSO-d6) δ: 8.26 (s, 2H), 7.29-7.25 (m, 3H), 7.12-7.07 (m, 3H), 6.86 (s, 1H), 6.38-6.35 (m, 1H), 6.27 (s, 2H), 5.25 (s, 1H), 4.84 (s, 2H), 4.41 (s, 2H), 2.30 (s, 3H).<br>LCMS Method C: m/z 491 $(M + H)^+$ (ES+), at 1.12 min, UV active |
| 1-61 | 5-amino-7-(4-fluorophenyl)-8-[2-(hydroxymethyl)-6-methyl-4-pyridyl]-2-[(5-methyl-2-pyridyl)methyl]- | Intermediate: 41 & 50 (step 1), 42 (step 2)<br>Route p (Step 1 product was not columned, but the reaction mixture was poured into ice water and the precipitate filtered) |

TABLE 3-continued

| Ex. | Name | Details |
| --- | --- | --- |
| | Data for Examples 1-1 to 3-10 | |
| | [1,2,4]triazolo[4,3-c]pyrimidin-3-one | $^1$H NMR: (MHz, DMSO-d6) δ: 8.33 (s, 1H), 7.58 (d, J = 8.0 Hz, 1H), 7.32-7.29 (m, 2H), 7.20 (d, J = 8.0 Hz, 1H), 7.12-7.06 (m, 3H), 6.85 (s, 1H), 5.24-5.22 (m, 1H), 5.06 (s, 2H), 4.41 (d, J = 4.0 Hz, 2H), 2.33-2.26 (m, 6H). Exchangeable —$NH_2$ protons were not observed.<br>LCMS Method C: m/z 472 $(M + H)^+$ (ES+), at 1.09 min, UV active |
| 1-62 | 5-amino-2-[(5-chloro-2-pyridyl)methyl]-7-(4-fluorophenyl)-8-[2-(hydroxymethyl)-6-methyl-4-pyridyl]-[1,2,4]triazolo[4,3-c]pyrimidin-3-one | Intermediate: 41 & 55 (step 1), 42 (step 2)<br>Route p (Step 1 Purified by Prep-HPLC (Method A). The product was partitioned between EtOAc (5 mL) and 10% sodium bicarbonate solution (5 mL). The organic layer was separated, dried over anhydrous $Na_2SO_4$ and concentrated under reduced pressure)<br>$^1$H NMR: (MHz, DMSO-d6) δ: 8.58 (s, 1H), 7.93-7.90 (m, 1H), 7.39 (d, J = 12.2 Hz, 1H), 7.32-7.28 (m, 2H), 7.12-7.07 (m, 3H), 6.85 (s, 1H), 5.24 (s, 1H), 5.13 (s, 2H), 4.40 (s, 2H), 2.30 (s, 3H). Exchangeable —$NH_2$ protons were not observed.<br>LCMS Method C: m/z 492 $(M + H)^+$ (ES+), at 1.27 min, UV active |
| 1-63 | 6-[[5-amino-7-(4-fluorophenyl)-8-[2-(hydroxymethyl)-6-methyl-4-pyridyl]-3-oxo-[1,2,4]triazolo[4,3-c]pyrimidin-2-yl]methyl]pyridine-3-carbonitrile | Route u<br>$^1$H NMR: (MHz, DMSO-d6) δ: 8.97 (s, 1H), 8.32-8-28 (m, 1H), 7.56 (d, J = 8.3 Hz, 1H), 7.33-7.29 (m, 2H), 7.12-7.07 (m, 3H), 6.85 (s, 1H), 5.25-5.22 (m, 3H), 4.40 (d, J = 5.6 Hz, 2H), 2.29 (s, 3H). Exchangeable —NH2 protons were not observed.<br>LCMS Method C: m/z 483 $(M + H)^+$ (ES+), at 1.14 min, UV active |
| 1-64 | 5-amino-2-[(6-amino-5-fluoro-2-pyridyl)methyl]-8-[2-(hydroxymethyl)-6-methoxy-4-pyridyl]-7-phenyl-[1,2,4]triazolo[4,3-c]pyrimidin-3-one | Intermediate: 1 & 38 (step 1), 57 (step 2)<br>Route m<br>$^1$H NMR: (MHz, DMSO-d6) δ: 8.36 (s, 2H), 7.76 (s, 5H), 7.31-7.25 (m, 1H), 6.84 (s, 1H), 6.45 (s, 1H), 6.38-6.36 (m, 1H), 6.28 (s, 2H), 5.23 (s, 1H), 4.84 (s, 2H), 4.35 (s, 2H), 3.74 (s, 3H).<br>LCMS Method C: m/z 489 $(M + H)^+$ (ES+), at 1.44 min, UV active |
| 1-65 | 5-amino-2-[(5-chloro-2-pyridyl)methyl]-8-[2-(hydroxymethyl)-6-methoxy-4-pyridyl]-7-phenyl-[1,2,4]triazolo[4,3-c]pyrimidin-3-one | Intermediate: 60 & 55<br>Route d (Purified by Prep-HPLC (Method A). The product was partitioned between EtOAc (5 mL) and 10% sodium bicarbonate solution (5 mL). The organic layer was separated, dried over anhydrous $Na_2SO_4$ and concentrated under reduced pressure)<br>$^1$H NMR: (MHz, DMSO-d6) δ: 8.58 (d, J = 2.3 Hz, 1H), 7.93-7.90 (m, 1H), 7.39 (d, J = 8.7 Hz, 1H), 7.31-7.26 (m, 5H), 7.27 (s, 1H), 6.43 (s, 1H), 5.21 (t, J = 8.0 Hz, 1H), 5.13 (s, 2H), 4.34 (d, J = 8.0 Hz, 2H), 3.73 (s, 3H). Exchangeable —$NH_2$ protons were not observed.<br>LCMS Method D: m/z 490 $(M + H)^+$ (ES+), at 2.42 min, UV active |
| 1-66 | 5-amino-8-[2-(hydroxymethyl)-6-methoxy-4-pyridyl]-2-[(5-methyl-2-pyridyl)methyl]-7-phenyl-[1,2,4]triazolo[4,3-c]pyrimidin-3-one | Intermediate: 1 & 50 (step 1), 57 (step 2)<br>Route p (Step 3 purified by flash column chromatography by using silica (230-400) mesh and was eluted with (0-100)% EtOAc in pet ether gradient)<br>$^1$H NMR: (MHz, DMSO-d6) δ: 8.33 (s, 2H), 7.59 (s, 1H), 7.31-7.24 (m, 6H), 6.82 (s, 1H), 6.42 (s, 1H), 5.21 (t, J = 6.8 Hz, 1H), 5.06 (s, 2H), 4.33 (d, J = 6.8 Hz, 2H), 3.72 (s, 3H), 2.26 (s, 3H). Exchangeable —NH proton was not observed.<br>LCMS Method C: m/z 470 $(M + H)^+$ (ES+), at 1.60 min, UV active |
| 1-67 | 5-amino-7-(4-fluorophenyl)-8-[2-(hydroxymethyl)-6-methoxy-4-pyridyl]-2-[(5-methyl-2-pyridyl)methyl]-[1,2,4]triazolo[4,3-c]pyrimidin-3-one | Intermediate: 41 & 50 (step 1), 57 (step 2)<br>Route p<br>$^1$H NMR: (MHz, DMSO-d6) δ: 8.33 (s, 1H), 7.57 (d, J = 9.2 Hz, 1H), 7.35-7-31 (m, 2H), 7.19 (d, J = 7.6 Hz, 1H), 7.12-7.09 (m, 2H), 6.78 (s, 1H), 6.47 (s, 1H), 5.21 (t, J = 5.6 Hz, 1H), 5.05 (s, 2H), 4.34 (d, J = 5.6 Hz, 2H), 3.73 (s, 3H), 2.26 (s, 3H). Exchangeable —$NH_2$ protons were not observed.<br>LCMS Method C: m/z 488 $(M + H)^+$ (ES+), at 1.70 min, UV active |
| 1-68 | 5-amino-2-[(5-chloro-2-pyridyl)methyl]-7-(4-fluorophenyl)-8-[2-(hydroxymethyl)-6-methoxy-4-pyridyl]-[1,2,4]triazolo[4,3-c]pyrimidin-3-one | Intermediate: 41 & 55 (step 1), 57 (step 2)<br>Route p<br>$^1$H NMR: (MHz, DMSO-d6) δ: 8.57 (d, J = 2.4 Hz, 1H), 7.92-7.90 (m, 1H), 7.35-7.31 (m, 3H), 7.14-7.11 (m, 2H), 6.14 (s, 1H), 6.47 (s, 1H), 5.22 (t, J = 6.0 Hz, 1H), 5.12 (s, 2H), 4.34 (d, J = 6.0 Hz, 2H), 3.74 (s, 3H). Exchangeable |

TABLE 3-continued

| Data for Examples 1-1 to 3-10 | | |
|---|---|---|
| Ex. | Name | Details |
| | | —$NH_2$ protons were not observed.<br>LCMS Method E: m/z 508 $(M + H)^+$ (ES+), at 1.96 min, UV active |
| 1-69 | 5-amino-8-[2-chloro-6-(hydroxymethyl)-4-pyridyl]-2-[(5-fluoro-2-pyridyl)methyl]-7-phenyl-[1,2,4]triazolo[4,3-c]pyrimidin-3-one | Intermediate: 1 & 4 (step 1), 61 (step 2)<br>Route p<br>$^1$H NMR: (MHz, DMSO-d6) δ: 8.53 (d, J = 2.6 Hz, 1H), 7.76-7.70 (m, 1H), 7.46-7.43 (m, 1H), 7.34-7.29 (m, 6H), 7.03 (s, 1H), 5.45-5.42 (m, 1H), 5.14 (s, 2H), 4.40 (d, J = 5.6 Hz, 2H). Exchangeable —$NH_2$ protons were not observed.<br>LCMS Method A: m/z 478 $(M + H)^+$ (ES+), at 3.46 min, UV active |
| 1-70 | 5-amino-2-[(6-amino-5-fluoro-2-pyridyl)methyl]-8-[2-chloro-6-(hydroxymethyl)-4-pyridyl]-7-phenyl-[1,2,4]triazolo[4,3-c]pyrimidin-3-one | Intermediate: 1 & 38 (step 1), 61 (step 2)<br>Route m<br>$^1$H NMR: (MHz, DMSO-d6) δ: 8.53 (s, 1H), 7.82 (s, 1H), 7.34-7.26 (m, 7H), 7.04 (s, 1H), 6.39 (t, J = 2.4 Hz, 1H), 6.29 (s, 2H), 5.44 (t, J = 5.2 Hz, 1H), 4.86 (s, 2H), 4.41 (d, J = 5.2 Hz, 2H).<br>LCMS Method A: m/z 493 $(M + H)^+$ (ES+), at 1.49 min, UV active |
| 1-71 | 5-amino-8-[2-(dimethylamino)-6-methyl-4-pyridyl]-2-[(5-fluoro-2-pyridyl)methyl]-7-phenyl-[1,2,4]triazolo[4,3-c]pyrimidin-3-one | Route v<br>$^1$H NMR: (MHz, DMSO-d6) δ: 8.75 (s, 1H), 8.35 (s, 1H), 8.20 (d, J = 11.2 Hz, 1H), 7.57-7.50 (m, 1H), 7.36-7.31 (m, 4H), 6.73 (s, 1H), 6.49 (s, 1H), 5.6-5.66 (m, 2H), 3.10-3.08 (m, 6H), 2.39 (s, 3H). Exchangeable —$NH_2$ Protons were not observed.<br>LCMS Method D: m/z 471 $(M + H)^+$ (ES+), at 2.63 min, UV active |
| 1-72 | 5-amino-2-[(5-fluoro-2-pyridyl)methyl]-8-[2-methyl-6-(trifluoromethyl)-4-pyridyl]-7-phenyl-[1,2,4]triazolo[4,3-c]pyrimidin-3-one | Intermediate: 1 & 4 (step 1), 66 (step 2)<br>Route b (Step 2 purified by Prep-HPLC (Method A). The product was partitioned between EtOAc (5 mL) and 10% sodium bicarbonate solution (5 mL). The organic layer was separated, dried over anhydrous $Na_2SO_4$ and concentrated under reduced pressure)<br>$^1$H NMR: (MHz, DMSO-d6) δ: 8.53 (s, 1H), 7.73 (d, J = 2.8 Hz, 1H), 7.47-7.46 (d, J = 4.4 Hz, 1H), 7.36-7.24 (m, 7H), 5.14 (s, 2H), 2.40 (s, 3H). Exchangeable —$NH_2$ Protons were not observed.<br>LCMS Method A: m/z 496 $(M + H)^+$ (ES+), at 4.63 min, UV active |
| 1-73 | 5-amino-2-[(5-fluoro-2-pyridyl)methyl]-8-[2-(hydroxymethyl)-6-methoxy-4-pyridyl]-7-phenyl-[1,2,4]triazolo[4,3-c]pyrimidin-3-one | Intermediate: 1 & 4 (step 1), 57 (step 2)<br>Route p<br>$^1$H NMR: (MHz, DMSO-d6) δ: 8.52 (s, 1H), 7.74-7.70 (m, 1H), 7.44-7.41 (m, 1H), 7.29-7.28 (m, 5H), 6.83 (s, 1H), 6.43 (s, 1H), 5.23-5.20 (m, 1H), 5.12 (s, 2H), 4.34 (d, J = 5.6 Hz, 2H), 3.73 (s, 3H). Exchangeable —$NH_2$ Protons were not observed.<br>LCMS Method A: m/z 474 $(M + H)^+$ (ES+), at 2.37 min, UV active |
| 1-74 | 5-amino-2-[(5-fluoro-2-pyridyl)methyl]-8-(2-hydroxy-6-methyl-4-pyridyl)-7-phenyl-[1,2,4]triazolo[4,3-c]pyrimidin-3-one | Intermediate: Example 1-78<br>Route e (Purified by Prep HPLC (Method A), the fractions were concentrated and the residue was diluted with EtOAc (10 mL) and washed with 10% sodium bicarbonate solution (10 mL). The organic layer was separated, dried over anhydrous $Na_2SO_4$)<br>$^1$H NMR: (MHz, DMSO-d6) δ: 11.41 (s, 1H), 8.53 (d, J = 2.8 Hz, 1H), 7.76-7.71 (m, 1H), 7.45-7.39 (m, 3H), 7.34-7.30 (m, 3H), 5.99 (s, 1H), 5.64 (s, 1H), 5.14 (s, 2H), 1.99 (s, 3H). Exchangeable —$NH_2$ Protons were not observed.<br>LCMS Method E: m/z 442 $(M - H)^-$ (ES−), at 4.19 min, UV active |
| 1-75 | 5-amino-8-[2-(azetidin-1-yl)-6-methyl-4-pyridyl]-2-[(5-fluoro-2-pyridyl)methyl]-7-phenyl-[1,2,4]triazolo[4,3-c]pyrimidin-3-one | Intermediate: 5 & 63 (step 1), 68 (step 2)<br>Route v<br>$^1$H NMR: (MHz, DMSO-d6) δ: 8.53 (s, 1H), 7.76-7.71 (m, 1H), 7.46-7.43 (m, 1H), 7.31-7.25 (m, 5H), 6.27 (s, 1H), 5.85 (s, 1H), 5.13 (s, 2H), 3.72-3.68 (m, 4H), 2.23-2.19 (m, 2H), 2.14 (s, 3H). Exchangeable —$NH_2$ Protons were not observed.<br>LCMS Method B: m/z 483 $(M + H)^+$ (ES+), at 1.21 min, UV active |
| 1-76 | 5-amino-8-(2-chloro-6-methyl-4-pyridyl)-2-[(5-fluoro-2-pyridyl)methyl]-7-phenyl-[1,2,4]triazolo[4,3-c]pyrimidin-3-one | Intermediate: 1 & 4 (step 1), 69 (step 2)<br>Route b (Step 2 performed using $K_3PO_4$ and $Pd(amphos)Cl_2$)<br>$^1$H NMR: (MHz, DMSO-d6) δ: 8.52 (d, J = 2.8 Hz, 1H), 7.76-7.71 (m, 1H), 7.45-7.41 (m, 1H), 7.34-7.26 (m, 5H), 6.98 (d, J = 11.6 Hz, 2H), 5.13 (s, 2H), 2.51-2.50 (m, 3H). |

TABLE 3-continued

| Data for Examples 1-1 to 3-10 | | |
|---|---|---|
| Ex. | Name | Details |
| | | Exchangeable —$NH_2$ Protons were not observed. LCMS Method A: m/z 462 $(M + H)^+$ (ES+), at 4.10 min, UV active |
| 1-77 | 5-amino-8-(2-chloro-6-methyl-4-pyridyl)-2-[(5-methoxy-2-pyridyl)methyl]-7-phenyl-[1,2,4]triazolo[4,3-c]pyrimidin-3-one | Route w $^1$H NMR: (MHz, DMSO-d6) δ: 8.30 (s, 1H), 7.36-7.27 (m, 7H), 7.03 (s, 1H), 6.89 (s, 1H), 5.23 (s, 2H), 3.89 (s, 3H), 2.42 (s, 3H). Exchangeable —$NH_2$ Protons were not observed. LCMS Method A: m/z 474 $(M + H)^+$ (ES+), at 3.60 min, UV active |
| 1-78 | 5-amino-2-[(5-fluoro-2-pyridyl)methyl]-8-(2-methoxy-6-methyl-4-pyridyl)-7-phenyl-[1,2,4]triazolo[4,3-c]pyrimidin-3-one | Intermediate: 1 & 4 (step 1), 70 (step 2) Route b $^1$H NMR: (MHz, DMSO-d6) δ: 8.51 (d, J = 2.8 Hz, 1H), 7.72 (d, J = 2.8 Hz, 1H), 7.43-7.41 (m, 1H), 7.29 7. 26 (m, 5H), 6.51 (s, 1H), 6.41 (s, 1H), 5.12 (s, 2H), 3.73 (s, 3H), 2.20 (s, 3H). Exchangeable —$NH_2$ Protons were not observed. LCMS Method A: m/z 458 $(M + H)^+$ (ES+), at 2.90 min, UV active |
| 1-79 | 5-amino-8-[2-chloro-6-(trifluoromethyl)-4-pyridyl]-2-[(5-fluoro-2-pyridyl)methyl]-7-phenyl-[1,2,4]triazolo[4,3-c]pyrimidin-3-one | Intermediate: 1 & 4 (step 1), 72 (step 2) Route b (Purified by Prep HPLC (Method A), the fractions were concentrated and the residue was diluted with EtOAc (10 mL) and washed with 10% sodium bicarbonate solution (10 mL). The organic layer was separated, dried over anhydrous $Na_2SO_4$) $^1$H NMR: (MHz, DMSO-d6) δ: 8.79 (s, 1H), 8.53 (d, J = 2.8 Hz, 1H), 7.96 (s, 1H), 7.77-7.72 (m, 1H), 7.60 (s, 1H), 7.4 (s, 1H), 7.41-7.29 (m, 4H), 5.16 (s, 2H). Exchangeable —$NH_2$ Protons were not observed. LCMS Method A: m/z 516 $(M + H)^+$ (ES+), at 5.19 min, UV active |
| 1-80 | 5-amino-8-(2,6-dimethyl-4-pyridyl)-7-phenyl-2-(2-phenylethyl)-[1,2,4]triazolo[4,3-c]pyrimidin-3-one | Route x $^1$H NMR: (MHz, DMSO-d6) δ: 7.30-7.21 (m, 10H), 6.79 (s, 2H), 4.02 (t, J = 14.5 Hz, 2H), 2.99 (t, J = 14.5 Hz, 2H), 2.30 (s, 6H). Exchangeable —$NH_2$ Protons were not observed. LCMS Method E: m/z 437 $(M + H)^+$ (ES+), at 5.64 min, UV active |
| 1-81 | 5-amino-8-(2,6-dimethyl-4-pyridyl)-2-(1-methyl-2-phenyl-ethyl)-7-phenyl-[1,2,4]triazolo[4,3-c]pyrimidin-3-one | Intermediate: 74 & 76 (step 1), 3 (step 5) Route x $^1$H NMR: (MHz, DMSO-d6) δ: 7.30-7.15 (m, 10H), 6.81 (s, 2H), 4.55-4.50 (m, 1H), 3.05-2.93 (m, 2H), 2.31 (s, 6H), 1.33 (d, J = 6.8 Hz, 3H). Exchangeable —$NH_2$ Protons were not observed. LCMS Method E: m/z 451 $(M + H)^+$ (ES+), at 6.01 min, UV active |
| 1-82 | 5-amino-8-(2,6-dimethyl-4-pyridyl)-2-[2-(4-hydroxyphenyl)ethyl]-7-phenyl-[1,2,4]triazolo[4,3-c]pyrimidin-3-one | Intermediate: 1 & 77 (step 1), 3 (step 2) Route a $^1$H NMR: (MHz, DMSO-d6) δ: 9.22 (s, 1H), 7.27-7.26 (m, 5H), 6.98 (d, J = 8.4 Hz, 2H), 6.98 (br s, 2H), 6.67 (d, J = 8.0 Hz, 2H), 3.92 (t, J = 3.8 Hz, 2H), 2.87 (t, J = 3.8 Hz, 2H), 2.34 (s, 6H). Exchangeable —$NH_2$ Protons were not observed. LCMS Method A: m/z 453 $(M + H)^+$ (ES+), at 2.62 min, UV active |
| 1-83 | 5-amino-8-(2,6-dimethyl-4-pyridyl)-2-[2-(4-fluorophenyl)ethyl]-7-phenyl-[1,2,4]triazolo[4,3-c]pyrimidin-3-one | Intermediate: 1 & 78 (step 1), 3 (step 2) Route a $^1$H NMR: (MHz, DMSO-d6) δ: 7.28-7.22 (m, 7H), 7.13-7.09 (m, 2H), 6.76 (s, 2H), 4.00 (t, J = 7.2 Hz, 2H), 2.97 (t, J = 7.2 Hz, 2H), 2.29 (s, 6H). Exchangeable —$NH_2$ Protons were not observed. LCMS Method A: m/z 455 $(M + H)^+$ (ES+), at 3.29 min, UV active |
| 1-84 | methyl 4-[2-[5-amino-8-(2,6-dimethyl-4-pyridyl)-3-oxo-7-phenyl-[1,2,4]triazolo[4,3-c]pyrimidin-2-yl]ethyl]benzoate | Intermediate: 1 & 79 (step 1), 3 (step 2) Route a $^1$H NMR: (MHz, DMSO-d6) δ: 7.88 (d, J = 8.4 Hz, 2H), 7.36 (d, J = 8.4 Hz, 2H), 7.28-7.23 (m, 5H), 6.74 (s, 2H), 4.06 (t, J = 6.6 Hz, 2H), 3.83 (s, 3H), 3.06 (t, J = 6.6 Hz, 2H), 2.27 (s, 6H). Exchangeable —$NH_2$ protons not observed LCMS Method A: m/z 495 $(M + H)^+$ (ES+), at 3.13 min, UV active |
| 1-85 | 4-[2-[5-amino-8-(2,6-dimethyl-4-pyridyl)-3-oxo-7-phenyl-[1,2,4]triazolo[4,3-c]pyrimidin-2-yl]ethyl]benzoic acid | Route y $^1$H NMR: (MHz, DMSO-d6) δ: 7.86 (d, J = 8.0 Hz, 2H), 7.32 (d, J = 8.0 Hz, 2H), 7.27-7.25 (m, 5H), 6.76 (s, 2H), 4.06 (t, J = 8.2 Hz, 2H), 3.06 (t, J = 8.2 Hz, 2H), 2.29 (s, 6H). Exchangeable —$NH_2$ and COOH protons not observed |

TABLE 3-continued

Data for Examples 1-1 to 3-10

| Ex. | Name | Details |
| --- | --- | --- |
| | | LCMS Method A: m/z 481 $(M + H)^+$ (ES+), at 2.89 min, UV active |
| 1-86 | 5-amino-8-(2,6-dimethyl-4-pyridyl)-7-phenyl-2-[2-(2-pyridyl)ethyl]-[1,2,4]triazolo[4,3-c]pyrimidin-3-one | Intermediate: 1 & 81 (step 1), 3 (step 2)<br>Route c<br>$^1$H NMR: (MHz, DMSO-d6) δ: 8.50 (d, J = 4.0 Hz, 1H), 7.75-7.71 (m, 1H), 7.30-7.26 (m, 7H), 6.76 (s, 2H), 4.15 (t, J = 7.2 Hz, 2H), 3.13 (t, J = 7.2 Hz, 2H), 2.29 (s, 6H). Exchangeable —$NH_2$ protons were not observed<br>LCMS Method A: m/z 438 $(M + H)^+$ (ES+), at 1.99 min, UV active |
| 1-87 | 5-amino-8-(2,6-dimethyl-4-pyridyl)-7-(4-fluorophenyl)-2-(2-phenylethyl)-[1,2,4]triazolo[4,3-c]pyrimidin-3-one | Intermediate: 41 & 82 (step 1), 3 (step 2)<br>Route a<br>$^1$H NMR: (MHz, DMSO-d6) δ: 8.04-7.85 (m, 2H), 7.30-7.27 (m, 4H), 7.23-7.20 (m, 3H), 7.11-7.08 (m, 2H), 6.79 (s, 2H), 4.01 (t, J = 7.2 Hz, 2H), 2.98 (t, J = 7.2 Hz, 2H), 2.31 (s, 6H).<br>LCMS Method A: m/z 455 $(M + H)^+$ (ES+), at 3.28 min, UV active |
| 1-88 | 5-amino-8-[2-methyl-6-(trifluoromethyl)-4-pyridyl]-7-phenyl-2-(2-phenylethyl)-[1,2,4]triazolo[4,3-c]pyrimidin-3-one | Intermediate: 1 & 82 (step 1), 66 (step 2)<br>Route a<br>$^1$H NMR: (MHz, DMSO-d6) δ: 8.54 (br s, 1H), 7.75 (br s, 1H), 7.38 (s, 1H), 7.34-7.22 (m, 11H), 4.04 (t, J = 7.2 Hz, 2H), 3.01 (t, J = 7.2 Hz, 2H), 2.33 (s, 3H).<br>LCMS Method A: m/z 491 $(M + H)^+$ (ES+), at 5.36 min, UV active |
| 1-89 | 5-amino-8-(2-chloro-6-methyl-4-pyridyl)-7-phenyl-2-(2-phenylethyl)-[1,2,4]triazolo[4,3-c]pyrimidin-3-one | Intermediate: 1 & 82 (step 1), 69 (step 2)<br>Route a (Step 2 performed using $K_3PO_4$ and Pd(amphos)$Cl_2$)<br>$^1$H NMR: (MHz, DMSO-d6) δ: 7.33-7.21 (m, 10H), 6.99 (s, 2H), 4.03 (t, J = 6.8 Hz, 2H), 2.99 (t, J = 6.8 Hz, 2H), 2.32 (s, 3H). Exchangeable —$NH_2$ protons not observed.<br>LCMS Method A: m/z 457 $(M + H)^+$ (ES+), at 4.71 min, UV active |
| 1-90 | 5-amino-8-[2-(azetidin-1-yl)-6-methyl-4-pyridyl]-7-phenyl-2-(2-phenylethyl)-[1,2,4]triazolo[4,3-c]pyrimidin-3-one | Route z<br>$^1$H NMR: (MHz, DMSO-d6) δ: 7.35-7.32 (m, 8H), 7.27-7.27 (m, 2H), 6.34 (s, 1H), 5.95 (s, 1H), 4.14 (t, J = 8.0 Hz, 2H), 3.92-3.88 (m, 4H), 3.14 (t, J = 8.0 Hz, 2H), 2.33-2.30 (m, 5H). Exchangeable —NH2 protons not observed.<br>LCMS Method A: m/z 478 $(M + H)^+$ (ES+), at 3.47 min, UV active |
| 1-91 | 5-[2-[5-amino-8-(2,6-dimethyl-4-pyridyl)-3-oxo-7-phenyl-[1,2,4]triazolo[4,3-c]pyrimidin-2-yl]ethylamino]-2-chloro-N-methyl-benzamide | Route aa<br>$^1$H NMR: (MHz, Chloroform-d) δ: 7.30-7.18 (m, 7H), 7.11 (d, J = 8.7 Hz, 1H), 6.92 (d, J = 3.0 Hz, 1H), 6.80 (s, 2H), 6.55-6.53 (m, 1H), 6.31 (s, 1H), 4.34 (s, 1H), 4.12 (t, J = 5.6 Hz, 2H), 3.55-3.51 (m, 2H), 2.99-2.97 (m, 3H), 2.42 (s, 6H).<br>LCMS Method F: m/z 543 $(M + H)^+$ (ES+), at 0.90 min, UV active |
| 1-92 | 5-amino-8-(2,6-dimethyl-4-pyridyl)-7-phenyl-2-[2-[1-([1,2,4]triazolo[4,3-a]pyrimidin-3-yl)ethylamino]ethyl]-[1,2,4]triazolo[4,3-c]pyrimidin-3-one | Intermediate: 87<br>Route aa<br>$^1$H NMR: (MHz, Chloroform-d) δ: 8.75 (d, J = 5.4 Hz, 2H), 7.37-7.13 (m, 5H), 7.03 (dd, J = 7.3, 3.7 Hz, 1H), 6.79 (s, 2H), 4.19 (d, J = 7.1 Hz, 1H), 4.06-3.86 (m, 2H), 3.10-2.88 (m, 2H), 2.37 (s, 6H), 2.11 (s, 1H), 1.54 (d, J = 6.7 Hz, 3H). Exchangeable —$NH_2$ protons not observed.<br>LCMS Method F: m/z 522 $(M + H)^+$ (ES+), at 0.68 min, UV active |
| 1-93 | 5-amino-8-(2,6-dimethyl-4-pyridyl)-2-[2-[methyl-(1-phenyl-4-piperidyl)amino]ethyl]-7-phenyl-[1,2,4]triazolo[4,3-c]pyrimidin-3-one | Intermediate: 88<br>Route aa<br>$^1$H NMR: (MHz, Chloroform-d) δ: 8.30 (br. s, 1H), 7.64 (br. s, 1H), 7.29-7.16 (m, 5H), 7.13 (t, J = 7.9 Hz, 2H), 6.82 (d, J = 7.9 Hz, 2H), 6.74-6.66 (m, 3H), 3.91-3.82 (m, 2H), 3.69-3.60 (m, 2H), 2.83-2.76 (m, 2H), 2.70-2.59 (m, 2H), 2.54-2.53 (m, 1H), 2.35-2.28 (m, 9H), 1.78-1.71 (m, 2H), 1.63-1.47 (m, 2H).<br>LCMS Method F: m/z 549 $(M + H)^+$ (ES+), at 0.82 min, UV active |
| 1-94 | 5-amino-8-(2,6-dimethyl-4-pyridyl)-2-[2-[[(1S)-1-(6-methyl-2-pyridyl)ethyl]amino]ethyl]-7-phenyl-[1,2,4]triazolo[4,3-c]pyrimidin-3-one | Intermediate: 89<br>Route aa<br>$^1$H NMR: (MHz, Chloroform-d) δ: 7.45 (t, J = 7.7 Hz, 1H), 7.32-7.18 (m, 6H), 7.05 (d, J = 7.7 Hz, 1H), 6.96 (d, J = 7.7 Hz, 1H), 6.79 (s, 2H), 4.05-3.82 (m, 3H), 2.97-2.79 (m, 2H), 2.48 (s, 3H), 2.38 (s, 6H), 2.08-1.89 (m, 2H), 1.34 (d, J = 6.6 Hz, 3H).<br>LCMS Method F: m/z 495 $(M + H)^+$ (ES+), at 0.76 min, UV active |

TABLE 3-continued

| Data for Examples 1-1 to 3-10 | | |
|---|---|---|
| Ex. | Name | Details |
| 1-95 | 5-amino-8-(2,6-dimethyl-4-pyridyl)-2-[2-[[1-(3-methyl-1H-pyrazol-5-yl)-4-piperidyl]amino]ethyl]-7-phenyl-[1,2,4]triazolo[4,3-c]pyrimidin-3-one | Intermediate: 90<br>Route aa<br>$^1$H NMR: (MHz, Chloroform-d) δ: 9.89 (s, 1H), 7.65 (s, 2H), 7.30-7.18 (m, 5H), 6.79 (s, 2H), 5.45 (s, 1H), 4.03-3.95 (m, 2H), 3.63-3.55 (m, 2H), 3.10-3.02 (m, 2H), 2.78-2.67 (m, 2H), 2.66-2.61 (m, 1H), 2.39 (s, 6H), 2.02 (s, 3H), 1.93-1.87 (m, 1H), 1.47-1.36 (m, 2H), 1.19 (d, J = 6.2 Hz, 1H).<br>LCMS Method F: m/z 439 $(M + H)^+$ (ES+), at 0.70 min, UV active |
| 1-96 | 5-amino-8-(2,6-dimethyl-4-pyridyl)-2-[2-[2-(1-methylpyrrol-2-yl)azepan-1-yl]ethyl]-7-phenyl-[1,2,4]triazolo[4,3-c]pyrimidin-3-one | Intermediate: 91<br>Route aa<br>$^1$H NMR: (MHz, Chloroform-d) δ: 7.32-7.22 (m, 6H), 6.79 (s, 2H), 6.31 (t, J = 2.2 Hz, 1H), 5.98-5.86 (m, 2H), 3.87-3.76 (m, 2H), 3.55-3.51 (m, 4.0 Hz, 1H), 3.46 (s, 3H), 3.29-3.27 (m, 1H), 3.07-2.96 (m, 1H), 2.90-2.77 (m, 2H), 2.40 (s, 6H), 2.11-1.97 (m, 1H), 1.94-1.76 (m, 2H), 1.74-1.50 (m,6H).<br>LCMS Method F: m/z 537 $(M + H)^+$ (ES+), at 0.79 min, UV active |
| 1-97 | 5-amino-8-(2,6-dimethyl-4-pyridyl)-2-[2-[4-[(5-methyl-2-pyridyl)amino]-1-piperidyl]ethyl]-7-phenyl-[1,2,4]triazolo[4,3-c]pyrimidin-3-one | Intermediate: 92<br>Route aa<br>$^1$H NMR: (MHz, Chloroform-d) δ: 7.88 (s, 1H), 7.34-7.13 (m, 6H), 6.80 (s, 2H), 6.29 (d, J = 8.5 Hz, 1H), 4.21 (d, J = 8.2 Hz, 1H), 4.08-3.90 (m, 2H), 3.57 (d, J = 9.7 Hz, 1H), 2.90 (d, J = 11.1 Hz, 2H), 2.81-2.70 (m, 2H), 2.60 (s, 2H), 2.39 (s, 6H), 2.26 (t, J = 11.1 Hz, 2H), 2.15 (s, 2H), 2.07-1.96 (m, 2H), 1.81 (s, 1H), 1.54-1.37 (m, 2H).<br>LCMS Method F: m/z 550 $(M + H)^+$ (ES+), at 0.65 min, UV active |
| 1-98 | 5-amino-8-(2,6-dimethyl-4-pyridyl)-2-[2-[3-(3-methyl-5-oxo-4H-pyrazol-1-yl)anilino]ethyl]-7-phenyl-[1,2,4]triazolo[4,3-c]pyrimidin-3-one | Intermediate: 93<br>Route aa<br>$^1$H NMR: (MHz, Chloroform-d) d 7.32-7.18 (m, 5H), 7.09 (d, J = 2.4 Hz, 1H), 7.08-6.97 (m, 2H), 6.73 (s, 2H), 6.47-6.39 (m, 1H), 5.48 (s, 1H), 4.37 (t, J = 5.0 Hz, 2H), 4.28 (t, J = 5.0 Hz, 2H), 3.72 (s, 2H), 2.38 (s, 6H), 2.24 (s, 3H), 1.20-1.18 (s, 1H). Exchangeable NH not observed.<br>LCMS Method F: m/z 548 $(M + H)^+$ (ES+), at 0.89 min, UV active |
| 1-99 | 5-amino-8-(2,6-dimethyl-4-pyridyl)-2-[2-[[2-(hydroxymethyl)tetralin-2-yl]-methyl-amino]ethyl]-7-phenyl-[1,2,4]triazolo[4,3-c]pyrimidin-3-one | Intermediate: 94<br>Route aa<br>$^1$H NMR: (MHz, Chloroform-d) δ 7.35-7.19 (m, 7H), 7.08-6.98 (m, 3H), 6.93 (d, J = 6.8 Hz, 1H), 6.88 (s, 2H), 3.95-3.91 (m, 2H), 3.50 (d, J = 11.2 Hz, 1H), 3.35 (d, J = 11.2 Hz, 1H), 3.02-2.89 (m, 2H), 2.89-2.65 (m, 3H), 2.65-2.56 (m, 2H), 2.45 (s, 6H), 2.41 (s, 3H), 1.88-1.84 (m, 1H), 1.75-1.64 (m, 1H).<br>LCMS Method F: m/z 550 $(M + H)^+$ (ES+), at 0.80 min, UV active |
| 1-100 | 5-amino-2-[1-(aminomethyl)-2-(2,4-difluorophenyl)ethyl]-8-(2,6-dimethyl-4-pyridyl)-7-phenyl-[1,2,4]triazolo[4,3-c]pyrimidin-3-one | Intermediate: 95<br>Route h<br>$^1$H NMR: (MHz, Chloroform-d) δ 7.33-7.16 (m, 6H), 7.09-6.99 (m, 1H), 6.83-6.71 (m, 5H), 4.52-4.41 (m, 1H), 3.44 (s, 1H), 3.18-2.97 (m, 5H), 2.40 (s, 6H).<br>LCMS Method F: m/z 502 $(M + H)^+$ (ES+), at 0.98 min, UV active |
| 1-101 | 5-amino-2-[[(3R)-4-benzylmorpholin-3-yl]methyl]-8-(2,6-dimethyl-4-pyridyl)-7-phenyl-[1,2,4]triazolo[4,3-c]pyrimidin-3-one | Intermediate: 96<br>Route d (purified by prep HPLC method C)<br>$^1$H NMR: (MHz, DMSO-d6) δ: 8.23 (s, 2H), 7.27-7.21 (m, 10H), 6.75 (s, 2H), 4.16-4.13 (m, 1H), 4.05 (d, J = 13.2 Hz, 1H), 3.96-3.92 (m, 1H), 3.70 (d, J = 8.4 Hz, 1H), 3.56-3.54 (m, 1H), 3.53-3.49 (m, 3H), 2.79-2.63 (m, 2H), 2.25-2.25 (m, 1H), 2.24 (s, 6H).<br>LCMS Method A: m/z 522 $(M + H)^+$ (ES+), at 2.37 min, UV active |
| 1-102 | 5-amino-2-[(4-benzyl-4-piperidyl)methyl]-8-(2,6-dimethyl-4-pyridyl)-7-phenyl-[1,2,4]triazolo[4,3-c]pyrimidin-3-one | Intermediate: 97<br>Route h<br>$^1$H NMR: (MHz, Chloroform-d) δ: 7.42-7.10 (m, 12H), 6.86 (s, 2H), 3.80 (s, 2H), 3.45 (s, 1H), 3.04-2.87 (m, 4H), 2.84 (s, 2H), 2.35 (s, 6H), 1.59-1.41 (m, 4H).<br>LCMS Method F: m/z 520 $(M + H)^+$ (ES+), at 0.98 min, UV active |
| 1-103 | 5-amino-8-(2,6-dimethyl-4-pyridyl)-2-(2-morpholin-3-yl-1-phenyl-ethyl)-7-phenyl-[1,2,4]triazolo[4,3-c]pyrimidin-3- | Intermediate: 98<br>Route h<br>$^1$H NMR: (MHz, Chloroform-d) δ 7.52-7.39 (m, 2H), 7.39-7.13 (m, 8H), 6.86-6.73 (m, 2H), 5.51-5.33 (m, 1H), |

TABLE 3-continued

| Data for Examples 1-1 to 3-10 | | |
|---|---|---|
| Ex. | Name | Details |
| | one | 3.86-3.64 (m, 2H), 3.55-3.38 (m, 1H), 3.25-3.10 (m, 1H), 2.92-2.78 (m, 2H), 2.76-2.58 (m, 1H), 2.48-2.32 (m, 6H), 2.33-2.04 (m, 1H), 1.97-1.77 (m, 2H). Exchangeable —$NH_2$ protons were not observed<br>LCMS Method F: m/z 522 $(M + H)^+$ (ES+), at 0.97 min, UV active |
| 1-104 | 5-amino-2-(5-aminoindan-2-yl)-8-(2,6-dimethyl-4-pyridyl)-7-phenyl-[1,2,4]triazolo[4,3-c]pyrimidin-3-one | Intermediate: 99<br>Route h<br>$^1$H NMR: (MHz, Chloroform-d) δ 7.32-7.17 (m, 7H), 6.98 (d, J = 7.9 Hz, 1H), 6.79 (s, 2H), 6.62-6.46 (m, 2H), 5.23-5.06 (m, 1H), 3.48 (s, 2H), 3.44-3.25 (m, 2H), 3.24-3.11 (m, 2H), 2.38 (s, 6H).<br>LCMS Method F: m/z 464 $(M + H)^+$ (ES+), at 0.93 min, UV active |
| 2-1 | 5-amino-8-(2,6-dimethyl-4-pyridyl)-7-phenyl-2H-[1,2,4]triazolo[4,3-c]pyrimidin-3-one | Intermediate: 7<br>Route 2<br>$^1$H NMR: (MHz, DMSO-d6) δ: 12.25 (s, 1H), 8.14 (s, 2H), 7.29-7.25 (m, 5H), 6.82 (s, 2H), 2.29 (s, 6H).<br>LCMS Method A: m/z 333 $(M + H)^+$ $(ES^+)$, at 1.98 min, UV active |
| 2-2 | 5-amino-8-(2,6-dimethyl-4-pyridyl)-2-methyl-7-phenyl-[1,2,4]triazolo[4,3-c]pyrimidin-3-one | Intermediate: 1 & 100 (step 1), 3 (step 2)<br>Route a<br>$^1$H NMR: (MHz, DMSO-d6) δ: 7.31-7.19 (m, 5H), 6.81 (s, 2H), 3.40 (s, 3H), 2.29 (s, 6H) Exchangeable —$NH_2$ protons were not observed<br>LCMS Method E: m/z 347 $(M + H)^+$ $(ES^+)$, at 4.32 min, UV active |
| 2-3 | 5-amino-8-(2,6-dimethyl-4-pyridyl)-2-ethyl-7-phenyl-[1,2,4]triazolo[4,3-c]pyrimidin-3-one | Intermediate: 1 & 101 (step 1), 3 (step 2)<br>Route a<br>$^1$H NMR: (MHz, DMSO-d6) δ: 7.25-7.24 (m, 5H), 6.81 (s, 2H), 3.80 (q, J = 7.2 Hz, 2H), 1.98 (s, 6H), 1.22 (t, J = 7.2 Hz, 3H). Exchangeable —$NH_2$ protons were not observed<br>LCMS Method A: m/z 361 $(M + H)^+$ $(ES^+)$, at 2.31 min, UV active |
| 2-4 | 5-amino-8-(2,6-dimethyl-4-pyridyl)-2-isopropyl-7-phenyl-[1,2,4]triazolo[4,3-c]pyrimidin-3-one | Intermediate: 1 & 102 (step 1), 3 (step 2)<br>Route a<br>$^1$H NMR: (MHz, DMSO-d6) δ: 7.82 (br s, 2H), 7.25 (br s, 5H), 6.82 (s, 2H), 4.42-4.38 (m, 1H), 2.32 (s, 6H), 1.29 (d, J = 6.0 Hz, 6H).<br>LCMS Method A: m/z 375 $(M + H)^+$ $(ES^+)$, at 2.59 min, UV active |
| 2-5 | 5-amino-8-(2,6-dimethyl-4-pyridyl)-2-isopentyl-7-phenyl-[1,2,4]triazolo[4,3-c]pyrimidin-3-one | Intermediate: 1 & 103 (step 1), 3 (step 2)<br>Route a<br>$^1$H NMR: (MHz, DMSO-d6) δ: 8.50 (br s, 2H), 7.27-7.25 (m, 5H), 6.82 (s, 2H), 3.79 (t, J = 8.8 Hz, 2H), 2.29 (s, 6H), 1.55-1.53 (m, 3H), 0.90 (d, J = 8.0 Hz, 6H)<br>LCMS Method A: m/z 403 $(M + H)^+$ $(ES^+)$, at 3.18 min, UV active |
| 2-6 | 5-amino-8-(2,6-dimethyl-4-pyridyl)-7-phenyl-2-(3,3,3-trifluoropropyl)-[1,2,4]triazolo[4,3-c]pyrimidin-3-one | Intermediate: 74 & 104 (step 1)<br>Route x<br>$^1$H NMR: (MHz, DMSO-d6) δ: 7.29-7.24 (m, 5H), 6.82 (s, 2H), 4.04 (t, J = 6.7 Hz, 2H), 2.76-2.70 (m, 2H), 2.28 (s, 6H). Exchangeable —$NH_2$ protons were not observed<br>LCMS Method A: m/z 429 $(M + H)^+$ $(ES^+)$, at 2.79 min, UV active |
| 2-7 | 5-amino-8-(2,6-dimethyl-4-pyridyl)-2-(2-hydroxyethyl)-7-phenyl-[1,2,4]triazolo[4,3-c]pyrimidin-3-one | Intermediate: 1 & 85 (step 1), 3 (step 2)<br>Route a<br>$^1$H NMR: (MHz, DMSO-d6) δ: 7.27-7.25 (m, 5H), 6.83 (s, 2H), 4.80 (t, J = 6.0 Hz, 1H), 3.84-3.80 (m, 2H), 3.65 (t, J = 5.6 Hz, 2H), 2.30 (s, 6H). Exchangeable —$NH_2$ protons were not observed<br>LCMS Method A: m/z 377 $(M + H)^+$ $(ES^+)$, at 1.94 min, UV active |
| 2-8 | 5-amino-8-(2,6-dimethyl-4-pyridyl)-2-(3-fluoropropyl)-7-phenyl-[1,2,4]triazolo[4,3-c]pyrimidin-3-one | Intermediate: 1 & 105 (step 1), 3 (step 2)<br>Route c<br>$^1$H NMR: (MHz, DMSO-d6) δ: 8.30-7.92 (m, 2H), 7.30-7.26 (m, 5H), 6.82 (s, 2H), 4.57-4.45 (m, 2H), 3.89 (t, J = 6.8 Hz, 2H), 2.98 (s, 6H), 2.09-2.01 (m, 2H).<br>LCMS Method A: m/z 393 $(M + H)^+$ $(ES^+)$, at 2.44 min, UV active |
| 2-9 | 2-[5-amino-8-(2,6-dimethyl-4-pyridyl)-3-oxo-7-phenyl-[1,2,4]triazolo[4,3-c]pyrimidin-2-yl]ethyl methanesulfonate | Intermediate: 83<br>Route 9<br>$^1$H NMR: (MHz, DMSO-d6 δ: 7.28-7.27 (m, 5H), 6.84 (s, 2H), 4.47 (t, J = 4.5 Hz, 2H), 4.13 (t, J = 4.5 Hz, 2H), 3.17 (s, 3H), 2.30 (s, 6H). Exchangeable —$NH_2$ protons not observed. |

TABLE 3-continued

Data for Examples 1-1 to 3-10

| Ex. | Name | Details |
|---|---|---|
| | | LCMS Method A: m/z 455 (M + H)+ (ES+), at 2.34 min, UV active. |
| 2-10 | 5-amino-8-(2,6-dimethyl-4-pyridyl)-2-(2-methoxyethyl)-7-phenyl-[1,2,4]triazolo[4,3-c]pyrimidin-3-one | Intermediate: 1 & 106 (step 1), 3 (step 2)<br>Route a<br>$^1$H NMR: (MHz, DMSO-d6) δ: 8.50-7.80 (m, 2H), 7.27-7.26 (m, 5H), 6.83 (s, 2H), 3.98-3.91 (m, 1H), 3.65-3.56 (m, 1H), 3.24 (s, 3H), 2.30 (s, 6H).<br>LCMS Method A: m/z 391 $(M + H)^+$ $(ES^+)$, at 2.23 min, UV active |
| 2-11 | 3-[5-amino-8-(2,6-dimethyl-4-pyridyl)-3-oxo-7-phenyl-[1,2,4]triazolo[4,3-c]pyrimidin-2-yl]propanenitrile | Intermediate: 1 & 107 (step 1), 3 (step 2)<br>Route a (step 2 purified by prep HPLC method A)<br>$^1$H NMR: (MHz, DMSO-d6) δ: 8.20-7.70 (m, 2H), 7.27-7.27 (m, 5H), 6.85 (s, 2H), 4.08 (t, J = 6.2 Hz, 2H), 2.95 (t, J = 6.2 Hz, 2H), 2.29 (s, 6H).<br>LCMS Method A: m/z 386 $(M + H)^+$ $(ES^+)$, at 4.6 min, UV active |
| 2-12 | ethyl N-[2-[5-amino-8-(2,6-dimethyl-4-pyridyl)-3-oxo-7-phenyl-[1,2,4]triazolo[4,3-c]pyrimidin-2-yl]ethyl]carbamate | Intermediate: 1 & 108 (step 1), 3 (step 2)<br>Route a<br>$^1$H NMR: (MHz, DMSO-d6) δ: 7.29-7.15 (m, 6H), 6.81 (s, 2H), 3.94-3.94 (q, J = 7.2 Hz, 2H), 3.81 (t, J = 5.2 Hz, 2H), 3.27 (d, J = 5.2 Hz, 2H), 2.28 (s, 6H), 1.09 (t, J = 7.2 Hz, 3H). Exchangeable —$NH_2$ protons were not observed<br>LCMS Method A: m/z 448 $(M + H)^+$ $(ES^+)$, at 2.51 min, UV active |
| 2-13 | ethyl N-[2-[5-amino-8-(2,6-dimethyl-4-pyridyl)-3-oxo-7-phenyl-[1,2,4]triazolo[4,3-c]pyrimidin-2-yl]ethyl]-N-methyl-carbamate | Intermediate: 1 & 109 (step 1), 3 (step 2)<br>Route c<br>$^1$H NMR: (MHz, DMSO-d6) δ: 7.27-7.24 (m, 5H), 6.83 (s, 2H), 3.95-3.93 (m, 4H), 3.51 (m, 2H), 2.84 (s, 3H), 2.28 (s, 6H), 1.11-0.96 (m, 3H). Exchangeable —$NH_2$ protons were not observed<br>LCMS Method A: m/z 462 $(M + H)^+$ $(ES^+)$, at 2.69 min, UV active |
| 2-14 | tert-butyl N-[2-[5-amino-8-(2,6-dimethyl-4-pyridyl)-3-oxo-7-phenyl-[1,2,4]triazolo[4,3-c]pyrimidin-2-yl]ethyl]carbamate | Intermediate: 1 & 110 (step 1), 3 (step 2)<br>Route a<br>$^1$H NMR: (MHz, DMSO-d6) δ: 8.34 (br s, 2H), 7.27-7.24 (m, 5H), 6.88 (s, 1H), 6.82 (s, 2H), 3.81-3.79 (m, 2H), 3.22-3.21 (m, 2H), 2.28 (s, 6H), 1.31 (s, 9H)<br>LCMS Method A: m/z 476 $(M + H)^+$ $(ES^+)$, at 2.94 min, UV active |
| 2-15 | methyl 3-[5-amino-8-(2,6-dimethyl-4-pyridyl)-3-oxo-7-phenyl-[1,2,4]triazolo[4,3-c]pyrimidin-2-yl]propanoate | Intermediate: 1 & 111 (step 1), 3 (step 2)<br>Route a (step 2 purified by prep HPLC method A)<br>$^1$H NMR: (MHz, DMSO-d6) δ: 7.27-7.26 (m, 5H), 6.79 (s, 2H), 4.02 (t, J = 6.4 Hz, 2H), 3.57 (s, 3H), 2.74 (t, J = 6.4 Hz, 2H), 2.28 (s, 6H). Exchangeable —$NH_2$ protons were not observed<br>LCMS Method A: m/z 419 $(M + H)^+$ $(ES^+)$, at 2.38 min, UV active |
| 2-16 | 2-[5-amino-8-(2,6-dimethyl-4-pyridyl)-3-oxo-7-phenyl-[1,2,4]triazolo[4,3-c]pyrimidin-2-yl]ethyl N-ethylcarbamate | Route ab<br>$^1$H NMR: (MHz, DMSO-d6) δ: 7.28-7.25 (m, 5H), 7.21 (s, 1H), 6.82 (s, 2H), 4.21 (d, J = 7.2 Hz, 2H), 3.99-3.98 (m, 2H), 2.97-2.94 (m, 2H), 2.33 (s, 6H), 0.97 (t, J = 7.2 Hz, 3H). Exchangeable —$NH_2$ protons were not observed<br>LCMS Method A: m/z 448 $(M + H)^+$ $(ES^+)$, at 2.42 min, UV active |
| 2-17 | 5-amino-2-(3,3-difluoropropyl)-8-(2,6-dimethyl-4-pyridyl)-7-phenyl-[1,2,4]triazolo[4,3-c]pyrimidin-3-one | Route ac<br>$^1$H NMR: (MHz, DMSO-d6) δ: 8.30 (s, 2H), 7.30-7.25 (m, 5H), 6.82 (s, 2H), 6.33-6.02 (m, 1H), 3.94 (t, J = 6.4 Hz, 2H), 2.29 (s, 6H), 2.28-2.16 (m, 2H).<br>LCMS Method A: m/z 411 $(M + H)^+$ $(ES^+)$, at 2.65 min, UV active |
| 2-18 | 5-amino-8-(2,6-dimethyl-4-pyridyl)-2-[2-[ethyl(methyl)amino]ethyl]-7-phenyl-[1,2,4]triazolo[4,3-c]pyrimidin-3-one | Intermediate: 112<br>Route aa<br>$^1$H NMR: (MHz, Chloroform-d) δ: 8.28 (br. s, 1H), 7.62 (br. s, 1H), 7.33-7.14 (m, 5H), 6.71 (s, 2H), 3.87 (t, J = 6.5 Hz, 2H), 2.67 (t, J = 6.5 Hz, 2H), 2.56-2.38 (m, 11H), 1.01 (t, J = 7.1 Hz, 3H).<br>LCMS Method F: m/z 418 $(M + H)^+$ (ES+), at 0.63 min, UV active |
| 2-19 | 5-amino-2-[2-[cyclopropyl(methyl)amino]ethyl]-8-(2,6-dimethyl-4-pyridyl)-7-phenyl-[1,2,4]triazolo[4,3-c]pyrimidin-3-one | Intermediate: 113<br>Route aa<br>$^1$H NMR: (MHz, Chloroform-d) δ 7.42-7.11 (m, 5H), 6.80 (s, 2H), 4.01-3.98 (t, J = 6.6 Hz, 2H), 2.95 (t, J = 6.6 Hz, 2H), 2.40 (s, 6H), 2.41-2.37 (m, 3H), 1.73-1.69 (m, 1H), 0.48-0.44 (m, 2H), 0.43-0.29 (m, 2H). Exchangeable —NH2 protons were not observed |

TABLE 3-continued

Data for Examples 1-1 to 3-10

| Ex. | Name | Details |
|---|---|---|
| | | LCMS Method F: m/z 430 (M + H)$^+$ (ES+), at 0.69 min, UV active |
| 2-20 | 5-amino-8-(2,6-dimethyl-4-pyridyl)-7-phenyl-2-propyl-[1,2,4]triazolo[4,3-c]pyrimidin-3-one | Route ad<br>$^1$H NMR: (MHz, DMSO-d6) δ: 8.10 (s, 2H), 7.20-7.30 (m, 5H), 6.83 (s, 2H), 3.74 (t, J = 6.7 Hz, 2H), 2.30 (s, 6H), 1.71-1.65 (m, 2H), 0.89-0.88 (m, 3H).<br>LCMS Method A: m/z 375 (M + H)$^+$ (ES$^+$), at 2.60 min, UV active |
| 2-21 | 5-amino-8-(2,6-dimethyl-4-pyridyl)-2-isobutyl-7-phenyl-[1,2,4]triazolo[4,3-c]pyrimidin-3-one | Intermediate: 7 & 115<br>Route ad<br>$^1$H NMR: (MHz, DMSO-d6) δ: 8.10 (s, 2H), 7.26-7.25 (m, 5H), 6.82-6.81 (m, 2H), 3.59-3.57 (m, 2H), 2.29-2.28 (m, 6H), 2.05-2.04 (m, 1H), 0.90-0.87 (m, 6H).<br>LCMS Method A: m/z 389 (M + H)$^+$ (ES$^+$), at 2.89 min, UV active |
| 2-22 | 2-[5-amino-8-(2,6-dimethyl-4-pyridyl)-3-oxo-7-phenyl-[1,2,4]triazolo[4,3-c]pyrimidin-2-yl]acetamide | Intermediate: 7 & 116<br>Route ad<br>$^1$H NMR: (MHz, DMSO-d6) δ: 8.10 (s, 2H), 7.49 (s, 2H), 7.30-7.26 (m, 5H), 6.80 (s, 2H), 4.37 (s, 2H), 2.29 (s, 6H).<br>LCMS Method A: m/z 390 (M + H)$^+$ (ES$^+$), at 1.86 min, UV active |
| 2-23 | 3-[5-amino-8-(2,6-dimethyl-4-pyridyl)-3-oxo-7-phenyl-[1,2,4]triazolo[4,3-c]pyrimidin-2-yl]-N,N-dimethyl-propanamide | Route ae<br>$^1$H NMR: (MHz, DMSO-d6) δ: 7.29-7.28 (m, 5H), 6.82 (s, 2H), 3.98 (t, J = 4.0 Hz, 2H), 2.80-2.77 (m, 3H), 2.75-2.73 (m, 3H), 2.51-2.49 (m, 2H), 2.30 (s, 6H).<br>Exchangeable —NH2 protons were not observed.<br>LCMS Method A: m/z 432 (M + H)$^+$ (ES$^+$), at 2.17 min, UV active |
| 2-24 | 5-amino-8-(2,6-dimethyl-4-pyridyl)-2-[3-hydroxy-2-(hydroxymethyl)propyl]-7-phenyl-[1,2,4]triazolo[4,3-c]pyrimidin-3-one | Route af<br>$^1$H NMR: (MHz, DMSO-d6) δ: 8.65 (s, 2H), 7.30-7.26 (m, 5H), 6.83 (s, 2H), 4.48 (t, J = 5.0 Hz, 2H), 3.78 (d, J = 7.0 Hz, 2H), 3.47-3.41 (m, 4H), 2.30 (s, 6H), 2.03-2.02 (m, 1H).<br>LCMS Method A: m/z 421 (M + H)$^+$ (ES$^+$), at 1.96 min, UV active |
| 2-25 | 2-[5-amino-8-(2,6-dimethyl-4-pyridyl)-3-oxo-7-phenyl-[1,2,4]triazolo[4,3-c]pyrimidin-2-yl]-N,N-dimethyl-acetamide | Intermediate: 7 & 118<br>Route ad<br>$^1$H NMR: (MHz, DMSO-d6) δ: 7.29-7.27 (m, 5H), 6.82 (s, 2H), 4.79 (s, 2H), 3.01 (s, 3H), 2.83 (s, 3H), 2.29 (s, 6H).<br>Exchangeable —$NH_2$ protons were not observed.<br>LCMS Method A: m/z 418 (M + H)$^+$ (ES$^+$), at 2.00 min, UV active |
| 2-26 | 5-amino-2-[(3,3-difluorocyclopentyl)methyl]-8-(2,6-dimethyl-4-pyridyl)-7-phenyl-[1,2,4]triazolo[4,3-c]pyrimidin-3-one | Intermediate: 119<br>Route g<br>$^1$H NMR: (MHz, Chloroform-d) δ: 7.32-7.22 (m, 5H), 6.80 (s, 2H), 3.93-3.81 (m, 2H), 2.69-2.67 (m, 1H), 2.40 (s, 6H) 2.32-1.84 (m, 5H), 1.69-1.55 (m, 1H). Exchangeable —$NH_2$ protons were not observed.<br>LCMS Method F: m/z 451 (M + H)$^+$ (ES+), at 1.02 min, UV active |
| 2-27 | 5-amino-8-(2,6-dimethyl-4-pyridyl)-2-[(2-ethyl-2-methyl-cyclopropyl)methyl]-7-phenyl-[1,2,4]triazolo[4,3-c]pyrimidin-3-one | Intermediate: 120<br>Route g<br>$^1$H NMR: (MHz, Chloroform-d) δ 7.36-7.19 (m, 5H), 6.85 (s, 2H), 4.05-3.71 (m, 2H), 2.42 (s, 6H), 1.78-1.55 (m, 2H), 1.53-1.01 (m, 4H), 1.02-0.84 (m, 3H), 0.71-0.15 (m, 2H).<br>Exchangeable —$NH_2$ protons were not observed.<br>LCMS Method F: m/z 429 (M + H)$^+$ (ES+), at 1.20 min, UV active |
| 2-28 | 2-[5-amino-8-(2,6-dimethyl-4-pyridyl)-3-oxo-7-phenyl-[1,2,4]triazolo[4,3-c]pyrimidin-2-yl]-N-cyclopropyl-N-methyl-acetamide | Intermediate: 121<br>Route g<br>$^1$H NMR: (MHz, Chloroform-d) δ 7.37-7.08 (m, 5H), 6.84 (s, 2H), 4.90 (s, 2H), 2.97 (s, 3H), 2.85-2.65 (m, 1H), 2.41 (s, 6H), 1.08-0.71 (m, 4H). Exchangeable —$NH_2$ protons were not observed.<br>LCMS Method F: m/z 444 (M + H)$^+$ (ES+), at 0.93 min, UV active |
| 2-29 | methyl 1-[[5-amino-8-(2,6-dimethyl-4-pyridyl)-3-oxo-7-phenyl-[1,2,4]triazolo[4,3-c]pyrimidin-2-yl]methyl]cyclopentanecarboxylate | Intermediate: 122<br>Route g<br>$^1$H NMR: (MHz, Chloroform-d) δ: 7.35-7.19 (m, 5H), 6.80 (s, 2H), 4.09 (s, 2H), 3.57 (s, 3H), 2.41 (s, 6H) 2.14-2.06 (m, 2H), 1.80-1.56 (m, 6H). Exchangeable —$NH_2$ protons were not observed.<br>LCMS Method F: m/z 473 (M + H)$^+$ (ES+), at 1.35 min, UV active |
| 2-30 | 5-amino-8-(2,6-dimethyl-4-pyridyl)-7-phenyl-2-[2- | Intermediate: 7 & 123<br>Route ad |

TABLE 3-continued

| Data for Examples 1-1 to 3-10 | | |
|---|---|---|
| Ex. | Name | Details |
| | (trifluoromethoxy)ethyl]-[1,2,4]triazolo[4,3-c]pyrimidin-3-one | $^1$H NMR: (MHz, DMSO-d6) δ: 7.86 (s, 2H), 7.33-7.24 (m, 5H), 6.82 (s, 2H), 4.36 (t, J = 5.2 Hz, 2H), 4.13 (t, J = 5.2 Hz, 2H), 2.29 (s, 6H).<br>LCMS Method A: m/z 445 $(M + H)^+$ $(ES^+)$, at 2.60 min, UV active |
| 2-31 | 3-[5-amino-8-(2,6-dimethyl-4-pyridyl)-3-oxo-7-phenyl-[1,2,4]triazolo[4,3-c]pyrimidin-2-yl]propanamide | Route ag<br>$^1$H NMR: (MHz, DMSO-d6) δ: 7.41 (m, 2H), 7.29 (s, 1H), 7.27-7.26 (m, 5H), 6.88 (s, 1H), 6.82-6.79 (m, 2H), 3.98-3.94 (m, 2H), 2.33 (s, 6H). 2 protons under DMSO peak<br>LCMS Method A: m/z 404 $(M + H)^+$ $(ES^+)$, at 1.93 min, UV active |
| 2-32 | 5-amino-8-(2,6-dimethyl-4-pyridyl)-7-(2,3,4,5,6-pentadeuteriophenyl)-2-(3,3,3-trifluoropropyl)-[1,2,4]triazolo[4,3-c]pyrimidin-3-one | Intermediate: 125 & 126 (step 1), 48 (step 2)<br>Route b<br>$^1$H NMR: (MHz, DMSO-d6) δ: 6.83 (s, 2H), 4.05 (t, J = 6.8 Hz, 2H), 2.74 (t, J = 6.8 Hz, 2H), 2.50 (s, 6H).<br>Exchangeable $NH_2$— protons were not observed.<br>LCMS Method A: m/z 434 $(M + H)^+$ $(ES^+)$, at 2.86 min, UV active |
| 2-33 | 5-amino-8-(2,6-dimethyl-4-pyridyl)-7-(4-fluorophenyl)-2-(3,3,3-trifluoropropyl)-[1,2,4]triazolo[4,3-c]pyrimidin-3-one | Intermediate: 41 & 126 (step 1), 3 (step 2)<br>Route b<br>$^1$H NMR: (MHz, DMSO-d6) δ: 7.32-7.31 (m, 2H), 7.13-7.11 (m, 2H), 6.84 (s, 2H), 4.07-4.05 (m, 2H), 2.77-2.75 (m, 2H), 2.32 (s, 6H). Exchangeable $NH_2$— protons were not observed.<br>LCMS Method A: m/z 447 $(M + H)^+$ $(ES^+)$, at 3.04 min, UV active |
| 2-34 | 5-amino-7-(2,4-difluorophenyl)-8-(2,6-dimethyl-4-pyridyl)-2-(3,3,3-trifluoropropyl)-[1,2,4]triazolo[4,3-c]pyrimidin-3-one | Intermediate: 127 & 126 (step 1), 3 (step 2)<br>Route b<br>$^1$H NMR: (MHz, DMSO-d6) δ: 8.48-8.45 (m, 2H), 7.43 (d, J = 7.0 Hz, 1H), 7.39-7.37 (m, 2H), 7.12-7.10 (m, 2H), 4.07-4.04 (m, 2H), 2.73-2.72 (m, 2H), 2.33 (s, 6H).<br>LCMS Method A: m/z 465 $(M + H)^+$ $(ES^+)$, at 3.07 min, UV active |
| 2-35 | 5-amino-8-(2,6-dimethyl-4-pyridyl)-7-(4-methoxyphenyl)-2-(3,3,3-trifluoropropyl)-[1,2,4]triazolo[4,3-c]pyrimidin-3-one | Intermediate: 125 & 126 (step 1), 129 (step 2)<br>Route b (Step 2 using $K_3PO_4$ and $[PdCl_2(amphos)]$)<br>$^1$H NMR: (MHz, DMSO-d6) δ: 7.22 (d, J = 4.8 Hz, 2H), 6.85 (s, 2H), 6.81 (d, J = 4.8 Hz, 2H), 4.03 (t, J = 6.4 Hz, 2H), 3.73 (s, 3H), 2.71 (t, J = 6.4 Hz, 2H), 2.34 (s, 6H).<br>Exchangeable —$NH_2$ protons were not observed.<br>LCMS Method A: m/z 459 $(M + H)^+$ $(ES^+)$, at 2.98 min, UV active |
| 2-36 | 4-[5-amino-8-(2,6-dimethyl-4-pyridyl)-3-oxo-2-(3,3,3-trifluoropropyl)-[1,2,4]triazolo[4,3-c]pyrimidin-7-yl]benzonitrile | Intermediate: 125 & 126 (step 1), 130 (step 2)<br>Route b (Step 2 using $K_3PO_4$ and $[PdCl_2(amphos)]$)<br>$^1$H NMR: (MHz, DMSO-d6) δ: 8.47 (s, 2H), 7.76 (d, J = 1.6 Hz, 2H), 7.44 (d, J = 1.6 Hz, 2H), 6.84 (s, 2H), 4.06 (t, J = 6.8 Hz, 2H), 2.75-2.72 (m, 2H), 2.31(s, 6H).<br>LCMS Method A: m/z 454 $(M + H)^+$ $(ES^+)$, at 2.80 min, UV active |
| 2-37 | 5-amino-8-(2,6-dimethyl-4-pyridyl)-7-(2-pyridyl)-2-(3,3,3-trifluoropropyl)-[1,2,4]triazolo[4,3-c]pyrimidin-3-one | Route ah<br>$^1$H NMR: (MHz, DMSO-d6) δ: 8.35 (d, J = 4.8 Hz, 1H), 7.81-7.78 (m, 1H), 7.53 (d, J = 8.0 Hz, 1H), 7.32-7.30 (m, 1H), 6.75 (s, 2H), 4.07 (t, J = 6.8 Hz, 2H), 2.70-2.68 (m, 2H), 2.28 (s, 6H). Exchangeable —$NH_2$ Protons were not observed.<br>LCMS Method A: m/z 430 $(M + H)^+$ $(ES^+)$, at 2.10 min, UV active |
| 2-38 | 5-amino-8-(2,6-dimethyl-4-pyridyl)-7-(4-pyridyl)-2-(3,3,3-trifluoropropyl)-[1,2,4]triazolo[4,3-c]pyrimidin-3-one | Intermediate: 133 (step 2)<br>Route ah<br>$^1$H NMR: (MHz, DMSO-d6) δ: 8.48 (d, J = 6.0 Hz, 2H), 7.90 (s, 1H), 7.23-7.21 (m, 1H), 6.86 (s, 2H), 4.06 (t, J = 6.8 Hz, 2H), 2.71 (t, J = 6.8 Hz, 2H), 2.51 (s, 6H).<br>Exchangeable —$NH_2$ Protons were not observed.<br>LCMS Method A: m/z 430 $(M + H)^+$ $(ES^+)$, at 1.97 min, UV active |
| 2-39 | 5-amino-8-(2,6-dimethyl-4-pyridyl)-7-(3-pyridyl)-2-(3,3,3-trifluoropropyl)-[1,2,4]triazolo[4,3-c]pyrimidin-3-one | Intermediate: 134 (step 2)<br>Route ah<br>$^1$H NMR: (MHz, DMSO-d6) δ: 8.46 (s, 1H), 8.40 (s, 1H), 7.67-7.68 (m, 1H), 7.34-7.32 (m, 1H), 7.30 (s, 1H), 6.86 (s, 1H), 4.06 (t, J = 6.8 Hz, 2H), 2.51 (t, J = 6.8 Hz, 2H), 2.50 (s, 6H). Exchangeable —$NH_2$ Protons were not observed.<br>LCMS Method A: m/z 430 $(M + H)^+$ $(ES^+)$, at 2.00 min, UV active |
| 2-40 | 5-amino-8-(2,6-dimethyl-4-pyridyl)-7-(5-fluoro-2-pyridyl)-2-(3,3,3-trifluoropropyl)-[1,2,4]triazolo[4,3-c]pyrimidin-3- | Intermediate: 135 (step 2)<br>Route ah<br>$^1$H NMR: (MHz, DMSO-d6) δ: 8.35 (d, J = 2.8 Hz, 1H), 7.77-7.75 (m, 1H), 7.66 (d, J = 4.4 Hz, 1H), 6.79 (s, 2H), |

TABLE 3-continued

| Ex. | Name | Details |
|---|---|---|
| | Data for Examples 1-1 to 3-10 | |
| | one | 4.06 (t, J = 6.8 Hz, 2H), 2.51 (t, J = 6.8 Hz, 2H), 2.30 (s, 6H). Exchangeable —$NH_2$ Protons were not observed. LCMS Method A: m/z 448 $(M + H)^+$ $(ES^+)$, at 2.54 min, UV active |
| 2-41 | 5-amino-8-(2,6-dimethyl-4-pyridyl)-7-(4-methylpyrazol-1-yl)-2-(3,3,3-trifluoropropyl)-[1,2,4]triazolo[4,3-c]pyrimidin-3-one | Route ai $^1H$ NMR: (MHz, DMSO-d6) δ: 8.65 (s, 1H), 7.82 (s, 1H), 7.33 (s, 1H), 6.73 (s, 2H), 4.03 (t, J = 6.8 Hz, 2H), 2.71 (t, J = 6.8 Hz, 2H), 2.34 (s, 6H), 2.03 (s, 3H). Exchangeable —NH Proton was not observed. LCMS Method A: m/z 433 $(M + H)^+$ $(ES^+)$, at 2.76 min, UV active |
| 2-42 | 5-amino-8-(2,6-dimethyl-4-pyridyl)-7-(2-furyl)-2-(3,3,3-trifluoropropyl)-[1,2,4]triazolo[4,3-c]pyrimidin-3-one | Intermediate: 136 (step 2) Route ah $^1H$ NMR: (MHz, DMSO-d6) δ: 7.58 (s, 1H), 6.95 (s, 2H), 6.51-6.50 (m, 2H), 4.01 (t, J = 6.7 Hz, 2H), 2.68 (t, J = 6.7 Hz, 2H), 2.51 (s, 6H). Exchangeable —$NH_2$ Protons were not observed. LCMS Method A: m/z 419 $(M + H)^+$ $(ES^+)$, at 2.72 min, UV active |
| 2-43 | 5-amino-8-(2,6-dimethyl-4-pyridyl)-7-(5-methyl-2-furyl)-2-(3,3,3-trifluoropropyl)-[1,2,4]triazolo[4,3-c]pyrimidin-3-one | Intermediate: 137 (step 2) Route ah $^1H$ NMR: (MHz, DMSO-d6) δ: 7.77 (s, 2H), 6.97 (s, 2H), 6.34 (d, J = 3.2 Hz, 1H), 6.11 (d, J = 3.2 Hz, 1H), 4.01 (t, J = 6.8 Hz, 2H), 2.71 (t, J = 6.8 Hz, 2H), 2.51 (s, 6H), 2.34 (s, 3H). LCMS Method A: m/z 433 $(M + H)^+$ $(ES^+)$, at 2.94 min, UV active |
| 2-44 | 5-amino-8-(2,6-dimethyl-4-pyridyl)-7-(4-methylthiazol-2-yl)-2-(3,3,3-trifluoropropyl)-[1,2,4]triazolo[4,3-c]pyrimidin-3-one | Intermediate: 138 (step 2) Route ah $^1H$ NMR: (MHz, DMSO-d6) δ: 7.33 (s, 1H), 6.95 (s, 2H), 4.03 (t, J = 6.4 Hz, 2H), 2.68 (d, J = 6.4 Hz, 2H), 2.50 (s, 6H), 2.11 (s, 3H). Exchangeable —$NH_2$ protons were not observed. LCMS Method A: m/z 450 $(M + H)^+$ $(ES^+)$, at 2.91 min, UV active |
| 2-45 | 5-amino-8-[2-chloro-6-(hydroxymethyl)-4-pyridyl]-7-phenyl-2-(3,3,3-trifluoropropyl)-[1,2,4]triazolo[4,3-c]pyrimidin-3-one | Intermediate: 1 & 126 (step 1), 61 (step 2) Route p $^1H$ NMR: (MHz, DMSO-d6) δ: 8.86-7.80 (s, 2H), 7.31-7.27 (m, 6H), 7.05 (s, 1H), 5.45 (d, J = 4.6 Hz, 1H), 4.42 (d, J = 4.6 Hz, 2H), 4.05 (m, 2H), 2.67 (m, 2H). LCMS Method C: m/z 465 $(M + H)^+$ $(ES^+)$, at 1.97 min, UV active |
| 2-46 | 5-amino-8-[2-(hydroxymethyl)-6-methoxy-4-pyridyl]-7-phenyl-2-(3,3,3-trifluoropropyl)-[1,2,4]triazolo[4,3-c]pyrimidin-3-one | Intermediate: 1 & 126 (step 1), 57 (step 2) Route p $^1H$ NMR: (MHz, DMSO-d6) δ:7.28-7.23 (m, 5H), 6.87 (s, 1H), 6.45 (s, 1H), 5.25-5.22 (m, 1H), 4.37-4.36 (d, J = 3.5 Hz, 2H), 4.05-4.02 (m, 2H), 3.75 (s, 3H), 2.75 (m, 2H). Exchangeable —$NH_2$ protons were not observed. LCMS Method C: m/z 461 $(M + H)^+$ $(ES^+)$, at 1.93 min, UV active |
| 2-47 | 5-amino-7-(4-fluorophenyl)-8-[2-(hydroxymethyl)-6-methoxy-4-pyridyl]-2-(3,3,3-trifluoropropyl)-[1,2,4]triazolo[4,3-c]pyrimidin-3-one | Intermediate: 41 & 126 (step 1), 57 (step 2) Route p $^1H$ NMR: (MHz, DMSO-d6) δ: 7.35-7.32 (m, 2H), 7.12 (t, J = 8.8 Hz, 2H), 6.83 (s, 1H), 6.51 (s, 1H), 5.25 (t, J = 5.8 Hz, 1H), 4.38 (d, J = 5.6 Hz, 2H), 4.05 (t, J = 5.8 Hz, 2H), 3.78 (s, 3H), 2.76-2.68 (m, 2H). Exchangeable —$NH_2$ protons were not observed. LCMS Method C: m/z 479 $(M + H)^+$ $(ES^+)$, at 1.96 min, UV active |
| 2-48 | 5-amino-8-(2-chloro-6-methyl-4-pyridyl)-7-phenyl-2-(3,3,3-trifluoropropyl)-[1,2,4]triazolo[4,3-c]pyrimidin-3-one | Intermediate: 1 & 126 (step 1), 139 (step 2) Route b (Step 2 using $K_3PO_4$and [$PdCl_2$(amphos)], and purified by Prep HPLC (Method A), the fractions were concentrated and the residue was diluted with EtOAc (10 mL) and washed with 10% sodium bicarbonate solution (10 mL). The organic layer was separated, dried over anhydrous $Na_2SO_4$) $^1H$ NMR: (MHz, DMSO-d6) δ: 8.56 (s, 1H), 7.80 (s, 1H), 7.30 (s, 5H), 7.04 (d, J = 5.6 Hz, 2H), 4.06 (t, J = 6.4 Hz, 2H), 2.79-2.66 (m, 2H), 2.32 (s, 3H). LCMS Method A: m/z 449 $(M + H)^+$ $(ES^+)$, at 4.61 min, UV active |
| 2-49 | 5-amino-8-(2-chloro-6-methyl-4-pyridyl)-7-(4-fluorophenyl)-2-methyl-[1,2,4]triazolo[4,3-c]pyrimidin-3-one | Intermediate: 41 & 100 (step 1), 139 (step2) Route a (Step 2 using $K_3PO_4$ and [$PdCl_2$(amphos)]) $^1H$ NMR: (MHz, DMSO-d6) δ: 8.52-7.76 (m, 2H), 7.33-7.30 (m, 2H), 7.16-7.12 (m, 2H), 7.06-7.03 (m, 2H), 3.42 (s, 3H), 2.33 (s, 3H). |

TABLE 3-continued

| Ex. | Name | Details |
|---|---|---|
| Data for Examples 1-1 to 3-10 | | |
| | | LCMS Method A: m/z 385 $(M + H)^+$ $(ES^+)$, at 3.82 min, UV active |
| 2-50 | 5-amino-8-(2-chloro-6-methyl-4-pyridyl)-7-(4-fluorophenyl)-2-(3,3,3-trifluoropropyl)-[1,2,4]triazolo[4,3-c]pyrimidin-3-one | Intermediate: 41 & 126 (step 1), 139 (step 2)<br>Route b (Step 2 using $K_3PO_4$and [$PdCl_2$(amphos)], and purified by Prep HPLC (Method A), fractions were concentrated and the residue was diluted with EtOAc (10 mL) and washed with 10% sodium bicarbonate solution (10 mL). The organic layer was separated, dried over anhydrous $Na_2SO_4$)<br>$^1$H NMR: (MHz, DMSO-d6) δ: 8.51 (s, 2H), 7.33-7.32 (m, 2H), 7.17-7.15 (m, 2H), 7.05 (d, J = 4.0 Hz, 2H), 4.08-4.06 (m, 2H), 2.67-2.65 (m, 2H), 2.35 (S, 3H).<br>LCMS Method A: m/z 467 $(M + H)^+$ $(ES^+)$, at 4.88 min, UV active |
| 2-51 | 5-amino-8-[2-(hydroxymethyl)-6-methyl-4-pyridyl]-7-phenyl-2-(3,3,3-trifluoropropyl)-[1,2,4]triazolo[4,3-c]pyrimidin-3-one | Route aj<br>$^1$H NMR: (MHz, DMSO-d6) δ: 7.32-7.19 (m, 5H), 7.15-7.09 (m, 1H), 6.89-6.79 (m, 1H), 5.26 (t, J = 5.9 Hz, 1H), 4.43 (d, J = 5.9 Hz, 2H), 4.11-3.99 (m, 2H), 2.84-2.63 (m, 2H), 2.31 (s, 3H).Exchangeable —$NH_2$ protons were not observed.<br>LCMS Method A: m/z 445 $(M + H)^+$ $(ES^+)$, at 3.66 min, UV active |
| 2-52 | methyl 4-[5-amino-3-oxo-7-phenyl-2-(3,3,3-trifluoropropyl)-[1,2,4]triazolo[4,3-c]pyrimidin-8-yl]-6-methyl-pyridine-2-carboxylate | Intermediate: 1 & 126 (step 1), 42 (step 2)<br>Route b<br>$^1$H NMR: (MHz, DMSO-d6) δ: 7.67 (s, 1H), 7.30-7.26 (m, 6H), 4.06 (t, J = 6.5 Hz, 2H), 3.81 (s, 3H), 2.76-2.73 (m, 2H), 2.41 (s, 3H). Exchangeable —$NH_2$ protons were not observed.<br>LCMS Method A: m/z 473 $(M + H)^+$ $(ES^+)$, at 3.52 min, UV active |
| 2-53 | 5-amino-8-[2-(hydroxymethyl)-6-(trifluoromethyl)-4-pyridyl]-7-phenyl-2-(3,3,3-trifluoropropyl)-[1,2,4]triazolo[4,3-c]pyrimidin-3-one | Intermediate: 1 & 126 (step 1), 140 (step 2)<br>Route p<br>$^1$H NMR: (MHz, DMSO-d6) δ: 7.73 (s, 1H), 7.32-7.29 (m, 6H), 5.56 (t, J = 5.7 Hz, 1H), 4.55 (d, J = 5.7 Hz, 2H), 4.07 (t, J = 6.6 Hz, 2H), 2.73 (t, J = 6.6 Hz, 2H). Exchangeable —$NH_2$ protons were not observed.<br>LCMS Method C: m/z 499 $(M + H)^+$ $(ES^+)$, at 2.14 min, UV active |
| 2-54 | tert-butyl 3-[5-amino-8-(2,6-dimethyl-4-pyridyl)-3-oxo-7-phenyl-[1,2,4]triazolo[4,3-c]pyrimidin-2-yl]piperidine-1-carboxylate | Intermediate: 1 and 142 (step 1), 3 (step 2)<br>Route c<br>$^1$H NMR: (MHz, DMSO-d6) δ: 7.29-7.24 (m, 5H), 6.83 (s, 2H), 4.23-4.06 (m, 3H), 3.23 (br s, 1H), 2.81 (t, J = 11.6 Hz, 1H), 2.61 (s, 6H), 2.03-1.87 (m, 3H), 1.57-1.54 (m, 1H), 1.29 (s, 9H).<br>LCMS Method A: m/z 516 $(M + H)^+$ $(ES^+)$, at 3.62 min, UV active |
| 2-55 | 5-amino-8-(2,6-dimethyl-4-pyridyl)-7-phenyl-2-(3-piperidyl)-[1,2,4]triazolo[4,3-c]pyrimidin-3-one | Route ak<br>$^1$H NMR: (MHz, DMSO-d6) δ: 7.33-7.26 (m, 5H), 6.95 (s, 2H), 4.24 (br s, 1H), 3.15-3.11 (m, 1H), 3.00-2.94 (m, 2H), 2.63-2.59 (m, 1H), 2.38 (s, 6H), 2.02 (d, J = 3.6 Hz, 2H), 1.87-1.84 (m, 1H), 1.65 (br s, 1H). Exchangeable —NH, —$NH_2$ protons were not observed<br>LCMS Method A: m/z 416 $(M + H)^+$ $(ES^+)$, at 2.04 min, UV active |
| 2-56 | 5-amino-8-(2,6-dimethyl-1-oxido-pyridin-1-ium-4-yl)-7-phenyl-2-(3,3,3-trifluoropropyl)-[1,2,4]triazolo[4,3-c]pyrimidin-3-one | Route al<br>$^1$H NMR: (MHz, DMSO-d6) δ: 7.32-7.30 (m, 5H), 7.13 (s, 2H), 4.08-4.05 (m, 2H), 2.78-2.75 (m, 2H), 2.25 (s, 6H). Exchangeable —$NH_2$ Protons were not observed.<br>LCMS Method C: m/z 445 $(M + H)^+$ $(ES^+)$, at 1.62 min, UV active |
| 2-57 | 5-amino-8-(2,6-dimethyl-1-oxido-pyridin-1-ium-4-yl)-2-isobutyl-7-phenyl-[1,2,4]triazolo[4,3-c]pyrimidin-3-one | Intermediate: Example 2-21<br>Route al<br>$^1$H NMR: (MHz, DMSO-d6) δ: 7.33-7.30 (m, 5H), 7.11 (s, 2H), 3.60 (d, J = 8.0 Hz, 2H), 2.24 (s, 6H), 2.09-2.02 (m, 1H), 0.89 (d, J = 8.0 Hz, 6H). Exchangeable —$NH_2$ Protons were not observed.<br>LCMS Method C: m/z 405 $(M + H)^+$ $(ES^+)$, at 1.62 min, UV active |
| 2-58 | 5-amino-8-(2,6-dimethyl-1-oxido-pyridin-1-ium-4-yl)-7-(4-fluorophenyl)-2-(3,3,3-trifluoropropyl)-[1,2,4]triazolo[4,3-c]pyrimidin-3-one | Intermediate: Example 2-33<br>Route al<br>$^1$H NMR: (MHz, DMSO-d6) δ: 7.39-7.36 (m, 2H), 7.18-7.16 (m, 4H), 4.07 (t, J = 12.0 Hz, 2H), 2.76 (t, J = 12.0 Hz, 2H), 2.27 (s, 6H). Exchangeable —$NH_2$ Protons were not observed.<br>LCMS Method D: m/z 463 $(M + H)^+$ $(ES^+)$, at 2.08 min, UV active |

TABLE 3-continued

| Data for Examples 1-1 to 3-10 | | |
|---|---|---|
| Ex. | Name | Details |
| 2-59 | 5-amino-2-[(3-fluoro-1-bicyclo[1.1.1]pentanyl)methyl]-8-[2-(hydroxymethyl)-6-methyl-4-pyridyl]-7-phenyl-[1,2,4]triazolo[4,3-c]pyrimidin-3-one | Intermediate: 45 & 143 (step 1)<br>Route o<br>$^{1}$H NMR: (MHz, DMSO-d6) δ: 7.29-7.25 (m, 5H), 7.14 (s, 1H), 6.84 (s, 1H), 5.25-5.22 (m, 1H), 4.42 (d, J = 5.6 Hz, 2H), 4.11 (s, 2H), 2.30 (s, 3H), 2.04 (d, J = 2.4 Hz, 6H). Exchangeable —$NH_2$ Protons were not observed.<br>LCMS Method A: m/z 447 $(M + H)^+$ $(ES^+)$, at 1.67 min, UV active |
| 2-60 | 5-amino-2-[(4-fluorocuban-1-yl)methyl]-8-[2-(hydroxymethyl)-6-methyl-4-pyridyl]-7-phenyl-[1,2,4]triazolo[4,3-c]pyrimidin-3-one | Intermediate: 45 & 144 (step 1)<br>Route q (step 1 performed in DCM)<br>$^{1}$H NMR: (MHz, DMSO-d6) δ: 7.71 (s, 1H), 7.33-7.29 (m, 5H), 7.17 (s, 1H), 4.23 (d, J = 3.6 Hz, 3H), 4.04 (s, 2H), 3.81 (s, 6H), 2.36 (s, 3H). Exchangeable —$NH_2$ Protons were not observed.<br>LCMS Method A: m/z 483 $(M + H)^+$ $(ES^+)$, at 2.24 min, UV active |
| 2-61 | 5-amino-8-[2-(hydroxymethyl)-6-methyl-4-pyridyl]-7-(2,3,4,5,6-pentadeuteriophenyl)-2-(3,3,3-trifluoropropyl)-[1,2,4]triazolo[4,3-c]pyrimidin-3-one | Intermediate: 49 & 126 (step 1)<br>Route s<br>$^{1}$H NMR: (MHz, DMSO-d6) δ: 7.12 (s, 1H), 6.85 (s, 1H), 5.26 (s, 1H), 4.34 (d, J = 7.0 Hz, 2H), 4.06-4.03 (m, 2H), 3.34-3.33 (m, 1H), 3.31 (s, 1H), 2.75-2.68 (m, 2H), 2.34-2.31 (m, 2H). Exchangeable —OH proton was not observed.<br>LCMS Method C: m/z 450 $(M + H)^+$ $(ES^+)$, at 1.20 min, UV active |
| 2-62 | 5-amino-2-(cuban-1-ylmethyl)-8-[2-(hydroxymethyl)-6-methyl-4-pyridyl]-7-phenyl-[1,2,4]triazolo[4,3-c]pyrimidin-3-one | Intermediate: 45 & 145 (step 1)<br>Route q (step 1 performed in DCM)<br>$^{1}$H NMR: (MHz, DMSO-d6) δ: 7.34-7.21 (m, 5H), 7.15-7.08 (m, 1H), 6.88-6.80 (m, 1H), 5.22 (t, J = 5.6 Hz, 1H), 4.41 (d, J = 5.6 Hz, 2H), 3.99 (d, J = 3.1 Hz, 3H), 3.95-3.85 (m, 6H), 2.31-2.25 (m, 3H). Exchangeable —$NH_2$ protons were not observed.<br>LCMS Method C: m/z 465 $(M + H)^+$ $(ES^+)$, at 1.49 min, UV active |
| 2-63 | 5-amino-2-(3-bicyclo[1.1.1]pentanylmethyl)-8-[2-(hydroxymethyl)-6-methyl-4-pyridyl]-7-phenyl-[1,2,4]triazolo[4,3-c]pyrimidin-3-one | Intermediate: 45 & 146 (step 1)<br>Route q (step 1 performed in DCM)<br>$^{1}$H NMR: (MHz, DMSO-d6) δ: 7.27-7.25 (m, 5H), 7.11 (s, 1H), 6.85 (s, 1H), 5.21 (s, 1H), 4.41 (d, J = 5.6 Hz, 2H), 3.80 (s, 2H), 2.50-2.47 (m, 1H), 2.29 (s, 3H), 1.73 (s, 6H). Exchangeable —$NH_2$ protons were not observed.<br>LCMS Method C: m/z 429 $(M + H)^+$ $(ES^+)$, at 1.30 min, UV active |
| 2-64 | 5-amino-7-(4-fluorophenyl)-8-[2-(hydroxymethyl)-6-methyl-4-pyridyl]-2-(3,3,3-trifluoropropyl)-[1,2,4]triazolo[4,3-c]pyrimidin-3-one | Intermediate: 56 & 126 (step 1)<br>Route s<br>$^{1}$H NMR: (MHz, DMSO-d6) δ: 7.32-7.29 (m, 2H), 7.113-7.10 (m, 3H), 6.90 (s, 1H), 5.26 (t, J = 6.0 Hz, 1H), 4.44 (d, J = 6.0 Hz, 2H), 4.05 (t, J = 6.8 Hz, 2H), 2.75-2.67 (m, 2H), 2.34 (s, 3H). Exchangeable —NH2 protons were not observed.<br>LCMS Method C: m/z 463 $(M + H)^+$ $(ES^+)$, at 1.27 min, UV active |
| 2-65 | tert-butyl (R)-2-((5-amino-8-(2,6-dimethylpyridin-4-yl)-3-oxo-7-phenyl-[1,2,4]triazolo[4,3-c]pyrimidin-2(3H)-yl)methyl)morpholine-4-carboxylate | Intermediate: 1 & 147 (step 1), 3 (step 2)<br>Route c<br>$^{1}$H NMR: (MHz, DMSO-d6) δ: 8.23-7.89 (m, 2H), 7.27-7.25 (m, 5H), 6.83 (s, 2H), 3.94-3.79 (m, 4H), 3.66 (d, J = 12.4 Hz, 2H), 3.39-3.36 (m, 1H), 2.82-2.68 (m, 2H), 2.29 (s, 6H), 1.39 (s, 9H).<br>LCMS Method A: m/z 532 $(M + H)^+$ $(ES^+)$, at 3.33 min, UV active |
| 2-66 | (R)-5-amino-8-(2,6-dimethylpyridin-4-yl)-2-(morpholin-2-ylmethyl)-7-phenyl-[1,2,4]triazolo[4,3-c]pyrimidin-3(2H)-one | Intermediate: Example 2-65<br>Route ak<br>$^{1}$H NMR: (MHz, DMSO-d6) δ: 8.23-7.89 (m, 2H), 7.27-7.25 (m, 5H), 6.83 (s, 2H), 3.89-3.84 (m, 1H), 3.72-3.69 (m, 3H), 3.38-3.34 (m, 1H), 2.83 (d, J = 12.2 Hz, 1H), 2.68-2.61 (m, 2H), 2.45-2.34 (m, 2H), 2.30 (s, 6H).<br>LCMS Method A: m/z 432 $(M + H)^+$ $(ES^+)$, at 1.92 min, UV active |
| 2-67 | tert-butyl 4-[[5-amino-8-(2,6-dimethyl-4-pyridyl)-3-oxo-7-phenyl-[1,2,4]triazolo[4,3-c]pyrimidin-2-yl]methyl]piperidine-1-carboxylate | Intermediate: 1 & 148 (step 1), 3 (step 2)<br>Route c<br>$^{1}$H NMR: (MHz, DMSO-d6) δ: 8.02 (s, 2H), 2.51-7.26 (m, 5H), 6.81 (s, 2H), 3.91-3.89 (m, 2H), 3.70-3.66 (m, 2H), 2.33 (s, 6H), 2.29-2.26 (m, 1H), 2.61-2.52 (m, 2H), 2.33-2.32 (m, 2H), 2.29-2.25 (m, 2H), 1.39 (s, 9H).<br>LCMS Method A: m/z 530 $(M + H)^+$ $(ES^+)$, at 3.60 min, UV active |

TABLE 3-continued

| Data for Examples 1-1 to 3-10 | | |
|---|---|---|
| Ex. | Name | Details |
| 2-68 | 5-amino-8-(2,6-dimethyl-4-pyridyl)-7-phenyl-2-(4-piperidylmethyl)-[1,2,4]triazolo[4,3-c]pyrimidin-3-one | Intermediate: Example 2-67<br>Route ak<br>$^1$H NMR: (MHz, DMSO-d6) δ: 7.45 (s, 1H), 7.29-7.28 (m, 5H), 6.82 (s, 2H), 3.65-3.47 (m, 2H), 2.68-2.68 (m, 2H), 2.55-2.50 (m, 2H), 2.33 (s, 6H), 2.48-2.46 (m, 1H), 1.60-1.59 (m, 2H), 1.24-1.18 (m, 2H). Exchangeable —$NH_2$ protons were not observed<br>LCMS Method A: m/z 430 (M + H)$^+$ (ES$^+$), at 1.97 min, UV active |
| 2-69 | tert-butyl (2S)-2-[[5-amino-8-(2,6-dimethyl-4-pyridyl)-3-oxo-7-phenyl-[1,2,4]triazolo[4,3-c]pyrimidin-2-yl]methyl]morpholine-4-carboxylate | Intermediate: 1 & 149 (step 1), 3 (step 2)<br>Route c<br>$^1$H NMR: (MHz, DMSO-d6) δ: 7.80 (s, 2H), 7.28-7.27 (m, 5H), 6.83 (s, 2H), 3.95-3.90 (m, 4H), 3.86 (d, J = 4.3 Hz, 2H), 3.40-3.25 (m, 2H), 2.97-2.95 (m, 1H), 2.29 (s, 6H), 1.39 (s, 9H).<br>LCMS Method A: m/z 532 (M + H)$^+$ (ES$^+$), at 3.35 min, UV active |
| 2-70 | 5-amino-8-(2,6-dimethyl-4-pyridyl)-2-(1-methyl-3-piperidyl)-7-phenyl-[1,2,4]triazolo[4,3-c]pyrimidin-3-one | Intermediate: 1 & 150 (step 1), 3 (step 2)<br>Route c<br>$^1$H NMR: (MHz, DMSO-d6) δ: 7.31-7.26 (m, 5H), 6.82 (s, 2H), 3.86-3.84 (m, 1H), 3.71 (br s, 1H), 2.94 (br s, 1H), 2.29 (s, 10H), 2.16-2.13 (m, 1H), 1.83 (br s, 1H), 1.70-1.63 (m, 3H). Exchangeable —$NH_2$ protons not observed.<br>LCMS Method A: m/z 430 (M + H)$^+$ (ES$^+$), at 1.92 min, UV active |
| 2-71 | (S)-5-amino-8-(2,6-dimethylpyridin-4-yl)-2-(morpholin-2-ylmethyl)-7-phenyl-[1,2,4]triazolo[4,3-c]pyrimidin-3(2H)-one | Intermediate: Example 2-69<br>Route ak<br>$^1$H NMR: (MHz, DMSO-d6) δ: 8.40 (s, 2H), 7.26-7.25 (m, 5H), 7.04 (s, 2H), 3.87-3.86 (m, 1H), 3.73-3.69 (m, 3H), 3.39-3.36 (m, 1H), 2.82 (d, J = 12.4 Hz, 1H), 2.67-2.61 (m, 3H), 2.43 (t, J = 9.6 Hz, 1H), 2.30 (s, 6H).<br>LCMS Method A: m/z 432 (M + H)$^+$ (ES$^+$), at 1.94 min, UV active |
| 2-72 | 5-amino-8-(2,6-dimethyl-4-pyridyl)-2-[[(2S)-4-methylmorpholin-2-yl]methyl]-7-phenyl-[1,2,4]triazolo[4,3-c]pyrimidin-3-one | Route am<br>$^1$H NMR: (MHz, DMSO-d6) δ: 8.60 (s, 2H), 7.64-7.27 (m, 5H), 6.85 (s, 2H), 3.94-3.78 (m, 4H), 3.49-3.34 (m, 1H), 2.76-2.67 (m, 2H), 2.33 (s, 6H), 2.20 (s, 3H), 2.04-1.92 (m, 1H), 1.87-1.83 (m, 1H).<br>LCMS Method A: m/z 446 (M + H)$^+$ (ES$^+$), at 1.94 min, UV active |
| 2-73 | 5-amino-8-(2,6-dimethyl-4-pyridyl)-7-phenyl-2-(tetrahydropyran-4-ylmethyl)-[1,2,4]triazolo[4,3-c]pyrimidin-3-one | Intermediate: 1 & 151 (step 1), 3 (step 2)<br>Route c<br>$^1$H NMR: (MHz, DMSO-d6) δ : 8.60 (s, 2H), 7.30-7.25 (m, 5H), 6.82 (s, 2H), 3.83-3.81 (m, 2H), 3.68 (d, J = 7.0 Hz, 2H), 3.25 (t, J = 11.7 Hz, 2H), 2.29 (s, 6H), 1.98-1.95 (m, 1H), 1.55-1.52 (m, 2H), 1.29-1.23 (m, 2H).<br>LCMS Method A: m/z 431 (M + H)$^+$ (ES$^+$), at 2.46 min, UV active |
| 2-74 | 5-amino-8-(2,6-dimethyl-4-pyridyl)-2-[[(2R)-4-methylmorpholin-2-yl]methyl]-7-phenyl-[1,2,4]triazolo[4,3-c]pyrimidin-3-one | Intermediate: Example 2-66<br>Route am (purification by trituration with methanol)<br>$^1$H NMR: (MHz, DMSO-d6) δ: 7.29-7.25 (m, 5H), 6.82 (s, 2H), 3.93-3.86 (m, 1H), 3.78-3.75 (m, 3H), 3.45 (t, J = 12.0 Hz, 1H), 2.74-2.71 (m, 1H), 2.55-2.55 (m, 1H), 2.29 (s, 6H), 2.17 (s, 3H), 2.05-1.98 (m, 1H), 1.84 (br s, 1H). Exchangeable —$NH_2$ protons were not observed.<br>LCMS Method A: m/z 446 (M + H)$^+$ (ES$^+$), at 1.93 min, UV active |
| 2-75 | tert-butyl (3S)-3-[[5-amino-8-(2,6-dimethyl-4-pyridyl)-3-oxo-7-phenyl-[1,2,4]triazolo[4,3-c]pyrimidin-2-yl]methyl]morpholine-4-carboxylate | Intermediate: 1 & 152 (step 1), 3 (step 2)<br>Route c<br>$^1$H NMR: (MHz, DMSO-d6) δ: 7.27-7.19 (m, 5H), 6.83 (s, 2H), 4.31 (br s, 1H), 4.15-4.12 (m, 1H), 4.06-4.02 (m, 1H), 3.90-3.66 (m, 3H), 3.52-3.47 (m, 1H), 3.41-3.37 (m, 2H), 2.28 (s, 6H), 1.28-1.18 (m, 9H). Exchangeable —$NH_2$ protons were not observed.<br>LCMS Method A: m/z 532 (M + H)$^+$ (ES$^+$), at 3.11 min, UV active |
| 2-76 | 5-amino-8-(2,6-dimethyl-4-pyridyl)-2-[[(3S)-morpholin-3-yl]methyl]-7-phenyl-[1,2,4]triazolo[4,3-c]pyrimidin-3-one | Intermediate: Example 2-75<br>Route ak<br>$^1$H NMR: (MHz, DMSO-d6) δ: 8.23 (s, 2H), 7.28-7.25 (m, 5H), 6.82 (s, 2H), 3.81-3.76 (m, 1H), 3.72-3.59 (m, 3H), 3.45-3.34 (m, 1H), 3.25-3.16 (m, 1H), 3.07-2.96 (m, 1H), 2.84-2.73 (m, 1H), 2.66-2.63 (m, 1H), 2.29 (s, 6H). Exchangeable —NH proton was not observed.<br>LCMS Method A: m/z 432 (M + H)$^+$ (ES$^+$), at 1.91 min, UV active |

TABLE 3-continued

| Data for Examples 1-1 to 3-10 | | |
|---|---|---|
| Ex. | Name | Details |
| 2-77 | 5-amino-8-(2,6-dimethyl-4-pyridyl)-2-[[(3S)-4-methylmorpholin-3-yl]methyl]-7-phenyl-[1,2,4]triazolo[4,3-c]pyrimidin-3-one | Intermediate: Example 2-76<br>Route am (purification by trituration with methanol)<br>$^1$H NMR: (MHz, DMSO-d6) δ: 8.23-7.70 (m, 2H), 7.29-7.25 (m, 5H), 6.82 (s, 2H), 3.96-3.91 (m, 1H), 3.79-3.76 (m, 1H), 3.68-3.63 (m, 2H), 3.49-3.44 (m, 1H), 3.36-3.34 (m, 1H), 2.66 (d, J = 12.0 Hz, 1H), 2.42 (t, J = 8.0 Hz, 1H), 2.31 (s, 3H), 2.28 (s, 6H), 2.23-2.17 (m, 1H).<br>LCMS Method A: m/z 446 $(M + H)^+$ $(ES^+)$, at 1.92 min, UV active |
| 2-78 | 5-amino-8-(2,6-dimethyl-4-pyridyl)-2-[(1-methyl-4-piperidyl)methyl]-7-phenyl-[1,2,4]triazolo[4,3-c]pyrimidin-3-one | Intermediate: Example 2-68<br>Route am<br>$^1$H NMR: (MHz, DMSO-d6) δ: 8.20 (s, 2H), 7.27-7.24 (m, 5H), 6.82 (s, 2H), 3.66 (d, J = 6.8 Hz, 2H), 2.73-2.70 (m, 2H), 2.29 (s, 6H), 2.12 (s, 3H), 1.82-1.76 (m, 2H), 1.68-1.60 (m, 1H), 1.59-1.56 (m, 2H), 1.24-1.20 (m, 2H).<br>LCMS Method A: m/z 444 $(M + H)^+$ $(ES^+)$, at 1.96 min, UV active |
| 2-79 | (R)-5-amino-8-(2,6-dimethylpyridin-4-yl)-2-(morpholin-3-ylmethyl)-7-phenyl-[1,2,4]triazolo[4,3-c]pyrimidin-3(2H)-one | Route an<br>$^1$H NMR: (MHz, DMSO-d6) δ: 8.25 (s, 2H), 7.29-7.26 (m, 5H), 6.82 (s, 2H), 3.78-3.76 (m, 1H), 3.72-3.69 (m, 3H), 3.40-3.38 (m, 1H), 3.21-3.12 (m, 1H), 3.09 (s, 1H), 2.79-2.71 (m, 1H), 2.68-2.58 (m, 1H), 2.30 (s, 6H).<br>Exchangeable —NH proton was not observed.<br>LCMS Method A: m/z 432 $(M + H)^+$ $(ES^+)$, at 2.04 min, UV active |
| 2-80 | 5-amino-8-(2,6-dimethyl-4-pyridyl)-2-[[(3R)-4-methylmorpholin-3-yl]methyl]-7-phenyl-[1,2,4]triazolo[4,3-c]pyrimidin-3-one | Intermediate: Example 2-79<br>Route am (Purification by prep HPLC (Method A))<br>$^1$H NMR: (MHz, DMSO-d6) δ: 8.23-7.70 (m, 2H), 7.30-7.27 (m, 5H), 6.82 (s, 2H), 3.97-3.92 (m, 1H), 3.79-3.75 (m, 1H), 3.69-3.64 (m, 2H), 3.50-3.45 (m, 1H), 2.66 (d, J = 12.0 Hz, 1H), 2.42-2.35 (m, 2H), 2.29 (s, 9H), 2.23-2.08 (m, 1H).<br>LCMS Method A: m/z 446 $(M + H)^+$ $(ES^+)$, at 1.89 min, UV active |
| 2-81 | 5-amino-8-(2,6-dimethyl-4-pyridyl)-7-phenyl-2-(tetrahydropyran-3-ylmethyl)-[1,2,4]triazolo[4,3-c]pyrimidin-3-one | Route ao<br>$^1$H NMR: (MHz, DMSO-d6) δ: 7.30-7.26 (m, 5H), 6.86 (s, 2H), 3.74-3.67 (m, 4H), 3.18 (d, J = 8.8 Hz, 1H), 2.68 (d, J = 3.6 Hz, 1H), 2.50-2.33 (m, 6H), 1.98 (s, 1H), 1.72 (d, J = 4.4 Hz, 1H), 1.61-1.59 (m, 1H), 1.47-1.43 (m, 1H), 1.33-1.24 (m, 1H). Exchangeable —$NH_2$ Protons were not observed.<br>LCMS Method A: m/z 431 $(M + H)^+$ $(ES^+)$, at 1.93 min, UV active |
| 2-81 iso-1 | 5-amino-8-(2,6-dimethyl-4-pyridyl)-7-phenyl-2-(tetrahydropyran-3-ylmethyl)-[1,2,4]triazolo[4,3-c]pyrimidin-3-one | Route ao<br>$^1$H NMR: (MHz, DMSO-d6) δ: 7.30-7.26 (m, 5H), 6.86 (s, 2H), 3.74-3.67 (m, 4H), 3.18 (d, J = 8.8 Hz, 1H), 2.68 (d, J = 3.6 Hz, 1H), 2.50-2.33 (m, 6H), 1.98 (s, 1H), 1.72 (d, J = 4.4 Hz, 1H), 1.61-1.59 (m, 1H), 1.47-1.43 (m, 1H), 1.33-1.24 (m, 1H). Exchangeable —$NH_2$ Protons were not observed.<br>LCMS Method A: m/z 431 $(M + H)^+$ $(ES^+)$, at 1.93 min, UV active |
| 2-81 iso-2 | 5-amino-8-(2,6-dimethyl-4-pyridyl)-7-phenyl-2-(tetrahydropyran-3-ylmethyl)-[1,2,4]triazolo[4,3-c]pyrimidin-3-one | Route ao<br>$^1$H NMR: (MHz, DMSO-d6) δ: 7.30-7.26 (m, 5H), 6.86 (s, 2H), 3.74-3.67 (m, 4H), 3.18 (d, J = 8.8 Hz, 1H), 2.68 (d, J = 3.6 Hz, 1H), 2.50-2.33 (m, 6H), 1.98 (s, 1H), 1.72 (d, J = 4.4 Hz, 1H), 1.61-1.59 (m, 1H), 1.47-1.43 (m, 1H), 1.33-1.24 (m, 1H). Exchangeable —$NH_2$ Protons were not observed.<br>LCMS Method A: m/z 431 $(M + H)^+$ $(ES^+)$, at 1.93 min, UV active |
| 2-82 | 5-amino-8-(2,6-dimethyl-4-pyridyl)-7-phenyl-2-(tetrahydropyran-2-ylmethyl)-[1,2,4]triazolo[4,3-c]pyrimidin-3-one | Intermediate: 155<br>Route ao<br>$^1$H NMR: (MHz, DMSO-d6) δ: 8.06 (s, 2H), 7.28-7.25 (m, 5H), 6.82 (s, 2H), 3.87-3.81 (m, 2H), 3.72-3.67 (m, 1H), 3.62 (d, J = 8.8 Hz, 1H), 3.33 (s, 1H), 2.51-2.46 (m, 6H), 2.34 (s, 1H), 2.33 (d, J = 2.0 Hz, 1H), 2.30-2.08 (m, 3H), 1.76 (s, 1H).<br>LCMS Method B: m/z 431 $(M + H)^+$ $(ES^+)$, at 2.02 min, UV active |
| 2-82 iso-1 | 5-amino-8-(2,6-dimethyl-4-pyridyl)-7-phenyl-2-(tetrahydropyran-2-ylmethyl)-[1,2,4]triazolo[4,3-c]pyrimidin-3-one | Intermediate: 155<br>Route ao (First eluting peak from chiral SFC separation (method E))<br>$^1$H NMR: (MHz, DMSO-d6) δ: 8.06 (s, 2H), 7.28-7.25 (m, 5H), 6.82 (s, 2H), 3.87-3.81 (m, 2H), 3.72-3.67 (m, 1H), 3.62 (d, J = 8.8 Hz, 1H), 3.33 (s, 1H), 2.51-2.46 (m, 6H), |

TABLE 3-continued

| Data for Examples 1-1 to 3-10 | | |
|---|---|---|
| Ex. | Name | Details |
| | | 2.34 (s, 1H), 2.33 (d, J = 2.0 Hz, 1H), 2.30-2.08 (m, 3H), 1.76 (s, 1H).<br>LCMS Method B: m/z 431 $(M + H)^+$ $(ES^+)$, at 2.02 min, UV active |
| 2-82 iso-2 | 5-amino-8-(2,6-dimethyl-4-pyridyl)-7-phenyl-2-(tetrahydropyran-2-ylmethyl)-[1,2,4]triazolo[4,3-c]pyrimidin-3-one | Intermediate: 155<br>Route ao (Second eluting peak from chiral SFC separation (method E))<br>$^1H$ NMR: (MHz, DMSO-d6) δ: 8.06 (s, 2H), 7.28-7.25 (m, 5H), 6.82 (s, 2H), 3.87-3.81 (m, 2H), 3.72-3.67 (m, 1H), 3.62 (d, J = 8.8 Hz, 1H), 3.33 (s, 1H), 2.51-2.46 (m, 6H), 2.34 (s, 1H), 2.33 (d, J = 2.0 Hz, 1H), 2.30-2.08 (m, 3H), 1.76 (s, 1H).<br>LCMS Method B: m/z 431 $(M + H)^+$ $(ES^+)$, at 2.02 min, UV active |
| 2-83 | tert-butyl (S)-3-((5-amino-8-(2,6-dimethylpyridin-4-yl)-3-oxo-7-phenyl-[1,2,4]triazolo[4,3-c]pyrimidin-2(3H)-yl)methyl)-4-methylpiperazine-1-carboxylate | Intermediate: 156<br>Route d (Purified by Prep HPLC (Method A), the fractions were concentrated and the residue was diluted with EtOAc (10 mL) and washed with 10% sodium bicarbonate solution (10 mL). The organic layer was separated, dried over anhydrous $Na_2SO_4$)<br>$^1H$ NMR: (MHz, DMSO-d6) δ: 7.87 (s, 2H), 7.29-7.27 (m, 5H), 6.83 (s, 2H), 3.92-3.98 (m, 1H), 3.74-3.79 (m, 1H), 3.69-3.55 (m, 2H), 3.01-3.03 (m, 2H), 2.73-2.70 (m, 1H), 2.68-2.67 (m, 1H), 2.25 (s, 9H), 2.09-2.11 (m, 1H), 1.40 (s, 9H).<br>LCMS Method A: m/z 545 $(M + H)^+$ $(ES^+)$, at 2.60 min, UV active |
| 2-84 | tert-butyl (R)-3-((5-amino-8-(2,6-dimethylpyridin-4-yl)-3-oxo-7-phenyl-[1,2,4]triazolo[4,3-c]pyrimidin-2(3H)-yl)methyl)-4-methylpiperazine-1-carboxylate | Intermediate: 157<br>Route d (Purified by Prep HPLC (Method A), the fractions were concentrated and the residue was diluted with EtOAc (10 mL) and washed with 10% sodium bicarbonate solution (10 mL). The organic layer was separated, dried over anhydrous $Na_2SO_4$)<br>$^1H$ NMR: (MHz, DMSO-d6) δ: 7.85 (s, 2H), 7.28-7.27 (m, 5H), 6.81 (s, 2H), 3.92-3.95 (m, 1H), 3.74-3.77 (m, 1H), 3.69-3.54 (m, 2H), 3.01-3.04 (m, 2H), 2.73-2.71 (m, 1H), 2.65-2.68 (m, 1H), 2.24 (s, 9H), 2.1-2.113 (m, 1H), 1.41 (s, 9H).<br>LCMS Method A: m/z 545 $(M + H)^+$ $(ES^+)$, at 2.63 min, UV active |
| 2-85 | (R)-5-amino-2-((1,4-dimethylpiperazin-2-yl)methyl)-8-(2,6-dimethylpyridin-4-yl)-7-phenyl-[1,2,4]triazolo[4,3-c]pyrimidin-3(2H)-one | Intermediate: Example 2-86<br>Route am (Purification by prep HPLC (Method A))<br>$^1H$ NMR: (MHz, DMSO-d6) δ: 7.31-7.27 (m, 5H), 6.83 (s, 2H), 3.94 (s, 1H), 3.34 (d, J = 2.9 Hz, 1H), 2.68 (d, J = 1.6 Hz, 1H), 2.51 (s, 1H), 2.51 (s, 3H), 2.33-2.29 (m, 1H), 2.27 (s, 9H), 2.24 (s, 4H). Exchangeable —$NH_2$ Protons were not observed.<br>LCMS Method A: m/z 459 $(M + H)^+$ $(ES^+)$, at 1.94 min, UV active |
| 2-86 | 5-amino-8-(2,6-dimethyl-4-pyridyl)-2-[[(2R)-1-methylpiperazin-2-yl]methyl]-7-phenyl-[1,2,4]triazolo[4,3-c]pyrimidin-3-one | Route ap<br>$^1H$ NMR: (MHz, DMSO-d6) δ: 7.30-7.26 (m, 5H), 6.82 (s, 2H), 3.96 (d, J = 4.0 Hz, 1H), 3.79 (d, J = 1.6 Hz, 1H), 2.76-2.73 (m, 2H), 2.67-2.66 (m, 2H), 2.46-2.34 (m, 2H), 2.28 (s, 9H), 2.15-2.11 (m, 1H). Exchangeable —$NH_2$ and —NH protons were not observed.<br>LCMS Method A: m/z 445 $(M + H)^+$ $(ES^+)$, at 1.90 min, UV active |
| 2-87 | (S)-5-amino-2-((1,4-dimethylpiperazin-2-yl)methyl)-8-(2,6-dimethylpyridin-4-yl)-7-phenyl-[1,2,4]triazolo[4,3-c]pyrimidin-3(2H)-one | Intermediate: Example 2-88<br>Route am (Purification by prep HPLC (Method A))<br>$^1H$ NMR: (MHz, DMSO-d6) δ: 7.27 (m, 5H), 6.83 (s, 2H), 3.95 (d, J = 14.8 Hz, 1H), 3.80 (d, J = 4.0 Hz, 1H), 2.68 (d, J = 1.2 Hz, 2H), 2.60 (s, 2H), 2.33 (s, 1H), 2.22-2.20 (m, 9H), 2.15-2.09 (m, 5H). Exchangeable —$NH_2$ Protons were not observed.<br>LCMS Method A: m/z 459 $(M + H)^+$ $(ES^+)$, at 1.95 min, UV active |
| 2-88 | 5-amino-8-(2,6-dimethyl-4-pyridyl)-2-[[(2S)-1-methylpiperazin-2-yl]methyl]-7-phenyl-[1,2,4]triazolo[4,3-c]pyrimidin-3-one | Intermediate: Example 2-83<br>Route ap<br>$^1H$ NMR: (MHz, DMSO-d6) δ: 7.31-7.26 (m, 5H), 6.82 (s, 2H), 3.99-3.95 (m, 1H), 3.78-3.73 (m, 1H), 2.76-2.68 (m, 4H), 2.34-2.27 (m, 11H), 2.10 (s, 1H). Exchangeable —$NH_2$ and —NH protons were not observed.<br>LCMS Method A: m/z 445 $(M + H)^+$ $(ES^+)$, at 1.91 min, UV active |
| 2-89 iso-1 | 5-amino-8-(2,6-dimethyl-4-pyridyl)-2-[(1,1-dioxothian-3- | Intermediate: 158<br>Route ao (First eluting peak from chiral SFC separation |

TABLE 3-continued

| Ex. | Name | Details |
|---|---|---|
| | yl)methyl]-7-phenyl-[1,2,4]triazolo[4,3-c]pyrimidin-3-one | (method D))<br>$^1$H NMR: (MHz, DMSO-d6) δ: 8.17 (s, 2H), 7.29-2.25 (m, 5H), 6.82-3.77 (m, 2H), 3.80-3.76 (m, 2H) 3.33 (s, 1H), 3.08-3.00 (m, 3H), 2.61 (s, 1H), 2.29 (s, 6H), 2.09-2.04 (m, 1H), 1.79-1.72 (m, 2H), 1.38-1.28 (m, 1H).<br>LCMS Method D: m/z 479 $(M + H)^+$ $(ES^+)$, at 1.86 min, UV active |
| 2-89 iso-2 | 5-amino-8-(2,6-dimethyl-4-pyridyl)-2-[(1,1-dioxothian-3-yl)methyl]-7-phenyl-[1,2,4]triazolo[4,3-c]pyrimidin-3-one | Intermediate: 158<br>Route ao (Second eluting peak from chiral SFC separation (method D))<br>$^1$H NMR: (MHz, DMSO-d6) δ: 8.17 (s, 2H), 7.29-2.25 (m, 5H), 6.82-3.77 (m, 2H), 3.80-3.76 (m, 2H) 3.33 (s, 1H), 3.08-3.00 (m, 3H), 2.61 (s, 1H), 2.29 (s, 6H), 2.09-2.04 (m, 1H), 1.79-1.72 (m, 2H), 1.38-1.28 (m, 1H).<br>LCMS Method D: m/z 479 $(M + H)^+$ $(ES^+)$, at 1.86 min, UV active |
| 2-90 | 5-amino-8-(2,6-dimethyl-4-pyridyl)-2-[(1,1-dioxothietan-3-yl)methyl]-7-phenyl-[1,2,4]triazolo[4,3-c]pyrimidin-3-one | Intermediate: 159<br>Route ao (No chiral separation)<br>$^1$H NMR: (MHz, DMSO-d6) δ: 7.30-7.25 (m, 5H), 6.82 (s, 2H), 4.29-4.23 (m, 2H), 4.09-4.00 (m, 4H), 2.88 (s, 1H), 2.29 (s, 6H). Exchangeable —$NH_2$ Protons were not observed.<br>LCMS Method C: m/z 451 $(M + H)^+$ $(ES^+)$, at 0.99 min, UV active |
| 2-91 iso-1 | 5-amino-8-[2-(hydroxymethyl)-6-methyl-4-pyridyl]-7-phenyl-2-(tetrahydropyran-2-ylmethyl)-[1,2,4]triazolo[4,3-c]pyrimidin-3-one | Route aq<br>$^1$H NMR: (MHz, DMSO-d6) δ: 7.29-7.25 (m, 5H), 7.13 (s, 1H), 6.84 (s, 1H), 5.27 (t, J = 5.60 Hz, 1H), 4.43 (d, J = 5.60 Hz, 2H), 3.85-3.82 (m, 2H), 3.71-3.67 (m, 1H), 3.62-3.60 (m, 1H), 3.33-3.29 (d, J = 5.60, 1H), 2.30 (s, 3H), 1.76 (s, 1H), 1.64-1.61 (m, 1H), 1.44 (m, 3H), 1.24 (m, 1H). Exchangeable —$NH_2$ Protons were not observed.<br>LCMS Method A: m/z 447 $(M + H)^+$ $(ES^+)$, at 1.95 min, UV active |
| 2-91 iso-2 | 5-amino-8-[2-(hydroxymethyl)-6-methyl-4-pyridyl]-7-phenyl-2-(tetrahydropyran-2-ylmethyl)-[1,2,4]triazolo[4,3-c]pyrimidin-3-one | Route aq<br>$^1$H NMR: (MHz, DMSO-d6) δ: 7.29-7.25 (m, 5H), 7.13 (s, 1H), 6.84 (s, 1H), 5.27 (t, J = 5.60 Hz, 1H), 4.43 (d, J = 5.60 Hz, 2H), 3.85-3.82 (m, 2H), 3.71-3.67 (m, 1H), 3.62-3.60 (m, 1H), 3.33-3.29 (d, J = 5.60, 1H), 2.30 (s, 3H), 1.76 (s, 1H), 1.64-1.61 (m, 1H), 1.44 (m, 3H), 1.24 (m, 1H). Exchangeable —$NH_2$ Protons were not observed.<br>LCMS Method A: m/z 447 $(M + H)^+$ $(ES^+)$, at 1.95 min, UV active |
| 2-92 iso-1 | 5-amino-8-[2-(hydroxymethyl)-6-methyl-4-pyridyl]-7-phenyl-2-(tetrahydropyran-3-ylmethyl)-[1,2,4]triazolo[4,3-c]pyrimidin-3-one | Intermediate: 1 & 154 (step 1), 42 (step 2)<br>Route aq (First eluting peak from chiral SFC separation (method D))<br>$^1$H NMR: (MHz, DMSO-d6) δ : δ 7.26-7.22 (m, 5H), 7.12 (s, 1H), 6.84 (s, 1H), 5.26 (d, J = 5.20 Hz, 1H), 4.43 (d, J = 5.20 Hz, 2H), 3.73-3.67 (m, 4H), 3.34 (s, 1H), 2.30 (s, 3H), 3.19 (t, J = 12.0 Hz, 1H), 1.98 (s, 1H), 1.72 (d, J = 12.0 Hz, 1H), 1.59-1.57 (m, 1H), 1.46-1.43 (m, 1H), 1.33-1.24 (m, 1H). Exchangeable —$NH_2$ Protons were not observed.<br>LCMS Method A: m/z 447 $(M + H)^+$ $(ES^+)$, at 1.88 min, UV active |
| 2-92 iso-2 | 5-amino-8-[2-(hydroxymethyl)-6-methyl-4-pyridyl]-7-phenyl-2-(tetrahydropyran-3-ylmethyl)-[1,2,4]triazolo[4,3-c]pyrimidin-3-one | Intermediate: 1 & 154 (step 1), 42 (step 2)<br>Route aq (Second eluting peak from chiral SFC separation (method D))<br>$^1$H NMR: (MHz, DMSO-d6) δ : δ 7.26-7.22 (m, 5H), 7.12 (s, 1H), 6.84 (s, 1H), 5.26 (d, J = 5.20 Hz, 1H), 4.43 (d, J = 5.20 Hz, 2H), 3.73-3.67 (m, 4H), 3.34 (s, 1H), 2.30 (s, 3H), 3.19 (t, J = 12.0 Hz, 1H), 1.98 (s, 1H), 1.72 (d, J = 12.0 Hz, 1H), 1.59-1.57 (m, 1H), 1.46-1.43 (m, 1H), 1.33-1.24 (m, 1H). Exchangeable —$NH_2$ Protons were not observed.<br>LCMS Method A: m/z 447 $(M + H)^+$ $(ES^+)$, at 1.88 min, UV active |
| 2-93 | 5-amino-7-(4-fluorophenyl)-8-[2-(hydroxymethyl)-6-methyl-4-pyridyl]-2-(3,4,5,6-tetrahydropyridazin-3-ylmethyl)-[1,2,4]triazolo[4,3-c]pyrimidin-3-one | Intermediate: 41 & 160 (step 1), 42 (step 2)<br>isolated as a by-product from route p<br>$^1$H NMR: (MHz, DMSO-d6) δ :7.40-7.36 (m, 2H), 7.27 (s, 1H), 7.02-6.98 (m, 3H), 4.59 (s, 2H), 4.48 (s, 2H), 3.4-3.6 (m, 1H), 3.00-2.98 (m, 2H), 2.46-2.39 (m, 4H), 2.19-2.16 (m, 2H), 1.93-1.90 (m, 2H). Exchangeable —$NH_2$ Protons were not observed.<br>LCMS Method A: m/z 463 $(M + H)^+$ $(ES^+)$, at 1.93 min, UV active |
| 2-94 | 5-amino-2-[2-(azetidin-1-yl)ethyl]-8-(2,6-dimethyl-4-pyridyl)-7-phenyl- | Intermediate: 161<br>Route aa<br>$^1$H NMR: (MHz, Chloroform-d) δ: 7.36-7.11 (m, 5H), |

TABLE 3-continued

| Ex. | Name | Details |
|---|---|---|
| | Data for Examples 1-1 to 3-10 | |
| | [1,2,4]triazolo[4,3-c]pyrimidin-3-one | 6.80 (s, 2H), 3.83 (t, J = 6.2 Hz, 2H), 3.27-3.24 (m, 4H), 2.79 (t, J = 6.2 Hz, 2H), 2.39 (s, 6H), 2.09-2.04 (m, 2H). Exchangeable —$NH_2$ Protons were not observed.<br>LCMS Method F: m/z 416 $(M + H)^+$ (ES+), at 0.70 min, UV active |
| 2-95 | 2-(2-(2-azabicyclo[3.1.0]hexan-2-yl)ethyl)-5-amino-8-(2,6-dimethylpyridin-4-yl)-7-phenyl-[1,2,4]triazolo[4,3-c]pyrimidin-3(2H)-one | Intermediate: 162<br>Route aa<br>$^1$H NMR: (MHz, DMSO-dg) δ 8.55-7.75 (m, 2H), 7.29-7.04 (m, 6H), 6.72 (s, 2H), 4.05-3.85 (m, 2H), 2.95 (s, 1H), 2.77 (s, 2H), 2.32 (s, 6H), 1.95-1.75 (m, 3H), 1.38 (s, 1H), 1.05 (d, J = 6.1 Hz, 1H), 0.61 (s, 1H).<br>LCMS Method F: m/z 442 $(M + H)^+$ (ES+), at 0.80 min, UV active |
| 2-96 | 5-amino-8-(2,6-dimethyl-4-pyridyl)-7-phenyl-2-[2-(1-piperidyl)ethyl]-[1,2,4]triazolo[4,3-c]pyrimidin-3-one | Intermediate: 1 & 163 (step 1), 3 (step 2)<br>Route a<br>$^1$H NMR: (MHz, DMSO-d6) δ: 7.30-7.25 (m, 5H), 6.82 (s, 2H), 3.89-2.86 (m, 2H), 2.56-2.53 (m, 2H), 2.38-2.34 (m, 4H), 2.29 (s, 6H), 1.46-1.36 (m, 6H). Exchangeable —$NH_2$ Protons were not observed.<br>LCMS Method E: m/z 444 $(M + H)^+$ $(ES^+)$, at 5.02 min, UV active |
| 2-97 | 5-amino-8-(2,6-dimethyl-4-pyridyl)-2-[2-(1-methyl-4-piperidyl)ethyl]-7-phenyl-[1,2,4]triazolo[4,3-c]pyrimidin-3-one | Intermediate: 1 & 164 (step 1), 3 (step 2)<br>Route c<br>$^1$H NMR: (MHz, DMSO-d6) δ: 7.25-7.22 (m, 5H), 6.81 (s, 2H), 3.79 (t, J = 6.0 Hz, 2H), 2.73-2.67 (m, 2H), 2.29 (s, 6H), 2.12 (s, 3H), 1.79 (t, J = 10.8 Hz, 2H), 1.67-1.56 (m, 4H), 1.23-1.12 (m, 3H). Exchangeable —$NH_2$ Protons were not observed.<br>LCMS Method A: m/z 458 $(M + H)^+$ $(ES^+)$, at 2.09 min, UV active |
| 2-98 | 5-amino-8-(2,6-dimethyl-4-pyridyl)-2-[2-(3-methyl-1-piperidyl)ethyl]-7-phenyl-[1,2,4]triazolo[4,3-c]pyrimidin-3-one | Route ar<br>$^1$H NMR: (MHz, DMSO-d6) δ: 7.26-7.23 (m, 5H), 6.82 (s, 2H), 3.88 (t, J = 4.0 Hz, 2H), 2.78 (t, J = 4.0 Hz, 2H), 2.30-2.29 (m, 1H), 2.30 (s, 6H), 1.89-1.55 (m, 7H), 0.82-0.8 (m, 4H). Exchangeable —$NH_2$ Protons were not observed.<br>LCMS Method A: m/z 458 $(M + H)^+$ $(ES^+)$, at 2.18 min, UV active |
| 2-99 | 5-amino-8-(2,6-dimethyl-4-pyridyl)-2-(2-morpholinoethyl)-7-phenyl-[1,2,4]triazolo[4,3-c]pyrimidin-3-one | Intermediate: 1 & 85 (step 1), 166 (step 2)<br>Route ar<br>$^1$H NMR: (MHz, DMSO-d6) δ: 7.27-7.24 (m, 5H), 6.81 (s, 2H), 3.90 (t, J = 6.0 Hz, 2H), 3.54-3.52 (m, 4H), 2.59 (t, J = 6.0 Hz, 2H), 2.32-2.28 (m, 4H), 2.07 (s, 6H). Exchangeable —$NH_2$ Protons were not observed.<br>LCMS Method A: m/z 446 $(M + H)^+$ $(ES^+)$, at 1.92 min, UV active |
| 2-100 | 5-amino-2-[2-((ds)-2,6-dimethylmorpholin-4-yl)ethyl]-8-(2,6-dimethyl-4-pyridyl)-7-phenyl-[1,2,4]triazolo[4,3-c]pyrimidin-3-one | Intermediate: 167<br>Route aa (purified by Biotage-Isolera using 10 g silica snap and eluted with gradient 1-5% MeOH in DCM)<br>$^1$H NMR: (MHz, DMSO-d6) δ: 7.28-7.25 (m, 5H), 6.80 (s, 2H), 3.89 (t, J = 6.0 Hz, 2H), 3.48 (t, J = 6.0 Hz, 2H), 2.79-2.76 (m, 2H), 2.58-2.56 (m, 2H), 2.28 (s, 6H), 1.64 (t, J = 10.4 Hz, 2H), 1.04-1.00 (m, 6H). Exchangeable —$NH_2$ Protons were not observed.<br>LCMS Method A: m/z 474 $(M + H)^+$ $(ES^+)$, at 2.15 min, UV active |
| 2-101 | 5-amino-2-[2-(4,4-difluoro-1-piperidyl)ethyl]-8-(2,6-dimethyl-4-pyridyl)-7-phenyl-[1,2,4]triazolo[4,3-c]pyrimidin-3-one | Intermediate: 168<br>Route aa (purified by Biotage-Isolera using 10 g silica snap and eluted with gradient 1-5% MeOH in DCM)<br>$^1$H NMR: (MHz, DMSO-d6) δ: 7.28-7.25 (m, 5H), 6.82 (s, 2H), 3.91 (t, J = 6.4 Hz, 2H), 2.69 (t, J = 6.4 Hz, 2H), 2.56-2.55 (m, 4H), 2.29 (s, 6H), 1.96-1.86 (m, 4H). Exchangeable —$NH_2$ Protons were not observed.<br>LCMS Method A: m/z 480 $(M + H)^+$ $(ES^+)$, at 2.18 min, UV active |
| 2-102 | 5-amino-8-(2,6-dimethyl-4-pyridyl)-2-[2-(4-methylpiperazin-1-yl)ethyl]-7-phenyl-[1,2,4]triazolo[4,3-c]pyrimidin-3-one | Intermediate: 169<br>Route aa (purified by Biotage-Isolera using 10 g silica snap and eluted with gradient 1-5% MeOH in DCM)<br>$^1$H NMR: (MHz, DMSO-d6) δ: 7.27-7.25 (m, 5H), 6.81 (s, 2H), 3.87 (t, J = 6.0 Hz, 2H), 2.58 (t, J = 6.0 Hz, 2H), 2.44-2.32 (m, 4H), 2.31-2.28 (m, 10H), 2.13 (s, 3H). Exchangeable —$NH_2$ Protons were not observed.<br>LCMS Method A: m/z 459 $(M + H)^+$ $(ES^+)$, at 1.92 min, UV active |
| 2-103 | 5-amino-2-[2-(8-azabicyclo[3.2.1]octan-8-yl)ethyl]-8-(2,6-dimethyl-4- | Intermediate: 170<br>aa (purified by Biotage-Isolera usinG 10 g silica snap and eluted with gradient 1-5% MeOH in DCM) |

TABLE 3-continued

| Data for Examples 1-1 to 3-10 | | |
|---|---|---|
| Ex. | Name | Details |
| | pyridyl)-7-phenyl-[1,2,4]triazolo[4,3-c]pyrimidin-3-one | $^1$H NMR: (MHz, DMSO-d6) δ: 7.30-7.25 (m, 5H), 6.82 (s, 2H), 3.83 (t, J = 6.4 Hz, 2H), 3.13-3.11 (m, 2H), 2.68 (t, J = 2.0 Hz, 2H), 2.33 (s, 6H), 1.83-1.81 (m, 2H), 1.60-1.20 (m, 8H). Exchangeable —$NH_2$ Protons were not observed. LCMS Method A: m/z 470 $(M + H)^+$ $(ES^+)$, at 2.11 min, UV active |
| 2-104 | 5-amino-8-(2,6-dimethyl-4-pyridyl)-7-(4-fluorophenyl)-2-[2-(1-piperidyl)ethyl]-[1,2,4]triazolo[4,3-c]pyrimidin-3-one | Intermediate: 41 & 163 (step 1), 3 (step 2) Route a $^1$H NMR: (MHz, DMSO-d6) δ: 7.32-7.28 (m, 2H), 7.13-7.08 (m, 2H), 6.83 (s, 2H), 3.88 (t, J = 5.6 Hz, 2H), 2.37-2.31 (m, 12H), 1.46-1.40 (m, 4H), 1.37-1.34 (m, 2H). Exchangeable —$NH_2$ Protons were not observed. LCMS Method A: m/z 462 $(M + H)^+$ $(ES^+)$, at 2.17 min, UV active |
| 2-105 | 5-amino-8-(2-chloro-6-methyl-4-pyridyl)-7-(4-fluorophenyl)-2-[2-(1-piperidyl)ethyl]-[1,2,4]triazolo[4,3-c]pyrimidin-3-one | 41 & 163 (step 1), 139 (step 2) Route a (Step 2 using $K_3PO_4$ and $[PdCl_2(amphos)]$) $^1$H NMR: (MHz, DMSO-d6) δ: 8.46-7.76 (m, 2H), 7.33-7.30 (m, 2H), 7.16-7.12 (m, 2H), 7.06-7.02 (m, 2H), 3.88 (br s, 2H), 2.50 (br s, 2H), 2.37-2.33 (m, 7H), 1.45 (br s, 4H), 1.36 (brs, 2H). LCMS Method A: m/z 482 $(M + H)^+$ $(ES^+)$, at 3.40 min, UV active |
| 2-106 | methyl 3-[2-[5-amino-8-(2,6-dimethyl-4-pyridyl)-3-oxo-7-phenyl-[1,2,4]triazolo[4,3-c]pyrimidin-2-yl]ethylamino]piperidine-1-carboxylate | Intermediate: 171 Route aa $^1$H NMR: (MHz, Chloroform-d) δ 7.37-7.11 (m, 5H), 6.80 (s, 2H), 4.06-3.88 (m, 2H), 3.78 (s, 2H), 3.65 (s, 3H), 3.15-2.97 (m, 2H), 2.95-2.91 (m, 1H), 2.70 (t, J = 11.9 Hz, 1H), 2.65-2.52 (m, 1H), 2.40 (s, 6H), 1.91-1.60 (m, 2H), 1.51-1.38 (m, 1H), 1.28 (t, J = 10.8 Hz, 1H). Exchangeable protons were not observed. LCMS Method F: m/z 517 $(M + H)^+$ (ES+), at 0.71 min, UV active |
| 2-107 | 5-amino-8-(2,6-dimethyl-4-pyridyl)-2-[2-[[2-(4-hydroxy-1-piperidyl)-2-oxo-ethyl]-methyl-amino]ethyl]-7-phenyl-[1,2,4]triazolo[4,3-c]pyrimidin-3-one | Intermediate: 172 Route aa $^1$H NMR: (MHz, Chloroform-d) δ: 8.24 (br. s, 1H), 7.65 (br. s, 1H), 7.30-7.15 (m, 5H), 6.73 (s, 2H), 4.42 (d, J = 3.9 Hz, 1H), 3.94-3.84 (m, 2H), 3.82-3.70 (m, 1H), 3.65-3.55 (m, 2H), 3.22-3.09 (m, 2H), 2.85-2.74 (m, 2H), 2.54 (s, 2H), 2.35-2.30 (m, 9H), 1.68-1.49 (m, 2H), 1.33-1.20 (m, 2H). LCMS Method F: m/z 531 $(M + H)^+$ (ES+), at 0.66 min, UV active |
| 2-108 | 3-[2-[5-amino-8-(2,6-dimethyl-4-pyridyl)-3-oxo-7-phenyl-[1,2,4]triazolo[4,3-c]pyrimidin-2-yl]ethylamino]-N-cyclopropyl-cyclohexanecarboxamide | Intermediate: 173 Route aa $^1$H NMR: (MHz, Chloroform-d) δ 7.31-7.17 (m, 5H), 6.78 (s, 2H), 5.73-5.68 (m, 1H), 3.94 (t, J = 6.0 Hz, 2H), 3.44 (s, 1H), 3.07-2.97 (m, 2H), 2.73-2.61 (m, 1H), 2.51-2.41 (m, 1H), 2.38 (s, 6H), 2.09-1.69 (m, 7H), 1.39-1.09 (m, 3H), 1.06-0.92 (m, 1H), 0.78-0.68 (m, 2H), 0.47-0.35 (m, 2H). LCMS Method F: m/z 541 $(M + H)^+$ (ES+), at 0.78 min, UV active |
| 2-109 | methyl 3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl]propanoate | Route as $^1$H NMR: (MHz, DMSO-d6) δ: 7.94 (s, 2H), 7.30-7.26 (m, 5H), 6.82 (s, 2H), 3.83-3.78 (m, 2H), 3.34-2.81 (m, 2H), 2.55 (m, 2H), 2.47 (s, 3H), 2.34 (s, 6H), 1.90 (t, J = 6.4 Hz, 2H), 1.86-1.83 (m, 2H), 1.68-1.68 (m, 2H), 1.67-1.64 (m, 1H), 1.60-1.58 (m, 2H). Exchangeable —$NH_2$ Protons were not observed. LCMS Method A: m/z 530 $(M + H)^+$ $(ES^+)$, at 2.17 min, UV active |
| 2-110 | 3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl]propanoic acid | Route as $^1$H NMR: (MHz, DMSO-d6) δ: 8.00 (s, 1H), 7.30-7.26 (m, 5H), 6.82 (s, 2H), 3.82 (t, J = 6.8 Hz, 2H), 2.68 (t, J = 6.8 Hz, 2H), 2.45-2.43 (m, 2H), 2.41-2.34 (m, 2H), 2.34 (s, 6H), 2.33-2.30 (m, 2H), 2.19-1.92 (m, 2H), 1.78-1.75 (m, 2H), 1.74-1.75 (m, 1H), 1.61-1.59 (m, 2H). Exchangeable —$NH_2$ Protons were not observed. LCMS Method A: m/z 516 $(M + H)^+$ $(ES^+)$, at 2.04 min, UV active |
| 2-111 | 5-amino-8-(2,6-dimethyl-4-pyridyl)-7-phenyl-2-[3-(1-piperidyl)propyl]-[1,2,4]triazolo[4,3-c]pyrimidin-3-one | Intermediate: 1 & 174 (step 1), 3 (step 2) Route c (purified by prep HPLC (Method A). Fractions were concentrated, residue obtained was dissolved in MeOH and passed through DSC-SCX cartridge and eluted with 2M Methanolic ammonia) $^1$H NMR: (MHz, DMSO-d6) δ: 7.28-7.25 (m, 5H), 6.81 (s, 2H), 3.81 (t, J = 7.2 Hz, 2H), 2.29-2.27 (m, 12H), 1.79-1.78 (m, 2H), 1.43-1.31 (m, 6H). Exchangeable —$NH_2$ |

TABLE 3-continued

| Data for Examples 1-1 to 3-10 | | |
|---|---|---|
| Ex. | Name | Details |
| | | Protons were not observed.<br>LCMS Method A: m/z 458 (M + H)+ (ES+), at 2.11 min, UV active |
| 2-112 | 5-amino-8-(2,6-dimethylpyridin-4-yl)-2-(3-(2-oxopyridin-1(2H)-yl)propyl)-7-phenyl-[1,2,4]triazolo[4,3-c]pyrimidin-3(2H)-one | Intermediate: 175<br>Route g<br>$^1$H NMR: (MHz, Chloroform-d) δ: 7.42-7.38 (m, 1H), 7.35-7.23 (m, 6H), 6.93 (s, 2H), 6.55 (d, J = 9.1 Hz, 1H), 6.15-6.10 (m, 1H) 4.02 (t, J = 6.7 Hz, 2H), 3.94 (t, J 6.7 = Hz, 2H), 2.50 (s, 6H), 2.30-2.27 (m, 2H). Exchangeable —$NH_2$ Protons were not observed.<br>LCMS Method F: m/z 468 (M + H)+ (ES+), at 0.85 min, UV active |
| 2-113 | 3-(5-amino-8-(2,6-dimethylpyridin-4-yl)-3-oxo-7-phenyl-[1,2,4]triazolo[4,3-c]pyrimidin-2(3H)-yl)-N-methylpropanamide | Intermediate: 176 (step 3)<br>Route ae (step 3 purified by Biotage-Isolera using 10 g silica snap, eluted with gradient 0-10% MeOH in DCM)<br>$^1$H NMR: (MHz, $CD_3OD$) δ: 7.34-7.26 (m, 5H), 6.95 (s, 2H), 4.15 (t, J = 6.8 Hz, 2H), 2.69-2.64 (m, 5H), 2.38 (s, 6H). Exchangeable —NH and —$NH_2$ protons not observed<br>LCMS Method A: m/z 418 (M + H)+ (ES+), at 1.99 min, UV active |
| 3-1 | 5-amino-8-(2,6-dimethyl-4-pyridyl)-7-morpholino-2-(3,3,3-trifluoropropyl)-[1,2,4]triazolo[4,3-c]pyrimidin-3-one | Route at<br>$^1$H NMR: (MHz, DMSO-d6) δ: 7.18 (s, 2H), 3.96 (t, J = 6.6 Hz, 2H), 3.56-3.46 (m, 4H), 3.20-3.07 (m, 4H), 2.82-2.63 (m, 2H), 2.42 (s, 6H). Exchangeable —$NH_2$ protons not observed<br>LCMS Method A: m/z 438 (M + H)+ (ES+), at 2.84 min, UV active |
| 3-2 | 5-amino-8-(2,6-dimethyl-4-pyridyl)-7-(1-piperidyl)-2-(3,3,3-trifluoropropyl)-[1,2,4]triazolo[4,3-c]pyrimidin-3-one | Intermediate: 177<br>Route at<br>$^1$H NMR: (MHz, DMSO-d6) δ: 7.72 (s, 2H), 7.14 (s, 2H), 4.01-3.88 (m, 2H), 3.13 (s, 4H), 2.81-2.58 (m, 2H), 2.40 (s, 6H), 1.70-1.33 (m, 6H).<br>LCMS Method A: m/z 436 (M + H)+ (ES+), at 3.55 min, UV active |
| 3-3 | 5-amino-8-(2,6-dimethyl-4-pyridyl)-7-ethoxy-2-(3,3,3-trifluoropropyl)-[1,2,4]triazolo[4,3-c]pyrimidin-3-one | Intermediate: 178 (2 eq used and reaction performed in DMSO)<br>Route at (Purified by Prep HPLC (Method A), the fractions were concentrated and the residue was diluted with EtOAc (10 mL) and washed with 10% sodium bicarbonate solution (10 mL). The organic layer was separated, dried over anhydrous $Na_2SO_4$)<br>$^1$H NMR: (MHz, DMSO-d6) δ: 8.74 (s, 1H), 7.92 (s, 1H), 7.41 (s, 2H), 4.35 (t, J = 7.2 Hz, 2H), 4.01 (t, J = 2.0 Hz, 2H), 2.52 (t, J = 2.0 Hz, 2H), 2.50 (s, 6H), 1.29 (t, J = 7.2 Hz, 3H).<br>LCMS Method A: m/z 397 (M + H)+ (ES+), at 3.13 min, UV active |
| 3-4 | 5-amino-8-(2,6-dimethyl-4-pyridyl)-7-[ethyl(methyl)amino]-2-(3,3,3-trifluoropropyl)-[1,2,4]triazolo[4,3-c]pyrimidin-3-one | Intermediate: 179<br>Route at<br>$^1$H NMR: (MHz, DMSO-d6) δ: 7.74 (s, 2H), 7.00 (s, 2H), 3.94 (t, J = 6.6 Hz, 2H), 3.36 (t, J = 7.1 Hz, 2H), 2.69 (t, J = 6.6 Hz, 2H), 2.51 (s, 3H), 2.40 (s, 6H), 1.06 (t, J = 7.1 Hz, 3H).<br>LCMS Method A: m/z 410 (M + H)+ (ES+), at 3.22 min, UV active |
| 3-5 | 5-amino-7-chloro-8-(2,6-dimethyl-4-pyridyl)-2-(3,3,3-trifluoropropyl)-[1,2,4]triazolo[4,3-c]pyrimidin-3-one | Intermediate: 125 & 126<br>Route b (step 1 only)<br>$^1$H NMR: (MHz, DMSO-d6) δ: 8.82 (s, 1H), 7.86 (s, 1H), 7.09 (s, 2H), 4.00 (t, J = 9.2 Hz, 2H), 2.71 (t, J = 9.2 Hz, 2H), 2.50 (s, 6H).<br>LCMS Method A: m/z 387 (M + H)+ (ES+), at 2.39 min, UV active |
| 3-6 | methyl 5-amino-8-(2,6-dimethyl-4-pyridyl)-3-oxo-2-(3,3,3-trifluoropropyl)-[1,2,4]triazolo[4,3-c]pyrimidine-7-carboxylate | Route au<br>$^1$H NMR: (MHz, DMSO-d6) δ: 8.70 (s, 1H), 7.76 (s, 1H), 6.99 (s, 2H), 4.05 (t, J = 6.8 Hz, 2H), 3.61 (s, 3H), 2.50 (t, J = 6.8 Hz, 2H), 2.44 (s, 6H).<br>LCMS Method A: m/z 411 (M + H)+ (ES+), at 2.29 min, UV active |
| 3-7 | 5-amino-8-(2,6-dimethyl-4-pyridyl)-7-prop-1-ynyl-2-(3,3,3-trifluoropropyl)-[1,2,4]triazolo[4,3-c]pyrimidin-3-one | Intermediate: 180 (step 2)<br>Route ah<br>$^1$H NMR: (MHz, DMSO-d6) δ: 7.39 (s, 2H), 4.13 (t, J = 7.2 Hz, 2H), 2.72 (t, J = 7.2 Hz, 2H), 2.69 (s, 6H), 1.97 (s, 3H). Exchangeable —$NH_2$ protons were not observed.<br>LCMS Method A: m/z 391 (M + H)+ (ES+), at 2.63 min, UV active |
| 3-8 | 5-amino-8-(2,6-dimethyl-4-pyridyl)-7-methoxy-2-(3,3,3- | Route av<br>$^1$H NMR: (MHz, DMSO-d6) δ: 7.39 (s, 2H), 4.00 (t, J = 6.8 |

TABLE 3-continued

| Data for Examples 1-1 to 3-10 | | |
|---|---|---|
| Ex. | Name | Details |
| | trifluoropropyl)-[1,2,4]triazolo[4,3-c]pyrimidin-3-one | Hz, 2H), 3.33 (s, 3H), 2.72 (t, J = 6.8 Hz, 2H), 2.51 (s, 6H). Exchangeable $NH_2$— Protons were not observed. LCMS Method A: m/z 383 $(M + H)^+$ $(ES^+)$, at 2.88 min, UV active |
| 3-9 | 5-amino-8-(2,6-dimethyl-4-pyridyl)-7-[(Z)-1-methylprop-1-enyl]-2-(3,3,3-trifluoropropyl)-[1,2,4]triazolo[4,3-c]pyrimidin-3-one | Route aw $^1H$ NMR: (MHz, DMSO-d6) δ: 6.99 (s, 2H), 5.29-5.17 (m, 1H), 4.03 (t, J = 6.7 Hz, 2H), 2.81-2.63 (m, 2H), 2.41 (s, 6H), 1.92-1.84 (m,3H), 1.24-1.15 (m, 3H). Exchangeable —$NH_2$ Protons were not observed. LCMS Method A: m/z 407 $(M + H)^+$ $(ES^+)$, at 2.66 min, UV active |
| 3-10 | 5-amino-8-(2,6-dimethyl-4-pyridyl)-7-[(E)-1-methylprop-1-enyl]-2-(3,3,3-trifluoropropyl)-[1,2,4]triazolo[4,3-c]pyrimidin-3-one | Route aw $^1H$ NMR: (MHz, DMSO-d6) δ: 6.97 (s, 2H), 5.40-5.28 (m, 1H), 4.02 (t, J = 6.6 Hz, 2H), 2.80-2.64 (m, 2H), 2.41 (s, 6H), 1.82-1.70 (m, 3H), 1.55-1.43 (m, 3H). Exchangeable —$NH_2$ Protons were not observed. LCMS Method A: m/z 407 $(M + H)^+$ $(ES^+)$, at 2.74 min, UV active |

Example 4: Adenosine Receptor Assays

Inhibition binding assays were performed using 0.2 μg of membranes prepared from HEK293 cells infected with BacMam human adenosine $A_{2A}$ receptor or 1.4 μg of membranes prepared from HEK293 cells infected with BacMam human adenosine A1 receptor. Membranes were incubated in 50 mM Tris-HCl (HEK293-h$A_{2A}$; pH 7.4) or 50 mM Tris-HCl, 100 mM NaCl, 10 mM MgCl2 (CHO-h$A_1$; pH 7.4) in the presence of varying concentrations of test compound and 1 nM [$^3$H]ZM241385 (HEK293-h$A_{2A}$) or [$^3$H] DPCPX (CHO-h$A_1$) at 25° C. for 1 h. The assay was then terminated by rapid filtration onto GF/B grade Unifilter plates using a TomTec cell harvester, followed by 5×0.5 ml washes with ddH2O. Nonspecific binding was defined in the presence of 1 μM CGS15943 (HEK293-h$A_{2A}$) or 1 μM DPCPX (CHO-h$A_1$). Bound radioactivity was determined by liquid scintillation counting and inhibition curves were analysed using a four-parameter logistic equation. $IC_{50}$ values were converted to Ki values with the Cheng-Prusoff equation using a KD value derived from saturation binding studies. Results are summarized in Table 4.

TABLE 4

| Adenosine receptor binding | | |
|---|---|---|
| Example no. | $A_1$ pKi | $A_{2A}$ pKi |
| 1-1 | 7.5 | 9.4 |
| 1-2 | 6.5 | 9.1 |
| 1-3 | 7.6 | 8.2 |
| 1-4 | 6.3 | 8.9 |
| 1-5 | 6.6 | 8.6 |
| 1-6 | 6.7 | 9.1 |
| 1-7 | 6.4 | 8.4 |
| 1-8 | 6.5 | 7.6 |
| 1-9 | 6.9 | 7.9 |
| 1-10 | 6.1 | 7.7 |
| 1-11 | 6.4 | 8.2 |
| 1-12 | 6.1 | 8.0 |
| 1-13 | 6.8 | 8.9 |
| 1-14 | 7.7 | 8.5 |
| 1-15 | 7.1 | 8.8 |
| 1-16 | 9.0 | 9.6 |
| 1-17 | 9.0 | 9.5 |
| 1-18 | 8.0 | 10.1 |
| 1-19 | 7.0 | 8.9 |
| 1-20 | 6.5 | 7.9 |

TABLE 4-continued

| Adenosine receptor binding | | |
|---|---|---|
| Example no. | $A_1$ pKi | $A_{2A}$ pKi |
| 1-21 | 8.0 | 9.3 |
| 1-22 | 8.7 | 9.8 |
| 1-23 | 8.5 | 10.0 |
| 1-24 | 7.8 | 9.9 |
| 1-25 | 8.2 | 9.7 |
| 1-26 | 6.1 | 7.8 |
| 1-27 | 6.6 | 8.0 |
| 1-28 | 7.2 | 9.7 |
| 1-29 | 7.9 | 9.3 |
| 1-30 | 7.4 | 9.3 |
| 1-31 | 6.5 | 8.0 |
| 1-32 | 8.4 | 9.9 |
| 1-33 | 6.0 | 7.6 |
| 1-34 | 7.0 | 9.0 |
| 1-35 | 6.0 | 7.8 |
| 1-36 | 7.0 | 9.6 |
| 1-37 | <5.5 | 7.2 |
| 1-38 | 6.0 | 7.0 |
| 1-38 iso-1 | 6.3 | 7.2 |
| 1-38-iso-2 | <5.7 | 6.7 |
| 1-39 | 7.2 | 9.2 |
| 1-40 | 7.4 | 9.1 |
| 1-41 | 6.4 | 8.6 |
| 1-42 | 6.6 | 7.8 |
| 1-43 | 6.5 | 7.5 |
| 1-44 | 6.4 | 8.8 |
| 1-45 | 6.9 | 9.1 |
| 1-46 iso-1 | <5.5 | 6.4 |
| 1-46 iso-2 | <5.6 | 7.0 |
| 1-47 | 6.3 | 8.1 |
| 1-48 | <5.6 | 8.0 |
| 1-49 | 6.4 | 8.8 |
| 1-50 | 6.7 | 9.0 |
| 1-51 | 6.6 | 8.7 |
| 1-52 | 6.3 | 9.2 |
| 1-53 | 6.3 | 8.6 |
| 1-54 | 5.5 | 6.8 |
| 1-55 | 6.3 | 8.8 |
| 1-56 | 6.7 | 8.4 |
| 1-57 | 6.9 | 9.2 |
| 1-58 | 6.2 | 7.9 |
| 1-59 | 5.9 | 8.8 |
| 1-60 | 6.1 | 8.8 |
| 1-61 | <5.8 | 8.8 |
| 1-62 | 6.0 | 8.4 |
| 1-63 | <5.4 | 6.2 |
| 1-64 | 6.8 | 9.5 |
| 1-65 | 6.1 | 9.1 |

TABLE 4-continued

| Adenosine receptor binding | | |
|---|---|---|
| Example no. | $A_1$ pKi | $A_{2A}$ pKi |
| 1-66 | 6.3 | 9.2 |
| 1-67 | 5.9 | 9.1 |
| 1-68 | <5.8 | 8.9 |
| 1-69 | 6.6 | 9.1 |
| 1-70 | 7.3 | 9.5 |
| 1-71 | 6.2 | 7.7 |
| 1-72 | 6.9 | 8.6 |
| 1-73 | 6.4 | 8.6 |
| 1-74 | <5.5 | 6.5 |
| 1-75 | 6.9 | 8.5 |
| 1-76 | 7.1 | 9.9 |
| 1-77 | 6.7 | 9.4 |
| 1-78 | 6.8 | 9.9 |
| 1-79 | 6.6 | 8.6 |
| 1-80 | 6.9 | 8.7 |
| 1-81 | 6.2 | 7.6 |
| 1-82 | 6.6 | 7.9 |
| 1-83 | 6.6 | 7.7 |
| 1-84 | 6.1 | 7.5 |
| 1-85 | <5.4 | 6.7 |
| 1-86 | 6.1 | 8.3 |
| 1-87 | 6.3 | 7.8 |
| 1-88 | 7.0 | 7.9 |
| 1-89 | 6.9 | 8.3 |
| 1-90 | 6.4 | 7.9 |
| 1-91 | 6.0 | 7.4 |
| 1-92 | <5.4 | 6.9 |
| 1-93 | 6.2 | 7.5 |
| 1-94 | 6.4 | 8.0 |
| 1-95 | <5.7 | 6.5 |
| 1-96 | 6.6 | 8.4 |
| 1-97 | <5.4 | 7.2 |
| 1-98 | 6.0 | 7.1 |
| 1-99 | 5.9 | 7.4 |
| 1-100 | 6.5 | 6.8 |
| 1-101 | 8.0 | 9.2 |
| 1-102 | 7.9 | 9.3 |
| 1-103 | 6.0 | 7.8 |
| 1-104 | 7.0 | 8.7 |
| 2-1 | 7.1 | 8.3 |
| 2-2 | 6.7 | 8.3 |
| 2-3 | 6.2 | 7.7 |
| 2-4 | 5.9 | 7.3 |
| 2-5 | 7.4 | 9.1 |
| 2-6 | 6.3 | 8.7 |
| 2-7 | 6.0 | 7.0 |
| 2-8 | 6.5 | 8.8 |
| 2-9 | 6.2 | 7.7 |
| 2-10 | 6.6 | 8.0 |
| 2-11 | 6.1 | 7.8 |
| 2-12 | 6.3 | 8.0 |
| 2-13 | 6.3 | 7.8 |
| 2-14 | 6.1 | 7.0 |
| 2-15 | 6.3 | 8.3 |
| 2-16 | 5.9 | 7.7 |
| 2-17 | 6.0 | 8.7 |
| 2-18 | 5.7 | 8.2 |
| 2-19 | 6.4 | 8.4 |
| 2-20 | 6.3 | 8.4 |
| 2-21 | 6.0 | 8.6 |
| 2-22 | 6.0 | 6.7 |
| 2-23 | 6.0 | 7.9 |
| 2-24 | 6.1 | 8.0 |
| 2-25 | 5.8 | 8.0 |
| 2-26 | 7.0 | 9.4 |
| 2-27 | 7.5 | 9.2 |
| 2-28 | 6.7 | 8.8 |
| 2-29 | 6.9 | 9.3 |
| 2-30 | 6.6 | 8.6 |
| 2-31 | 5.6 | 7.6 |
| 2-32 | 6.4 | 9.3 |
| 2-33 | 6.2 | 8.9 |
| 2-34 | <5.4 | 7.8 |
| 2-35 | 7.1 | 8.9 |
| 2-36 | <5.5 | 7.7 |
| 2-37 | <5.5 | 7.5 |

TABLE 4-continued

| Adenosine receptor binding | | |
|---|---|---|
| Example no. | $A_1$ pKi | $A_{2A}$ pKi |
| 2-38 | <5.4 | 7.4 |
| 2-39 | <5.4 | 7.3 |
| 2-40 | <5.5 | 7.4 |
| 2-41 | 5.7 | 7.5 |
| 2-42 | 5.7 | 9.0 |
| 2-43 | 6.3 | 8.7 |
| 2-44 | 5.6 | 7.7 |
| 2-45 | 6.5 | 9.6 |
| 2-46 | 5.9 | 9.0 |
| 2-47 | <5.4 | 8.8 |
| 2-48 | 8.2 | 9.1 |
| 2-49 | 6.3 | 7.4 |
| 2-50 | 7.1 | 9.1 |
| 2-51 | 6.3 | 8.9 |
| 2-52 | 6.7 | 9.2 |
| 2-53 | 6.3 | 8.9 |
| 2-54 | 6.4 | 8.2 |
| 2-55 | <5.5 | 6.6 |
| 2-56 | 6.5 | 7.9 |
| 2-57 | 6.6 | 8.0 |
| 2-58 | 6.0 | 7.3 |
| 2-59 | 6.5 | 8.4 |
| 2-60 | 6.7 | 8.1 |
| 2-61 | 6.2 | 8.9 |
| 2-62 | 7.5 | 9.5 |
| 2-63 | 6.5 | 8.9 |
| 2-64 | <5.9 | 8.8 |
| 2-65 | 6.3 | 7.9 |
| 2-66 | 6.0 | 8.2 |
| 2-67 | 6.0 | 8.2 |
| 2-68 | <5.5 | 6.4 |
| 2-69 | 6.4 | 8.2 |
| 2-70 | 6.3 | 8.4 |
| 2-71 | 5.7 | 7.5 |
| 2-72 | 6.2 | 7.8 |
| 2-73 | 6.0 | 8.7 |
| 2-74 | 5.8 | 7.8 |
| 2-75 | 5.9 | 7.0 |
| 2-76 | 6.2 | 7.8 |
| 2-77 | 6.4 | 8.5 |
| 2-78 | <5.5 | 6.7 |
| 2-79 | 6.1 | 7.8 |
| 2-80 | 6.7 | 8.1 |
| 2-81 | 6.5 | 9.3 |
| 2-81-iso-1 | 6.8 | 8.7 |
| 2-81-iso-2 | 6.9 | 9.0 |
| 2-82 | 6.6 | 9.5 |
| 2-82-iso-1 | 6.9 | 8.8 |
| 2-82-iso-2 | 6.9 | 8.8 |
| 2-83 | 6.0 | 8.0 |
| 2-84 | 6.5 | 8.2 |
| 2-85 | 5.8 | 8.1 |
| 2-86 | 5.8 | 7.6 |
| 2-87 | 5.7 | 7.0 |
| 2-88 | 5.7 | 7.1 |
| 2-89-iso-1 | 6.4 | 8.0 |
| 2-89-iso-2 | 6.5 | 7.6 |
| 2-90 | 6.1 | 7.3 |
| 2-91-iso-1 | 6.2 | 8.9 |
| 2-91-iso-2 | 6.6 | 8.8 |
| 2-92-iso-1 | 6.6 | 8.6 |
| 2-92-iso-2 | 6.5 | 8.9 |
| 2-93 | 5.8 | 7.5 |
| 2-94 | <5.6 | 7.6 |
| 2-95 | 5.7 | 8.2 |
| 2-96 | 5.7 | 7.8 |
| 2-97 | 6.2 | 8.2 |
| 2-98 | 5.8 | 7.7 |
| 2-99 | 6.1 | 7.5 |
| 2-100 | <5.5 | 6.5 |
| 2-101 | 6.2 | 7.8 |
| 2-102 | <5.5 | 6.9 |
| 2-103 | 6.0 | 8.2 |
| 2-104 | <5.4 | 7.1 |
| 2-105 | <5.6 | 7.5 |
| 2-106 | 5.7 | 7.0 |

TABLE 4-continued

| Adenosine receptor binding | | |
|---|---|---|
| Example no. | $A_1$ pKi | $A_{2A}$ pKi |
| 2-107 | <5.5 | 7.2 |
| 2-108 | <5.4 | 6.7 |
| 2-109 | 6.4 | 7.7 |
| 2-110 | 5.6 | 6.9 |
| 2-111 | <5.4 | 6.4 |
| 2-112 | 6.7 | 8.5 |
| 2-113 | 5.9 | 7.6 |
| 3-1 | <5.5 | 6.5 |
| 3-2 | <5.5 | 8.2 |
| 3-3 | <5.5 | 6.8 |
| 3-4 | <5.5 | 6.9 |
| 3-5 | <5.5 | 6.2 |
| 3-6 | <5.5 | 6.7 |
| 3-7 | <5.4 | 7.5 |
| 3-8 | <5.5 | 5.9 |
| 3-9 | <5.5 | 6.4 |
| 3-10 | <5.5 | 8.0 |

Example 5: CB1 Receptor Binding and Antagonism

Receptor binding: Evaluation of the affinity of compounds for the agonist site of the human CB-1 cannabinoid receptor in transfected CHO cells determined in a radioligand binding assay: Cell membrane homogenates (20 μg protein) are incubated for 120 min at 37° C. with 0.5 nM [$^3$H]CP 55940 in the absence or presence of the test compound in a buffer containing 50 mM Tris-HCl (pH 7.4), 5 mM MgCl2, 2.5 mM EDTA and 0.3% BSA. Nonspecific binding is determined in the presence of 10 μM WIN 55212-2.

Following incubation, the samples are filtered rapidly under vacuum through glass fiber filters (GF/B, Packard) presoaked with 0.3% PEI and rinsed several times with an ice-cold buffer containing 50 mM Tris-HCl (pH 7.4) and 0.5% BSA using a 96-sample cell harvester (Unifilter, Packard). The filters are dried then counted for radioactivity in a scintillation counter (Topcount, Packard) using a scintillation cocktail (Microscint 0, Packard).

The standard reference compound is CP 55940 which is tested in each experiment at several concentrations to obtain a competition curve from which its $IC_{50}$ is calculated.

Receptor antagonism: Evaluation of the antagonist activity of compounds at the human CB1 receptor expressed in transfected CHO cells, determined by measuring their effects on agonist-induced cAMP modulation using the HTRF detection method.

The cells are suspended in HBSS buffer (Invitrogen) complemented with 20 mM HEPES (pH 7.4), then distributed in microplates at a density of $5.10^3$ cells/well and preincubated for 5 min at room temperature in the presence of either of the following: HBSS (stimulated control), the reference antagonist AM 281 at 3 μM (basal control) or various concentrations ($IC_{50}$ determination), or the test compounds.

Thereafter, the reference agonist CP 55940 and the adenylyl cyclase activator NKH 477 are added at respective final concentrations of 3 nM and 3 μM.

For basal control measurements, CP 55940 is omitted from the wells containing 3 μM AM 281.

Following 20 min incubation at 37° C., the cells are lysed and the fluorescence acceptor (D2-labeled cAMP) and fluorescence donor (anti-cAMP antibody labeled with europium cryptate) are added.

After 60 min at room temperature, the fluorescence transfer is measured at $\lambda_{ex}$=337 nm and $\lambda_{em}$=620 and 665 nm using a microplate reader (Rubystar, BMG). The cAMP concentration is determined by dividing the signal measured at 665 nm by that measured at 620 nm (ratio).

The results are expressed as a percent inhibition of the control response to 3 nM CP 55940.

The standard reference antagonist is AM 281, which is tested in each experiment at several concentrations to generate a concentration-response curve from which its $IC_{50}$ value is calculated.

In Table 5, blank entries for $K_i$ indicate that the observed binding was too weak to measure a $K_i$ value.

TABLE 5

| CB1 receptor binding and functional assay | | |
|---|---|---|
| Example | Binding Ki (μM) | Antag IC50 (μM) |
| 1-1 | 3.6 | 1.7 |
| 1-2 | 20.1 | >4.9 |
| 1-7 | | 3.2 |
| 1-11 | 2.6 | 5 |
| 1-40 | 24.1 | 7.4 |
| 1-41 | 45.6 | 43.1 |
| 1-42 | 73.4 | >100 |
| 1-44 | 40.0 | 63.3 |
| 1-45 | | >100 |
| 1-52 | 46.1 | 39.4 |
| 1-57 | 62.6 | >100 |
| 1-64 | 23.5 | >100 |
| 1-65 | 19.9 | 9.3 |
| 1-70 | 61.3 | >100 |
| 1-75 | 39.1 | 17.9 |
| 1-80 | 10.8 | 10.2 |
| 1-101 | 4.0 | 2.7 |
| 2-6 | 22.0 | 26.5 |
| 2-10 | | >100 |
| 2-13 | | >100 |
| 2-18 | | >100 |
| 2-25 | | >100 |
| 2-26 | 3.9 | 3.5 |
| 2-30 | 26.5 | 19.5 |
| 2-35 | 18.8 | 4.9 |
| 2-37 | | >100 |
| 2-40 | 75.7 | >100 |
| 2-44 | | >100 |
| 2-46 | 61.0 | >100 |
| 2-51 | 85.0 | >100 |
| 2-53 | 37.7 | >100 |
| 2-54 | 8.2 | 1.1 |
| 2-56 | | >100 |
| 2-57 | 72.7 | >100 |
| 2-60 | 14.6 | 2.4 |
| 2-64 | | 37.4 |
| 2-66 | | >100 |
| 2-73 | 52.0 | >100 |
| 2-80 | | >100 |
| 3-4 | | >100 |

Other embodiments are within the scope of the following claims.

What is claimed is:

1. A compound of Formula (I):

(I)

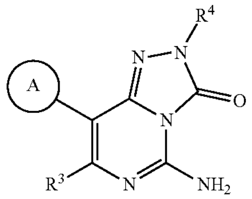

or a pharmaceutically acceptable salt thereof, wherein:
ring A is:

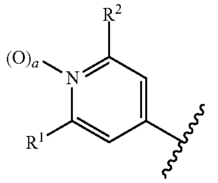

each $R^1$ and each $R^2$, independently, is halo, $C_{1-3}$alkyl, —O—$C_{1-3}$alkyl, —$CO_2R^a$, or —$NR^7R^8$;

wherein alkyl is optionally substituted with one or more substituents independently selected from —$OR^a$ and halo;

$R^3$ is $C_{1-6}$alkyl, $C_{2-6}$alkenyl, $C_{2-6}$alkynyl, aryl, heterocyclyl, heteroaryl, halo, —$OR^a$, —$NR^aR^b$, —$CO_2R^a$, —$CONR^aR^b$, —$NR^a$C(O)—$R^a$, or —NHC(O)—$OR^a$;

wherein heterocyclyl is selected from pyrrolidinyl, piperidinyl, piperazinyl, tetrahydrofuranyl, morpholinyl, thiomorphonlinyl, dihydropyranyl, dihydropyridinyl, tetrahydropyranyl, octahydroquinolinyl, octahydroindolizinyl, and decahydroquinolinyl;

wherein heteroaryl is selected from pyrrolyl, furanyl, pyridyl, imidazolyl, oxazolyl thiazolyl, pyrimidinyl, 5,6,7,8-tetrahydroquinolinyl, benzofuranyl, pyrrolopyridinyl, pyrrolopyrimidinyl, triazinyl, and tetrazolyl; and wherein $R^3$ is optionally substituted with from one to three substituents selected from halo, cyano, —$R^a$, and —$OR^a$;

$R^4$ is H or —$(CHR^c)_i$—$(NR^a)_j$—$R^5$;

$R^5$ is:

(1) $C_{3-8}$cycloalkyl, aryl, 3-, 4-, 6-, or 7-membered heterocyclyl, or 3-, 4-, 6-, or 7-membered heteroaryl;

wherein heterocyclyl and heteroaryl, independently, include from 1 to 4 heteroatoms independently selected from N, O, and $S(O)_k$; and wherein one or two ring atoms of $R^5$ is optionally replaced by —C(═O)—;

(2) a multicyclic, 6- to 11-membered, cycloalkyl, aryl, heterocyclyl, or heteroaryl ring system;

wherein heterocyclyl and heteroaryl, independently, include from 1 to 4 heteroatoms independently selected from N, O, and $S(O)_k$; and wherein one or two ring atoms of $R^5$ is optionally replaced by —C(═O)—; or (3) $C_{1-6}$alkyl, —$OR^a$, —$NR^aR^b$, cyano, —$OS(O)_2$—$C_{1-3}$alkyl, —$CO_2R^a$, —C(O)$NR^aR^b$, —$NR^a$—C(O)—$OR^a$, or —O—C(O)—$NR^aR^b$; and wherein $R^5$ is optionally substituted with from one to four groups —X—$R^6$;

each X, independently, is a bond, —O—, —$NR^a$—, —S(O)—, —$(CH_2)_m$—, or —C(O)—;

each $R^6$, independently, is H, halo, —$OR^a$, $C_{1-6}$alkyl, $C_{3-8}$cycloalkyl, heterocyclyl, heteroaryl, aryl, —$CO_2R^a$, —C(O)$NR^aR^b$, —$(CH_2)_n$—$NR^aR^b$, or cyano;

wherein heterocyclyl and heteroaryl, independently, include from 1 to 4 heteroatoms independently selected from N, O, and $S(O)_k$;

wherein one or two ring atoms of each $C_{3-8}$cycloalkyl, heterocyclyl, heteroaryl, or aryl, independently, is optionally replaced by —C(═O)—;

wherein each of alkyl, cycloalkyl, heterocyclyl, heteroaryl, and aryl is optionally substituted with one or more substituents independently selected from —$R^a$, —$OR^a$, —$(CH_2)_n$—$NR^aR^b$, and halo;

each $R^7$ and each $R^8$, independently, is $R^a$;

or $R^7$ and $R^8$ together with the atom to which they are attached form a 3- to 8-membered heterocyclyl optionally substituted with one or more substituents independently selected from —$OR^a$ and halo;

each $R^a$ and each $R^b$, independently, is H, $C_{1-6}$alkyl, $C_{3-8}$cycloalkyl, or $C_{4-9}$cycloalkylalkyl;

wherein each $R^a$ and each $R^b$, independently, is optionally substituted with one or more substituents independently selected from —OH and halo;

each $R^c$, independently, is H, halo, $C_{1-3}$alkyl, or —$(CH_2)_n$—$NR^aR^b$;

wherein alkyl is optionally substituted with one or more substituents independently selected from —$OR^a$ and halo;

a is 0 or 1;

i is 0, 1, 2, or 3;

j is 0 or 1;

each k, independently, is 0, 1, or 2;

each m, independently, is 1 or 2; and each n, independently, is 0 or 1.

2. The compound of claim 1, wherein $R^5$ is $C_{1-6}$alkyl, —$OR^a$, —$NR^aR^b$, cyano, —$OS(O)_2$-$C_{1-3}$alkyl, —$CO_2R^a$, —C(O)$NR^aR^b$, —$NR^a$—C(O)—$OR^a$, or —O—C(O)—$NR^aR^b$.

3. The compound of claim 1, wherein $R^5$ is aryl, 6-membered heterocyclyl, or 6-membered heteroaryl.

4. The compound of claim 1, wherein $R^5$ is a multicyclic, 6- to 11-membered, cycloalkyl, aryl, heterocyclyl, or heteroaryl ring system.

5. The compound of claim 1, wherein $R^3$ is $C_{1-6}$alkyl, $C_{2-6}$alkenyl, $C_{2-6}$alkynyl, heterocyclyl, heteroaryl, halo, —$OR^a$, —$NR^aR^b$, —$CO_2R^a$, —$CONR^aR^b$, —$NR^a$C(O)—$R^a$, or —NHC(O)—$OR^a$.

6. The compound of claim 1, wherein i is 1 and $R^c$ is H or $C_{1-3}$alkyl; or wherein i is 2 and each $R^c$ is H.

7. A compound which is either a compound of Formula (II):

(II)

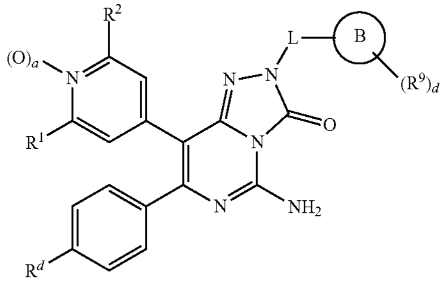

or a pharmaceutically acceptable salt thereof, wherein:

each $R^1$ and each $R^2$, independently, is halo, $C_{1-3}$alkyl, or —O—$C_{1-3}$alkyl;

wherein alkyl is optionally substituted with one or more substituents independently selected from —OH and halo;

ring B is $C_{3-8}$cycloalkyl, aryl, 6- or 7-membered heterocyclyl, or 6- or 7-membered heteroaryl;

wherein heterocyclyl and heteroaryl, independently, include from 1 to 4 heteroatoms independently selected from N and O;

each $R^9$, independently, is halo, —$R^a$, or —$OR^a$;

each $R^a$ and each $R^b$, independently, is H, $C_{1-6}$alkyl, $C_{3-8}$cycloalkyl, or $C_{4-9}$cycloalkylalkyl;

wherein each $R^a$ and each $R^b$, independently, is optionally substituted with one or more substituents independently selected from —OH and halo;

L is —$(CHR^c)_e$—;

each $R^c$, independently, is H, halo, $C_{1-3}$alkyl, or —$(CH_2)_n$—$NR^aR^b$;

wherein alkyl is optionally substituted with one or more substituents independently selected from —$OR^a$ and halo;

$R^d$ is H or halo;

a is 0 or 1;

b is 0, 1, or 2;

d is 0, 1, 2, 3, or 4;

e is 1 or 2; and n is 0 or 1;

or a compound of Formula (III):

(III)

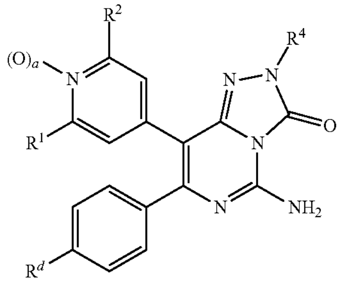

or a pharmaceutically acceptable salt thereof, wherein:

each $R^1$ and each $R^2$, independently, is halo, $C_{1-3}$alkyl, —O—$C_{1-3}$alkyl, —$CO_2R^a$, or —$NR^7R^8$;

wherein alkyl is optionally substituted with one or more substituents independently selected from —$OR^a$ and halo;

$R^4$ is —$(CHR^c)_2$—$R^5$;

$R^5$ is H, halo, $C_{1-3}$alkyl, —$OR^e$, —$COR^e$, —$COOR^e$, —$OS(O)_2R^e$, —OCO—$NR^eR^f$, or —CO—$NR^eR^f$;

wherein alkyl is optionally substituted with one or more substituents independently selected from —OH and halo;

each $R^a$ and each $R^b$, independently, is H, $C_{1-6}$alkyl, $C_{3-8}$cycloalkyl, or $C_{4-9}$cycloalkylalkyl;

wherein each $R^a$ and each $R^b$, independently, is optionally substituted with one or more substituents independently selected from —OH and halo;

each $R^c$, independently, is H, halo, $C_{1-3}$alkyl, or —$(CH_2)_n$—$NR^aR^b$;

wherein alkyl is optionally substituted with one or more substituents independently selected from —$OR^a$ and halo;

$R^d$ is H or halo;

each $R^e$ and each $R^f$, independently, is H or $C_{1-6}$alkyl;

wherein alkyl is optionally substituted with one or more substituents independently selected from —OH and halo;

a is 0 or 1; and each n, independently, is 0 or 1.

8. The compound of claim 7, wherein $R^5$ is H, —$CH_3$, —$CH_2F$, —$CHF_2$, or —$CF_3$.

9. A compound of claim 1, or pharmaceutically acceptable salt thereof, selected from the group consisting of:

5-amino-8-(2,6-dimethyl-4-pyridyl)-2-[(4-fluorophenyl)methyl]-7-phenyl-[1,2,4]triazolo[4,3-c]pyrimidin-3-one;

5-amino-8-(2,6-dimethyl-4-pyridyl)-2-[(5-fluoro-2-pyridyl)methyl]-7-phenyl-[1,2,4]triazolo[4,3-c]pyrimidin-3-one;

5-amino-8-(2,6-dimethyl-4-pyridyl)-2-[(4-methoxyphenyl)methyl]-7-phenyl-[1,2,4]triazolo[4,3-c]pyrimidin-3-one;

5-amino-8-(2,6-dimethyl-4-pyridyl)-2-[(4-hydroxyphenyl)methyl]-7-phenyl-[1,2,4]triazolo[4,3-c]pyrimidin-3-one;

5-amino-8-(2,6-dimethyl-4-pyridyl)-7-phenyl-2-(pyridazin-3-ylmethyl)-[1,2,4]triazolo[4,3-c]pyrimidin-3-one;

5-amino-8-(2,6-dimethyl-4-pyridyl)-2-[(6-methoxy-2-pyridyl)methyl]-7-phenyl-[1,2,4]triazolo[4,3-c]pyrimidin-3-one;

5-amino-8-(2,6-dimethyl-4-pyridyl)-2-[(5-fluoro-6-methoxy-2-pyridyl)methyl]-7-phenyl-[1,2,4]triazolo[4,3-c]pyrimidin-3-one;

5-amino-8-(2,6-dimethyl-4-pyridyl)-2-[(5-fluoro-6-oxo-1H-pyridin-2-yl)methyl]-7-phenyl-[1,2,4]triazolo[4,3-c]pyrimidin-3-one;

5-amino-8-(2,6-dimethyl-4-pyridyl)-2-[(6-oxo-1H-pyridin-2-yl)methyl]-7-phenyl-[1,2,4]triazolo[4,3-c]pyrimidin-3-one;

5-amino-8-(2,6-dimethyl-4-pyridyl)-2-[(5-fluoro-1-methyl-6-oxo-2-pyridyl)methyl]-7-phenyl-[1,2,4]triazolo[4,3-c]pyrimidin-3-one;

5-amino-2-[1-(2,4-difluorophenyl)ethyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-7-phenyl-2-(4-pyridylmethyl)-[1,2,4]triazolo[4,3-c]pyrimidin-3-one;

5-amino-8-(2,6-dimethyl-4-pyridyl)-2-isothiochroman-4-yl-7-phenyl-[1,2,4]triazolo[4,3-c]pyrimidin-3-one;

(R)-5-amino-8-(2,6-dimethyl-4-pyridyl)-2-(7-fluorotetralin-1-yl)-7-phenyl-[1,2,4]triazolo[4,3-c]pyrimidin-3-one;

5-amino-2-[1-(2,5-difluorophenyl)ethyl]-8-(2,6-dimethyl-4-pyridyl)-7-phenyl-[1,2,4]triazolo[4,3-c]pyrimidin-3-one;

5-amino-2-[[2-(difluoromethylsulfanyl)phenyl]methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-(o-tolylmethyl)-7-phenyl-[1,2,4]triazolo[4,3-c]pyrimidin-3-one;

5-amino-8-(2,6-dimethyl-4-pyridyl)-2-[(4-fluoro-2-methyl-phenyl)methyl]-7-phenyl-[1,2,4]triazolo[4,3-c]pyrimidin-3-one;

5-amino-8-(2,6-dimethyl-4-pyridyl)-7-phenyl-2-[(2-pyrazol-1-yl-3-pyridyl)methyl]-[1,2,4]triazolo[4,3-c]pyrimidin-3-one;

5-amino-8-(2,6-dimethyl-4-pyridyl)-7-phenyl-2-[1-(2-pyridyl)ethyl]-[1,2,4]triazolo[4,3-c]pyrimidin-3-one;

5-amino-2-[(2-chloro-3-fluoro-phenyl)methyl]-8-(2,6-dimethyl-4-pyridyl)-7-phenyl-[1,2,4]triazolo[4,3-c]pyrimidin-3-one;

5-amino-2-[[2-(cyclopropylmethoxy)phenyl]methyl]-8-(2,6-dimethyl-4-pyridyl)-7-phenyl-[1,2,4]triazolo[4,3-c]pyrimidin-3-one;

5-amino-2-[(2,6-difluorophenyl)methyl]-8-(2,6-dimethyl-4-pyridyl)-7-phenyl-[1,2,4]triazolo[4,3-c]pyrimidin-3-one;

5-amino-2-[[2-[(dimethylamino)methyl]phenyl]methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[(2-ethoxyphenyl)methyl]-7-phenyl-[1,2,4]triazolo[4,3-c]pyrimidin-3-one;

(R)-5-amino-8-(2,6-dimethyl-4-pyridyl)-7-phenyl-2-[1-(4-pyridyl)ethyl]-[1,2,4]triazolo[4,3-c]pyrimidin-3-one;

5-amino-8-(2,6-dimethyl-4-pyridyl)-7-phenyl-2-[1-(3-pyridyl)ethyl]-[1,2,4]triazolo[4,3-c]pyrimidin-3-one;

5-amino-8-(2,6-dimethyl-4-pyridyl)-2-[(2-methoxy-3-pyridyl)methyl]-7-phenyl-[1,2,4]triazolo[4,3-c]pyrimidin-3-one;

5-amino-8-(2,6-dimethyl-4-pyridyl)-2-[(4-methoxy-6-methyl-2-pyridyl)methyl]-7-phenyl-[1,2,4]triazolo[4,3-c]pyrimidin-3-one;

5-amino-8-(2,6-dimethyl-4-pyridyl)-7-phenyl-2-[[2-(4-piperidyl)phenyl]methyl]-[1,2,4]triazolo[4,3-c]pyrimidin-3-one;

5-amino-8-(2,6-dimethyl-4-pyridyl)-7-phenyl-2-[1-phenyl-2-(2,2,2-trifluoroethylamino)ethyl]-[1,2,4]triazolo[4,3-c]pyrimidin-3-one;

5-amino-8-(2,6-dimethyl-4-pyridyl)-7-phenyl-2-[[2-(4-piperidylmethyl)phenyl]methyl]-[1,2,4]triazolo[4,3-c]pyrimidin-3-one;

5-amino-8-(2,6-dimethyl-4-pyridyl)-2-[(6-methoxypyridazin-3-yl)methyl]-7-phenyl-[1,2,4]triazolo[4,3-c]pyrimidin-3-one;

5-amino-2-(2-amino-1-(2,6-difluorophenyl)ethyl)-8-(2,6-dimethylpyridin-4-yl)-7-phenyl-[1,2,4]triazolo[4,3-c]pyrimidin-3 (2H)-one;

5-amino-8-(2,6-dimethyl-4-pyridyl)-2-[(5-fluoropyrimidin-2-yl)methyl]-7-phenyl-[1,2,4]triazolo[4,3-c]pyrimidin-3-one;

5-amino-2-[(6-amino-5-fluoro-2-pyridyl)methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[(6-hydroxypyridazin-3-yl)methyl]-7-phenyl-[1,2,4]triazolo[4,3-c]pyrimidin-3-one;

5-amino-8-(2,6-dimethyl-4-pyridyl)-2-[1-(5-fluoro-2-pyridyl) propyl]-7-phenyl-[1,2,4]triazolo[4,3-c]pyrimidin-3-one;

5-amino-8-(2,6-dimethyl-4-pyridyl)-2-[1-(5-fluoro-2-pyridyl) propyl]-7-phenyl-[1,2,4]triazolo[4,3-c]pyrimidin-3-one;

5-amino-8-(2,6-dimethyl-4-pyridyl)-2-[1-(5-fluoro-2-pyridyl) propyl]-7-phenyl-[1,2,4]triazolo[4,3-c]pyrimidin-3-one;

5-amino-2-[(3-chloro-5-fluoro-2-pyridyl)methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[(5-fluoro-2-methoxy-3-pyridyl)methyl]-7-phenyl-[1,2,4]triazolo[4,3-c]pyrimidin-3-one;

5-amino-8-(2,6-dimethyl-4-pyridyl)-7-(4-fluorophenyl)-2-(pyridazin-3-ylmethyl)-[1,2,4]triazolo[4,3-c]pyrimidin-3-one;

5-amino-8-(2,6-dimethyl-1-oxido-pyridin-1-ium-4-yl)-2-[(5-fluoro-2-pyridyl)methyl]-7-phenyl-[1,2,4]triazolo[4,3-c]pyrimidin-3-one;

5-amino-8-(2,6-dimethyl-1-oxido-pyridin-1-ium-4-yl)-7-phenyl-2-(pyridazin-3-ylmethyl)-[1,2,4]triazolo[4,3-c]pyrimidin-3-one;

5-amino-2-[(5-fluoro-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[(6-amino-5-fluoro-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[1-(5-fluoro-2-pyridyl) propyl]-8-[2-(hydroxymethyl)-6-methyl-4-pyridyl]-7-phenyl-[1,2,4]triazolo[4,3-c]pyrimidin-3-one;

5-amino-2-[1-(5-fluoro-2-pyridyl) propyl]-8-[2-(hydroxymethyl)-6-methyl-4-pyridyl]-7-phenyl-[1,2,4]triazolo[4,3-c]pyrimidin-3-one;

5-amino-2-[(3-fluoro-5-methoxy-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[(5-fluoro-6-hydroxy-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[(5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one;

5-amino-2-[(3-chloro-5-fluoro-2-pyridyl)methyl]-8-[2-(hydroxymethyl)-6-methyl-4-pyridyl]-7-phenyl-[1,2,4]triazolo[4,3-c]pyrimidin-3-one;

5-amino-2-[(6-amino-5-fluoro-2-pyridyl)methyl]-8-[2-(hydroxymethyl)-6-methyl-4-pyridyl]-7-(2,3,4,5,6-pentadeuteriophenyl)-[1,2,4]triazolo[4,3-c]pyrimidin-3-one;

5-amino-8-[2-(hydroxymethyl)-6-methyl-4-pyridyl]-2-[(5-methyl-2-pyridyl)methyl]-7-phenyl-[1,2,4]triazolo[4,3-c]pyrimidin-3-one;

5-amino-2-[(5-bromo-2-pyridyl)methyl]-8-[2-(hydroxymethyl)-6-methyl-4-pyridyl]-7-phenyl-[1,2,4]triazolo[4,3-c]pyrimidin-3-one;

6-[[5-amino-8-[2-(hydroxymethyl)-6-methyl-4-pyridyl]-3-oxo-7-phenyl-[1,2,4]triazolo[4,3-c]pyrimidin-2-yl]methyl] pyridine-3-carbonitrile;

5-amino-2-[(5-chloro-2-pyridyl)methyl]-8-[2-(hydroxymethyl)-6-methyl-4-pyridyl]-7-phenyl-[1,2,4]triazolo[4,3-c]pyrimidin-3-one;

5-amino-8-[2-(hydroxymethyl)-6-methyl-4-pyridyl]-7-phenyl-2-(pyridazin-3-ylmethyl)-[1,2,4]triazolo[4,3-c]pyrimidin-3-one;

5-amino-8-[2-(hydroxymethyl)-6-methyl-4-pyridyl]-2-[(2-methoxy-3-pyridyl)methyl]-7-phenyl-[1,2,4]triazolo[4,3-c]pyrimidin-3-one;

5-amino-7-(4-fluorophenyl)-8-[2-(hydroxymethyl)-6-methyl-4-pyridyl]-2-(pyridazin-3-ylmethyl)-[1,2,4]triazolo[4,3-c]pyrimidin-3-one;

5-amino-7-(4-fluorophenyl)-2-[(5-fluoro-2-pyridyl)methyl]-8-[2-(hydroxymethyl)-6-methyl-4-pyridyl]-[1,2,4]triazolo[4,3-c]pyrimidin-3-one;

5-amino-2-[(6-amino-5-fluoro-2-pyridyl)methyl]-7-(4-fluorophenyl)-8-[2-(hydroxymethyl)-6-methyl-4-pyridyl]-[1,2,4]triazolo[4,3-c]pyrimidin-3-one;

5-amino-7-(4-fluorophenyl)-8-[2-(hydroxymethyl)-6-methyl-4-pyridyl]-2-[(5-methyl-2-pyridyl)methyl]-[1,2,4]triazolo[4,3-c]pyrimidin-3-one;

5-amino-2-[(5-chloro-2-pyridyl)methyl]-7-(4-fluorophenyl)-8-[2-(hydroxymethyl)-6-methyl-4-pyridyl]-[1,2,4]triazolo[4,3-c]pyrimidin-3-one;

6-[[5-amino-7-(4-fluorophenyl)-8-[2-(hydroxymethyl)-6-methyl-4-pyridyl]-3-oxo-[1,2,4]triazolo[4,3-c]pyrimidin-2-yl]methyl] pyridine-3-carbonitrile;

5-amino-2-[(6-amino-5-fluoro-2-pyridyl)methyl]-8-[2-(hydroxymethyl)-6-methoxy-4-pyridyl]-7-phenyl-[1,2,4]triazolo[4,3-c]pyrimidin-3-one;

5-amino-2-[(5-chloro-2-pyridyl)methyl]-8-[2-(hydroxymethyl)-6-methoxy-4-pyridyl]-7-phenyl-[1,2,4]triazolo[4,3-c]pyrimidin-3-one;

5-amino-8-[2-(hydroxymethyl)-6-methoxy-4-pyridyl]-2-[(5-methyl-2-pyridyl)methyl]-7-phenyl-[1,2,4]triazolo[4,3-c]pyrimidin-3-one;

5-amino-7-(4-fluorophenyl)-8-[2-(hydroxymethyl)-6-methoxy-4-pyridyl]-2-[(5-methyl-2-pyridyl)methyl]-[1,2,4]triazolo[4,3-c]pyrimidin-3-one;

5-amino-2-[(5-chloro-2-pyridyl)methyl]-7-(4-fluorophenyl)-8-[2-(hydroxymethyl)-6-methoxy-4-pyridyl]-[1,2,4]triazolo[4,3-c]pyrimidin-3-one;

5-amino-8-[2-chloro-6-(hydroxymethyl)-4-pyridyl]-2-[(5-fluoro-2-pyridyl)methyl]-7-phenyl-[1,2,4]triazolo[4,3-c]pyrimidin-3-one;

5-amino-2-[(6-amino-5-fluoro-2-pyridyl)methyl]-8-[2-chloro-6-(hydroxymethyl)-4-pyridyl]-7-phenyl-[1,2,4]triazolo[4,3-c]pyrimidin-3-one;

5-amino-8-[2-(dimethylamino)-6-methyl-4-pyridyl]-2-[(5-fluoro-2-pyridyl)methyl]-7-phenyl-[1,2,4]triazolo[4,3-c]pyrimidin-3-one;

5-amino-2-[(5-fluoro-2-pyridyl)methyl]-8-[2-methyl-6-(trifluoromethyl)-4-pyridyl]-7-phenyl-[1,2,4]triazolo[4,3-c]pyrimidin-3-one;

5-amino-2-[(5-fluoro-2-pyridyl)methyl]-8-[2-(hydroxymethyl)-6-methoxy-4-pyridyl]-7-phenyl-[1,2,4]triazolo[4,3-c]pyrimidin-3-one;

5-amino-2-[(5-fluoro-2-pyridyl)methyl]-8-(2-hydroxy-6-methyl-4-pyridyl)-7-phenyl-[1,2,4]triazolo[4,3-c]pyrimidin-3-one;

5-amino-8-[2-(azetidin-1-yl)-6-methyl-4-pyridyl]-2-[(5-fluoro-2-pyridyl)methyl]-7-phenyl-[1,2,4]triazolo[4,3-c]pyrimidin-3-one;

5-amino-8-(2-chloro-6-methyl-4-pyridyl)-2-[(5-fluoro-2-pyridyl)methyl]-7-phenyl-[1,2,4]triazolo[4,3-c]pyrimidin-3-one;

5-amino-8-(2-chloro-6-methyl-4-pyridyl)-2-[(5-methoxy-2-pyridyl)methyl]-7-phenyl-[1,2,4]triazolo[4,3-c]pyrimidin-3-one;

5-amino-2-[(5-fluoro-2-pyridyl)methyl]-8-(2-methoxy-6-methyl-4-pyridyl)-7-phenyl-[1,2,4]triazolo[4,3-c]pyrimidin-3-one;

5-amino-8-[2-chloro-6-(trifluoromethyl)-4-pyridyl]-2-[(5-fluoro-2-pyridyl)methyl]-7-phenyl-[1,2,4]triazolo[4,3-c]pyrimidin-3-one;

5-amino-8-(2,6-dimethyl-4-pyridyl)-7-phenyl-2-(2-phenylethyl)-[1,2,4]triazolo[4,3-c]pyrimidin-3-one;

5-amino-8-(2,6-dimethyl-4-pyridyl)-2-(1-methyl-2-phenyl-ethyl)-7-phenyl-[1,2,4]triazolo[4,3-c]pyrimidin-3-one;

5-amino-8-(2,6-dimethyl-4-pyridyl)-2-[2-(4-hydroxyphenyl)ethyl]-7-phenyl-[1,2,4]triazolo[4,3-c]pyrimidin-3-one;

5-amino-8-(2,6-dimethyl-4-pyridyl)-2-[2-(4-fluorophenyl)ethyl]-7-phenyl-[1,2,4]triazolo[4,3-c]pyrimidin-3-one;

methyl 4-[2-[5-amino-8-(2,6-dimethyl-4-pyridyl)-3-oxo-7-phenyl-[1,2,4]triazolo[4,3-c]pyrimidin-2-yl]ethyl]benzoate;

4-[2-[5-amino-8-(2,6-dimethyl-4-pyridyl)-3-oxo-7-phenyl-[1,2,4]triazolo[4,3-c]pyrimidin-2-yl]ethyl]benzoic acid;

5-amino-8-(2,6-dimethyl-4-pyridyl)-7-phenyl-2-[2-(2-pyridyl)ethyl]-[1,2,4]triazolo[4,3-c]pyrimidin-3-one;

5-amino-8-(2,6-dimethyl-4-pyridyl)-7-(4-fluorophenyl)-2-(2-phenylethyl)-[1,2,4]triazolo[4,3-c]pyrimidin-3-one;

5-amino-8-[2-methyl-6-(trifluoromethyl)-4-pyridyl]-7-phenyl-2-(2-phenylethyl)-[1,2,4]triazolo[4,3-c]pyrimidin-3-one;

5-amino-8-(2-chloro-6-methyl-4-pyridyl)-7-phenyl-2-(2-phenylethyl)-[1,2,4]triazolo[4,3-c]pyrimidin-3-one;

5-amino-8-[2-(azetidin-1-yl)-6-methyl-4-pyridyl]-7-phenyl-2-(2-phenylethyl)-[1,2,4]triazolo[4,3-c]pyrimidin-3-one;

5-[2-[5-amino-8-(2,6-dimethyl-4-pyridyl)-3-oxo-7-phenyl-[1,2,4]triazolo[4,3-c]pyrimidin-2-yl]ethylamino]-2-chloro-N-methyl-benzamide;

5-amino-8-(2,6-dimethyl-4-pyridyl)-7-phenyl-2-[2-[1-([1,2,4]triazolo[4,3-a]pyrimidin-3-yl)ethylamino]ethyl]-[1,2,4]triazolo[4,3-c]pyrimidin-3-one;

5-amino-8-(2,6-dimethyl-4-pyridyl)-2-[2-[methyl-(1-phenyl-4-piperidyl)amino]ethyl]-7-phenyl-[1,2,4]triazolo[4,3-c]pyrimidin-3-one;

5-amino-8-(2,6-dimethyl-4-pyridyl)-2-[2-[[(1S)-1-(6-methyl-2-pyridyl)ethyl]amino]ethyl]-7-phenyl-[1,2,4]triazolo[4,3-c]pyrimidin-3-one;

5-amino-8-(2,6-dimethyl-4-pyridyl)-2-[2-[[1-(3-methyl-1H-pyrazol-5-yl)-4-piperidyl]amino]ethyl]-7-phenyl-[1,2,4]triazolo[4,3-c]pyrimidin-3-one;

5-amino-8-(2,6-dimethyl-4-pyridyl)-2-[2-[2-(1-methylpyrrol-2-yl)azepan-1-yl]ethyl]-7-phenyl-[1,2,4]triazolo[4,3-c]pyrimidin-3-one;

5-amino-8-(2,6-dimethyl-4-pyridyl)-2-[2-[4-[(5-methyl-2-pyridyl)amino]-1-piperidyl]ethyl]-7-phenyl-[1,2,4]triazolo[4,3-c]pyrimidin-3-one;

5-amino-8-(2,6-dimethyl-4-pyridyl)-2-[2-[3-(3-methyl-5-oxo-4H-pyrazol-1-yl)anilino]ethyl]-7-phenyl-[1,2,4]triazolo[4,3-c]pyrimidin-3-one;

5-amino-8-(2,6-dimethyl-4-pyridyl)-2-[2-[[2-(hydroxymethyl)tetralin-2-yl]-methyl-amino]ethyl]-7-phenyl-[1,2,4]triazolo[4,3-c]pyrimidin-3-one;

5-amino-2-[1-(aminomethyl)-2-(2,4-difluorophenyl)ethyl]-8-(2,6-dimethyl-4-pyridyl)-7-phenyl-[1,2,4]triazolo[4,3-c]pyrimidin-3-one;

5-amino-2-[[(3R)-4-benzylmorpholin-3-yl]methyl]-8-(2,6-dimethyl-4-pyridyl)-7-phenyl-[1,2,4]triazolo[4,3-c]pyrimidin-3-one;

5-amino-2-[(4-benzyl-4-piperidyl)methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-(2-morpholin-3-yl-1-phenyl-ethyl)-7-phenyl-[1,2,4]triazolo[4,3-c]pyrimidin-3-one;

5-amino-2-(5-aminoindan-2-yl)-8-(2,6-dimethyl-4-pyridyl)-7-phenyl-[1,2,4]triazolo[4,3-c]pyrimidin-3-one;

5-amino-8-(2,6-dimethyl-4-pyridyl)-7-phenyl-2H-[1,2,4]triazolo[4,3-c]pyrimidin-3-one;

5-amino-8-(2,6-dimethyl-4-pyridyl)-2-methyl-7-phenyl-[1,2,4]triazolo[4,3-c]pyrimidin-3-one;

5-amino-8-(2,6-dimethyl-4-pyridyl)-2-ethyl-7-phenyl-[1,2,4]triazolo[4,3-c]pyrimidin-3-one;

5-amino-8-(2,6-dimethyl-4-pyridyl)-2-isopropyl-7-phenyl-[1,2,4]triazolo[4,3-c]pyrimidin-3-one;

5-amino-8-(2,6-dimethyl-4-pyridyl)-2-isopentyl-7-phenyl-[1,2,4]triazolo[4,3-c]pyrimidin-3-one;

5-amino-8-(2,6-dimethyl-4-pyridyl)-7-phenyl-2-(3,3,3-trifluoropropyl)-[1,2,4]triazolo[4,3-c]pyrimidin-3-one;

5-amino-8-(2,6-dimethyl-4-pyridyl)-2-(2-hydroxyethyl)-7-phenyl-[1,2,4]triazolo[4,3-c]pyrimidin-3-one;

5-amino-8-(2,6-dimethyl-4-pyridyl)-2-(3-fluoropropyl)-7-phenyl-[1,2,4]triazolo[4,3-c]pyrimidin-3-one;

2-[5-amino-8-(2,6-dimethyl-4-pyridyl)-3-oxo-7-phenyl-[1,2,4]triazolo[4,3-c]pyrimidin-2-yl]ethyl methanesulfonate;

5-amino-8-(2,6-dimethyl-4-pyridyl)-2-(2-methoxyethyl)-7-phenyl-[1,2,4]triazolo[4,3-c]pyrimidin-3-one;

3-[5-amino-8-(2,6-dimethyl-4-pyridyl)-3-oxo-7-phenyl-[1,2,4]triazolo[4,3-c]pyrimidin-2-yl] propanenitrile;

ethyl N-[2-[5-amino-8-(2,6-dimethyl-4-pyridyl)-3-oxo-7-phenyl-[1,2,4]triazolo[4,3-c]pyrimidin-2-yl]ethyl] carbamate;

ethyl N-[2-[5-amino-8-(2,6-dimethyl-4-pyridyl)-3-oxo-7-phenyl-[1,2,4]triazolo[4,3-c]pyrimidin-2-yl]ethyl]-N-methyl-carbamate;

tert-butyl N-[2-[5-amino-8-(2,6-dimethyl-4-pyridyl)-3-oxo-7-phenyl-[1,2,4]triazolo[4,3-c]pyrimidin-2-yl] ethyl] carbamate;

methyl 3-[5-amino-8-(2,6-dimethyl-4-pyridyl)-3-oxo-7-phenyl-[1,2,4]triazolo[4,3-c]pyrimidin-2-yl] propanoate;

2-[5-amino-8-(2,6-dimethyl-4-pyridyl)-3-oxo-7-phenyl-[1,2,4]triazolo[4,3-c]pyrimidin-2-yl]ethyl N-ethylcarbamate;

5-amino-2-(3,3-difluoropropyl)-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[2-[ethyl(methyl) amino]ethyl]-7-phenyl-[1,2,4]triazolo[4,3-c]pyrimidin-3-one;

5-amino-2-[2-[cyclopropyl(methyl)amino]ethyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-7-phenyl-2-propyl-[1,2,4]triazolo[4,3-c]pyrimidin-3-one;

5-amino-8-(2,6-dimethyl-4-pyridyl)-2-isobutyl-7-phenyl-[1,2,4]triazolo[4,3-c]pyrimidin-3-one;

2-[5-amino-8-(2,6-dimethyl-4-pyridyl)-3-oxo-7-phenyl-[1,2,4]triazolo[4,3-c]pyrimidin-2-yl] acetamide;

3-[5-amino-8-(2,6-dimethyl-4-pyridyl)-3-oxo-7-phenyl-[1,2,4]triazolo[4,3-c]pyrimidin-2-yl]-N,N-dimethyl-propanamide;

5-amino-8-(2,6-dimethyl-4-pyridyl)-2-[3-hydroxy-2-(hydroxymethyl) propyl]-7-phenyl-[1,2,4]triazolo[4,3-c] pyrimidin-3-one;

2-[5-amino-8-(2,6-dimethyl-4-pyridyl)-3-oxo-7-phenyl-[1,2,4]triazolo[4,3-c]pyrimidin-2-yl]-N,N-dimethyl-acetamide;

5-amino-2-[(3,3-difluorocyclopentyl)methyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[(2-ethyl-2-methyl-cyclopropyl)methyl]-7-phenyl-[1,2,4]triazolo [4,3-c]pyrimidin-3-one;

2-[5-amino-8-(2,6-dimethyl-4-pyridyl)-3-oxo-7-phenyl-[1,2,4]triazolo[4,3-c]pyrimidin-2-yl]-N-cyclopropyl-N-methyl-acetamide;

methyl 1-[[5-amino-8-(2,6-dimethyl-4-pyridyl)-3-oxo-7-phenyl-[1,2,4]triazolo[4,3-c]pyrimidin-2-yl]methyl] cyclopentanecarboxylate;

5-amino-8-(2,6-dimethyl-4-pyridyl)-7-phenyl-2-[2-(trifluoromethoxy)ethyl]-[1,2,4]triazolo[4,3-c]pyrimidin-3-one;

3-[5-amino-8-(2,6-dimethyl-4-pyridyl)-3-oxo-7-phenyl-[1,2,4]triazolo[4,3-c]pyrimidin-2-yl] propanamide;

5-amino-8-(2,6-dimethyl-4-pyridyl)-7-(2,3,4,5,6-pentadeuteriophenyl)-2-(3,3,3-trifluoropropyl)-[1,2,4]triazolo[4,3-c]pyrimidin-3-one;

5-amino-8-(2,6-dimethyl-4-pyridyl)-7-(4-fluorophenyl)-2-(3,3,3-trifluoropropyl)-[1,2,4]triazolo[4,3-c]pyrimidin-3-one;

5-amino-7-(2,4-difluorophenyl)-8-(2,6-dimethyl-4-pyridyl)-2-(3,3,3-trifluoropropyl)-[1,2,4]triazolo[4,3-c]pyrimidin-3-one;

5-amino-8-(2,6-dimethyl-4-pyridyl)-7-(4-methoxyphenyl)-2-(3,3,3-trifluoropropyl)-[1,2,4]triazolo[4,3-c]pyrimidin-3-one;

4-[5-amino-8-(2,6-dimethyl-4-pyridyl)-3-oxo-2-(3,3,3-trifluoropropyl)-[1,2,4]triazolo[4,3-c]pyrimidin-7-yl] benzonitrile;

5-amino-8-(2,6-dimethyl-4-pyridyl)-7-(2-pyridyl)-2-(3,3,3-trifluoropropyl)-[1,2,4]triazolo[4,3-c]pyrimidin-3-one;

5-amino-8-(2,6-dimethyl-4-pyridyl)-7-(4-pyridyl)-2-(3,3,3-trifluoropropyl)-[1,2,4]triazolo[4,3-c]pyrimidin-3-one;

5-amino-8-(2,6-dimethyl-4-pyridyl)-7-(3-pyridyl)-2-(3,3,3-trifluoropropyl)-[1,2,4]triazolo[4,3-c]pyrimidin-3-one;

5-amino-8-(2,6-dimethyl-4-pyridyl)-7-(5-fluoro-2-pyridyl)-2-(3,3,3-trifluoropropyl)-[1,2,4]triazolo[4,3-c]pyrimidin-3-one;

5-amino-8-(2,6-dimethyl-4-pyridyl)-7-(4-methylpyrazol-1-yl)-2-(3,3,3-trifluoropropyl)-[1,2,4]triazolo[4,3-c] pyrimidin-3-one;

5-amino-8-(2,6-dimethyl-4-pyridyl)-7-(2-furyl)-2-(3,3,3-trifluoropropyl)-[1,2,4]triazolo[4,3-c]pyrimidin-3-one;

5-amino-8-(2,6-dimethyl-4-pyridyl)-7-(5-methyl-2-furyl)-2-(3,3,3-trifluoropropyl)-[1,2,4]triazolo[4,3-c]pyrimidin-3-one;

5-amino-8-(2,6-dimethyl-4-pyridyl)-7-(4-methylthiazol-2-yl)-2-(3,3,3-trifluoropropyl)-[1,2,4]triazolo[4,3-c] pyrimidin-3-one;

5-amino-8-[2-chloro-6-(hydroxymethyl)-4-pyridyl]-7-phenyl-2-(3,3,3-trifluoropropyl)-[1,2,4]triazolo[4,3-c] pyrimidin-3-one;

5-amino-8-[2-(hydroxymethyl)-6-methoxy-4-pyridyl]-7-phenyl-2-(3,3,3-trifluoropropyl)-[1,2,4]triazolo[4,3-c] pyrimidin-3-one;

5-amino-7-(4-fluorophenyl)-8-[2-(hydroxymethyl)-6-methoxy-4-pyridyl]-2-(3,3,3-trifluoropropyl)-[1,2,4] triazolo[4,3-c]pyrimidin-3-one;

5-amino-8-(2-chloro-6-methyl-4-pyridyl)-7-phenyl-2-(3,3,3-trifluoropropyl)-[1,2,4]triazolo[4,3-c]pyrimidin-3-one;

5-amino-8-(2-chloro-6-methyl-4-pyridyl)-7-(4-fluorophenyl)-2-methyl-[1,2,4]triazolo[4,3-c]pyrimidin-3-one;

5-amino-8-(2-chloro-6-methyl-4-pyridyl)-7-(4-fluorophenyl)-2-(3,3,3-trifluoropropyl)-[1,2,4]triazolo[4,3-c] pyrimidin-3-one;

5-amino-8-[2-(hydroxymethyl)-6-methyl-4-pyridyl]-7-phenyl-2-(3,3,3-trifluoropropyl)-[1,2,4]triazolo[4,3-c] pyrimidin-3-one;

methyl 4-[5-amino-3-oxo-7-phenyl-2-(3,3,3-trifluoropropyl)-[1,2,4]triazolo[4,3-c]pyrimidin-8-yl]-6-methyl-pyridine-2-carboxylate;

5-amino-8-[2-(hydroxymethyl)-6-(trifluoromethyl)-4-pyridyl]-7-phenyl-2-(3,3,3-trifluoropropyl)-[1,2,4]triazolo[4,3-c]pyrimidin-3-one;

tert-butyl 3-[5-amino-8-(2,6-dimethyl-4-pyridyl)-3-oxo-7-phenyl-[1,2,4]triazolo[4,3-c]pyrimidin-2-yl]piperidine-1-carboxylate;

5-amino-8-(2,6-dimethyl-4-pyridyl)-7-phenyl-2-(3-piperidyl)-[1,2,4]triazolo[4,3-c]pyrimidin-3-one;

5-amino-8-(2,6-dimethyl-1-oxido-pyridin-1-ium-4-yl)-7-phenyl-2-(3,3,3-trifluoropropyl)-[1,2,4]triazolo[4,3-c]pyrimidin-3-one;

5-amino-8-(2,6-dimethyl-1-oxido-pyridin-1-ium-4-yl)-2-isobutyl-7-phenyl-[1,2,4]triazolo[4,3-c]pyrimidin-3-one;

5-amino-8-(2,6-dimethyl-1-oxido-pyridin-1-ium-4-yl)-7-(4-fluorophenyl)-2-(3,3,3-trifluoropropyl)-[1,2,4]triazolo[4,3-c]pyrimidin-3-one;

5-amino-2-[(3-fluoro-1-bicyclo[1.1.1]pentanyl)methyl]-8-[2-(hydroxymethyl)-6-methyl-4-pyridyl]-7-phenyl-[1,2,4]triazolo[4,3-c]pyrimidin-3-one;

5-amino-2-[(4-fluorocuban-1-yl)methyl]-8-[2-(hydroxymethyl)-6-methyl-4-pyridyl]-7-phenyl-[1,2,4]triazolo[4,3-c]pyrimidin-3-one;

5-amino-8-[2-(hydroxymethyl)-6-methyl-4-pyridyl]-7-(2,3,4,5,6-pentadeuteriophenyl)-2-(3,3,3-trifluoropropyl)-[1,2,4]triazolo[4,3-c]pyrimidin-3-one;

5-amino-2-(cuban-1-ylmethyl)-8-[2-(hydroxymethyl)-6-methyl-4-pyridyl]-7-phenyl-[1,2,4]triazolo[4,3-c]pyrimidin-3-one;

5-amino-2-(3-bicyclo[1.1.1]pentanylmethyl)-8-[2-(hydroxymethyl)-6-methyl-4-pyridyl]-7-phenyl-[1,2,4]triazolo[4,3-c]pyrimidin-3-one;

5-amino-7-(4-fluorophenyl)-8-[2-(hydroxymethyl)-6-methyl-4-pyridyl]-2-(3,3,3-trifluoropropyl)-[1,2,4]triazolo[4,3-c]pyrimidin-3-one;

tert-butyl (R)-2-((5-amino-8-(2,6-dimethylpyridin-4-yl)-3-oxo-7-phenyl-[1,2,4]triazolo[4,3-c]pyrimidin-2 (3H)-yl)methyl) morpholine-4-carboxylate;

(R)-5-amino-8-(2,6-dimethylpyridin-4-yl)-2-(morpholin-2-ylmethyl)-7-phenyl-[1,2,4]triazolo[4,3-c]pyrimidin-3 (2H)-one;

tert-butyl 4-[[5-amino-8-(2,6-dimethyl-4-pyridyl)-3-oxo-7-phenyl-[1,2,4]triazolo[4,3-c]pyrimidin-2-yl]methyl] piperidine-1-carboxylate;

5-amino-8-(2,6-dimethyl-4-pyridyl)-7-phenyl-2-(4-piperidylmethyl)-[1,2,4]triazolo[4,3-c]pyrimidin-3-one;

tert-butyl (2S)-2-[[5-amino-8-(2,6-dimethyl-4-pyridyl)-3-oxo-7-phenyl-[1,2,4]triazolo[4,3-c]pyrimidin-2-yl] methyl]morpholine-4-carboxylate;

5-amino-8-(2,6-dimethyl-4-pyridyl)-2-(1-methyl-3-piperidyl)-7-phenyl-[1,2,4]triazolo[4,3-c]pyrimidin-3-one;

(S)-5-amino-8-(2,6-dimethylpyridin-4-yl)-2-(morpholin-2-ylmethyl)-7-phenyl-[1,2,4]triazolo[4,3-c]pyrimidin-3 (2H)-one;

5-amino-8-(2,6-dimethyl-4-pyridyl)-2-[[(2S)-4-methylmorpholin-2-yl]methyl]-7-phenyl-[1,2,4]triazolo[4,3-c]pyrimidin-3-one;

5-amino-8-(2,6-dimethyl-4-pyridyl)-7-phenyl-2-(tetrahydropyran-4-ylmethyl)-[1,2,4]triazolo[4,3-c]pyrimidin-3-one;

5-amino-8-(2,6-dimethyl-4-pyridyl)-2-[[(2R)-4-methylmorpholin-2-yl]methyl]-7-phenyl-[1,2,4]triazolo[4,3-c]pyrimidin-3-one;

tert-butyl (3S)-3-[[5-amino-8-(2,6-dimethyl-4-pyridyl)-3-oxo-7-phenyl-[1,2,4]triazolo[4,3-c]pyrimidin-2-yl] methyl]morpholine-4-carboxylate;

5-amino-8-(2,6-dimethyl-4-pyridyl)-2-[[(3S)-morpholin-3-yl]methyl]-7-phenyl-[1,2,4]triazolo[4,3-c]pyrimidin-3-one;

5-amino-8-(2,6-dimethyl-4-pyridyl)-2-[[(3S)-4-methylmorpholin-3-yl]methyl]-7-phenyl-[1,2,4]triazolo[4,3-c]pyrimidin-3-one;

5-amino-8-(2,6-dimethyl-4-pyridyl)-2-[(1-methyl-4-piperidyl)methyl]-7-phenyl-[1,2,4]triazolo[4,3-c]pyrimidin-3-one;

(R)-5-amino-8-(2,6-dimethylpyridin-4-yl)-2-(morpholin-3-ylmethyl)-7-phenyl-[1,2,4]triazolo[4,3-c]pyrimidin-3 (2H)-one;

5-amino-8-(2,6-dimethyl-4-pyridyl)-2-[[(3R)-4-methylmorpholin-3-yl]methyl]-7-phenyl-[1,2,4]triazolo[4,3-c]pyrimidin-3-one;

5-amino-8-(2,6-dimethyl-4-pyridyl)-7-phenyl-2-(tetrahydropyran-3-ylmethyl)-[1,2,4]triazolo[4,3-c]pyrimidin-3-one;

5-amino-8-(2,6-dimethyl-4-pyridyl)-7-phenyl-2-(tetrahydropyran-3-ylmethyl)-[1,2,4]triazolo[4,3-c]pyrimidin-3-one;

5-amino-8-(2,6-dimethyl-4-pyridyl)-7-phenyl-2-(tetrahydropyran-3-ylmethyl)-[1,2,4]triazolo[4,3-c]pyrimidin-3-one;

5-amino-8-(2,6-dimethyl-4-pyridyl)-7-phenyl-2-(tetrahydropyran-2-ylmethyl)-[1,2,4]triazolo[4,3-c]pyrimidin-3-one;

5-amino-8-(2,6-dimethyl-4-pyridyl)-7-phenyl-2-(tetrahydropyran-2-ylmethyl)-[1,2,4]triazolo[4,3-c]pyrimidin-3-one;

5-amino-8-(2,6-dimethyl-4-pyridyl)-7-phenyl-2-(tetrahydropyran-2-ylmethyl)-[1,2,4]triazolo[4,3-c]pyrimidin-3-one;

tert-butyl(S)-3-((5-amino-8-(2,6-dimethylpyridin-4-yl)-3-oxo-7-phenyl-[1,2,4]triazolo[4,3-c]pyrimidin-2 (3H)-yl)methyl)-4-methylpiperazine-1-carboxylate;

tert-butyl (R)-3-((5-amino-8-(2,6-dimethylpyridin-4-yl)-3-oxo-7-phenyl-[1,2,4]triazolo[4,3-c]pyrimidin-2 (3H)-yl)methyl)-4-methylpiperazine-1-carboxylate;

(R)-5-amino-2-((1,4-dimethylpiperazin-2-yl)methyl)-8-(2,6-dimethylpyridin-4-yl)-7-phenyl-[1,2,4]triazolo[4,3-c]pyrimidin-3 (2H)-one;

5-amino-8-(2,6-dimethyl-4-pyridyl)-2-[[(2R)-1-methylpiperazin-2-yl]methyl]-7-phenyl-[1,2,4]triazolo[4,3-c]pyrimidin-3-one;

(S)-5-amino-2-((1,4-dimethylpiperazin-2-yl)methyl)-8-(2,6-dimethylpyridin-4-yl)-7-phenyl-[1,2,4]triazolo[4,3-c]pyrimidin-3 (2H)-one;

5-amino-8-(2,6-dimethyl-4-pyridyl)-2-[[(2S)-1-methylpiperazin-2-yl]methyl]-7-phenyl-[1,2,4]triazolo[4,3-c]pyrimidin-3-one;

5-amino-8-(2,6-dimethyl-4-pyridyl)-2-[(1, 1-dioxothian-3-yl)methyl]-7-phenyl-[1,2,4]triazolo[4,3-c]pyrimidin-3-one;

5-amino-8-(2,6-dimethyl-4-pyridyl)-2-[(1, 1-dioxothian-3-yl)methyl]-7-phenyl-[1,2,4]triazolo[4,3-c]pyrimidin-3-one;

5-amino-8-(2,6-dimethyl-4-pyridyl)-2-[(1,1-dioxothietan-3-yl)methyl]-7-phenyl-[1,2,4]triazolo[4,3-c]pyrimidin-3-one;

5-amino-8-[2-(hydroxymethyl)-6-methyl-4-pyridyl]-7-phenyl-2-(tetrahydropyran-2-ylmethyl)-[1,2,4]triazolo[4,3-c]pyrimidin-3-one;

5-amino-8-[2-(hydroxymethyl)-6-methyl-4-pyridyl]-7-phenyl-2-(tetrahydropyran-2-ylmethyl)-[1,2,4]triazolo[4,3-c]pyrimidin-3-one;

5-amino-8-[2-(hydroxymethyl)-6-methyl-4-pyridyl]-7-phenyl-2-(tetrahydropyran-3-ylmethyl)-[1,2,4]triazolo[4,3-c]pyrimidin-3-one;

5-amino-8-[2-(hydroxymethyl)-6-methyl-4-pyridyl]-7-phenyl-2-(tetrahydropyran-3-ylmethyl)-[1,2,4]triazolo[4,3-c]pyrimidin-3-one;

5-amino-7-(4-fluorophenyl)-8-[2-(hydroxymethyl)-6-methyl-4-pyridyl]-2-(3,4,5,6-tetrahydropyridazin-3-ylmethyl)-[1,2,4]triazolo[4,3-c]pyrimidin-3-one;

5-amino-2-[2-(azetidin-1-yl)ethyl]-8-(2,6-dimethyl-4-pyridyl)-7-phenyl-[1,2,4]triazolo[4,3-c]pyrimidin-3-one;

2-(2-(2-azabicyclo[3.1.0] hexan-2-yl)ethyl)-5-amino-8-(2,6-dimethylpyridin-4-yl)-7-phenyl-[1,2,4]triazolo[4,3-c]pyrimidin-3 (2H)-one;

5-amino-8-(2,6-dimethyl-4-pyridyl)-7-phenyl-2-[2-(1-piperidyl)ethyl]-[1,2,4]triazolo[4,3-c]pyrimidin-3-one;

5-amino-8-(2,6-dimethyl-4-pyridyl)-2-[2-(1-methyl-4-piperidyl)ethyl]-7-phenyl-[1,2,4]triazolo[4,3-c]pyrimidin-3-one;

5-amino-8-(2,6-dimethyl-4-pyridyl)-2-[2-(3-methyl-1-piperidyl)ethyl]-7-phenyl-[1,2,4]triazolo[4,3-c]pyrimidin-3-one;

5-amino-8-(2,6-dimethyl-4-pyridyl)-2-(2-morpholinoethyl)-7-phenyl-[1,2,4]triazolo[4,3-c]pyrimidin-3-one;

5-amino-2-[2-((cis)-2,6-dimethylmorpholin-4-yl)ethyl]-8-(2,6-dimethyl-4-pyridyl)-7-phenyl-[1,2,4]triazolo[4,3-c]pyrimidin-3-one;

5-amino-2-[2-(4,4-difluoro-1-piperidyl)ethyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-2-[2-(4-methylpiperazin-1-yl)ethyl]-7-phenyl-[1,2,4]triazolo[4,3-c]pyrimidin-3-one;

5-amino-2-[2-(8-azabicyclo[3.2.1] octan-8-yl)ethyl]-8-(2,6-dimethyl-4-pyridyl)-7-phenyl-[1,2,4]triazolo[4,3-c]pyrimidin-3-one;

5-amino-8-(2,6-dimethyl-4-pyridyl)-7-(4-fluorophenyl)-2-[2-(1-piperidyl)ethyl]-[1,2,4]triazolo[4,3-c]pyrimidin-3-one;

5-amino-8-(2-chloro-6-methyl-4-pyridyl)-7-(4-fluorophenyl)-2-[2-(1-piperidyl)ethyl]-[1,2,4]triazolo[4,3-c]pyrimidin-3-one;

methyl 3-[2-[5-amino-8-(2,6-dimethyl-4-pyridyl)-3-oxo-7-phenyl-[1,2,4]triazolo[4,3-c]pyrimidin-2-yl]ethylamino]piperidine-1-carboxylate;

5-amino-8-(2,6-dimethyl-4-pyridyl)-2-[2-[[2-(4-hydroxy-1-piperidyl)-2-oxo-ethyl]-methyl-amino]ethyl]-7-phenyl-[1,2,4]triazolo[4,3-c]pyrimidin-3-one;

3-[2-[5-amino-8-(2,6-dimethyl-4-pyridyl)-3-oxo-7-phenyl-[1,2,4]triazolo[4,3-c]pyrimidin-2-yl]ethylamino]-N-cyclopropyl-cyclohexanecarboxamide;

methyl 3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl] propanoate;

3-[4-[2-[5-amino-8-(2,6-dimethyl-4-pyridyl)-3-oxo-7-phenyl-[1,2,4]triazolo[4,3-c]pyrimidin-2-yl]ethyl]-1-piperidyl] propanoic acid;

5-amino-8-(2,6-dimethyl-4-pyridyl)-7-phenyl-2-[3-(1-piperidyl) propyl]-[1,2,4]triazolo[4,3-c]pyrimidin-3-one;

5-amino-8-(2,6-dimethylpyridin-4-yl)-2-(3-(2-oxopyridin-1 (2H)-yl) propyl)-7-phenyl-[1,2,4]triazolo[4,3-c]pyrimidin-3 (2H)-one;

3-(5-amino-8-(2,6-dimethylpyridin-4-yl)-3-oxo-7-phenyl-[1,2,4]triazolo[4,3-c]pyrimidin-2 (3H)-yl)-N-methylpropanamide;

5-amino-8-(2,6-dimethyl-4-pyridyl)-7-morpholino-2-(3,3,3-trifluoropropyl)-[1,2,4]triazolo[4,3-c]pyrimidin-3-one;

5-amino-8-(2,6-dimethyl-4-pyridyl)-7-(1-piperidyl)-2-(3,3,3-trifluoropropyl)-[1,2,4]triazolo[4,3-c]pyrimidin-3-one;

5-amino-8-(2,6-dimethyl-4-pyridyl)-7-ethoxy-2-(3,3,3-trifluoropropyl)-[1,2,4]triazolo[4,3-c]pyrimidin-3-one;

5-amino-8-(2,6-dimethyl-4-pyridyl)-7-[ethyl(methyl) amino]-2-(3,3,3-trifluoropropyl)-[1,2,4]triazolo[4,3-c]pyrimidin-3-one;

5-amino-7-chloro-8-(2,6-dimethyl-4-pyridyl)-2-(3,3,3-trifluoropropyl)-[1,2,4]triazolo[4,3-c]pyrimidin-3-one;

methyl 5-amino-8-(2,6-dimethyl-4-pyridyl)-3-oxo-2-(3,3,3-trifluoropropyl)-[1,2,4]triazolo[4,3-c]pyrimidine-7-carboxylate;

5-amino-8-(2,6-dimethyl-4-pyridyl)-7-prop-1-ynyl-2-(3,3,3-trifluoropropyl)-[1,2,4]triazolo[4,3-c]pyrimidin-3-one;

5-amino-8-(2,6-dimethyl-4-pyridyl)-7-methoxy-2-(3,3,3-trifluoropropyl)-[1,2,4]triazolo[4,3-c]pyrimidin-3-one;

5-amino-8-(2,6-dimethyl-4-pyridyl)-7-[(Z)-1-methylprop-1-enyl]-2-(3,3,3-trifluoropropyl)-[1,2,4]triazolo[4,3-c]pyrimidin-3-one; and 5-amino-8-(2,6-dimethyl-4-pyridyl)-7-[(E)-1-methylprop-1-enyl]-2-(3,3,3-trifluoropropyl)-[1,2,4]triazolo[4,3-c]pyrimidin-3-one.

10. A pharmaceutical composition comprising a compound of claim 1, or a pharmaceutically acceptable salt thereof, and a pharmaceutically acceptable carrier, diluent, or excipient.

11. A method for treating a disease or condition mediated by an adenosine receptor which comprises administering a compound of claim 1, or a pharmaceutically acceptable salt thereof, to a patient in need thereof, wherein the disease or condition mediated by the adenosine receptor is lung cancer, pancreatic cancer, prostate cancer, ovarian cancer, cervical cancer, colorectal cancer, breast cancer, brain cancer, gastric cancer, liver cancer, renal cancer, endometrial cancer, thyroid cancer, bladder cancer, glial cancer, melanoma, or other solid tumor.

* * * * *